US 8,816,079 B2

(12) United States Patent
Maeda et al.

(10) Patent No.: US 8,816,079 B2
(45) Date of Patent: Aug. 26, 2014

(54) AMIDE DERIVATIVE AND USE THEREOF AS MEDICINE

(75) Inventors: Kazuhiro Maeda, Osaka (JP); Jun-ichi Endoh, Osaka (JP); Akiko Tarao, Osaka (JP); Kaoru Tashiro, Osaka (JP); Seigo Ishibuchi, Osaka (JP); Hidemasa Hikawa, Funabashi (JP)

(73) Assignee: Mitsubishi Tanabe Pharma Corporation, Osaka (JP)

(*) Notice: Subject to any disclaimer, the term of this patent is extended or adjusted under 35 U.S.C. 154(b) by 0 days.

(21) Appl. No.: 13/643,790

(22) PCT Filed: Apr. 27, 2011

(86) PCT No.: PCT/JP2011/060307
§ 371 (c)(1),
(2), (4) Date: Oct. 26, 2012

(87) PCT Pub. No.: WO2011/136292
PCT Pub. Date: Nov. 3, 2011

(65) Prior Publication Data
US 2013/0040930 A1      Feb. 14, 2013

(30) Foreign Application Priority Data

Apr. 27, 2010    (JP) .................................. 2010-101953

(51) Int. Cl.
| | |
|---|---|
| C07D 251/00 | (2006.01) |
| C07D 253/00 | (2006.01) |
| C07D 241/02 | (2006.01) |
| C07D 403/00 | (2006.01) |
| C07D 413/00 | (2006.01) |
| C07D 211/68 | (2006.01) |
| C07D 401/00 | (2006.01) |
| A61K 31/55 | (2006.01) |
| A61K 31/497 | (2006.01) |
| A61K 31/445 | (2006.01) |
| A61K 31/41 | (2006.01) |

(52) U.S. Cl.
USPC ........... 544/364; 544/180; 544/182; 544/357; 544/369; 546/194; 546/209; 514/218; 514/252.11; 514/252.12; 514/253.01; 514/254.02; 514/318; 514/326; 514/383

(58) Field of Classification Search
USPC .......... 544/180, 182, 357, 364, 369; 546/194, 546/209; 514/218, 252.11, 253.01, 254.02, 514/318, 326, 383
See application file for complete search history.

(56) References Cited

U.S. PATENT DOCUMENTS

| | | | |
|---|---|---|---|
| 8,354,401 B2 * | 1/2013 | Ishibuchi et al. | ............. 514/218 |
| 2003/0191317 A1 | 10/2003 | Bedell et al. | |
| 2011/0263571 A1 * | 10/2011 | Ishibuchi et al. | ............. 514/218 |

FOREIGN PATENT DOCUMENTS

| | | |
|---|---|---|
| EP | 1 714 961 A1 | 10/2006 |
| EP | 2 077 271 A1 | 7/2009 |
| EP | 2 364 975 A1 | 9/2011 |
| JP | 2004-359657 A1 | 12/2004 |
| WO | WO 2004/069816 A1 | 8/2004 |
| WO | WO 2005/023260 A1 | 3/2005 |
| WO | WO 2005035534 A1 * | 4/2005 |
| WO | WO 2005/077912 A1 | 8/2005 |
| WO | WO 2007/012646 A1 | 11/2007 |
| WO | WO 2009/138438 A1 | 11/2009 |
| WO | WO 2009138438 A1 * | 11/2009 |
| WO | WO 2010/050461 A1 | 5/2010 |
| WO | WO 2010050461 A1 * | 5/2010 |

OTHER PUBLICATIONS

CAS#930684-79-0. Enamine Library. Published online Apr. 18, 2007.*
Ainiala et al., *Arthritis and Rheumatism*, 50(3): 858-865 (2004).
Cheng et al., *Bioorganic and Medicinal Chemistry*, 17: 3018-3024 (2009).
Huang et al., *Journal of the National Cancer Institute*, 94(15): 1134-1142 (2002).
Itoh et al., *The Journal of Immunology*, 169: 2643-2647 (2002).
Konttinen et al., *Ann. Rheum, Dis.*, 58: 691-697 (1999).
Masuhara et al., *Arthritis and Rheumatism*, 46(10): 2625-2631 (2002).
McQuibban et al., *Science*, 289: 1202-1206 (2000).
Medina et al., *Journal of Leukocyte Biology*, 79: 954-962 (2006).
Mohtai et al., *J. Clin. Invest*, 92: 179-185 (1993).
Opdenakker et al., *The Lancet Neurology*, 2: 747-756 (2003).

(Continued)

*Primary Examiner* — Paul Zarek
*Assistant Examiner* — George W Kosturko
(74) *Attorney, Agent, or Firm* — Leydig, Voit & Mayer, Ltd.

(57) ABSTRACT

Provided are a novel low-molecular-weight compound that suppresses production of induction type MMPs, particularly MMP-9, rather than production of hemostatic type MMP-2, as well as a prophylactic/therapeutic drug for autoimmune diseases or osteoarthritis. An amide derivative represented by the following formula (I)

(I)

$$R^a-N(R^b)-W-A-C(=O)-N(-(CH_2)_m-R^{4a})(-CHR^{4b}-CHR^{4c}-X-Y-\text{aryl}(R^1,R^2,R^3,Z^1,Z^2,Z^3))$$

wherein each symbol is as defined in the specification, or a pharmacologically acceptable salt thereof.

14 Claims, No Drawings

(56) References Cited

OTHER PUBLICATIONS

Pinard et al., *Bioorganic and Medicinal Letters*, 18: 5134-5139 (2008).
RN 899965-48-1, ED entered STN: Aug. 9, 2006, SR Chemical Library Registry [online—retrieved on May 24, 2011].
RN 1018135-60-8, ED entered STN: Apr. 29, 2008, SR Chemical Library Registry [online—retrieved on May 24, 2011].
Japanese Patent Office, International Search Report for International Patent Application No. PCT/JP2011/060307 (Jun. 7, 2011).
Chemical Abstracts Service, Database Registry (on-line), Database Accession No. 339320-85-3 (Jun. 4, 2001).
Chemical Abstracts Service, Database Registry (on-line), Database Accession No. 886148-20-5 (May 31, 2006).
Chemical Abstracts Service, Database Registry (on-line), Database Accession No. 1209436-76-9 (Mar. 12, 2010).
Ledour et al., *Bioorganic & Medicinal Chemistry*, 16(18): 8745-8759 (2008).
European Patent Office, Supplemental European Search Report in European Patent Application No. 11775073 (Oct. 31, 2013).

* cited by examiner

AMIDE DERIVATIVE AND USE THEREOF AS MEDICINE

CROSS-REFERENCE TO RELATED APPLICATIONS

This patent application is the U.S. national phase of PCT/JP2011/060307, filed on Apr. 27, 2011, which claims the benefit of Japanese Patent Application No. 2010/101953, filed on Apr. 27, 2010, which are incorporated by reference in their entireties herein.

TECHNICAL FIELD

The present invention relates to a novel amide derivative showing a selective MMP-9 production suppressive action and pharmaceutical use thereof.

BACKGROUND ART

Matrix metalloprotease (MMPs) is an enzyme group playing a key role in the binding tissue degradation in living organisms. The activity of MMPs is controlled by each step of 1) production of latent enzyme (proMMP) by gene expression, 2) activation of proMMP, 3) activity inhibition by TIMP which is an inhibitor of active enzymes. MMPs includes two types of hemostatic type and induction type, the former includes MMP-2 and MMP-14, and the latter includes many MMPs such as MMP-1, 3, 9, 13 etc. Particularly, promoted production or expression in rheumatoid arthritis, osteoarthritis, multiple sclerosis, systemic lupus erythematosus and inflammatory bowel diseases (ulcerative colitis, Crohn's disease) by MMP-9 has been acknowledged, and the involvement of MMP-9 in these pathologies has been suggested [Ann. Rheum. Dis., vol. 58, page 691-697 (1999) (non-patent document 1), J. Clin. Invest., vol. 92, page 179-185 (1993) (non-patent document 2), Arthritis Rheum., vol. 46, page 2625-2631 (2002) (non-patent document 3), Lancet Neurol., vol. 2, page 747-756 (2003) (non-patent document 4), Arthritis Rheum., vol. 50, page 858-865 (2004) (non-patent document 5), Journal of Leukocyte Biology, vol. 79, page 954-962 (2006) (non-patent document 9)].

In addition, it has been suggest from the studies of MMP knockout mouse that MMP-9 is involved in the formation and progression of cancer, MMP-9 plays an important role in the progression of arthritis and articular destruction [J. Natl. Cancer Inst., vol. 94, 1134-1142 (2002) (non-patent document 6), J. Immunol., vol. 169, 2643-2647 (2002) (non-patent document 7)]. On the other hand, MMP-2 shows an anti-inflammatory action and the action mechanism thereof is considered to be degradation of MCP-3 and the like [Science, vol. 289, page 1202-1206 (2000) (non-patent document 8)]. Therefore, a medicament that does not influence MMP-2 production and selectively suppresses MMP-9 production can be expected as a novel therapeutic drug.

JP-A-2004-359657 (patent document 1) discloses leptomycin B, which is a medicament that inhibits MMP-9 production, and a derivative thereof.

DOCUMENT LIST

Patent Document patent document 1: JP-A-2004-359657

Non-Patent Documents non-patent document 1: Ann. Rheum. Dis., vol. 58, page 691-697 (1999)

non-patent document 2: J. Clin. Invest., vol. 92, page 179-185 (1993)

non-patent document 3: Arthritis Rheum., vol. 46, page 2625-2631 (2002)

non-patent document 4: Lancet Neurol., vol. 2, page 747-756 (2003)

non-patent document 5: Arthritis Rheum., vol. 50, page 858-865 (2004)

non-patent document 6: J. Natl. Cancer Inst., vol. 94, page 1134-1142 (2002)

non-patent document 7: J. Immunol., vol. 169, page 2643-2647 (2002)

non-patent document 8: Science, vol. 289, page 1202-1206 (2000)

non-patent document 9: Journal of Leukocyte Biology, vol. 79, page 954-962 (2006)

SUMMARY OF THE INVENTION

Problems to be Solved by the Invention

The problem of the present invention is to provide a novel low-molecular-weight compound that suppresses production of induction type MMPs, particularly MMP-9, rather than production of hemostatic type MMP-2.

Means of Solving the Problems

In view of the above-mentioned problems, the present inventors have conducted intensive studies in an attempt to find a low-molecular-weight compound showing an MMP-9 production suppressive action. As a result, they have found that the amide derivative of the present invention suppresses production of induction type MMPs, particularly MMP-9, rather than production of hemostatic type MMP-2, which resulted in the completion of the present invention.

Accordingly, the present invention is as described below.

[1] An amide derivative represented by the following formula (I)

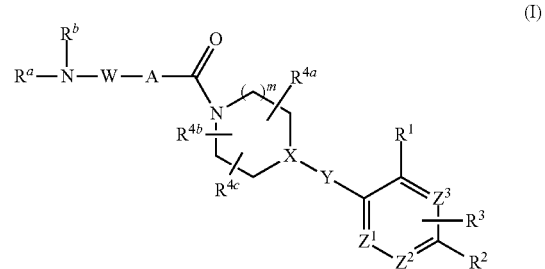

wherein A is a 5-membered heteroarylene containing 1-3 atoms selected from a nitrogen atom, an oxygen atom and a sulfur atom or phenylene or a 6-membered heteroarylene represented by the following formula

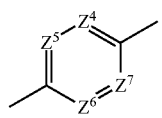

wherein $Z^4$, $Z^5$, $Z^6$ and $Z^7$ are each a carbon atom or a nitrogen atom, these phenylene and heteroarylene are optionally substituted by one or the same or different 2 or 3 substituents selected from a halogen atom; a hydroxyl group; nitro; cyano; mercapto; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ acyloxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; $C_3$-$C_6$ cycloalkylthio; $C_3$-$C_6$ cycloalkylsulfinyl; $C_3$-$C_6$ cycloalkylsulfonyl; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; aminocarbonyl wherein the amino moiety is optionally mono- or di-substituted by $C_1$-$C_6$ alkyl (wherein $C_1$-$C_6$ alkyl is optionally substituted by a halogen atom, a hydroxyl group, cyano, $C_1$-$C_6$ alkoxy, amino optionally mono- or di-substituted by $C_1$-$C_6$ alkyl, $C_6$-$C_{10}$ aryl optionally substituted by substituent B shown below or heteroaryl containing 1-6 atoms selected from a nitrogen atom, an oxygen atom and a sulfur atom and having 5-10 ring-constituting atoms, which is optionally substituted by substituent B shown below), $C_3$-$C_6$ cycloalkyl (wherein $C_3$-$C_6$ cycloalkyl is optionally substituted by substituent B shown below), $C_2$-$C_7$ alkoxycarbonyl, $C_6$-$C_{10}$ aryl optionally substituted by substituent B shown below, heteroaryl containing 1-6 atoms selected from a nitrogen atom, an oxygen atom and a sulfur atom and having 5-10 ring-constituting atoms, which is optionally substituted by substituent B shown below, or a nonaromatic heterocyclic group containing 1-4 atoms selected from a nitrogen atom, an oxygen atom and a sulfur atom and having 3-7 ring-constituting atoms, which is optionally substituted by substituent B shown below; $C_1$-$C_6$ alkylsulfonylamino wherein the amino moiety is optionally substituted by $C_1$-$C_6$ alkyl; $C_3$-$C_6$ cycloalkylsulfonylamino wherein the amino moiety is optionally substituted by $C_1$-$C_6$ alkyl; a nonaromatic heterocyclic group containing 1-4 atoms selected from a nitrogen atom, an oxygen atom and a sulfur atom, and having 3-7 ring-constituting atoms, which is optionally substituted by a halogen atom, a hydroxyl group, oxo, dioxo, $C_1$-$C_6$ alkyl (which is optionally substituted by amino optionally mono- or di-substituted by $C_1$-$C_6$ alkyl, a halogen atom, a hydroxyl group, $C_1$-$C_6$ alkoxy, arylalkyl wherein the $C_6$-$C_{10}$ aryl moiety is optionally substituted by substituent B shown below and the alkyl moiety has 1-6 carbon atoms, arylalkyloxy wherein the $C_6$-$C_{10}$ aryl moiety is optionally substituted by substituent B shown below and the alkyl moiety has 1-6 carbon atoms, heteroarylalkyl wherein the heteroaryl moiety containing 1-6 atoms selected from a nitrogen atom, an oxygen atom and a sulfur atom, and having 5-10 ring-constituting atoms is optionally substituted by substituent B shown below and the alkyl moiety has 1-6 carbon atoms or heteroarylalkyloxy wherein the heteroaryl moiety containing 1-6 atoms selected from a nitrogen atom, an oxygen atom and a sulfur atom, and having 5-10 ring-constituting atoms is optionally substituted by substituent B shown below and the alkyl moiety has 1-6 carbon atoms), $C_1$-$C_6$ alkoxy (which is optionally substituted by amino optionally mono- or di-substituted by $C_1$-$C_6$ alkyl, a halogen atom, a hydroxyl group or $C_1$-$C_6$ alkoxy) or $C_2$-$C_7$ acyl; carbonyl substituted by a nonaromatic heterocyclic group containing at least one nitrogen atom and 0-3 atoms selected from a nitrogen atom, an oxygen atom and a sulfur atom, and having 3-7 ring-constituting atoms, which is optionally substituted by substituent B shown below (wherein the carbonyl is bonded to a nitrogen atom on a nonaromatic heterocyclic group); and R'—NH—CO—NH— (wherein R' is $C_1$-$C_6$ alkyl optionally substituted by a halogen atom; $C_3$-$C_6$ cycloalkyl optionally substituted by a halogen atom; a nonaromatic heterocyclic group containing 1-4 atoms selected from a nitrogen atom, an oxygen atom and a sulfur atom, and having 3-7 ring-constituting atoms, which is optionally substituted by a halogen atom; $C_6$-$C_{10}$ aryl optionally substituted by substituent B shown below; or heteroaryl containing 1-6 atoms selected from a nitrogen atom, an oxygen atom and a sulfur atom and having 5-10 ring-constituting atoms, which is optionally substituted by substituent B shown below), the right bond is bonded to carbonyl, and the left bond is bonded to substituent W, $R^1$ is a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ alkoxycarbonyl; carboxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; $C_1$-$C_6$ alkylsulfonylamino wherein the amino moiety is optionally substituted by $C_1$-$C_6$ alkyl; or $C_3$-$C_6$ cycloalkylsulfonylamino wherein the amino moiety is optionally substituted by $C_1$-$C_6$ alkyl, $R^2$ is a halogen atom; a hydroxyl group; nitro; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkylthio wherein the alkyl moiety is optionally substituted by a halogen atom or a hydroxyl group; C$_1$-C$_6$ alkylsulfinyl wherein the alkyl moiety is optionally substituted by a halogen atom or a hydroxyl group; C$_1$-C$_6$ alkylsulfonyl wherein the alkyl moiety is optionally substituted by a halogen atom or a hydroxyl group; amino optionally mono- or di-substituted by C$_1$-C$_6$ alkyl or C$_3$-C$_6$ cycloalkyl; C$_2$-C$_7$ acylamino wherein the amino moiety is optionally substituted by C$_1$-C$_6$ alkyl; C$_1$-C$_6$ alkylsulfonylamino wherein the amino moiety is optionally substituted by C$_1$-C$_6$ alkyl; or C$_3$-C$_6$ cycloalkylsulfonylamino wherein the amino moiety is optionally substituted by C$_1$-C$_6$ alkyl, R$^3$ is a hydrogen atom; a halogen atom; a hydroxyl group; nitro; cyano; C$_1$-C$_6$ alkyl optionally substituted by amino optionally mono- or di-substituted by C$_1$-C$_6$ alkyl, a halogen atom, a hydroxyl group or C$_1$-C$_6$ alkoxy; C$_2$-C$_6$ alkenyl; C$_2$-C$_6$ alkynyl; C$_3$-C$_6$ cycloalkyl optionally substituted by a halogen atom, a hydroxyl group or amino; C$_1$-C$_6$ alkoxy optionally substituted by amino optionally mono- or di-substituted by C$_1$-C$_6$ alkyl, a halogen atom, a hydroxyl group or C$_1$-C$_6$ alkoxy; C$_2$-C$_7$ alkoxycarbonyl; or carboxy, R$^{4a}$, R$^{4b}$ and R$^{4c}$ are the same or different and each is a hydrogen atom, C$_1$-C$_6$ alkyl, oxo or C$_1$-C$_6$ alkoxy, W is a bond, C$_1$-C$_6$ alkylene or C$_3$-C$_6$ cycloalkylidene, X is a carbon atom (any of R$^{4a}$, R$^{4b}$ and R$^{4c}$ may be bonded to the carbon atom, but the carbon atom is not substituted by oxo) or a nitrogen atom (when Y is a bond, the nitrogen atom may be oxidized to form N-oxide), Y is a bond, carbonyl, C$_1$-C$_6$ alkylene, an oxygen atom or —NH—, m is 1 or 2, Z$^1$, Z$^2$ and Z$^3$ are the same or different and each is a carbon atom or a nitrogen atom, wherein Z$^1$, Z$^2$ and Z$^3$ are not nitrogen atoms at the same time, R$^a$ and R$^b$ are the same or different and each is a hydrogen atom; C$_1$-C$_6$ alkyl optionally substituted by amino optionally mono- or di-substituted by C$_1$-C$_6$ alkyl, a halogen atom, a hydroxyl group or C$_1$-C$_6$ alkoxy; C$_3$-C$_6$ cycloalkyl optionally substituted by a halogen atom, a hydroxyl group or amino; C$_6$-C$_{10}$ aryl optionally substituted by substituent B shown below; arylalkyl wherein the C$_6$-C$_{10}$ aryl moiety is optionally substituted by substituent B shown below and the alkyl moiety has 1-6 carbon atoms; heteroaryl containing 1-6 atoms selected from a nitrogen atom, an oxygen atom and a sulfur atom and having 5-10 ring-constituting atoms, which is optionally substituted by substituent B shown below; heteroarylalkyl wherein the heteroaryl moiety containing 1-6 atoms selected from a nitrogen atom, an oxygen atom and a sulfur atom and having 5-10 ring-constituting atoms is optionally substituted by substituent B shown below and the alkyl moiety has 1-6 carbon atoms; formyl; C$_2$-C$_7$ acyl; alkylcarbonyl wherein the C$_1$-C$_6$ alkyl moiety is substituted by amino optionally mono- or di-substituted by C$_1$-C$_6$ alkyl, a halogen atom, a hydroxyl group or C$_1$-C$_6$ alkoxy; arylcarbonyl wherein the C$_6$-C$_{10}$ aryl moiety is substituted by substituent B shown below; heteroarylcarbonyl wherein the heteroaryl moiety containing 1-6 atoms selected from a nitrogen atom, an oxygen atom and a sulfur atom and having 5-10 ring-constituting atoms is optionally substituted by substituent B shown below; C$_2$-C$_7$ alkoxycarbonyl; C$_1$-C$_6$ alkylsulfonyl wherein the alkyl moiety is optionally substituted by a halogen atom or a hydroxyl group; C$_3$-C$_6$ cycloalkylsulfonyl; aminocarbonyl wherein the amino moiety is optionally mono- or di-substituted by C$_1$-C$_6$ alkyl or C$_3$-C$_6$ cycloalkyl; C7-C11 arylaminocarbonyl wherein the aryl moiety is optionally substituted by substituent B shown below; heteroarylaminocarbonyl wherein the heteroaryl moiety containing 1-6 atoms selected from a nitrogen atom, an oxygen atom and a sulfur atom and having 5-10 ring-constituting atoms is optionally substituted by substituent B shown below; aminosulfonyl wherein the amino moiety is optionally mono- or di-substituted by C$_1$-C$_6$ alkyl; or carbonyl which is substituted by a nonaromatic heterocyclic group containing 1-4 atoms selected from a nitrogen atom, an oxygen atom and a sulfur atom and having 3-7 ring-constituting atoms, or R$^a$ and R$^b$ show, together with the adjacent nitrogen atom, heteroaryl containing 1-2 nitrogen atoms and 0-1 atom selected from an oxygen atom and a sulfur atom, and having 5 ring-constituting atoms, which is optionally substituted by substituent B shown below or oxo; heteroaryl containing 1-6 atoms selected from a nitrogen atom, an oxygen atom and a sulfur atom and always one or more nitrogen atoms, and having 6-10 ring-constituting atoms, which is optionally substituted by substituent B shown below or oxo; a saturated nonaromatic heterocyclic group containing 1-4 atoms selected from a nitrogen atom, an oxygen atom and a sulfur atom and always one or more nitrogen atoms, and having 3-7 ring-constituting atoms, which is optionally substituted by substituent B shown below, or a nitrogen-containing cyclic group shown below

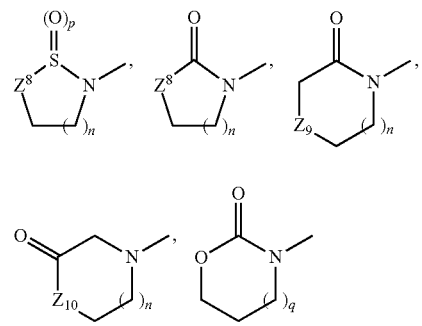

wherein Z$^8$ is a carbon atom or a nitrogen atom, Z$^9$ is a nitrogen atom or an oxygen atom, Z$^{10}$ is a carbon atom, a nitrogen atom or an oxygen atom, n is 0, 1, 2 or 3, p is 1 or 2, and q is 1 or 2, when A is 5-membered heteroarylene or any two or more of Z$^4$, Z$^5$, Z$^6$ and Z$^7$ are nitrogen atoms, Z$^2$ is a nitrogen atom, and one of Z$^1$ and Z$^3$ is a carbon atom and the other is a nitrogen atom, or W is C$_1$-C$_6$ alkylene or C$_3$-C$_6$ cycloalkylidene, then it may be a nitrogen-containing cyclic group shown below

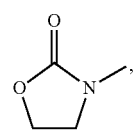

the above-mentioned nitrogen-containing cyclic group is optionally substituted by 1-6 substituents selected from a halogen atom; a hydroxyl group; oxo; C$_1$-C$_6$ alkyl optionally substituted by amino optionally mono- or di-substituted by C$_1$-C$_6$ alkyl, a halogen atom, a hydroxyl group, C$_1$-C$_6$ alkoxy, arylalkyloxy wherein the $C_6$-$C_{10}$ aryl moiety is optionally substituted by substituent B shown below and the alkyl moiety has 1-6 carbon atoms or heteroarylalkyloxy wherein the heteroaryl moiety containing 1-6 atoms selected from a nitrogen atom, an oxygen atom and a sulfur atom and having 5-10 ring-constituting atoms is optionally substituted by substituent B shown below, and the alkyl moiety has 1-6 carbon atoms; $C_3$-$C_6$ cycloalkyl optionally substituted by a halogen atom, a hydroxyl group or amino; $C_6$-$C_{10}$ aryl optionally substituted by substituent B shown below; arylalkyl wherein the $C_6$-$C_{10}$ aryl moiety is optionally substituted by substituent B shown below and the alkyl moiety has 1-6 carbon atoms; heteroaryl containing 1-6 atoms selected from a nitrogen atom, an oxygen atom and a sulfur atom and having 5-10 ring-constituting atoms, which is optionally substituted by substituent B shown below; heteroarylalkyl wherein the heteroaryl moiety containing 1-6 atoms selected from a nitrogen atom, an oxygen atom and a sulfur atom and having 5-10 ring-constituting atoms is optionally substituted by substituent B shown below and the alkyl moiety has 1-6 carbon atoms; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ acyl; alkylcarbonyl wherein the $C_1$-$C_6$ alkyl moiety is substituted by amino optionally mono- or di-substituted by $C_1$-$C_6$ alkyl, a halogen atom, a hydroxyl group or $C_1$-$C_6$ alkoxy; arylcarbonyl wherein the $C_6$-$C_{10}$ aryl moiety is substituted by substituent B shown below; $C_2$-$C_7$ acyloxy; $C_2$-$C_7$ alkoxycarbonyl; carboxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; aminocarbonyl wherein the amino moiety is optionally mono- or di-substituted by $C_1$-$C_6$ alkyl or $C_3$-$C_6$ cycloalkyl; $C_1$-$C_6$ alkylsulfonylamino wherein the amino moiety is optionally substituted by $C_1$-$C_6$ alkyl; $C_1$-$C_6$ alkyl which is substituted by a nonaromatic heterocyclic group containing 1-4 atoms selected from a nitrogen atom, an oxygen atom and a sulfur atom and having 3-7 ring-constituting atoms, wherein the nonaromatic heterocyclic group moiety is optionally substituted by amino optionally mono- or di-substituted by $C_1$-$C_6$ alkyl, a halogen atom, or pyrrolidinylalkyl wherein the alkyl moiety has 1 to 6 carbon atoms; and carbonyl which is substituted by a nonaromatic heterocyclic group containing 1-4 atoms selected from a nitrogen atom, an oxygen atom and a sulfur atom and having 3-7 ring-constituting atoms, wherein the nonaromatic heterocyclic group moiety is optionally substituted by amino or aminocarbonyl wherein the amino moiety is optionally mono- or di-substituted by $C_1$-$C_6$ alkyl, a halogen atom, a hydroxyl group, $C_1$-$C_6$ alkyl, piperidine, piperazine or morpholine, further, the carbon atom of the above-mentioned nitrogen-containing cyclic group optionally form a spiro bond with $C_3$-$C_6$ cycloalkane or a hetero ring containing 1 or 2 atoms selected from a nitrogen atom and an oxygen atom and having 3-6 ring-constituting atoms, further, two atoms from the atoms contained in the above-mentioned nitrogen-containing cyclic group, to which two atoms substituent(s) are bondable, are optionally bonded via methylene, ethylene or vinylene to form a fused ring or a crosslinked ring, when the formula (I) is the following compound

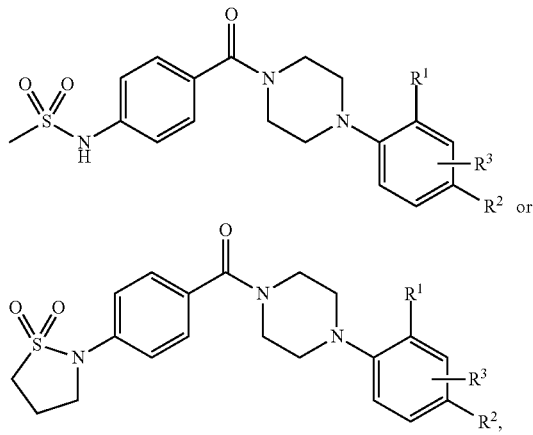

then $R^1$ and $R^2$ are not methyl groups at the same time:

Substituent B a halogen atom; a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group or amino; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl or $C_3$-$C_6$ cycloalkyl; aminocarbonyl wherein the amino moiety is optionally mono- or di-substituted by $C_1$-$C_6$ alkyl or $C_3$-$C_6$ cycloalkyl; or carbonyl which is substituted by a nonaromatic heterocyclic group containing 1-4 atoms selected from a nitrogen atom, an oxygen atom and a sulfur atom and having 3-7 ring-constituting atoms and optionally substituted by a halogen atom, a hydroxyl group, oxo, dioxo, $C_1$-$C_6$ alkyl or $C_1$-$C_6$ alkoxy, or a pharmacologically acceptable salt thereof.

[2] The amide derivative of [1], wherein X is a nitrogen atom or N-oxide wherein nitrogen atom is oxidized and Y is a bond, or a pharmacologically acceptable salt thereof.

[3] The amide derivative of [1] or [2], wherein A is 5-membered heteroarylene containing 1-3 atoms selected from a nitrogen atom, an oxygen atom and a sulfur atom, or phenylene or 6-membered heteroarylene represented by the following formula

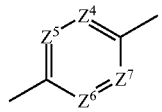

wherein $Z^4$, $Z^5$, $Z^6$ and $Z^7$ are each a carbon atom or a nitrogen atom, these phenylene and heteroarylene are optionally substituted by one or the same or different 2 or 3 substituents selected from a halogen atom; a hydroxyl group; nitro; cyano; mercapto; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ acyloxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; $C_3$-$C_6$ cycloalkylthio; $C_3$-$C_6$ cycloalkylsulfinyl; $C_3$-$C_6$ cycloalkylsulfonyl; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; aminocarbonyl wherein the amino moiety is optionally mono- or di-substituted by $C_1$-$C_6$ alkyl or $C_3$-$C_6$ cycloalkyl; $C_1$-$C_6$ alkylsulfonylamino wherein the amino moiety is optionally substituted by $C_1$-$C_6$ alkyl; $C_3$-$C_6$ cycloalkylsulfonylamino wherein the amino moiety is optionally substituted by $C_1$-$C_6$ alkyl; a nonaromatic heterocyclic group containing 1-4 atoms selected from a nitrogen atom, an oxygen atom and a sulfur atom, and having 3-7 ring-constituting atoms, which is optionally substituted by a halogen atom, a hydroxyl group, oxo, dioxo, $C_1$-$C_6$ alkyl or $C_1$-$C_6$ alkoxy; and R'—NH—CO—NH— (wherein R' is $C_1$-$C_6$ alkyl optionally substituted by a halogen atom; $C_3$-$C_6$ cycloalkyl optionally substituted by a halogen atom; a nonaromatic heterocyclic group containing 1-4 atoms selected from a nitrogen atom, an oxygen atom and a sulfur atom, and having 3-7 ring-constituting atoms, which is optionally substituted by a halogen atom; $C_6$-$C_{10}$ aryl optionally substituted by substituent B shown below; or heteroaryl containing 1-6 atoms selected from a nitrogen atom, an oxygen atom and a sulfur atom and having 5-10 ring-constituting atoms, which is optionally substituted by substituent B shown below, the right bond is bonded to carbonyl, and the left bond is bonded to substituent W, $R^a$ and $R^b$ are the same or different and each is a hydrogen atom; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group or amino; $C_6$-$C_{10}$ aryl optionally substituted by substituent B shown below; arylalkyl wherein the $C_6$-$C_{10}$ aryl moiety is optionally substituted by substituent B shown below and the alkyl moiety has 1-6 carbon atoms; heteroaryl containing 1-6 atoms selected from a nitrogen atom, an oxygen atom and a sulfur atom and having 5-10 ring-constituting atoms, which is optionally substituted by substituent B shown below; heteroarylalkyl wherein the heteroaryl moiety containing 1-6 atoms selected from a nitrogen atom, an oxygen atom and a sulfur atom and having 5-10 ring-constituting atoms is optionally substituted by substituent B shown below and the alkyl moiety has 1-6 carbon atoms; formyl; $C_2$-$C_7$ acyl; alkylcarbonyl wherein the $C_1$-$C_6$ alkyl moiety is substituted by amino optionally mono- or di-substituted by $C_1$-$C_6$ alkyl, a halogen atom, a hydroxyl group or $C_1$-$C_6$ alkoxy; arylcarbonyl wherein the $C_6$-$C_{10}$ aryl moiety is substituted by substituent B shown below; heteroarylcarbonyl wherein the heteroaryl moiety containing 1-6 atoms selected from a nitrogen atom, an oxygen atom and a sulfur atom and having 5-10 ring-constituting atoms is optionally substituted by substituent B shown below; $C_2$-$C_7$ alkoxycarbonyl; $C_1$-$C_6$ alkylsulfonyl wherein the alkyl moiety is optionally substituted by a halogen atom or a hydroxyl group; $C_3$-$C_6$ cycloalkylsulfonyl; aminocarbonyl wherein the amino moiety is optionally mono- or di-substituted by $C_1$-$C_6$ alkyl or $C_3$-$C_6$ cycloalkyl; $C_7$-$C_{11}$ arylaminocarbonyl wherein the aryl moiety is optionally substituted by substituent B shown below;

heteroarylaminocarbonyl wherein the heteroaryl moiety containing 1-6 atoms selected from a nitrogen atom, an oxygen atom and a sulfur atom and having 5-10 ring-constituting atoms is optionally substituted by substituent B shown below; aminosulfonyl wherein the amino moiety is optionally mono- or di-substituted by $C_1$-$C_6$ alkyl; or carbonyl which is substituted by a nonaromatic heterocyclic group containing 1-4 atoms selected from a nitrogen atom, an oxygen atom and a sulfur atom and having 3-7 ring-constituting atoms, or $R^a$ and $R^b$ show, together with the adjacent nitrogen atom, heteroaryl containing 1-2 nitrogen atoms and 0-1 atom selected from an oxygen atom and a sulfur atom, and having 5-ring-constituting atoms, which is optionally substituted by substituent B shown below or oxo; heteroaryl containing 1-6 atoms selected from a nitrogen atom, an oxygen atom and a sulfur atom and always one or more nitrogen atoms, and having 6-10 ring-constituting atoms, which is optionally substituted by substituent B shown below or oxo; a saturated nonaromatic heterocyclic group containing 1-4 atoms selected from a nitrogen atom, an oxygen atom and a sulfur atom and always one or more nitrogen atoms, and having 3-7 ring-constituting atoms, which is optionally substituted by substituent B shown below, or a nitrogen-containing cyclic group shown below

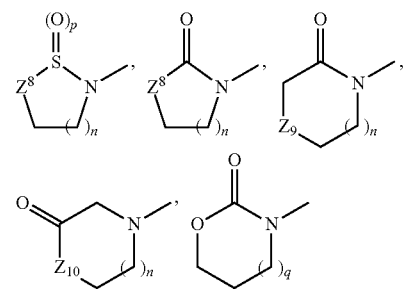

wherein $Z^6$ is a carbon atom or a nitrogen atom, $Z^9$ is a nitrogen atom or an oxygen atom, $Z^{10}$ is a carbon atom, a nitrogen atom or an oxygen atom, n is 0, 1, 2 or 3, p is 1 or 2, and q is 1 or 2, when A is 5-membered heteroarylene or any two or more of $Z^4$, $Z^5$, $Z^6$ and $Z^7$ are nitrogen atoms, $Z^2$ is a nitrogen atom, and one of $Z^1$ and $Z^3$ is a carbon atom and the other is a nitrogen atom, or W is $C_1$-$C_6$ alkylene or $C_3$-$C_6$ cycloalkylidene, then it may be a nitrogen-containing cyclic group shown below

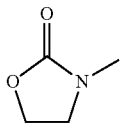

the above-mentioned nitrogen-containing cyclic group is optionally substituted by 1-3 substituents selected from a halogen atom; a hydroxyl group; oxo; $C_1$-$C_6$ alkyl optionally substituted by amino optionally mono- or di-substituted by $C_1$-$C_6$ alkyl, a halogen atom, a hydroxyl group, $C_1$-$C_6$ alkoxy, arylalkyloxy wherein the $C_6$-$C_{10}$ aryl moiety is optionally substituted by substituent B shown below and the alkyl moiety has 1-6 carbon atoms or heteroarylalkyloxy wherein the heteroaryl moiety containing 1-6 atoms selected from a nitrogen atom, an oxygen atom and a sulfur atom and having 5-10 ring-constituting atoms is optionally substituted by substituent B shown below, and the alkyl moiety has 1-6 carbon atoms; $C_3$-$C_6$ cycloalkyl optionally substituted by a halogen atom, a hydroxyl group or amino; $C_6$-$C_{10}$ aryl optionally substituted by substituent B shown below; arylalkyl wherein the $C_6$-$C_{10}$ aryl moiety is optionally substituted by substituent B shown below and the alkyl moiety has 1-6 carbon atoms; heteroaryl containing 1-6 atoms selected from a nitrogen atom, an oxygen atom and a sulfur atom and having 5-10 ring-constituting atoms, which is optionally substituted by substituent B shown below; heteroarylalkyl wherein the heteroaryl moiety containing 1-6 atoms selected from a nitrogen atom, an oxygen atom and a sulfur atom and having 5-10 ring-constituting atoms is optionally substituted by substituent B shown below and the alkyl moiety has 1-6 carbon atoms; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ acyl; alkylcarbonyl wherein the $C_1$-$C_6$ alkyl moiety is substituted by amino optionally mono- or di-substituted by $C_1$-$C_6$ alkyl, a halogen atom, a hydroxyl group or $C_1$-$C_6$ alkoxy; arylcarbonyl wherein the $C_6$-$C_{10}$ aryl moiety is substituted by substituent B shown below; $C_2$-$C_7$ acyloxy; $C_2$-$C_7$ alkoxycarbonyl; carboxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; aminocarbonyl wherein the amino moiety is optionally mono- or di-substituted by $C_1$-$C_6$ alkyl or $C_3$-$C_6$ cycloalkyl; $C_1$-$C_6$ alkylsulfonylamino wherein the amino moiety is optionally substituted by $C_1$-$C_6$ alkyl; $C_1$-$C_6$ alkyl which is substituted by a nonaromatic heterocyclic group containing 1-4 atoms selected from a nitrogen atom, an oxygen atom and a sulfur atom and having 3-7 ring-constituting atoms, wherein the nonaromatic heterocyclic group moiety is optionally substituted by amino optionally mono- or di-substituted by $C_1$-$C_6$ alkyl, a halogen atom, or pyrrolidinylalkyl wherein the alkyl moiety has 1 to 6 carbon atoms; and carbonyl which is substituted by a nonaromatic heterocyclic group containing 1-4 atoms selected from a nitrogen atom, an oxygen atom and a sulfur atom and having 3-7 ring-constituting atoms, wherein the nonaromatic heterocyclic group moiety is optionally substituted by amino or aminocarbonyl wherein the amino moiety is optionally mono- or di-substituted by $C_1$-$C_6$ alkyl, a halogen atom, a hydroxyl group, $C_1$-$C_6$ alkyl, piperidine, piperazine or morpholine, further, the carbon atom of the above-mentioned nitrogen-containing cyclic group optionally form a Spiro bond with $C_3$-$C_6$ cycloalkane or a hetero ring containing 1 or 2 atoms selected from a nitrogen atom and an oxygen atom and having 3-6 ring-constituting atoms, further, two atoms from the atoms contained in the above-mentioned nitrogen-containing cyclic group, to which two atoms substituent(s) are bondable, are optionally bonded via methylene, ethylene or vinylene to form a fused ring or a crosslinked ring, Substituent B a halogen atom; a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group or amino; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl or $C_3$-$C_6$ cycloalkyl; aminocarbonyl wherein the amino moiety is optionally mono- or di-substituted by $C_1$-$C_6$ alkyl or $C_3$-$C_6$ cycloalkyl; or carbonyl which is substituted by a nonaromatic heterocyclic group containing 1-4 atoms selected from a nitrogen atom, an oxygen atom and a sulfur atom and having 3-7 ring-constituting atoms and optionally substituted by a halogen atom, a hydroxyl group, oxo, dioxo, $C_1$-$C_6$ alkyl or $C_1$-$C_6$ alkoxy, or a pharmacologically acceptable salt thereof.

[4] The amide derivative of any one of [1] to [3], wherein A is phenylene or 6-membered heteroarylene, or a pharmacologically acceptable salt thereof.

[5] The amide derivative of any one of [1] to [4], wherein $R^a$ is $C_2$-$C_7$ acyl; $C_2$-$C_7$ alkoxycarbonyl; $C_1$-$C_6$ alkylsulfonyl wherein the alkyl moiety is optionally substituted by a halogen atom or a hydroxyl group; or carbonyl which is substituted by a nonaromatic heterocyclic group containing 1-4 atoms selected from a nitrogen atom, an oxygen atom and a sulfur atom, and having 3-7 ring-constituting atoms, $R^b$ is a hydrogen atom; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; or $C_3$-$C_6$ cycloalkyl optionally substituted by a halogen atom, a hydroxyl group or amino, or $R^a$ and $R^b$ show, together with the adjacent nitrogen atom, a nitrogen-containing cyclic group shown below

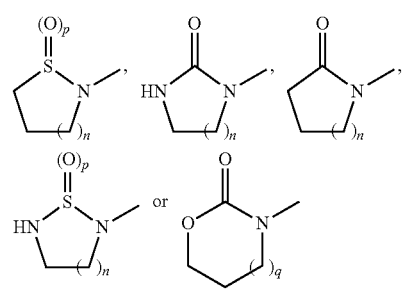

wherein n is 0, 1, 2 or 3, p is 1 or 2 and q is 1 or 2, which is optionally substituted by $C_1$-$C_6$ alkyl optionally substituted by amino optionally mono- or di-substituted by $C_1$-$C_6$ alkyl, a halogen atom, a hydroxyl group or $C_1$-$C_6$ alkoxy or oxo, or a pharmacologically acceptable salt thereof.

[6] The amide derivative of any one of [1] to [5], wherein $R^a$ and $R^b$ show, together with the adjacent nitrogen atom, a nitrogen-containing cyclic group shown below

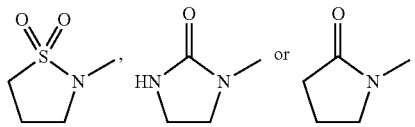

which is optionally substituted by $C_1$-$C_6$ alkyl optionally substituted by a hydroxyl group or $C_1$-$C_6$ alkoxy or oxo, or a pharmacologically acceptable salt thereof.

[7] The amide derivative of any one of [1] to [6], wherein W is a bond, or a pharmacologically acceptable salt thereof.

[8] The amide derivative of any one of [1] to [7], wherein $Z^2$ and $Z^3$ are carbon atoms, or a pharmacologically acceptable salt thereof.

[9] The amide derivative of any one of [1] to [8], wherein $R^1$ is $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino,
$R^2$ is $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino, and
$R^3$ is a hydrogen atom; a halogen atom; $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino, or a pharmacologically acceptable salt thereof.

[10] The amide derivative of any one of [1] to [9], wherein $R^{4a}$, $R^{4b}$ and $R^{4c}$ are hydrogen atoms, or a pharmacologically acceptable salt thereof.

[11] [4-(3,5-dimethylpyridin-2-yl)piperazin-1-yl][4-(1,1-dioxo-1$\lambda^6$-isothiazolidin-2-yl)-2-fluorophenyl]methanone,
[4-(5-cyclopropyl-3-methylpyridin-2-yl)piperazin-1-yl][6-(1,1-dioxo-1$\lambda^6$-isothiazolidin-2-yl)-2-methylpyridin-3-yl]methanone,
1-{4-[4-(3,5-dimethylpyridin-2-yl)piperazine-1-carbonyl]-3-fluorophenyl}imidazolidin-2-one, or
1-{4-[4-(3,5-dimethylpyridin-2-yl)piperazine-1-carbonyl]-3-fluorophenyl}-3,5-dimethylimidazolidine-2,4-dione.

[12] A pharmaceutical composition comprising the amide derivative of any one of [1] to [11], or a pharmacologically acceptable salt thereof, and a pharmaceutically acceptable additive.

[13] An agent for suppressing MMP-9 production, comprising the amide derivative of any one of [1] to [11], or a pharmacologically acceptable salt thereof.

[14] A medicament for the prophylaxis and/or treatment of an autoimmune disease or inflammatory bowel disease comprising the amide derivative of any one of [1] to [11], or a pharmacologically acceptable salt thereof.

[15] The medicament of [14], wherein the autoimmune disease is rheumatoid arthritis, multiple sclerosis or systemic lupus erythematosus.

[16] The medicament of [14], wherein the inflammatory bowel disease is Crohn's disease or ulcerative colitis.

[17] A medicament for the prophylaxis and/or treatment of osteoarthritis, comprising the amide derivative of any one of [1] to [11], or a pharmacologically acceptable salt thereof.

Effect of the Invention

Since the compound of the present invention selectively suppresses production of induction type MMPs, particularly MMP-9, rather than production of hemostatic type MMP-2, it is useful as a medicament for the prophylaxis and/or treatment of autoimmune diseases such as rheumatoid arthritis and the like, inflammatory bowel diseases (ulcerative colitis, Crohn's disease) and osteoarthritis.

DESCRIPTION OF EMBODIMENTS

The compound of the present invention is the above-mentioned amide derivative represented by the formula (I), a pharmacologically acceptable salt thereof or a hydrate or solvate thereof. In the following, the meanings of the terms used in the present specification are described, and the present invention is explained in more detail. The explanation of the following terms does not limit the present invention in any way.

The halogen atom is a fluorine atom, a chlorine atom, a bromine atom or an iodine atom.

The $C_1$-$C_6$ alkyl is straight chain or branched chain alkyl, and methyl, ethyl, propyl, isopropyl, butyl, isobutyl, secondary butyl, tertiary butyl, pentyl, 3-methylbutyl, neopentyl, hexyl, 2-ethylbutyl and the like can be mentioned.

The $C_1$-$C_3$ alkyl is straight chain or branched chain alkyl, and methyl, ethyl, propyl, isopropyl and the like can be mentioned.

The $C_2$-$C_6$ alkenyl is straight chain or branched chain alkenyl, and vinyl, allyl, 1-propenyl, isopropenyl, 2-butenyl, 3-butenyl, 2-pentenyl, 4-pentenyl, 3-methyl-2-butenyl, 5-hexenyl, 4-methyl-3-pentenyl and the like can be mentioned.

The $C_2$-$C_6$ alkynyl is straight chain or branched chain alkynyl, and ethynyl, propynyl, butynyl, pentynyl, hexynyl and the like can be mentioned.

Examples of the $C_3$-$C_6$ cycloalkyl include cyclopropyl, cyclobutyl, cyclopentyl, cyclohexyl and the like.

Examples of the $C_6$-$C_{10}$ aryl include phenyl, naphthyl and the like.

The arylalkyl is the aforementioned $C_1$-$C_6$ alkyl substituted by the aforementioned $C_6$-$C_{10}$ aryl, and benzyl, phenethyl, phenylpropyl, naphthylmethyl, naphthylethyl and the like can be mentioned.

The heteroaryl containing 1-6 nitrogen atoms, an oxygen atom and a sulfur atom, and having 5-10 ring-constituting atoms is a monovalent group induced from a monocyclic aromatic heterocycle containing 1 to 3 from a nitrogen atom, an oxygen atom and a sulfur atom, and having 5 or 6 ring-constituting atoms, a fused ring of this monocyclic aromatic heterocycle and benzene and a fused ring of the same or different these two monocyclic aromatic heterocycles. Specific examples include pyrrolyl, furyl, thienyl, pyrazolyl, imidazolyl, triazolyl, tetrazolyl, oxazolyl, isoxazolyl, oxadiazolyl, thiazolyl, isothiazolyl, thiadiazolyl, furazanyl, pyridyl, pyranyl, thiopyranyl, pyridazinyl, pyrimidinyl, pyrazinyl, triazinyl, tetrazinyl, indolyl, isoindolyl, benzofuryl, benzothienyl, indazolyl, benzoxazolyl, benzimidazolyl, benzothiazolyl, pyrrolopyridyl, pyrazolopyridyl, imidazopyridyl, pyrrolopyrimidinyl, pyrazolopyrimidinyl, quinolyl, isoquinolyl, quinoxalyl, quinazolyl and the like.

Examples of the heteroaryl containing 1 or 2 nitrogen atoms and 0 or 1 atom selected from an oxygen atom and a sulfur atom, and having 5 ring-constituting atoms include pyrrolyl, pyrazolyl, imidazolyl and the like.

The heteroarylalkyl is the aforementioned $C_1$-$C_6$ alkyl substituted by the aforementioned heteroaryl containing 1-6 nitrogen atoms, oxygen atoms and sulfur atoms, and having 5-10 ring-constituting atoms.

Examples of the heteroaryl containing 1-6 atoms selected from a nitrogen atom, an oxygen atom and a sulfur atom, and always containing one or more nitrogen atoms, and having 6-10 ring-constituting atoms include indolyl, isoindolyl, indazolyl, benzimidazolyl, pyrrolopyridyl, pyrazolopyridyl, imidazopyridyl, pyrrolopyrimidinyl, pyrazolopyrimidinyl and the like.

The nonaromatic heterocyclic group containing 1-4 atoms selected from a nitrogen atom, an oxygen atom and a sulfur atom, and having 3-7 ring-constituting atoms is a monovalent group derived from a monocyclic heterocycle containing 1 to 4 atoms from a nitrogen atom, an oxygen atom and a sulfur atom, and having 3-7 ring-constituting atoms. Specific examples include aziridinyl, azetidinyl, oxetyl, thietyl, pyrrolidinyl, tetrahydrofuryl, tetrahydrothienyl, imidazolidinyl, pyrazolidinyl, oxazolidinyl, isoxazolidinyl, thiazolidinyl, isothiazolidinyl, piperidinyl, tetrahydropyranyl, tetrahydrothiopyranyl, piperazinyl, morpholinyl, thiomorpholinyl, azepyl, diazepyl, oxazepyl, thiazepyl and the like. Besides these, a monovalent group derived from an aromatic heterocycle containing 1-4 atoms selected from a nitrogen atom, an oxygen atom and a sulfur atom, and having 3-7 ring-constituting atoms, which is partially or entirely reduced, such as pyrrolyl, furyl, thienyl, pyrazolyl, imidazolyl, triazolyl, tetrazolyl, oxazolyl, isoxazolyl, thiazolyl, isothiazolyl, thiadiazolyl and the like is also included.

Specific examples of the nonaromatic heterocyclic group containing 1-4 atoms selected from a nitrogen atom, an oxygen atom and a sulfur atom and having 3-7 ring-constituting atoms, which is substituted by oxo or dioxo, include 1,1-dioxoisothiazolidinyl, 2-oxopyrrolidinyl, 2-oxoimidazolidinyl, 2-oxooxazolidinyl, 2,4-dioxoimidazolidinyl, 1-oxoisothiazolidinyl, 1-oxo-[1,2]thiazinanyl, 1,1-dioxo-[1,2]thiazinanyl and the like.

The carbonyl substituted by a nonaromatic heterocyclic group containing at least one nitrogen atom and 0-3 atoms selected from a nitrogen atom, an oxygen atom and a sulfur atom, and having 3-7 ring-constituting atoms is a carbonyl which is substituted by the above-mentioned nonaromatic heterocyclic group containing 1-4 atoms selected from a nitrogen atom, an oxygen atom and a sulfur atom, and having 3-7 ring-constituting atoms, which contains at least one nitrogen atom, and which is bonded to a nitrogen atom on the nonaromatic heterocyclic group. Here, specific examples of the nonaromatic heterocyclic group containing at least one nitrogen atom and 0-3 atoms selected from a nitrogen atom, an oxygen atom and a sulfur atom, and having 3-7 ring-constituting atoms include monovalent groups derived from aziridinyl, azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, azepyl, diazepyl, oxazepyl, thiazepyl, pyrrolyl, pyrazolyl, imidazolyl, triazolyl, tetrazolyl, oxazolyl, isoxazolyl, thiazolyl, isothiazolyl and thiadiazolyl, which are partially or entirely reduced, and the like.

The saturated nonaromatic heterocyclic group containing 1-4 atoms selected from a nitrogen atom, an oxygen atom and a sulfur atom and always containing one or more nitrogen atoms, and having 3-7 ring-constituting atoms is the aforementioned nonaromatic heterocyclic group containing 1-4 atoms selected from a nitrogen atom, an oxygen atom and a sulfur atom, having 3-7 ring-constituting atoms, always containing one or more nitrogen atoms as ring-constituting atoms, and free of a double bond in the ring. Examples thereof include aziridinyl, azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, azepyl, diazepyl, oxazepyl, thiazepyl, triazolidinyl, hexahydropyridazinyl, hexahydropyrimidinyl, hexahydrotriazinyl, hexahydrotetrazinyl and the like.

The $C_1$-$C_6$ alkoxy is straight chain or branched chain alkoxy, and methoxy, ethoxy, propoxy, isopropoxy, butoxy, isobutoxy, secondary butoxy, tertiary butoxy, pentoxy, 3-methylbutoxy, neopentoxy, hexyloxy, 2-ethylbutoxy or the like.

The $C_2$-$C_7$ acyl is carbonyl substituted by the aforementioned $C_1$-$C_6$ alkyl, carbonyl substituted by the aforementioned $C_3$-$C_6$ cycloalkyl, or carbonyl substituted by phenyl. Examples thereof include acetyl, propionyl, butyryl, isobutyryl, valeryl, isovaleryl, hexanoyl, cyclopropylcarbonyl, cyclopentylcarbonyl, cyclohexylcarbonyl, benzoyl and the like.

The alkylcarbonyl is carbonyl substituted by the aforementioned $C_1$-$C_6$ alkyl.

The arylcarbonyl is carbonyl substituted by the aforementioned $C_6$-$C_{10}$ aryl.

The heteroarylcarbonyl is carbonyl substituted by the aforementioned heteroaryl containing 1-6 atoms selected from a nitrogen atom, an oxygen atom and a sulfur atom, and having 5-10 ring-constituting atoms.

Examples of the $C_2$-$C_7$ acyloxy include acetoxy, ethylcarbonyloxy, propylcarbonyloxy, isopropylcarbonyloxy, butylcarbonyloxy, isobutylcarbonyloxy, secondary butylcarbonyloxy, tertiary butylcarbonyloxy, pentylcarbonyloxy, neopentylcarbonyloxy, hexylcarbonyloxy, cyclopropylcarbonyloxy, cyclobutylcarbonyloxy, cyclopentylcarbonyloxy, cyclohexylcarbonyloxy, benzoyloxy and the like.

Examples of the $C_2$-$C_7$ alkoxycarbonyl include a group wherein the aforementioned $C_1$-$C_6$ alkoxy is bonded to carbonyl, and methoxycarbonyl, ethoxycarbonyl, propoxycarbonyl, isopropoxycarbonyl, butoxycarbonyl, isobutoxycarbonyl, secondary butoxycarbonyl, tertiary butoxycarbonyl, pentoxycarbonyl, 3-methylbutoxycarbonyl, neopentoxycarbonyl, hexyloxycarbonyl, 2-ethylbutoxycarbonyl and the like.

The $C_1$-$C_6$ alkylthio is straight chain or branched chain alkylthio. Examples thereof include methylthio, ethylthio, propylthio, isopropylthio, butylthio, isobutylthio, secondary butylthio, tertiary butylthio, pentylthio, 3-methylbutylthio, neopentylthio, hexylthio, 2-ethylbutylthio and the like.

The $C_1$-$C_6$ alkylsulfinyl is straight chain or branched chain alkylsulfinyl. Examples thereof include methanesulfinyl, ethylsulfinyl, propylsulfinyl, butylsulfinyl, pentylsulfinyl, hexylsulfinyl and the like.

The $C_1$-$C_6$ alkylsulfonyl is straight chain or branched chain alkylsulfonyl. Examples thereof include methanesulfonyl, ethylsulfonyl, propylsulfonyl, butylsulfonyl, pentylsulfonyl, hexylsulfonyl and the like.

Examples of the $C_3$-$C_6$ cycloalkylthio include cyclopropylthio, cyclobutylthio, cyclopentylthio, cyclohexylthio and the like.

Examples of the $C_3$-$C_6$ cycloalkylsulfinyl include cyclopropylsulfinyl, cyclobutylsulfinyl, cyclopentylsulfinyl, cyclohexylsulfinyl and the like.

Examples of the $C_3$-$C_6$ cycloalkylsulfonyl include cyclopropylsulfonyl, cyclobutylsulfonyl, cyclopentylsulfonyl, cyclohexylsulfonyl and the like.

The $C_2$-$C_7$ acylamino is amino substituted by the aforementioned $C_2$-$C_7$ acyl. Examples thereof include acetylamino, propionylamino, butyrylamino, isobutyrylamino, valerylamino, isovalerylamino, hexanoylamino, cyclopropylcarbonylamino, cyclobutylcarbonylamino, cyclopentylcarbonylamino, cyclohexylcarbonylamino, benzoylamino and the like.

The $C_7$-$C_{17}$ arylaminocarbonyl is aminocarbonyl wherein the amino moiety is substituted by the aforementioned $C_6$-$C_{10}$ aryl. Examples thereof include and phenylaminocarbonyl, naphthylaminocarbonyl and the like.

The heteroarylaminocarbonyl is aminocarbonyl wherein the amino moiety is substituted by the aforementioned heteroaryl containing 1-6 atoms selected from a nitrogen atom, an oxygen atom and a sulfur atom, and having 5-10 ring-constituting atoms.

The $C_1$-$C_6$ alkylsulfonylamino is amino mono-substituted by the aforementioned $C_1$-$C_6$ alkylsulfonyl. Examples thereof include methanesulfonylamino, ethylsulfonylamino, propylsulfonylamino, butylsulfonylamino, pentylsulfonylamino, hexylsulfonylamino and the like.

The $C_3$-$C_6$ cycloalkylsulfonylamino is amino mono-substituted by the aforementioned $C_3$-$C_6$ cycloalkylsulfonyl. Examples thereof include cyclopropylsulfonylamino, cyclobutylsulfonylamino, cyclopentylsulfonylamino, cyclohexylsulfonylamino and the like.

Examples of the amino optionally mono- or di-substituted by $C_1$-$C_6$ alkyl include amino, methylamino, ethylamino, propylamino, isopropylamino, butylamino, isobutylamino, secondary butylamino, tertiary butylamino, pentylamino, 3-methylbutylamino, neopentylamino, hexylamino, 2-ethylbutylamino, dimethylamino, ethylmethylamino, diethylamino, methylpropylamino, ethylpropylamino, dipropylamino and the like.

Examples of the amino optionally mono- or di-substituted by $C_1$-$C_6$ alkyl or $C_3$-$C_6$ cycloalkyl include, in addition to the aforementioned amino optionally mono- or di-substituted by $C_1$-$C_6$ alkyl, cyclopropylamino, cyclobutylamino, cyclopentylamino, cyclohexylamino, dicyclopropylamino, methylcyclopropylamino and the like.

The aminocarbonyl wherein the amino moiety is optionally mono- or di-substituted by $C_1$-$C_6$ alkyl or $C_3$-$C_6$ cycloalkyl is carbonyl substituted by the aforementioned amino optionally mono- or di-substituted by $C_1$-$C_6$ alkyl or $C_3$-$C_6$ cycloalkyl.

The $C_1$-$C_6$ alkylene is straight chain or branched chain alkylene. Examples thereof include methylene, ethylene, trimethylene, tetramethylene, pentamethylene, hexamethylene, propylene, ethylethylene and the like.

Examples of the $C_3$-$C_6$ cycloalkylidene include cyclopropylidene, cyclobutylidene, cyclopentylidene, cyclohexylidene.

The arylalkyloxy is the aforementioned $C_1$-$C_6$ alkoxy substituted by the aforementioned $C_6$-$C_{10}$ aryl.

The heteroarylalkyloxy is the aforementioned $C_1$-$C_6$ alkoxy substituted by the aforementioned heteroaryl containing 1-6 atoms selected from a nitrogen atom, an oxygen atom and a sulfur atom, and having 5-10 ring-constituting atoms.

The dioxo means that two oxos are bonded as substituents to one atom.

In the present specification, the number of the substituents when "optionally substituted" is one or more unless particularly specified, and the kind of the substituents may be the same or different.

Now preferable embodiments of the above-mentioned formula (I) are explained.

Preferred as X is a nitrogen atom or N-oxide wherein nitrogen atom is oxidized, more preferably a nitrogen atom.

Y is preferably a bond, carbonyl or an oxygen atom, more preferably a bond.

A is preferably phenylene or 6-membered heteroarylene, more preferably

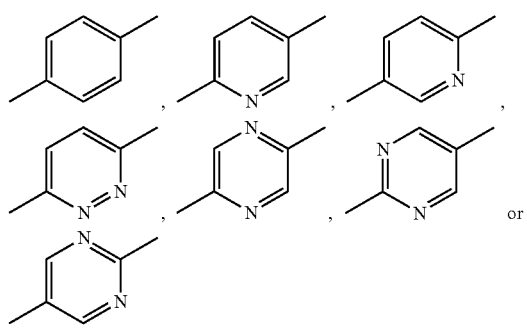

further preferably

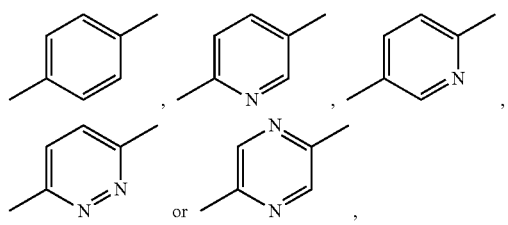

and
particularly preferably

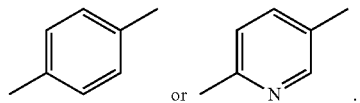

The substituent when A has substituent(s) is preferably one or the same or different 2 or 3 substituents selected from
a halogen atom;
a hydroxyl group;
nitro;
cyano;
$C_1$-$C_6$ alkyl optionally substituted by amino optionally mono- or di-substituted by $C_1$-$C_6$ alkyl, a halogen atom, a hydroxyl group or $C_1$-$C_6$ alkoxy;
$C_2$-$C_6$ alkenyl;
$C_2$-$C_6$ alkynyl;
$C_3$-$C_6$ cycloalkyl optionally substituted by a halogen atom, a hydroxyl group or amino;
$C_1$-$C_6$ alkoxy optionally substituted by amino optionally mono- or di-substituted by $C_1$-$C_6$ alkyl, a halogen atom, a hydroxyl group or $C_1$-$C_6$ alkoxy;
$C_1$-$C_6$ alkylthio wherein the alkyl moiety is optionally substituted by a halogen atom or a hydroxyl group;
$C_1$-$C_6$ alkylsulfinyl wherein the alkyl moiety is optionally substituted by a halogen atom or a hydroxyl group;
$C_1$-$C_6$ alkylsulfonyl wherein the alkyl moiety is optionally substituted by a halogen atom or a hydroxyl group;
amino optionally mono- or di-substituted by $C_1$-$C_6$ alkyl or $C_3$-$C_6$ cycloalkyl;
$C_2$-$C_7$ acylamino wherein the amino moiety is optionally substituted by $C_1$-$C_6$ alkyl;
aminocarbonyl wherein the amino moiety is optionally mono- or di-substituted by
$C_1$-$C_6$ alkyl (wherein $C_1$-$C_6$ alkyl is substituted by a halogen atom, a hydroxyl group, cyano, $C_1$-$C_6$ alkoxy, amino optionally mono- or di-substituted by $C_1$-$C_6$ alkyl, $C_6$-$C_{10}$ aryl optionally substituted by substituent B, or heteroaryl containing 1-6 atoms selected from a nitrogen atom, an oxygen atom and a sulfur atom, and having 5-10 ring-constituting atoms, which is optionally substituted by substituent B), $C_3$-$C_6$ cycloalkyl (wherein $C_3$-$C_6$ cycloalkyl is optionally substituted by substituent B), or a nonaromatic heterocyclic group containing 1-4 atoms selected from a nitrogen atom, an oxygen atom and a sulfur atom, and having 3-7 ring-constituting atoms, which is optionally substituted by substituent B;

$C_1$-$C_6$ alkylsulfonylamino wherein the amino moiety is optionally substituted by $C_1$-$C_6$ alkyl;

$C_3$-$C_6$ cycloalkylsulfonylamino wherein the amino moiety is optionally substituted by $C_1$-$C_6$ alkyl;

a nonaromatic heterocyclic group containing 1-4 atoms selected from a nitrogen atom, an oxygen atom and a sulfur atom, and having 3-7 ring-constituting atoms, which is optionally substituted by a halogen atom, a hydroxyl group, oxo, dioxo, $C_1$-$C_6$ alkyl (which is optionally substituted by amino optionally mono- or di-substituted by $C_1$-$C_6$ alkyl, a halogen atom, a hydroxyl group, $C_1$-$C_6$ alkoxy, arylalkyl wherein the $C_6$-$C_{10}$ aryl moiety is optionally substituted by substituent B and the alkyl moiety has 1-6 carbon atoms, arylalkyloxy wherein the $C_6$-$C_{10}$ aryl moiety is optionally substituted by substituent B and the alkyl moiety has 1-6 carbon atoms, heteroarylalkyl wherein the heteroaryl moiety containing 1-6 atoms selected from a nitrogen atom, an oxygen atom and a sulfur atom and having 5-10 ring-constituting atoms is optionally substituted by substituent B and the alkyl moiety has 1-6 carbon atoms or heteroarylalkyloxy wherein the heteroaryl moiety containing 1-6 atoms selected from a nitrogen atom, an oxygen atom and a sulfur atom and having 5-10 ring-constituting atoms is optionally substituted by substituent B and the alkyl moiety has 1-6 carbon atoms); and carbonyl substituted by a nonaromatic heterocyclic group containing at least one nitrogen atom and 0-3 atoms selected from a nitrogen atom, an oxygen atom and a sulfur atom, and having 3-7 ring-constituting atoms, which is optionally substituted by substituent B (wherein the carbonyl is bonded to a nitrogen atom on a nonaromatic heterocyclic group), more preferably, one or the same or different 2 or 3 substituents selected from a halogen atom;

cyano;

$C_1$-$C_6$ alkyl optionally substituted by amino optionally mono- or di-substituted by $C_1$-$C_6$ alkyl, a halogen atom, a hydroxyl group or $C_1$-$C_6$ alkoxy;

$C_3$-$C_6$ cycloalkyl optionally substituted by a halogen atom, a hydroxyl group or amino;

$C_1$-$C_6$ alkoxy optionally substituted by amino optionally mono- or di-substituted by $C_1$-$C_6$ alkyl, a halogen atom, a hydroxyl group or $C_1$-$C_6$ alkoxy;

$C_1$-$C_6$ alkylsulfonyl wherein the alkyl moiety is optionally substituted by a halogen atom or a hydroxyl group;

amino;

$C_2$-$C_7$ acylamino wherein the amino moiety is optionally substituted by $C_1$-$C_6$ alkyl;

aminocarbonyl wherein the amino moiety is optionally mono- or di-substituted by $C_1$-$C_6$ alkyl (which is optionally substituted by a halogen atom, a hydroxyl group, cyano, $C_1$-$C_6$ alkoxy, amino optionally mono- or di-substituted by $C_1$-$C_6$ alkyl, $C_6$-$C_{10}$ aryl optionally substituted by substituent B or heteroaryl containing 1-6 atoms selected from a nitrogen atom, an oxygen atom and a sulfur atom, and having 5-10 ring-constituting atoms, which is optionally substituted by substituent B), $C_3$-$C_6$ cycloalkyl (which is optionally substituted by substituent B), or a nonaromatic heterocyclic group containing 1-4 atoms selected from a nitrogen atom, an oxygen atom and a sulfur atom, and having 3-7 ring-constituting atoms, which is optionally substituted by substituent B;

$C_1$-$C_6$ alkylsulfonylamino wherein the amino moiety is optionally substituted by $C_1$-$C_6$ alkyl;

a nonaromatic heterocyclic group containing 1-4 atoms selected from a nitrogen atom, an oxygen atom and a sulfur atom, and having 3-7 ring-constituting atoms, which is optionally substituted by a halogen atom, a hydroxyl group, oxo, dioxo, $C_1$-$C_6$ alkyl (which is optionally substituted by amino optionally mono- or di-substituted by $C_1$-$C_6$ alkyl, a halogen atom, a hydroxyl group, $C_1$-$C_6$ alkoxy, arylalkyl wherein the $C_6$-$C_{10}$ aryl moiety is optionally substituted by substituent B and the alkyl moiety has 1-6 carbon atoms, arylalkyloxy wherein the $C_6$-$C_{10}$ aryl moiety is optionally substituted by substituent B and the alkyl moiety has 1-6 carbon atoms, heteroarylalkyl wherein the heteroaryl moiety containing 1-6 atoms selected from a nitrogen atom, an oxygen atom and a sulfur atom and having 5-10 ring-constituting atoms is optionally substituted by substituent B and the alkyl moiety has 1-6 carbon atoms or heteroarylalkyloxy wherein the heteroaryl moiety containing 1-6 atoms selected from a nitrogen atom, an oxygen atom and a sulfur atom and having 5-10 ring-constituting atoms is optionally substituted by substituent B and the alkyl moiety has 1-6 carbon atoms), $C_1$-$C_6$ alkoxy (which is optionally substituted by amino optionally mono- or di-substituted by $C_1$-$C_6$ alkyl, a halogen atom, a hydroxyl group or $C_1$-$C_6$ alkoxy or $C_2$-$C_7$ acyl; and carbonyl substituted by a nonaromatic heterocyclic group containing at least one nitrogen atom, 0-3 atoms selected from a nitrogen atom, an oxygen atom and a sulfur atom, and having 3-7 ring-constituting atoms, which is optionally substituted by substituent B (wherein the carbonyl is bonded to a nitrogen atom on a nonaromatic heterocyclic group).

Further preferred is a halogen atom; $C_1$-$C_6$ alkyl; $C_1$-$C_6$ alkylsulfonyl; or 1,1-dioxoisothiazolidinyl, 2-oxopyrrolidinyl, 2-oxoimidazolidinyl, 2-oxooxazolidinyl or 2,4-dioxoimidazolidinyl, which is optionally substituted by $C_1$-$C_6$ alkyl optionally substituted by amino optionally mono- or di-substituted by $C_1$-$C_6$ alkyl, a halogen atom, a hydroxyl group or $C_1$-$C_6$ alkoxy, and particularly preferred is a halogen atom or C1-3 alkyl.

The substituent when A has a substituent is as mentioned above and, in a preferable embodiment, A is unsubstituted.

$R^a$ is $C_2$-$C_7$ acyl; $C_2$-$C_7$ alkoxycarbonyl; $C_1$-$C_6$ alkylsulfonyl wherein the alkyl moiety is optionally substituted by a halogen atom or a hydroxyl group; or carbonyl which is substituted by a nonaromatic heterocyclic group containing 1-4 atoms selected from a nitrogen atom, an oxygen atom and a sulfur atom, and having 3-7 ring-constituting atoms, $R^b$ is a hydrogen atom; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; or $C_3$-$C_6$ cycloalkyl optionally substituted by a halogen atom, a hydroxyl group or amino, or $R^a$ and $R^b$ show, together with the adjacent nitrogen atom, a nitrogen-containing cyclic group shown below

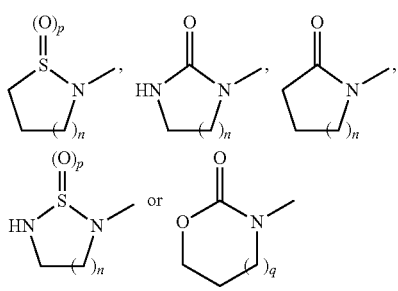

wherein n is 0, 1, 2 or 3, p is 1 or 2 and q is 1 or 2, which is optionally substituted by one or the same or different 2-6 substituents, more preferably one or the same or different 2-4 substituents, selected from $C_1$-$C_6$ alkyl optionally substituted by amino optionally mono- or di-substituted by $C_1$-$C_6$ alkyl, a halogen atom, a hydroxyl group or $C_1$-$C_6$ alkoxy, and oxo. Furthermore, $R^a$ and $R^b$ preferably show, together with the adjacent nitrogen atom, the following nitrogen-containing cyclic group shown below

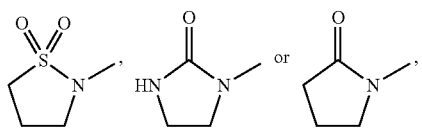

which is optionally substituted by one or the same or different 2-6 substituents, more preferably one or the same or different 2-4 substituents, selected from oxo and $C_1$-$C_6$ alkyl optionally substituted by a hydroxyl group or $C_1$-$C_6$ alkoxy.

W is preferably a bond.

$Z^2$ and $Z^3$ are preferably carbon atoms. Furthermore, in the most preferable embodiment of the combination of $Z^1$, $Z^2$ and $Z^3$, $Z^1$ is a nitrogen atom, and $Z^2$ and $Z^3$ are carbon atoms.

$R^1$ is preferably $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino, more preferably, $C_1$-$C_6$ alkyl optionally substituted by a halogen atom or $C_3$-$C_6$ cycloalkyl optionally substituted by a halogen atom. Further preferably, $R^1$ is $C_1$-$C_6$ alkyl or $C_3$-$C_6$ cycloalkyl, particularly preferably C1-3 alkyl, most preferably methyl.

$R^2$ is preferably $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino, more preferably, $C_1$-$C_6$ alkyl optionally substituted by a halogen atom or $C_3$-$C_6$ cycloalkyl optionally substituted by a halogen atom. Further preferably, $R^2$ is $C_1$-$C_6$ alkyl or $C_3$-$C_6$ cycloalkyl, more preferably C1-3 alkyl or $C_3$-$C_6$ cycloalkyl, particularly preferably methyl, ethyl or cyclopropyl.

$R^3$ is preferably a hydrogen atom; a halogen atom; $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino, and a hydrogen atom or $C_1$-$C_6$ alkyl is more preferable. Further preferably, $R^3$ is a hydrogen atom or $C_1$-$C_3$ alkyl, particularly preferably a hydrogen atom.

$R^{4a}$, $R^{4b}$ and $R^{4c}$ are each preferably a hydrogen atom.

m is preferably 1.

Preferable examples of the compound of the present invention include

[4-(3,5-dimethylpyridin-2-yl)piperazin-1-yl][4-(1,1-dioxo-1λ⁶-isothiazolidin-2-yl)-2-fluorophenyl]methanone,

[4-(5-cyclopropyl-3-methylpyridin-2-yl)piperazin-1-yl][6-(1,1-dioxo-1λ⁶-isothiazolidin-2-yl)-2-methylpyridin-3-yl]methanone, 1-{4-[4-(3,5-dimethylpyridin-2-yl)piperazine-1-carbonyl]-3-fluorophenyl}imidazolidin-2-one, and 1-{4-[4-(3,5-dimethylpyridin-2-yl)piperazine-1-carbonyl]-3-fluorophenyl}-3,5-dimethylimidazolidine-2,4-dione.

In the present invention, the "pharmacologically acceptable salt" is not particularly limited as long as it is acceptable as a medicament, and salt with inorganic acid, salt with organic acid, salt with alkali metal, salt with alkaline earth metal, salt with inorganic base, and salt with organic base can be mentioned.

The "pharmaceutically acceptable" in the present specification means being generally safe and harmless, and may be biologically undesirable but preferable in other aspects, and include those useful for the preparation of pharmaceutical compositions usable as medicament for human as well as veterinary medicine.

While the compound of the present invention can be produced by the following methods, the production methods are note limited.

The compound (1) of the present invention can be produced by the following Method A, B, C, D or E.

(Method A)

Step 1

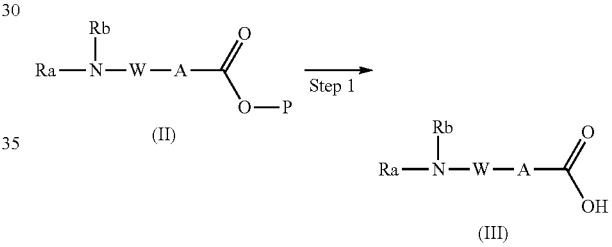

wherein P is a carboxyl protecting group that can be removed by hydrolysis, and other symbols are as defined above.

By hydrolyzing a compound represented by the formula (II), the corresponding compound represented by the formula (III) can be obtained. The reaction proceeds using a base or an acid in a suitable solvent at room temperature –100° C. Examples of the base include aqueous sodium hydroxide solution and the like. Examples of the acid include trifluoroacetic acid and the like. Examples of the solvent include methanol, ethanol, 1,4-dioxane, dichloromethane, toluene and the like.

Step 2

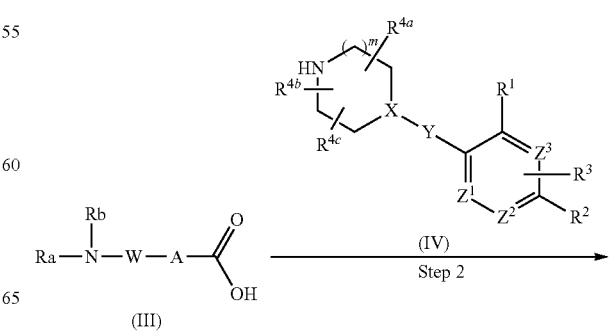

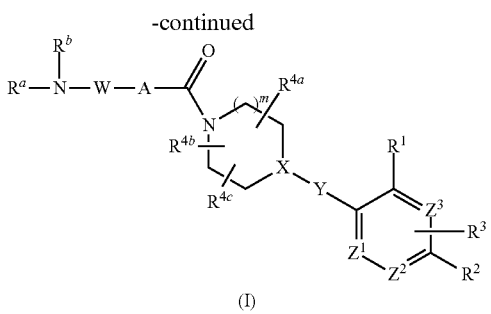

(I)

wherein the symbols are as defined above.

By reacting a compound represented by the formula (III) with a compound represented by the formula (IV), the corresponding compound represented by the formula (I) can be obtained. The reaction proceeds using a condensing agent in a suitable solvent at 0° C.-room temperature. Examples of the condensing agent include 4-(4,6-dimethoxy[1.3.5]triazin-2-yl)-4-methylmorpholinium chloride hydrate (DMT-MM), 1-ethyl-3-(3'-dimethylaminopropyl)carbodiimide hydrochloride (WSC HCl) and the like. Examples of the solvent include methanol, N,N-dimethylformamide, chloroform, tetrahydrofuran and the like.

The reaction may be promoted by the addition of 1-hydroxybenzotriazole (HOBt). When a compound represented by the formula (IV) forms a salt with an acid, the reaction proceeds by neutralization by the addition of a base.

In addition, a compound represented by the formula (I) can also be obtained in one pot from the formula (II) by reacting, after hydrolysis of the formula (II), a compound represented by the formula (III) with a compound represented by the formula (IV) without isolation and purification.

(Method B)

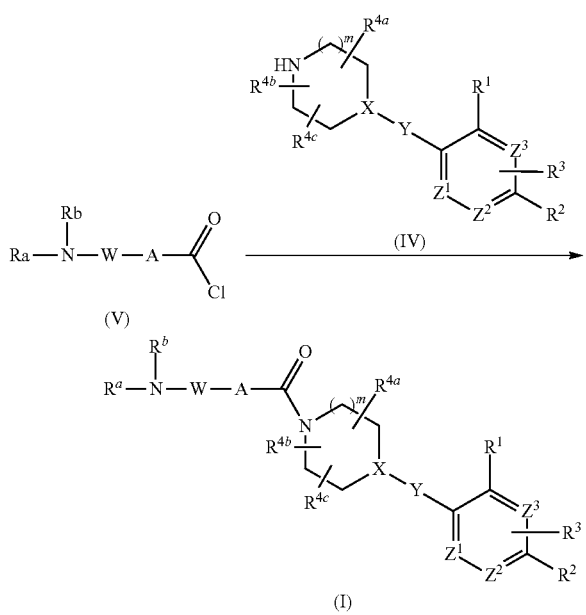

wherein the symbols are as defined above.

By reacting a compound represented by the formula (V) with a compound represented by the formula (IV), the corresponding compound represented by the formula (I) is obtained. The reaction proceeds by using a base in a suitable solvent at 0° C.-room temperature. Examples of the base include aqueous sodium hydroxide solution, triethylamine, N-methylmorpholine and the like. Examples of the solvent include tetrahydrofuran, dimethoxyethane, ethyl acetate and the like.

A compound represented by the formula (I) wherein W is a bond can also be produced by the following method.

(Method C)

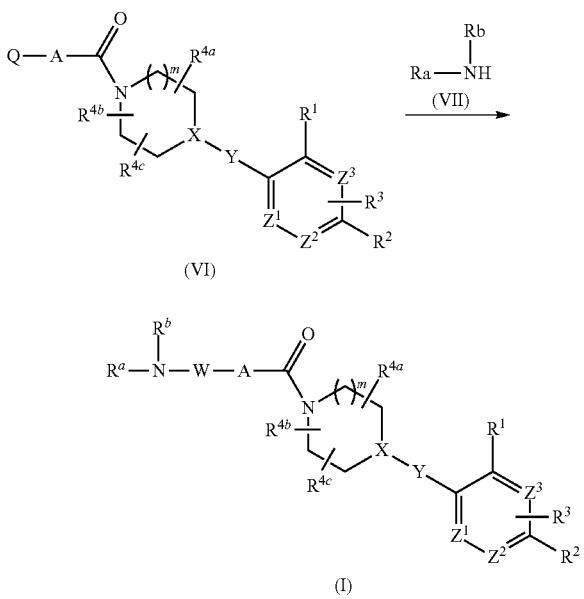

wherein Q is a chlorine atom, a bromine atom or an iodine atom, and other symbols are as defined above.

By reacting a compound represented by the formula (VI) with a compound represented by the formula (VII), the corresponding compound represented by the formula (I) is obtained. The reaction proceeds by heating with a copper catalyst, a ligand and a base in a suitable solvent. Examples of the copper catalyst include copper (I) iodide and the like. Examples of the ligand include N,N'-dimethylethylenediamine and the like. Examples of the base include potassium carbonate, tripotassium phosphate, cesium carbonate and the like. Examples of the solvent include toluene, 1,4-dioxane and the like.

The reaction also proceeds by heating with a palladium catalyst, a phosphine ligand and a base in a suitable solvent. Examples of the palladium catalyst include palladium (II) acetate, tris(dibenzylideneacetone)dipalladium (0) and the like. Examples of the phosphine ligand include 2-dicyclohexylphosphinobiphenyl, 2-di-tert-butylphosphinobiphenyl, 2-di-tert-butylphosphino-3,4,5,6-tetramethyl-2',4',6'-triisopropyl-1,1'-biphenyl, 4,5-bis(diphenylphosphino)-9,9-dimethylxanthene and the like. Examples of the base include tripotassium phosphate, cesium carbonate and the like. Examples of the solvent include toluene, tetrahydrofuran, 1,4-dioxane, tert-butanol and the like.

A compound represented by the formula (I) wherein $NR^aR^b$ is 1,1-dioxo-1$\lambda^6$-isothiazolidine, 1,1-dioxo-1$\lambda^6$-[1,2]thiazinane ring, pyrrolidin-2-one, piperidin-2-one or the like, can also be produced by the following method.

(Method D)

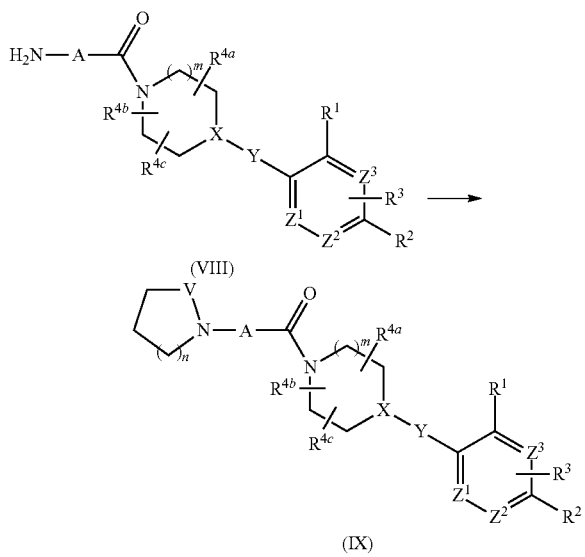

wherein n is 1 or 2, V is SO$_2$ or C(=O), and other symbols are as defined above.

By amidating and cyclizing a compound represented by the formula (VIII), the corresponding compound represented by the formula (IX) is obtained. The amidation reaction proceeds using a corresponding acid halide and a base in a suitable solvent at 0° C.-room temperature. Examples of the acid halide include sulfonic acid halide such as 3-chloropropane-1-sulfonyl chloride, 4-chlorobutane-1-sulfonyl chloride and the like, carboxylic acid halide such as 4-chlorobutyryl chloride, 5-bromovaleryl chloride and the like. Examples of the base include triethylamine, N-methylmorpholine, pyridine, disodium hydrogen phosphate and the like. Examples of the solvent include tetrahydrofuran, dichloromethane, dichloroethane, dimethoxyethane and the like. The cyclization reaction proceeds using a base in a suitable solvent at 0° C.-100° C. Examples of the base include 1,8-diazabicyclo[5.4.0]undec-7-ene, sodium methoxide, sodium ethoxide, potassium tert-butoxide, potassium carbonate, sodium hydrogen carbonate, sodium hydroxide and the like. Examples of the solvent include N,N-dimethylformamide, ethyl acetate, tetrahydrofuran, methanol, ethanol and the like.

The compound represented by of the formula (I) wherein the substituent of the phenylene moiety for A is aminocarbonyl can also be produced by the following method.

(Method E)
Step 1

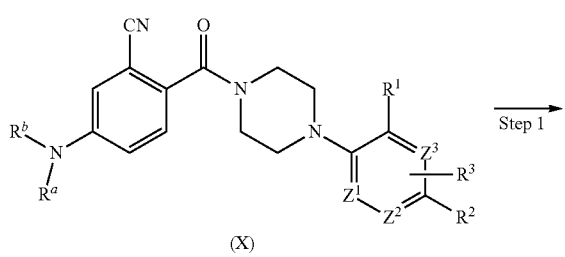

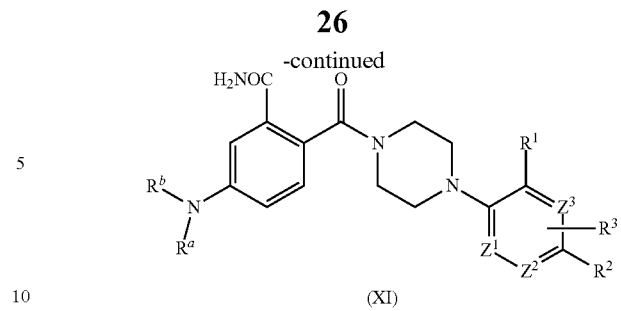

wherein the symbols are as defined above.

By hydrolyzing a compound represented by the formula (X), the corresponding compound represented by the formula (XI) is obtained. The reaction proceeds in a mixture of inorganic acid and organic acid at –30° C. to 100° C. Examples of the inorganic acid include concentrated sulfuric acid, hydrochloric acid and the like, and examples of the organic acid include trifluoroacetic acid, acetic acid and the like.

Step 2

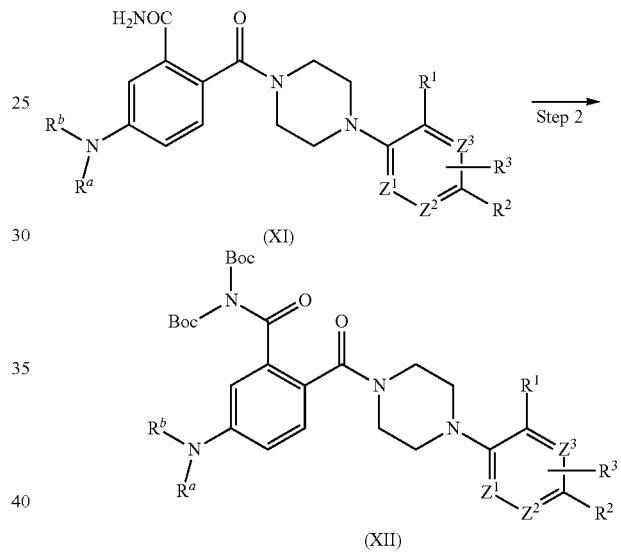

wherein the symbols are as defined above.

By reacting a compound represented by the formula (XI) with di-tert-butyl dicarbonate, the corresponding compound represented by the formula (XII) is obtained. The reaction proceeds in a suitable solvent and using a reaction promoter at 0° C.-100° C. Examples of the solvent include acetonitrile, dichloromethane, tetrahydrofuran and the like. Examples of the reaction promoter include 4-dimethylaminopyridine and the like.

Step 3

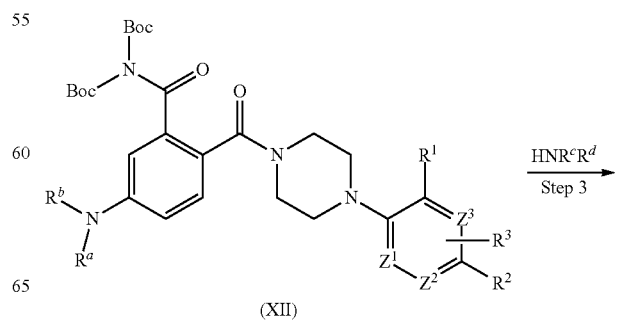

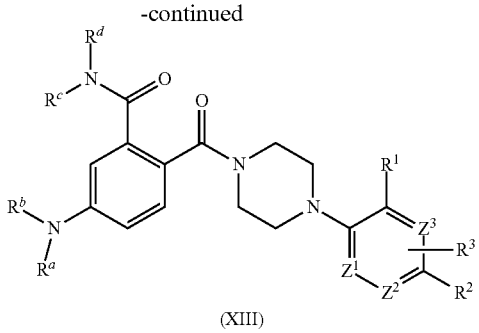

(XIII)

wherein the symbols are as defined above.

By reacting a compound represented by the formula (XII) with amine represented by the formula: HNR$^c$R$^d$, the corresponding compound represented by the formula (XIII) is obtained. The reaction proceeds in a suitable solvent at −30° C. to 100° C. Examples of the solvent include acetonitrile, dichloromethane, tetrahydrofuran and the like.

The amide derivative of the formula (I), which was produced by the aforementioned method, can be purified to any purity by a conventionally-used purification means, for example, concentration, extraction, chromatography, reprecipitation, recrystallization and the like. In addition, it can be converted to a pharmacologically acceptable salt as necessary by treatment with an acid or base etc. in a suitable solvent (water, alcohol, ether etc.). Furthermore, the obtained compound of the present invention or a pharmacologically acceptable salt thereof can be converted to a hydrate or solvate thereof by treatment with water, water-containing solvent or other solvent (e.g., alcohol etc.).

The amide derivative and a pharmacologically acceptable salt thereof of the present invention include racemic compounds, stereoisomers, and mixture of these compounds, and includes isotope-labeled and radioactivity-labeled compounds. Such isomers can be isolated by a standard separation technique including fractional crystallization and chiral column chromatography. In addition, the compound of the present invention has an asymmetric carbon atom. Therefore, it includes enantiomer and diastereomer. A diastereomer mixture can be separated into each diastereomer based on their physical/chemical differences by a method well known in the art, for example, chromatography and/or fractional crystallization. Enantiomer can be separated by chiral column chromatography or by reacting an enantiomer compound with an appropriate optically active compound to give a diastereomer mixture, separating each diastereomer and converting each diastereomer to a corresponding enantiomer. All such isomers including diastereomer, enantiomer and a mixture thereof are a part of the compound of the present invention.

The compound of the present invention has a MMP-9 selective production suppressive action, and can be used as a prophylactic medicament or a therapeutic drug for autoimmune diseases represented by rheumatoid arthritis, multiple sclerosis, systemic lupus erythematosus and the like, inflammatory bowel diseases (ulcerative colitis, Crohn's disease) or osteoarthritis.

In the present invention, "prophylaxis" means an act of administering the compound of the present invention or a pharmaceutical composition containing the compound to an individual who has not developed a disease, condition or symptom. In addition, "treatment" means an act of administering the compound of the present invention or a pharmaceutical composition containing the compound to an individual who has developed a disease, condition or symptom. Therefore, an act of administration to an individual who has developed a disease, condition or symptom, for the prevention of aggravation of the symptom and the like, and for the prevention of attack and recurrence is one embodiment of the "treatment".

When the compound of the present invention is used as a medicament, the compound of the present invention is mixed with a pharmaceutically acceptable additive (excipient, binder, disintegrant, corrigent, flavor, emulsifier, diluent, solubilizing agents and the like) to give a pharmaceutical composition which can be orally or parenterally administered. A pharmaceutical composition can be formulated by a general method.

In the present specification, parenteral includes subcutaneous injection, intravenous injection, intramuscular injection, intraperitoneal injection, drip or topical administration (transdermal administration, transocular administration, transpulmonary or bronchial administration, transnasal administration, transrectal administration and the like) and the like.

The dose of the compound of the present invention is determined according to the age, body weight, general health condition, sex, diet, administration time, administration method, clearance rate, and the level of disease for which patients are undergoing treatments at that time, or further in consideration of other factors. While the daily dose of the compound of the present invention varies depending on the condition and body weight of patient, the kind of the compound, administration route and the like, it is parenterally administered at, for example, about 0.01 to 100 mg/patient/day by subcutaneous, intravenous, intramuscular, transdermal, transocular, transpulmonary or bronchial, transnasal or rectal administration, or about 0.01 to 1000 mg/patient/day by oral administration.

EXAMPLES

The present invention is explained in detail in the following by referring to Preparation Examples, Examples and Experimental Examples, which are not to be construed as limitative.

Preparation Example 1

Preparation of (S)-3-benzyloxymethylisothiazolidine 1,1-dioxide

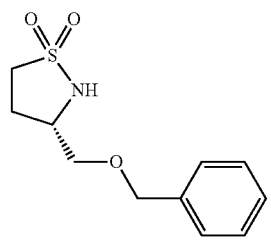 [SMILES: O=S1(=O)CC[C@@H](COCc2ccccc2)N1]

A mixture of (S)-2-amino-3-benzyloxy-1-propanol (5.0 g) and triethylamine (7.9 mL) was dissolved in tetrahydrofuran (40 mL), methanesulfonyl chloride (4.4 mL) was added under ice-cooling, and the mixture was stirred at room temperature overnight. Water was added to the reaction mixture, and the mixture was extracted with ethyl acetate, the organic layer was washed with saturated brine, and the solvent was evaporated. The obtained residue was dissolved in N,N-dimethylformamide (10 mL), sodium chloride (3.2 g) was added, and the mixture was stirred at 80° C. for 5 hr. The reaction mixture was cooled, water was added, and the mixture was extracted with ethyl acetate. The organic layer was washed with saturated brine, and the solvent was evaporated. A mixture of the obtained residue and 1,10-phenanthroline (28 mg) was dissolved in tetrahydrofuran (80 mL), diisopropylamine (3.9 mL) was added at −70° C., and n-butyllithium (38 mL) was further added. The reaction mixture was heated to room temperature, and stirred overnight. Water was added to the reaction mixture, and the mixture was extracted with ethyl acetate, the organic layer was washed with saturated brine, and the solvent was evaporated. The obtained residue was purified by column chromatography (hexane:ethyl acetate) to give the title compound (4.49 g).

Preparation Example 2

Preparation of (R)-3-methylisothiazolidine 1,1-dioxide

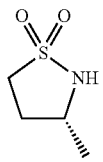

Using (R)-2-amino-1-propanol (1.50 g) and methanesulfonyl chloride (3.2 mL) and by the reaction and treatment in the same manner as in Preparation Example 1, the title compound (0.27 g) was obtained.

Preparation Example 3

Preparation of (R)-3-ethylisothiazolidine 1,1-dioxide

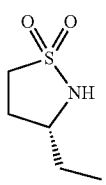

Using (R)-2-amino-1-butanol (1.78 g) and methanesulfonyl chloride (3.2 mL) and by the reaction and treatment in the same manner as in Preparation Example 1, the title compound (1.54 g) was obtained.

Preparation Example 4

Preparation of (S)-4-methylisothiazolidine 1,1-dioxide

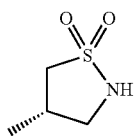

Using (S)-1-amino-2-propanol (2.0 g) and methanesulfonyl chloride (4.2 mL) and by the reaction and treatment in the same manner as in Preparation Example 1, the title compound (650 mg) was obtained.

Preparation Example 5

Preparation of 5-methylisothiazolidine 1,1-dioxide

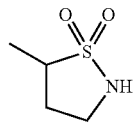

Using 2-aminoethanol (2.4 g) and ethanesulfonyl chloride (7.8 mL) and by the reaction and treatment in the same manner as in Preparation Example 1, the title compound (360 mg) was obtained.

Preparation Example 6

Preparation of (S)-3-isopropylisothiazolidine 1,1-dioxide

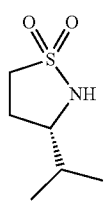

Using (R)-2-amino-3-methyl-1-butanol (5.0 g) and methanesulfonyl chloride (7.7 mL) and by the reaction and treatment in the same manner as in Preparation Example 1, the title compound (3.48 g) was obtained.

Preparation Example 7

Preparation of (R)-4-methylisothiazolidine 1,1-dioxide

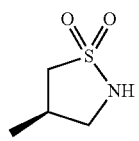

Using (R)-1-amino-2-propanol (3.0 g) and methanesulfonyl chloride (6.3 mL) and by the reaction and treatment in the same manner as in Preparation Example 1, the title compound (990 mg) was obtained.

Preparation Example 8

Preparation of (R)-3-isopropylisothiazolidine 1,1-dioxide

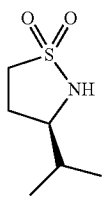

Using (S)-2-amino-3-methyl-1-butanol (5.0 g) and methanesulfonyl chloride (7.7 mL) and by the reaction and treatment in the same manner as in Preparation Example 1, the title compound (1.55 g) was obtained.

Preparation Example 9

Preparation of 4-methylisothiazolidine 1,1-dioxide

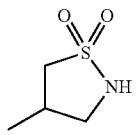

Using 1-amino-2-propanol (6.0 g) and methanesulfonyl chloride (12.7 mL) and by the reaction and treatment in the same manner as in Preparation Example 1, the title compound (324 mg) was obtained.

Preparation Example 10

Preparation of (R)-3-benzyloxymethylisothiazolidine 1,1-dioxide

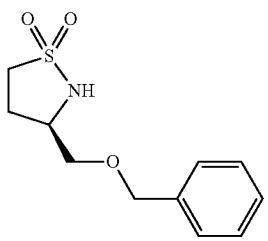 [SMILES: O=S1(=O)CC[C@H](COCc2ccccc2)N1]

Using (R)-2-amino-3-benzyloxy-1-propanol (2.0 g) and methanesulfonyl chloride (1.8 mL) and by the reaction and treatment in the same manner as in Preparation Example 1, the title compound (370 mg) was obtained.

Preparation Example 11

Preparation of 3,3-dimethylisothiazolidine 1,1-dioxide

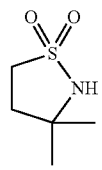

Using 2-amino-2-methyl-1-propanol (1.5 g) and methanesulfonyl chloride (2.7 mL) and by the reaction and treatment in the same manner as in Preparation Example 1, the title compound (130 mg) was obtained.

Preparation Example 12

Preparation of methyl (S)-4-(3-benzyloxymethyl-1,1-dioxo-1$\lambda^6$-isothiazolidin-2-yl)-2-methoxybenzoate

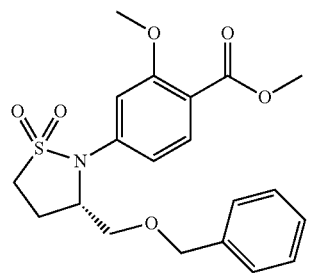 [SMILES: COC(=O)c1ccc(N2[C@H](COCc3ccccc3)CCS2(=O)=O)cc1OC]

To a mixture of methyl 4-bromo-2-methoxybenzoate (245 mg), (S)-3-benzyloxymethylisothiazolidine 1,1-dioxide (241 mg) described in Preparation Example 1, potassium carbonate (276 mg), potassium iodide (166 mg) and copper(I) iodide (95 mg) were added toluene (3 mL) and N,N'-dimethylethylenediamine (110 μL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give the title compound (380 mg).

MS (ESI) m/z: 406(M+H)$^+$.

Preparation Example 13

Preparation of methyl 4-bromo-2-(1,1-dioxo-1$\lambda^6$-isothiazolidin-2-yl)benzoate

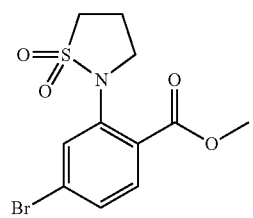 [SMILES: COC(=O)c1ccc(Br)cc1N1CCCS1(=O)=O]

Methyl 2-amino-4-bromobenzoate (5 g) and triethylamine (5.73 mL) were dissolved in methylene chloride (39 mL), 3-chloropropane-1-sulfonyl chloride (3.44 mL) was added under ice-cooling, and the mixture was stirred at room temperature. After completion of the reaction, water was added to the reaction mixture, and the mixture was extracted with chloroform. The organic layer was washed with dilute hydrochloric acid and saturated brine, and the solvent was evaporated. To the obtained residue were added 1,8-diazabicyclo [5.4.0]undec-7-ene (DBU)(3.9 mL) and N,N-dimethylformamide (29 mL), and the mixture was stirred at room temperature. After completion of the reaction, water was added to the reaction mixture, and the mixture was extracted with ethyl acetate. The organic layer was washed with dilute hydrochloric acid and saturated brine, and the solvent was evaporated. To the obtained residue was added diisopropyl ether, and the precipitate was collected by filtration to give the title compound (5.05 g).

Preparation Example 14

Preparation of methyl (S)-4-(3-benzyloxymethyl-1,1-dioxo-1$\lambda^6$-isothiazolidin-2-yl)-2-(1,1-dioxo-1$\lambda^6$-isothiazolidin-2-yl)benzoate

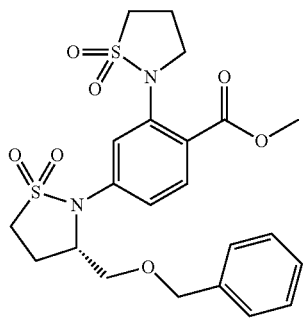 [SMILES: COC(=O)c1ccc(N2[C@H](COCc3ccccc3)CCS2(=O)=O)cc1N1CCCS1(=O)=O]

Using methyl 4-bromo-2-(1,1-dioxo-1$\lambda^6$-isothiazolidin-2-yl)benzoate (334 mg) described in Preparation Example 13 and (S)-3-benzyloxymethylisothiazolidine 1,1-dioxide (241 mg) described in Preparation Example 1 and by the reaction and treatment in the same manner as in Preparation Example 12, the title compound (430 mg) was obtained.
MS (ESI) m/z: 495(M+H)$^+$.

Preparation Example 15

Preparation of 4-(4-methyl-1,1-dioxo-1$\lambda^6$-isothiazolidin-2-yl)benzoic acid

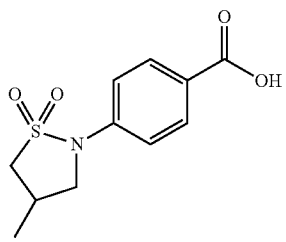 [SMILES: CC1CN(c2ccc(C(=O)O)cc2)S(=O)(=O)C1]

To a mixture of ethyl 4-iodobenzoate (571 mg), 4-methylisothiazolidine 1,1-dioxide (280 mg) described in Preparation Example 9, potassium carbonate (572 mg) and copper(I) iodide (197 mg) were added toluene (6 mL) and N,N'-dimethylethylenediamine (230 μL), and the mixture was stirred with heating under reflux for 9 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give ethyl 4-(4-methyl-1,1-dioxo-1$\lambda^6$-isothiazolidin-2-yl)benzoate. The obtained ethyl 4-(4-methyl-1,1-dioxo-1$\lambda^6$-isothiazolidin-2-yl)benzoate was dissolved in tetrahydrofuran (5 mL), 1N aqueous sodium hydroxide solution was added, and the mixture was stirred at room temperature for 1 hr. The solvent was evaporated from the reaction mixture, 1N hydrochloric acid was added, and the mixture was extracted with ethyl acetate. The organic layer was washed with saturated brine, and the solvent was evaporated. To the obtained residue was added diethyl ether, and the precipitate was collected by filtration to give the title compound (210 mg).
MS (ESI) m/z: 256(M+H)$^+$.

Preparation Example 16

Preparation of 4-(1,1-dioxo-1$\lambda^6$-isothiazolidin-2-yl)benzoic acid

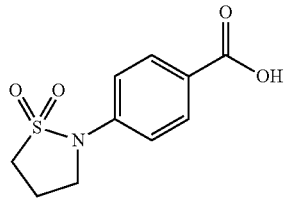 [SMILES: O=C(O)c1ccc(N2CCCS2(=O)=O)cc1]

Ethyl 4-aminobenzoate (0.92 g) and triethylamine (1.5 mL) were dissolved in dichloromethane (10 mL), 3-chloropropane-1-sulfonyl chloride (0.9 mL) was added under ice-cooling, and the mixture was stirred at room temperature overnight. After completion of the reaction, 1N hydrochloric acid was added, and the mixture was extracted with chloroform. The organic layer was washed with saturated brine, and the solvent was evaporated. The obtained residue was dissolved in N,N-dimethylformamide (8 mL), 1,8-diazabicyclo [5.4.0]undec-7-ene (DBU) (1 mL) was added, and the mixture was stirred at room temperature for 3 hr. To the reaction mixture was added 1N hydrochloric acid, and the mixture was extracted with ethyl acetate. The organic layer was washed with saturated brine, and the solvent was evaporated. The obtained residue (1.5 g) was dissolved in ethanol (20 mL), 1N aqueous sodium hydroxide solution (8.4 mL) was added, and the mixture was stirred at 60° C. for 3 hr. To the reaction mixture were added 1N hydrochloric acid (9.2 mL) and water, and the precipitate was collected by filtration to give the title compound (0.98 g).
MS (ESI) m/z: 242(M+H)$^+$.

Preparation Example 17

Preparation of methyl 4-(1,1-dioxo-1λ⁶-isothiazolidin-2-ylmethyl)benzoate

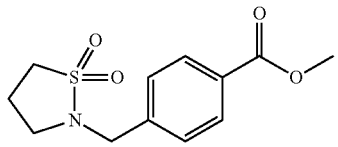 [SMILES: COC(=O)c1ccc(CN2CCCS2(=O)=O)cc1]

Methyl 4-aminomethylbenzoate hydrochloride (1.61 g) and triethylamine (2.45 mL) were dissolved in dichloromethane (40 mL), 3-chloropropane-1-sulfonyl chloride (1.17 mL) was added under ice-cooling, and the mixture was stirred at room temperature overnight. After completion of the reaction, the solvent was evaporated, 1N hydrochloric acid was added, and the mixture was extracted with ethyl acetate. The organic layer was washed with water and saturated brine, and the solvent was evaporated. The obtained residue was dissolved in N,N-dimethylformamide (8 mL), 1,8-diazabicyclo[5.4.0]undec-7-ene (DBU) (1.46 mL) was added, and the mixture was stirred at room temperature overnight. To the reaction mixture was added 0.5N hydrochloric acid, and the mixture was extracted with ethyl acetate, the organic layer was washed with water and saturated brine, and the solvent was evaporated. The obtained residue was purified by column chromatography (chloroform:ethyl acetate) to give the title compound (1.95 g).

MS (ESI) m/z: 270(M+H)⁺.

Preparation Example 18

Preparation of 4-(1,1-dioxo-1λ⁶-isothiazolidin-2-ylmethyl)benzoic acid

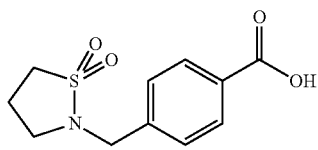 [SMILES: O=C(O)c1ccc(CN2CCCS2(=O)=O)cc1]

Methyl 4-(1,1-dioxo-1λ⁶-isothiazolidin-2-ylmethyl)benzoate (1.95 g) described in Preparation Example 17 was dissolved in a solution of tetrahydrofuran (20 mL) and methanol (20 mL), 1N aqueous sodium hydroxide solution was added, and the mixture was stirred at room temperature. The reaction mixture was neutralized with 1N hydrochloric acid, and the solvent was evaporated. To the obtained residue was added water, and the insoluble material was collected by filtration to give the title compound (1.62 g).

MS (ESI) m/z: 256(M+H)⁺.

Preparation Example 19

Preparation of 4-(1,1-dioxo-1λ⁶-isothiazolidin-2-yl)-2-methoxybenzoic acid

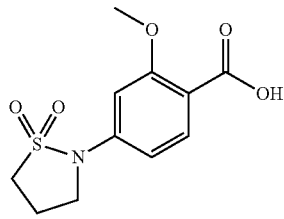 [SMILES: COc1cc(N2CCCS2(=O)=O)ccc1C(=O)O]

Using methyl 4-amino-2-methoxybenzoate (1.01 g) and 3-chloropropane-1-sulfonyl chloride (0.9 mL) and by the reaction and treatment in the same manner as in Preparation Example 16, the title compound (839 mg) was obtained.

MS (ESI) m/z: 272(M+H)⁺.

Preparation Example 20

Preparation of 4-(1,1-dioxo-1λ⁶-isothiazolidin-2-yl)-3-methylbenzoic acid

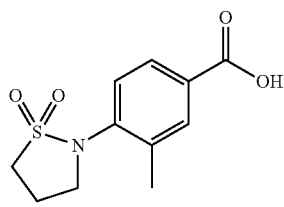 [SMILES: Cc1cc(C(=O)O)ccc1N1CCCS1(=O)=O]

Using ethyl 4-amino-3-methylbenzoate (1.0 g) and 3-chloropropane-1-sulfonyl chloride (0.9 mL) and by the reaction and treatment in the same manner as in Preparation Example 16, the title compound (463 mg) was obtained.

MS (ESI) m/z: 256(M+H)⁺.

Preparation Example 21

Preparation of 4-(1,1-dioxo-1λ⁶-isothiazolidin-2-yl)-3-methoxybenzoic acid

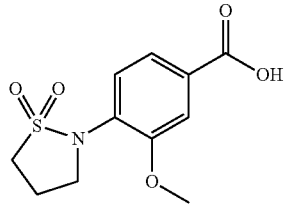 [SMILES: COc1cc(C(=O)O)ccc1N1CCCS1(=O)=O]

Using methyl 4-amino-3-methoxybenzoate (1.22 g) and 3-chloropropane-1-sulfonyl chloride (1.1 mL) and by the reaction and treatment in the same manner as in Preparation Example 16, the title compound (1.05 g) was obtained.

MS (ESI) m/z: 272(M+H)⁺.

Preparation Example 22

Preparation of 4-(1,1-dioxo-1λ$^6$-isothiazolidin-2-yl)-2-methanesulfonylbenzoic acid

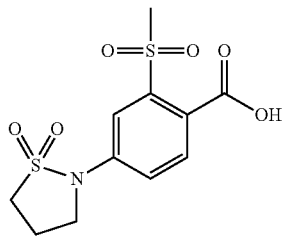 [SMILES: CS(=O)(=O)c1cc(N2CCCS2(=O)=O)ccc1C(=O)O]

To 4-bromo-2-methanesulfonylbenzoic acid (5 g) were added methanol (45 mL) and concentrated sulfuric acid (1.8 mL), and the mixture was stirred with heating under reflux. After completion of the reaction, the solvent was evaporated, and the residue was neutralized with 1N aqueous sodium hydroxide solution, and the mixture was extracted with ethyl acetate. The organic layer was washed with saturated brine, and the solvent was evaporated to give methyl 4-bromo-2-methanesulfonylbenzoate (3.34 g). To a mixture of the obtained methyl 4-bromo-2-methanesulfonylbenzoate (3.34 g), tris(dibenzylideneacetone)dipalladium(0)-chloroform adduct (295 mg), 2-(dicyclohexylphosphino)biphenyl (399 mg), tripotassium phosphate (3.39 g) and benzophenonimine (2.5 mL) was added 1,2-dimethoxyethane (25 mL), and the mixture was stirred with heating under reflux. After completion of the reaction, water was added to the reaction mixture, and the mixture was extracted with ethyl acetate. The organic layer was washed with saturated brine, and the solvent was evaporated. The obtained residue was dissolved in tetrahydrofuran (26 mL), 1N hydrochloric acid (100 mL) was added, and the mixture was stirred at room temperature for 1 hr. The reaction mixture was neutralized with sodium hydrogen carbonate, and the mixture was extracted with ethyl acetate. The organic layer was washed with saturated brine, and the solvent was evaporated to give methyl 4-amino-2-methanesulfonylbenzoate (1.46 g). Using the obtained methyl 4-amino-2-methanesulfonylbenzoate (1.46 g) and 3-chloropropane-1-sulfonyl chloride (1.03 mL) and by the reaction and treatment in the same manner as in Preparation Example 16, the title compound (0.53 g) was obtained.

Preparation Example 23

Preparation of 4-(1,1-dioxo-1λ$^6$-isothiazolidin-2-yl)-2-fluorobenzoic acid

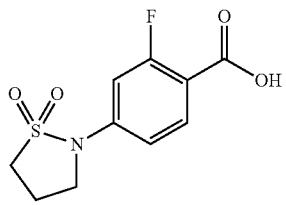 [SMILES: O=C(O)c1ccc(N2CCCS2(=O)=O)cc1F]

Using methyl 4-amino-2-fluorobenzoate (1.02 g) and 3-chloropropane-1-sulfonyl chloride (0.97 mL) and by the reaction and treatment in the same manner as in Preparation Example 16, the title compound (1.09 g) was obtained.

MS (ESI) m/z: 260(M+H)$^+$.

Preparation Example 24

Preparation of 4-(1,1-dioxo-1λ$^6$-isothiazolidin-2-yl)-2-nitrobenzoic acid

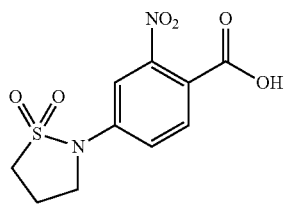 [SMILES: O=C(O)c1ccc(N2CCCS2(=O)=O)cc1[N+](=O)[O-]]

Using methyl 4-amino-2-nitrobenzoate (750 mg) and 3-chloropropane-1-sulfonyl chloride (0.61 mL) and by the reaction and treatment in the same manner as in Preparation Example 16, the title compound (967 mg) was obtained.

Preparation Example 25

Preparation of ethyl 6-(1,1-dioxo-1λ$^6$-isothiazolidin-2-yl)nicotinate

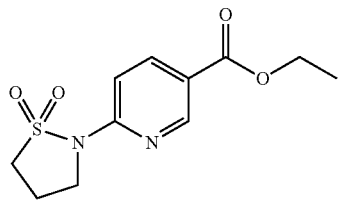 [SMILES: CCOC(=O)c1ccc(N2CCCS2(=O)=O)nc1]

Using ethyl 6-aminonicotinate (2.02 g) and 3-chloropropane-1-sulfonyl chloride (1.8 mL) and by the reaction and treatment in the same manner as in Preparation Example 17, the title compound (2.29 g) was obtained.

Preparation Example 26

Preparation of 4-(1,1-dioxo-1λ$^6$-isothiazolidin-2-yl)-3-fluorobenzoic acid

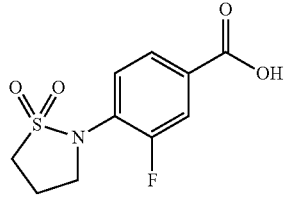

Using methyl 4-amino-3-fluorobenzoate (1.12 g) and 3-chloropropane-1-sulfonyl chloride (1.06 mL) and by the reaction and treatment in the same manner as in Preparation Example 16, the title compound (1.04 g) was obtained.

Preparation Example 27

Preparation of (S)-3-phenylisothiazolidine 1,1-dioxide

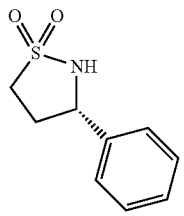 [SMILES: O=S1(=O)CC[C@@H](c2ccccc2)N1]

Using (R)-2-amino-2-phenylethanol (1.37 g) and methanesulfonyl chloride (1.6 mL) and by the reaction and treatment in the same manner as in Preparation Example 1, the title compound (391 mg) was obtained.

Preparation Example 28

Preparation of ethyl (R)-2-methanesulfonyl-4-(3-methyl-1,1-dioxo-1$\lambda^6$-isothiazolidin-2-yl)benzoate

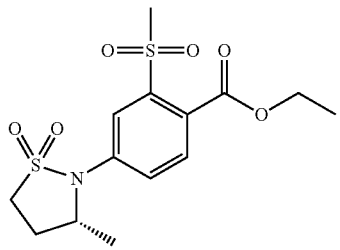 [SMILES: CCOC(=O)c1ccc(N2[C@H](C)CCS2(=O)=O)cc1S(C)(=O)=O]

To a mixture of ethyl 4-bromo-2-methanesulfonylbenzoate (13.88 g), sodium iodide (13.54 g) and copper(I) iodide (4.30% g) were added toluene (46 mL) and N,N'-dimethylethylenediamine (4.86 mL), and the mixture was stirred with heating under reflux for 8 hr under a nitrogen stream. The reaction mixture was cooled, water was added, and the mixture was extracted with ethyl acetate. The solvent was evaporated from the organic layer, the obtained residue was purified by column chromatography (hexane:ethyl acetate) to give ethyl 4-iodo-2-methanesulfonylbenzoate (10.32 g). To a mixture of the obtained ethyl 4-iodo-2-methanesulfonylbenzoate (3.22 g), (R)-3-methylisothiazolidine 1,1-dioxide (1.23 g) described in Preparation Example 2, copper(I) iodide (4.30 g), N,N'-dimethylethylenediamine (0.92 mL) and potassium carbonate (2.52 g) was added toluene (9.2 mL), and the mixture was stirred with heating under reflux for 8 hr under a nitrogen stream. The reaction mixture was cooled, water was added, and the mixture was extracted with ethyl acetate. The solvent was evaporated from the organic layer, and the obtained residue was purified by column chromatography (hexane:ethyl acetate) to give the title compound (1.7 g).

MS (ESI) m/z: 362(M+H)$^+$.

Preparation Example 29

Preparation of 4-(1,1-dioxo-1$\lambda^6$-isothiazolidin-2-yl)-2-methylbenzoic acid

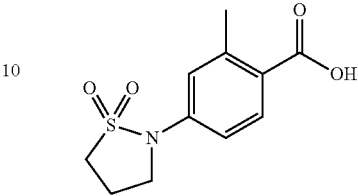

Using ethyl 4-amino-2-methylbenzoate (5.3 g) and 3-chloropropane-1-sulfonyl chloride (4.8 mL) and by the reaction and treatment in the same manner as in Preparation Example 16, the title compound (6.49 g) was obtained.

Preparation Example 30

Preparation of ethyl 4-(4,4-dimethyl-1,1-dioxo-1$\lambda^6$-isothiazolidin-2-yl)benzoate

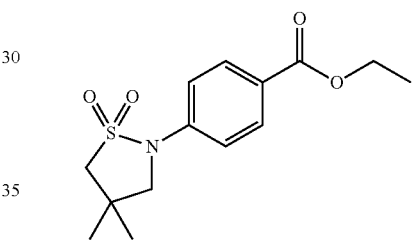

To a mixture of 3-bromo-2,2-dimethyl-1-propanol (5 mL) and triethylamine (15 mL) was added tetrahydrofuran (50 mL), acetyl chloride (3.8 mL) was added dropwise under ice-cooling, and the mixture was stirred at room temperature overnight. Water was added to the reaction mixture, and the mixture was extracted with ethyl acetate. The organic layer was washed with saturated brine, and the solvent was evaporated to give acetic acid (3-bromo-2,2-dimethyl-1-propyl) ester (8.37 g). The obtained acetic acid (3-bromo-2,2-dimethyl-1-propyl)ester (8.37 g) were added sodium sulfite (5.05 g) and water (20 mL), and the mixture was stirred with heating under reflux for 20 hr. To the reaction mixture was added concentrated hydrochloric acid (5.81 mL), and the mixture was stirred with heating under reflux for 1 hr. The reaction mixture was cooled, neutralized with 4N aqueous sodium hydroxide solution (20.5 mL), and the mixture was concentrated to about 10 mL. The precipitated precipitate was collected by filtration, and the filtrate was concentrated. To the obtained residue was added phosphorus pentachloride (18.35 g) under ice-cooling, and the mixture was stirred at room temperature for 1 hr. Into the reaction mixture was poured ice water, and the mixture was extracted with dichloromethane. The solvent was evaporated from the organic layer to give crude 3-chloro-2,2-dimethylpropane-1-sulfonyl chloride (3.99 g). Using the obtained crude 3-chloro-2,2-dimethylpropane-1-sulfonyl chloride (3.99 g) and ethyl 4-aminobenzoate (3.21 g) and by the reaction and treatment in the same manner as in Preparation Example 17, the title compound (127 mg) was obtained.

Preparation Example 31

Preparation of 4-[1-(1,1-dioxo-1λ⁶-isothiazolidin-2-yl)cyclopropyl]benzoic acid

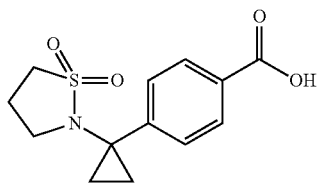 [SMILES: O=C(O)c1ccc(C2(N3CCCS3(=O)=O)CC2)cc1]

Using methyl 4-(1-aminocyclopropyl)benzoate (532 mg) and 3-chloropropane-1-sulfonyl chloride (0.44 mL) and by the reaction and treatment in the same manner as in Preparation Example 16, the title compound (559 mg) was obtained.

Preparation Example 32

Preparation of methyl 4-(1,1-dioxo-1λ⁶-isothiazolidin-2-yl)-2-(2-oxooxazolidin-3-yl)benzoate

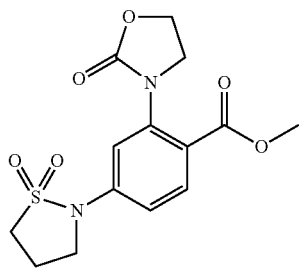 [SMILES: COC(=O)c1ccc(N2CCCS2(=O)=O)cc1N1CCOC1=O]

To a mixture of methyl 2-bromo-4-nitrobenzoate (2 g), oxazolidin-2-one (0.67 g), potassium carbonate (2.06 g), copper(I) iodide (0.73 g) and N,N'-dimethylethylenediamine (0.83 mL) was added toluene (16 mL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give methyl 4-nitro-2-(2-oxo-oxazolidin-3-yl)benzoate (960 mg). To a solution of ethanol (24 mL) and water (5 mL) were added ammonium chloride (0.11 g) and iron (0.79 g), and a solution of the obtained methyl 4-nitro-2-(2-oxooxazolidin-3-yl)benzoate (960 mg) in ethanol (19 mL) was added while stirring at 60° C.-70° C. After completion of the reaction, the insoluble material was collected by filtration, and the filtrate was concentrated. To the obtained residue was added aqueous sodium hydrogen carbonate solution, and the mixture was extracted with ethyl acetate. The solvent was evaporated from the organic layer to give methyl 4-amino-2-(2-oxooxazolidin-3-yl)benzoate (730 mg). Using the obtained methyl 4-amino-2-(2-oxooxazolidin-3-yl)benzoate (730 mg) and 3-chloropropane-1-sulfonyl chloride (0.49 mL) and by the reaction and treatment in the same manner as in Preparation Example 17, the title compound (495 mg) was obtained.
MS (ESI) m/z: 341(M+H)⁺.

Preparation Example 33

Preparation of methyl 4-(1,1-dioxo-1λ⁶-isothiazolidin-2-yl)-2-(2-oxopyrrolidin-1-yl)benzoate

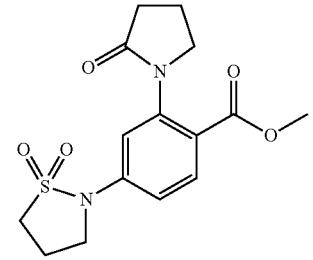 [SMILES: COC(=O)c1ccc(N2CCCS2(=O)=O)cc1N1CCCC1=O]

Using methyl 2-bromo-4-nitrobenzoate (2 g) and pyrrolidin-2-one (655 mg) and by the reaction and treatment in the same manner as in Preparation Example 32, the title compound (296 mg) was obtained.
MS (ESI) m/z: 339(M+H)⁺.

Preparation Example 34

Preparation of 2,4-bis(1,1-dioxo-1λ⁶-isothiazolidin-2-yl)benzoic acid

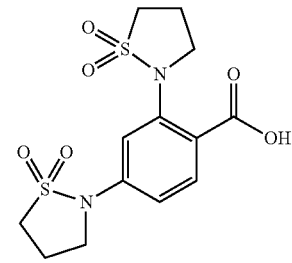 [SMILES: O=C(O)c1ccc(N2CCCS2(=O)=O)cc1N1CCCS1(=O)=O]

Using ethyl 2,4-diaminobenzoate (2.21 g) and 3-chloropropane-1-sulfonyl chloride (4 mL) and by the reaction and treatment in the same manner as in Preparation Example 16, the title compound (1.33 g) was obtained.

Preparation Example 35

Preparation of methyl 2-cyclopropyl-4-(1,1-dioxo-1λ⁶-isothiazolidin-2-yl)benzoate

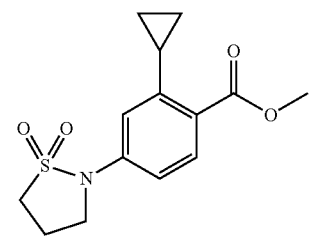 [SMILES: COC(=O)c1ccc(N2CCCS2(=O)=O)cc1C1CC1]

To a mixture of methyl 2-bromo-4-nitrobenzoate (871 mg), bis(tricyclohexylphosphine)palladium(II)dichloride (136 mg), tripotassium phosphate (3.98 g) and cyclopropylboronic acid (863 mg) were added toluene (10 mL) and water (0.4 mL), and the mixture was stirred with heating under reflux for 8 hr. The reaction mixture was cooled, water was added, and the mixture was extracted with ethyl acetate. The solvent was evaporated from the organic layer, and the obtained residue was purified by column chromatography (ethyl acetate:hexane) to give methyl 2-cyclopropyl-4-nitrobenzoate (285 mg). The obtained methyl 2-cyclopropyl-4-nitrobenzoate (285 mg) was dissolved in a solution of ethyl acetate and ethanol, and catalytic hydrogenation was performed using palladium carbon to give methyl 4-amino-2-cyclopropylbenzoate (189 mg). Using the obtained methyl 4-amino-2-cyclopropylbenzoate (189 mg) and 3-chloropropane-1-sulfonyl chloride (0.156 mL) and by the reaction and treatment in the same manner as in Preparation Example 17, the title compound (168 mg) was obtained.

MS (ESI) m/z: 296(M+H)$^+$.

Preparation Example 36

Preparation of methyl 6-amino-2-methylnicotinate

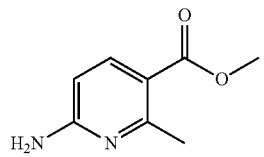

6-Amino-2-methylnicotinic acid (1.00 g) was suspended in methanol (15 mL), concentrated sulfuric acid (0.5 mL) was added, and the mixture was stirred with heating under reflux for 18 hr. The reaction mixture was cooled, aqueous sodium hydroxide solution was added, and the mixture was extracted with chloroform. The organic layer was washed with saturated brine, and the solvent was evaporated to give the title compound (0.82 g).

MS (ESI) m/z: 167(M+H)$^+$.

Preparation Example 37

Preparation of methyl 6-(1,1-dioxo-1$\lambda^6$-isothiazolidin-2-yl)-2-methylnicotinate

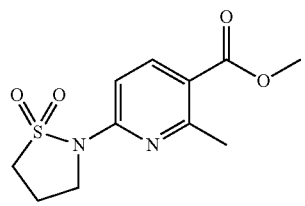 [SMILES: COC(=O)c1ccc(N2CCCS2(=O)=O)nc1C]

Using methyl 6-amino-2-methylnicotinate (170 mg) described in Preparation Example 36 and 3-chloropropane-1-sulfonyl chloride (0.25 mL) and by the reaction and treatment in the same manner as in Preparation Example 17, the title compound (220 mg) was obtained.

MS (ESI) m/z: 271(M+H)$^+$.

Preparation Example 38

Preparation of methyl 4-[1-(1,1-dioxo-1$\lambda^6$-isothiazolidin-2-yl)-1-methylethyl]benzoate

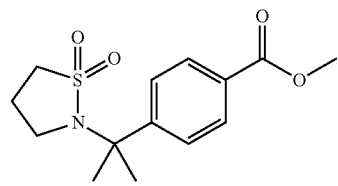 [SMILES: COC(=O)c1ccc(C(C)(C)N2CCCS2(=O)=O)cc1]

Using methyl 4-(1-amino-1-methylethyl)benzoate (570 mg) and 3-chloropropane-1-sulfonyl chloride (0.47 mL) and by the reaction and treatment in the same manner as in Preparation Example 17, the title compound (862 mg) was obtained.

Preparation Example 39

Preparation of 4-[1-(1,1-dioxo-1$\lambda^6$-isothiazolidin-2-yl)-1-methylethyl]benzoic acid

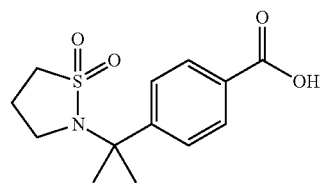 [SMILES: CC(C)(c1ccc(C(=O)O)cc1)N1CCCS1(=O)=O]

Using methyl 4-[1-(1,1-dioxo-1$\lambda^6$-isothiazolidin-2-yl)-1-methylethyl]benzoate (860 mg) described in Preparation Example 38 and by the reaction and treatment in the same manner as in Preparation Example 18, the title compound (671 mg) was obtained.

MS (ESI) m/z: 284(M+H)$^+$.

Preparation Example 40

Preparation of methyl 4-[2-(1,1-dioxo-1$\lambda^6$-isothiazolidin-2-yl)ethyl]benzoate

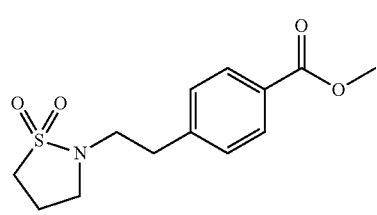

Using methyl 4-(2-aminoethyl)benzoate (0.78 g) and 3-chloropropane-1-sulfonyl chloride (0.69 mL) and by the

Preparation Example 41

Preparation of 4-[2-(1,1-dioxo-1λ⁶-isothiazolidin-2-yl)ethyl]benzoic acid

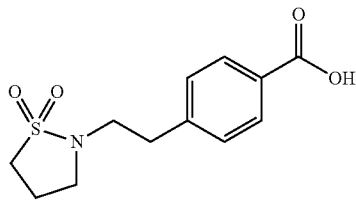

Using methyl 4-[2-(1,1-dioxo-1λ⁶-isothiazolidin-2-yl)ethyl]benzoate (1.00 g) described in Preparation Example 40 and by the reaction and treatment in the same manner as in Preparation Example 18, the title compound (0.91 g) was obtained.
MS (ESI) m/z: 270(M+H)⁺.

Preparation Example 42

Preparation of methyl (R)-4-(3-methyl-1,1-dioxo-1λ⁶-isothiazolidin-2-ylmethyl)benzoate

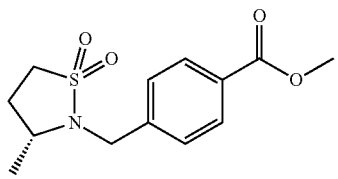

Under a nitrogen stream, (R)-3-methylisothiazolidine 1,1-dioxide (149 mg) described in Preparation Example 2 was dissolved in a solution of tetrahydrofuran (5 mL) and N,N-dimethylformamide (4 mL), sodium hydride (44 mg) was added under ice-cooling, and the mixture was stirred at the same temperature for 15 min. Then, a solution of methyl 4-bromomethylbenzoate (229 mg) in tetrahydrofuran (5 mL) was added, and the mixture was stirred under ice-cooling for 1.5 hr, and at room temperature for 2 hr. To the reaction mixture was added 0.5N hydrochloric acid, and the mixture was extracted with ethyl acetate. The organic layer was washed with water and saturated brine, and the solvent was evaporated. The obtained residue was purified by column chromatography (hexane:ethyl acetate) to give the title compound (159 mg).
MS (ESI) m/z: 284(M+H)⁺.

Preparation Example 43

Preparation of methyl (S)-4-[1-(1,1-dioxo-1λ⁶-isothiazolidin-2-yl)ethyl]benzoate

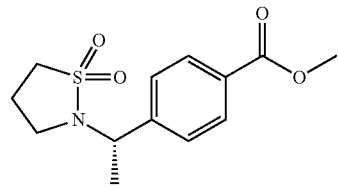

Using methyl (S)-4-(1-aminoethyl)benzoate (0.61 g) and 3-chloropropane-1-sulfonyl chloride (0.54 mL) and by the reaction and treatment in the same manner as in Preparation Example 17, the title compound (0.90 g) was obtained.
MS (ESI) m/z: 284(M+H)⁺.

Preparation Example 44

Preparation of (S)-4-[1-(1,1-dioxo-1λ⁶-isothiazolidin-2-yl)ethyl]benzoic acid

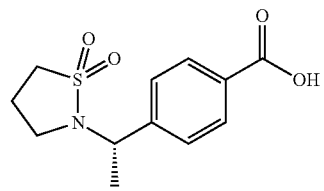

Using methyl (S)-4-[1-(1,1-dioxo-1λ⁶-isothiazolidin-2-yl)ethyl]benzoate (0.90 g) described in Preparation Example 43 and by the reaction and treatment in the same manner as in Preparation Example 18, the title compound (0.77 g) was obtained.
MS (ESI) m/z: 270(M+H)⁺.

Preparation Example 45

Preparation of methyl 6-(1,1-dioxo-1λ⁶-isothiazolidin-2-ylmethyl)nicotinate

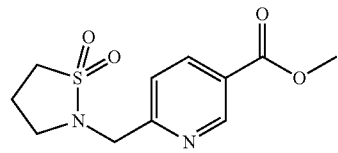

Using methyl 6-bromomethylnicotinate (500 mg) and 1,1-dioxo-1λ⁶-isothiazolidine (290 mg) and by the reaction and treatment in the same manner as in Preparation Example 42, the title compound (429 mg) was obtained.
MS (ESI) m/z: 271(M+H)⁺.

Preparation Example 46

Preparation of ethyl 4-(1,1-dioxo-1λ⁶-[1,2,5]thiadiazolidin-2-yl)benzoate

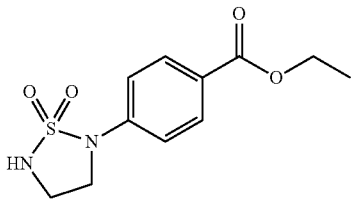 [SMILES: CCOC(=O)c1ccc(N2CCNS2(=O)=O)cc1]

To 2-chloroethylamine hydrochloride (1.16 g) were added acetonitrile (15 mL) and sulfuryl chloride (6.08 mL), and the mixture was stirred at 80° C. for 8 hr. The solvent was evaporated from the reaction mixture, and to the obtained to residue was added tetrahydrofuran (10 mL). A solution of a mixture of ethyl 4-aminobenzoate (826 mg) and triethylamine (2.8 mL) in tetrahydrofuran (5 mL) was added dropwise under ice-cooling. The reaction mixture was stirred at room temperature overnight, and water was added. The mixture was extracted with ethyl acetate, and the solvent was evaporated. The obtained residue was dissolved in dimethylsulfoxide (15 mL), potassium carbonate (1.38 g) was added, and the mixture was stirred at room temperature. Water was added to the reaction mixture, the mixture was extracted with ethyl acetate, and the solvent was evaporated. The obtained residue was purified by column chromatography (ethyl acetate:hexane) to give the title compound (195 mg).

Preparation Example 47

Preparation of ethyl 4-(1,1-dioxo-1λ⁶-[1,2,6]thiadiazinan-2-yl)benzoate

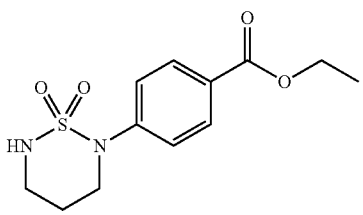 [SMILES: CCOC(=O)c1ccc(N2CCCNS2(=O)=O)cc1]

Using ethyl 4-aminobenzoate (826 mg) and 3-chloropropylamine hydrochloride (1.3 g) and by the reaction and treatment in the same manner as in Preparation Example 46, the title compound (534 mg) was obtained.

MS (ESI) m/z: 285(M+H)⁺.

Preparation Example 48

Preparation of ethyl 4-(4-methyl-2-oxopyrrolidin-1-yl)benzoate

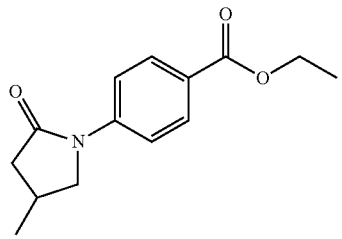 [SMILES: CCOC(=O)c1ccc(N2CC(C)CC2=O)cc1]

To a mixture of ethyl 4-iodobenzoate (552 mg), 4-methylpyrrolidin-2-one (198 mg), potassium carbonate (536 mg) and copper(I) iodide (190 mg) were added toluene (2 mL) and N,N'-dimethylethylenediamine (215 µL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give the title compound (377 mg).

MS (ESI) m/z: 248(M+H)⁺.

Preparation Example 49

Preparation of ethyl 4-(4,4-dimethyl-2-oxopyrrolidin-1-yl)benzoate

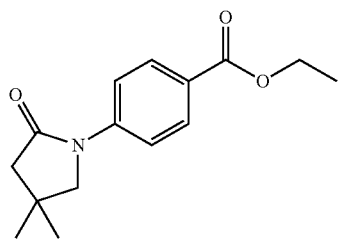 [SMILES: CCOC(=O)c1ccc(N2CC(C)(C)CC2=O)cc1]

Using ethyl 4-iodobenzoate (552 mg) and 4,4-dimethylpyrrolidin-2-one (226 mg) and by the reaction and treatment in the same manner as in Preparation Example 48, the title compound (538 mg) was obtained.

MS (ESI) m/z: 262(M+H)⁺.

Preparation Example 50

Preparation of 4-(2-methyl-5-oxopyrrolidin-1-yl)benzoic acid

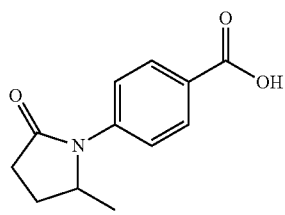 [SMILES: CC1CCC(=O)N1c1ccc(C(=O)O)cc1]

Using ethyl 4-iodobenzoate (1.70 mL) and 5-methylpyrrolidin-2-one (0.98 g) and by the reaction and treatment in the same manner as in Preparation Example 15, the title compound (1.80 g) was obtained.

Preparation Example 51

Preparation of 3-(4-methoxybenzyl)-5-methylimidazolidine-2,4-dione

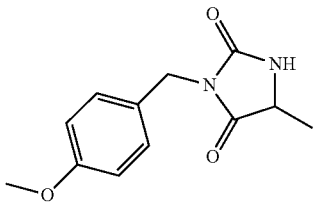

To a mixture of 5-methylimidazolidine-2,4-dione (2.00 g), 4-methoxybenzyl chloride (2.85 mL) and potassium carbonate (3.15 g) were added N,N-dimethylformamide (20 mL) and potassium iodide (0.29 g), and the mixture was stirred at 90° C. for 9 hr. The reaction mixture was cooled, water was added, and the mixture was extracted with ethyl acetate. The organic layer was washed with water and saturated brine, and the solvent was evaporated. The obtained residue was recrystallized from ethyl acetate/diisopropyl ether to give the title compound (2.82 g).
MS (ESI) m/z: 235(M+H)$^+$.

Preparation Example 52

Preparation of 1-(4-methoxybenzyl)-4-methylimidazolidin-2-one

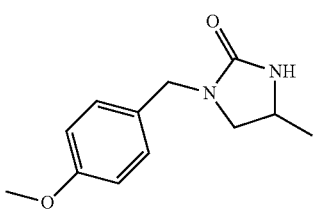

Under a nitrogen stream, sodium borohydride (0.65 g) was suspended in tetrahydrofuran (25 mL), boron trifluoride diethyl ether complex (2.63 mL) was added dropwise under ice-cooling, and the mixture was stirred at the same temperature for 15 min. Then, a solution of 3-(4-methoxybenzyl)-5-methylimidazolidine-2,4-dione (2.00 g) described in Preparation Example 51 in tetrahydrofuran (25 ml) was added under ice-cooling, and the mixture was stirred at the same temperature for 30 min and at room temperature overnight. To the reaction mixture were added dropwise methanol and 0.5N hydrochloric acid, and the mixture was stirred at room temperature for 1 hr. The solvent was evaporated from the reaction mixture, water was added, and the mixture was extracted with ethyl acetate. The organic layer was washed with 1N hydrochloric acid, water and saturated brine, and the solvent was evaporated. The obtained residue was purified by column chromatography (hexane:ethyl acetate) to give the title compound (1.16 g).
MS (ESI) m/z: 221(M+H)$^+$.

Preparation Example 53

Preparation of 3-(4-methoxybenzyl)-5,5-dimethylimidazolidine-2,4-dione

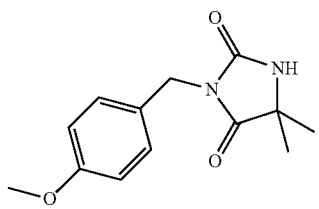

Using 5,5-dimethylimidazolidine-2,4-dione (3.00 g) and 4-methoxybenzyl chloride (3.81 mL) and by the reaction and treatment in the same manner as in Preparation Example 51, the title compound (4.32 g) was obtained.
MS (ESI) m/z: 249(M+H)$^+$.

Preparation Example 54

Preparation of 1-(4-methoxybenzyl)-4,4-dimethylimidazolidin-2-one

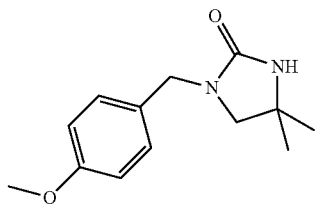

Using 3-(4-methoxybenzyl)-5,5-dimethylimidazolidine-2,4-dione (2.00 g) described in Preparation Example 53 and by the reaction and treatment in the same manner as in Preparation Example 52, the title compound (1.02 g) was obtained.
MS (ESI) m/z: 235(M+H)$^+$.

Preparation Example 55

Preparation of 3-benzoyl-1-(4-methoxybenzyl)-4-methylimidazolidin-2-one

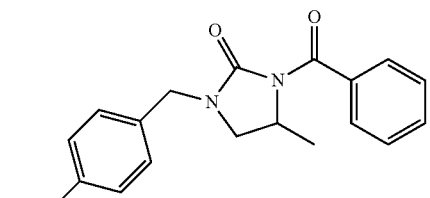

Under a nitrogen stream, 1-(4-methoxybenzyl)-4-methylimidazolidin-2-one (300 mg) described in Preparation Example 52 was dissolved in N,N-dimethylformamide (3 mL), sodium hydride (60 mg) was added under ice-cooling, and the mixture was stirred at room temperature for 30 min. Then, benzoyl chloride (0.17 mL) was added under ice-cool-

Preparation Example 56

Preparation of
1-benzoyl-5-methylimidazolidin-2-one

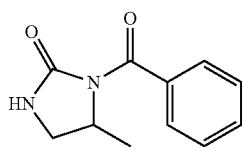

3-Benzoyl-1-(4-methoxybenzyl)-4-methylimidazolidin-2-one (220 mg) described in Preparation Example 55 was dissolved in trifluoroacetic acid (2 mL), and the mixture was stirred for 4 hr under heated reflux. The solvent was evaporated from the reaction mixture, 5% aqueous sodium hydrogen carbonate solution was added, and the mixture was extracted with ethyl acetate. The organic layer was washed with 5% aqueous sodium hydrogen carbonate solution and saturated brine, and the solvent was evaporated. The obtained residue was purified by column chromatography (hexane:ethyl acetate) to give the title compound (135 mg).

MS (ESI) m/z: 205(M+H)$^+$.

Preparation Example 57

Preparation of 3-benzoyl-1-(4-methoxybenzyl)-4,4-dimethylimidazolidin-2-one

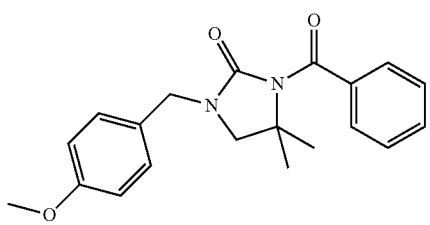 [SMILES: COc1ccc(CN2CC(C)(C)N(C(=O)c3ccccc3)C2=O)cc1]

Using 1-(4-methoxybenzyl)-4,4-dimethylimidazolidin-2-one (500 mg) described in Preparation Example 54 and benzoyl chloride (0.28 mL) and by the reaction and treatment in the same manner as in Preparation Example 55, the title compound (500 mg) was obtained.

MS (ESI) m/z: 339(M+H)$^+$.

ing, and the mixture was stirred at the same temperature for 30 min and at room temperature for 2 hr. To the reaction mixture was added 1N hydrochloric acid, and the mixture was extracted with ethyl acetate. The organic layer was washed with water, 5% aqueous sodium hydrogen carbonate solution and saturated brine, and the solvent was evaporated. The obtained residue was purified by column chromatography (hexane:ethyl acetate) to give the title compound (220 mg).

MS (ESI) m/z: 325(M+H)$^+$.

Preparation Example 58

Preparation of
1-benzoyl-5,5-dimethylimidazolidin-2-one

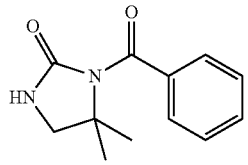 [SMILES: CC1(C)CNC(=O)N1C(=O)c1ccccc1]

3-Benzoyl-1-(4-methoxybenzyl)-4,4-dimethylimidazolidin-2-one (500 mg) described in Preparation Example 57 was dissolved in dichloromethane (5 mL), trifluoromethanesulfonic acid (0.39 mL) was added, and the mixture was stirred at room temperature for 3 hr. To the reaction mixture was added 5% aqueous sodium hydrogen carbonate solution, the solvent was evaporated, and the mixture was extracted with ethyl acetate. The organic layer was washed with saturated brine, and the solvent was evaporated. The obtained residue was purified by column chromatography (hexane:ethyl acetate) to give the title compound (146 mg).

MS (ESI) m/z: 219(M+H)$^+$.

Preparation Example 59

Preparation of methyl
4-(3-acetyl-2-oxoimidazolidin-1-yl)benzoate

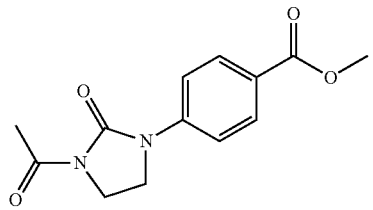 [SMILES: COC(=O)c1ccc(N2CCN(C(C)=O)C2=O)cc1]

To a mixture of p-(methoxycarbonyl)phenylboronic acid (2.45 g), 1-acetylimidazolidin-2-one (870 mg) and copper(II) acetate (1.23 g) were added methylene chloride (20 mL) and triethylamine (1.9 mL), and the mixture was stirred at room temperature overnight. Water was added to the reaction mixture, and the insoluble material was collected by filtration. The filtrate was extracted with chloroform, and the solvent was evaporated from the organic layer. The obtained residue was purified by column chromatography (chloroform) to give the title compound (292 mg).

Preparation Example 60

Preparation of ethyl
4-(2-oxotetrahydropyrimidin-1-yl)benzoate

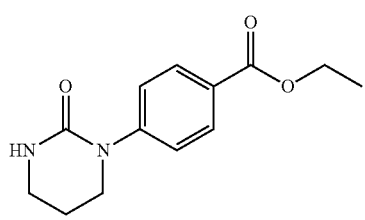 [SMILES: CCOC(=O)c1ccc(N2CCCNC2=O)cc1]

A mixture of ethyl 4-aminobenzoate (496 mg) and pyridine (60 µL) was dissolved in dichloromethane (3 mL), 1-chloro-3-isocyanatopropane (323 µL) was added, and the mixture was stirred at room temperature. Water was added to the reaction mixture, and the mixture was extracted with ethyl acetate. The organic layer was washed with dilute hydrochloric acid and saturated brine, and the solvent was evaporated. The obtained residue was purified by column chromatography (ethyl acetate:hexane) to give ethyl 4-[3-(3-chloropropyl)ureido]benzoate (810 mg). The obtained ethyl 4-[3-(3-chloropropyl)ureido]benzoate (810 mg) was dissolved in N,N-dimethylformamide (10 mL), sodium hydride (250 mg) was added under ice-cooling, and the mixture was stirred at room temperature for 3 hr. Water was added to the reaction mixture, the mixture was extracted with ethyl acetate, and the solvent was evaporated from the organic layer. To the obtained residue was added diisopropyl ether, and the precipitate was collected by filtration to give the title compound (84 mg).

MS (ESI) m/z: 249(M+H)$^+$

Preparation Example 61

Preparation of methyl 4-(2-oxooxazolidin-3-ylmethyl)benzoate

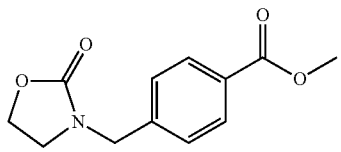 [SMILES: COC(=O)c1ccc(CN2CCOC2=O)cc1]

Using methyl 4-bromomethylbenzoate (1.83 g) and oxazolidin-2-one (0.77 g) and by the reaction and treatment in the same manner as in Preparation Example 42, the title compound (1.65 g) was obtained.

MS (ESI) m/z: 236(M+H)$^+$.

Preparation Example 62

Preparation of 4-(2-oxooxazolidin-3-ylmethyl)benzoic acid

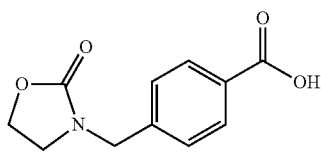 [SMILES: O=C(O)c1ccc(CN2CCOC2=O)cc1]

Using methyl 4-(2-oxooxazolidin-3-ylmethyl)benzoate (1.65 g) described in Preparation Example 61 and by the reaction and treatment in the same manner as in Preparation Example 18, the title compound (1.33 g) was obtained.

MS (ESI) m/z: 222(M+H)$^+$.

Preparation Example 63

Preparation of methyl (R)-4-(4-methyl-2-oxooxazolidin-3-ylmethyl)benzoate

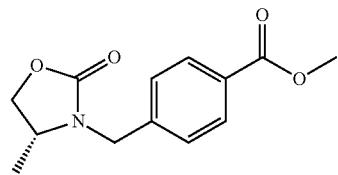 [SMILES: COC(=O)c1ccc(CN2C(=O)OC[C@H]2C)cc1]

Using methyl 4-bromomethylbenzoate (1.00 g) and (R)-4-methyloxazolidin-2-one (0.49 g) and by the reaction and treatment in the same manner as in Preparation Example 42, the title compound (0.81 g) was obtained.

MS (ESI) m/z: 250(M+H)$^+$.

Preparation Example 64

Preparation of (R)-4-(4-methyl-2-oxooxazolidin-3-ylmethyl)benzoic acid

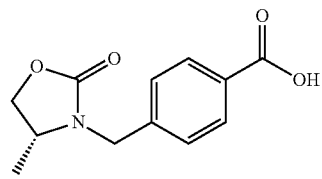 [SMILES: C[C@@H]1COC(=O)N1Cc1ccc(C(=O)O)cc1]

Using methyl (R)-4-(4-methyl-2-oxooxazolidin-3-ylmethyl)benzoate (0.81 g) described in Preparation Example 63 and by the reaction and treatment in the same manner as in Preparation Example 18, the title compound (0.69 g) was obtained.

MS (ESI) m/z: 236(M+H)$^+$.

Preparation Example 65

Preparation of methyl (S)-4-(4-methyl-2-oxooxazolidin-3-ylmethyl)benzoate

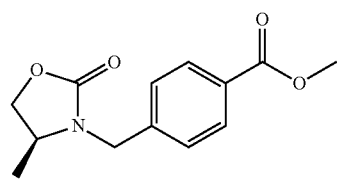 [SMILES: COC(=O)c1ccc(CN2C(=O)OC[C@@H]2C)cc1]

Using methyl 4-bromomethylbenzoate (500 mg) and (S)-4-methyloxazolidin-2-one (243 mg) and by the reaction and treatment in the same manner as in Preparation Example 42, the title compound (440 mg) was obtained.

MS (ESI) m/z: 250(M+H)$^+$.

Preparation Example 66

Preparation of (S)-4-(4-methyl-2-oxooxazolidin-3-ylmethyl)benzoic acid

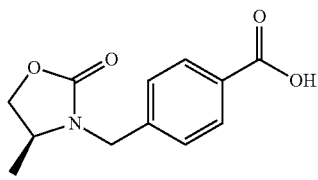 [SMILES: C[C@H]1COC(=O)N1Cc1ccc(C(=O)O)cc1]

Using methyl (S)-4-(4-methyl-2-oxooxazolidin-3-ylmethyl)benzoate (440 mg) described in Preparation Example 65 and by the reaction and treatment in the same manner as in Preparation Example 18, the title compound (353 mg) was obtained.
MS (ESI) m/z: 236(M+H)$^+$.

Preparation Example 67

Preparation of methyl 4-(1-ethoxycarbonylaminocyclopropyl)benzoate

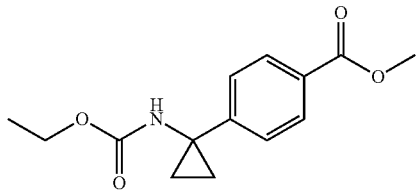 [SMILES: CCOC(=O)NC1(c2ccc(C(=O)OC)cc2)CC1]

Methyl 4-(1-aminocyclopropyl)benzoate (1.84 g) and triethylamine (2.82 mL) were dissolved in dichloromethane (40 mL), ethyl chlorocarbonate (1.01 mL) was added under ice-cooling, and the mixture was stirred at the same temperature for 30 min and at room temperature for 1 hr. After completion of the reaction, the solvent was evaporated, to the residue was added 0.5N hydrochloric acid, and the mixture was extracted with ethyl acetate. The organic layer was washed with saturated brine, and the solvent was evaporated. The obtained residue was purified by column chromatography (hexane:ethyl acetate) to give the title compound (0.86 g).
MS (ESI) m/z: 264(M+H)$^+$.

Preparation Example 68

Preparation of methyl 4-(1-{ethoxycarbonyl-[2-(tetrahydropyran-2-yloxy)ethyl]amino}cyclopropyl)benzoate

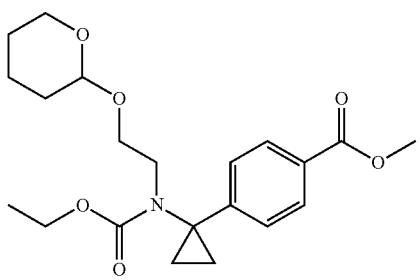 [SMILES: CCOC(=O)N(CCOC1CCCCO1)C1(c2ccc(C(=O)OC)cc2)CC1]

Under a nitrogen stream, methyl 4-(1-ethoxycarbonylaminocyclopropyl)benzoate (430 mg) described in Preparation Example 67 was dissolved in a solution of tetrahydrofuran (10 mL) and N,N-dimethylformamide (5 mL), sodium hydride (72 mg) were added under ice-cooling, and the mixture was stirred for 15 min. Then, 2-(2-bromoethoxy)tetrahydrofuran (0.30 mL) and sodium iodide (catalytic amount) were added, and the mixture was stirred for 30 min under ice-cooling and at room temperature overnight. Furthermore, sodium hydride (72 mg) was added under ice-cooling, and the mixture was stirred for 15 min. 2-(2-Bromoethoxy)tetrahydrofuran (0.30 mL) was added, and the mixture was stirred at room temperature overnight. To the reaction mixture was added saturated aqueous ammonium chloride solution, and the mixture was extracted with ethyl acetate. The organic layer was washed with water and saturated brine, and the solvent was evaporated. The obtained residue was purified by column chromatography (hexane:ethyl acetate) to give the title compound (129 mg).

Preparation Example 69

Preparation of methyl 4-[1-(2-oxooxazolidin-3-yl)cyclopropyl]benzoate

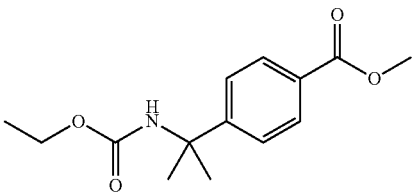 [SMILES: CCOC(=O)NC(C)(C)c1ccc(C(=O)OC)cc1]

Methyl 4-(1-{ethoxycarbonyl-[2-(tetrahydropyran-2-yloxy)ethyl]amino}cyclopropyl)benzoate (128 mg) described in Preparation Example 68 was dissolved in methanol (4 mL), 5% hydrogen chloride/methanol was added under ice-cooling, and the mixture was stirred at room temperature for 3.5 hr. The solvent was evaporated from the reaction mixture, N,N-dimethylformamide (4 mL) and potassium carbonate (9 mg) were added, and the mixture was stirred at 140° C. for 6 hr. The reaction mixture was cooled, water was added, and the mixture was extracted with ethyl acetate. The organic layer was washed with water and saturated brine, and the solvent was evaporated. The obtained residue was purified by column chromatography (hexane:ethyl acetate) to give the title compound (53 mg).
MS (ESI) m/z: 262(M+H)$^+$.

Preparation Example 70

Preparation of methyl 4-(1-ethoxycarbonylamino-1-methylethyl)benzoate

To a solution of methyl 4-(1-amino-1-methylethyl)benzoate (410 mg) in dichloromethane (15 mL) was added saturated aqueous sodium hydrogen carbonate solution (3 mL), a solution of ethyl chlorocarbonate (0.24 mL) in dichloromethane (5 mL) was added dropwise under ice-cooling, and the mixture was stirred at the same temperature for 1 hr and at room temperature for 1 hr. Water was added to the reaction mixture, and the mixture was extracted with dichloromethane. The organic layer was dried over sodium sulfate, and the solvent was evaporated. The obtained residue was purified by column chromatography (hexane:ethyl acetate) to give the title compound (551 mg).

MS (ESI) m/z: 266(M+H)$^+$.

Preparation Example 71

Preparation of methyl 4-(1-methanesulfonylamino-1-methylethyl)benzoate

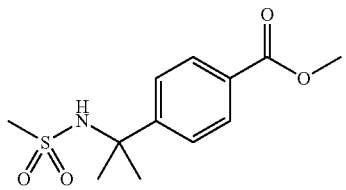

Methyl 4-(1-amino-1-methylethyl)benzoate (200 mg) and triethylamine (0.30 mL) were dissolved in dichloromethane (10 mL), methanesulfonyl chloride (88 μL) was added under ice-cooling, and the mixture was stirred at the same temperature for 30 min and at room temperature for 2 hr. After completion of the reaction, the solvent was evaporated, 0.5N hydrochloric acid was added to the residue, and the mixture was extracted with ethyl acetate. The organic layer was washed with saturated brine, and the solvent was evaporated. The obtained residue was purified by column chromatography (hexane:ethyl acetate) to give the title compound (252 mg).

Preparation Example 72

Preparation of methyl (S)-4-(1-methanesulfonylaminoethyl)benzoate

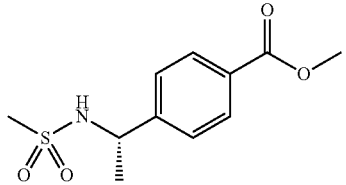

Using methyl (S)-4-(1-aminoethyl)benzoate (0.61 g) and methanesulfonyl chloride (0.29 mL) and by the reaction and treatment in the same manner as in Preparation Example 71, the title compound (0.81 g) was obtained.

Preparation Example 73

Preparation of (S)-4-(1-methanesulfonylaminoethyl)benzoic acid

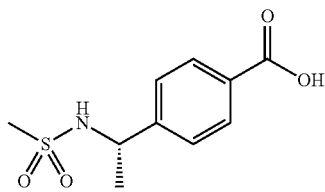 [SMILES: C[C@H](NS(C)(=O)=O)c1ccc(C(=O)O)cc1]

Using methyl (S)-4-(1-methanesulfonylaminoethyl)benzoate (805 mg) described in Preparation Example 72 and by the reaction and treatment in the same manner as in Preparation Example 18, the title compound (621 mg) was obtained.

Preparation Example 74

Preparation of methyl 4-bromo-2-iodobenzoate

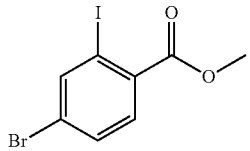

To methyl 2-amino-4-bromobenzoate (5.75 g) was added cooled 20% sulfuric acid (75 mL), sodium nitrite (2.07 g) was added by small portions under ice-cooling, and the mixture was stirred at the same temperature for 40 min. To this reaction mixture was added dropwise a solution of potassium iodide (8.3 g) in water (25 mL) under cooling to 5° C., 20% sulfuric acid (30 mL) was added, and the mixture was stirred at 5° C. for 2 hr. This reaction mixture was neutralized with 4N aqueous sodium hydroxide solution under ice-cooling, 10% aqueous sodium sulfite solution (45 mL) and sodium chloride were added, and the mixture was extracted with ethyl acetate. The organic layer was washed with 10% aqueous sodium sulfite solution added saturated brine and saturated brine, dried over sodium sulfate, and the solvent was evaporated. The obtained residue was purified by column chromatography (hexane:ethyl acetate) to give the title compound (7.05 g).

Preparation Example 75

Preparation of methyl 4-bromo-2-cyanobenzoate

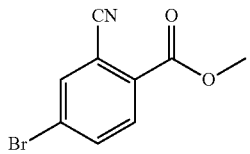

To a mixture of methyl 4-bromo-2-iodobenzoate (3.52 g) described in Preparation Example 74 and copper cyanide (1.16 g) was added N-methylpyrrolidone (21 mL), and the mixture was stirred at 60° C. for 1 hr. The reaction mixture was cooled, a solution of saturated aqueous ammonium chloride solution and aqueous ammonia (1:1) was added, and the mixture was extracted with ethyl acetate. The organic layer was washed with a solution of saturated aqueous ammonium chloride solution and aqueous ammonia (1:1), saturated aqueous ammonium chloride solution, and saturated brine. The organic layer was dried over sodium sulfate, and the solvent was evaporated to give the title compound (2.39 g).

MS (ESI) m/z: 240(M+H)⁺.

Preparation Example 76

Preparation of 4-bromo-2-cyanobenzoic acid

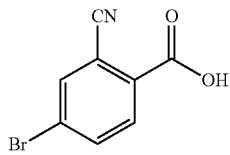

Methyl 4-bromo-2-cyanobenzoate (8.53 g) described in Preparation Example 75 was dissolved in dimethoxyethane (140 mL), a solution of lithium hydroxide 1 hydrate (2.24 g) in water (54 mL) was added dropwise under ice-cooling, and the mixture was stirred at the same temperature for 30 min. To the reaction mixture was added dropwise 1N hydrochloric acid (60 mL) under ice-cooling, saturated brine was added, and the mixture was extracted with ethyl acetate. The organic layer was washed with saturated brine, dried over sodium sulfate, and the solvent was evaporated to give the title compound (7.97 g).

MS (ESI) m/z: 226(M+H)⁺

Preparation Example 77

Preparation of ethyl 4-(imidazo[4,5-b]pyridin-3-yl)benzoate

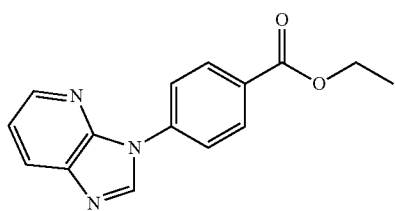 [SMILES: CCOC(=O)c1ccc(-n2cnc3cccnc32)cc1]

To phenol (22.92 g) were added 2-chloro-3-nitropyridine (13.22 g) and potassium iodide (0.42 g), and the mixture was stirred at 100° C. for 10 min. Ethyl 4-aminobenzoate (13.2 g) were added, and the mixture was stirred at 100° C.-150° C. for 6 hr. The reaction mixture was poured into ice water, and 4N aqueous sodium hydroxide solution (63 mL) and ethyl acetate (100 mL) were added. The precipitated solid was collected by filtration, and recrystallized from ethanol to give ethyl 4-(3-nitropyridin-2-ylamino)benzoate (15.48 g). Then, to a solution of ethanol (186 mL) and water (46 mL) were added ammonium chloride (1.12 g) and iron (8.1 g), the mixture was stirred at 60° C.-70° C., and the obtained ethyl 4-(3-nitropyridin-2-ylamino)benzoate (10.67 g) was added. After completion of the reaction, the insoluble material was collected by filtration, and the filtrate was concentrated. To the residue was added aqueous sodium hydrogen carbonate solution, and the mixture was extracted with ethyl acetate, and the solvent was evaporated to give ethyl 4-(3-aminopyridin-2-ylamino)benzoate (8.77 g). To the obtained ethyl 4-(3-aminopyridin-2-ylamino)benzoate (8.77 g) was added triethyl orthoformate (87 mL), and the mixture was stirred with heating under reflux for 4 hr. The solvent was evaporated from the reaction mixture, and toluene (35 mL) and a small amount of p-toluenesulfonic acid hydrate were added to the residue, and the mixture was stirred with heating under reflux for 2 hr. Water was added to the reaction mixture, and the mixture was extracted with chloroform. The solvent was evaporated from the organic layer, and to the residue were added ethylether and hexane, and the precipitated solid was collected by filtration to give the title compound (7.926 g).

Preparation Example 78

Preparation of ethyl 6-(benzimidazol-1-yl)nicotinate

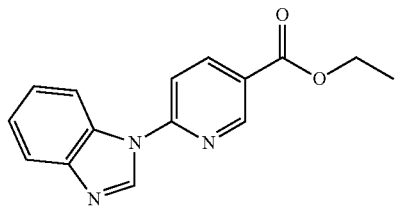 [SMILES: CCOC(=O)c1ccc(-n2cnc3ccccc32)nc1]

To a mixture of ethyl 6-chloronicotinate (2.43 g), 1H-benzimidazole (1.7 g) and potassium carbonate (5.43 g) was added N,N-dimethylformamide (20 mL), and the mixture was stirred at 50° C.-60° C. for 9 hr. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (2.28 g).

Preparation Example 79

Preparation of 1-(3,5-dimethylpyridin-2-yl)piperazine

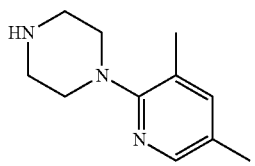

To a mixture of 2,3,5-trichloropyridine (25 g), 1-Boc-piperazine (28.13 g) and potassium carbonate (37.86 g) were added N,N-dimethylformamide (25 mL) and toluene (50 mL), and the mixture was stirred at 100° C. After completion of the reaction, water was added to the reaction mixture, and the mixture was extracted with ethyl acetate. The organic layer was washed with saturated brine, and the solvent was evaporated. The obtained residue was purified by column chromatography (hexane:ethyl acetate) to give 4-(3,5-dichloropyridin-2-yl)piperazine-1-carboxylic acid tert-butyl ester (39.13 g). To a mixture of the obtained 4-(3,5-dichloropyridin-2-yl)piperazine-1-carboxylic acid tert-butyl ester (6.35 g), palladium(II) acetate (0.46 g), 2-dicyclohexylphosphino-2',6'-dimethoxybiphenyl (1.71 g), potassium fluoride (9.56 g) and methylboronic acid (5 g) was added tetrahydrofuran (202 mL), and the mixture was stirred with heating under reflux for 8 hr under a nitrogen stream. Water was added to the reaction mixture, and the mixture was extracted with ethyl acetate. The organic layer was washed with saturated brine, and the solvent was evaporated. The obtained residue was purified by column chromatography (hexane:ethyl acetate) to give 4-(3,5-dimethylpyridin-2-yl)piperazine-1-carboxylic acid tert-butyl ester (5.45 g). The obtained 4-(3,5-dimethylpyridin-2-yl)piperazine-1-carboxylic acid tert-butyl ester (5.45 g) was dissolved in chloroform (46 mL), 4N hydrogen chloride/ethyl acetate (18 ml) was added, and the mixture was stirred at room temperature. After completion of the reaction, to the reaction mixture were added water and potassium carbonate, the mixture was extracted with ethyl acetate, and the solvent was evaporated to give the title compound (3.3 g).

Preparation Example 80

Preparation of
1-(3,5-dimethylpyridin-2-yl)piperazine hydrochloride

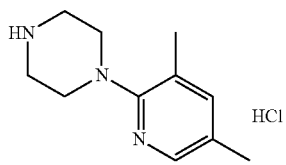

To a mixture of 4-(5-bromo-3-methylpyridin-2-yl)piperazine-1-carboxylic acid tert-butyl ester (25 g), methylboronic acid (8.4 g), [1,1'-bis(diphenylphosphino)ferrocene]palladium(II)dichloride dichloromethane complex (1:1, 2.9 g) and potassium fluoride (16 g) was added tetrahydrofuran (140 mL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give 4-(3,5-dimethylpyridin-2-yl)piperazine-1-carboxylic acid tert-butyl ester (16 g). The obtained 4-(3,5-dimethylpyridin-2-yl)piperazine-1-carboxylic acid tert-butyl ester (16 g) was dissolved in chloroform (100 mL), 4N hydrogen chloride/ethyl acetate (50 mL) was added, and the mixture was stirred at room temperature overnight. To the reaction mixture was added ethyl acetate (200 mL), and the precipitate was collected by filtration to give the title compound (10 g).

Preparation Example 81

Preparation of
1-(5-ethyl-3-methylpyridin-2-yl)piperazine

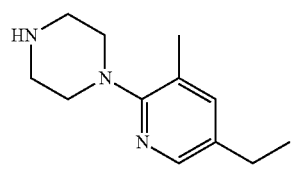

To a mixture of 4-(5-bromo-3-methylpyridin-2-yl)piperazine-1-carboxylic acid tert-butyl ester (3.3 g), bis(tricyclohexylphosphine)palladium(II)dichloride (332 mg), tripotassium phosphate (11 g) and vinylboronic acid pinacol ester (3 g) were added toluene (27 mL) and water (1.4 mL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give 4-(3-methyl-5-vinylpyridin-2-yl)piperazine-1-carboxylic acid tert-butyl ester (1.3 g). The obtained 4-(3-methyl-5-vinylpyridin-2-yl)piperazine-1-carboxylic acid tert-butyl ester (1.3 g) was dissolved in ethanol (20 mL), 5% palladium carbon-ethylenediamine complex (600 mg) was added, and the mixture was stirred at room temperature for 8 hr under hydrogen atmosphere. The mixture was filtered through celite, and the solvent was evaporated from the filtrate to give 4-(5-ethyl-3-methylpyridin-2-yl)piperazine-1-carboxylic acid tert-butyl ester (870 mg). The obtained 4-(5-ethyl-3-methylpyridin-2-yl)piperazine-1-carboxylic acid tert-butyl ester (870 mg) was dissolved in chloroform (2 mL), 4N hydrogen chloride/ethyl acetate (1.5 mL) was added, and the mixture was stirred at room temperature overnight. To the reaction mixture was added 1N aqueous sodium hydroxide solution (7 ml), and the mixture was extracted with chloroform. The organic layer was washed with saturated brine, and the solvent was evaporated to give the title compound (441 mg).

Preparation Example 82

Preparation of
1-(5-cyclopropyl-3-methylpyridin-2-yl)piperazine hydrochloride

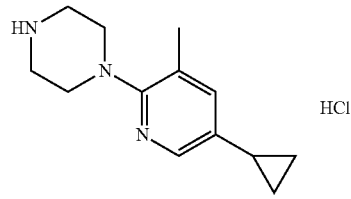 [SMILES: Cc1cc(C2CC2)cnc1N1CCNCC1 ; Cl]

To a mixture of 4-(5-bromo-3-methylpyridin-2-yl)piperazine-1-carboxylic acid tert-butyl ester (3.6 g), bis(tricyclohexylphosphine)palladium(II)dichloride (396 mg), tripotassium phosphate (12 g) and cyclopropylboronic acid (2.1 g) were added toluene (30 mL) and water (1.5 mL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (chloroform) to give 4-(5-cyclopropyl-3-methylpyridin-2-yl)piperazine-1-carboxylic acid tert-butyl ester (2.2 g). The obtained 4-(5-cyclopropyl-3-methylpyridin-2-yl)piperazine-1-carboxylic acid tert-butyl ester (2.2 g) was dissolved in chloroform (5 mL), 4N hydrogen chloride/ethyl acetate (5 mL) was added, and the mixture was stirred at room temperature overnight. To the reaction mixture was added ethyl acetate (20 mL), and the precipitate was collected by filtration to give the title compound (1.3 g).

Preparation Example 83

Preparation of 1-(5-cyclopropyl-3-methylpyridin-2-yl)piperazine

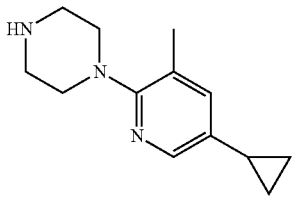 [SMILES: Cc1cc(C2CC2)cnc1N1CCNCC1]

1-(5-Cyclopropyl-3-methylpyridin-2-yl)piperazine hydrochloride described in Preparation Example 82 was suspended in ethyl acetate (50 mL), 1N aqueous sodium hydroxide solution (10 mL) was added under cooling, and the mixture was stirred. To the reaction mixture were added under cooling sodium chloride and water, and the mixture was extracted twice with ethyl acetate. The organic layer was dried over sodium sulfate, and the solvent was evaporated to give the title compound (1.43 g).

MS (ESI) m/z: 218(M+H)⁺.

Preparation Example 84

Preparation of 1-(3-methyl-5-trifluoromethylpyridin-2-yl)piperazine

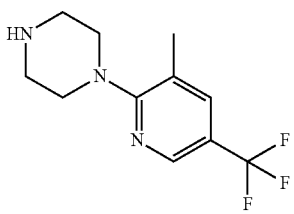 [SMILES: Cc1cc(C(F)(F)F)cnc1N1CCNCC1]

Using 2,3-dichloro-5-trifluoromethylpyridine (25 g) and 1-Boc-piperazine (23.84 g) and by the reaction and treatment in the same manner as in Preparation Example 79, the title compound (6.38 g) was obtained.

MS (ESI) m/z: 246(M+H)⁺.

Preparation Example 85

Preparation of 1-(3-cyclopropyl-5-methylpyridin-2-yl)piperazine hydrochloride

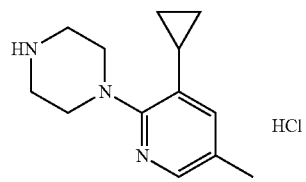 [SMILES: Cc1cnc(N2CCNCC2)c(C2CC2)c1 ; Cl]

To a mixture of 1-Boc-piperazine (7.2 g), 2,3-dichloro-5-methylpyridine (5 g), palladium(II) acetate (179 mg), rac-2,2'-bis(diphenylphosphino)-1,1'-binaphthyl (499 mg) and sodium tert-butoxide (4.1 g) was added toluene (30 mL), and the mixture was stirred with heating under reflux for 5 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give 4-(3-chloro-5-methylpyridin-2-yl)piperazine-1-carboxylic acid tert-butyl ester (9 g). To a mixture of the obtained 4-(3-chloro-5-methylpyridin-2-yl)piperazine-1-carboxylic acid tert-butyl ester (9 g), bis(tricyclohexylphosphine)palladium(II)dichloride (1 g), tripotassium phosphate (30 g) and cyclopropylboronic acid (5.5 g) were added toluene (80 mL) and water (4 mL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give 4-(3-cyclopropyl-5-methylpyridin-2-yl)piperazine-1-carboxylic acid tert-butyl ester (9 g). The obtained 4-(3-cyclopropyl-5-methylpyridin-2-yl)piperazine-1-carboxylic acid tert-butyl ester (9 g) was dissolved in chloroform (25 mL), 4N hydrogen chloride/ethyl acetate (25 mL) was added, and the mixture was stirred at room temperature overnight. To the reaction mixture was added ethyl acetate (100 mL), and the precipitate was collected by filtration to give the title compound (4.6 g).

Preparation Example 86

Preparation of 1-(3-cyclopropyl-5-methylpyridin-2-yl)piperazine

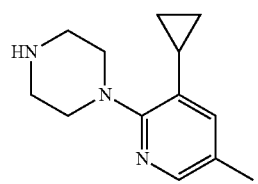 [SMILES: Cc1cnc(N2CCNCC2)c(C2CC2)c1]

To 1-(3-cyclopropyl-5-methylpyridin-2-yl)piperazine hydrochloride obtained by using 1-Boc-piperazine (7.2 g) and 2,3-dichloro-5-methylpyridine (5 g) and by the reaction and treatment in the same manner as in Preparation Example 85 was added saturated aqueous sodium hydrogen carbonate, and the mixture was extracted with ethyl acetate. The organic layer was washed with saturated brine, and the solvent was evaporated to give the title compound (1.32 g).

Preparation Example 87

Preparation of 1-(3,5-dicyclopropylpyridin-2-yl)piperazine hydrochloride

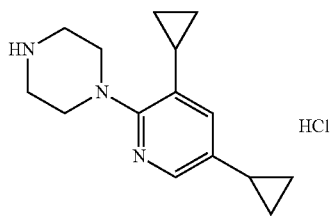 [SMILES: c1nc(N2CCNCC2)c(C2CC2)cc1C1CC1 ; Cl]

To a mixture of 2,3,5-tribromopyridine (10 g), 1-Boc-piperazine (6 g) and potassium carbonate (20 g) was added 2-butanone (80 mL), and the mixture was stirred with heating under reflux for 8 hr. The reaction mixture was cooled, water was added, and the mixture was extracted with ethyl acetate. The organic layer was washed with saturated brine, and the solvent was evaporated to give 4-(3,5-dibromopyridin-2-yl)piperazine-1-carboxylic acid tert-butyl ester (13 g). To a mixture of the obtained 4-(3,5-dibromopyridin-2-yl)piperazine-1-carboxylic acid tert-butyl ester (13 g), bis(tricyclohexylphosphine)palladium(II)dichloride (1.3 g), tripotassium phosphate (38 g) and cyclopropylboronic acid (8.4 g) were added toluene (100 mL) and water (5 mL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give 4-(3,5-dicyclopropylpyridin-2-yl)piperazine-1-carboxylic acid tert-butyl ester (7 g). The obtained 4-(3,5-dicyclopropylpyridin-2-yl)piperazine-1-carboxylic acid tert-butyl ester (7 g) was dissolved in chloroform (25 mL), 4N hydrogen chloride/ethyl acetate (25 mL) was added, and the mixture was stirred at room temperature overnight. To the reaction mixture was added 1N aqueous sodium hydroxide solution (100 mL), and the mixture was extracted with chloroform. The organic layer was washed with saturated brine, and the solvent was evaporated. The obtained residue was dissolved in ethyl acetate (50 mL), 4N hydrogen chloride/ethyl acetate (8 mL) was added, and the precipitate was collected by filtration to give the title compound (3.2 g).

Preparation Example 88

Preparation of 1-(3,5-dicyclopropylpyridin-2-yl)piperazine

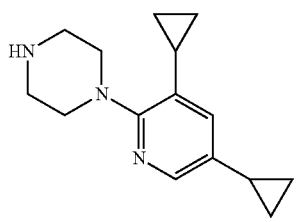 [SMILES: c1nc(N2CCNCC2)c(C2CC2)cc1C1CC1]

The intermediate 4-(3,5-dicyclopropylpyridin-2-yl)piperazine-1-carboxylic acid tert-butyl ester (7.4 g) described in Preparation Example 87 was dissolved in chloroform (54 mL), 4N hydrogen chloride/ethyl acetate (22 mL) was added, and the mixture was stirred at room temperature overnight. To the reaction mixture was added saturated aqueous sodium hydrogen carbonate solution, the mixture was extracted with chloroform, and the solvent was evaporated to give the title compound (4.6 g).

Preparation Example 89

Preparation of 1-(3-cyclopropyl-5-trifluoromethylpyridin-2-yl)piperazine hydrochloride

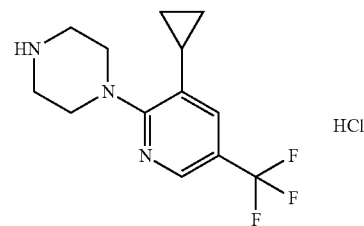 [SMILES: FC(F)(F)c1cnc(N2CCNCC2)c(C2CC2)c1 ; Cl]

Using the intermediate 4-(3-chloro-5-trifluoromethylpyridin-2-yl)piperazine-1-carboxylic acid tert-butyl ester (7.3 g) described in Preparation Example 84 and cyclopropylboronic acid (4.2 g) and by the reaction and treatment in the same manner as in Preparation Example 82, the title compound (5.8 g) was obtained.

Preparation Example 90

Preparation of 1-(3-cyclopropyl-5-trifluoromethylpyridin-2-yl)piperazine

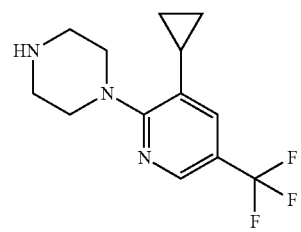 [SMILES: FC(F)(F)c1cnc(N2CCNCC2)c(C2CC2)c1]

To 1-(3-cyclopropyl-5-trifluoromethylpyridin-2-yl)piperazine hydrochloride obtained by using the intermediate 4-(3-chloro-5-trifluoromethylpyridin-2-yl)piperazine-1-carboxylic acid tert-butyl ester (5.86 g) described in Preparation Example 84 and cyclopropylboronic acid (5 g) and by the reaction and treatment in the same manner as in Preparation Example 82 was added saturated aqueous sodium hydrogen carbonate, and the mixture was extracted with ethyl acetate. The organic layer was washed with saturated brine, and the solvent was evaporated to give the title compound (3.62 g).

MS (ESI) m/z: 272(M+H)$^+$.

Preparation Example 91

Preparation of
1-(3,5,6-trimethylpyridin-2-yl)piperazine hydrochloride

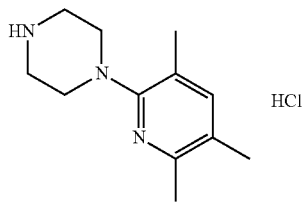

To a mixture of 2,3,5,6-tetrachloropyridine (10 g), t-Boc-piperazine (8.6 g) and potassium carbonate (13 g) was added 2-butanone (140 mL), and the mixture was stirred with heating under reflux for 8 hr. The reaction mixture was cooled, water was added, and the mixture was extracted with ethyl acetate. The organic layer was washed with saturated brine, and the solvent was evaporated to give 4-(3,5,6-trichloropyridin-2-yl)piperazine-1-carboxylic acid tert-butyl ester (17 g). To a mixture of the obtained 4-(3,5,6-trichloropyridin-2-yl)piperazine-1-carboxylic acid tert-butyl ester (17 g), palladium(II) acetate (516 mg), 2-dicyclohexylphosphino-2',6'-dimethoxybiphenyl (1.9 g), potassium fluoride (24 g) and methylboronic acid (12 g) was added tetrahydrofuran (140 ml), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give 4-(3,5,6-trimethylpyridin-2-yl)piperazine-1-carboxylic acid tert-butyl ester (14 g). The obtained 4-(3,5,6-trimethylpyridin-2-yl)piperazine-1-carboxylic acid tert-butyl ester (14 g) was dissolved in chloroform (28 mL), 4N hydrogen chloride/ethyl acetate (25 ml) was added, and the mixture was stirred at room temperature overnight. To the reaction mixture was added ethyl acetate (100 mL), and the precipitate was collected by filtration to give the title compound (11 g).

Preparation Example 92

Preparation of
1-(3,5,6-trimethylpyridin-2-yl)piperazine

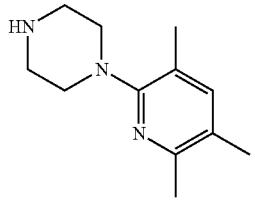

Using the intermediate 4-(3,5,6-trimethylpyridin-2-yl)piperazine-1-carboxylic acid tert-butyl ester (7.49 g) described in Preparation Example 91 and by the reaction and treatment in the same manner as in Preparation Example 88, the title compound (5.10 g) was obtained.
MS (ESI) m/z: 206(M+H)$^+$.

Preparation Example 93

Preparation of
1-(2,4-dimethylphenyl)-[1,4]diazepane hydrochloride

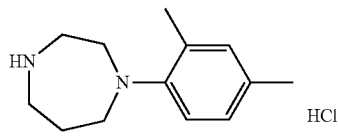

To a mixture of 1-bromo-2,4-dimethylbenzene (1.85 g), 1-Boc-[1,4]diazepane (2 g), palladium(II) acetate (0.12 g), rac-2,2'-bis(diphenylphosphino)-1,1'-binaphthyl (0.31 g) and sodium tert-butoxide (1.34 g) was added toluene (35 mL), and the mixture was stirred with heating under reflux for 9 hr. Water was added to the reaction mixture, and the mixture was extracted with ethyl acetate. The organic layer was washed with saturated brine, and the solvent was evaporated. The obtained residue was purified by column chromatography (chloroform:methanol) to give 4-(2,4-dimethylphenyl)-[1,4]diazepane-1-carboxylic acid tert-butyl ester (2.16 g). The obtained 4-(2,4-dimethylphenyl)-[1,4]diazepane-1-carboxylic acid tert-butyl ester (2.16 g) was dissolved in chloroform (17 mL), 4N hydrogen chloride/ethyl acetate solution (6.9 mL) was added, and the mixture was stirred at room temperature overnight. The solvent was evaporated from the reaction mixture to give the title compound (1.74 g).

Preparation Example 94

Preparation of
1-(2,6-dimethylpyridin-3-yl)piperazine

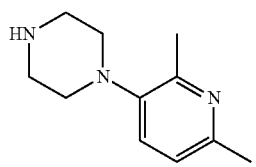

To a mixture of 3-bromo-2,6-dimethylpyridine (2.0 g), t-Boc-piperazine (2 g), palladium(II) acetate (0.12 g), rac-2,2'-bis(diphenylphosphino)-1,1'-binaphthyl (0.31 g) and sodium tert-butoxide (1.34 g) was added toluene (35 mL), and the mixture was stirred with heating under reflux for 9 hr. Water was added to the reaction mixture, and the mixture was extracted with ethyl acetate. The organic layer was washed with saturated brine, and the solvent was evaporated. The obtained residue was purified by column chromatography (chloroform:methanol) to give 4-(2,6-dimethylpyridin-3-yl)piperazine-1-carboxylic acid tert-butyl ester (3.06 g). The obtained 4-(2,6-dimethylpyridin-3-yl)piperazine-1-carboxylic acid tert-butyl ester (2.16 g) was dissolved in chloroform (21 mL), 4N hydrogen chloride/ethyl acetate solution (10 mL) was added, and the mixture was stirred at room temperature overnight. The reaction mixture was neutralized with aqueous potassium carbonate solution, the mixture was extracted with ethyl acetate, and the solvent was evaporated to give the title compound (2.01 g).

Preparation Example 95

Preparation of
1-(4,6-dimethylpyridin-3-yl)piperazine

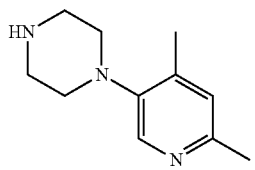

To 5-amino-2,4-dimethylpyridine (883 mg) were added N,N-diisopropylethylamine (2.1 mL) and N,N-bis(2-chloroethyl)-p-toluenesulfonamide (2.08 g), and the mixture was stirred with heating under reflux. After completion of the reaction, water was added to the reaction mixture, the mixture was extracted with chloroform, and the solvent was evaporated. The obtained residue was purified by column chromatography (chloroform:methanol) to give 1-(4,6-dimethylpyridin-3-yl)-4-(toluene-4-sulfonyl)piperazine (380 mg). The obtained 1-(4,6-dimethylpyridin-3-yl)-4-(toluene-4-sulfonyl)piperazine (380 mg) was dissolved in acetic acid (2 mL), 40% hydrobromic acid (2 mL) was added, and the mixture was stirred at 100° C. After completion of the reaction, the reaction mixture was neutralized with aqueous sodium hydroxide solution, and the mixture was extracted with ethyl acetate. The solvent was evaporated from the organic layer to give the title compound (131 mg).

Preparation Example 96

Preparation of
1-(4-methyl-2-trifluoromethylphenyl)piperazine

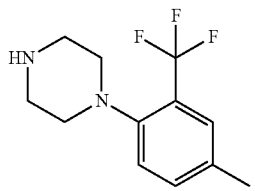 [SMILES: Cc1ccc(N2CCNCC2)c(C(F)(F)F)c1]

Using 4-methyl-2-trifluoromethylphenylamine (1 g) and N,N-bis(2-chloroethyl)-p-toluenesulfonamide (1.69 g) and by the reaction and treatment in the same manner as in Preparation Example 95, the title compound (368 mg) was obtained.

Preparation Example 97

Preparation of methyl
3-methyl-4-(piperazin-1-yl)benzoate

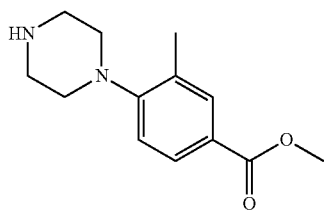 [SMILES: COC(=O)c1ccc(N2CCNCC2)c(C)c1]

Using methyl 4-bromo-3-methylbenzoate (5 g) and 1-Boc-piperazine (4.47 g) and by the reaction and treatment in the same manner as in Example 94, the title compound (1.05 g) was obtained via 4-(4-methoxycarbonyl-2-methylphenyl)piperazine-1-carboxylic acid tert-butyl ester.

Preparation Example 98

Preparation of
[3-methyl-4-(piperazin-1-yl)phenyl]methanol

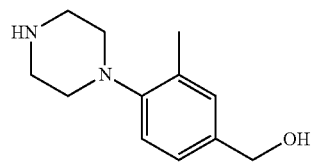

The intermediate 4-(4-methoxycarbonyl-2-methylphenyl)piperazine-1-carboxylic acid tert-butyl ester (1.42 g) described in Preparation Example 97 was dissolved in diethyl ether (18 mL), 0.99M diisobutylaluminum hydride (9 mL) was added under cooling to −78° C., and the mixture was stirred while rising the temperature to room temperature. The mixture was further stirred at room temperature for 2 hr, methanol (0.7 mL) was added, and aqueous solution (5 mL) of Rochelle salt was added. The precipitate was collected by filtration from the reaction mixture, and the filtrate was concentrated. The obtained residue was purified by column chromatography (ethyl acetate:hexane) to give 4-(4-hydroxymethyl-2-methylphenyl)piperazine-1-carboxylic acid tert-butyl ester (720 mg). The obtained 4-(4-hydroxymethyl-2-methylphenyl)piperazine-1-carboxylic acid tert-butyl ester (720 mg) was dissolved in chloroform (6 mL), 4N hydrogen chloride/ethyl acetate solution (2.3 mL) was added, and the mixture was stirred at room temperature overnight. The reaction mixture was neutralized with aqueous potassium carbonate solution, and the mixture was extracted with ethyl acetate. The solvent was evaporated from the organic layer to give the title compound (654 mg).

Preparation Example 99

Preparation of
[5-methyl-2-(piperazin-1-yl)phenyl]methanol

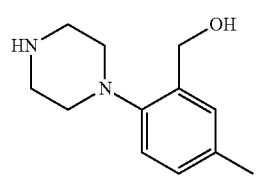

Using (2-amino-5-methylphenyl)methanol (1 g) and N,N-bis(2-chloroethyl)-p-toluenesulfonamide (2.1 g) and by the reaction and treatment in the same manner as in Preparation Example 95, the title compound (810 mg) was obtained.

Preparation Example 100

Preparation of 4-(2,4-dicyclopropylphenyl)piperazine-1-carboxylic acid tert-butyl ester

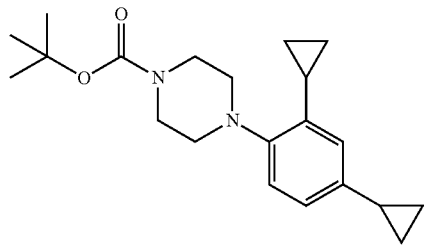 [SMILES: CC(C)(C)OC(=O)N1CCN(c2ccc(C3CC3)cc2C2CC2)CC1]

Under a nitrogen stream, to a mixture of 4-(2,4-dichlorophenyl)piperazine-1-carboxylic acid tert-butyl ester (3.31 g), palladium(II) acetate (0.44 g), 2-dicyclohexylphosphino-2',6'-dimethoxybiphenyl (0.81 g), tripotassium phosphate (11 g) and cyclopropylboronic acid (2.54 g) was added tetrahydrofuran (15 mL), and the mixture was stirred with heating under reflux. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give the title compound (3.30 g).

MS (ESI) m/z: 343(M+H)$^+$.

Preparation Example 101

Preparation of 1-(2,4-dicyclopropylphenyl)piperazine

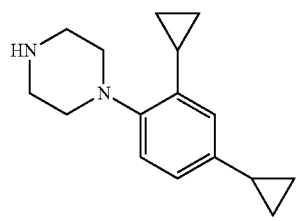

Using 4-(2,4-dicyclopropylphenyl)piperazine-1-carboxylic acid tert-butyl ester (3.30 g) described in Preparation Example 100 and by the reaction and treatment in the same manner as in Preparation Example 88, the title compound (1.60 g) was obtained.

MS (ESI) m/z: 243(M+H)$^+$.

Preparation Example 102

Preparation of 4-(5-cyano-3-methylpyridin-2-yl)piperazine-1-carboxylic acid tert-butyl ester

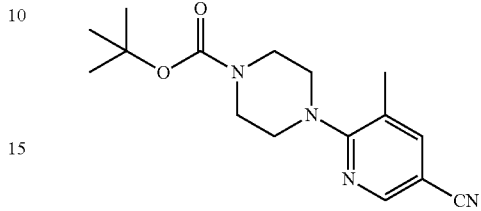

Under a nitrogen stream, 4-(5-bromo-3-methylpyridin-2-yl)piperazine-1-carboxylic acid tert-butyl ester (3.13 g) was dissolved in N,N-dimethylformamide (30 mL), zinc cyanide (1.03 g) and tetrakistriphenylphosphine palladium(0) (0.51 g) were added, and the mixture was stirred at 120° C. for 4 hr. After completion of the reaction, to the reaction mixture was added water/saturated aqueous ammonium chloride solution/28% aqueous ammonia (4:4:1), and the mixture was extracted with ethyl acetate. The organic layer was washed with water and saturated brine, and the solvent was evaporated. The obtained residue was purified by column chromatography (hexane:ethyl acetate) to give the title compound (2.46 g).

MS (ESI) m/z: 203 (M+H-100)$^+$ (detected as Boc-eliminated form).

Preparation Example 103

Preparation of 5-methyl-6-(piperazin-1-yl)nicotinonitrile

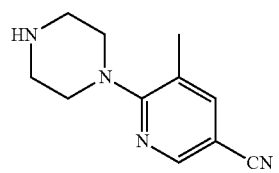

4-(5-Cyano-3-methylpyridin-2-yl)piperazine-1-carboxylic acid tert-butyl ester (2.45 g) described in Preparation Example 102 was dissolved in dichloromethane (15 mL), trifluoroacetic acid (5 mL) was added, and the mixture was stirred at room temperature for 6 hr. The solvent was evaporated from the reaction mixture, aqueous potassium carbonate solution was added, and the mixture was extracted with chloroform. The solvent was evaporated from the organic layer, the obtained residue was purified by NH-coated silica gel silica gel column chromatography (hexane:ethyl acetate) to give the title compound (1.07 g).

MS (ESI) m/z: 203(M+H)$^+$.

Preparation Example 104

Preparation of (3,5-dimethylpyrazin-2-yl)piperazine hydrochloride

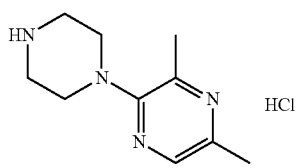

Under a nitrogen stream, to a mixture of 2-chloro-3,5-dimethylpyrazine (2.8 g), 1-Boc-piperazine (3.7 g), palladium(II) acetate (225 mg), 2-(dicyclohexylphosphino)-2',4',6'-triisopropyl-1,1'-biphenyl (953 mg) and sodium tert-butoxide (2.7 g) was added toluene (40 mL), and the mixture was stirred with heating under reflux for 8 hr. After cooling, the mixture was extracted with ethyl acetate. The organic layer was washed with saturated brine, and the solvent was evaporated. The obtained residue was purified by column chromatography (hexane:ethyl acetate) to give (3,5-dimethylpyrazin-2-yl)piperazine-1-carboxylic acid tert-butyl ester (5 g). The obtained (3,5-dimethylpyrazin-2-yl)piperazine-1-carboxylic acid tert-butyl ester (5 g) was dissolved in chloroform (15 mL), 4N hydrogen chloride/ethyl acetate (15 mL) was added, and the mixture was stirred at room temperature overnight. To the reaction mixture was added ethyl acetate (100 mL), and the precipitate was collected by filtration to give the title compound (3.3 g).

Preparation Example 105

Preparation of 4-(5-bromo-3-cyanopyridin-2-yl)piperazine-1-carboxylic acid tert-butyl ester

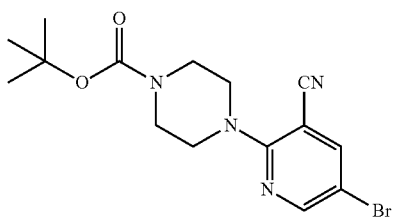 [SMILES: CC(C)(C)OC(=O)N1CCN(c2ncc(Br)cc2C#N)CC1]

To a mixture of 5-bromo-2-chloronicotinonitrile (1.00 g), 1-Boc-piperazine (0.94 g) and potassium carbonate (1.27 g) were added toluene (4.5 mL) and N,N-dimethylformamide (10 mL), and the mixture was stirred at 100° C. for 4 hr. After cooling, water was added to the reaction mixture, and the mixture was extracted with ethyl acetate. The organic layer was washed with water and saturated brine, and the solvent was evaporated. The obtained residue was purified by column chromatography (hexane:ethyl acetate) to give the title compound (1.52 g).

MS (ESI) m/z: 267 (M+H-100)$^+$ (detected as Boc-eliminated form).

Preparation Example 106

Preparation of 4-(3-cyano-5-methylpyridin-2-yl)piperazine-1-carboxylic acid tert-butyl ester

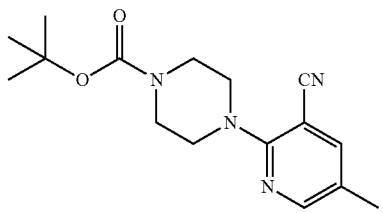 [SMILES: Cc1cnc(N2CCN(C(=O)OC(C)(C)C)CC2)c(C#N)c1]

Under a nitrogen stream, to a mixture of 4-(5-bromo-3-cyanopyridin-2-yl)piperazine-1-carboxylic acid tert-butyl ester (1.52 g) described in Preparation Example 105, methylboronic acid (0.50 g), palladium(II) acetate (46 mg), 2-dicyclohexylphosphino-2',6'-dimethoxybiphenyl (0.17 g) and potassium fluoride (0.96 g) was added tetrahydrofuran (40 mL), and the mixture was stirred with heating under reflux for 8 hr. Water was added to the reaction mixture, and the mixture was extracted with ethyl acetate. The organic layer was washed with saturated brine, and the solvent was evaporated. The obtained residue was purified by silica gel column chromatography (hexane:ethyl acetate) to give the title compound (1.36 g).

MS (ESI) m/z: 203 (M+H-100)$^+$ (detected as Boc-eliminated form).

Preparation Example 107

Preparation of 4-(3-cyano-5-methylpyridin-2-yl)piperazine

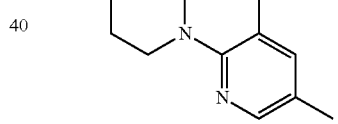

Using 4-(3-cyano-5-methylpyridin-2-yl)piperazine-1-carboxylic acid tert-butyl ester (1.35 g) described in Preparation Example 106 and by the reaction and treatment in the same manner as in Preparation Example 103, the title compound (0.89 g) was obtained.

MS (ESI) m/z: 203(M+H)$^+$.

Preparation Example 108

Preparation of [4-(2,4-dimethylphenyl)piperazin-1-yl](4-iodophenyl)methanone

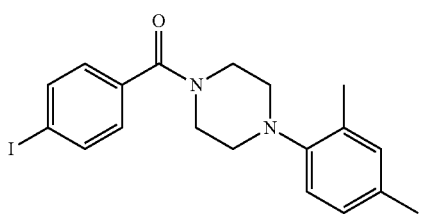 [SMILES: Cc1ccc(N2CCN(C(=O)c3ccc(I)cc3)CC2)c(C)c1]

To tetrahydrofuran (60 mL) were added 4-iodobenzoyl chloride (5 g), 1-(2,4-dimethylphenyl)piperazine (3.6 g) and 1N aqueous sodium hydroxide solution (20 mL), and the mixture was stirred at room temperature overnight. Ethyl acetate was added and the mixture was partitioned. The organic layer was washed with saturated brine, and the solvent was evaporated to give the title compound (8 g).

Preparation Example 109

Preparation of (4-bromo-2,6-difluorophenyl)[4-(2,4-dimethylphenyl)piperazin-1-yl]methanone

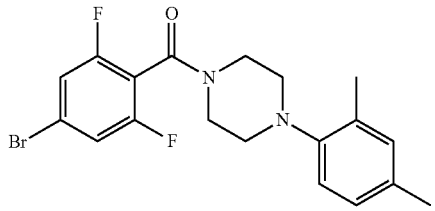 [SMILES: Cc1ccc(N2CCN(C(=O)c3c(F)cc(Br)cc3F)CC2)c(C)c1]

4-Bromo-2,6-difluorobenzoic acid (5 g) and 1-(2,4-dimethylphenyl)piperazine (4 g) were dissolved in a solution of chloroform (50 mL) and methanol (50 mL), 4-(4,6-dimethoxy[1.3.5]triazin-2-yl)-4-methylmorpholinium chloride hydrate (DMT-MM) (6.9 g) was added, and the mixture was stirred at room temperature overnight. The solvent was evaporated from the reaction mixture, ethyl acetate was added, and the insoluble material was collected by filtration. The solvent was evaporated from the obtained filtrate to give the title compound (7 g).

Preparation Example 110

Preparation of (4-bromo-2-methanesulfonylphenyl)[4-(2,4-dimethylphenyl)piperazin-1-yl]methanone

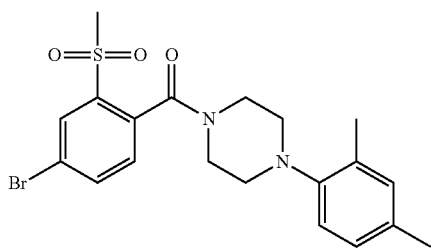 [SMILES: Cc1ccc(N2CCN(C(=O)c3ccc(Br)cc3S(C)(=O)=O)CC2)c(C)c1]

Using 4-bromo-2-methanesulfonylbenzoic acid (1 g) and 1-(2,4-dimethylphenyl)piperazine (684 mg) and by the reaction and treatment in the same manner as in Preparation Example 109, the title compound (1.3 g) was obtained.

Preparation Example 111

Preparation of (4-bromo-2,6-difluorophenyl)[4-(3,5-dimethylpyridin-2-yl)piperazin-1-yl]methanone

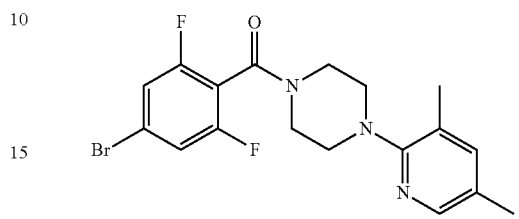

4-Bromo-2,6-difluorobenzoic acid (2.88 g), 1-(3,5-dimethylpyridin-2-yl)piperazine (2.32 g) described in Preparation Example 79 and 1-hydroxybenzotriazole 1 hydrate (1.64 g) were dissolved in N,N-dimethylformamide (50 mL), 1-ethyl-3-(3'-dimethylaminopropyl)carbodiimide hydrochloride (2.32 g) was added, and the mixture was stirred at room temperature overnight. To the reaction mixture was added saturated brine, and the mixture was extracted with ethyl acetate. The organic layer was washed with water and saturated brine, and the solvent was evaporated. The obtained residue was purified by column chromatography (chloroform:methanol) to give the title compound (4.33 g).

MS (ESI) m/z: 410(M+H)$^+$.

Preparation Example 112

Preparation of (4-bromo-2-methanesulfonylphenyl)[4-(3,5-dimethylpyridin-2-yl)piperazin-1-yl]methanone

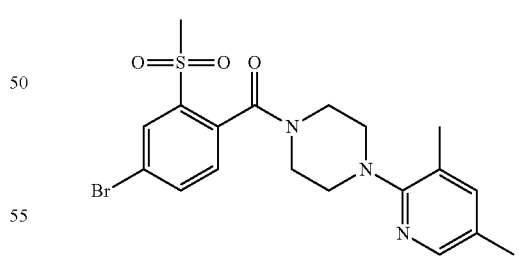

Using 4-bromo-2-methanesulfonylbenzoic acid (2.79 g) and 1-(3,5-dimethylpyridin-2-yl)piperazine (1.91 g) described in Preparation Example 79 and by the reaction and treatment in the same manner as in Preparation Example 111, the title compound (3.09 g) was obtained.

MS (ESI) m/z: 452(M+H)$^+$.

Preparation Example 113

Preparation of [4-(3,5-dimethylpyridin-2-yl)piperazin-1-yl](4-iodophenyl)methanone

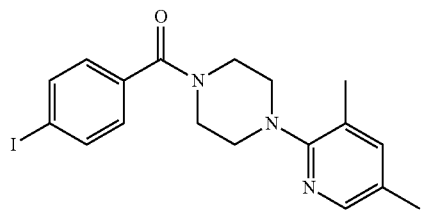 [SMILES: Cc1cnc(N2CCN(C(=O)c3ccc(I)cc3)CC2)c(C)c1]

Using 1-(3,5-dimethylpyridin-2-yl)piperazine (3.8 g) described in Preparation Example 79 and 4-iodobenzoyl chloride (5.3 g) and by the reaction and treatment in the same manner as in Preparation Example 108, the title compound (8 g) was obtained.

Preparation Example 114

Preparation of (4-bromo-2-fluorophenyl)[4-(3,5-dimethylpyridin-2-yl)piperazin-1-yl]methanone

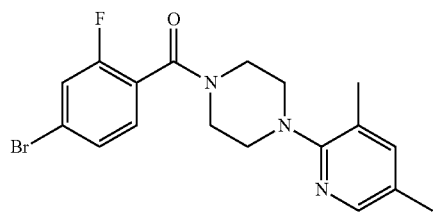 [SMILES: Cc1cnc(N2CCN(C(=O)c3ccc(Br)cc3F)CC2)c(C)c1]

1-(3,5-Dimethylpyridin-2-yl)piperazine (2.42 g) described in Preparation Example 79 was dissolved in tetrahydrofuran (32 mL), 4-bromo-2-fluorobenzoyl chloride (3.0 g) and 1N aqueous sodium hydroxide solution (15 mL) were added, and the mixture was stirred at room temperature. The reaction mixture was poured into water under cooling, 4N aqueous sodium hydroxide solution was added, and the mixture was extracted with ethyl acetate. The organic layer was washed with saturated brine added 4N aqueous sodium hydroxide solution and saturated brine, dried over sodium sulfate, and the solvent was evaporated. The obtained residue was purified by column chromatography (ethyl acetate:hexane) to give the title compound (4.39 g).
MS (ESI) m/z: 392(M+H)$^+$.

Preparation Example 115

Preparation of (6-bromopyridin-3-yl)[4-(2,4-dimethylphenyl)piperazin-1-yl]methanone

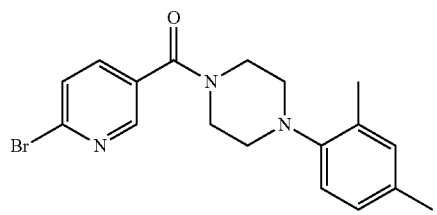 [SMILES: Cc1ccc(N2CCN(C(=O)c3ccc(Br)nc3)CC2)c(C)c1]

Using 6-bromonicotinic acid (2 g) and 1-(2,4-dimethylphenyl)piperazine (1.9 g) and by the reaction and treatment in the same manner as in Preparation Example 109, the title compound (3.8 g) was obtained.

Preparation Example 116:

Preparation of (4-bromo-2-fluorophenyl)[4-(2,4-dimethylphenyl)piperazin-1-yl]methanone

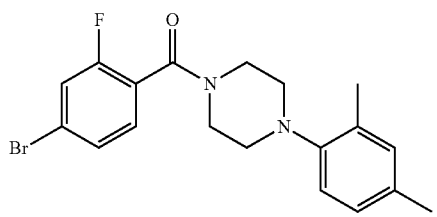 [SMILES: Cc1ccc(N2CCN(C(=O)c3ccc(Br)cc3F)CC2)c(C)c1]

Using 4-bromo-2-fluorobenzoic acid (5 g) and 1-(2,4-dimethylphenyl)piperazine (4.4 g) and by the reaction and treatment in the same manner as in Preparation Example 109, the title compound (9 g) was obtained.

Preparation Example 117

Preparation of [4-(5-cyclopropyl-3-methylpyridin-2-yl)piperazin-1-yl](4-iodophenyl)methanone

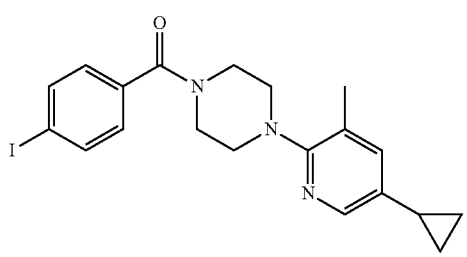 [SMILES: Cc1cc(C2CC2)cnc1N1CCN(C(=O)c2ccc(I)cc2)CC1]

Using 1-(5-cyclopropyl-3-methylpyridin-2-yl)piperazine (1.42 g) described in Preparation Example 83 and 4-iodobenzoyl chloride (1.83 g) and by the reaction and treatment in the same manner as in Preparation Example 114, the title compound (2.63 g) was obtained.
MS (ESI) m/z: 448(M+H)$^+$.

Preparation Example 118

Preparation of (4-bromo-2-methylphenyl)[4-(3,5-dimethylpyridin-2-yl)piperazin-1-yl]methanone

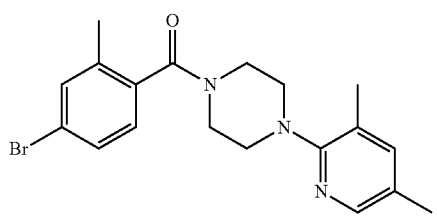 [SMILES: Cc1cnc(N2CCN(C(=O)c3ccc(Br)cc3C)CC2)c(C)c1]

1-(3,5-Dimethylpyridin-2-yl)piperazine (3.8 g) described in Preparation Example 79 and 4-bromo-2-methylbenzoic acid (4.3 g) were dissolved in a solution of chloroform (30 mL) and methanol (30 mL), 4-(4,6-dimethoxy[1.3.5]triazin-2-yl)-4-methylmorpholinium chloride hydrate (DMT-MM) (8.8 g) was added, and the mixture was stirred at room temperature overnight. The solvent was evaporated from the reaction mixture, ethyl acetate was added, and the insoluble material was collected by filtration. The solvent was evaporated from the obtained filtrate, and the residue was purified by column chromatography (hexane:ethyl acetate) to give the title compound (7 g).

Preparation Example 119

Preparation of (4-bromo-2-chlorophenyl)[4-(3,5-dimethylpyridin-2-yl)piperazin-1-yl]methanone

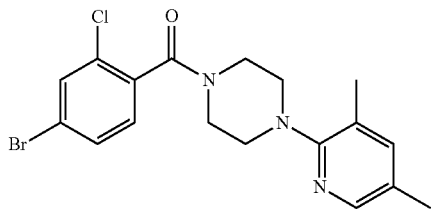 [SMILES: Cc1cnc(N2CCN(C(=O)c3ccc(Br)cc3Cl)CC2)c(C)c1]

A mixture of 1-(3,5-dimethylpyridin-2-yl)piperazine hydrochloride (956 mg) described in Preparation Example 80, 4-bromo-2-chlorobenzoic acid (1 g) and N-methylmorpholine (465 µL) was dissolved in a solution of chloroform (6 mL) and methanol (6 mL), 4-(4,6-dimethoxy[1.3.5]triazin-2-yl)-4-methylmorpholinium chloride hydrate (DMT-MM) (1.7 g) was added, and the mixture was stirred at room temperature overnight. Water was added to the reaction mixture, and the mixture was extracted with chloroform. The organic layer was washed with saturated brine, and the solvent was evaporated. The obtained residue was purified by column chromatography (hexane:ethyl acetate) to give the title compound (1.7 g).

Preparation Example 120

Preparation of (4-iodophenyl)[4-(3,5,6-trimethylpyridin-2-yl)piperazin-1-yl]methanone

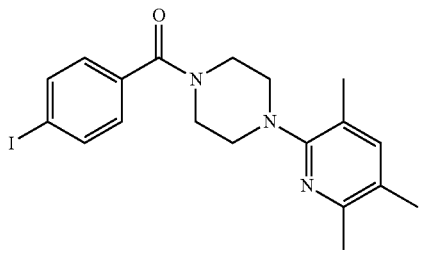 [SMILES: Cc1cc(C)c(N2CCN(C(=O)c3ccc(I)cc3)CC2)nc1C]

Using 1-(3,5,6-trimethylpyridin-2-yl)piperazine (4.39 g) described in Preparation Example 92 and 4-iodobenzoyl chloride (5.98 g) and by the reaction and treatment in the same manner as in Preparation Example 108, the title compound (8.82 g) was obtained.

MS (ESI) m/z: 436(M+H)$^+$.

Preparation Example 121

Preparation of (4-bromo-2-fluorophenyl)[4-(5-cyclopropyl-3-methylpyridin-2-yl)piperazin-1-yl]methanone

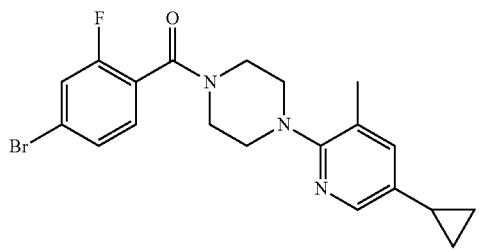

Using 4-bromo-2-fluorobenzoyl chloride (2.5 g) and 1-(5-cyclopropyl-3-methylpyridin-2-yl)piperazine hydrochloride (2.7 g) described in Preparation Example 82 and by the reaction and treatment in the same manner as in Preparation Example 108, the title compound (4.2 g) was obtained.

Preparation Example 122

Preparation of (4-bromo-2-methanesulfonylphenyl)[4-(3,5,6-trimethylpyridin-2-yl)piperazin-1-yl]methanone

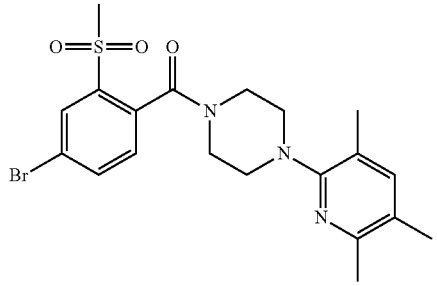 [SMILES: Cc1cc(C)c(N2CCN(C(=O)c3ccc(Br)cc3S(C)(=O)=O)CC2)nc1C]

Using 4-bromo-2-methanesulfonylbenzoic acid (3.5 g) and 1-(3,5,6-trimethylpyridin-2-yl)piperazine hydrochloride (3 g) described in Preparation Example 91 and by the reaction and treatment in the same manner as in Preparation Example 119, the title compound (3 g) was obtained.

Preparation Example 123

Preparation of (4-bromo-2-fluorophenyl)[4-(3-cyclopropyl-5-trifluoromethylpyridin-2-yl)piperazin-1-yl]methanone

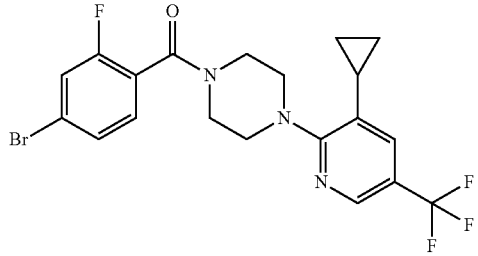 [SMILES: O=C(c1ccc(Br)cc1F)N1CCN(c2ncc(C(F)(F)F)cc2C2CC2)CC1]

Using 4-bromo-2-fluorobenzoyl chloride (2.5 g) and 1-(3-cyclopropyl-5-trifluoromethylpyridin-2-yl)piperazine hydrochloride (3.2 g) described in Preparation Example 89 and by the reaction and treatment in the same manner as in Preparation Example 108, the title compound (4.2 g) was obtained.

Preparation Example 124

Preparation of (4-bromo-2-methylphenyl)[4-(5-cyclopropyl-3-methylpyridin-2-yl)piperazin-1-yl]methanone

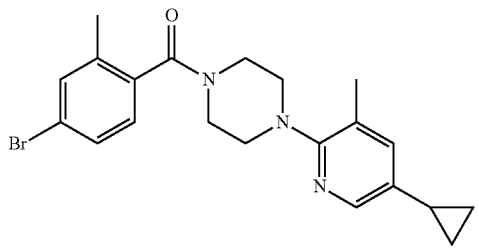

Using 4-bromo-2-methylbenzoic acid (1.00 g) and 1-(5-cyclopropyl-3-methylpyridin-2-yl)piperazine (1.52 g) described in Preparation Example 83 and by the reaction and treatment in the same manner as in Preparation Example 111, the title compound (1.04 g) was obtained.

MS (ESI) m/z: 414(M+H)$^+$.

Preparation Example 125

Preparation of (4-bromo-3-fluorophenyl)[4-(3,5-dimethylpyridin-2-yl)piperazin-1-yl]methanone

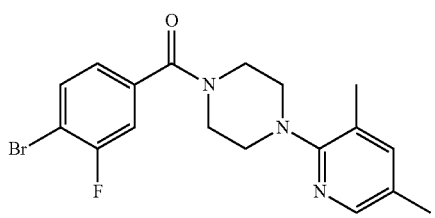

Using 1-(3,5-dimethylpyridin-2-yl)piperazine (2.87 g) described in Preparation Example 79 and 4-bromo-3-fluorobenzoic acid (3.29 g) and by the reaction and treatment in the same manner as in Preparation Example 111, the title compound (3.97 g) was obtained.

MS (ESI) m/z: 392(M+H)$^+$.

Preparation Example 126

Preparation of (4-bromo-2-methanesulfonylphenyl)[4-(5-cyclopropyl-3-methylpyridin-2-yl)piperazin-1-yl]methanone

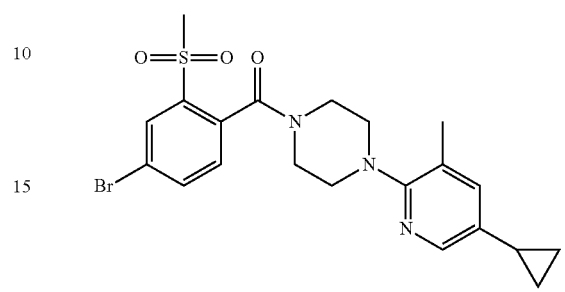

Using 4-bromo-2-methanesulfonylbenzoic acid (558 mg) and 1-(5-cyclopropyl-3-methylpyridin-2-yl)piperazine hydrochloride (508 mg) described in Preparation Example 82 and by the reaction and treatment in the same manner as in Preparation Example 119, the title compound (0.9 g) was obtained.

Preparation Example 127

Preparation of (6-bromopyridin-3-yl)[4-(3,5-dimethylpyridin-2-yl)piperazin-1-yl]methanone

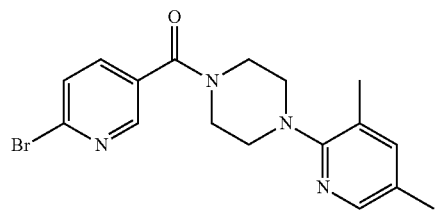

Using 6-bromonicotinic acid (808 mg) and 1-(3,5-dimethylpyridin-2-yl)piperazine (765 mg) described in Preparation Example 79 and by the reaction and treatment in the same manner as in Preparation Example 118, the title compound (1.5 g) was obtained.

Preparation Example 128

Preparation of (4-bromo-2-fluorophenyl)[4-(3,5,6-trimethylpyridin-2-yl)piperazin-1-yl]methanone

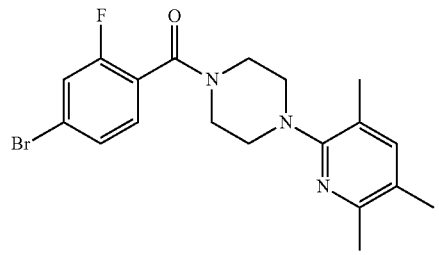 [SMILES: Cc1cc(C)c(N2CCN(C(=O)c3ccc(Br)cc3F)CC2)nc1C]

Using 4-bromo-2-fluorobenzoyl chloride (5 g) and 1-(3,5,6-trimethylpyridin-2-yl)piperazine hydrochloride (5 g) described in Preparation Example 91 and by the reaction and treatment in the same manner as in Preparation Example 108, the title compound (5 g) was obtained.

Preparation Example 129

Preparation of (4-bromo-2-fluorophenyl)[4-(3-cyclopropyl-5-methylpyridin-2-yl)piperazin-1-yl]methanone

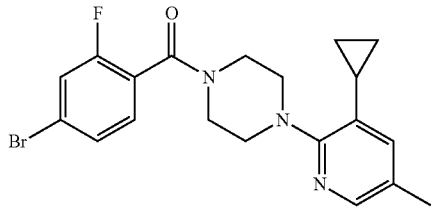 [SMILES: Cc1cnc(N2CCN(C(=O)c3ccc(Br)cc3F)CC2)c(C2CC2)c1]

Using 4-bromo-2-fluorobenzoyl chloride (2.6 g) and 1-(3-cyclopropyl-5-methylpyridin-2-yl)piperazine hydrochloride (2.8 g) described in Preparation Example 85 and by the reaction and treatment in the same manner as in Preparation Example 108, the title compound (2.5 g) was obtained.

Preparation Example 130

Preparation of (4-bromo-2-methylphenyl)[4-(2,4-dimethylphenyl)piperazin-1-yl]methanone

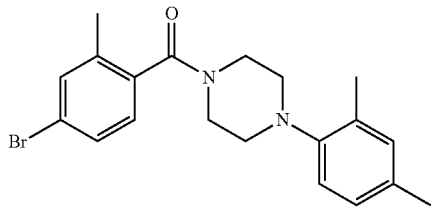

Using 4-bromo-2-methylbenzoic acid (5 g) and 1-(2,4-dimethylphenyl)piperazine (4.6 g) and by the reaction and treatment in the same manner as in Preparation Example 109, the title compound (8.9 g) was obtained.

Preparation Example 131

Preparation of (4-bromo-2-chlorophenyl)[4-(2,4-dimethylphenyl)piperazin-1-yl]methanone

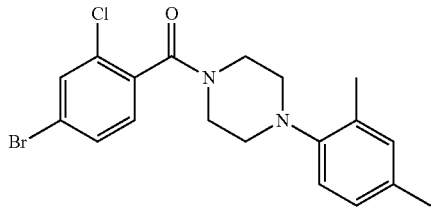

Using 4-bromo-2-chlorobenzoic acid (5 g) and 1-(2,4-dimethylphenyl)piperazine (4 g) and by the reaction and treatment in the same manner as in Preparation Example 109, the title compound (9 g) was obtained.

Preparation Example 132

Preparation of (4-bromo-3-fluorophenyl)[4-(2,4-dimethylphenyl)piperazin-1-yl]methanone

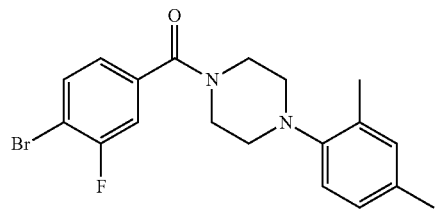 [SMILES: Cc1ccc(N2CCN(C(=O)c3ccc(Br)c(F)c3)CC2)c(C)c1]

Using 4-bromo-3-fluorobenzoic acid (5 g) and 1-(2,4-dimethylphenyl)piperazine (4 g) and by the reaction and treatment in the same manner as in Preparation Example 109, the title compound (7 g) was obtained.

Preparation Example 133

Preparation of [4-(5-ethyl-3-methylpyridin-2-yl)piperazin-1-yl](4-iodophenyl)methanone

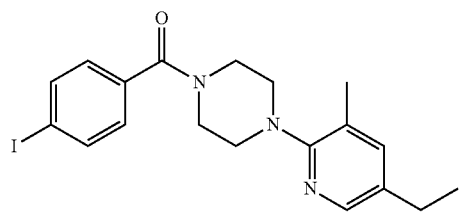 [SMILES: CCc1cnc(N2CCN(C(=O)c3ccc(I)cc3)CC2)c(C)c1]

Using 1-(5-ethyl-3-methylpyridin-2-yl)piperazine (2.46 g) described in Preparation Example 81 and 4-iodobenzoyl chloride (3.36 g) and by the reaction and treatment in the same manner as in Preparation Example 108, the title compound (4.72 g) was obtained.

MS (ESI) m/z: 436(M+H)$^+$.

Preparation Example 134

Preparation of (5-bromopyridin-2-yl) [4-(3,5-dimethylpyridin-2-yl)piperazin-1-yl]methanone

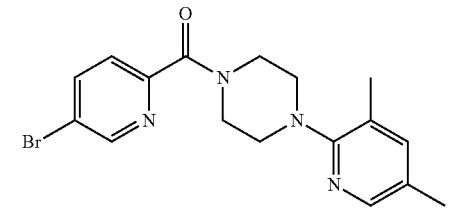

Using 5-bromo-2-picolinic acid (5.0 g) and 1-(3,5-dimethylpyridin-2-yl)piperazine (4.7 g) described in Preparation Example 79 and by the reaction and treatment in the same manner as in Preparation Example 111, the title compound (7.6 g) was obtained.

MS (ESI) m/z: 375(M+H)+.

Preparation Example 135

Preparation of (5-bromopyridin-2-yl)[4-(5-cyclopropyl-3-methylpyridin-2-yl)piperazin-1-yl]methanone

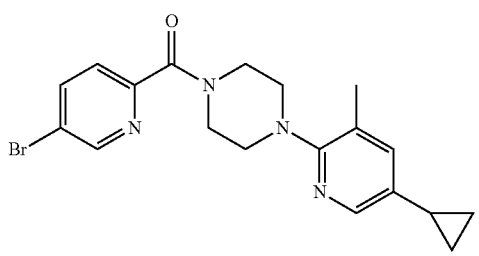

Using 5-bromo-2-picolinic acid (1.5 g) and 1-(5-cyclopropyl-3-methylpyridin-2-yl)piperazine (1.8 g) described in Preparation Example 83 and by the reaction and treatment in the same manner as in Preparation Example 111, the title compound (1.4 g) was obtained.

MS (ESI) m/z: 401(M+H)+.

Preparation Example 136

Preparation of (6-amino-2-methylpyridin-3-yl)[4-(2,4-dimethylphenyl)piperazin-1-yl]methanone

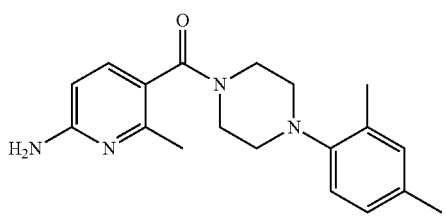 [SMILES: Cc1ccc(N2CCN(C(=O)c3ccc(N)nc3C)CC2)c(C)c1]

Using 6-amino-2-methylnicotinic acid (500 mg) and 1-(2,4-dimethylphenyl)piperazine (657 mg) and by the reaction and treatment in the same manner as in Preparation Example 109, the title compound (180 mg) was obtained.

MS (ESI) m/z: 325(M+H)+.

Preparation Example 137

Preparation of (5-bromopyridin-2-yl)[4-(2,4-dimethylphenyl)piperazin-1-yl]methanone

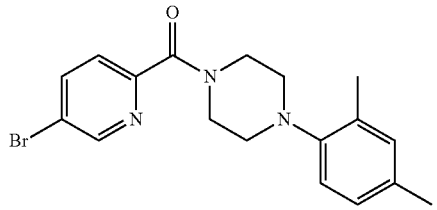 [SMILES: Cc1ccc(N2CCN(C(=O)c3ccc(Br)cn3)CC2)c(C)c1]

Using 5-bromopyridine-2-carboxylic acid (5 g) and 1-(2,4-dimethylphenyl)piperazine (4.8 g) and by the reaction and treatment in the same manner as in Preparation Example 109, the title compound (9.4 g) was obtained.

Preparation Example 138

Preparation of (5-bromopyridin-2-yl)[4-(5-ethyl-3-methylpyridin-2-yl)piperazin-1-yl]methanone

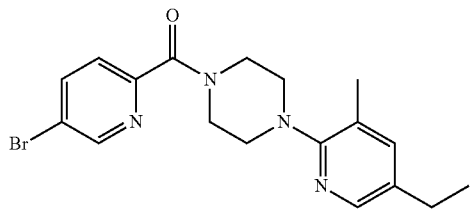

Using 5-bromo-2-picolinic acid (206 mg) and 1-(5-ethyl-3-methylpyridin-2-yl)piperazine (220 mg) described in Preparation Example 81 and by the reaction and treatment in the same manner as in Preparation Example 109, the title compound (170 mg) was obtained.

MS (ESI) m/z: 389(M+H)+.

Preparation Example 139

Preparation of [4-(5-bromo-3-methylpyridin-2-yl)piperazin-1-yl](6-fluoro-4-methylpyridin-3-yl)methanone

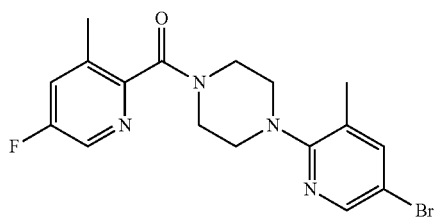 [SMILES: Cc1cc(F)cnc1C(=O)N1CCN(c2ncc(Br)cc2C)CC1]

Using 6-fluoro-4-methylnicotinic acid (1.00 g) and 1-(5-bromo-3-methylpyridin-2-yl)piperazine (1.65 g) and by the reaction and treatment in the same manner as in Preparation Example 111, the title compound (2.20 g) was obtained.

Preparation Example 140

Preparation of [4-(5-cyclopropyl-3-methylpyridin-2-yl)piperazin-1-yl](6-fluoro-4-methylpyridin-3-yl)methanone

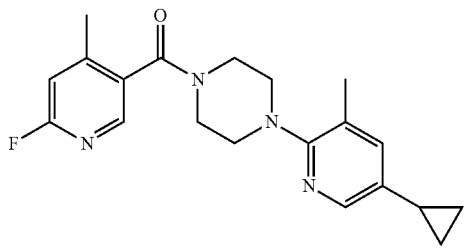

Using [4-(5-bromo-3-methylpyridin-2-yl)piperazin-1-yl](6-fluoro-4-methylpyridin-3-yl)methanone (2.2 g) described in Preparation Example 139 and cyclopropylboronic acid (721 mg) and by the reaction and treatment in the same manner as in Preparation Example 100, the title compound (2.39 g) was obtained.

MS (ESI) m/z: 355(M+H)$^+$.

Preparation Example 141

Preparation of (6-amino-4-methylpyridin-3-yl) [4-(5-cyclopropyl-3-methylpyridin-2-yl)piperazin-1-yl]methanone

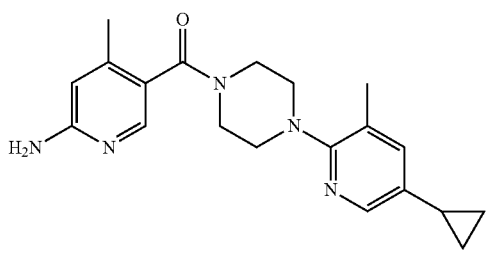 [SMILES: Cc1cc(N)ncc1C(=O)N1CCN(c2ncc(C3CC3)cc2C)CC1]

A mixture of [4-(5-cyclopropyl-3-methylpyridin-2-yl)piperazin-1-yl](6-fluoro-4-methylpyridin-3-yl)methanone (1.45 g) described in Preparation Example 140 and 4-methoxybenzylamine (1.12 g) was stirred at 100° C. for 5 hr. The reaction mixture was cooled, water was added, and the mixture was extracted with chloroform. The organic layer was washed with saturated brine, and the solvent was evaporated. The obtained residue was dissolved in dichloromethane (10 mL), trifluoroacetic acid (20 mL) was added, and the mixture was stirred at room temperature overnight. Water was added to the reaction mixture, and the mixture was extracted with dichloromethane. The organic layer was washed with saturated brine, and the solvent was evaporated. The obtained residue was purified by column chromatography (hexane:ethyl acetate) to give the title compound (1.07 g).

MS (ESI) m/z: 352(M+H)$^+$.

Preparation Example 142

Preparation of (5-bromopyridin-2-yl)[4-(3,5-dicyclopropylpyridin-2-yl)piperazin-1-yl]methanone

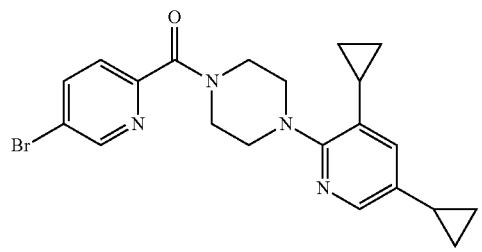 [SMILES: O=C(c1ccc(Br)cn1)N1CCN(c2ncc(C3CC3)cc2C2CC2)CC1]

Using 5-bromo-2-picolinic acid (378 mg) and 1-(3,5-dicyclopropylpyridin-2-yl)piperazine (500 mg) described in Preparation Example 88 and by the reaction and treatment in the same manner as in Preparation Example 109, the title compound (798 mg) was obtained.

MS (ESI) m/z: 427(M+H)$^+$.

Preparation Example 143

Preparation of (6-bromopyridin-3-yl)[4-(3,5-dicyclopropylpyridin-2-yl)piperazin-1-yl]methanone

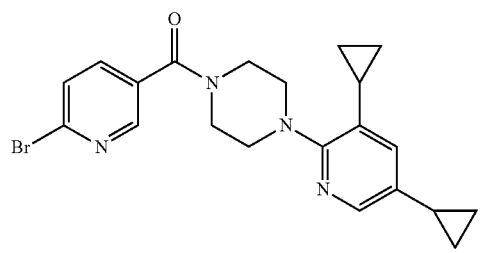

Using 6-bromonicotinic acid (2 g) and 1-(3,5-dicyclopropylpyridin-2-yl)piperazine hydrochloride (3.2 g) described in Preparation Example 87 and by the reaction and treatment in the same manner as in Preparation Example 119, the title compound (4.1 g) was obtained.

Preparation Example 144

Preparation of (6-bromopyridin-3-yl)[4-(5-cyclopropyl-3-methylpyridin-2-yl)piperazin-1-yl]methanone

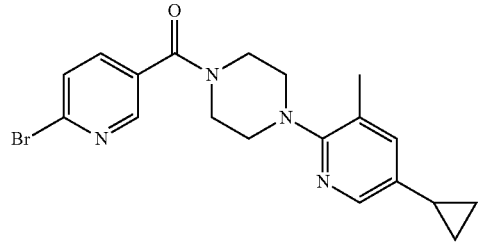

Using 6-bromonicotinic acid (2 g) and 1-(5-cyclopropyl-3-methylpyridin-2-yl)piperazine hydrochloride (2.5 g) described in Preparation Example 82 and by the reaction and treatment in the same manner as in Preparation Example 119, the title compound (3.4 g) was obtained.

Preparation Example 145

Preparation of (6-bromopyridin-3-yl)[4-(5-ethyl-3-methylpyridin-2-yl)piperazin-1-yl]methanone

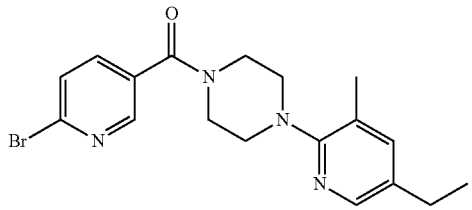

Using 6-bromonicotinic acid (2 g) and 1-(5-ethyl-3-methylpyridin-2-yl)piperazine (3.1 g) described in Preparation Example 81 and by the reaction and treatment in the same manner as in Preparation Example 109, the title compound (5 g) was obtained.

Preparation Example 146

Preparation of [4-(3,5-dimethylpyridin-2-yl)piperazin-1-yl](6-fluoro-4-methylpyridin-3-yl)methanone

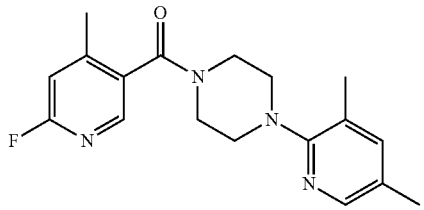

Using 6-fluoro-4-methylnicotinic acid (310 mg) and 1-(3,5-dimethylpyridin-2-yl)piperazine (383 mg) described in Preparation Example 79 and by the reaction and treatment in the same manner as in Preparation Example 109, the title compound (620 mg) was obtained.
MS (ESI) m/z: 329(M+H)$^+$.

Preparation Example 147

Preparation of (5-bromopyridin-2-yl)[4-(3,5,6-trimethylpyridin-2-yl)piperazin-1-yl]methanone

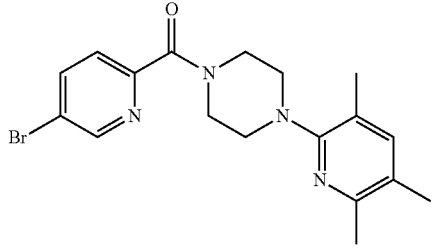

Using 1-(3,5,6-trimethylpyridin-2-yl)piperazine (1.5 g) described in Preparation Example 92 and 5-bromo-2-pi-colinic acid (1.5 g) and by the reaction and treatment in the same manner as in Preparation Example 118, the title compound (1.8 g) was obtained
MS (ESI) m/z: 474(M+H)$^+$.

Preparation Example 148

Preparation of (4-amino-2-methylphenyl)[4-(2,4-dimethylphenyl)piperazin-1-yl]methanone

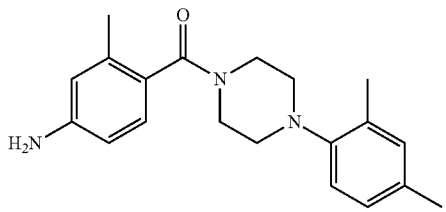 [SMILES: Cc1ccc(N2CCN(C(=O)c3ccc(N)cc3C)CC2)c(C)c1]

2-Methyl-4-nitrobenzoic acid (500 mg), 1-(2,4-dimethylphenyl)piperazine (523 mg) and 1-hydroxybenzotriazole 1 hydrate (373 mg) were dissolved in N,N-dimethylformamide (13 mL), 1-ethyl-3-(3'-dimethylaminopropyl)carbodiimide hydrochloride (531 mg) was added, and the mixture was stirred at room temperature. Water was added to the reaction mixture, and the mixture was extracted with ethyl acetate. The organic layer was washed with saturated brine, and the solvent was evaporated. The obtained residue was purified by column chromatography (chloroform:methanol) to give [4-(2,4-dimethylphenyl)piperazin-1-yl](2-methyl-4-nitrophenyl)methanone (771 mg). Then, to a mixed solution of ethanol (11 mL) and water (3 mL) were added ammonium chloride (660 mg) and iron (480 mg), and the obtained [4-(2,4-dimethylphenyl)piperazin-1-yl](2-methyl-4-nitrophenyl)methanone (771 mg) was added while stirring at 60° C.-70° C. After completion of the reaction, the insoluble material was collected by filtration, and the filtrate was concentrated. To the obtained residue was added aqueous sodium hydrogen carbonate solution, and the mixture was extracted with ethyl acetate. The solvent was evaporated from the organic layer to give the title compound (833 mg).
MS (ESI) m/z: 324(M+H)$^+$.

Preparation Example 149

Preparation of (4-amino-2-trifluoromethylphenyl)[4-(2,4-dimethylphenyl)piperazin-1-yl]methanone

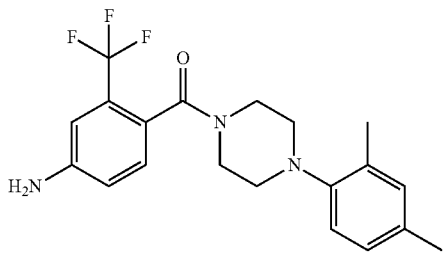 [SMILES: Cc1ccc(N2CCN(C(=O)c3ccc(N)cc3C(F)(F)F)CC2)c(C)c1]

Using 4-nitro-2-trifluoromethylbenzoic acid (500 mg) and 1-(2,4-dimethylphenyl)piperazine (403 mg) and by the reaction and treatment in the same manner as in Preparation Example 148, the title compound (850 mg) was obtained.

Preparation Example 150

Preparation of (2,4-diaminophenyl)[4-(2,4-dimethylphenyl)piperazin-1-yl]methanone

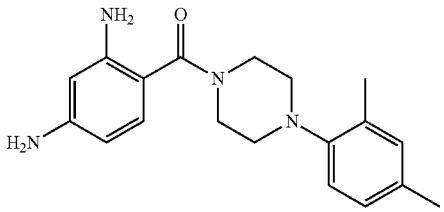 [SMILES: Cc1ccc(N2CCN(C(=O)c3ccc(N)cc3N)CC2)c(C)c1]

Using 2,4-dinitrobenzoic acid (585 mg) and 1-(2,4-dimethylphenyl)piperazine (523 mg) and by the reaction and treatment in the same manner as in Preparation Example 148, the title compound (847 mg) was obtained.

Preparation Example 151

Preparation of [4-amino-2-(morpholin-4-yl)phenyl][4-(2,4-dimethylphenyl)piperazin-1-yl]methanone

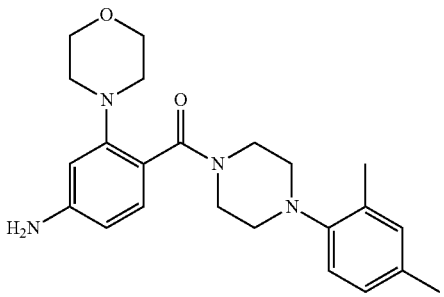 [SMILES: Cc1ccc(N2CCN(C(=O)c3ccc(N)cc3N3CCOCC3)CC2)c(C)c1]

To a mixture of ethyl 2-chloro-4-nitrobenzoate (1.5 g), palladium acetate (73.3 mg), 2-(dicyclohexylphosphino)biphenyl (229 mg), tripotassium phosphate (1.94 g) and morpholine (0.57 mL) was added 1,2-dimethoxyethane (23 mL), and the mixture was stirred with heating under reflux for 8 hr. Water was added to the reaction mixture, and the mixture was extracted with ethyl acetate. The organic layer was washed with saturated brine, and the solvent was evaporated. The obtained residue was purified by column chromatography (ethyl acetate:hexane) to give ethyl 2-(morpholin-4-yl)-4-nitrobenzoate (220 mg). The obtained ethyl 2-(morpholin-4-yl)-4-nitrobenzoate (220 mg) and 1-(2,4-dimethylphenyl)piperazine (149 mg) were dissolved in ethanol (3.5 mL), 1N aqueous sodium hydroxide solution (1.1 mL) was added, and the mixture was stirred at 50° C. To the reaction mixture was added 1N hydrochloric acid (1.1 mL), 1-(2,4-dimethylphenyl)piperazine (149 mg) and 4-(4,6-dimethoxy[1.3.5]triazin-2-yl)-4-methylmorpholinium chloride hydrate (DMT-MM) (218 mg) were added, and the mixture was stirred at room temperature overnight. To the reaction mixture was added saturated brine, and the mixture was extracted with ethyl acetate. The solvent was evaporated from the organic layer, the obtained residue was purified by silica gel column chromatography to give [4-(2,4-dimethylphenyl)piperazin-1-yl][2-(morpholin-4-yl)-4-nitrophenyl]methanone (206 mg). Then, to a solution of ethanol (3 mL) and water (1 mL) were added ammonium chloride (294 mg) and iron (211 mg), and the obtained [4-(2,4-dimethylphenyl)piperazin-1-yl][2-(morpholin-4-yl)-4-nitrophenyl]methanone (206 mg) was added while stirring at 60° C.-70° C. After completion of the reaction, the insoluble material was collected by filtration, and the filtrate was concentrated. To the obtained residue was added aqueous sodium hydrogen carbonate solution, and the mixture was extracted with ethyl acetate. The solvent was evaporated from the organic layer to give the title compound (188 mg).

Preparation Example 152

Preparation of [4-amino-2-(pyrrolidin-1-yl)phenyl][4-(2,4-dimethylphenyl)piperazin-1-yl]methanone

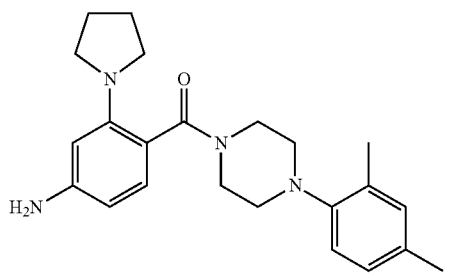 [SMILES: Cc1ccc(N2CCN(C(=O)c3ccc(N)cc3N3CCCC3)CC2)c(C)c1]

Using methyl 2-bromo-4-nitrobenzoate (1.7 g), pyrrolidine (0.54 mL) and 1-(2,4-dimethylphenyl)piperazine (999 mg) and by the reaction and treatment in the same manner as in Preparation Example 151, the title compound (268 mg) was obtained.

Preparation Example 153

Preparation of N-{5-amino-2-[4-(2,4-dimethylphenyl)piperazine-1-carbonyl]phenyl}methanesulfonamide

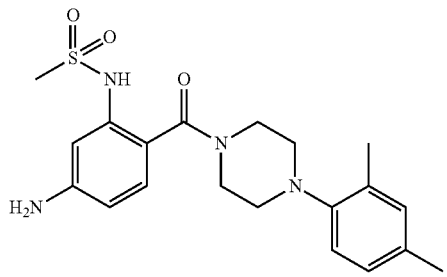 [SMILES: Cc1ccc(N2CCN(C(=O)c3ccc(N)cc3NS(C)(=O)=O)CC2)c(C)c1]

Methyl 2-amino-4-nitrobenzoate (600 mg) and triethylamine (2.9 mL) were dissolved in tetrahydrofuran (11 mL), methanesulfonyl chloride (0.51 mL) was added under ice-cooling, and the mixture was stirred at room temperature overnight. Water was added to the reaction mixture, and the mixture was extracted with chloroform. The organic layer was washed with saturated brine, and the solvent was evaporated. Methanol (18 mL) and 1N aqueous sodium hydroxide solution (9.1 mL) were added to the obtained residue, and the mixture was stirred at 50° C.-60° C. After completion of the reaction, to the reaction mixture was added aqueous sodium hydroxide solution, and the mixture was partitioned with ethyl acetate. The aqueous layer was neutralized with diluted hydrochloric acid, and the precipitated solid was collected by filtration to give 2-methanesulfonylamino-4-nitrobenzoic acid (358 mg). Using the obtained 2-methanesulfonylamino-4-nitrobenzoic acid (358 mg) and 1-(2,4-dimethylphenyl)piperazine (262 mg) and by the reaction and treatment in the same manner as in Preparation Example 111, N-{2-[4-(2,4-dimethylphenyl)piperazine-1-carbonyl]-5-nitrophenyl}methanesulfonamide (330 mg) was obtained. Then, to a solution of ethanol (5.4 mL) and water (1.8 mL) were added ammonium chloride (528 mg) and iron (379 mg), and the obtained N-{2-[4-(2,4-dimethylphenyl)piperazine-1-carbonyl]-5-nitrophenyl}methanesulfonamide (267 mg) was added while stirring at 60° C. After completion of the reaction, the insoluble material was collected by filtration, and the filtrate was concentrated. To the obtained residue was added aqueous sodium hydrogen carbonate solution, and the mixture was extracted with ethyl acetate. The solvent was evaporated from the organic layer to give the title compound (268 mg).

Preparation Example 154

Preparation of [4-(3,5-dimethylpyridin-2-yl)piperazin-1-yl](4-iodo-2-methylphenyl)methanone

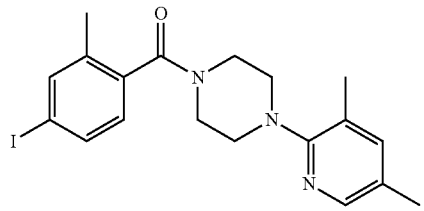

To a mixture of (4-bromo-2-methylphenyl)[4-(3,5-dimethylpyridin-2-yl)piperazin-1-yl]methanone (842 mg) described in Preparation Example 118, sodium iodide (650 mg) and copper(I) iodide (246 mg) were added toluene (2.2 mL) and N,N'-dimethylethylenediamine (1.62 mL), and the mixture was stirred with heating under reflux for 18 hr under a nitrogen stream. The reaction mixture was cooled, water was added, and the mixture was extracted with ethyl acetate. The solvent was evaporated from the organic layer, and the residue was purified by column chromatography (chloroform:methanol) to give the title compound (562 mg).

Preparation Example 155

Preparation of [4-(3,5-dimethylpyridin-2-yl)piperazin-1-yl](2-fluoro-4-iodophenyl)methanone

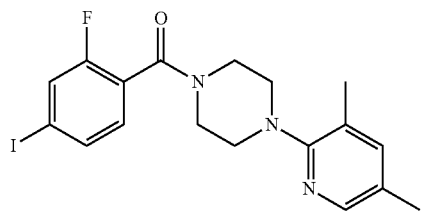

Using 1-(3,5-dimethylpyridin-2-yl)piperazine (1.44 g) described in Preparation Example 79 and 2-fluoro-4-iodobenzoic acid (2 g) and by the reaction and treatment in the same manner as in Preparation Example 111, the title compound (2.67 g) was obtained.

MS (ESI) m/z: 440(M+H)$^+$.

Preparation Example 156

Preparation of [4-(3,5-dimethylpyridin-2-yl)piperazin-1-yl](4-iodo-2-methanesulfonylphenyl)methanone

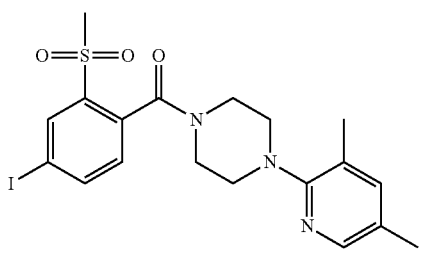 [SMILES: Cc1cnc(N2CCN(C(=O)c3ccc(I)cc3S(C)(=O)=O)CC2)c(C)c1]

Using (4-bromo-2-methanesulfonylphenyl)[4-(3,5-dimethylpyridin-2-yl)piperazin-1-yl]methanone (980 mg) described in Preparation Example 112, sodium iodide (650 mg) and copper(I) iodide (205 mg) and by the reaction and treatment in the same manner as in Preparation Example 154, the title compound (580 mg) was obtained.

Preparation Example 157

Preparation of [4-(2,4-dimethylphenyl)piperazin-1-yl](4-iodo-2-methanesulfonylphenyl)methanone

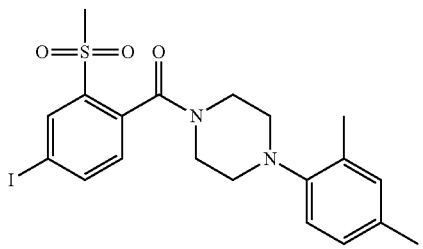 [SMILES: Cc1ccc(N2CCN(C(=O)c3ccc(I)cc3S(C)(=O)=O)CC2)c(C)c1]

Using (4-bromo-2-methanesulfonylphenyl)[4-(2,4-dimethylphenyl)piperazin-1-yl]methanone (979 mg) described in Preparation Example 110, sodium iodide (650 mg) and copper(I) iodide (205 mg) and by the reaction and treatment in the same manner as in Preparation Example 154, the title compound (886 mg) was obtained.

Preparation Example 158

Preparation of (2,6-difluoro-4-iodophenyl) [4-(3,5-dimethylpyridin-2-yl)piperazin-1-yl]methanone

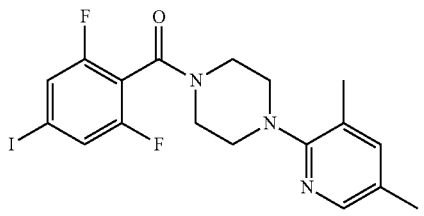 [SMILES: Cc1cnc(N2CCN(C(=O)c3c(F)cc(I)cc3F)CC2)c(C)c1]

Using (4-bromo-2,6-difluorophenyl)[4-(3,5-dimethylpyridin-2-yl)piperazin-1-yl]methanone (820 mg) described in Preparation Example 111, sodium iodide (599 mg) and copper(I) iodide (189 mg) and by the reaction and treatment in the same manner as in Preparation Example 154, the title compound (743 mg) was obtained.
MS (ESI) m/z: 458(M+H)$^+$.

Preparation Example 159

Preparation of [4-(3,5-dimethylpyridin-2-yl)piperazin-1-yl](3-fluoro-4-iodophenyl)methanone

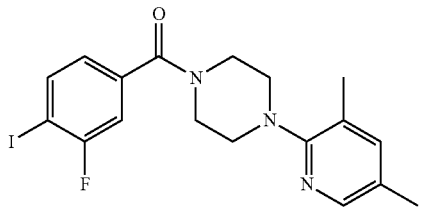

Using (4-bromo-3-fluorophenyl)[4-(3,5-dimethylpyridin-2-yl)piperazin-1-yl]methanone (760 mg) described in Preparation Example 125, sodium iodide (581 mg) and copper(I) iodide (184 mg) and by the reaction and treatment in the same manner as in Preparation Example 154, the title compound (600 mg) was obtained.

Preparation Example 160

Preparation of 6-[4-(6-bromopyridine-3-carbonyl)piperazin-1-yl]-5-methylnicotinonitrile

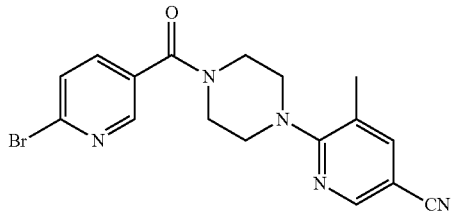 [SMILES: Cc1cc(C#N)cnc1N1CCN(C(=O)c2ccc(Br)nc2)CC1]

6-Bromonicotinic acid (500 mg), 1-(3,5-dimethylpyridin-2-yl)piperazine (501 mg) described in Preparation Example 79, 1-hydroxybenzotriazole 1 hydrate (379 mg) and triethylamine (0.69 mL) were dissolved in N,N-dimethylformamide (10 mL), 1-ethyl-3-(3'-dimethylaminopropyl)carbodiimide hydrochloride (569 mg) was added, and the mixture was stirred at room temperature overnight. To the reaction mixture was added 5% aqueous sodium hydrogen carbonate solution, and the mixture was extracted with ethyl acetate. The organic layer was washed with water and saturated brine, and the solvent was evaporated. The obtained residue was purified by column chromatography (hexane:ethyl acetate) to give the title compound (709 mg).
MS (ESI) m/z: 386(M+H)$^+$.

Preparation Example 161

Preparation of (2-fluoro-4-iodophenyl)[4-(3-methyl-5-trifluoromethylpyridin-2-yl)piperazin-1-yl]methanone

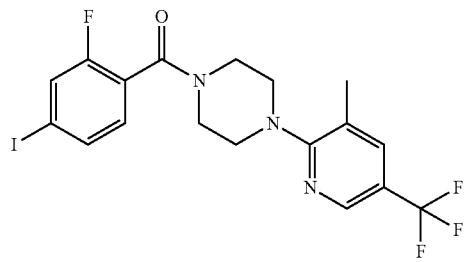 [SMILES: Cc1cc(C(F)(F)F)cnc1N1CCN(C(=O)c2ccc(I)cc2F)CC1]

Using 2-fluoro-4-iodobenzoic acid (266 mg) and 1-(3-methyl-5-trifluoromethylpyridin-2-yl)piperazine (245 mg) described in Preparation Example 84 and by the reaction and treatment in the same manner as in Preparation Example 111, the title compound (507 mg) was obtained.

Preparation Example 162

Preparation of [4-(2,4-dimethylphenyl)piperazin-1-yl](6-iodopyridin-3-yl)methanone

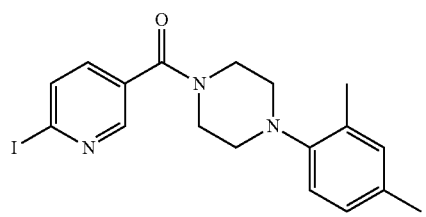

Using (6-bromopyridin-3-yl)[4-(2,4-dimethylphenyl)piperazin-1-yl]methanone (487 mg) described in Preparation Example 115, sodium iodide (389 mg) and copper(I) iodide (123 mg) and by the reaction and treatment in the same manner as in Preparation Example 154, the title compound (340.6 mg) was obtained.

Preparation Example 163

Preparation of [4-(5-cyclopropyl-3-methylpyridin-2-yl)piperazin-1-yl](2-fluoro-4-iodophenyl)methanone

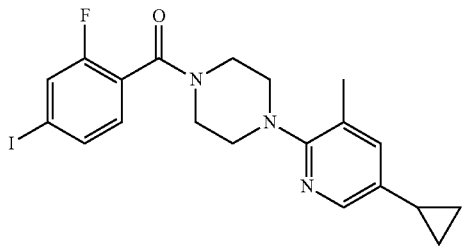 [SMILES: Cc1cc(C2CC2)cnc1N1CCN(C(=O)c2ccc(I)cc2F)CC1]

Using 2-fluoro-4-iodobenzoic acid (399 mg) and 1-(5-cyclopropyl-3-methylpyridin-2-yl)piperazine hydrochloride (381 mg) described in Preparation Example 82 and by the reaction and treatment in the same manner as in Preparation Example 160, the title compound (668.5 mg) was obtained.

Preparation Example 164

Preparation of [4-(3,5-dicyclopropylpyridin-2-yl)piperazin-1-yl](2-fluoro-4-iodophenyl)methanone

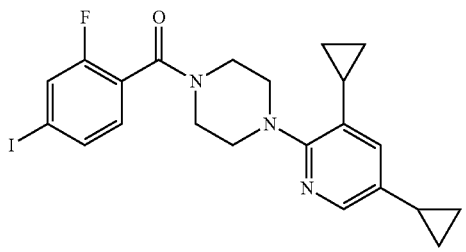 [SMILES: O=C(c1ccc(I)cc1F)N1CCN(c2ncc(C3CC3)cc2C2CC2)CC1]

Using 2-fluoro-4-iodobenzoic acid (2.027 g) and 1-(3,5-dicyclopropylpyridin-2-yl)piperazine (1.85 g) described in Preparation Example 88 and by the reaction and treatment in the same manner as in Preparation Example 111, the title compound (3.47 g) was obtained.

Preparation Example 165

Preparation of (4-bromophenyl)[4-(3,5-dimethylpyridin-2-yl)piperazin-1-yl]methanone

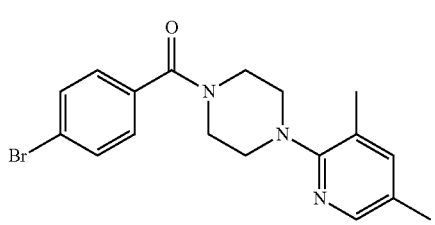

Using 4-bromobenzoic acid (0.50 g) and 1-(3,5-dimethylpyridin-2-yl)piperazine (0.48 g) described in Preparation Example 79 and by the reaction and treatment in the same manner as in Preparation Example 111, the title compound (0.84 g) was obtained.

MS (ESI) m/z: 374(M+H)$^+$.

Preparation Example 166

Preparation of [4-bromo-2-(1,1-dioxo-1$\lambda^6$-isothiazolidin-2-yl)phenyl][4-(3,5-dimethylpyridin-2-yl)piperazin-1-yl]methanone

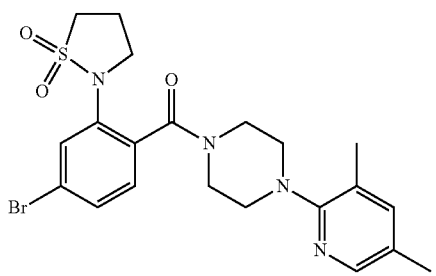 [SMILES: Cc1cnc(N2CCN(C(=O)c3ccc(Br)cc3N3CCCS3(=O)=O)CC2)c(C)c1]

Methyl 4-bromo-2-(1,1-dioxo-1$\lambda^6$-isothiazolidin-2-yl)benzoate (2 g) described in Preparation Example 13 was dissolved in methanol (18 mL), 1N aqueous sodium hydroxide solution (9 mL) was added, and the mixture was stirred at 60-70° C. To the reaction mixture was added 1N hydrochloric acid (9 mL), a solution of 1-(3,5-dimethylpyridin-2-yl)piperazine (1.14 g) described in Preparation Example 79 in methanol (2 mL) and 4-(4,6-dimethoxy[1.3.5]triazin-2-yl)-4-methylmorpholinium chloride hydrate (DMT-MM) (1.65 g) were added, and the mixture was stirred at room temperature overnight. Water was added to the reaction mixture, and the mixture was extracted with ethyl acetate. The solvent was evaporated from the organic layer, and the residue was purified by column chromatography (hexane:ethyl acetate) to give the title compound (2.4 g).

MS (ESI) m/z: 493(M+H)$^+$.

Preparation Example 167

Preparation of (2-bromo-4-chlorophenyl)[4-(3,5-dimethylpyridin-2-yl)piperazin-1-yl]methanone

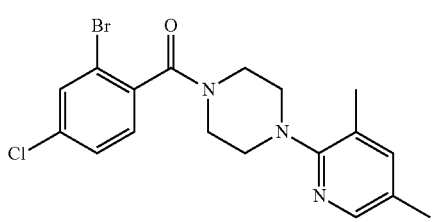 [SMILES: Cc1cnc(N2CCN(C(=O)c3ccc(Cl)cc3Br)CC2)c(C)c1]

Using 2-bromo-4-chlorobenzoic acid (2.09 g) and 1-(3,5-dimethylpyridin-2-yl)piperazine (1.7 g) described in Preparation Example 79 and by the reaction and treatment in the same manner as in Preparation Example 111, the title compound (3.58 g) was obtained.

MS (ESI) m/z: 408(M+H)$^+$.

Preparation Example 168

Preparation of 3-{5-chloro-2-[4-(3,5-dimethylpyridin-2-yl)piperazine-1-carbonyl]phenyl}oxazolidin-2-one

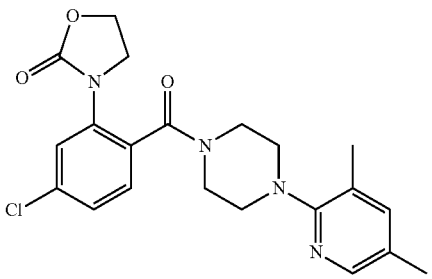 [SMILES: Cc1cnc(N2CCN(C(=O)c3ccc(Cl)cc3N3CCOC3=O)CC2)c(C)c1]

Using (2-bromo-4-chlorophenyl)[4-(3,5-dimethylpyridin-2-yl)piperazin-1-yl]methanone (1.79 g) described in Preparation Example 167 and oxazolidin-2-one (0.381 g) and by the reaction and treatment in the same manner as in Preparation Example 48, the title compound (1.023 g) was obtained.
MS (ESI) m/z: 415(M+H)$^+$.

Preparation Example 169

Preparation of 1-{5-chloro-2-[4-(3,5-dimethylpyridin-2-yl)piperazine-1-carbonyl]phenyl}pyrrolidin-2-one

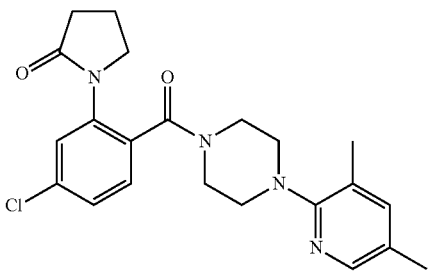 [SMILES: Cc1cnc(N2CCN(C(=O)c3ccc(Cl)cc3N3CCCC3=O)CC2)c(C)c1]

Using (2-bromo-4-chlorophenyl)[4-(3,5-dimethylpyridin-2-yl)piperazin-1-yl]methanone (1.57 g) described in Preparation Example 167 and pyrrolidin-2-one (327 mg) and by the reaction and treatment in the same manner as in Preparation Example 48, the title compound (720 mg) was obtained.
MS (ESI) m/z: 413(M+H)$^+$

Preparation Example 170

Preparation of (4-bromophenyl)[4-(2,4-dimethylphenyl)piperazin-1-yl]methanone

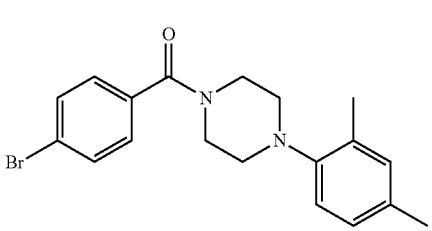

Using 4-bromobenzoyl chloride (25 g) and 1-(2,4-dimethylphenyl)piperazine (22 g) and by the reaction and treatment in the same manner as in Preparation Example 108, the title compound (31 g) was obtained.

Preparation Example 171

Preparation of (4-bromo-3-chlorophenyl)[4-(2,4-dimethylphenyl)piperazin-1-yl]methanone

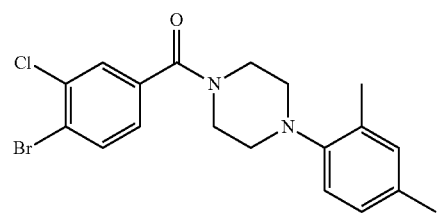 [SMILES: Cc1ccc(N2CCN(C(=O)c3ccc(Br)c(Cl)c3)CC2)c(C)c1]

Using 4-bromo-3-chlorobenzoic acid (2.4 g) and 1-(2,4-dimethylphenyl)piperazine (1.9 g) and by the reaction and treatment in the same manner as in Preparation Example 109, the title compound (4.1 g) was obtained.

Preparation Example 172

Preparation of 5-bromo-2-[4-(3,5,6-trimethylpyridin-2-yl)piperazine-1-carbonyl]benzonitrile

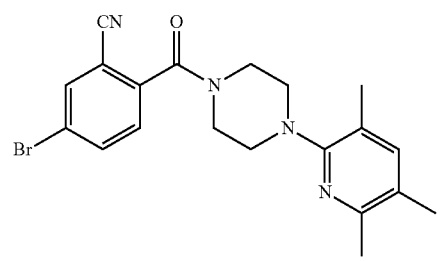

Using 4-bromo-2-cyanobenzoic acid (3.84 g) described in Preparation Example 76 and 1-(3,5,6-trimethylpyridin-2-yl)piperazine (3.66 g) described in Preparation Example 92 and by the reaction and treatment in the same manner as in Preparation Example 111, the title compound (6.17 g) was obtained.
MS (ESI) m/z: 413(M+H)$^+$.

Preparation Example 173

Preparation of (6-bromopyridin-3-yl)[4-(2,4,5-trimethylphenyl)piperazin-1-yl]methanone

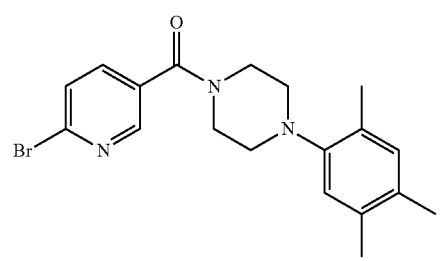

Using 6-bromonicotinic acid (412 mg) and 1-(2,4,5-trimethylphenyl)piperazine (440 mg) and by the reaction and treatment in the same manner as in Preparation Example 118, the title compound (800 mg) was obtained.

Preparation Example 174

Preparation of [4-(3,5-dicyclopropylpyridin-2-yl)piperazin-1-yl](6-fluoro-4-methylpyridin-3-yl)methanone

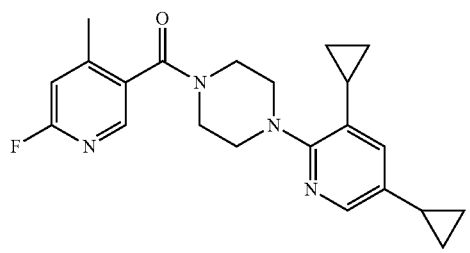

Using 6-fluoro-4-methylnicotinic acid (0.60 g) and 1-(3,5-dicyclopropylpyridin-2-yl)piperazine (0.92 g) described in Preparation Example 88 and by the reaction and treatment in the same manner as in Preparation Example 111, the title compound (1.23 g) was obtained.
MS (ESI) m/z: 381(M+H)$^+$.

Preparation Example 175

Preparation of [4-(2,4-dimethylphenyl)piperazin-1-yl](6-fluoro-4-methylpyridin-3-yl)methanone

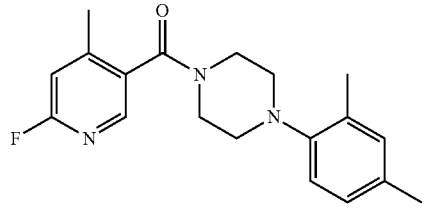 [SMILES: Cc1ccc(N2CCN(C(=O)c3cnc(F)cc3C)CC2)c(C)c1]

Using 6-fluoro-4-methylnicotinic acid (500 mg) and 1-(2,4-dimethylphenyl)piperazine (607 mg) and by the reaction and treatment in the same manner as in Preparation Example 111, the title compound (870 mg) was obtained.
MS (ESI) m/z: 328(M+H)$^+$.

Preparation Example 176

Preparation of [4-(5-ethyl-3-methylpyridin-2-yl)piperazin-1-yl](6-fluoro-4-methylpyridin-3-yl)methanone

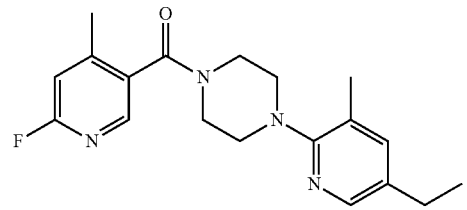

Using 6-fluoro-4-methylnicotinic acid (300 mg) and 1-(5-ethyl-3-methylpyridin-2-yl)piperazine (389 mg) described in Preparation Example 81 and by the reaction and treatment in the same manner as in Preparation Example 111, the title compound (340 mg) was obtained.
MS (ESI) m/z: 343(M+H)$^+$.

Preparation Example 177

Preparation of methyl 2-bromo-4-(1,1-dioxo-1$\lambda^6$-isothiazolidin-2-ylmethyl)benzoate

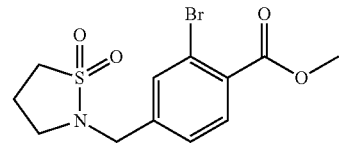 [SMILES: COC(=O)c1ccc(CN2CCCS2(=O)=O)cc1Br]

Using methyl 2-bromo-4-bromomethylbenzoate (500 mg) and isothiazolidine 1,1-dioxide (216 mg) and by the reaction and treatment in the same manner as in Preparation Example 42, the title compound (312 mg) was obtained.
MS (ESI) m/z: 348(M+H)$^+$.

Preparation Example 178

Preparation of [4-(3,5-dicyclopropylpyridin-2-yl)piperazin-1-yl](6-fluoro-4-methylpyridin-3-yl)methanone

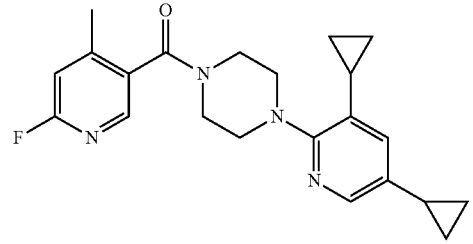 [SMILES: Cc1cc(F)ncc1C(=O)N1CCN(c2ncc(C3CC3)cc2C2CC2)CC1]

Using 6-fluoro-4-methylnicotinic acid (0.60 g) and 1-(3,5-dicyclopropylpyridin-2-yl)piperazine (0.92 g) described in Preparation Example 88 and by the reaction and treatment in the same manner as in Preparation Example 111, the title compound (1.23 g) was obtained.

MS (ESI) m/z: 381(M+H)⁺.

Preparation Example 179

Preparation of [4-(2,4-dicyclopropylphenyl)piperazin-1-yl](6-fluoro-4-methylpyridin-3-yl)methanone

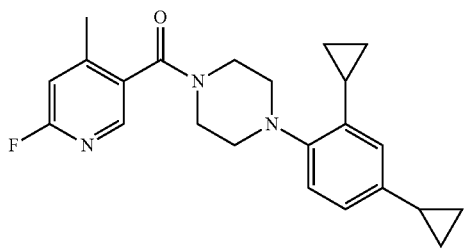

Using 6-fluoro-4-methylnicotinic acid (386 mg) and 1-(2,4-dicyclopropylphenyl)piperazine (650 mg) described in Preparation Example 101 and by the reaction and treatment in the same manner as in Preparation Example 118, the title compound (980 mg) was obtained.

MS (ESI) m/z: 380(M+H)⁺.

Preparation Example 180

Preparation of (6-fluoro-4-methylpyridin-3-yl)[4-(2,4,5-trimethylphenyl)piperazin-1-yl]methanone

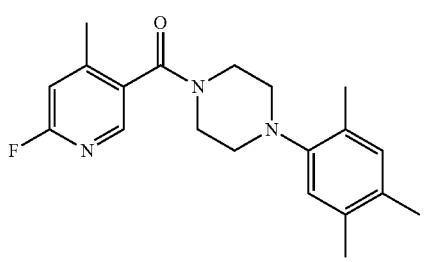 [SMILES: Cc1cc(C)c(N2CCN(C(=O)c3cnc(F)cc3C)CC2)cc1C]

Using 6-fluoro-4-methylnicotinic acid (162 mg) and 1-(2,4,5-trimethylphenyl)piperazine (230 mg) and by the reaction and treatment in the same manner as in Preparation Example 118, the title compound (310 mg) was obtained.

MS (ESI) m/z: 342(M+H)⁺.

Preparation Example 181

Preparation of [4-(3-cyclopropyl-5-methylpyridin-2-yl)piperazin-1-yl](6-fluoro-4-methylpyridin-3-yl)methanone

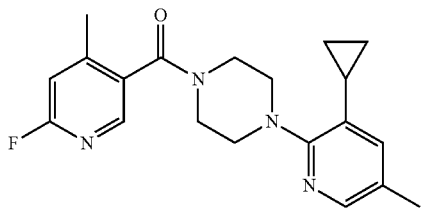

Using 6-fluoro-4-methylnicotinic acid (139 mg) and a free form (210 mg) of 1-(3-cyclopropyl-5-methylpyridin-2-yl)piperazine hydrochloride described in Preparation Example 85 with a base and by the reaction and treatment in the same manner as in Preparation Example 119, the title compound (180 mg) was obtained.

MS (ESI) m/z: 355(M+H)⁺.

Preparation Example 182

Preparation of (6-fluoro-4-methylpyridin-3-yl)[4-(3,5,6-trimethylpyridin-2-yl)piperazin-1-yl]methanone

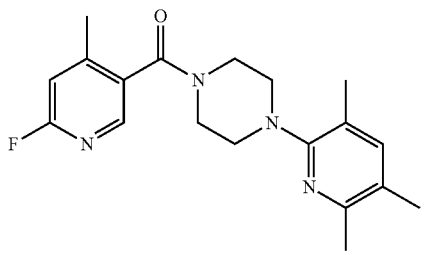 [SMILES: Cc1cc(F)ncc1C(=O)N1CCN(c2nc(C)c(C)cc2C)CC1]

Using 6-fluoro-4-methylnicotinic acid (119 mg) and 1-(3,5,6-trimethylpyridin-2-yl)piperazine (170 mg) described in Preparation Example 92 and by the reaction and treatment in the same manner as in Preparation Example 118, the title compound (220 mg) was obtained.

MS (ESI) m/z: 343(M+H)⁺.

Preparation Example 183

Preparation of [4-(3-cyclopropyl-5-methylpyridin-2-yl)piperazin-1-yl](2-fluoro-4-iodophenyl)methanone

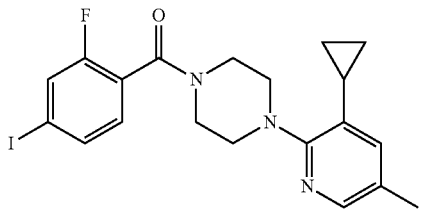 [SMILES: Cc1cnc(N2CCN(C(=O)c3ccc(I)cc3F)CC2)c(C2CC2)c1]

Using 2-fluoro-4-iodobenzoic acid (399 mg) and 1-(3-cyclopropyl-5-methylpyridin-2-yl)piperazine hydrochloride (381 mg) described in Preparation Example 85 and by the reaction and treatment in the same manner as in Preparation Example 111, the title compound (627 mg) was obtained.
MS (ESI) m/z: 466(M+H)+.

Preparation Example 184

Preparation of 2-[4-(6-bromopyridine-3-carbonyl)piperazin-1-yl]-5-methylnicotinonitrile

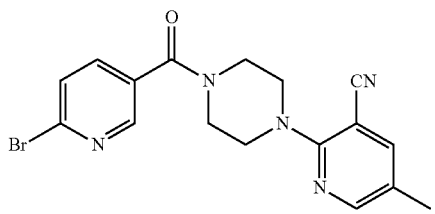 [SMILES: Cc1cnc(N2CCN(C(=O)c3ccc(Br)nc3)CC2)c(C#N)c1]

Using 6-bromonicotinic acid (303 mg) and 4-(3-cyano-5-methylpyridin-2-yl)piperazine (303 mg) described in Preparation Example 107 and by the reaction and treatment in the same manner as in Preparation Example 111, the title compound (458 mg) was obtained.
MS (ESI) m/z: 386(M+H)+.

Preparation Example 185

Preparation of (4-bromophenyl)[4-(5-cyclopropyl-3-methylpyridin-2-yl)piperazin-1-yl]methanone

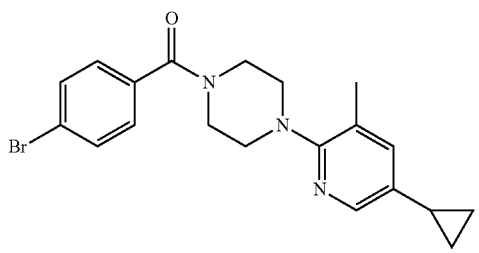 [SMILES: Cc1cc(C2CC2)cnc1N1CCN(C(=O)c2ccc(Br)cc2)CC1]

Using 4-bromobenzoic acid (0.50 g) and 1-(5-cyclopropyl-3-methylpyridin-2-yl)piperazine (0.54 g) described in Preparation Example 83 and by the reaction and treatment in the same manner as in Preparation Example 111, the title compound (0.70 g) was obtained.
MS (ESI) m/z: 400(M+H)+.

Preparation Example 186

Preparation of [4-(3,5-dicyclopropylpyridin-2-yl)piperazin-1-yl](4-iodophenyl)methanone

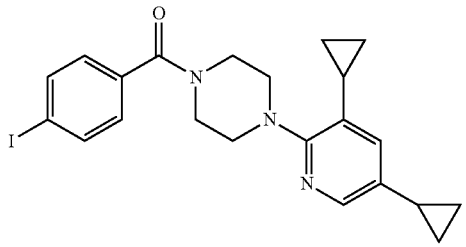 [SMILES: O=C(c1ccc(I)cc1)N1CCN(c2ncc(C3CC3)cc2C2CC2)CC1]

Using 1-(3,5-dicyclopropylpyridin-2-yl)piperazine (5.52 g) described in Preparation Example 88 and 4-iodobenzoyl chloride (6.35 g) and by the reaction and treatment in the same manner as in Preparation Example 114, the title compound (9.76 g) was obtained.
MS (ESI) m/z: 474(M+H)+.

Preparation Example 187

Preparation of 5-bromo-2-[4-(3,5-dimethylpyridin-2-yl)piperazine-1-carbonyl]benzonitrile

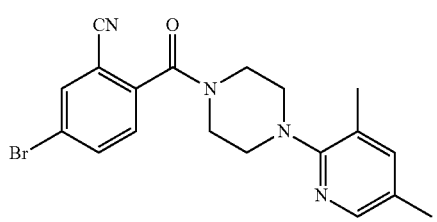

Using 4-bromo-2-cyanobenzoic acid (3.39 g) described in Preparation Example 76 and 1-(3,5-dimethylpyridin-2-yl)piperazine (3.01 g) described in Preparation Example 79 and by the reaction and treatment in the same manner as in Preparation Example 111, the title compound (4.86 g) was obtained.
MS (ESI) m/z: 399(M+H)+.

Preparation Example 188

Preparation of 5-bromo-2-[4-(2,4-dimethylphenyl)piperazine-1-carbonyl]benzonitrile

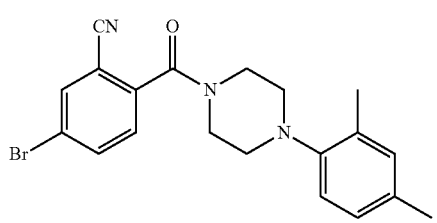 [SMILES: Cc1ccc(N2CCN(C(=O)c3ccc(Br)cc3C#N)CC2)c(C)c1]

Using 4-bromo-2-cyanobenzoic acid (1.81 g) described in Preparation Example 76 and 1-(2,4-dimethylphenyl)piperazine (1.67 g) and by the reaction and treatment in the same manner as in Preparation Example 111, the title compound (2.68 g) was obtained.
MS (ESI) m/z: 398(M+H)+.

Preparation Example 189

Preparation of 5-bromo-2-[4-(5-cyclopropyl-3-methylpyridin-2-yl)piperazine-1-carbonyl]benzonitrile

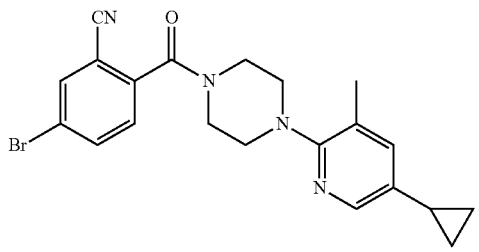

Using 4-bromo-2-cyanobenzoic acid (2.14 g) described in Preparation Example 76 and 1-(5-cyclopropyl-3-methylpyridin-2-yl)piperazine (2.16 g) described in Preparation Example 83 and by the reaction and treatment in the same manner as in Preparation Example 111, the title compound (3.31 g) was obtained.

MS (ESI) m/z: 425(M+H)⁺.

Preparation Example 190

Preparation of (6-bromopyridin-3-yl)[4-(4-chlorobenzoyl)piperidin-1-yl]methanone

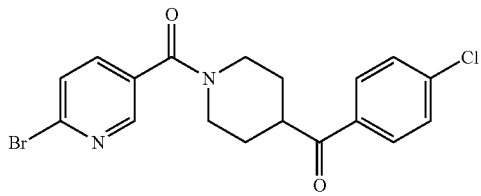 [SMILES: O=C(c1ccc(Cl)cc1)C1CCN(C(=O)c2ccc(Br)nc2)CC1]

(4-Chlorophenyl)(piperidin-4-yl)methanone hydrochloride (13 g) and 1N aqueous sodium hydroxide solution (50 mL) were added to chloroform (150 mL), and the mixture was stirred at room temperature for 10 min. The chloroform layer was partitioned, to the obtained organic layer were added methanol (50 mL), 6-bromonicotinic acid (10 g) and 4-(4,6-dimethoxy[1.3.5]triazin-2-yl)-4-methylmorpholinium chloride hydrate (DMT-MM) (16.6 g), and the mixture was stirred at room temperature overnight. The solvent was evaporated from the reaction mixture, ethyl acetate was added, and the insoluble material was collected by filtration. The solvent was evaporated from the obtained filtrate to give the title compound (16.4 g).

Preparation Example 191

Preparation of (4-bromo-2-methanesulfonylphenyl)[4-(4-chlorobenzoyl)piperidin-1-yl]methanone

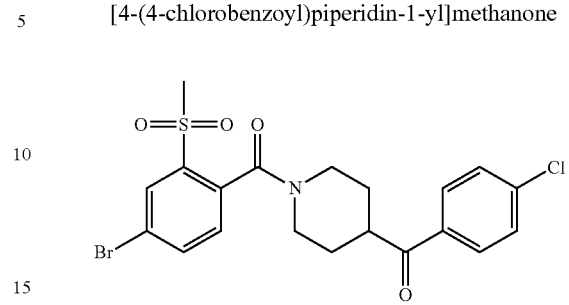

Using 4-bromo-2-methylsulfonylbenzoic acid (2.8 g) and (4-chlorophenyl)piperidin-4-ylmethanone (2.6 g) and by the reaction and treatment in the same manner as in Preparation Example 109, the title compound (4.8 g) was obtained.

Preparation Example 192

Preparation of (6-bromopyridin-3-yl)[4-(4-cyclopropylphenoxy)piperidin-1-yl]methanone

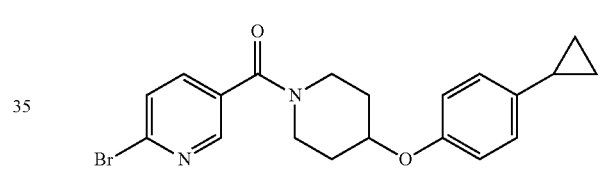

To a mixture of 1-Boc-4-(4-bromophenoxy)piperidine (5 g), dichlorobis(tricyclohexylphosphine)palladium(II) (725 mg), tripotassium phosphate (14.9 g) and cyclopropylboronic acid (1.81 g) was added toluene (70 mL), and the mixture was stirred with heating under reflux for 7 hr. The reaction mixture was cooled, water was added, and the insoluble material was collected by filtration. The filtrate was extracted with ethyl acetate. The organic layer was washed with saturated brine, and the solvent was evaporated. The obtained residue was purified by column chromatography to give 4-(4-cyclopropylphenoxy)piperidine-1-carboxylic acid tert-butyl ester. The obtained 4-(4-cyclopropylphenoxy)piperidine-1-carboxylic acid tert-butyl ester was dissolved in ethyl acetate (3 mL), 4N hydrogen chloride/ethyl acetate (7 mL) was added, and the mixture was stirred at room temperature overnight. Water was added to the reaction mixture, and the mixture was washed with ethyl acetate. To the obtained aqueous layer was added 1N aqueous sodium hydroxide solution, and the mixture was extracted with ethyl acetate. The organic layer was washed with saturated brine, and the solvent was evaporated to give 4-(4-cyclopropylphenoxy)piperidine (2.49 g). Using the obtained 4-(4-cyclopropylphenoxy)piperidine (1.4 g) and 6-bromonicotinic acid (1.2 g) and by the reaction and treatment in the same manner as in Preparation Example 111, the title compound (2.4 g) was obtained.

MS (ESI) m/z: 401(M+H)⁺.

Preparation Example 193

Preparation of (6-bromopyridin-3-yl)[4-(p-tolyloxy)piperidin-1-yl]methanone

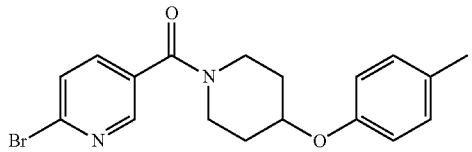 [SMILES: Cc1ccc(OC2CCN(C(=O)c3ccc(Br)nc3)CC2)cc1]

Using 4-(p-tolyloxy)piperidine (765 mg) and 6-bromonicotinic acid (808 mg) and by the reaction and treatment in the same manner as in Preparation Example 118, the title compound (1.5 g) was obtained.

Preparation Example 194

Preparation of [4-(3-chloro-5-trifluoromethylpyridin-2-yl)piperazin-1-yl][4-(1,1-dioxo-1$\lambda^6$-isothiazolidin-2-yl)phenyl]methanone

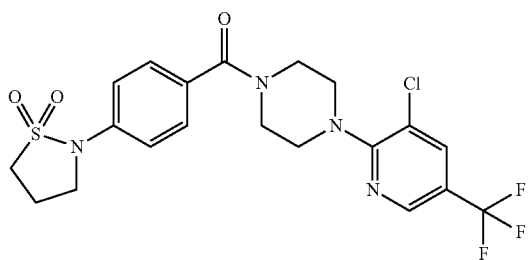 [SMILES: O=C(c1ccc(N2CCCS2(=O)=O)cc1)N1CCN(c2ncc(C(F)(F)F)cc2Cl)CC1]

Using 4-(1,1-dioxo-1$\lambda^6$-isothiazolidin-2-yl)benzoic acid (253 mg) described in Preparation Example 16 and 1-(3-chloro-hydrochloride (453 mg) and by the reaction and treatment in the same manner as in Preparation Example 119, the title compound (182 mg) was obtained.
MS (ESI) m/z: 489(M+H)$^+$.

Preparation Example 195

Preparation of [4-(3,5-dichloropyridin-2-yl)piperazin-1-yl][4-(1,1-dioxo-1$\lambda^6$-isothiazolidin-2-yl)phenyl]methanone

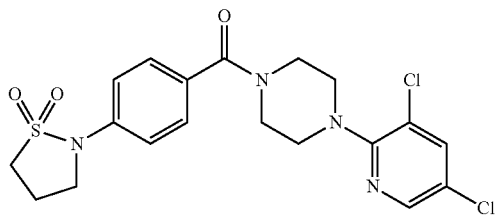 [SMILES: O=C(c1ccc(N2CCCS2(=O)=O)cc1)N1CCN(c2ncc(Cl)cc2Cl)CC1]

Using 4-(1,1-dioxo-1$\lambda^6$-isothiazolidin-2-yl)benzoic acid (253 mg) described in Preparation Example 16 and 1-(3,5-dichloropyridin-2-yl)piperazine (229 mg) and by the reaction and treatment in the same manner as in Preparation Example 111, the title compound (340 mg) was obtained.
MS (ESI) m/z: 455(M+H)$^+$.

Preparation Example 196

Preparation of [4-(3,5-dichloropyridin-2-yl)piperazin-1-yl][4-(1,1-dioxo-1$\lambda^6$-isothiazolidin-2-yl)-2-methanesulfonylphenyl]methanone

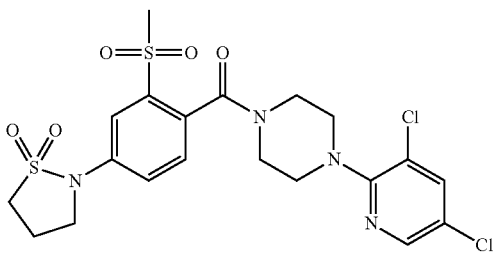 [SMILES: CS(=O)(=O)c1cc(N2CCCS2(=O)=O)ccc1C(=O)N1CCN(c2ncc(Cl)cc2Cl)CC1]

Using 4-(1,1-dioxo-1$\lambda^6$-isothiazolidin-2-yl)-2-methanesulfonylbenzoic acid (319 mg) described in Preparation Example 22 and 1-(3,5-dichloropyridin-2-yl)piperazine (232 mg) and by the reaction and treatment in the same manner as in Preparation Example 111, the title compound (68 mg) was obtained.
MS (ESI) m/z: 533(M+H)$^+$.

Preparation Example 197

Preparation of [4-(3,5-dichloropyridin-2-yl)piperazin-1-yl][4-(1,1-dioxo-1$\lambda^6$-isothiazolidin-2-yl)-2-fluorophenyl]methanone

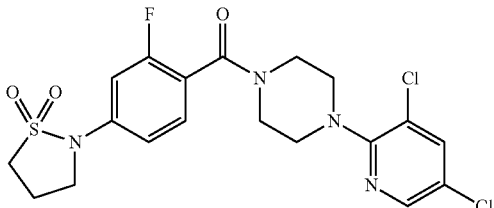

Using 4-(1,1-dioxo-1$\lambda^6$-isothiazolidin-2-yl)-2-fluorobenzoic acid (272 mg) described in Preparation Example 23 and 1-(3,5-dichloropyridin-2-yl)piperazine (244 mg) and by the reaction and treatment in the same manner as in Preparation Example 111, the title compound (508 mg) was obtained.
MS (ESI) m/z: 473(M+H)$^+$.

Preparation Example 198

Preparation of [4-(3,5-dichloropyridin-2-yl)piperazin-1-yl][4-(1,1-dioxo-1$\lambda^6$-isothiazolidin-2-yl)-2-methoxyphenyl]methanone

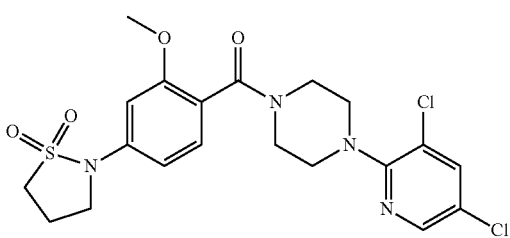 [SMILES: COc1cc(N2CCCS2(=O)=O)ccc1C(=O)N1CCN(c2ncc(Cl)cc2Cl)CC1]

Using 4-(1,1-dioxo-1λ⁶-isothiazolidin-2-yl)-2-methoxybenzoic acid (266 mg) described in Preparation Example 19 and 1-(3,5-dichloropyridin-2-yl)piperazine (227 mg) and by the reaction and treatment in the same manner as in Preparation Example 111, the title compound (507 mg) was obtained.
MS (ESI) m/z: 485(M+H)⁺.

Preparation Example 199

Preparation of methyl 4-aminomethyl-2-fluorobenzoate

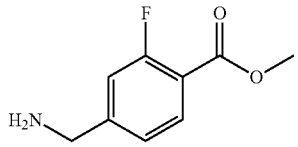

4-Aminomethyl-2-fluorobenzoic acid hydrochloride (500 mg) was dissolved in methanol (10 mL), concentrated sulfuric acid (6 μL) was added, and the mixture was stirred with heating under reflux for 9 hr. After completion of the reaction, the solvent was evaporated, saturated aqueous potassium carbonate solution was added, and the mixture was extracted with chloroform. The organic layer was dried over sodium sulfate, and the solvent was evaporated to give the title compound (181 mg).

Preparation Example 200

Preparation of methyl 4-(1,1-dioxo-1λ⁶-isothiazolidin-2-ylmethyl)-2-fluorobenzoate

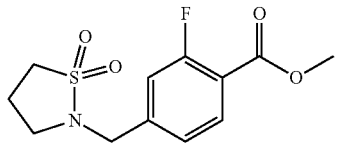 [SMILES: COC(=O)c1ccc(CN2CCCS2(=O)=O)cc1F]

Using methyl 4-aminomethyl-2-fluorobenzoate (181 mg) described in Preparation Example 199 and 3-chloropropane-1-sulfonyl chloride (0.14 mL) and by the reaction and treatment in the same manner as in Preparation Example 17, the title compound (233 mg) was obtained.
MS (ESI) m/z: 288(M+H)⁺.

Preparation Example 201

Preparation of (R)-3-(4-methoxybenzyl)-5-methylimidazolidine-2,4-dione

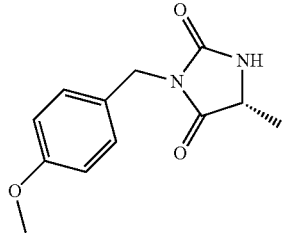 [SMILES: COc1ccc(CN2C(=O)N[C@H](C)C2=O)cc1]

Using (R)-5-methylimidazolidine-2,4-dione (2.00 g) and 4-methoxybenzyl chloride (2.85 mL) and by the reaction and treatment in the same manner as in Preparation Example 51, the title compound (2.95 g) was obtained.
MS (ESI) m/z: 235(M+H)⁺.

Preparation Example 202

Preparation of (R)-1-(4-methoxybenzyl)-4-methylimidazolidin-2-one

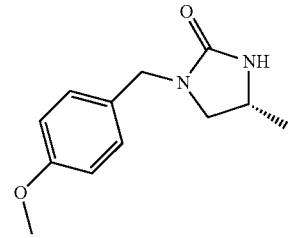 [SMILES: COc1ccc(CN2C[C@@H](C)NC2=O)cc1]

Using (R)-3-(4-methoxybenzyl)-5-methylimidazolidine-2,4-dione (1.50 g) described in Preparation Example 201 and by the reaction and treatment in the same manner as in Preparation Example 52, the title compound (0.72 g) was obtained.
MS (ESI) m/z: 221(M+H)⁺.

Preparation Example 203

Preparation of (S)-3-(4-methoxybenzyl)-5-methylimidazolidine-2,4-dione

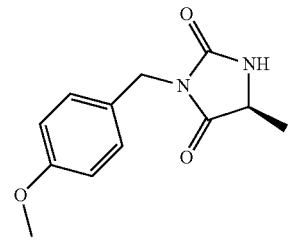 [SMILES: COc1ccc(CN2C(=O)N[C@@H](C)C2=O)cc1]

Using (S)-5-methylimidazolidine-2,4-dione (2.00 g) and 4-methoxybenzyl chloride (2.85 mL) and by the reaction and treatment in the same manner as in Preparation Example 51, the title compound (3.13 g) was obtained.
MS (ESI) m/z: 235(M+H)⁺.

Preparation Example 204

Preparation of (S)-1-(4-methoxybenzyl)-4-methylimidazolidin-2-one

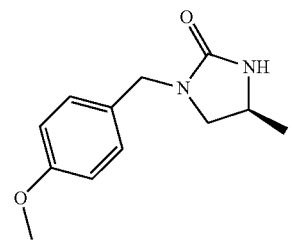 [SMILES: COc1ccc(CN2C[C@H](C)NC2=O)cc1]

Using (S)-3-(4-methoxybenzyl)-5-methylimidazolidine-2,4-dione (1.50 g) described in Preparation Example 203 and by the reaction and treatment in the same manner as in Preparation Example 52, the title compound (0.75 g) was obtained.
MS (ESI) m/z: 221(M+H)⁺.

Preparation Example 205

Preparation of (6-bromopyridin-3-yl)[4-(3,5,6-trimethylpyridin-2-yl)piperazin-1-yl]methanone

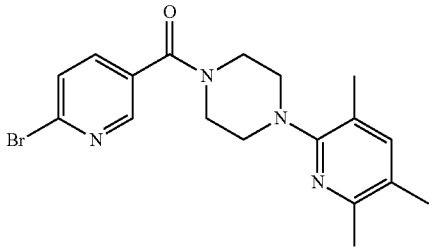 [SMILES: Cc1cc(C)c(N2CCN(C(=O)c3ccc(Br)nc3)CC2)nc1C]

Using 6-bromonicotinic acid (606 mg) and 1-(3,5,6-trimethylpyridin-2-yl)piperazine (616 mg) described in Preparation Example 92 and by the reaction and treatment in the same manner as in Preparation Example 111, the title compound (1.03 g) was obtained.

Preparation Example 206

Preparation of 3-benzyloxymethyl-5-methylimidazolidine-2,4-dione

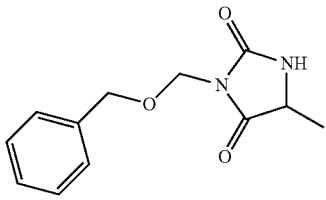 [SMILES: CC1NC(=O)N(COCc2ccccc2)C1=O]

5-Methylimidazolidine-2,4-dione (1.00 g) was dissolved in N,N-dimethylformamide (20 mL), potassium tert-butoxide (1.08 g) and benzyl chloromethyl ether (1.32 mL) were added under ice-cooling, and the mixture was stirred at room temperature for 5 hr. Water was added to the reaction mixture, and the mixture was extracted with ethyl acetate. The organic layer was washed with water and saturated brine, and the solvent was evaporated. The obtained residue was purified by silica gel column chromatography (hexane:ethyl acetate) to give the title compound (0.98 g).
MS (ESI) m/z: 235(M+H)$^+$.

Preparation Example 207

Preparation of 5-ethyl-3-(4-methoxybenzyl)imidazolidine-2,4-dione

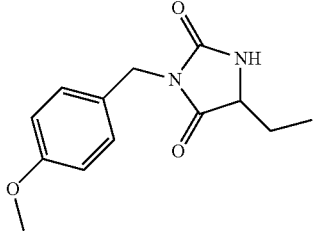 [SMILES: CCC1NC(=O)N(Cc2ccc(OC)cc2)C1=O]

Using 5-ethylimidazolidine-2,4-dione (2.00 g) and 4-methoxybenzyl chloride (2.54 mL) and by the reaction and treatment in the same manner as in Preparation Example 51, the title compound (3.08 g) was obtained.
MS (ESI) m/z: 249(M+H)$^+$.

Preparation Example 208

Preparation of 4-ethyl-1-(4-methoxybenzyl)imidazolidin-2-one

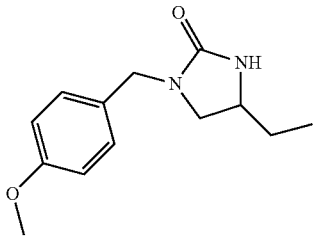 [SMILES: CCC1CN(Cc2ccc(OC)cc2)C(=O)N1]

Using 5-ethyl-3-(4-methoxybenzyl)imidazolidine-2,4-dione (2.00 g) described in Preparation Example 207 and by the reaction and treatment in the same manner as in Preparation Example 52, the title compound (1.07 g) was obtained.
MS (ESI) m/z: 235(M+H)$^+$.

Preparation Example 209

Preparation of 5-isopropyl-3-(4-methoxybenzyl)imidazolidine-2,4-dione

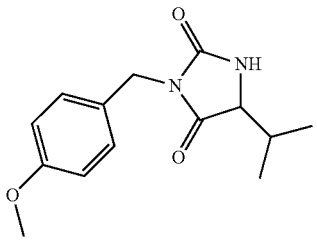 [SMILES: COc1ccc(CN2C(=O)NC(C(C)C)C2=O)cc1]

Using 5-isopropylimidazolidine-2,4-dione (2.00 g) and 4-methoxybenzyl chloride (2.29 mL) and by the reaction and treatment in the same manner as in Preparation Example 51, the title compound (2.72 g) was obtained.
MS (ESI) m/z: 263(M+H)$^+$.

Preparation Example 210

Preparation of 4-isopropyl-1-(4-methoxybenzyl)imidazolidin-2-one

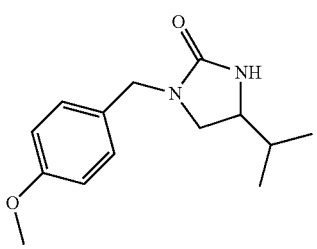 [SMILES: COc1ccc(CN2CC(C(C)C)NC2=O)cc1]

Using 5-isopropyl-3-(4-methoxybenzyl)imidazolidine-2,4-dione (2.00 g) described in Preparation Example 209 and

Preparation Example 211

Preparation of (4-bromo-2-fluorophenyl)[4-(5-ethyl-3-methylpyridin-2-yl)piperazin-1-yl]methanone

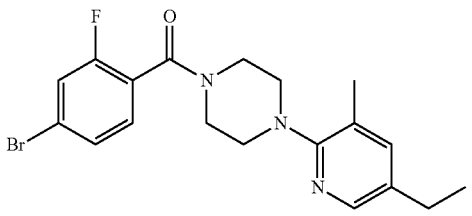 [SMILES: CCc1cnc(N2CCN(C(=O)c3ccc(Br)cc3F)CC2)c(C)c1]

Using 4-bromo-2-fluorobenzoic acid (1.08 g) and 1-(5-ethyl-3-methylpyridin-2-yl)piperazine (1.01 g) described in Preparation Example 81 and by the reaction and treatment in the same manner as in Preparation Example 111, the title compound (1.72 g) was obtained.
MS (ESI) m/z: 406(M+H)$^+$.

Preparation Example 212

Preparation of (4-bromophenyl)[4-(5-ethyl-3-methylpyridin-2-yl)piperazin-1-yl]methanone

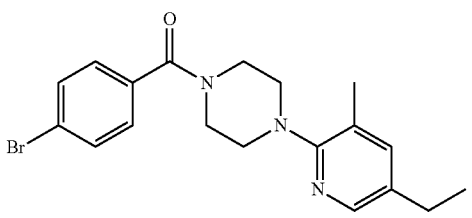 [SMILES: CCc1cnc(N2CCN(C(=O)c3ccc(Br)cc3)CC2)c(C)c1]

Using 4-bromobenzoic acid (1.01 g) and 1-(5-ethyl-3-methylpyridin-2-yl)piperazine (1.03 g) described in Preparation Example 81 and by the reaction and treatment in the same manner as in Preparation Example 111, the title compound (1.38 g) was obtained.
MS (ESI) m/z: 388(M+H)$^+$.

Preparation Example 213

Preparation of 3-(4-methoxybenzyl)imidazolidine-2,4-dione

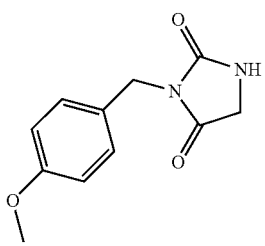 [SMILES: COc1ccc(CN2C(=O)CNC2=O)cc1]

Using imidazolidine-2,4-dione (1.00 g) and 4-methoxybenzyl chloride (1.63 mL) and by the reaction and treatment in the same manner as in Preparation Example 51, the title compound (1.68 g) was obtained.
MS (ESI) m/z: 221(M+H)$^+$.

Preparation Example 214

Preparation of 3-methylimidazolidine-2,4-dione

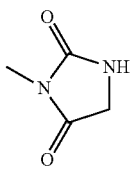

Imidazolidine-2,4-dione (1.00 g) was dissolved in N,N-dimethylformamide (20 mL), potassium tert-butoxide (1.11 g) and methyl iodide (0.65 mL) were used under ice-cooling, and the mixture was stirred at room temperature for 24 hr. The solvent was evaporated from the reaction mixture under reduced pressure, ethyl acetate was added, and the insoluble material was removed by filtration. The obtained mother liquor was concentrated under reduced pressure and the obtained residue was suspended and washed with ethyl acetate/diisopropyl ether to give the title compound (1.01 g).

Preparation Example 215

Preparation of 5-ethyl-3-methylimidazolidine-2,4-dione

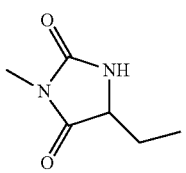

Using 5-ethylimidazolidine-2,4-dione (1.00 g) and methyl iodide (0.51 mL) and by the reaction and treatment in the same manner as in Preparation Example 214, the title compound (0.52 g) was obtained.
MS (ESI) m/z: 143(M+H)$^+$.

Preparation Example 216

Preparation of 5-isopropyl-3-methylimidazolidine-2,4-dione

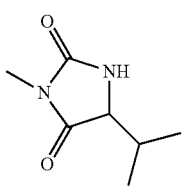

Using 5-isopropylimidazolidine-2,4-dione (1.00 g) and methyl iodide (0.46 mL) and by the reaction and treatment in the same manner as in Preparation Example 214, the title compound (0.88 g) was obtained.
MS (ESI) m/z: 157(M+H)$^+$.

Preparation Example 217

Preparation of 3,5-dimethylimidazolidine-2,4-dione

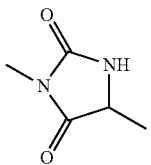

Using 5-methylimidazolidine-2,4-dione (1.00 g) and methyl iodide (0.57 mL) and by the reaction and treatment in the same manner as in Preparation Example 214, the title compound (1.66 g, containing DMF) was obtained.

Preparation Example 218

Preparation of 3,5,5-trimethylimidazolidine-2,4-dione

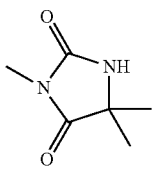

Using 5,5-dimethylimidazolidine-2,4-dione (1.00 g) and methyl iodide (0.53 mL) and by the reaction and treatment in the same manner as in Preparation Example 214, the title compound (1.03 g) was obtained.
MS (ESI) m/z: 143(M+H)$^+$.

Preparation Example 219

Preparation of toluene-4-sulfonic acid [(S)-5-oxopyrrolidin-2-yl]methyl ester

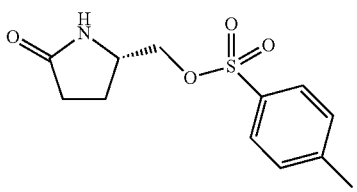 [SMILES: Cc1ccc(S(=O)(=O)OC[C@@H]2CCC(=O)N2)cc1]

(S)-5-hydroxymethylpyrrolidin-2-one (1.15 g) was dissolved in dichloromethane (40 mL), triethylamine (1.67 mL), p-toluenesulfonyl chloride (2.00 g) and dimethylaminopyridine (0.12 g) were added under ice-cooling, and the mixture was stirred at room temperature 18 hr. The reaction mixture was concentrated under reduced pressure, 0.5N hydrochloric acid was added, and the mixture was extracted with ethyl acetate. The organic layer was washed with 0.5N hydrochloric acid, water, saturated aqueous sodium hydrogen carbonate solution, and saturated brine, and the solvent was evaporated to give the title compound (1.88 g).
MS (ESI) m/z: 270(M+H)$^+$.

Preparation Example 220

Preparation of (S)-5-iodomethylpyrrolidin-2-one

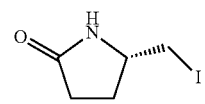

Toluene-4-sulfonic acid [(S)-5-oxopyrrolidin-2-yl]methyl ester (1.88 g) described in Preparation Example 219 was dissolved in acetonitrile (60 mL), sodium iodide (2.09 g) was added, and the mixture was stirred with heating under reflux for 8 hr. The reaction mixture was concentrated under reduced pressure, water was added, and the mixture was extracted with ethyl acetate. The organic layer was washed with aqueous sodium thiosulfate solution, water and saturated brine, and the solvent was evaporated to give the title compound (1.12 g).
MS (ESI) m/z: 226(M+H)$^+$.

Preparation Example 221

Preparation of (R)-5-methylpyrrolidin-2-one

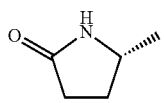

(S)-5-iodomethylpyrrolidin-2-one (1.12 g) described in Preparation Example 220 was dissolved in ethanol (30 mL), sodium carbonate (0.53 g) and 10% palladium carbon catalyst (0.22 g) were added, and the mixture was stirred for 8 hr under a hydrogen atmosphere. The catalyst was filtered through by celite from the reaction mixture, and the obtained mother liquor was concentrated under reduced pressure. To the obtained residue was added 5% aqueous sodium thiosulfate solution, and the mixture was extracted with chloroform. The organic layer was dried over sodium sulfate, and the solvent was evaporated to give the title compound (0.40 g).
MS (ESI) m/z: 100(M+H)$^+$.

Preparation Example 222

Preparation of toluene-4-sulfonic acid [(R)-5-oxopyrrolidin-2-yl]methyl ester

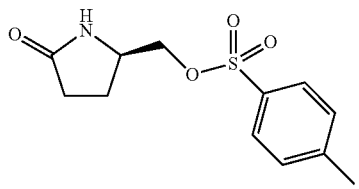 [SMILES: Cc1ccc(S(=O)(=O)OC[C@H]2CCC(=O)N2)cc1]

Using (R)-5-hydroxymethylpyrrolidin-2-one (1.68 g) and p-toluenesulfonyl chloride (2.92 g) and by the reaction and treatment in the same manner as in Preparation Example 219, the title compound (2.61 g) was obtained.

MS (ESI) m/z: 270(M+H)$^+$.

Preparation Example 223

Preparation of (R)-5-iodomethylpyrrolidin-2-one

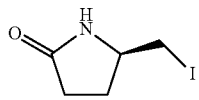

Using toluene-4-sulfonic acid [(R)-5-oxopyrrolidin-2-yl] methyl ester (2.61 g) described in Preparation Example 222 and sodium iodide (2.91 g) and by the reaction and treatment in the same manner as in Preparation Example 220, the title compound (1.30 g) was obtained.

MS (ESI) m/z: 226(M+H)$^+$.

Preparation Example 224

Preparation of (S)-5-methylpyrrolidin-2-one

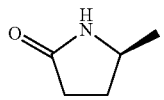

Using (R)-5-iodomethylpyrrolidin-2-one (1.30 g) described in Preparation Example 223 and by the reaction and treatment in the same manner as in Preparation Example 221, the title compound (0.17 g) was obtained.

MS (ESI) m/z: 100(M+H)$^+$.

Preparation Example 225

Preparation of 4-bromo-2-methanesulfonylaminobenzoic acid

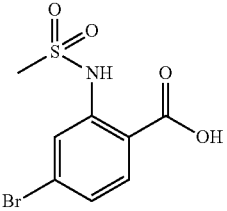

Methyl 2-amino-4-bromobenzoate (1 g) was dissolved in tetrahydrofuran (15 mL), triethylamine (4.2 mL) and methanesulfonyl chloride (0.74 mL) were added, and the mixture was stirred at room temperature for 6 hr. Water was added to the reaction mixture, and the mixture was extracted with chloroform. After evaporation of the solvent, to the residue were added methanol (20 mL) and 1N aqueous sodium hydroxide solution (13 mL), and the mixture was stirred at 50-60° C. After neutralizing with 1N hydrochloric acid, the precipitated solid was collected by filtration to give the title compound (964 mg).

Preparation Example 226

Preparation of N-{5-bromo-2-[4-(3,5-dimethylpyridin-2-yl)piperazine-1-carbonyl]phenyl}methanesulfonamide

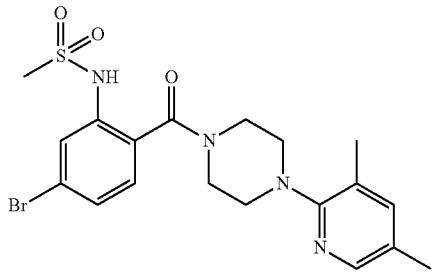 [SMILES: Cc1cnc(N2CCN(C(=O)c3ccc(Br)cc3NS(C)(=O)=O)CC2)c(C)c1]

Using 4-bromo-2-methanesulfonylaminobenzoic acid (964 mg) described in Preparation Example 225 and 1-(3,5-dimethylpyridin-2-yl)piperazine (629 mg) described in Preparation Example 79 and by the reaction and treatment in the same manner as in Preparation Example 111, the title compound (321 mg) was obtained.

MS (ESI) m/z: 467(M+H)$^+$.

Preparation Example 227

Preparation of N-{5-bromo-2-[4-(3,5-dimethylpyridin-2-yl)piperazine-1-carbonyl]phenyl}-N-methyl-methanesulfonamide

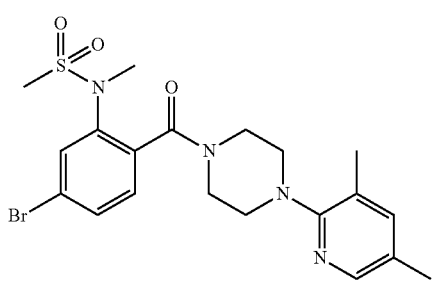 [SMILES: Cc1cnc(N2CCN(C(=O)c3ccc(Br)cc3N(C)S(C)(=O)=O)CC2)c(C)c1]

N-{5-bromo-2-[4-(3,5-dimethylpyridin-2-yl)piperazine-1-carbonyl]phenyl}methanesulfonamide (634 mg) described in Preparation Example 226 was dissolved in N,N-dimethylformamide (5 mL), and sodium hydride (65.1 mg, 60% in oil) was added under ice-cooling. After stirring at room temperature for 10 min, methyl iodide (93 μL) was added, and the mixture was stirred overnight. To the reaction mixture was added water under ice-cooling, and the mixture was extracted with ethyl acetate. The solvent was evaporated under reduced pressure, and the residue was purified by column chromatography (ethyl acetate:hexane) to give the title compound (670 mg).

MS (ESI) m/z: 481(M+H)$^+$.

Preparation Example 228

Preparation of (6-bromo-4-methylpyridin-3-yl)[4-(3,5-dimethylpyridin-2-yl)piperazin-1-yl]methanone

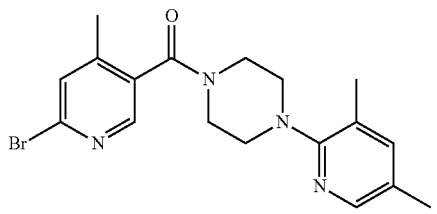

Using 6-bromo-4-methylnicotinic acid (500 mg) and 1-(3,5-dimethylpyridin-2-yl)piperazine (443 mg) described in Preparation Example 79 and by the reaction and treatment in the same manner as in Preparation Example 111, the title compound (880 mg) was obtained.

MS (ESI) m/z: 389(M+H)$^+$.

Preparation Example 229

Preparation of (5-bromopyrimidin-2-yl)[4-(3,5-dimethylpyridin-2-yl)piperazin-1-yl]methanone

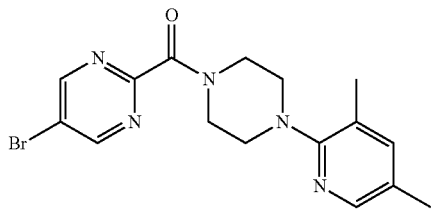 [SMILES: Cc1cnc(N2CCN(C(=O)c3ncc(Br)cn3)CC2)c(C)c1]

Using 5-bromopyrimidine-2-carboxylic acid (0.81 g) and 1-(3,5-dimethylpyridin-2-yl)piperazine (0.77 g) described in Preparation Example 79 and by the reaction and treatment in the same manner as in Preparation Example 111, the title compound (1.08 g) was obtained.

MS (ESI) m/z: 376(M+H)$^+$.

Preparation Example 230

Preparation of (6-chloropyridazin-3-yl)[4-(3,5-dimethylpyridin-2-yl)piperazin-1-yl]methanone

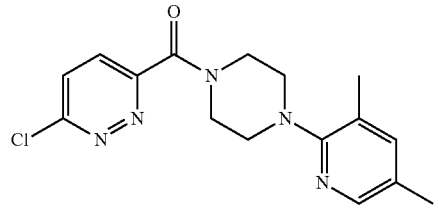

Using 6-chloropyridazine-3-carboxylic acid (1 g) and 1-(3,5-dimethylpyridin-2-yl)piperazine (1.2 g) described in Preparation Example 79 and by the reaction and treatment in the same manner as in Preparation Example 118, the title compound (1.44 g) was obtained.

MS (ESI) m/z: 332(M+H)$^+$.

Preparation Example 231

Preparation of methyl 2-(1,1-dioxo-1λ$^6$-isothiazolidin-2-yl)pyrimidine-5-carboxylate

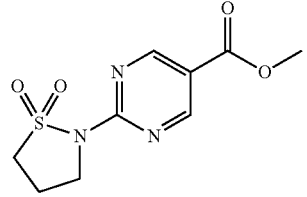 [SMILES: COC(=O)c1cnc(N2CCCS2(=O)=O)nc1]

Methyl 2-chloropyrimidine-5-carboxylate (173 mg) and isothiazolidine 1,1-dioxide (145 mg) were dissolved in N,N-dimethylformamide (1 mL), and sodium hydride (48 mg, 60% in oil) was added under ice-cooling. After stirring at room temperature for 6 hr, water was added, and the mixture was extracted with ethyl acetate. The solvent was evaporated, diisopropyl ether and ethyl acetate were added, and the precipitated solid was collected by filtration to give the title compound (185 mg).

MS (ESI) m/z: 258(M+H)$^+$.

Preparation Example 232

Preparation of (5-bromopyrazin-2-yl)[4-(3,5-dimethylpyridin-2-yl)piperazin-1-yl]methanone

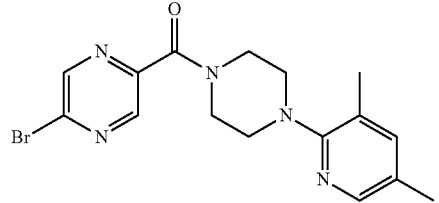

Using 5-bromopyrazine-2-carboxylic acid (203 mg) and 1-(3,5-dimethylpyridin-2-yl)piperazine (191 mg) described in Preparation Example 79 and by the reaction and treatment in the same manner as in Preparation Example 118, the title compound (261 mg) was obtained.

MS (ESI) m/z: 376(M+H)⁺.

Preparation Example 233

Preparation of (6-chloropyridazin-3-yl)[4-(5-cyclopropyl-3-methylpyridin-2-yl)piperazin-1-yl]methanone

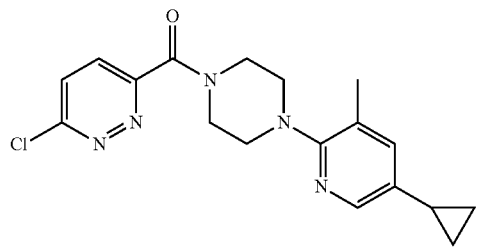 [SMILES: Cc1cc(C2CC2)cnc1N1CCN(C(=O)c2ccc(Cl)nn2)CC1]

Using 6-chloropyridazine-3-carboxylic acid (1 g) and 1-(5-cyclopropyl-3-methylpyridin-2-yl)piperazine (1.37 g) described in Preparation Example 83 and by the reaction and treatment in the same manner as in Preparation Example 118, the title compound (1.46 g) was obtained.

MS (ESI) m/z: 358(M+H)⁺.

Preparation Example 234

Preparation of 1-acetyl-3-{5-chloro-2-[4-(3,5-dimethylpyridin-2-yl)piperazine-1-carbonyl]phenyl}imidazolidin-2-one

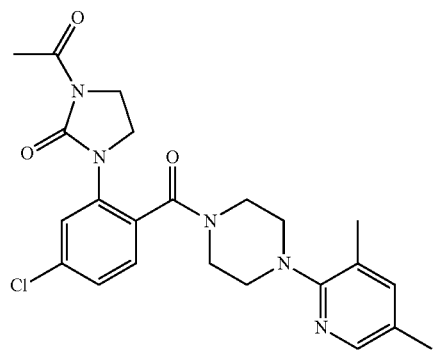 [SMILES: CC(=O)N1CCN(c2cc(Cl)ccc2C(=O)N2CCN(c3ncc(C)cc3C)CC2)C1=O]

To a mixture of (2-bromo-4-chlorophenyl)[4-(3,5-dimethylpyridin-2-yl)piperazin-1-yl]methanone (817 mg) described in Preparation Example 167, 1-acetylimidazolidin-2-one (384 mg), tripotassium phosphate (849 mg) and copper (I) iodide (191 mg) were added dioxane (4 mL) and N,N'-dimethylethylenediamine (215 μL), and the mixture was stirred at 8 hr under refluxing. After cooling, water was added to the reaction mixture, and the mixture was extracted with ethyl acetate. The solvent was evaporated, and the residue was purified by column chromatography (ethyl acetate: methanol) to give the title compound (639 mg).

MS (ESI) m/z: 456(M+H)⁺.

Preparation Example 235

Preparation of (2-bromo-4-chlorophenyl)[4-(5-cyclopropyl-3-methylpyridin-2-yl)piperazin-1-yl]methanone

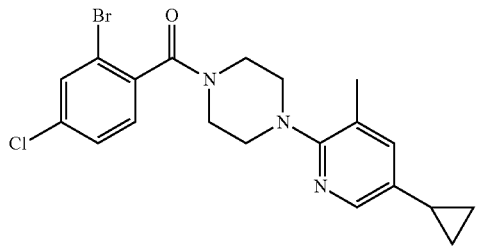

Using 2-bromo-4-chlorobenzoic acid (1 g) and 1-(5-cyclopropyl-3-methylpyridin-2-yl)piperazine (0.92 g) described in Preparation Example 83 and by the reaction and treatment in the same manner as in Preparation Example 111, the title compound (1.75 g) was obtained.

MS (ESI) m/z: 434(M+H)⁺.

Preparation Example 236

Preparation of 1-acetyl-3-{5-chloro-2-[4-(5-cyclopropyl-3-methylpyridin-2-yl)piperazine-1-carbonyl]phenyl}imidazolidin-2-one

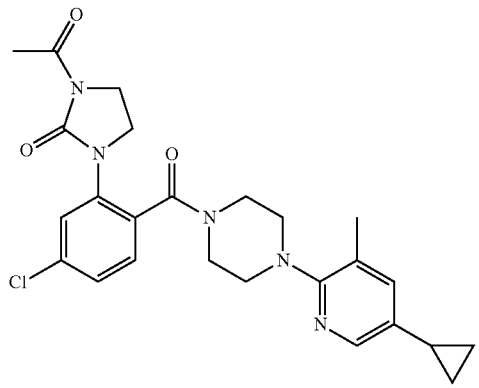

Using (2-bromo-4-chlorophenyl)[4-(5-cyclopropyl-3-methylpyridin-2-yl)piperazin-1-yl]methanone (870 mg) described in Preparation Example 235 and 1-acetylimidazolidin-2-one (384 mg) and by the reaction and treatment in the same manner as in Preparation Example 234, the title compound (560 mg) was obtained.

MS (ESI) m/z: 482(M+H)⁺.

Preparation Example 237

Preparation of (2,4-dibromophenyl)[4-(3,5-dimethylpyridin-2-yl)piperazin-1-yl]methanone

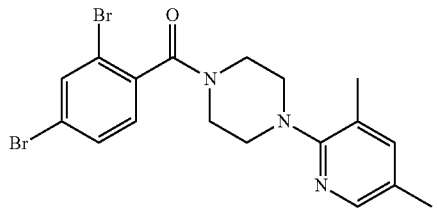

Using 2,4-dibromobenzoic acid (500 mg) and 1-(3,5-dimethylpyridin-2-yl)piperazine (343 mg) described in Preparation Example 79 and by the reaction and treatment in the same manner as in Preparation Example 118, the title compound (691 mg) was obtained.
MS (ESI) m/z: 452(M+H)+.

Preparation Example 238

Preparation of [4-(5-cyclopropyl-3-methylpyridin-2-yl)piperazin-1-yl](2,4-dibromophenyl)methanone

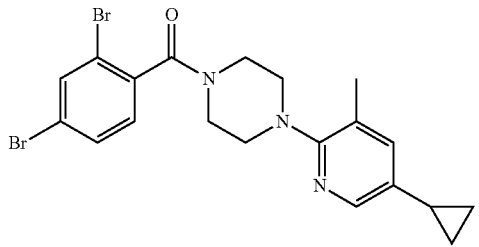 [SMILES: Cc1cc(C2CC2)cnc1N1CCN(C(=O)c2ccc(Cl)cc2Br)CC1]

Using 2,4-dibromobenzoic acid (530 mg) and 1-(5-cyclopropyl-3-methylpyridin-2-yl)piperazine (413 mg) described in Preparation Example 83 and by the reaction and treatment in the same manner as in Preparation Example 118, the title compound (630 mg) was obtained.
MS (ESI) m/z: 478(M+H)+.

Preparation Example 239

Preparation of methyl 4-bromo-2-(1,1-dioxo-1$\lambda^6$-isothiazolidin-2-yl)benzoate

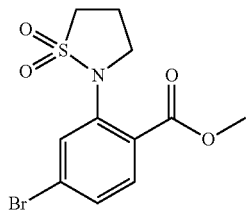 [SMILES: COC(=O)c1ccc(Br)cc1N1CCCS1(=O)=O]

Using methyl 2-amino-4-bromobenzoate (5 g) and 3-chloropropane-1-sulfonyl chloride (3.44 mL) and by the reaction and treatment in the same manner as in Preparation Example 17, the title compound (5.32 g) was obtained.
MS (ESI) m/z: 334(M+H)+.

Preparation Example 240

Preparation of [4-bromo-2-(1,1-dioxo-1$\lambda^6$-isothiazolidin-2-yl)phenyl][4-(5-cyclopropyl-3-methylpyridin-2-yl)piperazin-1-yl]methanone

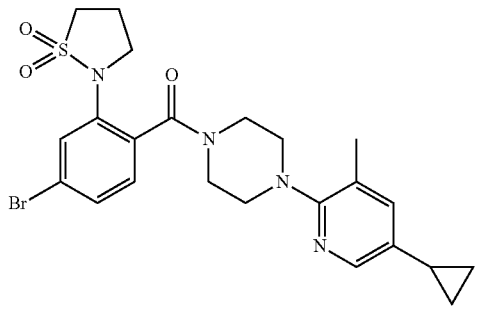 [SMILES: Cc1cc(C2CC2)cnc1N1CCN(C(=O)c2ccc(Br)cc2N2CCCS2(=O)=O)CC1]

Using methyl 4-bromo-2-(1,1-dioxo-1$\lambda^6$-isothiazolidin-2-yl)benzoate (1 g) described in Preparation Example 239 and 1-(5-cyclopropyl-3-methylpyridin-2-yl)piperazine (0.65 g) described in Preparation Example 83 and by the reaction and treatment in the same manner as in Preparation Example 166, the title compound (0.98 g) was obtained.
MS (ESI) m/z: 519(M+H)+.

Preparation Example 241

Preparation of 1-{5-chloro-2-[4-(3,5-dimethylpyridin-2-yl)piperazine-1-carbonyl]phenyl}-3-methylimidazolidin-2-one

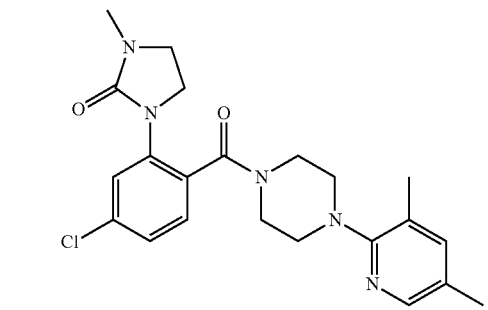 [SMILES: Cc1cnc(N2CCN(C(=O)c3ccc(Cl)cc3N3CCN(C)C3=O)CC2)c(C)c1]

To a mixture of (2-bromo-4-chlorophenyl)[4-(3,5-dimethylpyridin-2-yl)piperazin-1-yl]methanone (817 mg) described in Preparation Example 167, 1-methylimidazolidin-2-one (300 mg), cesium carbonate (1.30 g) and copper(I) iodide (191 mg) were added 1,4-dioxane (4 mL) and N,N'-dimethylethylenediamine (0.22 mL), and the mixture was stirred for 8 hr under refluxing. After cooling, water was added to the reaction mixture, and the mixture was extracted with ethyl acetate. The solvent was evaporated, and the residue was purified by column chromatography (ethyl acetate:methanol) to give the title compound (330 mg).
MS (ESI) m/z: 428(M+H)+.

Preparation Example 242

Preparation of 1-{5-chloro-2-[4-(5-cyclopropyl-3-methylpyridin-2-yl)piperazine-1-carbonyl]phenyl}-3-methylimidazolidin-2-one

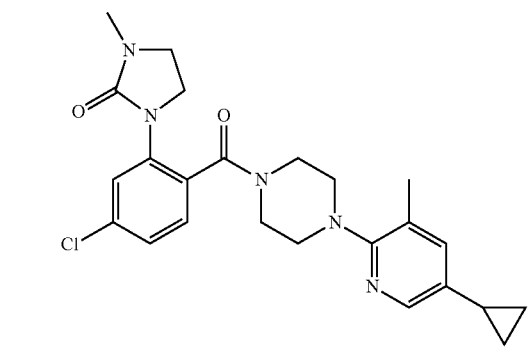 [SMILES: Cc1cc(C2CC2)cnc1N1CCN(C(=O)c2ccc(Cl)cc2N2CCN(C)C2=O)CC1]

Using (2-bromo-4-chlorophenyl)[4-(5-cyclopropyl-3-methylpyridin-2-yl)piperazin-1-yl]methanone (848 mg) described in Preparation Example 235 and 1-methylimidazolidin-2-one (293 mg) and by the reaction and treatment in the same manner as in Preparation Example 241, the title compound (250 mg) was obtained.
MS (ESI) m/z: 454(M+H)+.

Preparation Example 243

Preparation of (5-bromopyrazin-2-yl) [4-(5-cyclopropyl-3-methylpyridin-2-yl)piperazin-1-yl]methanone

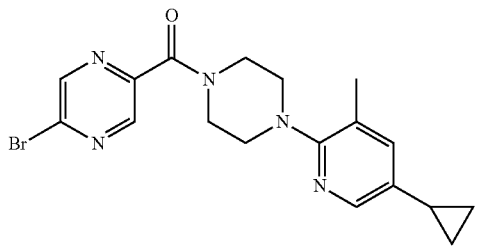 [SMILES: Cc1cc(C2CC2)cnc1N1CCN(C(=O)c2cnc(Br)cn2)CC1]

Using 5-bromopyrazine-2-carboxylic acid (1 g) and 1-(5-cyclopropyl-3-methylpyridin-2-yl)piperazine (1.07 g) described in Preparation Example 83 and by the reaction and treatment in the same manner as in Preparation Example 118, the title compound (1.3 g) was obtained.
MS (ESI) m/z: 402(M+H)$^+$.

Preparation Example 244

Preparation of (5-bromothiophen-3-yl)[4-(3,5-dimethylpyridin-2-yl)piperazin-1-yl]methanone

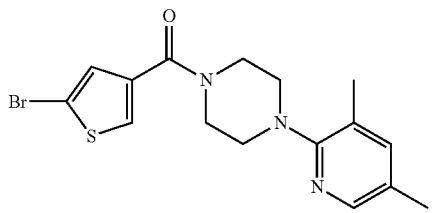 [SMILES: Cc1cnc(N2CCN(C(=O)c3csc(Br)c3)CC2)c(C)c1]

Using 5-bromothiophene-3-carboxylic acid (500 mg) and 1-(3,5-dimethylpyridin-2-yl)piperazine (462 mg) described in Preparation Example 79 and by the reaction and treatment in the same manner as in Preparation Example 118, the title compound (700 mg) was obtained.
MS (ESI) m/z: 380(M+H)$^+$.

Preparation Example 245

Preparation of 5-bromo-2-[4-(3,5-dicyclopropylpyridin-2-yl)piperazine-1-carbonyl]benzonitrile

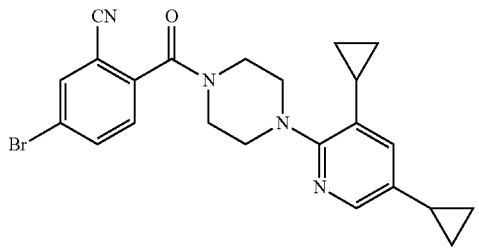 [SMILES: N#Cc1cc(Br)ccc1C(=O)N1CCN(c2ncc(C3CC3)cc2C2CC2)CC1]

Using 4-bromo-2-cyanobenzoic acid (3.39 g) described in Preparation Example 76 and 1-(3,5-dicyclopropylpyridin-2-yl)piperazine (4.02 g) described in Preparation Example 88 and by the reaction and treatment in the same manner as in Preparation Example 111, the title compound (6.28 g) was obtained.
MS (ESI) m/z: 451(M+H)$^+$.

Preparation Example 246

Preparation of 5-bromo-2-[4-(5-ethyl-3-methylpyridin-2-yl)piperazine-1-carbonyl]benzonitrile

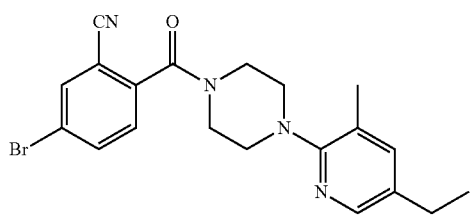

Using 4-bromo-2-cyanobenzoic acid (4.55 g) described in Preparation Example 76 and 1-(5-ethyl-3-methylpyridin-2-yl)piperazine (4.13 g) described in Preparation Example 81 and by the reaction and treatment in the same manner as in Preparation Example 111, the title compound (7.52 g) was obtained.
MS (ESI) m/z: 413(M+H)$^+$.

Preparation Example 247

Preparation of (6-bromo-2-methylpyridin-3-yl) [4-(3,5-dimethylpyridin-2-yl)piperazin-1-yl]methanone

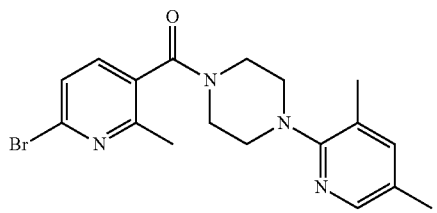 [SMILES: Cc1cnc(N2CCN(C(=O)c3ccc(Br)nc3C)CC2)c(C)c1]

Using 6-bromo-2-methylnicotinic acid (986 mg) and 1-(3,5-dimethylpyridin-2-yl)piperazine (917 mg) described in Preparation Example 79 and by the reaction and treatment in the same manner as in Preparation Example 111, the title compound (903 mg) was obtained.
MS (ESI) m/z: 389(M+H)$^+$.

Preparation Example 248

Preparation of (6-bromo-2-methylpyridin-3-yl)[4-(3,5,6-trimethylpyridin-2-yl)piperazin-1-yl]methanone

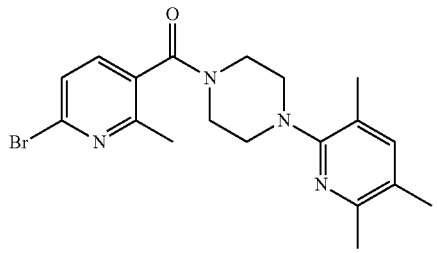 [SMILES: Cc1cc(C)c(N2CCN(C(=O)c3ccc(Br)nc3C)CC2)nc1C]

Using 6-bromo-2-methylnicotinic acid (745 mg) and 1-(3,5,6-trimethylpyridin-2-yl)piperazine (744 mg) described in Preparation Example 92 and by the reaction and treatment in the same manner as in Preparation Example 111, the title compound (801 mg) was obtained.

MS (ESI) m/z: 403(M+H)+.

Preparation Example 249

Preparation of (6-bromo-2-methylpyridin-3-yl)[4-(5-cyclopropyl-3-methylpyridin-2-yl)piperazin-1-yl]methanone

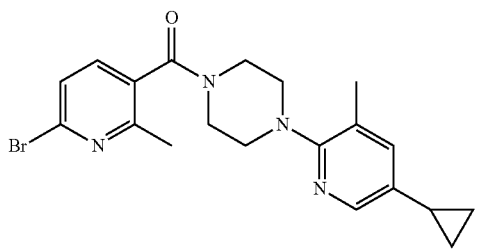 [SMILES: Cc1cc(C2CC2)cnc1N1CCN(C(=O)c2ccc(Br)nc2C)CC1]

Using 6-bromo-2-methylnicotinic acid (864 mg) and 1-(5-cyclopropyl-3-methylpyridin-2-yl)piperazine (913 mg) described in Preparation Example 83 and by the reaction and treatment in the same manner as in Preparation Example 111, the title compound (948 mg) was obtained.

MS (ESI) m/z: 415(M+H)+.

Preparation Example 250

Preparation of (6-bromo-2-methylpyridin-3-yl)[4-(5-ethyl-3-methylpyridin-2-yl)piperazin-1-yl]methanone

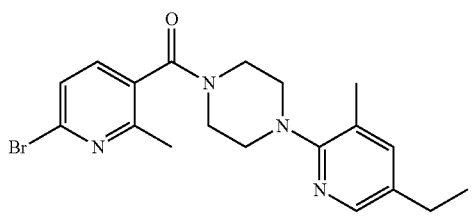

Using 6-bromo-2-methylnicotinic acid (675 mg) and 1-(5-ethyl-3-methylpyridin-2-yl)piperazine (611 mg) described in Preparation Example 81 and by the reaction and treatment in the same manner as in Preparation Example 111, the title compound (664 mg) was obtained.

MS (ESI) m/z: 403(M+H)+.

Preparation Example 251

Preparation of (6-bromo-2-methylpyridin-3-yl)[4-(3,5-dicyclopropylpyridin-2-yl)piperazin-1-yl]methanone

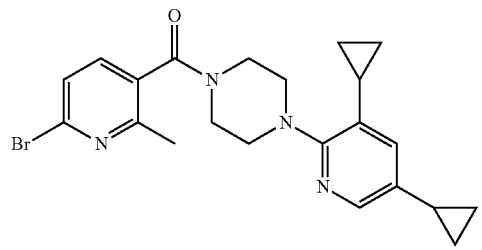 [SMILES: Cc1nc(Br)ccc1C(=O)N1CCN(c2ncc(C3CC3)cc2C2CC2)CC1]

Using 6-bromo-2-methylnicotinic acid (604 mg) and 1-(3,5-dicyclopropylpyridin-2-yl)piperazine (816 mg) described in Preparation Example 88 and by the reaction and treatment in the same manner as in Preparation Example 111, the title compound (695 mg) was obtained.

MS (ESI) m/z: 441(M+H)+.

Preparation Example 252

Preparation of (4-bromo-2-methoxyphenyl) [4-(3,5-dimethylpyridin-2-yl)piperazin-1-yl]methanone

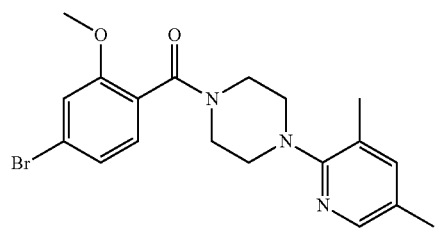 [SMILES: COc1cc(Br)ccc1C(=O)N1CCN(c2ncc(C)cc2C)CC1]

Using 4-bromo-2-methoxybenzoic acid (2.31 g) and 1-(3,5-dimethylpyridin-2-yl)piperazine (1.91 g) described in Preparation Example 79 and by the reaction and treatment in the same manner as in Preparation Example 111, the title compound (3.81 g) was obtained.

MS (ESI) m/z: 404(M+H)+.

Preparation Example 253

Preparation of (4-bromo-2-methylphenyl) [4-(5-ethyl-3-methylpyridin-2-yl)piperazin-1-yl]methanone

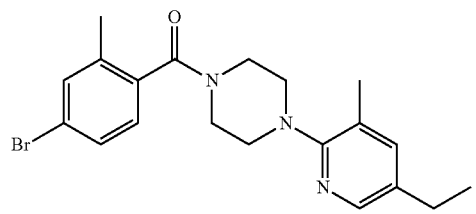

Using 4-bromo-2-methylbenzoic acid (1.42 g) and 1-(5-ethyl-3-methylpyridin-2-yl)piperazine (1.23 g) described in Preparation Example 81 and by the reaction and treatment in the same manner as in Preparation Example 111, the title compound (2.05 g) was obtained.

MS (ESI) m/z: 402(M+H)$^+$.

Preparation Example 254

Preparation of (4-bromo-2-methanesulfonylphenyl)[4-(5-ethyl-3-methylpyridin-2-yl)piperazin-1-yl]methanone

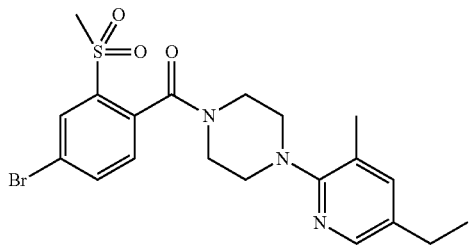 [SMILES: CCc1cnc(N2CCN(C(=O)c3ccc(Br)cc3S(C)(=O)=O)CC2)c(C)c1]

Using 4-bromo-2-methanesulfonylbenzoic acid (2.76 g) and 1-(5-ethyl-3-methylpyridin-2-yl)piperazine (1.85 g) described in Preparation Example 81 and by the reaction and treatment in the same manner as in Preparation Example 111, the title compound (3.20 g) was obtained.

MS (ESI) m/z: 466(M+H)$^+$.

Preparation Example 255

Preparation of methyl 6-(3,5-dimethyl-2,4-dioxoimidazolidin-1-yl)-2-methylnicotinate

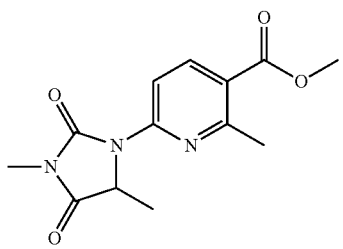

Using methyl 6-bromo-2-methylnicotinate (96 mg) and 3,5-dimethylimidazolidine-2,4-dione (107 mg) described in Preparation Example 217 and by the reaction and treatment in the same manner as in Preparation Example 48, the title compound (19 mg) was obtained.

MS (ESI) m/z: 278(M+H)$^+$.

Preparation Example 256

Preparation of 1-{5-chloro-2-[4-(3,5-dimethylpyridin-2-yl)piperazine-1-carbonyl]phenyl}-3-methylimidazolidine-2,4-dione

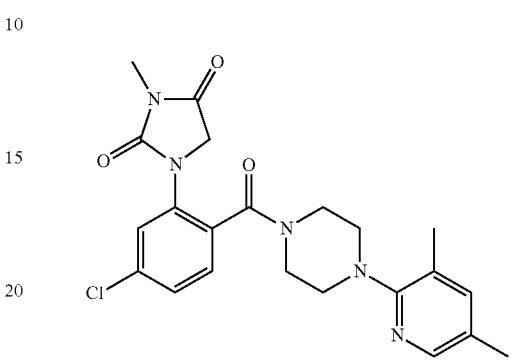

Using (2-bromo-4-chlorophenyl)[4-(3,5-dimethylpyridin-2-yl)piperazin-1-yl]methanone (817 mg) described in Preparation Example 167 and 3-methylimidazolidine-2,4-dione (339 mg) described in Preparation Example 214 and by the reaction and treatment in the same manner as in Preparation Example 241, the title compound (310 mg) was obtained.

MS (ESI) m/z: 442(M+H)$^+$.

Preparation Example 257

Preparation of (2-bromo-4-chlorophenyl)[4-(3,5,6-trimethylpyridin-2-yl)piperazin-1-yl]methanone

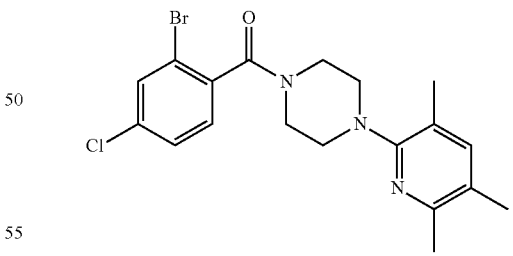

Using 2-bromo-4-chlorobenzoic acid (1 g) and 1-(3,5,6-trimethylpyridin-2-yl)piperazine (0.87 g) described in Preparation Example 92 and by the reaction and treatment in the same manner as in Preparation Example 111, the title compound (1.85 g) was obtained.

MS (ESI) m/z: 422(M+H)$^+$.

Preparation Example 258

Preparation of 1-acetyl-3-{5-chloro-2-[4-(3,5,6-trimethylpyridin-2-yl)piperazine-1-carbonyl]phenyl}imidazolidin-2-one

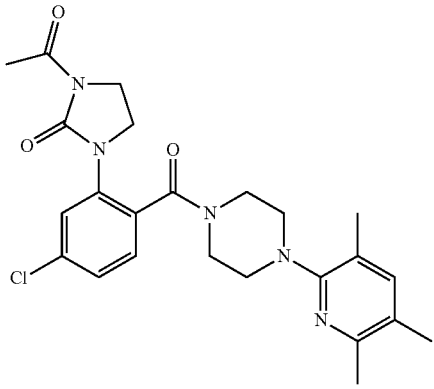 [SMILES: CC(=O)N1CCN(c2cc(Cl)ccc2C(=O)N2CCN(c3nc(C)c(C)cc3C)CC2)C1=O]

Using (2-bromo-4-chlorophenyl)[4-(3,5,6-trimethylpyridin-2-yl)piperazin-1-yl]methanone (846 mg) described in Preparation Example 257 and 1-acetylimidazolidin-2-one (384 mg) and by the reaction and treatment in the same manner as in Preparation Example 234, the title compound (579 mg) was obtained.

MS (ESI) m/z: 470(M+H)$^+$.

Preparation Example 259

Preparation of 1-{5-chloro-2-[4-(3,5,6-trimethylpyridin-2-yl)piperazine-1-carbonyl]phenyl}-3-methylimidazolidin-2-one

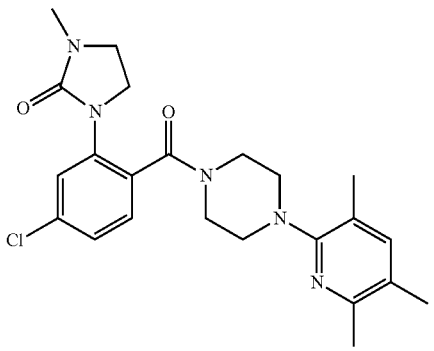 [SMILES: Cc1cc(C)c(N2CCN(C(=O)c3ccc(Cl)cc3N3CCN(C)C3=O)CC2)nc1C]

Using (2-bromo-4-chlorophenyl)[4-(3,5,6-trimethylpyridin-2-yl)piperazin-1-yl]methanone (846 mg) described in Preparation Example 257 and 1-methylimidazolidin-2-one (300 mg) and by the reaction and treatment in the same manner as in Preparation Example 241, the title compound (113 mg) was obtained.

MS (ESI) m/z: 442(M+H)$^+$.

Example 1

Synthesis of (R)-[4-(2,4-dimethylphenyl)piperazin-1-yl][4-(3-ethyl-1,1-dioxo-1$\lambda^6$-isothiazolidin-2-yl)phenyl]methanone

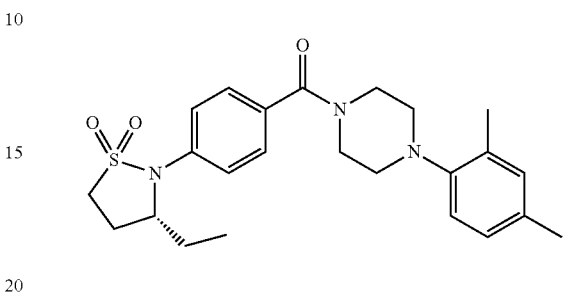

To a mixture of [4-(2,4-dimethylphenyl)piperazin-1-yl](4-iodophenyl)methanone (420 mg) described in Preparation Example 108, (R)-3-ethylisothiazolidine 1,1-dioxide (150 mg) described in Preparation Example 3, potassium carbonate (276 mg) and copper(I) iodide (95 mg) were added toluene (3 mL) and N,N'-dimethylethylenediamine (110 µL), and the mixture was stirred with heating under reflux for 8 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give the title compound (140 mg).

MS (ESI) m/z: 442(M+H)$^+$.

Example 2

Synthesis of (R)-[4-(3,5-dimethylpyridin-2-yl)piperazin-1-yl][4-(3-ethyl-1,1-dioxo-1$\lambda^6$-isothiazolidin-2-yl)phenyl]methanone

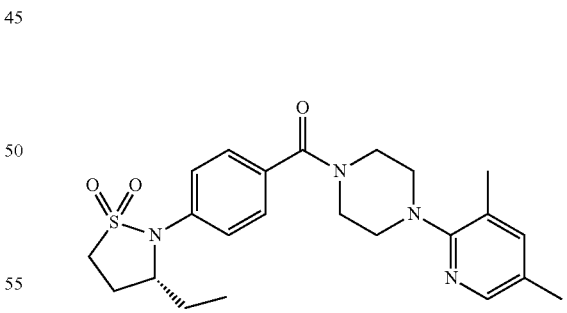

Using (R)-3-ethylisothiazolidine 1,1-dioxide (150 mg) described in Preparation Example 3 and [4-(3,5-dimethylpyridin-2-yl)piperazin-1-yl](4-iodophenyl)methanone (421 mg) described in Preparation Example 113 and by the reaction and treatment in the same manner as in Example 1, the title compound (57 mg) was obtained.

MS (ESI) m/z: 443(M+H)$^+$.

Example 3

Synthesis of (R)-[4-(3,5-dimethylpyridin-2-yl)piperazin-1-yl][4-(3-ethyl-1,1-dioxo-1λ⁶-isothiazolidin-2-yl)-2-fluorophenyl]methanone

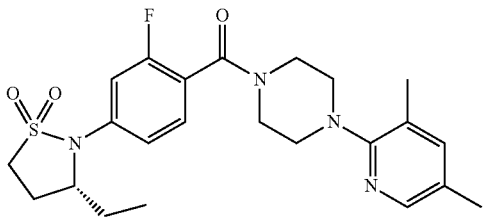 [SMILES: CC[C@@H]1CCS(=O)(=O)N1c1ccc(C(=O)N2CCN(c3ncc(C)cc3C)CC2)c(F)c1]

Using (R)-3-ethylisothiazolidine 1,1-dioxide (150 mg) described in Preparation Example 3 and (4-bromo-2-fluorophenyl)[4-(3,5-dimethylpyridin-2-yl)piperazin-1-yl]methanone (439 mg) described in Preparation Example 114 and by the reaction and treatment in the same manner as in Example 1, the title compound (60 mg) was obtained.

MS (ESI) m/z: 461(M+H)⁺.

Example 4

Synthesis of (R)-[4-(2,4-dimethylphenyl)piperazin-1-yl][4-(3-ethyl-1,1-dioxo-1λ⁶-isothiazolidin-2-yl)-2-methanesulfonylphenyl]methanone

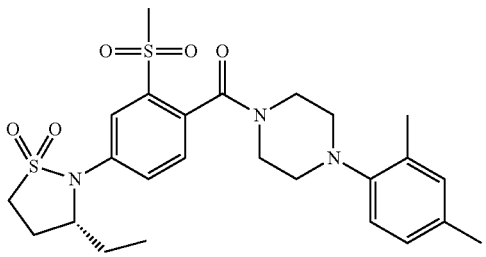 [SMILES: CC[C@@H]1CCS(=O)(=O)N1c1ccc(C(=O)N2CCN(c3ccc(C)cc3C)CC2)c(S(C)(=O)=O)c1]

To a mixture of (4-bromo-2-methanesulfonylphenyl)[4-(2,4-dimethylphenyl)piperazin-1-yl]methanone (451 mg) described in Preparation Example 110, (R)-3-ethylisothiazolidine 1,1-dioxide (150 mg) described in Preparation Example 3, potassium carbonate (276 mg), potassium iodide (332 mg) and copper(I) iodide (95 mg) were added toluene (3 mL) and N,N'-dimethylethylenediamine (110 μL), and the mixture was stirred with heating under reflux for 15 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give the title compound (44 mg).

MS (ESI) m/z: 520(M+H)⁺.

Example 5

Synthesis of (R)-[4-(3,5-dimethylpyridin-2-yl)piperazin-1-yl][4-(3-ethyl-1,1-dioxo-1λ⁶-isothiazolidin-2-yl)-2-methanesulfonylphenyl]methanone

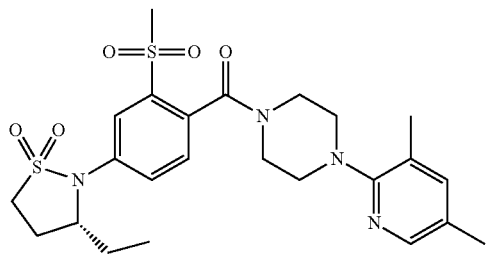 [SMILES: CC[C@@H]1CCS(=O)(=O)N1c1ccc(C(=O)N2CCN(c3ncc(C)cc3C)CC2)c(S(C)(=O)=O)c1]

Using (4-bromo-2-methanesulfonylphenyl)[4-(3,5-dimethylpyridin-2-yl)piperazin-1-yl]methanone (664 mg) described in Preparation Example 112 and (R)-3-ethylisothiazolidine 1,1-dioxide (238 mg) described in Preparation Example 3 and by the reaction and treatment in the same manner as in Example 1, the title compound (194 mg) was obtained.

MS (ESI) m/z: 521(M+H)⁺.

Example 6

Synthesis of (S)-[4-(3,5-dimethylpyridin-2-yl)piperazin-1-yl][4-(4-methyl-1,1-dioxo-1λ⁶-isothiazolidin-2-yl)phenyl]methanone

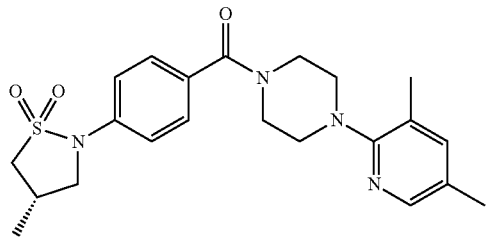 [SMILES: Cc1cnc(N2CCN(C(=O)c3ccc(N4C[C@H](C)CS4(=O)=O)cc3)CC2)c(C)c1]

Using [4-(3,5-dimethylpyridin-2-yl)piperazin-1-yl](4-iodophenyl)methanone (130 mg) described in Preparation Example 113 and (S)-4-methylisothiazolidine 1,1-dioxide (84 mg) described in Preparation Example 4 and by the reaction and treatment in the same manner as in Example 1, the title compound (32 mg) was obtained.

MS (ESI) m/z: 429(M+H)⁺.

Example 7

Synthesis of (S)-[4-(2,4-dimethylphenyl)piperazin-1-yl][4-(4-methyl-1,1-dioxo-1λ⁶-isothiazolidin-2-yl)phenyl]methanone

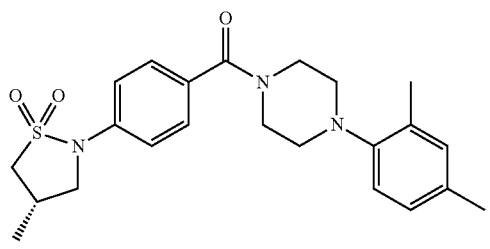 [SMILES: Cc1ccc(N2CCN(C(=O)c3ccc(N4C[C@H](C)CS4(=O)=O)cc3)CC2)c(C)c1]

Using (S)-4-methylisothiazolidine 1,1-dioxide (202 mg) described in Preparation Example 4 and [4-(2,4-dimethylphenyl)piperazin-1-yl](4-iodophenyl)methanone (420 mg) described in Preparation Example 108 and by the reaction and treatment in the same manner as in Example 1, the title compound (110 mg) was obtained.

MS (ESI) m/z: 428(M+H)$^+$.

Example 8

Synthesis of (S)-[4-(2,4-dimethylphenyl)piperazin-1-yl][2-methanesulfonyl-4-(4-methyl-1,1-dioxo-1λ$^6$-isothiazolidin-2-yl)phenyl]methanone

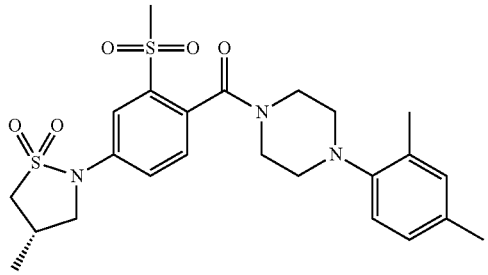 [SMILES: Cc1ccc(N2CCN(C(=O)c3ccc(N4C[C@H](C)CS4(=O)=O)cc3S(C)(=O)=O)CC2)c(C)c1]

Using (4-bromo-2-methanesulfonylphenyl)[4-(2,4-dimethylphenyl)piperazin-1-yl]methanone (534 mg) described in Preparation Example 110 and (S)-4-methylisothiazolidine 1,1-dioxide (320 mg) described in Preparation Example 4 and by the reaction and treatment in the same manner as in Example 4, the title compound (163 mg) was obtained.

MS (ESI) m/z: 506(M+H)$^+$.

Example 9

Synthesis of (R)-[4-(3,5-dimethylpyridin-2-yl)piperazin-1-yl][4-(3-ethyl-1, yl)-2,6-difluorophenyl]methanone

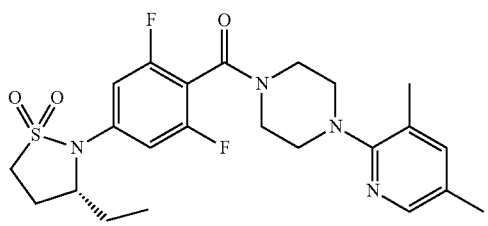 [SMILES: CC[C@@H]1CCS(=O)(=O)N1c1cc(F)c(C(=O)N2CCN(c3ncc(C)cc3C)CC2)c(F)c1]

Using (4-bromo-2,6-difluorophenyl)[4-(3,5-dimethylpyridin-2-yl)piperazin-1-yl]methanone (400 mg) described in Preparation Example 111 and (R)-3-ethylisothiazolidine 1,1-dioxide (150 mg) described in Preparation Example 3 and by the reaction and treatment in the same manner as in Example 4, the title compound (75 mg) was obtained.

MS (ESI) m/z: 479(M+H)$^+$.

Example 10

Synthesis of [4-(2,4-dimethylphenyl)piperazin-1-yl][2-methanesulfonyl-4-(5-methyl-1,1-dioxo-1λ$^6$-isothiazolidin-2-yl)phenyl]methanone

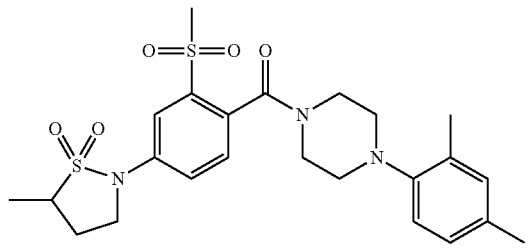

Using 5-methylisothiazolidine 1,1-dioxide (360 mg) described in Preparation Example 5 and (4-bromo-2-methanesulfonylphenyl)[4-(2,4-dimethylphenyl)piperazin-1-yl]methanone (803 mg) described in Preparation Example 110 and by the reaction and treatment in the same manner as in Example 4, the title compound (191 mg) was obtained.

MS (ESI) m/z: 506(M+H)$^+$.

Example 11

Synthesis of [4-(2,4-dimethylphenyl)piperazin-1-yl][4-(1,1-dioxo-1λ$^6$-isothiazolidin-2-yl)-2-methanesulfonylphenyl]methanone

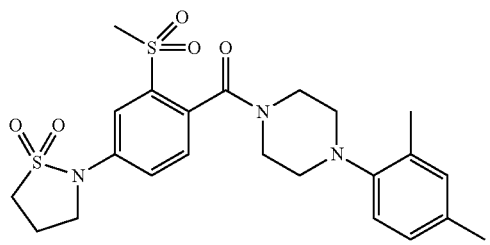 [SMILES: Cc1ccc(N2CCN(C(=O)c3ccc(N4CCCS4(=O)=O)cc3S(C)(=O)=O)CC2)c(C)c1]

4-(1,1-Dioxo-1λ$^6$-isothiazolidin-2-yl)-2-methanesulfonylbenzoic acid (335 mg) described in Preparation Example 22, 1-(2,4-dimethylphenyl)piperazine (199 mg), 1-hydroxybenzotriazole 1 hydrate (142 mg) were dissolved in N,N-dimethylformamide (5 mL), 1-ethyl-3-(3'-dimethylaminopropyl)carbodiimide hydrochloride (202 mg) was added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (436 mg).

MS (ESI) m/z: 492(M+H)$^+$.

Example 12

Synthesis of (S)-[4-(2,4-dimethylphenyl)piperazin-1-yl][4-(3-isopropyl-1,1-dioxo-1λ⁶-isothiazolidin-2-yl)phenyl]methanone

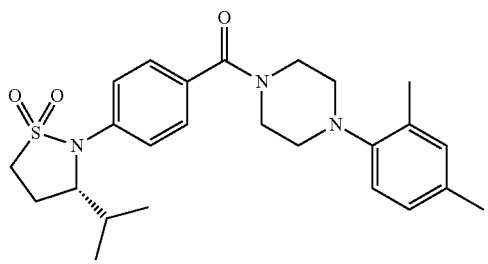 [SMILES: Cc1ccc(N2CCN(C(=O)c3ccc(N4[C@H](C(C)C)CCS4(=O)=O)cc3)CC2)c(C)c1]

Using (S)-3-isopropylisothiazolidine 1,1-dioxide (320 mg) described in Preparation Example 6 and [4-(2,4-dimethylphenyl)piperazin-1-yl](4-iodophenyl)methanone (420 mg) described in Preparation Example 108 and by the reaction and treatment in the same manner as in Example 1, the title compound (107 mg) was obtained.

MS (ESI) m/z: 456(M+H)⁺.

Example 13

Synthesis of (S)-[4-(2,4-dimethylphenyl)piperazin-1-yl][4-(3-isopropyl-1,1-dioxo-1λ⁶-isothiazolidin-2-yl)-2-methanesulfonylphenyl]methanone

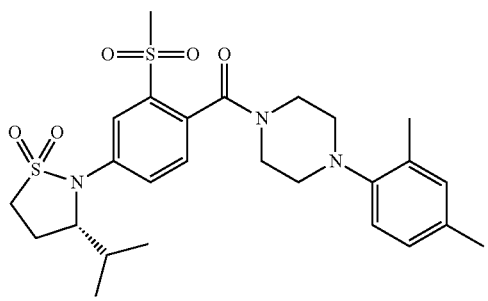 [SMILES: Cc1ccc(N2CCN(C(=O)c3ccc(N4[C@H](C(C)C)CCS4(=O)=O)cc3S(C)(=O)=O)CC2)c(C)c1]

Using (S)-3-isopropylisothiazolidine 1,1-dioxide (320 mg) described in Preparation Example 6 and (4-bromo-2-methanesulfonylphenyl)[4-(2,4-dimethylphenyl)piperazin-1-yl]methanone (451 mg) described in Preparation Example 110 and by the reaction and treatment in the same manner as in Example 4, the title compound (130 mg) was obtained.

MS (ESI) m/z: 534(M+H)⁺.

Example 14

Synthesis of (S)-[2,6-difluoro-4-(3-isopropyl-1,1-dioxo-1λ⁶-isothiazolidin-2-yl)phenyl][4-(3,5-dimethylpyridin-2-yl)piperazin-1-yl]methanone

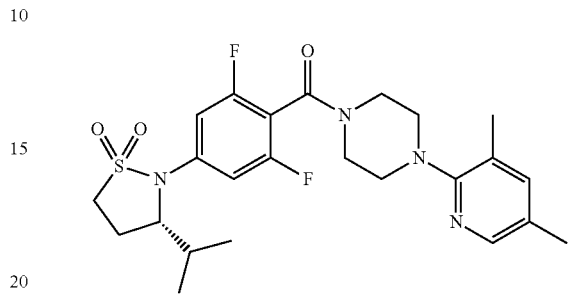

Using (S)-3-isopropylisothiazolidine 1,1-dioxide (320 mg) described in Preparation Example 6 and (4-bromo-2,6-difluorophenyl) [4-(3,5-dimethylpyridin-2-yl)piperazin-1-yl]methanone (410 mg) described in Preparation Example 111 and by the reaction and treatment in the same manner as in Example 4, the title compound (36 mg) was obtained.

MS (ESI) m/z: 493(M+H)⁺.

Example 15

Synthesis of (S)-[4-(4-chlorobenzoyl)piperidin-1-yl][6-(3-isopropyl-1,1-dioxo-1λ⁶-isothiazolidin-2-yl)pyridin-3-yl]methanone

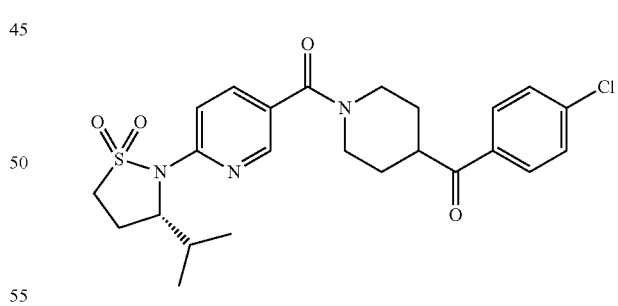

Using (S)-3-isopropylisothiazolidine 1,1-dioxide (320 mg) described in Preparation Example 6 and (6-bromopyridin-3-yl)[4-(4-chlorobenzoyl)piperidin-1-yl]methanone (408 mg) described in Preparation Example 190 and by the reaction and treatment in the same manner as in Example 4, the title compound (126 mg) was obtained.

MS (ESI) m/z: 490(M+H)⁺.

Example 16

Synthesis of (R)-[4-(2,4-dimethylphenyl)piperazin-1-yl][4-(4-methyl-1,1-dioxo-1λ⁶-isothiazolidin-2-yl)phenyl]methanone

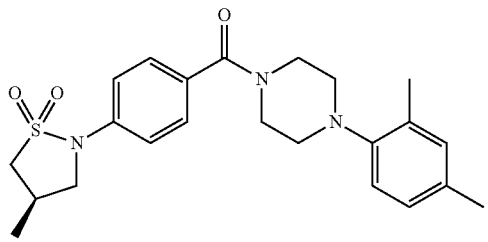

Using (R)-4-methylisothiazolidine 1,1-dioxide (203 mg) described in Preparation Example 7 and [4-(2,4-dimethylphenyl)piperazin-1-yl](4-iodophenyl)methanone (420 mg) described in Preparation Example 108 and by the reaction and treatment in the same manner as in Example 1, the title compound (39 mg) was obtained.

MS (ESI) m/z: 428(M+H)⁺.

Example 17

Synthesis of (R)-[4-(2,4-dimethylphenyl)piperazin-1-yl][2-methanesulfonyl-4-(4-methyl-1,1-dioxo-1λ⁶-isothiazolidin-2-yl)phenyl]methanone

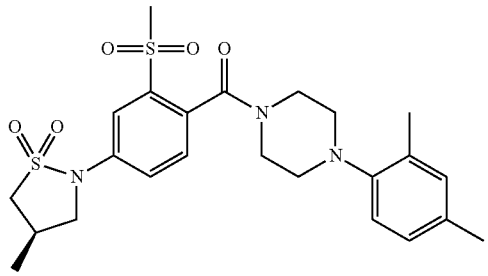

Using (R)-4-methylisothiazolidine 1,1-dioxide (203 mg) described in Preparation Example 7 and (4-bromo-2-methanesulfonylphenyl)[4-(2,4-dimethylphenyl)piperazin-1-yl]methanone (451 mg) described in Preparation Example 110 and by the reaction and treatment in the same manner as in Example 1, the title compound (23 mg) was obtained.

MS (ESI) m/z: 506(M+H)⁺.

Example 18

Synthesis of (R)-[4-(3,5-dimethylpyridin-2-yl)piperazin-1-yl][2-fluoro-4-(4-methyl-1,1-dioxo-1λ⁶-isothiazolidin-2-yl)phenyl]methanone

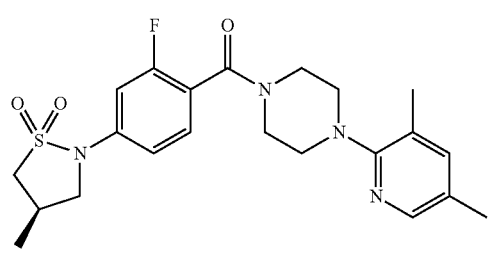 [SMILES: Cc1cnc(N2CCN(C(=O)c3ccc(N4C[C@@H](C)CS4(=O)=O)cc3F)CC2)c(C)c1]

Using (R)-4-methylisothiazolidine 1,1-dioxide (320 mg) described in Preparation Example 7 and (4-bromo-2-fluorophenyl)[4-(3,5-dimethylpyridin-2-yl)piperazin-1-yl]methanone (439 mg) described in Preparation Example 114 and by the reaction and treatment in the same manner as in Example 1, the title compound (63 mg) was obtained.

MS (ESI) m/z: 447(M+H)⁺.

Example 19

Synthesis of (S)-[4-(3,5-dimethylpyridin-2-yl)piperazin-1-yl][2-fluoro-4-(3-isopropyl-1,1-dioxo-1λ⁶-isothiazolidin-2-yl)phenyl]methanone

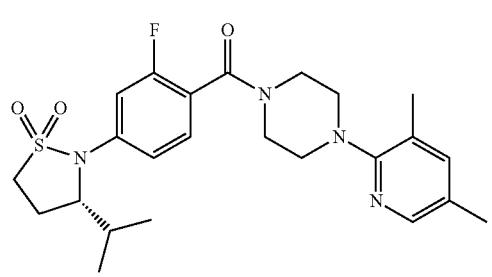 [SMILES: Cc1cnc(N2CCN(C(=O)c3ccc(N4[C@H](C(C)C)CCS4(=O)=O)cc3F)CC2)c(C)c1]

Using (S)-3-isopropylisothiazolidine 1,1-dioxide (400 mg) described in Preparation Example 6 and (4-bromo-2-fluorophenyl)[4-(3,5-dimethylpyridin-2-yl)piperazin-1-yl]methanone (392 mg) described in Preparation Example 114 and by the reaction and treatment in the same manner as in Example 4, the title compound (78 mg) was obtained.

MS (ESI) m/z: 475(M+H)⁺.

Example 20

Synthesis of (R)-[4-(2,4-dimethylphenyl)piperazin-1-yl][4-(3-isopropyl-1,1-dioxo-1λ⁶-isothiazolidin-2-yl)phenyl]methanone

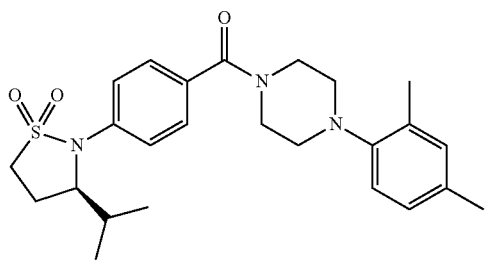 [SMILES: Cc1ccc(N2CCN(C(=O)c3ccc(N4[C@@H](C(C)C)CCS4(=O)=O)cc3)CC2)c(C)c1]

Using (R)-3-isopropylisothiazolidine 1,1-dioxide (300 mg) described in Preparation Example 8 and [4-(2,4-dimethylphenyl)piperazin-1-yl](4-iodophenyl)methanone (420 mg) described in Preparation Example 108 and by the reaction and treatment in the same manner as in Example 1, the title compound (19 mg) was obtained.

MS (ESI) m/z: 456(M+H)$^+$.

Example 21

Synthesis of (R)-[4-(2,4-dimethylphenyl)piperazin-1-yl][4-(3-isopropyl-1,1-dioxo-1λ⁶-isothiazolidin-2-yl)-2-methanesulfonylphenyl]methanone

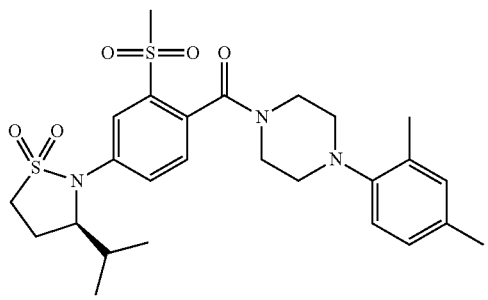

Using (R)-3-isopropylisothiazolidine 1,1-dioxide (300 mg) described in Preparation Example 8 and (4-bromo-2-methanesulfonylphenyl)[4-(2,4-dimethylphenyl)piperazin-1-yl]methanone (451 mg) described in Preparation Example 110 and by the reaction and treatment in the same manner as in Example 4, the title compound (41 mg) was obtained.

MS (ESI) m/z: 534(M+H)$^+$.

Example 22

Synthesis of (R)-[4-(3,5-dimethylpyridin-2-yl)piperazin-1-yl][2-fluoro-4-(3-isopropyl-1,1-dioxo-1λ⁶-isothiazolidin-2-yl)phenyl]methanone

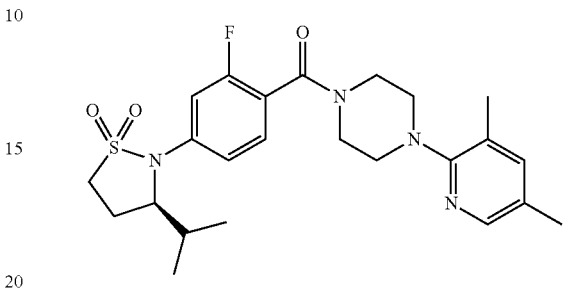

Using (R)-3-isopropylisothiazolidine 1,1-dioxide (300 mg) described in Preparation Example 8 and (4-bromo-2-fluorophenyl)[4-(3,5-dimethylpyridin-2-yl)piperazin-1-yl]methanone (440 mg) described in Preparation Example 114 and by the reaction and treatment in the same manner as in Example 4, the title compound (63 mg) was obtained.

MS (ESI) m/z: 475(M+H)$^+$.

Example 23

Synthesis of (S)-[4-(3,5-dimethylpyridin-2-yl)piperazin-1-yl][4-(3-isopropyl-1,1-dioxo-1λ⁶-isothiazolidin-2-yl)-2-methanesulfonylphenyl]methanone

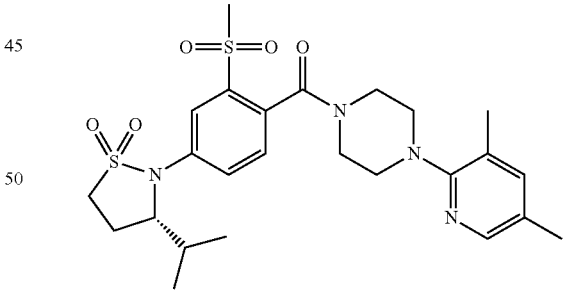

Using (S)-3-isopropylisothiazolidine 1,1-dioxide (240 mg) described in Preparation Example 6 and (4-bromo-2-methanesulfonylphenyl)[4-(3,5-dimethylpyridin-2-yl)piperazin-1-yl]methanone (452 mg) described in Preparation Example 112 and by the reaction and treatment in the same manner as in Example 4, the title compound (142 mg) was obtained.

MS (ESI) m/z: 535(M+H)$^+$.

Example 24

Synthesis of (S)-[4-(3,5-dimethylpyridin-2-yl)piperazin-1-yl][4-(3-isopropyl-1,1-dioxo-1λ⁶-isothiazolidin-2-yl)phenyl]methanone

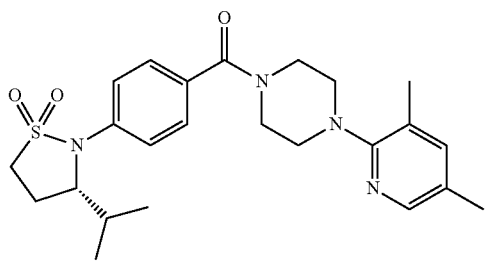

Using (S)-3-isopropylisothiazolidine 1,1-dioxide (300 mg) described in Preparation Example 6 and [4-(3,5-dimethylpyridin-2-yl)piperazin-1-yl](4-iodophenyl)methanone (421 mg) described in Preparation Example 113 and by the reaction and treatment in the same manner as in Example 4, the title compound (68 mg) was obtained.

MS (ESI) m/z: 457(M+H)$^+$.

Example 25

Synthesis of (S)-[4-(3,5-dimethylpyridin-2-yl)piperazin-1-yl][2-fluoro-4-(4-methyl-1,1-dioxo-1λ⁶-isothiazolidin-2-yl)phenyl]methanone

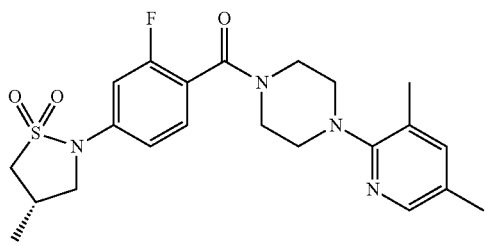

Using (S)-4-methylisothiazolidine 1,1-dioxide (150 mg) described in Preparation Example 4 and (4-bromo-2-fluorophenyl)[4-(3,5-dimethylpyridin-2-yl)piperazin-1-yl]methanone (219 mg) described in Preparation Example 114 and by the reaction and treatment in the same manner as in Example 4, the title compound (44 mg) was obtained.

MS (ESI) m/z: 447(M+H)$^+$.

Example 26

Synthesis of [4-(2,4-dimethylphenyl)piperazin-1-yl][4-(1,1-dioxo-1λ⁶-isothiazolidin-2-yl)-2-methanesulfonylphenyl]methanone sulfate

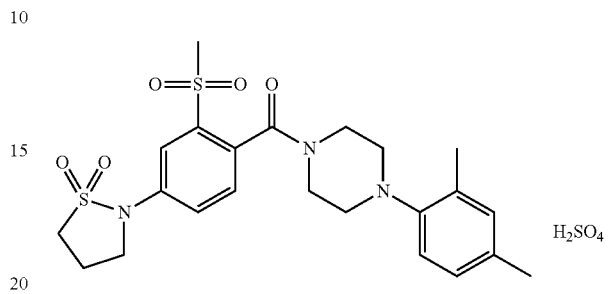

To a solution of [4-(2,4-dimethylphenyl)piperazin-1-yl][4-(1,1-dioxo-1λ⁶-isothiazolidin-2-yl)-2-methanesulfonylphenyl]methanone (100 mg) described in Example 11 in 1,4-dioxane (5 mL) was added sulfuric acid (2 drops), and the mixture was stirred at room temperature. To the reaction mixture was added ethyl acetate, and the precipitate was collected by filtration to give the title compound (81 mg).

MS (ESI) m/z: 492(M+H)$^+$.

Example 27

Synthesis of (S)-[4-(3-benzyloxymethyl-1,1-dioxo-1λ⁶-isothiazolidin-2-yl)-2-methanesulfonylphenyl][4-(2,4-dimethylphenyl)piperazin-1-yl]methanone

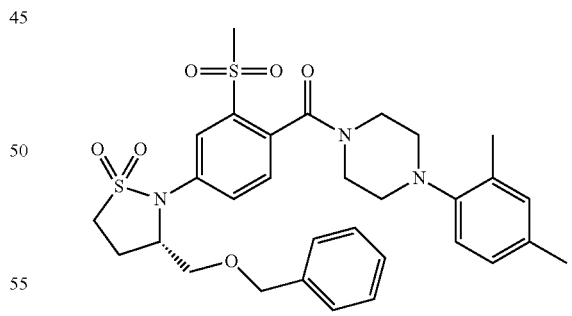

Using (S)-3-benzyloxymethylisothiazolidine 1,1-dioxide (536 mg) described in Preparation Example 1 and (4-bromo-2-methanesulfonylphenyl)[4-(2,4-dimethylphenyl)piperazin-1-yl]methanone (1.0 g) described in Preparation Example 110 and by the reaction and treatment in the same manner as in Example 4, the title compound (950 mg) was obtained.

MS (ESI) m/z: 612(M+H)$^+$.

Example 28

Synthesis of (S)-[4-(3-benzyloxymethyl-1,1-dioxo-1λ⁶-isothiazolidin-2-yl)phenyl][4-(3,5-dimethylpyridin-2-yl)piperazin-1-yl]methanone hydrochloride

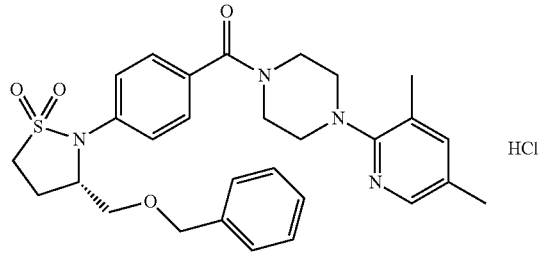 [SMILES: Cc1cnc(N2CCN(C(=O)c3ccc(N4[C@H](COCc5ccccc5)CCS4(=O)=O)cc3)CC2)c(C)c1 ; Cl]

Using (S)-3-benzyloxymethylisothiazolidine 1,1-dioxide (287 mg) described in Preparation Example 1 and [4-(3,5-dimethylpyridin-2-yl)piperazin-1-yl](4-iodophenyl)methanone (500 mg) described in Preparation Example 113 and by the reaction and treatment in the same manner as in Example 1, (S)-[4-(3-benzyloxymethyl-1,1-dioxo-1λ⁶-isothiazolidin-2-yl)phenyl][4-(3,5-dimethyl-pyridin-2-yl)piperazin-1-yl]methanone (490 mg) was obtained. The obtained (S)-[4-(3-benzyloxymethyl-1,1-dioxo-1λ⁶-isothiazolidin-2-yl)phenyl][4-(3,5-dimethyl-pyridin-2-yl)piperazin-1-yl]methanone (490 mg) was dissolved in ethyl acetate, 4N hydrogen chloride/ethyl acetate was added, and the precipitate was collected by filtration to give the title compound (410 mg).

MS (ESI) m/z: 535(M+H)⁺.

Example 29

Synthesis of (S)-[4-(2,4-dimethylphenyl)piperazin-1-yl][4-(3-hydroxymethyl-1,1-dioxo-1λ⁶-isothiazolidin-2-yl)-2-methanesulfonylphenyl]methanone

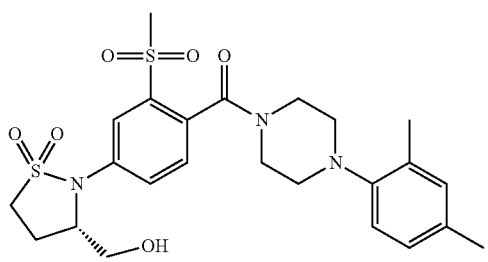 [SMILES: Cc1ccc(N2CCN(C(=O)c3ccc(N4[C@H](CO)CCS4(=O)=O)cc3S(C)(=O)=O)CC2)c(C)c1]

(S)-[4-(3-benzyloxymethyl-1,1-dioxo-1λ⁶-isothiazolidin-2-yl)-2-methanesulfonylphenyl][4-(2,4-dimethylphenyl)piperazin-1-yl]methanone (930 mg) described in Example 27 was dissolved in ethanol (50 mL), palladium carbon (200 mg) and 1N hydrochloric acid (2 mL) were added, and the mixture was stirred at room temperature for 3.5 hr under a hydrogen atmosphere. The insoluble material was separated by filtration from the reaction mixture, and the filtrate was concentrated. To the obtained residue was added 1N aqueous sodium hydroxide solution, and the mixture was extracted with ethyl acetate. The organic layer was washed with saturated brine, and the solvent was evaporated. The obtained residue was purified by column chromatography (hexane:ethyl acetate) to give the title compound (705 mg).

MS (ESI) m/z: 522(M+H)⁺.

Example 30

Synthesis of (S)-[6-(3-benzyloxymethyl-1,1-dioxo-1λ⁶-isothiazolidin-2-yl)pyridin-3-yl][4-(2,4-dimethylphenyl)piperazin-1-yl]methanone

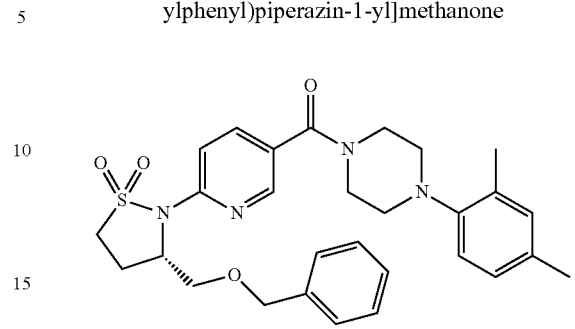

Using (S)-3-benzyloxymethylisothiazolidine 1,1-dioxide (536 mg) described in Preparation Example 1 and (6-bromopyridin-3-yl) [4-(2,4-dimethylphenyl)piperazin-1-yl]methanone (831 mg) described in Preparation Example 115 and by the reaction and treatment in the same manner as in Example 4, the title compound (729 mg) was obtained.

MS (ESI) m/z: 535(M+H)⁺.

Example 31

Synthesis of (S)-[4-(3,5-dimethylpyridin-2-yl)piperazin-1-yl][4-(3-hydroxymethyl-1,1-dioxo-1λ⁶-isothiazolidin-2-yl)phenyl]methanone

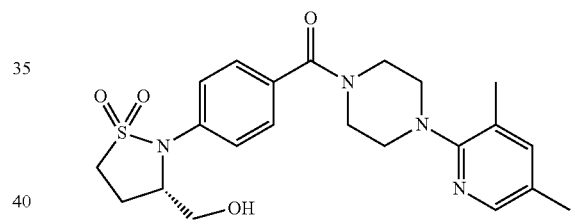

Using (S)-[4-(3-benzyloxymethyl-1,1-dioxo-1λ⁶-isothiazolidin-2-yl)phenyl][4-(3,5-dimethylpyridin-2-yl)piperazin-1-yl]methanone hydrochloride (355 mg) described in Example 28 and by the reaction and treatment in the same manner as in Example 29, the title compound (124 mg) was obtained.

MS (ESI) m/z: 445(M+H)⁺.

Example 32

Synthesis of (S)-[4-(2,4-dimethylphenyl)piperazin-1-yl][4-(3-hydroxymethyl-1,1-dioxo-1λ⁶-isothiazolidin-2-yl)phenyl]methanone

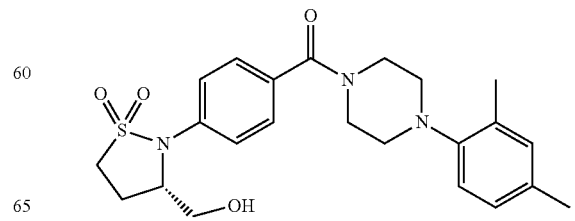

Using (S)-3-benzyloxymethylisothiazolidine 1,1-dioxide (536 mg) described in Preparation Example 1 and [4-(2,4-dimethylphenyl)piperazin-1-yl](4-iodophenyl)methanone (933 mg) described in Preparation Example 108 and by the reaction and treatment in the same manner as in Example 1, (S)-[4-(3-benzyloxymethyl-1,1-dioxo-1λ$^6$-isothiazolidin-2-yl)phenyl][4-(2,4-dimethylphenyl)piperazin-1-yl]methanone (1.05 g) was obtained. Using the obtained (S)-[4-(3-benzyloxymethyl-1,1-dioxo-1λ$^6$-isothiazolidin-2-yl)phenyl][4-(2,4-dimethylphenyl)piperazin-1-yl]methanone (1.05 g) and by the reaction and treatment in the same manner as in Example 29, the title compound (590 mg) was obtained.

MS (ESI) m/z: 444(M+H)$^+$.

Example 33

Synthesis of (S)-[4-(3-benzyloxymethyl-1,1-dioxo-1λ$^6$-isothiazolidin-2-yl)-2,6-difluorophenyl][4-(3,5-dimethylpyridin-2-yl)piperazin-1-yl]methanone

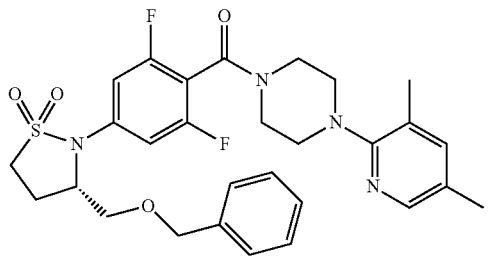 [SMILES: Cc1cnc(N2CCN(C(=O)c3c(F)cc(N4[C@H](COCc5ccccc5)CCS4(=O)=O)cc3F)CC2)c(C)c1]

Using (S)-3-benzyloxymethylisothiazolidine 1,1-dioxide (536 mg) described in Preparation Example 1 and (4-bromo-2,6-difluorophenyl)[4-(3,5-dimethylpyridin-2-yl)piperazin-1-yl]methanone (911 mg) described in Preparation Example 111 and by the reaction and treatment in the same manner as in Example 4, the title compound (760 mg) was obtained.

MS (ESI) m/z: 571(M+H)$^+$.

Example 34

Synthesis of (S)-[4-(2,4-dimethylphenyl)piperazin-1-yl][6-(3-hydroxymethyl-1,1-dioxo-1λ$^6$-isothiazolidin-2-yl)pyridin-3-yl]methanone

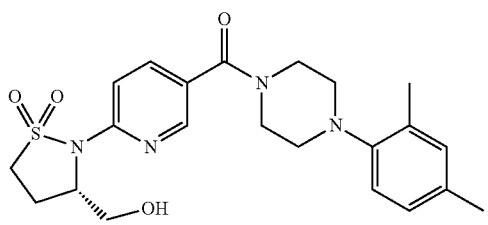 [SMILES: Cc1ccc(N2CCN(C(=O)c3ccc(N4[C@H](CO)CCS4(=O)=O)nc3)CC2)c(C)c1]

Using (S)-[6-(3-benzyloxymethyl-1,1-dioxo-1λ$^6$-isothiazolidin-2-yl)pyridin-3-yl][4-(2,4-dimethylphenyl)piperazin-1-yl]methanone (668 mg) described in Example 30 and by the reaction and treatment in the same manner as in Example 29, the title compound (501 mg) was obtained.

MS (ESI) m/z: 445(M+H)$^+$.

Example 35

Synthesis of (S)-[2,6-difluoro-4-(3-hydroxymethyl-1,1-dioxo-1λ$^6$-isothiazolidin-2-yl)phenyl][4-(3,5-dimethylpyridin-2-yl)piperazin-1-yl]methanone

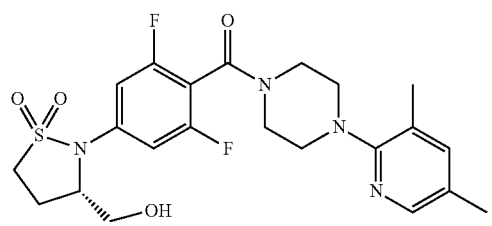 [SMILES: Cc1cnc(N2CCN(C(=O)c3c(F)cc(N4[C@H](CO)CCS4(=O)=O)cc3F)CC2)c(C)c1]

Using (S)-[4-(3-benzyloxymethyl-1,1-dioxo-1λ$^6$-isothiazolidin-2-yl)-2,6-difluorophenyl][4-(3,5-dimethylpyridin-2-yl)piperazin-1-yl]methanone (710 mg) described in Example 33 and by the reaction and treatment in the same manner as in Example 29, the title compound (320 mg) was obtained.

MS (ESI) m/z: 481(M+H)$^+$.

Example 36

Synthesis of (S)-[2,6-difluoro-4-(3-methoxymethyl-1,1-dioxo-1λ$^6$-isothiazolidin-2-yl)phenyl][4-(3,5-dimethylpyridin-2-yl)piperazin-1-yl]methanone

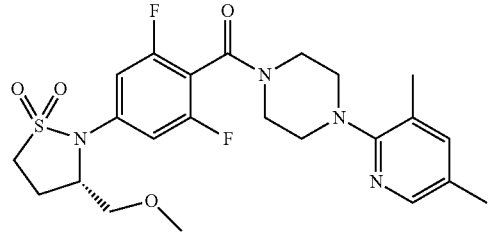 [SMILES: COC[C@@H]1CCS(=O)(=O)N1c1cc(F)c(C(=O)N2CCN(c3ncc(C)cc3C)CC2)c(F)c1]

(S)-[2,6-difluoro-4-(3-hydroxymethyl-1,1-dioxo-1λ$^6$-isothiazolidin-2-yl)phenyl][4-(3,5-dimethylpyridin-2-yl)piperazin-1-yl]methanone (270 mg) described in Example 35 was dissolved in tetrahydrofuran, sodium hydride (48 mg) was added, and the mixture was stirred at room temperature for 30 min. Then, to the reaction mixture was added methyl tosylate (203 mg), and the mixture was stirred at room temperature overnight. Water was added to the reaction mixture, and the mixture was extracted with ethyl acetate. The organic layer was washed with saturated brine, dried over sodium sulfate, and the solvent was evaporated. The obtained residue was purified by column chromatography (hexane:ethyl acetate) to give the title compound (5 mg).

MS (ESI) m/z: 495(M+H)$^+$.

Example 37

Synthesis of (S)-[4-(2,4-dimethylphenyl)piperazin-1-yl][4-(3-methoxymethyl-1,1-dioxo-1λ⁶-isothiazolidin-2-yl)phenyl]methanone

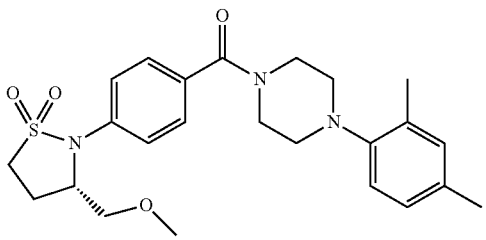 [SMILES: COC[C@@H]1CCS(=O)(=O)N1c1ccc(C(=O)N2CCN(c3ccc(C)cc3C)CC2)cc1]

Using (S)-[4-(2,4-dimethylphenyl)piperazin-1-yl][4-(3-hydroxymethyl-1,1-dioxo-1λ⁶-isothiazolidin-2-yl)phenyl]methanone (480 mg) described in Example 32 and methyl tosylate (0.16 mL) and by the reaction and treatment in the same manner as in Example 36, the title compound (177 mg) was obtained.

MS (ESI) m/z: 458(M+H)⁺.

Example 38

Synthesis of (S)-[4-(2,4-dimethylphenyl)piperazin-1-yl][2-methanesulfonyl-4-(3-methoxymethyl-1,1-dioxo-1λ⁶-isothiazolidin-2-yl)phenyl]methanone

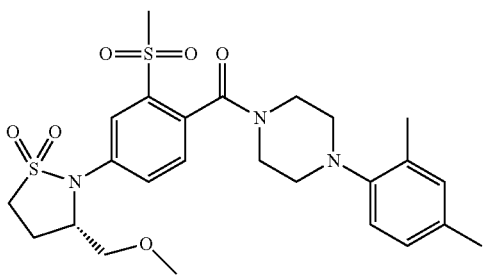 [SMILES: COC[C@@H]1CCS(=O)(=O)N1c1ccc(C(=O)N2CCN(c3ccc(C)cc3C)CC2)c(S(C)(=O)=O)c1]

Using (S)-[4-(2,4-dimethylphenyl)piperazin-1-yl][4-(3-hydroxymethyl-1,1-dioxo-1λ⁶-isothiazolidin-2-yl)-2-methanesulfonylphenyl]methanone (880 mg) described in Example 29 and methyl tosylate (0.25 mL) and by the reaction and treatment in the same manner as in Example 36, the title compound (71 mg) was obtained.

MS (ESI) m/z: 536(M+H)⁺.

Example 39

Synthesis of (S)-[4-(2,4-dimethylphenyl)piperazin-1-yl][2-fluoro-4-(3-hydroxymethyl-1,1-dioxo-1λ⁶-isothiazolidin-2-yl)phenyl]methanone

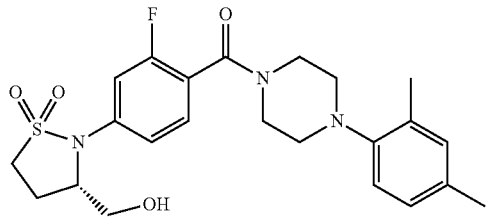 [SMILES: Cc1ccc(N2CCN(C(=O)c3ccc(N4[C@H](CO)CCS4(=O)=O)cc3F)CC2)c(C)c1]

Using (S)-3-benzyloxymethylisothiazolidine 1,1-dioxide (536 mg) described in Preparation Example 1 and (4-bromo-2-fluorophenyl)[4-(2,4-dimethylphenyl)piperazin-1-yl]methanone (869 mg) described in Preparation Example 116 and by the reaction and treatment in the same manner as in Example 32, the title compound (620 mg) was obtained.

MS (ESI) m/z: 462(M+H)⁺.

Example 40

Synthesis of (S)-[4-(2,4-dimethylphenyl)piperazin-1-yl][2-fluoro-4-(3-methoxymethyl-1,1-dioxo-1λ⁶-isothiazolidin-2-yl)phenyl]methanone

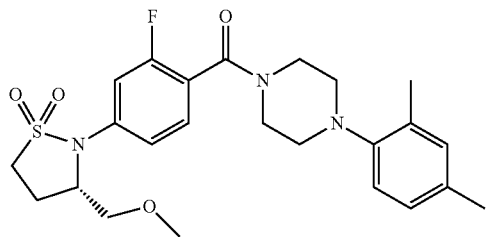 [SMILES: COC[C@@H]1CCS(=O)(=O)N1c1ccc(C(=O)N2CCN(c3ccc(C)cc3C)CC2)c(F)c1]

Using (S)-[4-(2,4-dimethylphenyl)piperazin-1-yl][2-fluoro-4-(3-hydroxymethyl-1,1-dioxo-1λ⁶-isothiazolidin-2-yl)phenyl]methanone (550 mg) described in Example 39 and methyl tosylate (0.18 mL) and by the reaction and treatment in the same manner as in Example 36, the title compound (48 mg) was obtained.

MS (ESI) m/z: 476(M+H)⁺.

Example 41

Synthesis of (S)-[4-(3,5-dicyclopropylpyridin-2-yl)piperazin-1-yl][2-fluoro-4-(3-hydroxymethyl-1,1-dioxo-1λ⁶-isothiazolidin-2-yl)phenyl]methanone

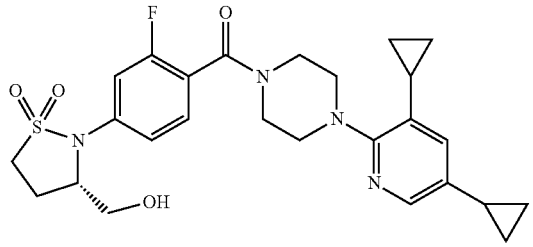 [SMILES: O=C(c1ccc(N2[C@H](CO)CCS2(=O)=O)cc1F)N1CCN(c2ncc(C3CC3)cc2C2CC2)CC1]

Using (S)-3-benzyloxymethylisothiazolidine 1,1-dioxide (393 mg) described in Preparation Example 1 and [4-(3,5-dicyclopropylpyridin-2-yl)piperazin-1-yl](2-fluoro-4-iodophenyl)methanone (800 mg) described in Preparation Example 164 and by the reaction and treatment in the same manner as in Example 32, the title compound (365 mg) was obtained.

MS (ESI) m/z: 515(M+H)⁺.

Example 42

Synthesis of (S)-[4-(5-cyclopropyl-3-methylpyridin-2-yl)piperazin-1-yl][4-(4-methyl-1,1-dioxo-1λ⁶-isothiazolidin-2-yl)phenyl]methanone

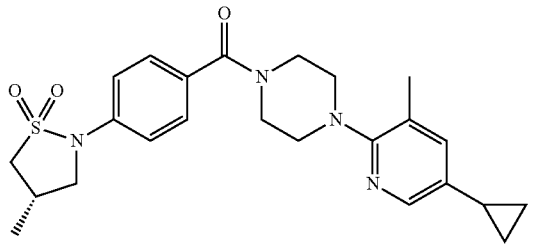 [SMILES: Cc1cc(C2CC2)cnc1N1CCN(C(=O)c2ccc(N3C[C@H](C)CS3(=O)=O)cc2)CC1]

Using (S)-4-methylisothiazolidine 1,1-dioxide (240 mg) described in Preparation Example 4 and [4-(5-cyclopropyl-3-methylpyridin-2-yl)piperazin-1-yl](4-iodophenyl)methanone (650 mg) described in Preparation Example 117 and by the reaction and treatment in the same manner as in Example 1, the title compound (264 mg) was obtained.

MS (ESI) m/z: 455(M+H)⁺.

Example 43

Synthesis of (R)-[4-(5-cyclopropyl-3-methylpyridin-2-yl)piperazin-1-yl][4-(4-methyl-1,1-dioxo-1λ⁶-isothiazolidin-2-yl)phenyl]methanone

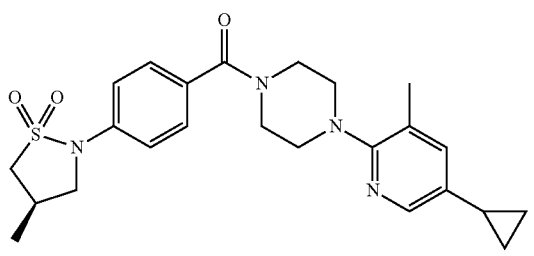 [SMILES: Cc1cc(C2CC2)cnc1N1CCN(C(=O)c2ccc(N3C[C@@H](C)CS3(=O)=O)cc2)CC1]

Using (R)-4-methylisothiazolidine 1,1-dioxide (91 mg) described in Preparation Example 7 and [4-(5-cyclopropyl-3-methylpyridin-2-yl)piperazin-1-yl](4-iodophenyl)methanone (200 mg) described in Preparation Example 117 and by the reaction and treatment in the same manner as in Example 1, the title compound (70 mg) was obtained.

MS (ESI) m/z: 455(M+H)⁺.

Example 44

Synthesis of (S)-[4-(3,5-dicyclopropylpyridin-2-yl)piperazin-1-yl][2-fluoro-4-(4-methyl-1,1-dioxo-1λ⁶-isothiazolidin-2-yl)phenyl]methanone

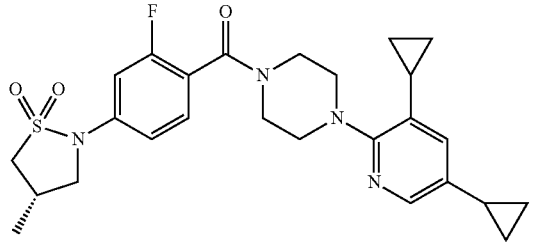

Using (S)-4-methylisothiazolidine 1,1-dioxide (235 mg) described in Preparation Example 4 and [4-(3,5-dicyclopropylpyridin-2-yl)piperazin-1-yl](2-fluoro-4-iodophenyl)methanone (570 mg) described in Preparation Example 164 and by the reaction and treatment in the same manner as in Example 1, the title compound (190 mg) was obtained.

MS (ESI) m/z: 499(M+H)⁺.

Example 45

Synthesis of (S)-[4-(3,5-dimethylpyridin-2-yl)piperazin-1-yl][2-methyl-4-(4-methyl-1,1-dioxo-1λ⁶-isothiazolidin-2-yl)phenyl]methanone

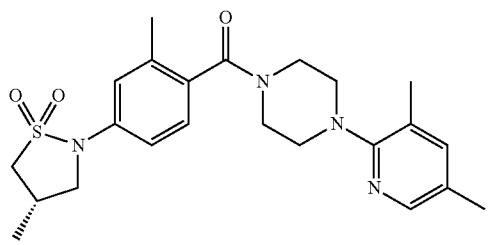 [SMILES: Cc1cnc(N2CCN(C(=O)c3ccc(N4C[C@H](C)CS4(=O)=O)cc3C)CC2)c(C)c1]

Using (S)-4-methylisothiazolidine 1,1-dioxide (110 mg) described in Preparation Example 4 and (4-bromo-2-methylphenyl)[4-(3,5-dimethylpyridin-2-yl)piperazin-1-yl]methanone (210 mg) described in Preparation Example 118 and by the reaction and treatment in the same manner as in Example 4, the title compound (42 mg) was obtained.

MS (ESI) m/z: 443(M+H)⁺.

Example 46

Synthesis of (S)-[4-(5-cyclopropyl-3-methylpyridin-2-yl)piperazin-1-yl][2-methanesulfonyl-4-(4-methyl-1,1-dioxo-1λ⁶-isothiazolidin-2-yl)phenyl]methanone

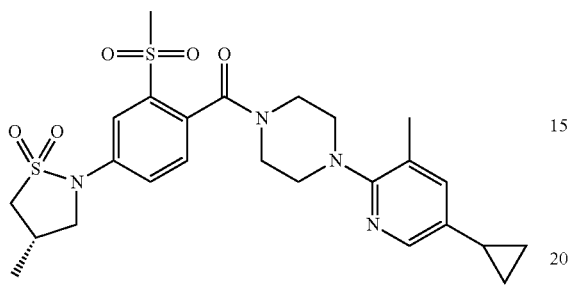

Using (S)-4-methylisothiazolidine 1,1-dioxide (140 mg) described in Preparation Example 4 and (4-bromo-2-methanesulfonylphenyl)[4-(5-cyclopropyl-3-methylpyridin-2-yl)piperazin-1-yl]methanone (330 mg) described in Preparation Example 126 and by the reaction and treatment in the same manner as in Example 4, the title compound (148 mg) was obtained.

MS (ESI) m/z: 533(M+H)$^+$.

Example 47

Synthesis of (S)-[4-(4-methyl-1,1-dioxo-1λ⁶-isothiazolidin-2-yl)phenyl][4-(3,5,6-trimethylpyridin-2-yl)piperazin-1-yl]methanone

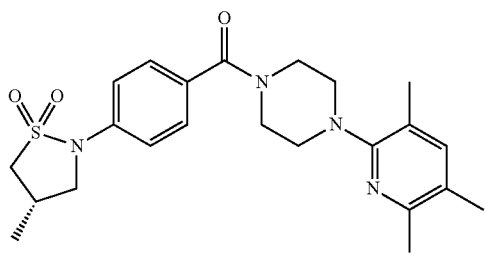 [SMILES: Cc1cc(C)c(N2CCN(C(=O)c3ccc(N4C[C@H](C)CS4(=O)=O)cc3)CC2)nc1C]

Using (S)-4-methylisothiazolidine 1,1-dioxide (90 mg) described in Preparation Example 4 and (4-iodophenyl)[4-(3,5,6-trimethylpyridin-2-yl)piperazin-1-yl]methanone (193 mg) described in Preparation Example 120 and by the reaction and treatment in the same manner as in Example 4, the title compound (108 mg) was obtained.

MS (ESI) m/z: 443(M+H)$^+$.

Example 48

Synthesis of (S)-[4-(3,5-dimethylpyridin-2-yl)piperazin-1-yl][2-methanesulfonyl-4-(4-methyl-1,1-dioxo-1λ⁶-isothiazolidin-2-yl)phenyl]methanone

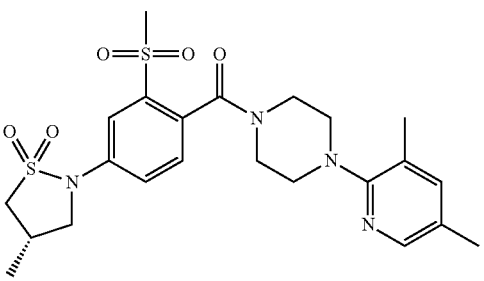

Using (S)-4-methylisothiazolidine 1,1-dioxide (100 mg) described in Preparation Example 4 and (4-bromo-2-methanesulfonylphenyl)[4-(3,5-dimethylpyridin-2-yl)piperazin-1-yl]methanone (220 mg) described in Preparation Example 112 and by the reaction and treatment in the same manner as in Example 4, the title compound (49 mg) was obtained.

MS (ESI) m/z: 507(M+H)$^+$.

Example 49

Synthesis of (S)-[4-(5-cyclopropyl-3-methylpyridin-2-yl)piperazin-1-yl][2-fluoro-4-(4-methyl-1,1-dioxo-1λ⁶-isothiazolidin-2-yl)phenyl]methanone

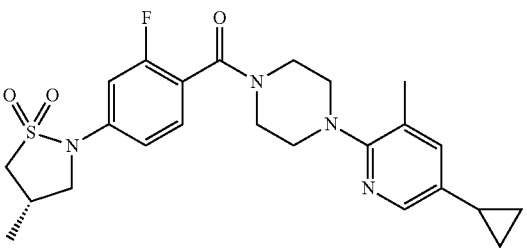

Using (S)-4-methylisothiazolidine 1,1-dioxide (110 mg) described in Preparation Example 4 and (4-bromo-2-fluorophenyl)[4-(5-cyclopropyl-3-methylpyridin-2-yl)piperazin-1-yl]methanone (227 mg) described in Preparation Example 121 and by the reaction and treatment in the same manner as in Example 4, the title compound (104 mg) was obtained.

MS (ESI) m/z: 473(M+H)$^+$.

Example 50

Synthesis of (S)-[2-methanesulfonyl-4-(4-methyl-1,1-dioxo-1λ⁶-isothiazolidin-2-yl)phenyl][4-(3,5,6-trimethylpyridin-2-yl)piperazin-1-yl]methanone

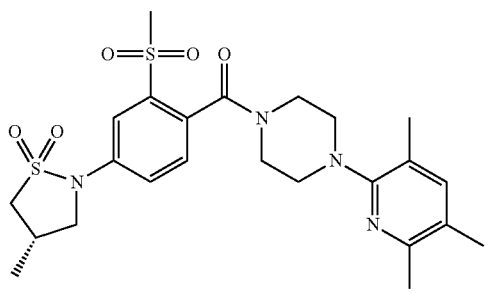

Using (S)-4-methylisothiazolidine 1,1-dioxide (110 mg) described in Preparation Example 4 and (4-bromo-2-methanesulfonylphenyl) [4-(3,5,6-trimethylpyridin-2-yl)piperazin-1-yl]methanone (253 mg) described in Preparation Example 122 and by the reaction and treatment in the same manner as in Example 4, the title compound (151 mg) was obtained.

MS (ESI) m/z: 521(M+H)⁺.

Example 51

Synthesis of (S)-[4-(3-cyclopropyl-5-trifluoromethylpyridin-2-yl)piperazin-1-yl][2-fluoro-4-(4-methyl-1,1-dioxo-1λ⁶-isothiazolidin-2-yl)phenyl]methanone

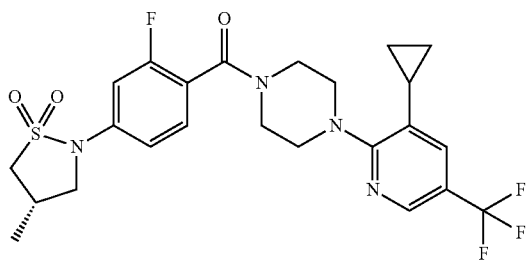 [SMILES: C[C@H]1CN(c2ccc(C(=O)N3CCN(c4ncc(C(F)(F)F)cc4C4CC4)CC3)c(F)c2)S(=O)(=O)C1]

Using (S)-4-methylisothiazolidine 1,1-dioxide (110 mg) described in Preparation Example 4 and (4-bromo-2-fluorophenyl)[4-(3-cyclopropyl-5-trifluoromethylpyridin-2-yl)piperazin-1-yl]methanone (256 mg) described in Preparation Example 123 and by the reaction and treatment in the same manner as in Example 4, the title compound (164 mg) was obtained.

MS (ESI) m/z: 527(M+H)⁺.

Example 52

Synthesis of (S)-[4-(5-cyclopropyl-3-methylpyridin-2-yl)piperazin-1-yl][2-methyl-4-(4-methyl-1,1-dioxo-1λ⁶-isothiazolidin-2-yl)phenyl]methanone

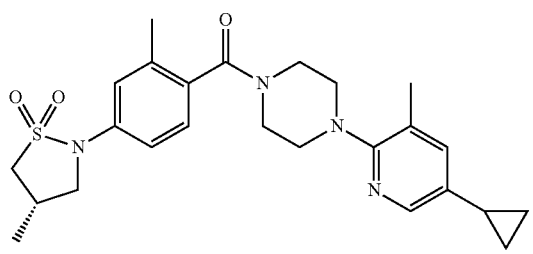

Using (S)-4-methylisothiazolidine 1,1-dioxide (110 mg) described in Preparation Example 4 and (4-bromo-2-methylphenyl)[4-(5-cyclopropyl-3-methylpyridin-2-yl)piperazin-1-yl]methanone (225 mg) described in Preparation Example 124 and by the reaction and treatment in the same manner as in Example 4, the title compound (150 mg) was obtained.

MS (ESI) m/z: 469(M+H)⁺.

Example 53

Synthesis of (R)-[4-(5-cyclopropyl-3-methylpyridin-2-yl)piperazin-1-yl][2-fluoro-4-(4-methyl-1,1-dioxo-1λ⁶-isothiazolidin-2-yl)phenyl]methanone

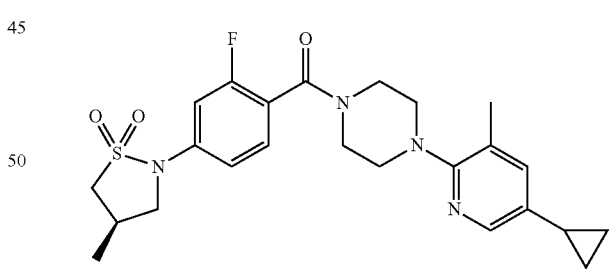

Using (R)-4-methylisothiazolidine 1,1-dioxide (180 mg) described in Preparation Example 7 and (4-bromo-2-fluorophenyl)[4-(5-cyclopropyl-3-methylpyridin-2-yl)piperazin-1-yl]methanone (371 mg) described in Preparation Example 121 and by the reaction and treatment in the same manner as in Example 4, the title compound (144 mg) was obtained.

MS (ESI) m/z: 473(M+H)⁺.

Example 54

Synthesis of (S)-[4-(3,5-dimethylpyridin-2-yl)piperazin-1-yl][3-fluoro-4-(4-methyl-1,1-dioxo-1λ⁶-isothiazolidin-2-yl)phenyl]methanone

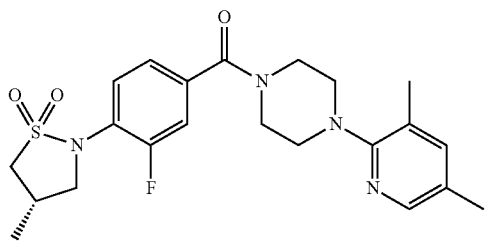 [SMILES: Cc1cnc(N2CCN(C(=O)c3ccc(N4C[C@H](C)CS4(=O)=O)c(F)c3)CC2)c(C)c1]

Using (S)-4-methylisothiazolidine 1,1-dioxide (119 mg) described in Preparation Example 4 and (4-bromo-3-fluorophenyl)[4-(3,5-dimethylpyridin-2-yl)piperazin-1-yl]methanone (230 mg) described in Preparation Example 125 and by the reaction and treatment in the same manner as in Example 4, the title compound (38 mg) was obtained.

MS (ESI) m/z: 447(M+H)$^+$.

Example 55

Synthesis of (S)-[2-chloro-4-(4-methyl-1,1-dioxo-1λ⁶-isothiazolidin-2-yl)phenyl][4-(3,5-dimethylpyridin-2-yl)piperazin-1-yl]methanone

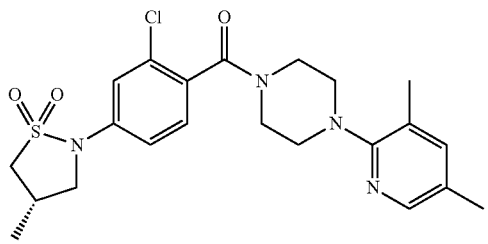

Using (S)-4-methylisothiazolidine 1,1-dioxide (101 mg) described in Preparation Example 4 and (4-bromo-2-chlorophenyl)[4-(3,5-dimethylpyridin-2-yl)piperazin-1-yl]methanone (204 mg) described in Preparation Example 119 and by the reaction and treatment in the same manner as in Example 4, the title compound (49 mg) was obtained.

MS (ESI) m/z: 463(M+H)$^+$.

Example 56

Synthesis of (S)-[4-(2,4-dimethylphenyl)piperazin-1-yl][2-fluoro-4-(4-methyl-1,1-dioxo-1λ⁶-isothiazolidin-2-yl)phenyl]methanone

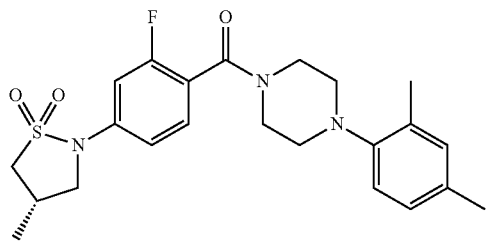 [SMILES: Cc1cnc(N2CCN(C(=O)c3ccc(N4C[C@H](C)CS4(=O)=O)cc3Cl)CC2)c(C)c1]

Using (S)-4-methylisothiazolidine 1,1-dioxide (101 mg) described in Preparation Example 4 and (4-bromo-2-fluorophenyl)[4-(2,4-dimethylphenyl)piperazin-1-yl]methanone (196 mg) described in Preparation Example 116 and by the reaction and treatment in the same manner as in Example 4, the title compound (62 mg) was obtained.

MS (ESI) m/z: 446(M+H)$^+$.

Example 57

Synthesis of (S)-[4-(3,5-dimethylpyridin-2-yl)piperazin-1-yl][6-(4-methyl-1,1-dioxo-1λ⁶-isothiazolidin-2-yl)pyridin-3-yl]methanone

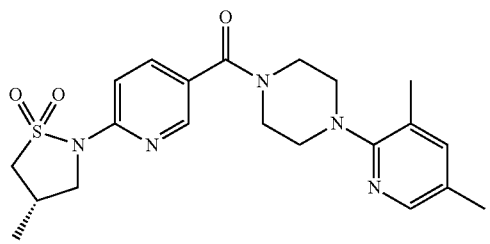

Using (S)-4-methylisothiazolidine 1,1-dioxide (203 mg) described in Preparation Example 4 and (6-bromopyridin-3-yl)[4-(3,5-dimethylpyridin-2-yl)piperazin-1-yl]methanone (375 mg) described in Preparation Example 127 and by the reaction and treatment in the same manner as in Example 1, the title compound (170 mg) was obtained.

MS (ESI) m/z: 430(M+H)$^+$.

Example 58

Synthesis of (S)-[4-(2,4-dimethylphenyl)piperazin-1-yl][6-(4-methyl-1,1-dioxo-1λ⁶-isothiazolidin-2-yl)pyridin-3-yl]methanone

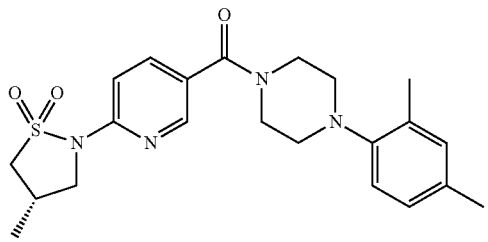 [SMILES: Cc1ccc(N2CCN(C(=O)c3ccc(N4C[C@H](C)CS4(=O)=O)nc3)CC2)c(C)c1]

Using (S)-4-methylisothiazolidine 1,1-dioxide (203 mg) described in Preparation Example 4 and (6-bromopyridin-3-yl) [4-(2,4-dimethylphenyl)piperazin-1-yl]methanone (374 mg) described in Preparation Example 115 and by the reaction and treatment in the same manner as in Example 1, the title compound (180 mg) was obtained.

MS (ESI) m/z: 429(M+H)⁺.

Example 59

Synthesis of (S)-[4-(5-cyclopropyl-3-methylpyridin-2-yl)piperazin-1-yl][2-fluoro-4-(3-hydroxymethyl-1,1-dioxo-1λ⁶-isothiazolidin-2-yl)phenyl]methanone

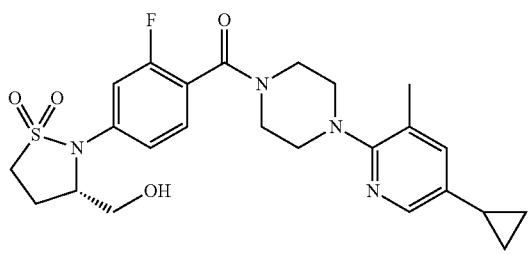

Using (S)-3-benzyloxymethylisothiazolidine 1,1-dioxide (241 mg) described in Preparation Example 1 and (4-bromo-2-fluorophenyl)[4-(5-cyclopropyl-3-methylpyridin-2-yl)piperazin-1-yl]methanone (418 mg) described in Preparation Example 121 and by the reaction and treatment in the same manner as in Example 32, the title compound (49 mg) was obtained.

MS (ESI) m/z: 489(M+H)⁺.

Example 60

Synthesis of (S)-[2-fluoro-4-(4-methyl-1,1-dioxo-1λ⁶-isothiazolidin-2-yl)phenyl][4-(3,5,6-trimethylpyridin-2-yl)piperazin-1-yl]methanone

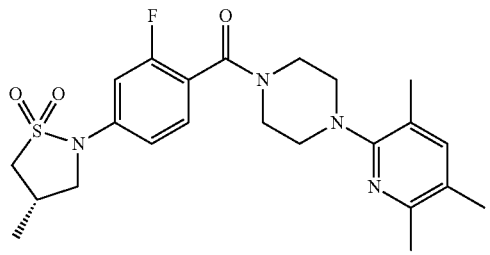 [SMILES: Cc1cc(C)c(N2CCN(C(=O)c3ccc(N4C[C@H](C)CS4(=O)=O)cc3F)CC2)nc1C]

Using (S)-4-methylisothiazolidine 1,1-dioxide (152 mg) described in Preparation Example 4 and (4-bromo-2-fluorophenyl)[4-(3,5,6-trimethylpyridin-2-yl)piperazin-1-yl]methanone (305 mg) described in Preparation Example 128 and by the reaction and treatment in the same manner as in Example 4, the title compound (112 mg) was obtained.

MS (ESI) m/z: 461(M+H)⁺.

Example 61

Synthesis of (S)-[4-(3-cyclopropyl-5-methylpyridin-2-yl)piperazin-1-yl][2-fluoro-4-(4-methyl-1,1-dioxo-1λ⁶-isothiazolidin-2-yl)phenyl]methanone

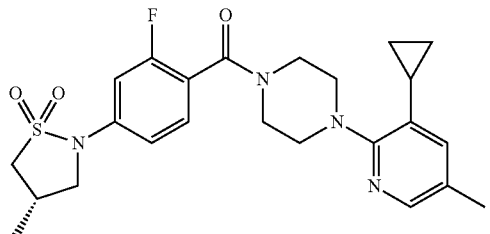

Using (S)-4-methylisothiazolidine 1,1-dioxide (203 mg) described in Preparation Example 4 and (4-bromo-2-fluorophenyl)[4-(3-cyclopropyl-5-methylpyridin-2-yl)piperazin-1-yl]methanone (418 mg) described in Preparation Example 129 and by the reaction and treatment in the same manner as in Example 4, the title compound (108 mg) was obtained.

MS (ESI) m/z: 473(M+H)⁺.

Example 62

Synthesis of (S)-[4-(2,4-dimethylphenyl)piperazin-1-yl][4-(3-hydroxymethyl-1,1-dioxo-1λ⁶-isothiazolidin-2-yl)-2-methylphenyl]methanone

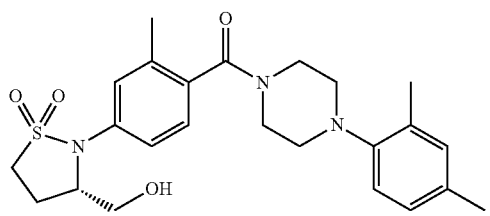 [SMILES: Cc1ccc(N2CCN(C(=O)c3ccc(N4[C@H](CO)CCS4(=O)=O)cc3C)CC2)c(C)c1]

Using (S)-3-benzyloxymethylisothiazolidine 1,1-dioxide (482 mg) described in Preparation Example 1 and (4-bromo-2-methylphenyl)[4-(2,4-dimethylphenyl)piperazin-1-yl]methanone (774 mg) described in Preparation Example 130 and by the reaction and treatment in the same manner as in Example 32, the title compound (662 mg) was obtained.

MS (ESI) m/z: 458(M+H)$^+$.

Example 63

Synthesis of (S)-[2,6-difluoro-4-(3-hydroxymethyl-1,1-dioxo-1$\lambda^6$-isothiazolidin-2-yl)phenyl][4-(2,4-dimethylphenyl)piperazin-1-yl]methanone

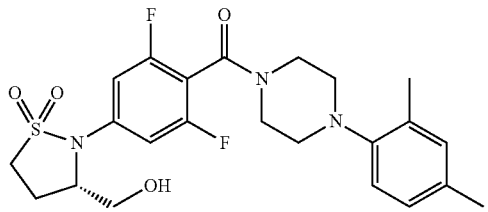 [SMILES: Cc1ccc(N2CCN(C(=O)c3c(F)cc(N4[C@H](CO)CCS4(=O)=O)cc3F)CC2)c(C)c1]

Using (S)-3-benzyloxymethylisothiazolidine 1,1-dioxide (482 mg) described in Preparation Example 1 and (4-bromo-2,6-difluorophenyl)[4-(2,4-dimethylphenyl)piperazin-1-yl]methanone (819 mg) described in Preparation Example 109 and by the reaction and treatment in the same manner as in Example 32, the title compound (498 mg) was obtained.

MS (ESI) m/z: 480(M+H)$^+$.

Example 64

Synthesis of (S)-[2-chloro-4-(3-hydroxymethyl-1,1-dioxo-1$\lambda^6$-isothiazolidin-2-yl)phenyl][4-(2,4-dimethylphenyl)piperazin-1-yl]methanone

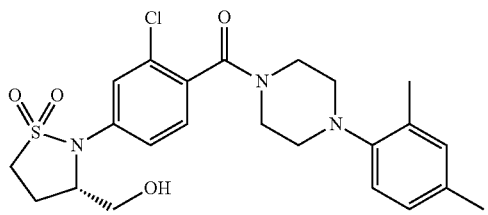 [SMILES: Cc1ccc(N2CCN(C(=O)c3ccc(N4[C@H](CO)CCS4(=O)=O)cc3Cl)CC2)c(C)c1]

Using (S)-3-benzyloxymethylisothiazolidine 1,1-dioxide (586 mg) described in Preparation Example 1 and (4-bromo-2-chlorophenyl)[4-(2,4-dimethylphenyl)piperazin-1-yl]methanone (990 mg) described in Preparation Example 131 and by the reaction and treatment in the same manner as in Example 32, the title compound (265 mg) was obtained.

MS (ESI) m/z: 478(M+H)$^+$.

Example 65

Synthesis of (S)-[4-(5-cyclopropyl-3-methylpyridin-2-yl)piperazin-1-yl][4-(3-hydroxymethyl-1,1-dioxo-1$\lambda^6$-isothiazolidin-2-yl)-2-methanesulfonylphenyl]methanone

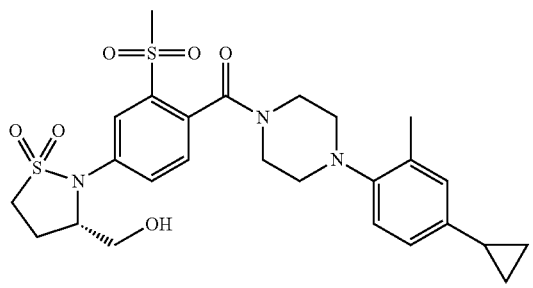 [SMILES: Cc1cc(C2CC2)ccc1N1CCN(C(=O)c2ccc(N3[C@H](CO)CCS3(=O)=O)cc2S(C)(=O)=O)CC1]

Using (S)-3-benzyloxymethylisothiazolidine 1,1-dioxide (241 mg) described in Preparation Example 1 and (4-bromo-2-methanesulfonylphenyl)[4-(5-cyclopropyl-3-methylpyridin-2-yl)piperazin-1-yl]methanone (478 mg) described in Preparation Example 126 and by the reaction and treatment in the same manner as in Example 32, the title compound (170 mg) was obtained.

MS (ESI) m/z: 549(M+H)$^+$.

Example 66

Synthesis of (S)-[4-(2,4-dimethylphenyl)piperazin-1-yl][3-fluoro-4-(3-hydroxymethyl-1,1-dioxo-1$\lambda^6$-isothiazolidin-2-yl)phenyl]methanone

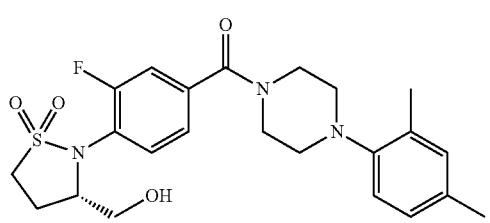 [SMILES: Cc1ccc(N2CCN(C(=O)c3ccc(N4[C@H](CO)CCS4(=O)=O)c(F)c3)CC2)c(C)c1]

Using (S)-3-benzyloxymethylisothiazolidine 1,1-dioxide (1.07 g) described in Preparation Example 1 and (4-bromo-3-fluorophenyl)[4-(2,4-dimethylphenyl)piperazin-1-yl]methanone (1.74 g) described in Preparation Example 132 and by the reaction and treatment in the same manner as in Example 32, the title compound (274 mg) was obtained.

MS (ESI) m/z: 462(M+H)$^+$.

Example 67

Synthesis of (S)-[4-(5-cyclopropyl-3-methylpyridin-2-yl)piperazin-1-yl][4-(3-hydroxymethyl-1,1-dioxo-1λ6-isothiazolidin-2-yl)phenyl]methanone

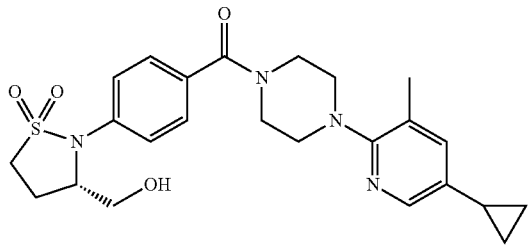 [SMILES: Cc1cc(C2CC2)cnc1N1CCN(C(=O)c2ccc(N3[C@H](CO)CCS3(=O)=O)cc2)CC1]

Using (S)-3-benzyloxymethylisothiazolidine 1,1-dioxide (241 mg) described in Preparation Example 1 and [4-(5-cyclopropyl-3-methylpyridin-2-yl)piperazin-1-yl](4-iodophenyl)methanone (447 mg) described in Preparation Example 117 and by the reaction and treatment in the same manner as in Example 32, the title compound (178 mg) was obtained.

MS (ESI) m/z: 471(M+H)+.

Example 68

Synthesis of (S)-[4-(2,4-dimethylphenyl)piperazin-1-yl][4-(3-hydroxymethyl-1,1-dioxo-1λ6-isothiazolidin-2-yl)-2-methoxyphenyl]methanone

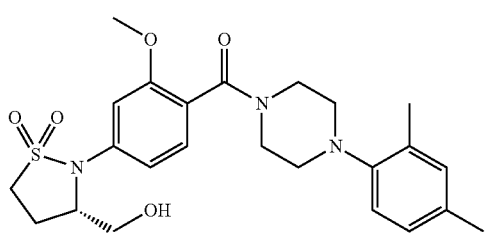 [SMILES: COc1cc(N2[C@H](CO)CCS2(=O)=O)ccc1C(=O)N1CCN(c2ccc(C)cc2C)CC1]

Methyl (S)-4-(3-benzyloxymethyl-1,1-dioxo-1λ6-isothiazolidin-2-yl)-2-methoxybenzoate (380 mg) described in Preparation Example 12 was dissolved in tetrahydrofuran (10 mL), 1N aqueous sodium hydroxide solution (2 mL) was added, and the mixture was stirred at room temperature for 4 hr. To the reaction mixture was added 1N hydrochloric acid, and the mixture was extracted with ethyl acetate. The organic layer was washed with saturated brine, and the solvent was evaporated. The obtained residue was dissolved in tetrahydrofuran (10 mL), 1-(2,4-dimethylphenyl)piperazine (178 mg), 1-hydroxybenzotriazole 1 hydrate (139 mg) and 1-ethyl-3-(3'-dimethylaminopropyl)carbodiimide hydrochloride (225 mg) were added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (hexane:ethyl acetate) to give (S)-[4-(3-benzyloxymethyl-1,1-dioxo-1λ6-isothiazolidin-2-yl)-2-methoxyphenyl][4-(2,4-dimethylphenyl)piperazin-1-yl]methanone. Using the obtained (S)-[4-(3-benzyloxymethyl-1,1-dioxo-1λ6-isothiazolidin-2-yl)-2-methoxyphenyl][4-(2,4-dimethylphenyl)piperazin-1-yl]methanone and by the reaction and treatment in the same manner as in Example 29, the title compound (209 mg) was obtained.

MS (ESI) m/z: 474(M+H)+.

Example 69

Synthesis of [4-(3,5-dimethylpyridin-2-yl)piperazin-1-yl][4-(4-methyl-1,1-dioxo-1λ6-isothiazolidin-2-yl)phenyl]methanone

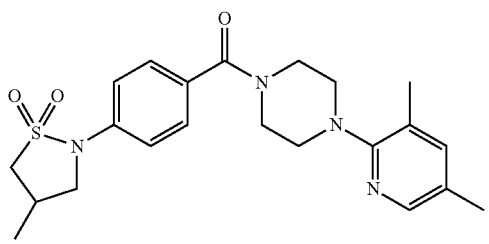

Using 4-methylisothiazolidine 1,1-dioxide (270 mg) described in Preparation Example 9 and [4-(3,5-dimethylpyridin-2-yl)piperazin-1-yl](4-iodophenyl)methanone (421 mg) described in Preparation Example 113 and by the reaction and treatment in the same manner as in Example 4, the title compound (134 mg) was obtained.

MS (ESI) m/z: 429(M+H)+.

Example 70

Synthesis of (S)-[4-(2,4-dimethylphenyl)piperazin-1-yl][2-(1,1-dioxo-1λ6-isothiazolidin-2-yl)-4-(3-hydroxymethyl-1,1-dioxo-1λ6-isothiazolidin-2-yl)phenyl]methanone

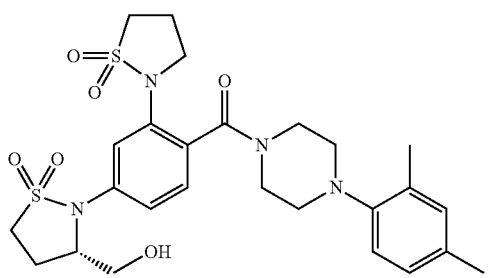 [SMILES: Cc1ccc(N2CCN(C(=O)c3ccc(N4[C@H](CO)CCS4(=O)=O)cc3N3CCCS3(=O)=O)CC2)c(C)c1]

Using methyl (S)-4-(3-benzyloxymethyl-1,1-dioxo-1λ6-isothiazolidin-2-yl)-2-(1,1-dioxo-1λ6-isothiazolidin-2-yl)benzoate (430 mg) described in Preparation Example 14 and by the reaction and treatment in the same manner as in Example 68, the title compound (359 mg) was obtained.

MS (ESI) m/z: 563(M+H)+.

Example 71

Synthesis of [4-(5-cyclopropyl-3-methylpyridin-2-yl)piperazin-1-yl][4-(4-methyl-1,1-dioxo-1$\lambda^6$-isothiazolidin-2-yl)phenyl]methanone

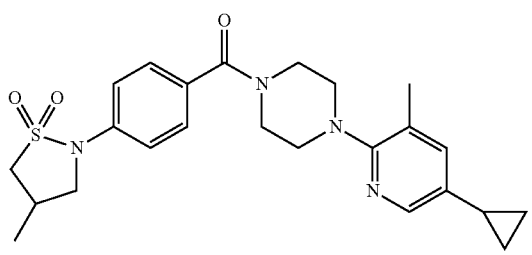

4-(4-Methyl-1,1-dioxo-1$\lambda^6$-isothiazolidin-2-yl)benzoic acid (200 mg) described in Preparation Example 15 and 1-(5-cyclopropyl-3-methylpyridin-2-yl)piperazine (170 mg) described in Preparation Example 83 were dissolved in tetrahydrofuran (10 mL), 1-hydroxybenzotriazole 1 hydrate (139 mg) and 1-ethyl-3-(3'-dimethylaminopropyl)carbodiimide hydrochloride (225 mg) were added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (hexane:ethyl acetate) to give the title compound (120 mg).

MS (ESI) m/z: 455(M+H)$^+$.

Example 72

Synthesis of (R)-[4-(2,4-dimethylphenyl)piperazin-1-yl][4-(3-hydroxymethyl-1,1-dioxo-1$\lambda^6$-isothiazolidin-2-yl)phenyl]methanone

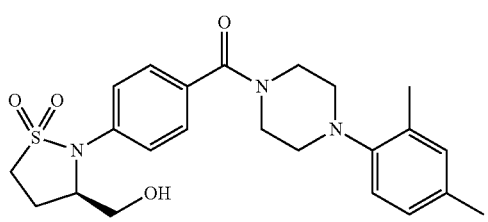 [SMILES: Cc1ccc(N2CCN(C(=O)c3ccc(N4[C@@H](CO)CCS4(=O)=O)cc3)CC2)c(C)c1]

Using (R)-3-benzyloxymethylisothiazolidine 1,1-dioxide (370 mg) described in Preparation Example 10 and [4-(2,4-dimethylphenyl)piperazin-1-yl](4-iodophenyl)methanone (643 mg) described in Preparation Example 108 and by the reaction and treatment in the same manner as in Example 32, the title compound (522 mg) was obtained.

MS (ESI) m/z: 444(M+H)$^+$.

Example 73

Synthesis of [4-(5-ethyl-3-methylpyridin-2-yl)piperazin-1-yl][4-(4-methyl-1,1-dioxo-1$\lambda^6$-isothiazolidin-2-yl)phenyl]methanone

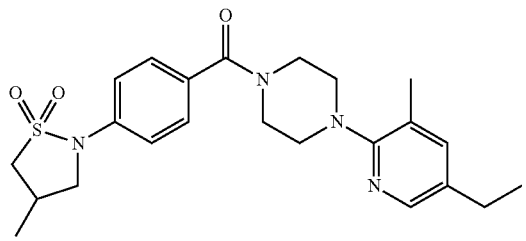 [SMILES: CCc1cnc(N2CCN(C(=O)c3ccc(N4CC(C)CS4(=O)=O)cc3)CC2)c(C)c1]

Using 4-methylisothiazolidine 1,1-dioxide (202 mg) described in Preparation Example 9 and [4-(5-ethyl-3-methylpyridin-2-yl)piperazin-1-yl](4-iodophenyl)methanone (500 mg) described in Preparation Example 133 and by the reaction and treatment in the same manner as in Example 1, the title compound (46 mg) was obtained.

MS (ESI) m/z: 443(M+H)$^+$.

Example 74

Synthesis of [4-(3,3-dimethyl-1,1-dioxo-1$\lambda^6$-isothiazolidin-2-yl)phenyl][4-(3,5-dimethylpyridin-2-yl)piperazin-1-yl]methanone

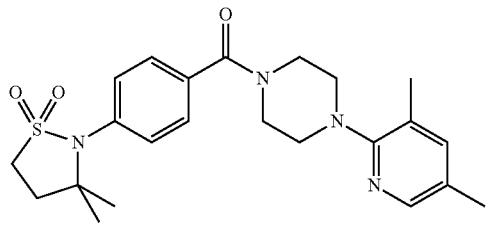 [SMILES: Cc1cnc(N2CCN(C(=O)c3ccc(N4C(C)(C)CCS4(=O)=O)cc3)CC2)c(C)c1]

Using 3,3-dimethylisothiazolidine 1,1-dioxide (130 mg) described in Preparation Example 11 and [4-(3,5-dimethylpyridin-2-yl)piperazin-1-yl](4-iodophenyl)methanone (367 mg) described in Preparation Example 113 and by the reaction and treatment in the same manner as in Example 1, the title compound (4.9 mg) was obtained.

MS (ESI) m/z: 443(M+H)$^+$.

Example 75

Synthesis of [4-(3,5-dimethylpyridin-2-yl)piperazin-1-yl][5-(1,1-dioxo-1$\lambda^6$-isothiazolidin-2-yl)pyridin-2-yl]methanone

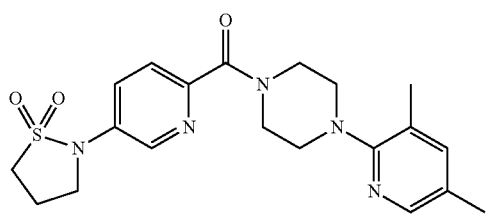 [SMILES: Cc1cnc(N2CCN(C(=O)c3ccc(N4CCCS4(=O)=O)cn3)CC2)c(C)c1]

Using isothiazolidine 1,1-dioxide (121 mg) and (5-bromopyridin-2-yl) [4-(3,5-dimethylpyridin-2-yl)piperazin-1-yl]methanone (375 mg) described in Preparation Example 134 and by the reaction and treatment in the same manner as in Example 1, the title compound (154 mg) was obtained.

MS (ESI) m/z: 416(M+H)$^+$.

Example 76

Synthesis of [4-(5-cyclopropyl-3-methylpyridin-2-yl)piperazin-1-yl][5-(1,1-dioxo-1λ$^6$-isothiazolidin-2-yl)pyridin-2-yl]methanone

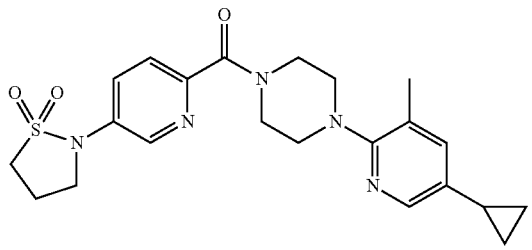

Using isothiazolidine 1,1-dioxide (94 mg) and (5-bromopyridin-2-yl) [4-(5-cyclopropyl-3-methylpyridin-2-yl)piperazin-1-yl]methanone (310 mg) described in Preparation Example 135 and by the reaction and treatment in the same manner as in Example 1, the title compound (139 mg) was obtained.

MS (ESI) m/z: 442(M+H)$^+$.

Example 77

Synthesis of [4-(4-cyclopropylphenoxy)piperidin-1-yl][6-(1,1-dioxo-1λ$^6$-isothiazolidin-2-yl)pyridin-3-yl]methanone

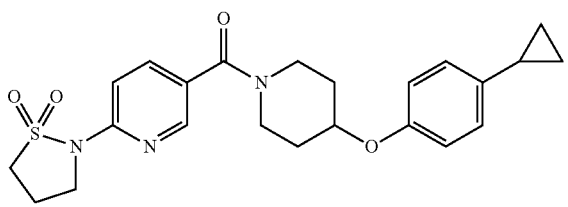 [SMILES: O=C(c1ccc(N2CCCS2(=O)=O)nc1)N1CCC(Oc2ccc(C3CC3)cc2)CC1]

Using isothiazolidine 1,1-dioxide (230 mg) and (6-bromopyridin-3-yl)[4-(4-cyclopropylphenoxy)piperidin-1-yl]methanone (635 mg) described in Preparation Example 192 and by the reaction and treatment in the same manner as in Example 1, the title compound (423 mg) was obtained.

MS (ESI) m/z: 442(M+H)$^+$.

Example 78

Synthesis of [4-(2,4-dimethylphenyl)piperazin-1-yl][6-(1,1-dioxo-1λ$^6$-isothiazolidin-2-yl)-2-methylpyridin-3-yl]methanone

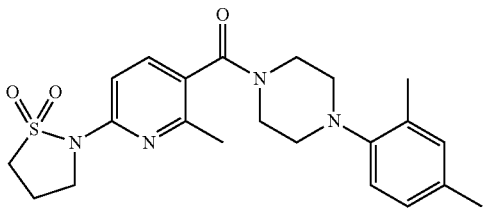 [SMILES: Cc1ccc(N2CCN(C(=O)c3ccc(N4CCCS4(=O)=O)nc3C)CC2)c(C)c1]

(6-Amino-2-methylpyridin-3-yl)[4-(2,4-dimethylphenyl)piperazin-1-yl]methanone (180 mg) described in Preparation Example 136 and triethylamine (0.19 mL) were dissolved in dichloromethane (5 mL), 3-chloropropane-1-sulfonyl chloride (0.14 mL) was added, and the mixture was stirred at room temperature overnight. Water was added to the reaction mixture, the mixture was extracted with dichloromethane, the extract was washed with saturated brine, and the solvent was evaporated. The obtained residue was dissolved in N,N-dimethylformamide (5 mL), 1,8-diazabicyclo[5.4.0]undec-7-ene (DBU) (0.12 mL) was added, and the mixture was stirred at room temperature overnight. Water was added to the reaction mixture, and the mixture was extracted with ethyl acetate, the extract was washed with saturated brine, and the solvent was evaporated. The obtained residue was purified by column chromatography (hexane:ethyl acetate) to give the title compound (57 mg).

MS (ESI) m/z: 429(M+H)$^+$.

Example 79

Synthesis of [4-(2,4-dimethylphenyl)piperazin-1-yl][5-(1,1-dioxo-1λ$^6$-isothiazolidin-2-yl)pyridin-2-yl]methanone

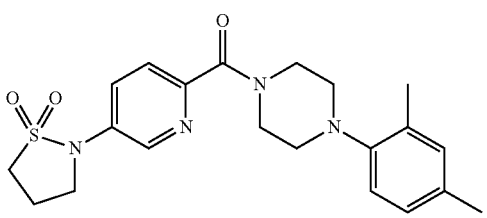 [SMILES: Cc1ccc(N2CCN(C(=O)c3ccc(N4CCCS4(=O)=O)cn3)CC2)c(C)c1]

Using isothiazolidine 1,1-dioxide (52 mg) and (5-bromopyridin-2-yl) [4-(2,4-dimethylphenyl)piperazin-1-yl]methanone (160 mg) described in Preparation Example 137 and by the reaction and treatment in the same manner as in Example 1, the title compound (67 mg) was obtained.

MS (ESI) m/z: 415(M+H)$^+$.

Example 80

Synthesis of [5-(1,1-dioxo-1λ⁶-isothiazolidin-2-yl)pyridin-2-yl][4-(5-ethyl-3-methylpyridin-2-yl)piperazin-1-yl]methanone

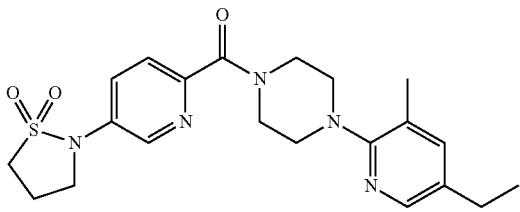 [SMILES: CCc1cnc(N2CCN(C(=O)c3ccc(N4CCCS4(=O)=O)cn3)CC2)c(C)c1]

Using isothiazolidine 1,1-dioxide (53 mg) and (5-bromopyridin-2-yl) [4-(5-ethyl-3-methylpyridin-2-yl)piperazin-1-yl]methanone (170 mg) described in Preparation Example 138 and by the reaction and treatment in the same manner as in Example 1, the title compound (130 mg) was obtained.
MS (ESI) m/z: 430(M+H)⁺.

Example 81

Synthesis of (S)-[4-(2,4-dimethylphenyl)piperazin-1-yl][5-(3-hydroxymethyl-1,1-dioxo-1λ⁶-isothiazolidin-2-yl)pyridin-2-yl]methanone

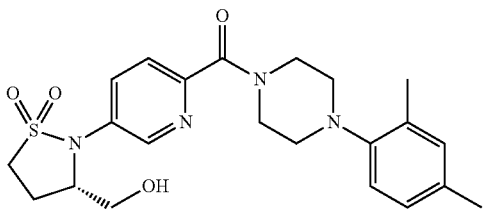 [SMILES: Cc1ccc(N2CCN(C(=O)c3ccc(N4[C@H](CO)CCS4(=O)=O)cn3)CC2)c(C)c1]

Using (S)-3-benzyloxymethylisothiazolidine 1,1-dioxide (439 mg) described in Preparation Example 1 and (5-bromopyridin-2-yl)[4-(2,4-dimethylphenyl)piperazin-1-yl]methanone (680 mg) described in Preparation Example 137 and by the reaction and treatment in the same manner as in Example 32, the title compound (338 mg) was obtained.
MS (ESI) m/z: 445(M+H)⁺.

Example 82

Synthesis of [4-(5-cyclopropyl-3-methylpyridin-2-yl)piperazin-1-yl][6-(1,1-dioxo-1λ⁶-isothiazolidin-2-yl)-4-methylpyridin-3-yl]methanone

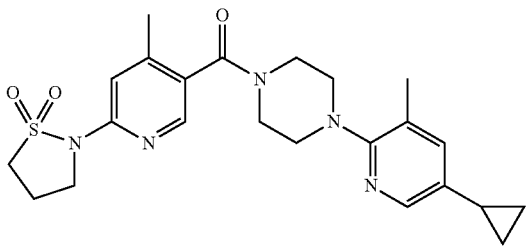 [SMILES: Cc1cc(N2CCCS2(=O)=O)ncc1C(=O)N1CCN(c2ncc(C3CC3)cc2C)CC1]

Using (6-amino-4-methylpyridin-3-yl) [4-(5-cyclopropyl-3-methylpyridin-2-yl)piperazin-1-yl]methanone (1.0 g) described in Preparation Example 141 and 3-chloropropane-1-sulfonyl chloride (0.69 mL) and by the reaction and treatment in the same manner as in Example 78, the title compound (636 mg) was obtained.
MS (ESI) m/z: 456(M+H)⁺.

Example 83

Synthesis of [4-(3,5-dicyclopropylpyridin-2-yl)piperazin-1-yl][5-(1,1-dioxo-1λ⁶-isothiazolidin-2-yl)pyridin-2-yl]methanone

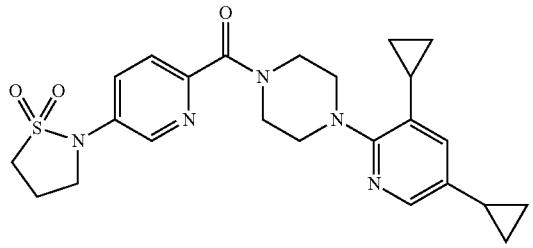 [SMILES: O=C(c1ccc(N2CCCS2(=O)=O)cn1)N1CCN(c2ncc(C3CC3)cc2C2CC2)CC1]

Using isothiazolidine 1,1-dioxide (105 mg) and (5-bromopyridin-2-yl)[4-(3,5-dicyclopropylpyridin-2-yl)piperazin-1-yl]methanone (338 mg) described in Preparation Example 142 and by the reaction and treatment in the same manner as in Example 1, the title compound (145 mg) was obtained.
MS (ESI) m/z: 468(M+H)⁺.

Example 84

Synthesis of (S)-[4-(3,5-dicyclopropylpyridin-2-yl)piperazin-1-yl][5-(3-hydroxymethyl-1,1-dioxo-1λ⁶-isothiazolidin-2-yl)pyridin-2-yl]methanone

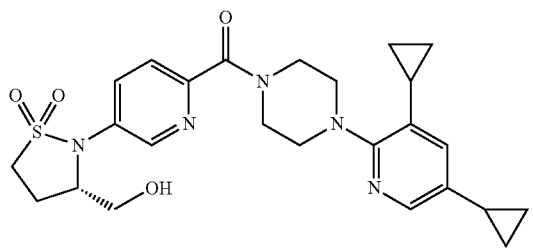 [SMILES: O=C(c1ccc(N2[C@H](CO)CCS2(=O)=O)cn1)N1CCN(c2ncc(C3CC3)cc2C2CC2)CC1]

Using (S)-3-benzyloxymethylisothiazolidine 1,1-dioxide (287 mg) described in Preparation Example 1 and (5-bromopyridin-2-yl)[4-(3,5-dicyclopropylpyridin-2-yl)piperazin-1-yl]methanone (460 mg) described in Preparation Example 142 and by the reaction and treatment in the same manner as in Example 1, (S)-5-[(3-benzyloxymethyl-1,1-dioxo-1λ⁶-isothiazolidin-2-yl)pyridin-2-yl][4-(3,5-dicyclopropylpyridin-2-yl)piperazin-1-yl]methanone (420 mg) was obtained. To a mixture of the obtained (S)-5-[(3-benzyloxymethyl-1,1-dioxo-1λ⁶-isothiazolidin-2-yl)pyridin-2-yl][4-(3, 5-dicyclopropylpyridin-2-yl)piperazin-1-yl]methanone (420 mg), palladium carbon (50 mg) and ammonium formate (500 mg) were added methanol (30 mL) and water (3 mL), and the mixture was stirred at 40° C. for 14 hr. Insoluble material was filtered off from the reaction mixture, and the filtrate was concentrated. To the obtained residue was added 1N aqueous sodium hydroxide solution, and the mixture was extracted with ethyl acetate. The organic layer was washed with saturated brine, and the solvent was evaporated. The obtained residue was purified by column chromatography (hexane: ethyl acetate) to give the title compound (46 mg).

MS (ESI) m/z: 498(M+H)$^+$.

Example 85

Synthesis of [4-(3,5-dimethylpyridin-2-yl)piperazin-1-yl][5-(1,1-dioxo-1$\lambda^6$-[1,2]thiazinan-2-yl)pyridin-2-yl]methanone

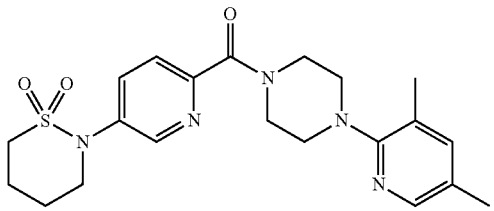 [SMILES: Cc1cnc(N2CCN(C(=O)c3ccc(N4CCCCS4(=O)=O)cn3)CC2)c(C)c1]

Using [1,2]thiazinane 1,1-dioxide (94 mg) and (5-bromopyridin-2-yl)[4-(3,5-dimethylpyridin-2-yl)piperazin-1-yl]methanone (260 mg) described in Preparation Example 134 and by the reaction and treatment in the same manner as in Example 1, the title compound (214 mg) was obtained.

MS (ESI) m/z: 430(M+H)$^+$.

Example 86

Synthesis of [4-(1,1-dioxo-1$\lambda^6$-isothiazolidin-2-yl)phenyl][4-(4-methylbenzoyl)piperidin-1-yl]methanone

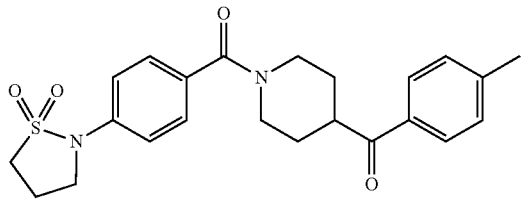 [SMILES: Cc1ccc(C(=O)C2CCN(C(=O)c3ccc(N4CCCS4(=O)=O)cc3)CC2)cc1]

4-(1,1-Dioxo-1$\lambda^6$-isothiazolidin-2-yl)benzoic acid (253 mg) described in Preparation Example 16, (piperidin-4-yl)(p-tolyl)methanone hydrochloride (252 mg), 1-hydroxybenzotriazole 1 hydrate (142 mg) and triethylamine (0.15 mL) were dissolved in N,N-dimethylformamide (5 mL), 1-ethyl-3-(3'-dimethylaminopropyl)carbodiimide hydrochloride (202 mg) was added, and the mixture was stirred at room temperature overnight. To the reaction mixture was added 5% aqueous sodium hydrogen carbonate solution, and the mixture was extracted with ethyl acetate. The organic layer was washed with water and saturated brine, and the solvent was evaporated. The obtained residue was purified by column chromatography (chloroform:methanol) to give the title compound (108 mg).

MS (ESI) m/z: 427(M+H)$^+$.

Example 87

Synthesis of [4-(2,4-dimethylphenyl)piperazin-1-yl][4-(1,1-dioxo-1$\lambda^6$-isothiazolidin-2-ylmethyl)phenyl]methanone

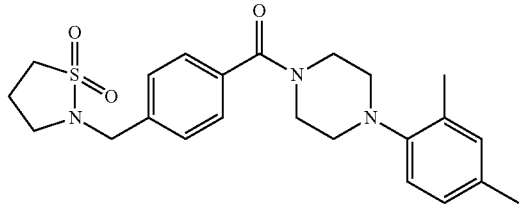 [SMILES: Cc1ccc(N2CCN(C(=O)c3ccc(CN4CCCS4(=O)=O)cc3)CC2)c(C)c1]

4-(1,1-Dioxo-1$\lambda^6$-isothiazolidin-2-ylmethyl)benzoic acid (268 mg) described in Preparation Example 18, 1-(2,4-dimethylphenyl)piperazine (199 mg), 1-hydroxybenzotriazole 1 hydrate (142 mg) were dissolved in N,N-dimethylformamide (5 mL), 1-ethyl-3-(3'-dimethylaminopropyl)carbodiimide hydrochloride (202 mg) was added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (256 mg).

MS (ESI) m/z: 428(M+H)$^+$.

Example 88

Synthesis of [4-(1,1-dioxo-1$\lambda^6$-isothiazolidin-2-ylmethyl)phenyl][4-(4-methylbenzoyl)piperidin-1-yl]methanone

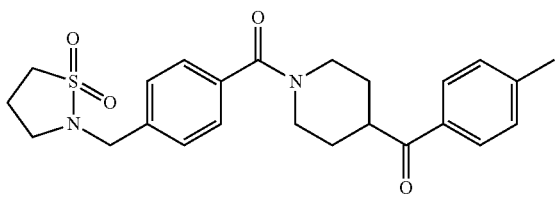 [SMILES: Cc1ccc(C(=O)C2CCN(C(=O)c3ccc(CN4CCCS4(=O)=O)cc3)CC2)cc1]

Using 4-(1,1-dioxo-1$\lambda^6$-isothiazolidin-2-ylmethyl)benzoic acid (268 mg) described in Preparation Example 18 and (piperidin-4-yl)(p-tolyl)methanone hydrochloride (252 mg) and by the reaction and treatment in the same manner as in Example 86, the title compound (235 mg) was obtained.

MS (ESI) m/z: 441(M+H)$^+$.

Example 89

Synthesis of [4-(2,4-dimethylphenyl)piperazin-1-yl][4-(1,1-dioxo-1$\lambda^6$-isothiazolidin-2-yl)-2-methoxyphenyl]methanone

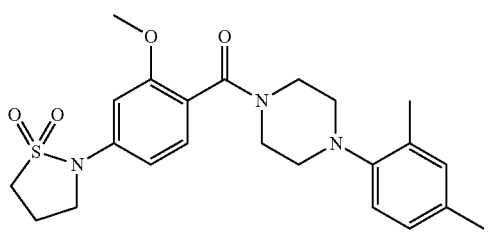 [SMILES: COc1cc(N2CCCS2(=O)=O)ccc1C(=O)N1CCN(c2ccc(C)cc2C)CC1]

Using 4-(1,1-dioxo-1λ⁶-isothiazolidin-2-yl)-2-methoxybenzoic acid (285 mg) described in Preparation Example 19 and 1-(2,4-dimethylphenyl)piperazine (199 mg) and by the reaction and treatment in the same manner as in Example 87, the title compound (377 mg) was obtained.
MS (ESI) m/z: 444(M+H)⁺.

Example 90

Synthesis of [4-(1,1-dioxo-1λ⁶-isothiazolidin-2-yl)-2-methoxyphenyl][4-(4-methylbenzoyl)piperidin-1-yl]methanone

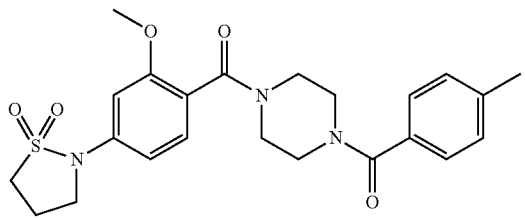 [SMILES: COc1cc(N2CCCS2(=O)=O)ccc1C(=O)N1CCN(C(=O)c2ccc(C)cc2)CC1]

Using 4-(1,1-dioxo-1λ⁶-isothiazolidin-2-yl)-2-methoxybenzoic acid (285 mg) described in Preparation Example 19 and (piperidin-4-yl)(p-tolyl)methanone hydrochloride (252 mg) and by the reaction and treatment in the same manner as in Example 86, the title compound (52 mg) was obtained.
MS (ESI) m/z: 457(M+H)⁺.

Example 91

Synthesis of [4-(2,4-dimethylphenyl)piperazin-1-yl][4-(1,1-dioxo-1λ⁶-isothiazolidin-2-yl)-3-methylphenyl]methanone

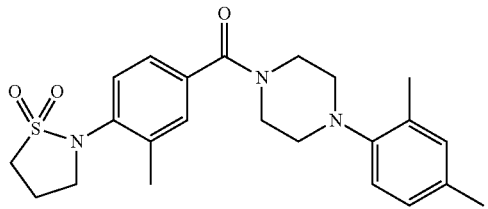 [SMILES: Cc1ccc(N2CCN(C(=O)c3ccc(N4CCCS4(=O)=O)c(C)c3)CC2)c(C)c1]

Using 4-(1,1-dioxo-1λ⁶-isothiazolidin-2-yl)-3-methylbenzoic acid (268 mg) described in Preparation Example and 1-(2,4-dimethylphenyl)piperazine (199 mg) and by the reaction and treatment in the same manner as in Example 87, the title compound (242 mg) was obtained.
MS (ESI) m/z: 428(M+H)⁺.

Example 92

Synthesis of [4-(1,1-dioxo-1λ⁶-isothiazolidin-2-yl)-3-methylphenyl][4-(4-methylbenzoyl)piperidin-1-yl]methanone

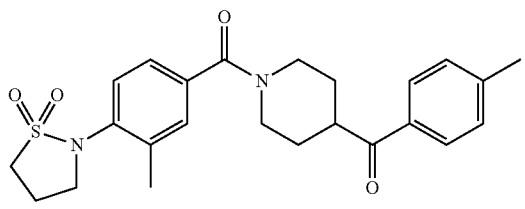 [SMILES: Cc1ccc(C(=O)C2CCN(C(=O)c3ccc(N4CCCS4(=O)=O)c(C)c3)CC2)cc1]

Using 4-(1,1-dioxo-1λ⁶-isothiazolidin-2-yl)-3-methylbenzoic acid (268 mg) described in Preparation Example and (piperidin-4-yl)(p-tolyl)methanone hydrochloride (252 mg) and by the reaction and treatment in the same manner as in Example 86, the title compound (50 mg) was obtained.
MS (ESI) m/z: 441(M+H)⁺.

Example 93

Synthesis of [4-(2,4-dimethylphenyl)piperazin-1-yl][4-(1,1-dioxo-1λ⁶-isothiazolidin-2-yl)-3-methoxyphenyl]methanone

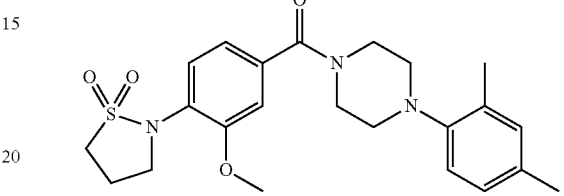

4-(1,1-Dioxo-1λ⁶-isothiazolidin-2-yl)-3-methoxybenzoic acid (285 mg) described in Preparation Example 21 and 1-(2,4-dimethylphenyl)piperazine (199 mg) were dissolved in a solution of chloroform (2.1 mL) and methanol (2.1 mL), 4-(4,6-dimethoxy[1.3.5]triazin-2-yl)-4-methylmorpholinium chloride hydrate (349 mg) was added, and the mixture was stirred at room temperature. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (411 mg).
MS (ESI) m/z: 444(M+H)⁺.

Example 94

Synthesis of [4-(1,1-dioxo-1λ⁶-isothiazolidin-2-yl)-3-methoxyphenyl][4-(4-methylbenzoyl)piperidin-1-yl]methanone

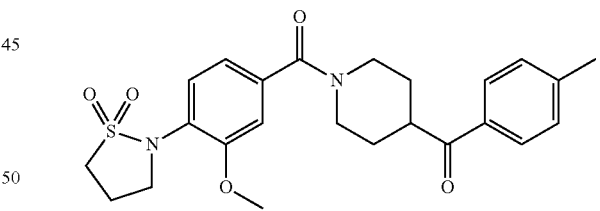

A mixture of 4-(1,1-dioxo-1λ⁶-isothiazolidin-2-yl)-3-methoxybenzoic acid (285 mg) described in Preparation Example 21, (piperidin-4-yl)(p-tolyl)methanone hydrochloride (252 mg) and N-methylmorpholine (0.12 mL) was dissolved in a solution of methanol (3 mL) and water (2 mL), 4-(4,6-dimethoxy[1.3.5]triazin-2-yl)-4-methylmorpholinium chloride hydrate (349 mg) was added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (344 mg).
MS (ESI) m/z: 457(M+H)⁺.

Example 95

Synthesis of [4-(2,4-dimethylphenyl)piperazin-1-yl][4-(1,1-dioxo-1λ$^6$-isothiazolidin-2-yl)-2-methylphenyl]methanone

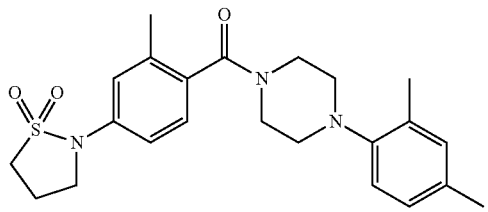 [SMILES: Cc1ccc(N2CCN(C(=O)c3ccc(N4CCCS4(=O)=O)cc3C)CC2)c(C)c1]

Using (4-amino-2-methylphenyl)[4-(2,4-dimethylphenyl)piperazin-1-yl]methanone (833 mg) described in Preparation Example 148 and 3-chloropropane-1-sulfonyl chloride (0.42 mL) and by the reaction and treatment in the same manner as in Example 78, the title compound (624 mg) was obtained.
MS (ESI) m/z: 428(M+H)$^+$.

Example 96

Synthesis of [4-(2,4-dimethylphenyl)piperazin-1-yl][4-(1,1-dioxo-1λ$^6$-isothiazolidin-2-yl)-2-methanesulfonylphenyl]methanone hydrobromide

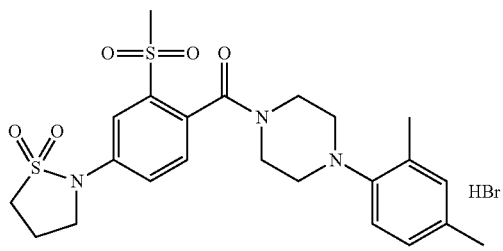 [SMILES: Cc1ccc(N2CCN(C(=O)c3ccc(N4CCCS4(=O)=O)cc3S(C)(=O)=O)CC2)c(C)c1 ; Br]

[4-(2,4-Dimethylphenyl)piperazin-1-yl][4-(1,1-dioxo-1λ$^6$-isothiazolidin-2-yl)-2-methanesulfonylphenyl]methanone (500 mg) described in Example 11 was dissolved in acetone (75 mL), hydrogen bromide/acetic acid solution (about 30%-containing, 0.3 mL) was added, and the mixture was stirred at room temperature. To the reaction mixture was added ethyl acetate, and the precipitate was collected by filtration to give the title compound (283 mg).

Example 97

Synthesis of [4-(2,4-dimethylphenyl)-[1,4]diazepan-1-yl][4-(1,1-dioxo-1λ$^6$-isothiazolidin-2-yl)phenyl]methanone

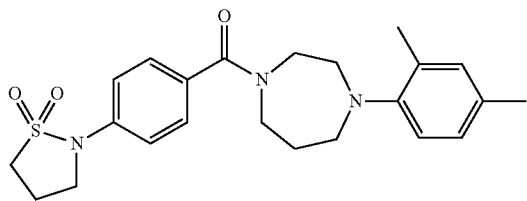 [SMILES: Cc1ccc(N2CCCN(C(=O)c3ccc(N4CCCS4(=O)=O)cc3)CC2)c(C)c1]

A mixture of 4-(1,1-dioxo-1λ$^6$-isothiazolidin-2-yl)benzoic acid (253 mg) described in Preparation Example 16, 1-(2,4-dimethylphenyl)-[1,4]diazepane hydrochloride (253 mg) described in Preparation Example 93 and N-methylmorpholine (0.12 mL) was dissolved in a solution of methanol (2 mL), 1,4-dioxane (2 mL) and water (0.5 mL), 4-(4,6-dimethoxy[1.3.5]triazin-2-yl)-4-methylmorpholinium chloride hydrate (349 mg) was added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (223 mg).
MS (ESI) m/z: 428(M+H)$^+$.

Example 98

Synthesis of [4-(2,4-dimethylphenyl)piperazin-1-yl][4-(1,1-dioxo-1λ$^6$-isothiazolidin-2-yl)-2-fluorophenyl]methanone

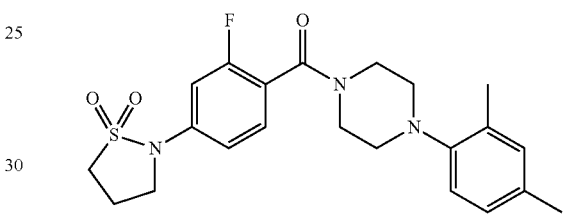

Using 4-(1,1-dioxo-1λ$^6$-isothiazolidin-2-yl)-2-fluorobenzoic acid (272 mg) described in Preparation Example 23 and 1-(2,4-dimethylphenyl)piperazine (199 mg) and by the reaction and treatment in the same manner as in Example 87, the title compound (371 mg) was obtained.
MS (ESI) m/z: 432(M+H)$^+$.

Example 99

Synthesis of [4-(2,4-dimethylphenyl)piperazin-1-yl][4-(1,1-dioxo-1λ$^6$-isothiazolidin-2-yl)-2-trifluoromethylphenyl]methanone

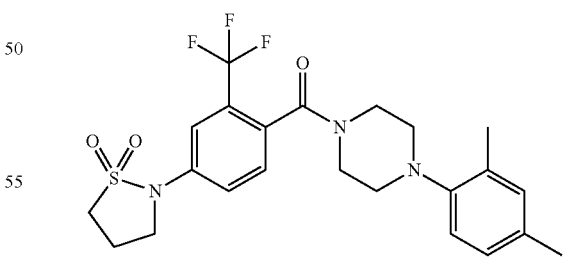

Using (4-amino-2-trifluoromethylphenyl)[4-(2,4-dimethylphenyl)piperazin-1-yl]methanone (850 mg) described in Preparation Example 149 and 3-chloropropane-1-sulfonyl chloride (0.37 mL) and by the reaction and treatment in the same manner as in Example 78, the title compound (544 mg) was obtained.
MS (ESI) m/z: 482(M+H)$^+$.

Example 100

Synthesis of [4-(2,4-dimethylphenyl)piperazin-1-yl][4-(1,1-dioxo-1λ⁶-isothiazolidin-2-yl)-2-nitrophenyl]methanone

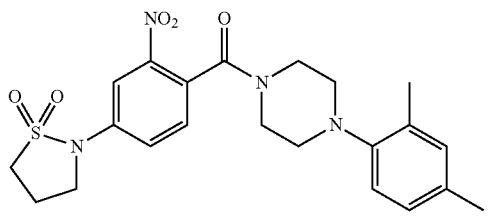 [SMILES: Cc1ccc(N2CCN(C(=O)c3ccc(N4CCCS4(=O)=O)cc3[N+](=O)[O-])CC2)c(C)c1]

Using 4-(1,1-dioxo-1λ⁶-isothiazolidin-2-yl)-2-nitrobenzoic acid (967 mg) described in Preparation Example 24 and 1-(2,4-dimethylphenyl)piperazine (639 mg) and by the reaction and treatment in the same manner as in Example 87, the title compound (250 mg) was obtained.
MS (ESI) m/z: 459(M+H)⁺.

Example 101

Synthesis of [2,4-bis(1,1-dioxo-1λ⁶-isothiazolidin-2-yl)phenyl][4-(2,4-dimethylphenyl)piperazin-1-yl]methanone

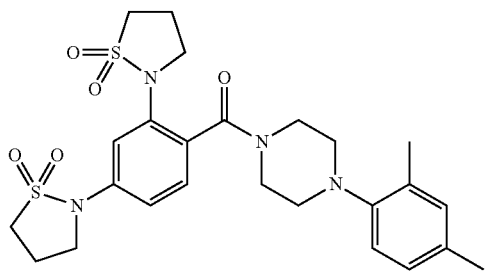 [SMILES: Cc1ccc(N2CCN(C(=O)c3ccc(N4CCCS4(=O)=O)cc3N3CCCS3(=O)=O)CC2)c(C)c1]

Using (2,4-diaminophenyl)[4-(2,4-dimethylphenyl)piperazin-1-yl]methanone (847 mg) described in Preparation Example 150 and 3-chloropropane-1-sulfonyl chloride (0.85 mL) and by the reaction and treatment in the same manner as in Example 78, the title compound (843 mg) was obtained.
MS (ESI) m/z: 533(M+H)⁺.

Example 102

Synthesis of [4-(1,1-dioxo-1λ⁶-isothiazolidin-2-yl)phenyl][4-(2,4,6-trimethylphenyl)piperazin-1-yl]methanone

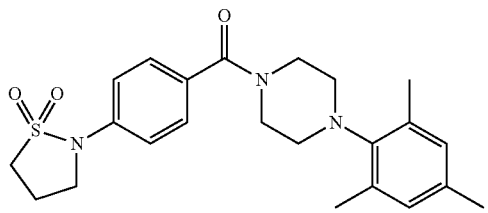 [SMILES: Cc1cc(C)c(N2CCN(C(=O)c3ccc(N4CCCS4(=O)=O)cc3)CC2)c(C)c1]

Using 4-(1,1-dioxo-1λ⁶-isothiazolidin-2-yl)benzoic acid (253 mg) described in Preparation Example 16 and 1-(2,4,6-trimethylphenyl)piperazine (215 mg) and by the reaction and treatment in the same manner as in Example 87, the title compound (103 mg) was obtained.
MS (ESI) m/z: 428(M+H)⁺.

Example 103

Synthesis of [2-amino-4-(1,1-dioxo-1λ⁶-isothiazolidin-2-yl)phenyl][4-(2,4-dimethylphenyl)piperazin-1-yl]methanone

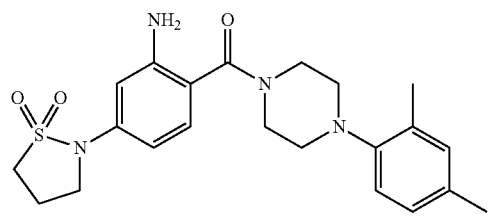

Ammonium chloride (504 mg) and iron (364 mg) were added to a solution of ethanol (9 mL) and water (2.3 mL), [4-(2,4-dimethylphenyl)piperazin-1-yl][4-(1,1-dioxo-1λ⁶-isothiazolidin-2-yl)-2-nitrophenyl]methanone (770 mg) described in Example 100 was added while stirring at 60° C.-70° C. After completion of the reaction, the insoluble material was collected by filtration, and the filtrate was concentrated. To the obtained residue was added aqueous sodium hydrogen carbonate solution, the mixture was extracted with ethyl acetate, and the solvent was evaporated. The obtained residue was purified by column chromatography (chloroform:methanol) to give the title compound (380 mg).
MS (ESI) m/z: 429(M+H)⁺.

Example 104

Synthesis of 1-{2-[4-(2,4-dimethylphenyl)piperazine-1-carbonyl]-5-(1,1-dioxo-1λ⁶-isothiazolidin-2-yl)phenyl}-3-(4-fluorophenyl)urea

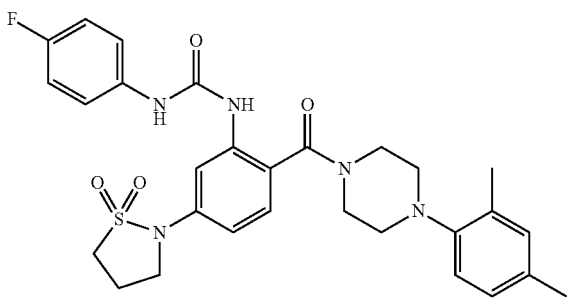 [SMILES: Cc1ccc(N2CCN(C(=O)c3ccc(N4CCCS4(=O)=O)cc3NC(=O)Nc3ccc(F)cc3)CC2)c(C)c1]

[2-Amino-4-(1,1-dioxo-1λ⁶-isothiazolidin-2-yl)phenyl][4-(2,4-dimethylphenyl)piperazin-1-yl]methanone (100 mg) described in Example 103 was dissolved in pyridine (2 mL), 4-fluorophenyl isocyanate (64 mg) was added, and the mixture was stirred at room temperature. After completion of the reaction, to the reaction mixture was added dilute hydrochloric acid, and the mixture was extracted with ethyl acetate. The organic layer was washed with saturated brine, and the sol-

Example 105

Synthesis of [4-(2,6-dimethylpyridin-3-yl)piperazin-1-yl][4-(1,1-dioxo-1$\lambda^6$-isothiazolidin-2-yl)-2-methanesulfonylphenyl]methanone

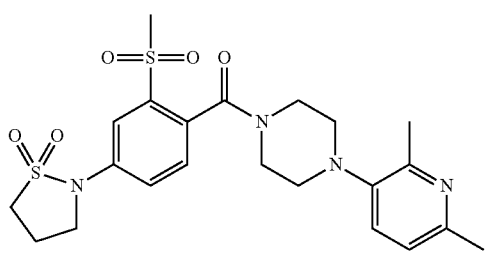 [SMILES: Cc1ccc(N2CCN(C(=O)c3ccc(N4CCCS4(=O)=O)cc3S(C)(=O)=O)CC2)c(C)n1]

Using 4-(1,1-dioxo-1$\lambda^6$-isothiazolidin-2-yl)-2-methanesulfonylbenzoic acid (189 mg) described in Preparation Example 22 and 1-(2,6-dimethylpyridin-3-yl)piperazine (113 mg) described in Preparation Example 94 and by the reaction and treatment in the same manner as in Example 87, the title compound (102 mg) was obtained.

MS (ESI) m/z: 493(M+H)⁺.

Example 106

Synthesis of [4-(2,6-dimethylpyridin-3-yl)piperazin-1-yl][4-(1,1-dioxo-1$\lambda^6$-isothiazolidin-2-yl)-2-fluorophenyl]methanone

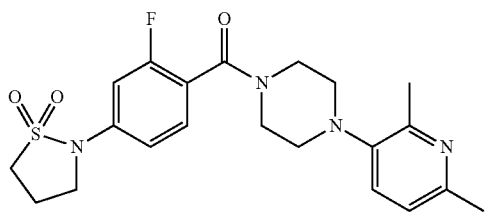

Using 4-(1,1-dioxo-1$\lambda^6$-isothiazolidin-2-yl)-2-fluorobenzoic acid (291 mg) described in Preparation Example 23 and 1-(2,6-dimethylpyridin-3-yl)piperazine (215 mg) described in Preparation Example 94 and by the reaction and treatment in the same manner as in Example 87, the title compound (175 mg) was obtained.

MS (ESI) m/z: 433(M+H)⁺.

Example 107

Synthesis of N-{2-[4-(2,4-dimethylphenyl)piperazine-1-carbonyl]-5-(1,1-dioxo-1$\lambda^6$-isothiazolidin-2-yl)phenyl}acetamide

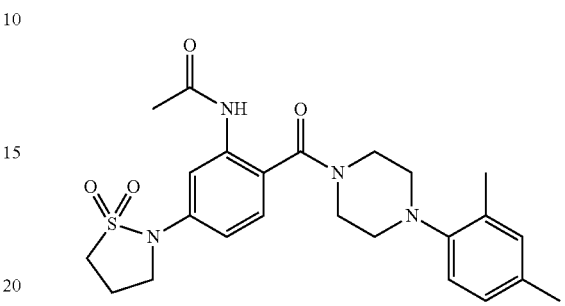

[2-Amino-4-(1,1-dioxo-1$\lambda^6$-isothiazolidin-2-yl)phenyl][4-(2,4-dimethylphenyl)piperazin-1-yl]methanone (100 mg) described in Example 103 was dissolved in dichloromethane (2 mL), triethylamine (0.07 mL) and acetyl chloride (0.03 mL) were added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (24 mg).

MS (ESI) m/z: 471(M+H)⁺.

Example 108

Synthesis of [4-(2,6-dimethylpyridin-3-yl)piperazin-1-yl][4-(1,1-dioxo-1$\lambda^6$-isothiazolidin-2-yl)phenyl]methanone

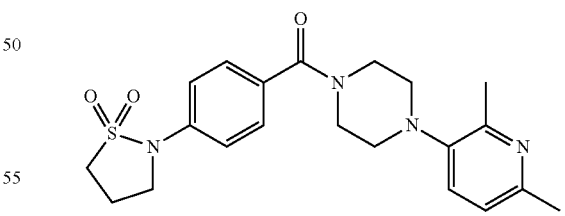

Using 4-(1,1-dioxo-1$\lambda^6$-isothiazolidin-2-yl)benzoic acid (270 mg) described in Preparation Example 16 and 1-(2,6-dimethylpyridin-3-yl)piperazine (215 mg) described in Preparation Example 94 and by the reaction and treatment in the same manner as in Example 87, the title compound (159 mg) was obtained.

MS (ESI) m/z: 415(M+H)⁺.

Example 109

Synthesis of [4-(2,4-dimethylphenyl)piperazin-1-yl][6-(1,1-dioxo-1λ⁶-isothiazolidin-2-yl)pyridin-3-yl]methanone

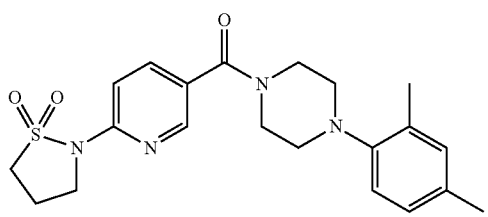

Ethyl 6-(1,1-dioxo-1λ⁶-isothiazolidin-2-yl)nicotinate (363 mg) described in Preparation Example 25 was dissolved in ethanol (6 mL), 1N aqueous sodium hydroxide solution (1.8 mL) was added, and the mixture was stirred at 50° C. for 3 hr. 1N Hydrochloric acid (1.8 mL), 1-(2,4-dimethylphenyl)piperazine (255 mg) and 4-(4,6-dimethoxy[1.3.5]triazin-2-yl)-4-methylmorpholinium chloride hydrate (372 mg) were added to the reaction mixture, and the mixture was stirred at room temperature overnight. To the reaction mixture was added saturated brine, the mixture was extracted with ethyl acetate, and the solvent was evaporated. The obtained residue was purified by silica gel column chromatography (chloroform:methanol) to give the title compound (271 mg).

MS (ESI) m/z: 415(M+H)⁺.

Example 110

Synthesis of [4-(2,4-dimethylphenyl)piperazin-1-yl][4-(1,1-dioxo-1λ⁶-isothiazolidin-2-yl)-3-fluorophenyl]methanone

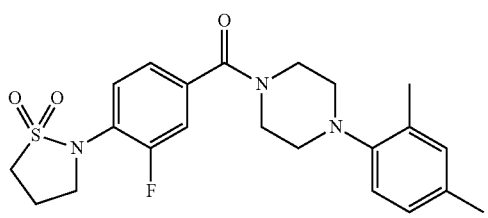

Using 4-(1,1-dioxo-1λ⁶-isothiazolidin-2-yl)-3-fluorobenzoic acid (272 mg) described in Preparation Example 26 and 1-(2,4-dimethylphenyl)piperazine (199 mg) and by the reaction and treatment in the same manner as in Example 87, the title compound (258 mg) was obtained.

MS (ESI) m/z: 432(M+H)⁺.

Example 111

Synthesis of [4-(2,4-dimethylphenyl)piperazin-1-yl][4-(1,1-dioxo-1λ⁶-isothiazolidin-2-yl)-2-(morpholin-4-yl)phenyl]methanone

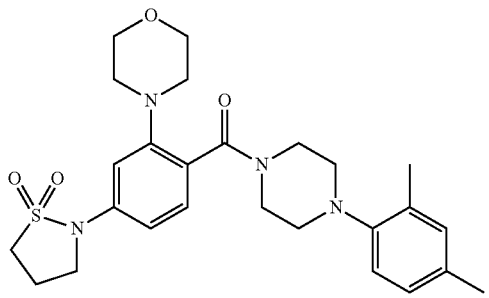 [SMILES: Cc1ccc(N2CCN(C(=O)c3ccc(N4CCCS4(=O)=O)cc3N3CCOCC3)CC2)c(C)c1]

Using [4-amino-2-(morpholin-4-yl)phenyl][4-(2,4-dimethylphenyl)piperazin-1-yl]methanone (188 mg) described in Preparation Example 151 and 3-chloropropane-1-sulfonyl chloride (0.08 mL) and by the reaction and treatment in the same manner as in Preparation Example 78, the title compound (82 mg) was obtained.

MS (ESI) m/z: 499(M+H)⁺.

Example 112

Synthesis of [4-(1,1-dioxo-1λ⁶-isothiazolidin-2-yl)phenyl][4-(5-trifluoromethylpyridin-2-yl)piperazin-1-yl]methanone

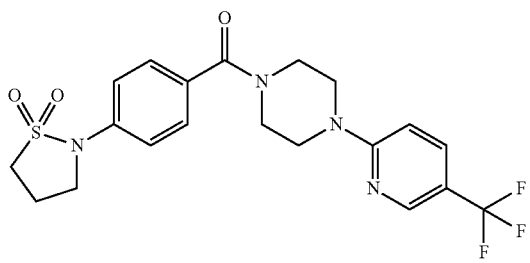 [SMILES: O=C(c1ccc(N2CCCS2(=O)=O)cc1)N1CCN(c2ccc(C(F)(F)F)cn2)CC1]

Using 4-(1,1-dioxo-1λ⁶-isothiazolidin-2-yl)benzoic acid (253 mg) described in Preparation Example 16 and 1-(5-trifluoromethylpyridin-2-yl)piperazine dihydrochloride (319 mg) and by the reaction and treatment in the same manner as in Example 94, the title compound (408 mg) was obtained.

MS (ESI) m/z: 455(M+H)⁺.

Example 113

Synthesis of [4-(2,4-dimethylphenyl)piperazin-1-yl][4-(imidazo[4,5-b]pyridin-3-yl)phenyl]methanone

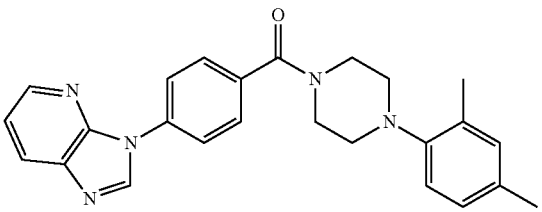 [SMILES: Cc1ccc(N2CCN(C(=O)c3ccc(-n4cnc5cccnc54)cc3)CC2)c(C)c1]

Using ethyl 4-(imidazo[4,5-b]pyridin-3-yl)benzoate (300 mg) described in Preparation Example 77 and 1-(2,4-dimethylphenyl)piperazine (214 mg) and by the reaction and treatment in the same manner as in Example 109, the title compound (338 mg) was obtained.
MS (ESI) m/z: 412(M+H)$^+$.

Example 114

Synthesis of [4-(2,4-dimethylphenyl)piperazin-1-yl][4-(1,1-dioxo-1λ$^6$-isothiazolidin-2-yl)-2-(methylamino)phenyl]methanone

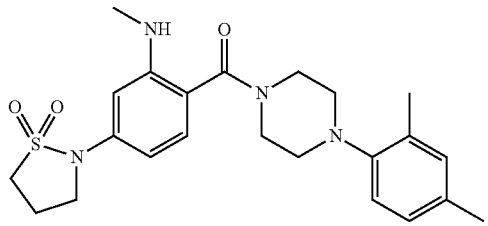

[2-Amino-4-(1,1-dioxo-1λ$^6$-isothiazolidin-2-yl)phenyl][4-(2,4-dimethylphenyl)piperazin-1-yl]methanone (210 mg) described in Example 103 was dissolved in dichloromethane (2 mL), 4-dimethylaminopyridine (0.3 mg) and di-tert-butyl dicarbonate (110 mg) were added, and the mixture was stirred at room temperature. After completion of the reaction, the solvent was evaporated, and the obtained residue was purified by column chromatography (chloroform:methanol) to give {2-[4-(2,4-dimethylphenyl)piperazine-1-carbonyl]-5-(1,1-dioxo-1λ$^6$-isothiazolidin-2-yl)phenyl}carbamic acid tert-butyl ester (283 mg). The obtained {2-[4-(2,4-dimethylphenyl)piperazine-1-carbonyl]-5-(1,1-dioxo-1λ$^6$-isothiazolidin-2-yl)phenyl}carbamic acid tert-butyl ester (282.6 mg) was dissolved in N,N-dimethylformamide (8 mL), sodium hydride (26 mg) was added, and the mixture was stirred at room temperature for 10 min. Methyl iodide (0.04 mL) was added, and the mixture was stirred at room temperature. After completion of the reaction, water was added to the reaction mixture, and the mixture was extracted with ethyl acetate. The organic layer was washed with saturated brine, and the solvent was evaporated. The obtained residue was dissolved in 1,4-dioxane (1 mL), 4N hydrogen chloride/1,4-dioxane (2.6 mL) was added, and the mixture was stirred at room temperature for 2 hr. To the reaction mixture was added aqueous sodium hydrogen carbonate solution, and the mixture was extracted with ethyl acetate. The organic layer was washed with water and saturated brine, and the solvent was evaporated. The obtained residue was purified by HPLC (ODS, 0.05% TFA aqueous solution-acetonitrile) to give the title compound (17 mg).
MS (ESI) m/z: 443(M+H)$^+$.

Example 115

Synthesis of [4-(1,1-dioxo-1λ$^6$-isothiazolidin-2-yl)phenyl][4-(3-methyl-5-trifluoromethylpyridin-2-yl)piperazin-1-yl]methanone

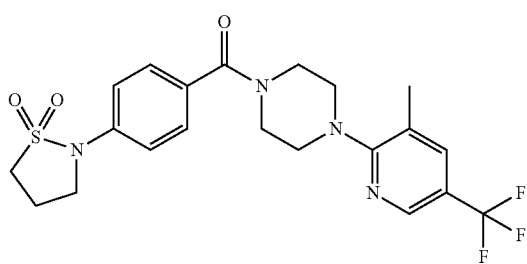 [SMILES: Cc1cc(C(F)(F)F)cnc1N1CCN(C(=O)c2ccc(N3CCCS3(=O)=O)cc2)CC1]

Under a nitrogen stream, to a mixture of [4-(3-chloro-5-trifluoromethylpyridin-2-yl)piperazin-1-yl][4-(1,1-dioxo-1λ$^6$-isothiazolidin-2-yl)phenyl]methanone (150 mg) described in Preparation Example 194, palladium(II) acetate (6.8 mg), 2-dicyclohexylphosphino-2',6'-dimethoxybiphenyl (25.2 mg), potassium fluoride (141.2 mg) and methylboronic acid (73.6 mg) was added tetrahydrofuran (1.5 mL), and the mixture was stirred with heating under reflux for 8 hr. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (50 mg).
MS (ESI) m/z: 469(M+H)$^+$.

Example 116

Synthesis of [4-(4-chlorobenzoyl)piperidin-1-yl][6-(1,1-dioxo-1λ$^6$-isothiazolidin-2-yl)pyridin-3-yl]methanone

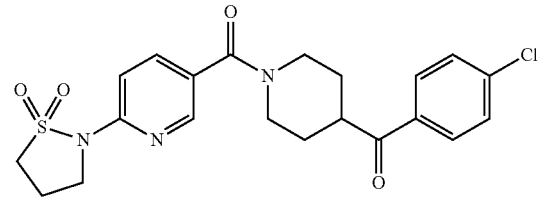 [SMILES: O=C(c1ccc(Cl)cc1)C1CCN(C(=O)c2ccc(N3CCCS3(=O)=O)nc2)CC1]

Using ethyl 6-(1,1-dioxo-1λ$^6$-isothiazolidin-2-yl)nicotinate (363 mg) described in Preparation Example 25 and 4-(4-chlorobenzoyl)piperidine (300 mg) and by the reaction and treatment in the same manner as in Example 109, the title compound (37 mg) was obtained.
MS (ESI) m/z: 448(M+H)$^+$.

Example 117

Synthesis of [4-(1,1-dioxo-1λ$^6$-isothiazolidin-2-yl)-2-methanesulfonylphenyl][4-(4-methylbenzoyl)piperidin-1-yl]methanone

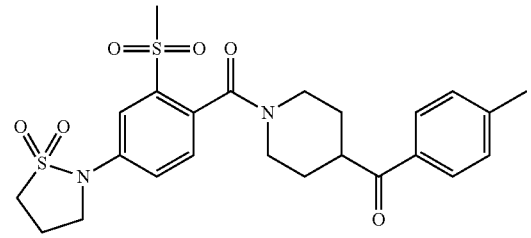 [SMILES: Cc1ccc(C(=O)C2CCN(C(=O)c3ccc(N4CCCS4(=O)=O)cc3S(C)(=O)=O)CC2)cc1]

Using 4-(1,1-dioxo-1λ$^6$-isothiazolidin-2-yl)-2-methanesulfonylbenzoic acid (138 mg) described in Preparation Example 22 and 4-(4-chlorobenzoyl)piperidine (97 mg) and by the reaction and treatment in the same manner as in Example 87, [4-(4-chlorobenzoyl)piperidin-1-yl][4-(1,1-dioxo-1λ$^6$-isothiazolidin-2-yl)-2-methanesulfonylphenyl]methanone (76 mg) was obtained. Using the obtained [4-(4-chlorobenzoyl)piperidin-1-yl][4-(1,1-dioxo-1λ$^6$-isothiazolidin-2-yl)-2-methanesulfonylphenyl]methanone (76 mg) and methylboronic acid (37 mg) and by the reaction and treatment in the same manner as in Example 115, the title compound (37 mg) was obtained.
MS (ESI) m/z: 505(M+H)$^+$.

Example 118

Synthesis of [6-(1,1-dioxo-1λ⁶-isothiazolidin-2-yl)pyridin-3-yl][4-(4-methylbenzoyl)piperidin-1-yl]methanone

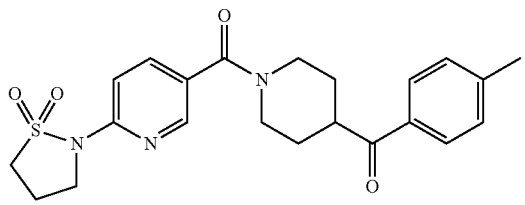 [SMILES: Cc1ccc(C(=O)C2CCN(C(=O)c3ccc(N4CCCS4(=O)=O)nc3)CC2)cc1]

Using [4-(4-chlorobenzoyl)piperidin-1-yl][6-(1,1-dioxo-1λ⁶-isothiazolidin-2-yl)pyridin-3-yl]methanone (194 mg) described in Example 116 and methylboronic acid (110 mg) and by the reaction and treatment in the same manner as in Example 115, the title compound (126 mg) was obtained.
MS (ESI) m/z: 428(M+H)⁺.

Example 119

Synthesis of [4-(2,4-dimethylphenyl)piperazin-1-yl][4-(pyrrolidin-1-yl)phenyl]methanone

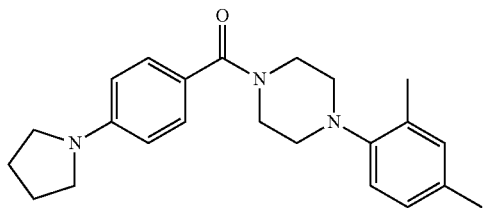 [SMILES: Cc1ccc(N2CCN(C(=O)c3ccc(N4CCCC4)cc3)CC2)c(C)c1]

Using 4-(pyrrolidin-1-yl)benzoic acid (200 mg) and 1-(2,4-dimethylphenyl)piperazine (199 mg) and by the reaction and treatment in the same manner as in Example 87, the title compound (15.8 mg) was obtained.
MS (ESI) m/z: 364(M+H)⁺.

Example 120

Synthesis of [4-(3,5-dimethylpyridin-2-yl)piperazin-1-yl][4-(1,1-dioxo-1λ⁶-isothiazolidin-2-yl)phenyl]methanone

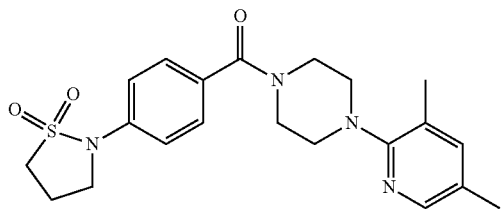 [SMILES: Cc1cnc(N2CCN(C(=O)c3ccc(N4CCCS4(=O)=O)cc3)CC2)c(C)c1]

Using [4-(3,5-dichloropyridin-2-yl)piperazin-1-yl][4-(1,1-dioxo-1λ⁶-isothiazolidin-2-yl)phenyl]methanone (446 mg) described in Preparation Example 195 and methylboronic acid (249 mg) and by the reaction and treatment in the same manner as in Example 115, the title compound (267 mg) was obtained.
MS (ESI) m/z: 415(M+H)⁺.

Example 121

Synthesis of [4-(2,4-dimethylphenyl)piperazin-1-yl][4-(1,1-dioxo-1λ⁶-isothiazolidin-2-yl)-2-(pyrrolidin-1-yl)phenyl]methanone

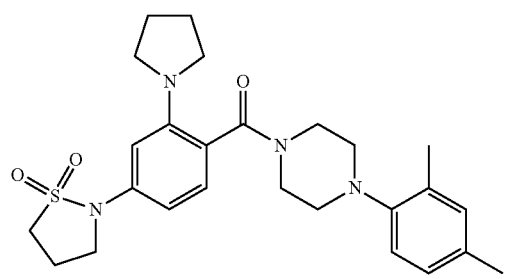 [SMILES: Cc1ccc(N2CCN(C(=O)c3ccc(N4CCCS4(=O)=O)cc3N3CCCC3)CC2)c(C)c1]

Using [4-amino-2-(pyrrolidin-1-yl)phenyl][4-(2,4-dimethylphenyl)piperazin-1-yl]methanone (268 mg) described in Preparation Example 152 and 3-chloropropane-1-sulfonyl chloride (0.11 mL) and by the reaction and treatment in the same manner as in Example 78, the title compound (31 mg) was obtained.
MS (ESI) m/z: 483(M+H)⁺.

Example 122

Synthesis of N-{2-[4-(2,4-dimethylphenyl)piperazine-1-carbonyl]-5-(1,1-dioxo-1λ⁶-isothiazolidin-2-yl)phenyl}methanesulfonamide

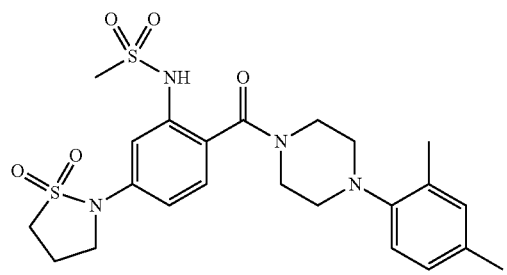 [SMILES: Cc1ccc(N2CCN(C(=O)c3ccc(N4CCCS4(=O)=O)cc3NS(C)(=O)=O)CC2)c(C)c1]

Using N-{5-amino-2-[4-(2,4-dimethylphenyl)piperazine-1-carbonyl]phenyl}methanesulfonamide (588 mg) described in Preparation Example 153 and 3-chloropropane-1-sulfonyl chloride (0.23 mL) and by the reaction and treatment in the same manner as in Example 78, the title compound (94 mg) was obtained.
MS (ESI) m/z: 507(M+H)⁺.

Example 123

Synthesis of [4-(2,4-dimethylphenyl)-4-oxypiperazin-1-yl][4-(1,1-dioxo-1λ⁶-isothiazolidin-2-yl)-2-methanesulfonylphenyl]methanone

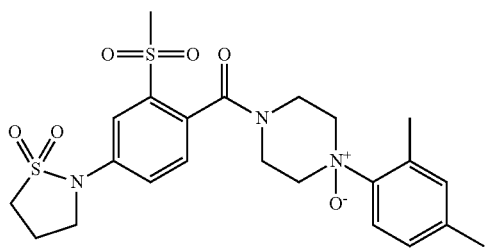 [SMILES: Cc1ccc([N+]2([O-])CCN(C(=O)c3ccc(N4CCCS4(=O)=O)cc3S(C)(=O)=O)CC2)c(C)c1]

[4-(2,4-Dimethylphenyl)piperazin-1-yl][4-(1,1-dioxo-1λ⁶-isothiazolidin-2-yl)-2-methanesulfonylphenyl]methanone described in Example 11 was dissolved in dichloromethane (5.4 mL), m-chloroperoxybenzoic acid (313 mg) was added under ice-cooling, and the mixture was stirred at room temperature for 3 hr. Water was added to the reaction mixture, the mixture was extracted with chloroform, and the solvent was evaporated. The obtained residue was purified by column chromatography (chloroform:methanol) to give the title compound (586 mg).

MS (ESI) m/z: 508(M+H)⁺.

Example 124

Synthesis of [4-(2,4-dimethylphenyl)piperazin-1-yl][4-(1,1-dioxo-1λ⁶-isothiazolidin-2-yl)-2-hydroxyphenyl]methanone

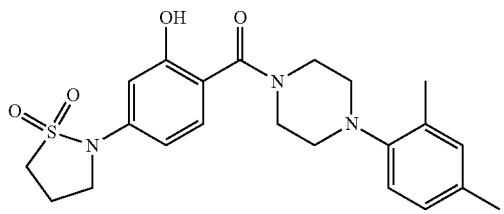 [SMILES: Cc1ccc(N2CCN(C(=O)c3ccc(N4CCCS4(=O)=O)cc3O)CC2)c(C)c1]

[4-(2,4-Dimethylphenyl)piperazin-1-yl][4-(1,1-dioxo-1λ⁶-isothiazolidin-2-yl)-2-methoxyphenyl]methanone (0.35 g) described in Example 89 was dissolved in dichloromethane (20 mL), 1 mol/L boron tribromide dichloromethane solution (4 mL) was added while stirring at −78° C. under cooling, and the mixture was stirred while rising the temperature to room temperature. Into the reaction mixture was poured ice water, and the mixture was neutralized with sodium hydrogen carbonate and extracted with chloroform. The organic layer was washed with saturated brine, and the solvent was evaporated. The obtained residue was purified by column chromatography (chloroform:methanol) to give the title compound (168 mg).

MS (ESI) m/z: 430(M+H)⁺.

Example 125

Synthesis of [4-(2,4-dimethylphenyl)piperazin-1-yl][4-(1,1-dioxo-1λ⁶-isothiazolidin-2-yl)-3-hydroxyphenyl]methanone

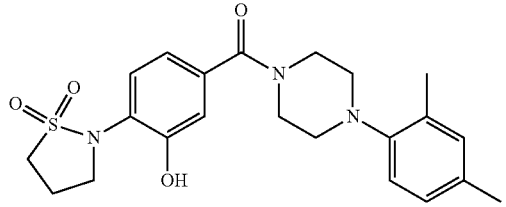 [SMILES: Cc1ccc(N2CCN(C(=O)c3ccc(N4CCCS4(=O)=O)c(O)c3)CC2)c(C)c1]

Using [4-(2,4-dimethylphenyl)piperazin-1-yl][4-(1,1-dioxo-1λ⁶-isothiazolidin-2-yl)-3-methoxyphenyl]methanone (388 mg) described in Example 93 and by the reaction and treatment in the same manner as in Example 124, the title compound (169 mg) was obtained.

MS (ESI) m/z: 430(M+H)⁺.

Example 126

Synthesis of [4-(2,4-dimethylphenyl)piperazin-1-yl]{4-[4-(4-methylpiperazine-1-carbonyl)pyrazol-1-yl]phenyl}methanone

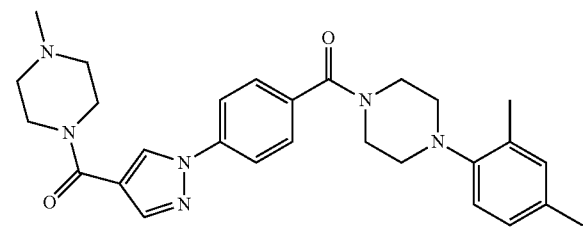 [SMILES: Cc1ccc(N2CCN(C(=O)c3ccc(-n4cc(C(=O)N5CCN(C)CC5)cn4)cc3)CC2)c(C)c1]

Using [4-(2,4-dimethylphenyl)piperazin-1-yl](4-iodophenyl)methanone (840 mg) described in Preparation Example 108 and 1H-pyrazole-4-carboxylic acid ethyl ester (320 mg) and by the reaction and treatment in the same manner as in Example 1, 1-{4-[4-(2,4-dimethylphenyl)piperazine-1-carbonyl]phenyl}-1H-pyrazole-4-carboxylic acid ethyl ester was obtained. Using this compound and 1-methylpiperazine (230 μL) and by the reaction and treatment in the same manner as in Example 109, the title compound (88 mg) was obtained.

MS (ESI) m/z: 487(M+H)⁺.

Example 127

Synthesis of [4-(3,5-dimethylpyridin-2-yl)piperazin-1-yl][4-(1,1-dioxo-1λ⁶-isothiazolidin-2-yl)-2-methanesulfonylphenyl]methanone

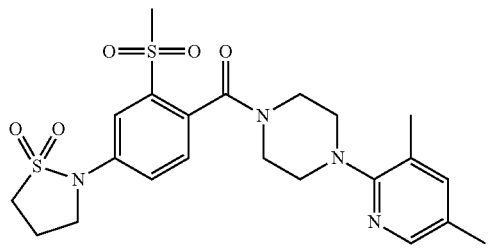 [SMILES: Cc1cnc(N2CCN(C(=O)c3ccc(N4CCCS4(=O)=O)cc3S(C)(=O)=O)CC2)c(C)c1]

Using [4-(3,5-dichloropyridin-2-yl)piperazin-1-yl][4-(1,1-dioxo-1λ⁶-isothiazolidin-2-yl)-2-methanesulfonylphenyl]methanone (216 mg) described in Preparation Example 196 and methylboronic acid (103 mg) and by the reaction and treatment in the same manner as in Example 115, the title compound (67 mg) was obtained.

MS (ESI) m/z: 493(M+H)⁺.

Example 128

Synthesis of [4-(2,4-dimethylphenyl)-4-oxypiperazin-1-yl][4-(1,1-dioxo-1λ⁶-isothiazolidin-2-yl)phenyl]methanone

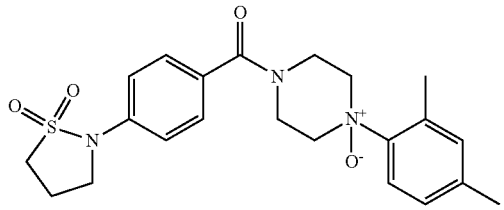 [SMILES: Cc1ccc([N+]2([O-])CCN(C(=O)c3ccc(N4CCCS4(=O)=O)cc3)CC2)c(C)c1]

Using 4-(1,1-dioxo-1λ⁶-isothiazolidin-2-yl)benzoic acid (253 mg) described in Preparation Example 16 and 1-(2,4-dimethylphenyl)piperazine (199 mg) and by the reaction and treatment in the same manner as in Example 87, [4-(2,4-dimethylphenyl)piperazin-1-yl][4-(1,1-dioxo-1λ⁶-isothiazolidin-2-yl)phenyl]methanone (384 mg) was obtained. Using the obtained [4-(2,4-dimethylphenyl)piperazin-1-yl][4-(1,1-dioxo-1λ⁶-isothiazolidin-2-yl)phenyl]methanone (303 mg) and by the reaction and treatment in the same manner as in Example 123, the title compound (264 mg) was obtained.

MS (ESI) m/z: 430(M+H)⁺.

Example 129

Synthesis of 1-{4-[4-(2,4-dimethylphenyl)piperazine-1-carbonyl]phenyl}azetidin-2-one

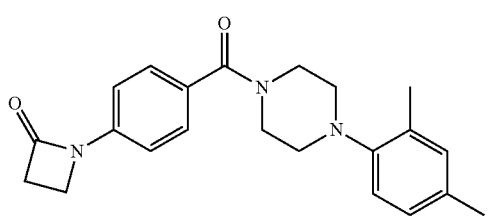 [SMILES: Cc1ccc(N2CCN(C(=O)c3ccc(N4CCC4=O)cc3)CC2)c(C)c1]

Using (4-bromophenyl)[4-(2,4-dimethylphenyl)piperazin-1-yl]methanone (747 mg) described in Preparation Example 170 and azetidin-2-one (142 mg) and by the reaction and treatment in the same manner as in Example 1, the title compound (200 mg) was obtained.

MS (ESI) m/z: 364(M+H)⁺.

Example 130

Synthesis of [4-(3,5-dimethylpyridin-2-yl)piperazin-1-yl][4-(1,1-dioxo-1λ⁶-isothiazolidin-2-yl)-2-fluorophenyl]methanone

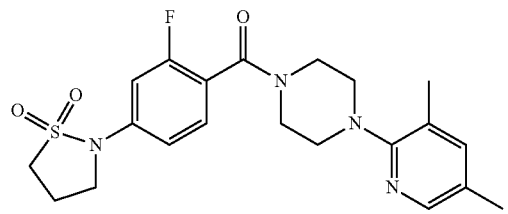 [SMILES: Cc1cnc(N2CCN(C(=O)c3ccc(N4CCCS4(=O)=O)cc3F)CC2)c(C)c1]

Using [4-(3,5-dichloropyridin-2-yl)piperazin-1-yl][4-(1,1-dioxo-1λ⁶-isothiazolidin-2-yl)-2-fluorophenyl]methanone (508 mg) described in Preparation Example 197 and methylboronic acid (272 mg) and by the reaction and treatment in the same manner as in Example 115, the title compound (295.5 mg) was obtained.

MS (ESI) m/z: 433(M+H)⁺.

Example 131

Synthesis of (R)-3-[2-[4-(3,5-dimethylpyridin-2-yl)piperazine-1-carbonyl]pyrimidin-5-yl]-4-methyloxazolidin-2-one hydrochloride

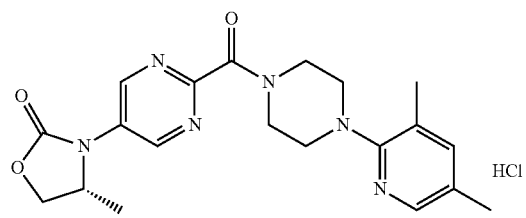 [SMILES: Cc1cnc(N2CCN(C(=O)c3ncc(N4C(=O)OC[C@H]4C)cn3)CC2)c(C)c1 ; Cl]

Using 1-(3,5-dimethylpyridin-2-yl)piperazine hydrochloride (528 mg) described in Preparation Example 80 and 5-bromopyrimidine-2-carboxylic acid (406 mg) and by the reaction and treatment in the same manner as in Example 97, (5-bromopyrimidin-2-yl)[4-(3,5-dimethylpyridin-2-yl)piperazin-1-yl]methanone (750 mg) was obtained. Using this compound (750 mg) and (R)-4-methyl-2-oxazolidinone (303 mg) and by the reaction and treatment in the same manner as in Example 1, (R)-3-[2-[4-(3,5-dimethylpyridin-2-yl)piperazine-1-carbonyl]pyrimidin-5-yl]-4-methyloxazolidin-2-one was obtained. The obtained (R)-3-[2-[4-(3,5-dimethylpyridin-2-yl)piperazine-1-carbonyl]pyrimidin-5-yl]-4-methyloxazolidin-2-one was dissolved in ethyl acetate, 4N hydrogen chloride/ethyl acetate (0.4 mL) was added, and the precipitate was collected by filtration to give the title compound (509 mg).

MS (ESI) m/z: 397(M+H)⁺.

Example 132

Synthesis of [4-(3,5-dimethylpyridin-2-yl)piperazin-1-yl][4-(1,1-dioxo-1λ$^6$-isothiazolidin-2-yl)-2-methoxyphenyl]methanone

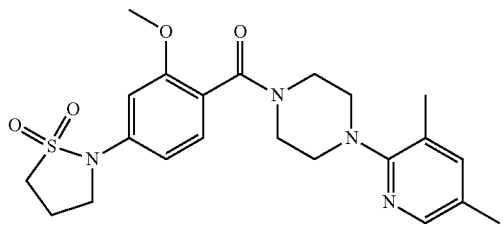 [SMILES: COc1cc(N2CCCS2(=O)=O)ccc1C(=O)N1CCN(c2ncc(C)cc2C)CC1]

Using [4-(3,5-dichloropyridin-2-yl)piperazin-1-yl][4-(1,1-dioxo-1λ$^6$-isothiazolidin-2-yl)-2-methoxyphenyl]methanone (507 mg) described in Preparation Example 198 and methylboronic acid (272 mg) and by the reaction and treatment in the same manner as in Example 115, the title compound (347 mg) was obtained.

MS (ESI) m/z: 445(M+H)$^+$.

Example 133

Synthesis of [4-(3,5-dimethylpyridin-2-yl)piperazin-1-yl][4-(1,1-dioxo-1λ$^6$-isothiazolidin-2-yl)-2-hydroxyphenyl]methanone

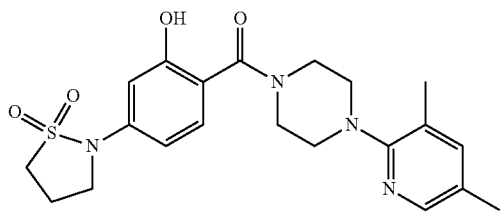 [SMILES: Cc1cnc(N2CCN(C(=O)c3ccc(N4CCCS4(=O)=O)cc3O)CC2)c(C)c1]

Using [4-(3,5-dimethylpyridin-2-yl)piperazin-1-yl][4-(1,1-dioxo-1λ$^6$-isothiazolidin-2-yl)-2-methoxyphenyl]methanone (347 mg) described in Example 132 and by the reaction and treatment in the same manner as in Example 124, the title compound (83 mg) was obtained.

MS (ESI) m/z: 431(M+H)$^+$.

Example 134

Synthesis of [4-(3,5-dimethylpyridin-2-yl)piperazin-1-yl][6-(1,1-dioxo-1λ$^6$-isothiazolidin-2-yl)pyridin-3-yl]methanone

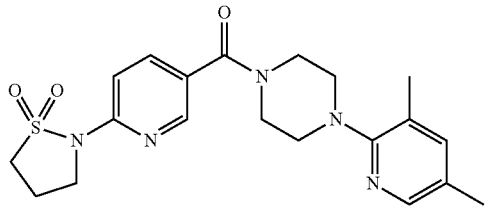

Using ethyl 6-(1,1-dioxo-1λ$^6$-isothiazolidin-2-yl)nicotinate (363 mg) described in Preparation Example 25 and 1-(3,5-dimethylpyridin-2-yl)piperazine (256 mg) described in Preparation Example 79 and by the reaction and treatment in the same manner as in Example 109, the title compound (257 mg) was obtained.

MS (ESI) m/z: 416(M+H)$^+$.

Example 135

Synthesis of [4-(3,5-dimethylpyridin-2-yl)piperazin-1-yl][4-(1,1-dioxo-1λ$^6$-isothiazolidin-2-yl)-2-nitrophenyl]methanone

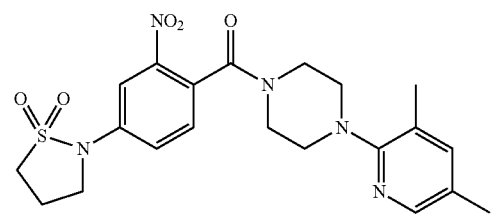

Using 4-(1,1-dioxo-1λ$^6$-isothiazolidin-2-yl)-2-nitrobenzoic acid (1.05 g) described in Preparation Example 24 and 1-(3,5-dimethylpyridin-2-yl)piperazine (0.70 g) described in Preparation Example 79 and by the reaction and treatment in the same manner as in Example 87, the title compound (1.06 g) was obtained.

MS (ESI) m/z: 460(M+H)$^+$.

Example 136

Synthesis of [2-amino-4-(1,1-dioxo-1λ$^6$-isothiazolidin-2-yl)phenyl][4-(3,5-dimethylpyridin-2-yl)piperazin-1-yl]methanone

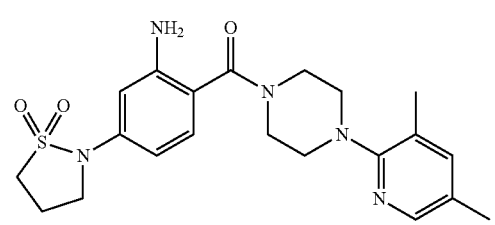

Using [4-(3,5-dimethylpyridin-2-yl)piperazin-1-yl][4-(1,1-dioxo-1λ$^6$-isothiazolidin-2-yl)-2-nitrophenyl]methanone (948 mg) described in Example 135 and by the reaction and treatment in the same manner as in Example 103, the title compound (734 mg) was obtained.

MS (ESI) m/z: 430(M+H)$^+$.

Example 137

Synthesis of N-{2-[4-(3,5-dimethylpyridin-2-yl)piperazine-1-carbonyl]-5-(1,1-dioxo-1λ⁶-isothiazolidin-2-yl)phenyl}acetamide

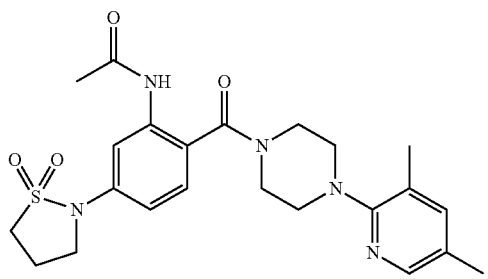

Using [2-amino-4-(1,1-dioxo-1λ⁶-isothiazolidin-2-yl)phenyl][4-(3,5-dimethylpyridin-2-yl)piperazin-1-yl]methanone (300 mg) described in Example 136 and acetyl chloride (0.07 mL) and by the reaction and treatment in the same manner as in Example 107, the title compound (279 mg) was obtained.

MS (ESI) m/z: 472(M+H)⁺.

Example 138

Synthesis of 2-{4-[4-(2,4-dimethylphenyl)piperazine-1-carbonyl]phenyl}-1,1-dioxo-1λ⁶-isothiazolidine-3-carboxylic acid methyl ester

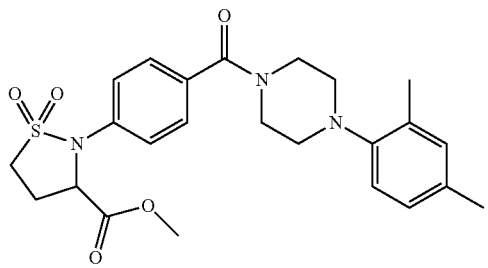 [SMILES: COC(=O)C1CCS(=O)(=O)N1c1ccc(C(=O)N2CCN(c3ccc(C)cc3C)CC2)cc1]

Using [4-(2,4-dimethylphenyl)piperazin-1-yl](4-iodophenyl)methanone (781 mg) described in Preparation Example 108 and 1,1-dioxo-1λ⁶-isothiazolidine-3-carboxylic acid methyl ester (580 mg) and by the reaction and treatment in the same manner as in Example 1, the title compound (41 mg) was obtained.

MS (ESI) m/z: 472(M+H)⁺.

Example 139

Synthesis of [4-(4,6-dimethylpyridin-3-yl)piperazin-1-yl][4-(1,1-dioxo-1λ⁶-isothiazolidin-2-yl)phenyl]methanone

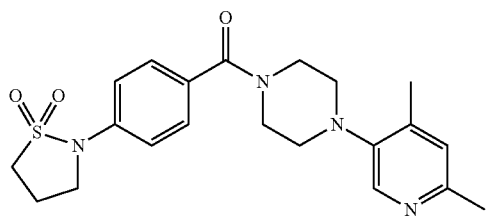 [SMILES: Cc1cc(C)c(N2CCN(C(=O)c3ccc(N4CCCS4(=O)=O)cc3)CC2)cn1]

Using 4-(1,1-dioxo-1λ⁶-isothiazolidin-2-yl)benzoic acid (165 mg) described in Preparation Example 16 and 1-(4,6-dimethylpyridin-3-yl)piperazine (131 mg) described in Preparation Example 95 and by the reaction and treatment in the same manner as in Example 87, the title compound (105 mg) was obtained.

MS (ESI) m/z: 415(M+H)⁺.

Example 140

Synthesis of (S)-[4-(3,5-dimethylpyridin-2-yl)piperazin-1-yl][4-(1,1-dioxo-3-phenyl-1λ⁶-isothiazolidin-2-yl)phenyl]methanone

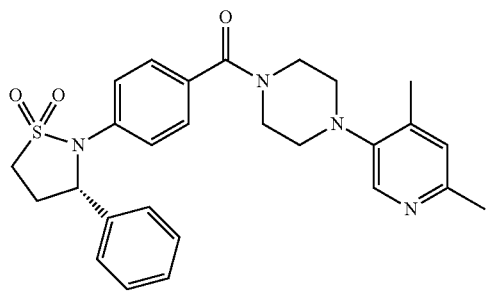 [SMILES: Cc1cc(C)c(N2CCN(C(=O)c3ccc(N4[C@H](c5ccccc5)CCS4(=O)=O)cc3)CC2)cn1]

Using [4-(3,5-dimethylpyridin-2-yl)piperazin-1-yl](4-iodophenyl)methanone (421 mg) described in Preparation Example 113 and (S)-3-phenylisothiazolidine 1,1-dioxide (197 mg) described in Preparation Example 27 and by the reaction and treatment in the same manner as in Example 1, the title compound (275 mg) was obtained.

MS (ESI) m/z: 491(M+H)⁺.

Example 141

Synthesis of (R)-[4-(3,5-dimethylpyridin-2-yl)piperazin-1-yl][4-(3-methyl-1,1-dioxo-1λ⁶-isothiazolidin-2-yl)phenyl]methanone hydrochloride

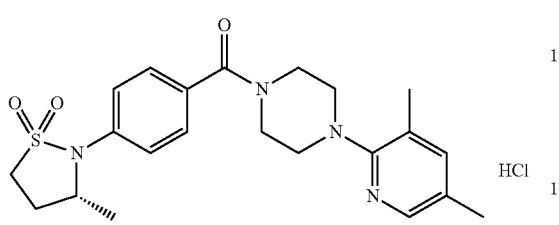

To a mixture of [4-(3,5-dimethylpyridin-2-yl)piperazin-1-yl](4-iodophenyl)methanone (848 mg) described in Preparation Example 113, (R)-3-methylisothiazolidine 1,1-dioxide (272 mg) described in Preparation Example 2, potassium carbonate (555 mg) and copper(I) iodide (192 mg) were added toluene (4 mL) and N,N'-dimethylethylenediamine (0.20 mL), and the mixture was stirred with heating under reflux for 8 hr. The reaction mixture was cooled, water was added, the mixture was extracted with chloroform, and the solvent was evaporated. The obtained residue was purified by column chromatography (chloroform:methanol) to give (R)-[4-(3,5-dimethylpyridin-2-yl)piperazin-1-yl][4-(3-methyl-1,1-dioxo-1λ⁶-isothiazolidin-2-yl)phenyl]methanone. The obtained (R)-[4-(3,5-dimethylpyridin-2-yl)piperazin-1-yl][4-(3-methyl-1,1-dioxo-1λ⁶-isothiazolidin-2-yl)phenyl]methanone (453 mg) was dissolved in ethyl acetate, 4N hydrogen chloride/ethyl acetate (0.26 mL) was added, and the precipitate was collected by filtration to give the title compound (372 mg).

MS (ESI) m/z: 429(M+H)⁺.

Example 142

Synthesis of [6-(1,1-dioxo-1λ⁶-isothiazolidin-2-yl)pyridin-3-yl][4-(p-tolyloxy)piperidin-1-yl]methanone

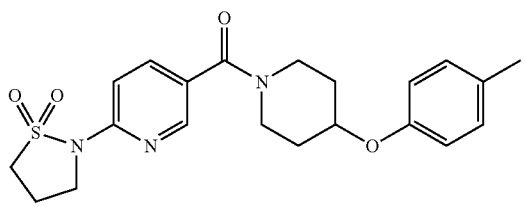 [SMILES: Cc1ccc(OC2CCN(C(=O)c3ccc(N4CCCS4(=O)=O)nc3)CC2)cc1]

Using (6-bromopyridin-3-yl)[4-(p-tolyloxy)piperidin-1-yl]methanone (548 mg) described in Preparation Example 193 and isothiazolidine 1,1-dioxide (177 mg) and by the reaction and treatment in the same manner as in Example 1, the title compound (146 mg) was obtained.

MS (ESI) m/z: 416(M+H)⁺.

Example 143

Synthesis of (R)-[4-(3,5-dimethylpyridin-2-yl)piperazin-1-yl][2-methyl-4-(3-methyl-1,1-dioxo-1λ⁶-isothiazolidin-2-yl)phenyl]methanone

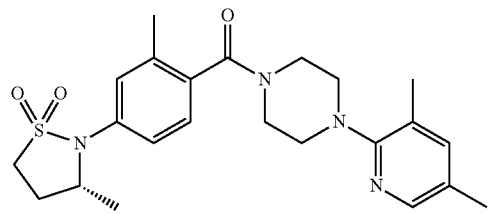 [SMILES: Cc1cnc(N2CCN(C(=O)c3ccc(N4[C@H](C)CCS4(=O)=O)cc3C)CC2)c(C)c1]

Using [4-(3,5-dimethylpyridin-2-yl)piperazin-1-yl](4-iodo-2-methylphenyl)methanone (562 mg) described in Preparation Example 154 and (R)-3-methylisothiazolidine 1,1-dioxide (175 mg) described in Preparation Example 2 and by the reaction and treatment in the same manner as in Example 1, the title compound (296 mg) was obtained.

MS (ESI) m/z: 443(M+H)⁺.

Example 144

Synthesis of (R)-[4-(3,5-dimethylpyridin-2-yl)piperazin-1-yl][2-fluoro-4-(3-methyl-1,1-dioxo-1λ⁶-isothiazolidin-2-yl)phenyl]methanone

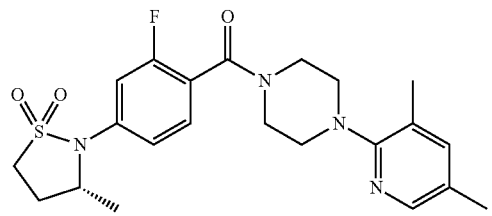 [SMILES: Cc1cnc(N2CCN(C(=O)c3ccc(N4[C@H](C)CCS4(=O)=O)cc3F)CC2)c(C)c1]

Using [4-(3,5-dimethylpyridin-2-yl)piperazin-1-yl](2-fluoro-4-iodophenyl)methanone (439 mg) described in Preparation Example 155 and (R)-3-methylisothiazolidine 1,1-dioxide (135 mg) described in Preparation Example 2 and by the reaction and treatment in the same manner as in Example 1, the title compound (242 mg) was obtained.

MS (ESI) m/z: 447(M+H)⁺.

Example 145

Synthesis of (R)-[4-(3,5-dimethylpyridin-2-yl)piperazin-1-yl][2-methanesulfonyl-4-(3-methyl-1,1-dioxo-1λ⁶-isothiazolidin-2-yl)phenyl]methanone

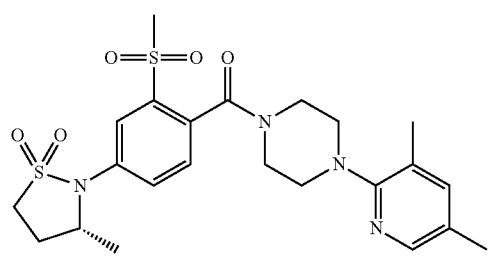 [SMILES: Cc1cnc(N2CCN(C(=O)c3ccc(N4[C@H](C)CCS4(=O)=O)cc3S(C)(=O)=O)CC2)c(C)c1]

Using [4-(3,5-dimethylpyridin-2-yl)piperazin-1-yl](4-iodo-2-methanesulfonylphenyl)methanone (580 mg) described in Preparation Example 156 and (R)-3-methylisothiazolidine 1,1-dioxide (157 mg) described in Preparation Example 2 and by the reaction and treatment in the same manner as in Example 1, the title compound (337 mg) was obtained.

MS (ESI) m/z: 507(M+H)+.

Example 146

Synthesis of (R)-[4-(2,4-dimethylphenyl)piperazin-1-yl][4-(3-methyl-1,1-dioxo-1λ6-isothiazolidin-2-yl)phenyl]methanone

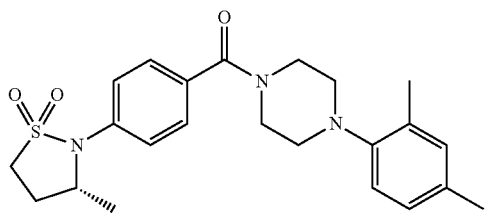 [SMILES: Cc1ccc(N2CCN(C(=O)c3ccc(N4[C@H](C)CCS4(=O)=O)cc3)CC2)c(C)c1]

Using [4-(2,4-dimethylphenyl)piperazin-1-yl](4-iodophenyl)methanone (294 mg) described in Preparation Example 108 and (R)-3-methylisothiazolidine 1,1-dioxide (94 mg) described in Preparation Example 2 and by the reaction and treatment in the same manner as in Example 1, the title compound (123 mg) was obtained.

MS (ESI) m/z: 428(M+H)+.

Example 147

Synthesis of [4-(3,5-dimethylpyridin-2-yl)piperazin-1-yl][4-(1,1-dioxo-1λ6-isothiazolidin-2-yl)-3-fluorophenyl]methanone

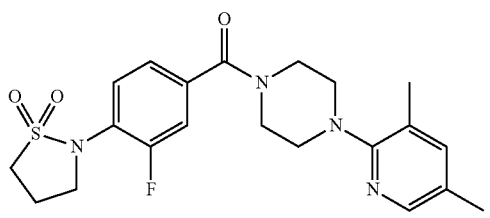

Using 4-(1,1-dioxo-1λ6-isothiazolidin-2-yl)-3-fluorobenzoic acid (223 mg) described in Preparation Example 26 and 1-(3,5-dimethylpyridin-2-yl)piperazine (164 mg) described in Preparation Example 79 and by the reaction and treatment in the same manner as in Example 87, the title compound (229 mg) was obtained.

MS (ESI) m/z: 433(M+H)+.

Example 148

Synthesis of [4-(5-cyclopropyl-3-methylpyridin-2-yl)piperazin-1-yl][4-(1,1-dioxo-1λ6-isothiazolidin-2-yl)phenyl]methanone

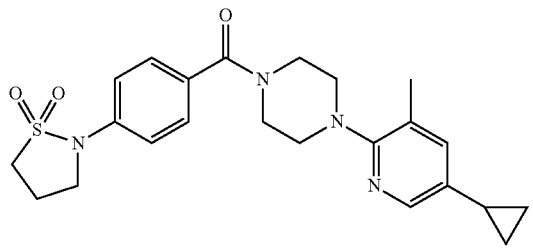

Using 4-(1,1-dioxo-1λ6-isothiazolidin-2-yl)benzoic acid (241 mg) described in Preparation Example 16 and 1-(5-cyclopropyl-3-methylpyridin-2-yl)piperazine hydrochloride (254 mg) described in Preparation Example 82 and by the reaction and treatment in the same manner as in Example 86, the title compound (231 mg) was obtained.

MS (ESI) m/z: 441(M+H)+.

Example 149

Synthesis of (R)-[4-(2,4-dimethylphenyl)piperazin-1-yl][2-methanesulfonyl-4-(3-methyl-1,1-dioxo-1λ6-isothiazolidin-2-yl)phenyl]methanone

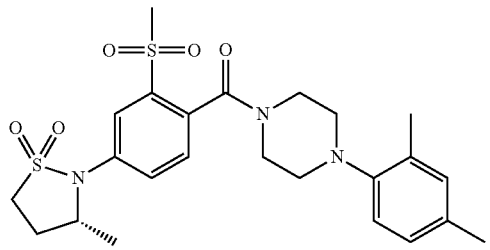

Using [4-(2,4-dimethylphenyl)piperazin-1-yl](4-iodo-2-methanesulfonylphenyl)methanone (886 mg) described in Preparation Example 157 and (R)-3-methylisothiazolidine 1,1-dioxide (240 mg) described in Preparation Example 2 and by the reaction and treatment in the same manner as in Example 1, the title compound (514 mg) was obtained.

MS (ESI) m/z: 506(M+H)+.

Example 150

Synthesis of [4-(3-cyclopropyl-5-methylpyridin-2-yl)piperazin-1-yl][4-(1,1-dioxo-1λ6-isothiazolidin-2-yl)phenyl]methanone

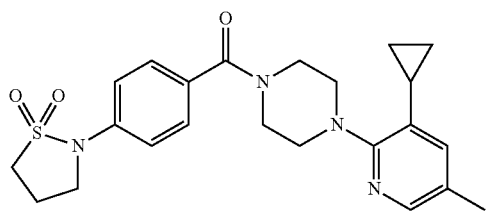 [SMILES: Cc1cnc(N2CCN(C(=O)c3ccc(N4CCCS4(=O)=O)cc3)CC2)c(C2CC2)c1]

Using 4-(1,1-dioxo-1λ⁶-isothiazolidin-2-yl)benzoic acid (241 mg) described in Preparation Example 16 and 1-(3-cyclopropyl-5-methylpyridin-2-yl)piperazine hydrochloride (254 mg) described in Preparation Example 85 and by the reaction and treatment in the same manner as in Example 86, the title compound (42 mg) was obtained.

MS (ESI) m/z: 441(M+H)⁺.

Example 151

Synthesis of (R)-[2,6-difluoro-4-(3-methyl-1,1-dioxo-1λ⁶-isothiazolidin-2-yl)phenyl][4-(3,5-dimethylpyridin-2-yl)piperazin-1-yl]methanone

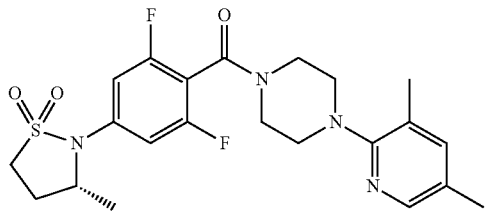 [SMILES: Cc1cnc(N2CCN(C(=O)c3c(F)cc(N4[C@H](C)CCS4(=O)=O)cc3F)CC2)c(C)c1]

Using (2,6-difluoro-4-iodophenyl)[4-(3,5-dimethylpyridin-2-yl)piperazin-1-yl]methanone (743 mg) described in Preparation Example 158 and (R)-3-methylisothiazolidine 1,1-dioxide (220 mg) described in Preparation Example 2 and by the reaction and treatment in the same manner as in Example 1, the title compound (421 mg) was obtained.

MS (ESI) m/z: 465(M+H)⁺.

Example 152

Synthesis of [4-(3-cyclopropyl-5-methylpyridin-2-yl)piperazin-1-yl][4-(1,1-dioxo-1λ⁶-isothiazolidin-2-yl)-2-fluorophenyl]methanone

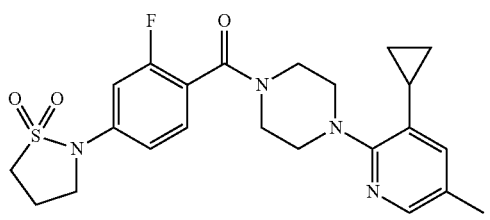 [SMILES: Cc1cnc(N2CCN(C(=O)c3ccc(N4CCCS4(=O)=O)cc3F)CC2)c(C2CC2)c1]

Using 4-(1,1-dioxo-1λ⁶-isothiazolidin-2-yl)-2-fluorobenzoic acid (259 mg) described in Preparation Example 23 and 1-(3-cyclopropyl-5-methylpyridin-2-yl)piperazine hydrochloride (254 mg) described in Preparation Example 85 and by the reaction and treatment in the same manner as in Example 86, the title compound (223 mg) was obtained.

MS (ESI) m/z: 459(M+H)⁺.

Example 153

Synthesis of [4-(5-cyclopropyl-3-methylpyridin-2-yl)piperazin-1-yl][4-(1,1-dioxo-1λ⁶-isothiazolidin-2-yl)-2-fluorophenyl]methanone

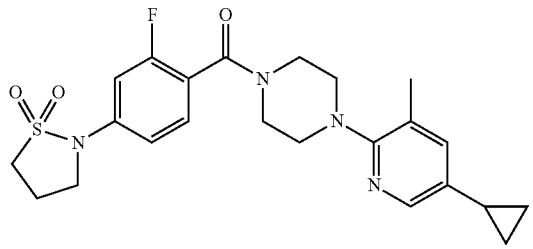 [SMILES: Cc1cc(C2CC2)cnc1N1CCN(C(=O)c2ccc(N3CCCS3(=O)=O)cc2F)CC1]

Using 4-(1,1-dioxo-1λ⁶-isothiazolidin-2-yl)-2-fluorobenzoic acid (259 mg) described in Preparation Example 23 and 1-(5-cyclopropyl-3-methylpyridin-2-yl)piperazine hydrochloride (254 mg) described in Preparation Example 82 and by the reaction and treatment in the same manner as in Example 86, the title compound (288 mg) was obtained.

MS (ESI) m/z: 459(M+H)⁺.

Example 154

Synthesis of [4-(3,5-dimethylpyridin-2-yl)piperazin-1-yl][4-(1,1-dioxo-1λ⁶-isothiazolidin-2-yl)-2-methylphenyl]methanone

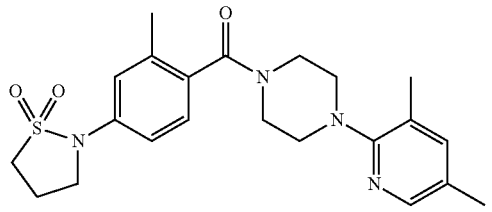 [SMILES: Cc1cnc(N2CCN(C(=O)c3ccc(N4CCCS4(=O)=O)cc3C)CC2)c(C)c1]

Using [4-(3,5-dimethylpyridin-2-yl)piperazin-1-yl](4-iodo-2-methylphenyl)methanone (487 mg) described in Preparation Example 154 and isothiazolidine 1,1-dioxide (136 mg) and by the reaction and treatment in the same manner as in Example 1, the title compound (279 mg) was obtained.

MS (ESI) m/z: 429(M+H)⁺.

Example 155

Synthesis of (R)-[4-(3,5-dimethylpyridin-2-yl)piperazin-1-yl][3-fluoro-4-(3-methyl-1,1-dioxo-1λ⁶-isothiazolidin-2-yl)phenyl]methanone

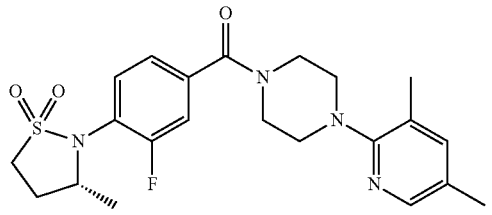 [SMILES: Cc1cnc(N2CCN(C(=O)c3ccc(N4[C@H](C)CCS4(=O)=O)c(F)c3)CC2)c(C)c1]

Using [4-(3,5-dimethylpyridin-2-yl)piperazin-1-yl](3-fluoro-4-iodophenyl)methanone (600 mg) described in Preparation Example 159 and (R)-3-methylisothiazolidine 1,1-dioxide (185 mg) described in Preparation Example 2 and by the reaction and treatment in the same manner as in Example 1, the title compound (51 mg) was obtained.

MS (ESI) m/z: 447(M+H)$^+$.

Example 156

Synthesis of [4-(1,1-dioxo-1$\lambda^6$-isothiazolidin-2-yl)-2-fluorophenyl][4-(3-methyl-5-trifluoromethylpyridin-2-yl)piperazin-1-yl]methanone

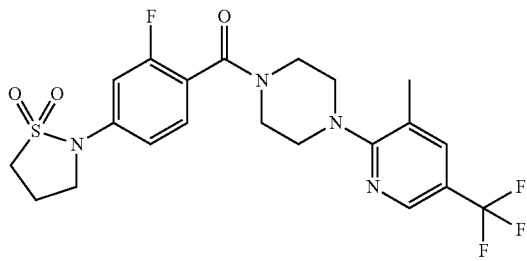 [SMILES: Cc1cc(C(F)(F)F)cnc1N1CCN(C(=O)c2ccc(N3CCCS3(=O)=O)cc2F)CC1]

Using 4-(1,1-dioxo-1$\lambda^6$-isothiazolidin-2-yl)-2-fluorobenzoic acid (259 mg) described in Preparation Example 23 and 1-(3-methyl-5-trifluoromethylpyridin-2-yl)piperazine (245 mg) described in Preparation Example 84 and by the reaction and treatment in the same manner as in Example 87, the title compound (332 mg) was obtained.

MS (ESI) m/z: 487(M+H)$^+$.

Example 157

Synthesis of (R)-[4-(3-cyclopropyl-5-methylpyridin-2-yl)piperazin-1-yl][2-fluoro-4-(3-methyl-1,1-dioxo-1$\lambda^6$-isothiazolidin-2-yl)phenyl]methanone

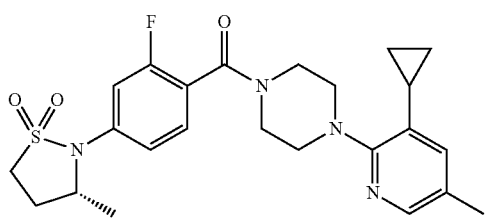 [SMILES: Cc1cnc(N2CCN(C(=O)c3ccc(N4[C@H](C)CCS4(=O)=O)cc3F)CC2)c(C2CC2)c1]

Using [4-(3-cyclopropyl-5-methylpyridin-2-yl)piperazin-1-yl](2-fluoro-4-iodophenyl)methanone (627 mg) described in Preparation Example 183 and (R)-3-methylisothiazolidine 1,1-dioxide (182 mg) described in Preparation Example 2 and by the reaction and treatment in the same manner as in Example 1, the title compound (291 mg) was obtained.

MS (ESI) m/z: 473(M+H)$^+$.

Example 158

Synthesis of (R)-[2-fluoro-4-(3-methyl-1,1-dioxo-1$\lambda^6$-isothiazolidin-2-yl)phenyl][4-(3-methyl-5-trifluoromethylpyridin-2-yl)piperazin-1-yl]methanone

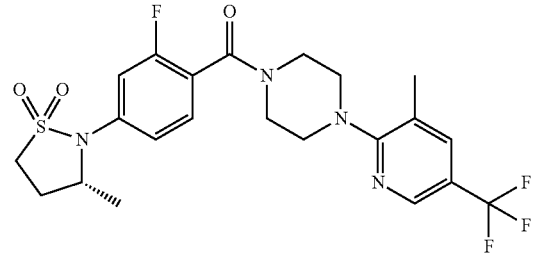 [SMILES: Cc1cc(C(F)(F)F)cnc1N1CCN(C(=O)c2ccc(N3[C@H](C)CCS3(=O)=O)cc2F)CC1]

Using (2-fluoro-4-iodophenyl)[4-(3-methyl-5-trifluoromethylpyridin-2-yl)piperazin-1-yl]methanone (507 mg) described in Preparation Example 161 and (R)-3-methylisothiazolidine 1,1-dioxide (139 mg) described in Preparation Example 2 and by the reaction and treatment in the same manner as in Example 1, the title compound (29 mg) was obtained.

MS (ESI) m/z: 501(M+H)$^+$.

Example 159

Synthesis of (R)-[4-(2,4-dimethylphenyl)piperazin-1-yl][6-(3-methyl-1,1-dioxo-1$\lambda^6$-isothiazolidin-2-yl)pyridin-3-yl]methanone

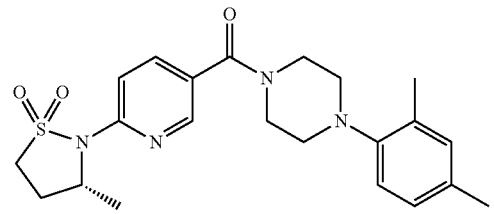

Using [4-(2,4-dimethylphenyl)piperazin-1-yl](6-iodopyridin-3-yl)methanone (341 mg) described in Preparation Example 162 and (R)-3-methylisothiazolidine 1,1-dioxide (123 mg) described in Preparation Example 2 and by the reaction and treatment in the same manner as in Example 1, the title compound (102 mg) was obtained.

MS (ESI) m/z: 429(M+H)$^+$.

Example 160

Synthesis of (R)-[4-(5-cyclopropyl-3-methylpyridin-2-yl)piperazin-1-yl][2-fluoro-4-(3-methyl-1,1-dioxo-1$\lambda^6$-isothiazolidin-2-yl)phenyl]methanone hydrochloride

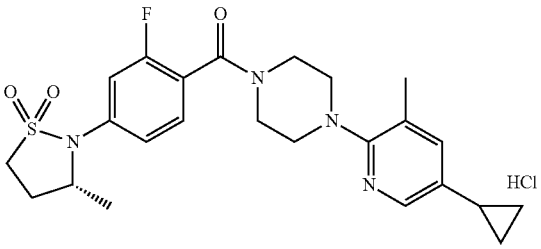 [SMILES: Cc1cc(C2CC2)cnc1N1CCN(C(=O)c2ccc(N3[C@H](C)CCS3(=O)=O)cc2F)CC1 ; Cl]

Using [4-(5-cyclopropyl-3-methylpyridin-2-yl)piperazin-1-yl](2-fluoro-4-iodophenyl)methanone (669 mg) described in Preparation Example 163 and (R)-3-methylisothiazolidine 1,1-dioxide (194 mg) described in Preparation Example 2 and by the reaction and treatment in the same manner as in Example 141, the title compound (330 mg) was obtained.

MS (ESI) m/z: 473(M+H)$^+$.

Example 161

Synthesis of [6-(1,1-dioxo-1$\lambda^6$-isothiazolidin-2-yl)pyridin-3-yl][4-(4-methyl-2-trifluoromethylphenyl)piperazin-1-yl]methanone

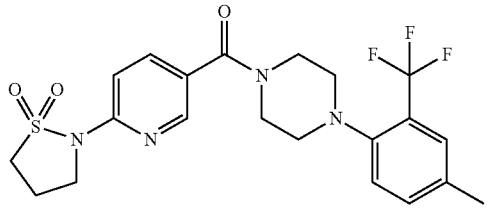 [SMILES: Cc1ccc(N2CCN(C(=O)c3ccc(N4CCCS4(=O)=O)nc3)CC2)c(C(F)(F)F)c1]

Using ethyl 6-(1,1-dioxo-1$\lambda^6$-isothiazolidin-2-yl)nicotinate (363 mg) described in Preparation Example 25 and 1-(4-methyl-2-trifluoromethylphenyl)piperazine (327 mg) described in Preparation Example 96 and by the reaction and treatment in the same manner as in Example 109, the title compound (172 mg) was obtained.

MS (ESI) m/z: 469(M+H)$^+$.

Example 162

Synthesis of [4-(3,5-dicyclopropylpyridin-2-yl)piperazin-1-yl][4-(1,1-dioxo-1$\lambda^6$-isothiazolidin-2-yl)-2-fluorophenyl]methanone

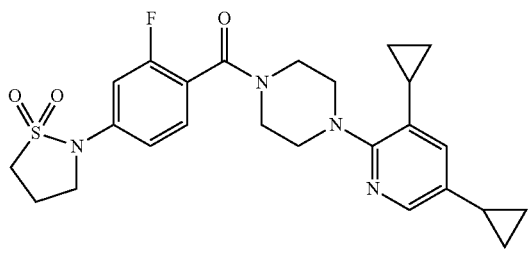 [SMILES: O=C(c1ccc(N2CCCS2(=O)=O)cc1F)N1CCN(c2ncc(C3CC3)cc2C2CC2)CC1]

Using 4-(1,1-dioxo-1$\lambda^6$-isothiazolidin-2-yl)-2-fluorobenzoic acid (259 mg) described in Preparation Example 23 and 1-(3,5-dicyclopropylpyridin-2-yl)piperazine hydrochloride (280 mg) described in Preparation Example 87 and to by the reaction and treatment in the same manner as in Example 86, the title compound (323 mg) was obtained.

MS (ESI) m/z: 485(M+H)$^+$.

Example 163

Synthesis of [4-(3,5-dicyclopropylpyridin-2-yl)piperazin-1-yl][4-(1,1-dioxo-1$\lambda^6$-isothiazolidin-2-yl)-2-methanesulfonylphenyl]methanone

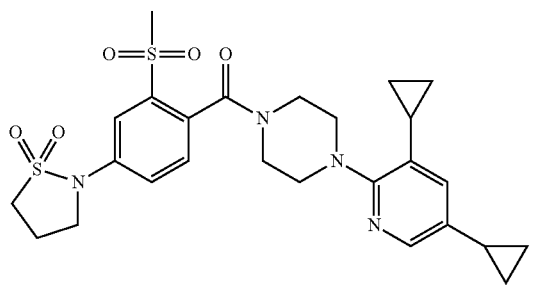 [SMILES: CS(=O)(=O)c1cc(N2CCCS2(=O)=O)ccc1C(=O)N1CCN(c2ncc(C3CC3)cc2C2CC2)CC1]

Using 4-(1,1-dioxo-1$\lambda^6$-isothiazolidin-2-yl)-2-methanesulfonylbenzoic acid (319 mg) described in Preparation Example 22 and 1-(3,5-dicyclopropylpyridin-2-yl)piperazine hydrochloride (280 mg) described in Preparation Example 87 and by the reaction and treatment in the same manner as in Example 86, the title compound (427 mg) was obtained.

MS (ESI) m/z: 545(M+H)$^+$.

Example 164

Synthesis of [4-(3-cyclopropyl-5-methylpyridin-2-yl)piperazin-1-yl][4-(1,1-dioxo-1$\lambda^6$-isothiazolidin-2-yl)-2-methanesulfonylphenyl]methanone

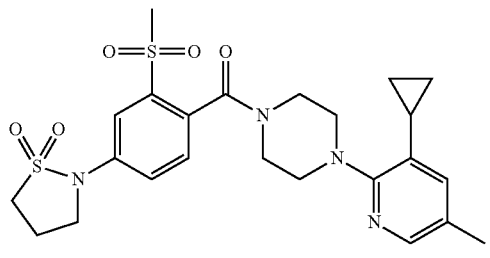 [SMILES: Cc1cnc(N2CCN(C(=O)c3ccc(N4CCCS4(=O)=O)cc3S(C)(=O)=O)CC2)c(C2CC2)c1]

Using 4-(1,1-dioxo-1$\lambda^6$-isothiazolidin-2-yl)-2-methanesulfonylbenzoic acid (319 mg) described in Preparation Example 22 and 1-(3-cyclopropyl-5-methylpyridin-2-yl)piperazine hydrochloride (254 mg) described in Preparation Example 85 and by the reaction and treatment in the same manner as in Example 86, the title compound (360 mg) was obtained.

MS (ESI) m/z: 519(M+H)$^+$.

Example 165

Synthesis of [4-(5-cyclopropyl-3-methylpyridin-2-yl)piperazin-1-yl][4-(1,1-dioxo-1λ$^6$-isothiazolidin-2-yl)-2-methanesulfonylphenyl]methanone

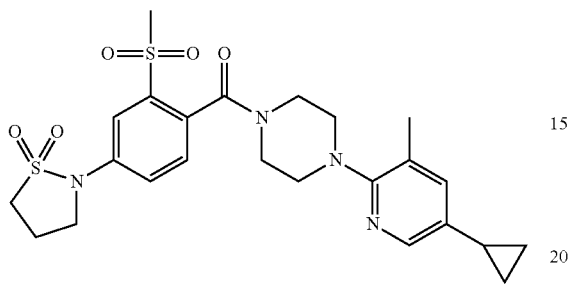

Using 4-(1,1-dioxo-1λ$^6$-isothiazolidin-2-yl)-2-methanesulfonylbenzoic acid (319 mg) described in Preparation Example 22 and 1-(5-cyclopropyl-3-methylpyridin-2-yl)piperazine hydrochloride (254 mg) described in Preparation Example 82 and by the reaction and treatment in the same manner as in Example 86, the title compound (424 mg) was obtained.

MS (ESI) m/z: 519(M+H)$^+$.

Example 166

Synthesis of [4-(3,5-dicyclopropylpyridin-2-yl)piperazin-1-yl][4-(1,1-dioxo-1λ$^6$-isothiazolidin-2-yl)phenyl]methanone

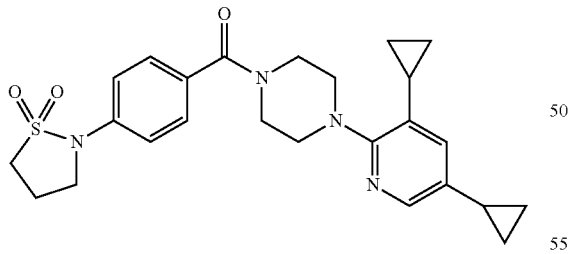

Using 4-(1,1-dioxo-1λ$^6$-isothiazolidin-2-yl)benzoic acid (241 mg) described in Preparation Example 16 and 1-(3,5-dicyclopropylpyridin-2-yl)piperazine hydrochloride (280 mg) described in Preparation Example 87 and by the reaction and treatment in the same manner as in Example 86, the title compound (323 mg) was obtained.

MS (ESI) m/z: 467(M+H)$^+$.

Example 167

Synthesis of (R)-[4-(3,5-dicyclopropylpyridin-2-yl)piperazin-1-yl][2-fluoro-4-(3-methyl-1,1-dioxo-1λ$^6$-isothiazolidin-2-yl)phenyl]methanone

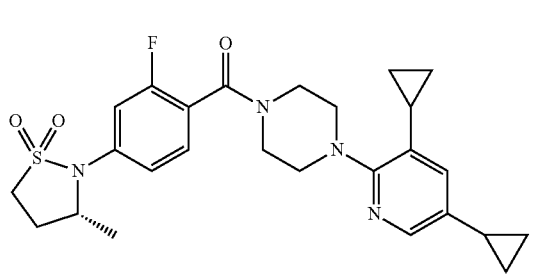 [SMILES: C[C@@H]1CCS(=O)(=O)N1c1ccc(C(=O)N2CCN(c3ncc(C4CC4)cc3C3CC3)CC2)c(F)c1]

Using [4-(3,5-dicyclopropylpyridin-2-yl)piperazin-1-yl](2-fluoro-4-iodophenyl)methanone (491 mg) described in Preparation Example 164 and (R)-3-methylisothiazolidine 1,1-dioxide (135 mg) described in Preparation Example 2 and by the reaction and treatment in the same manner as in Example 1, the title compound (210 mg) was obtained.

MS (ESI) m/z: 499(M+H)$^+$.

Example 168

Synthesis of [4-(1,1-dioxo-1λ$^6$-isothiazolidin-2-yl)-2-methanesulfonylphenyl][4-(3,5,6-trimethylpyridin-2-yl)piperazin-1-yl]methanone

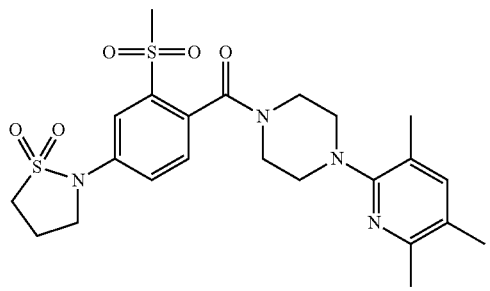 [SMILES: Cc1cc(C)c(N2CCN(C(=O)c3ccc(N4CCCS4(=O)=O)cc3S(C)(=O)=O)CC2)nc1C]

Using (4-bromo-2-methanesulfonylphenyl)[4-(3,5,6-trimethylpyridin-2-yl)piperazin-1-yl]methanone (370 mg) described in Preparation Example 122 and isothiazolidine 1,1-dioxide (96 mg) and by the reaction and treatment in the same manner as in Example 4, the title compound (212 mg) was obtained.

MS (ESI) m/z: 507(M+H)$^+$.

Example 169

Synthesis of (R)-[2-methanesulfonyl-4-(3-methyl-1,1-dioxo-1λ$^6$-isothiazolidin-2-yl)phenyl][4-(3,5,6-trimethylpyridin-2-yl)piperazin-1-yl]methanone

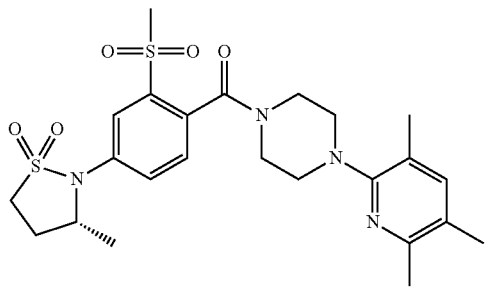 [SMILES: Cc1cc(C)c(N2CCN(C(=O)c3ccc(N4[C@H](C)CCS4(=O)=O)cc3S(C)(=O)=O)CC2)nc1C]

Using (4-bromo-2-methanesulfonylphenyl)[4-(3,5,6-trimethylpyridin-2-yl)piperazin-1-yl]methanone (370 mg) described in Preparation Example 122 and (R)-3-methylisothiazolidine 1,1-dioxide (107 mg) described in Preparation Example 2 and by the reaction and treatment in the same manner as in Example 4, the title compound (200 mg) was obtained.

MS (ESI) m/z: 521(M+H)$^+$.

Example 170

Synthesis of (R)-[4-(5-cyclopropyl-3-methylpyridin-2-yl)piperazin-1-yl][2-methanesulfonyl-4-(3-methyl-1,1-dioxo-1λ$^6$-isothiazolidin-2-yl)phenyl]methanone

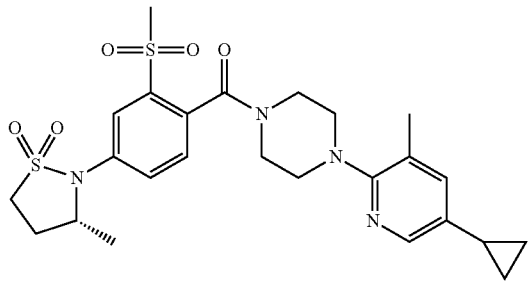 [SMILES: Cc1cc(C2CC2)cnc1N1CCN(C(=O)c2ccc(N3[C@H](C)CCS3(=O)=O)cc2S(C)(=O)=O)CC1]

Ethyl (R)-2-methanesulfonyl-4-(3-methyl-1,1-dioxo-1λ$^6$-isothiazolidin-2-yl)benzoate (361 mg) described in Preparation Example 28 was dissolved in ethanol (5 mL), 1N aqueous sodium hydroxide solution (1.5 mL) was added, and the mixture was stirred at 60° C. After completion of the reaction, the reaction mixture was neutralized with 1N hydrochloric acid (1.5 mL), 1-(5-cyclopropyl-3-methylpyridin-2-yl)piperazine hydrochloride (254 mg) described in Preparation Example 82, N-methylmorpholine (0.2 mL) and 4-(4,6-dimethoxy[1.3.5]triazin-2-yl)-4-methylmorpholinium chloride hydrate (277 mg) were added, and the mixture was stirred at room temperature overnight. Water was added to the reaction mixture, and the mixture was extracted with ethyl acetate. The organic layer was washed with saturated brine, and the solvent was evaporated. The obtained residue was purified by silica gel column chromatography (ethyl acetate:hexane) to give the title compound (292 mg).

MS (ESI) m/z: 533(M+H)$^+$.

Example 171

Synthesis of [4-(1,1-dioxo-1λ$^6$-isothiazolidin-2-yl)phenyl][4-(3,5,6-trimethylpyridin-2-yl)piperazin-1-yl]methanone

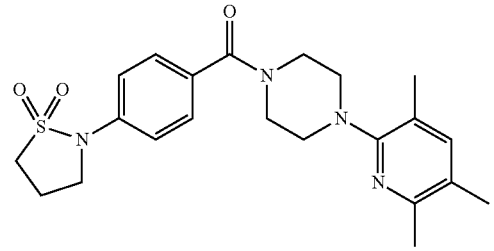 [SMILES: Cc1cc(C)c(N2CCN(C(=O)c3ccc(N4CCCS4(=O)=O)cc3)CC2)nc1C]

Using (4-iodophenyl) [4-(3,5,6-trimethylpyridin-2-yl)piperazin-1-yl]methanone (435 mg) described in Preparation Example 120 and isothiazolidine 1,1-dioxide (121 mg) and by the reaction and treatment in the same manner as in Example 1, the title compound (126 mg) was obtained.

MS (ESI) m/z: 429(M+H)$^+$.

Example 172

Synthesis of (R)-[4-(3,5-dicyclopropylpyridin-2-yl)piperazin-1-yl][2-methanesulfonyl-4-(3-methyl-1,1-dioxo-1λ$^6$-isothiazolidin-2-yl)phenyl]methanone

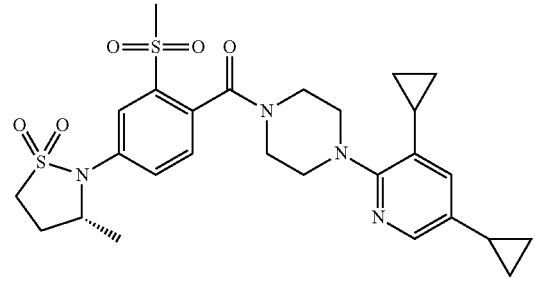 [SMILES: C[C@@H]1CCS(=O)(=O)N1c1ccc(C(=O)N2CCN(c3ncc(C4CC4)cc3C3CC3)CC2)c(S(C)(=O)=O)c1]

Using ethyl (R)-2-methanesulfonyl-4-(3-methyl-1,1-dioxo-1λ$^6$-isothiazolidin-2-yl)benzoate (361 mg) described in Preparation Example 28 and 1-(3,5-dicyclopropylpyridin-2-yl)piperazine (243 mg) described in Preparation Example 88 and by the reaction and treatment in the same manner as in Example 109, the title compound (172 mg) was obtained.

MS (ESI) m/z: 559(M+H)$^+$.

Example 173

Synthesis of [4-(3-cyclopropyl-5-trifluoromethylpyridin-2-yl)piperazin-1-yl][4-(1,1-dioxo-1λ$^6$-isothiazolidin-2-yl)-2-fluorophenyl]methanone

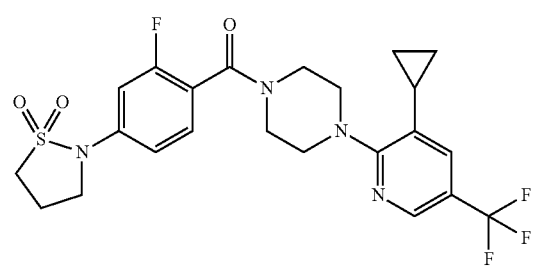 [SMILES: O=C(c1ccc(N2CCCS2(=O)=O)cc1F)N1CCN(c2ncc(C(F)(F)F)cc2C2CC2)CC1]

Using (4-bromo-2-fluorophenyl)[4-(3-cyclopropyl-5-trifluoromethylpyridin-2-yl)piperazin-1-yl]methanone (375 mg) described in Preparation Example 123 and isothiazolidine 1,1-dioxide (96 mg) and by the reaction and treatment in the same manner as in Example 4, the title compound (209 mg) was obtained.

MS (ESI) m/z: 513(M+H)$^+$.

Example 174

Synthesis of (R)-[4-(3-cyclopropyl-5-trifluoromethylpyridin-2-yl)piperazin-1-yl][2-fluoro-4-(3-methyl-1,1-dioxo-1$\lambda^6$-isothiazolidin-2-yl)phenyl]methanone

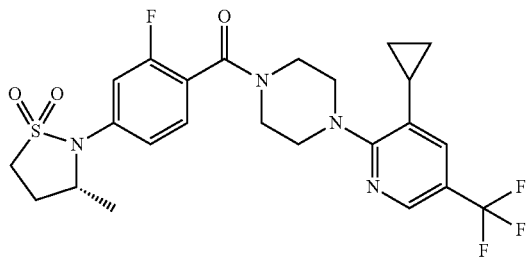 [SMILES: C[C@@H]1CCS(=O)(=O)N1c1ccc(C(=O)N2CCN(c3ncc(C(F)(F)F)cc3C3CC3)CC2)c(F)c1]

Using (4-bromo-2-fluorophenyl)[4-(3-cyclopropyl-5-trifluoromethylpyridin-2-yl)piperazin-1-yl]methanone (375 mg) described in Preparation Example 123 and (R)-3-methylisothiazolidine 1,1-dioxide (107 mg) described in Preparation Example 2 and by the reaction and treatment in the same manner as in Example 4, the title compound (122 mg) was obtained.

MS (ESI) m/z: 527(M+H)$^+$.

Example 175

Synthesis of (R)-[4-(3-methyl-1,1-dioxo-1$\lambda^6$-isothiazolidin-2-yl)phenyl][4-(3,5,6-trimethylpyridin-2-yl)piperazin-1-yl]methanone hydrochloride

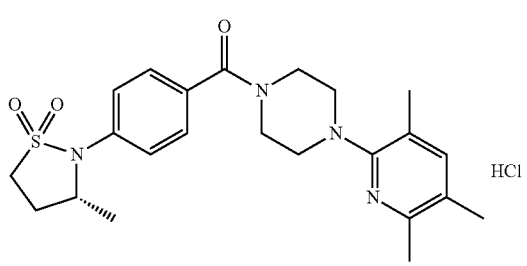 [SMILES: Cc1cc(C)c(N2CCN(C(=O)c3ccc(N4[C@H](C)CCS4(=O)=O)cc3)CC2)nc1C ; Cl]

Using (4-iodophenyl)[4-(3,5,6-trimethylpyridin-2-yl)piperazin-1-yl]methanone (435 mg) described in Preparation Example 120 and (R)-3-methylisothiazolidine 1,1-dioxide (135 mg) described in Preparation Example 2 and by the reaction and treatment in the same manner as in Example 141, the title compound (88 mg) was obtained.

MS (ESI) m/z: 443(M+H)$^+$.

Example 176

Synthesis of [4-(1,1-dioxo-1$\lambda^6$-isothiazolidin-2-yl)-2-methanesulfonylphenyl][4-(3-methyl-5-trifluoromethylpyridin-2-yl)piperazin-1-yl]methanone

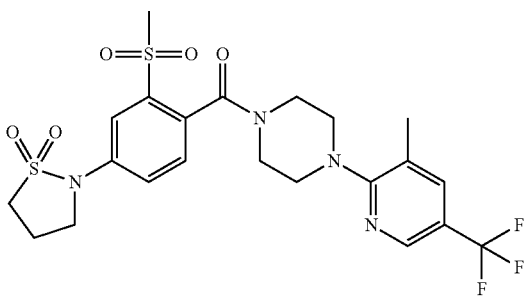 [SMILES: Cc1cc(C(F)(F)F)cnc1N1CCN(C(=O)c2ccc(N3CCCS3(=O)=O)cc2S(C)(=O)=O)CC1]

Using 4-(1,1-dioxo-1$\lambda^6$-isothiazolidin-2-yl)-2-methanesulfonylbenzoic acid (319 mg) described in Preparation Example 22 and 1-(3-methyl-5-trifluoromethylpyridin-2-yl)piperazine (245 mg) described in Preparation Example 84 and by the reaction and treatment in the same manner as in Example 87, the title compound (449 mg) was obtained.

MS (ESI) m/z: 547(M+H)$^+$.

Example 177

Synthesis of [4-(1,1-dioxo-1$\lambda^6$-isothiazolidin-2-yl)-2-fluorophenyl][4-(3,5,6-trimethylpyridin-2-yl)piperazin-1-yl]methanone

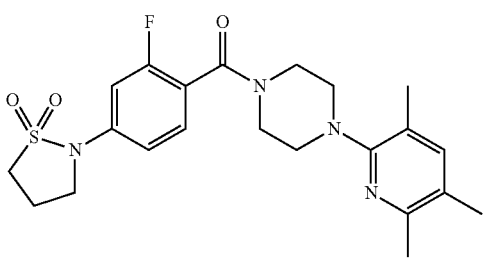

Using 4-(1,1-dioxo-1$\lambda^6$-isothiazolidin-2-yl)-2-fluorobenzoic acid (259 mg) described in Preparation Example 23 and 1-(3,5,6-trimethylpyridin-2-yl)piperazine (205 mg) described in Preparation Example 92 and by the reaction and treatment in the same manner as in Example 87, the title compound (282 mg) was obtained.

MS (ESI) m/z: 447(M+H)$^+$.

Example 178

Synthesis of (R)-[2-fluoro-4-(3-methyl-1,1-dioxo-1λ⁶-isothiazolidin-2-yl)phenyl][4-(3,5,6-trimethylpyridin-2-yl)piperazin-1-yl]methanone hydrochloride

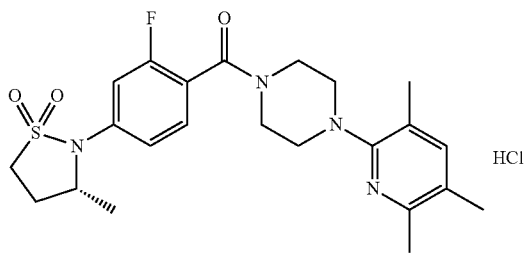 [SMILES: Cc1cc(C)c(N2CCN(C(=O)c3ccc(N4[C@H](C)CCS4(=O)=O)cc3F)CC2)nc1C ; Cl]

To a mixture of (4-bromo-2-fluorophenyl)[4-(3,5,6-trimethylpyridin-2-yl)piperazin-1-yl]methanone (322 mg) described in Preparation Example 128, (R)-3-methylisothiazolidine 1,1-dioxide (107 mg) described in Preparation Example 2, potassium carbonate (220 mg), copper(I) iodide (76 mg) and potassium iodide (132 mg) were added toluene (1 mL) and N,N'-dimethylethylenediamine (80 µL), and the mixture was stirred with heating under reflux for 8 hr. The reaction mixture was cooled, water was added, the mixture was extracted with chloroform, and the solvent was evaporated. The obtained residue was purified by column chromatography (ethyl acetate:hexane) to give (R)-[2-fluoro-4-(3-methyl-1,1-dioxo-1λ⁶-isothiazolidin-2-yl)phenyl][4-(3,5,6-trimethylpyridin-2-yl)piperazin-1-yl]methanone. The obtained (R)-[2-fluoro-4-(3-methyl-1,1-dioxo-1λ⁶-isothiazolidin-2-yl)phenyl][4-(3,5,6-trimethylpyridin-2-yl)piperazin-1-yl]methanone (140 mg) was dissolved in ethyl acetate, 4N hydrogen chloride/ethyl acetate (0.08 mL) was added, and the precipitate was collected by filtration to give the title compound (166 mg).

MS (ESI) m/z: 461(M+H)⁺.

Example 179

Synthesis of [4-(3-cyclopropyl-5-trifluoromethylpyridin-2-yl)piperazin-1-yl][4-(1,1-dioxo-1λ⁶-isothiazolidin-2-yl)phenyl]methanone

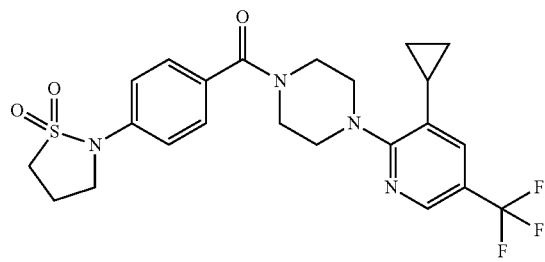 [SMILES: O=C(c1ccc(N2CCCS2(=O)=O)cc1)N1CCN(c2ncc(C(F)(F)F)cc2C2CC2)CC1]

Using 4-(1,1-dioxo-1λ⁶-isothiazolidin-2-yl)benzoic acid (241 mg) described in Preparation Example 16 and 1-(3-cyclopropyl-5-trifluoromethylpyridin-2-yl)piperazine (271 mg) described in Preparation Example 90 and by the reaction and treatment in the same manner as in Example 87, the title compound (401 mg) was obtained.

MS (ESI) m/z: 495(M+H)⁺.

Example 180

Synthesis of [4-(3-cyclopropyl-5-trifluoromethylpyridin-2-yl)piperazin-1-yl][4-(1,1-dioxo-1λ⁶-isothiazolidin-2-yl)-2-methanesulfonylphenyl]methanone

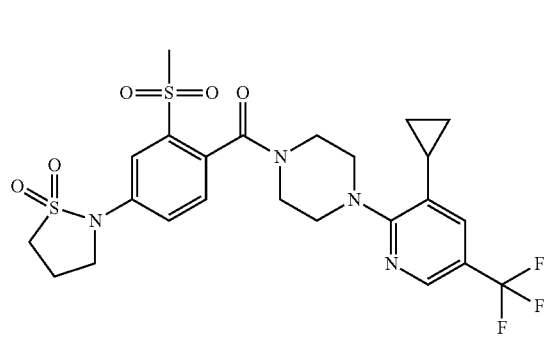 [SMILES: CS(=O)(=O)c1cc(N2CCCS2(=O)=O)ccc1C(=O)N1CCN(c2ncc(C(F)(F)F)cc2C2CC2)CC1]

Using 4-(1,1-dioxo-1λ⁶-isothiazolidin-2-yl)-2-methanesulfonylbenzoic acid (319 mg) described in Preparation Example 22 and 1-(3-cyclopropyl-5-trifluoromethylpyridin-2-yl)piperazine (271 mg) described in Preparation Example 90 and by the reaction and treatment in the same manner as in Example 87, the title compound (455 mg) was obtained.

MS (ESI) m/z: 573(M+H)⁺.

Example 181

Synthesis of [4-(5-cyclopropyl-3-methylpyridin-2-yl)piperazin-1-yl][4-(1,1-dioxo-1λ⁶-isothiazolidin-2-yl)-2-methoxyphenyl]methanone

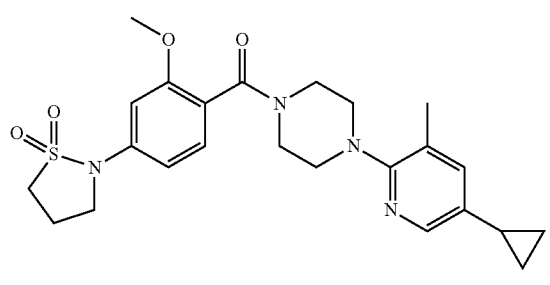 [SMILES: COc1cc(N2CCCS2(=O)=O)ccc1C(=O)N1CCN(c2ncc(C3CC3)cc2C)CC1]

Using 4-(1,1-dioxo-1λ⁶-isothiazolidin-2-yl)-2-methoxybenzoic acid (271 mg) described in Preparation Example 19 and 1-(5-cyclopropyl-3-methylpyridin-2-yl)piperazine hydrochloride (254 mg) described in Preparation Example 82 and by the reaction and treatment in the same manner as in Example 86, the title compound (343 mg) was obtained.

MS (ESI) m/z: 471(M+H)⁺.

Example 182

Synthesis of (R)-[2-methanesulfonyl-4-(3-methyl-1,1-dioxo-1λ⁶-isothiazolidin-2-yl)phenyl][4-(3-methyl-5-trifluoromethylpyridin-2-yl)piperazin-1-yl]methanone

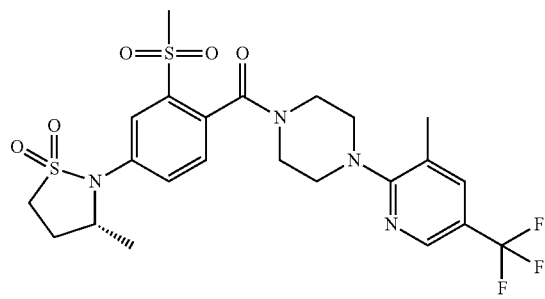 [SMILES: Cc1cc(C(F)(F)F)cnc1N1CCN(C(=O)c2ccc(N3[C@H](C)CCS3(=O)=O)cc2S(C)(=O)=O)CC1]

Using ethyl (R)-2-methanesulfonyl-4-(3-methyl-1,1-dioxo-1λ⁶-isothiazolidin-2-yl)benzoate (361 mg) described in Preparation Example 28 and 1-(3-methyl-5-trifluoromethylpyridin-2-yl)piperazine (245 mg) described in Preparation Example 84 and by the reaction and treatment in the same manner as in Example 109, the title compound (78 mg) was obtained.

MS (ESI) m/z: 561(M+H)⁺.

Example 183

Synthesis of (R)-[4-(3-cyclopropyl-5-methylpyridin-2-yl)piperazin-1-yl][2-methanesulfonyl-4-(3-methyl-1,1-dioxo-1λ⁶-isothiazolidin-2-yl)phenyl]methanone

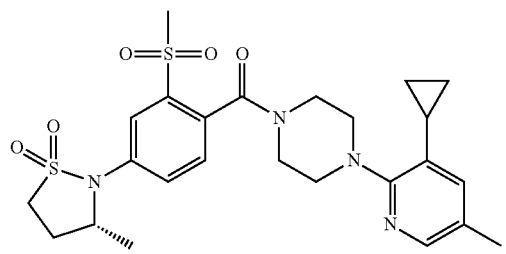 [SMILES: Cc1cnc(N2CCN(C(=O)c3ccc(N4[C@H](C)CCS4(=O)=O)cc3S(C)(=O)=O)CC2)c(C2CC2)c1]

Using ethyl (R)-2-methanesulfonyl-4-(3-methyl-1,1-dioxo-1λ⁶-isothiazolidin-2-yl)benzoate (181 mg) described in Preparation Example 28 and 1-(3-cyclopropyl-5-methylpyridin-2-yl)piperazine (109 mg) described in Preparation Example 86 and by the reaction and treatment in the same manner as in Example 109, the title compound (202 mg) was obtained.

MS (ESI) m/z: 533(M+H)⁺.

Example 184

Synthesis of (R)-[4-(3-cyclopropyl-5-trifluoromethylpyridin-2-yl)piperazin-1-yl][2-methanesulfonyl-4-(3-methyl-1,1-dioxo-1λ⁶-isothiazolidin-2-yl)phenyl]methanone

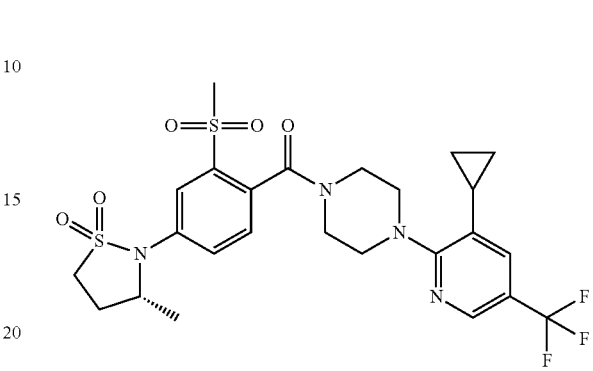

Using ethyl (R)-2-methanesulfonyl-4-(3-methyl-1,1-dioxo-1λ⁶-isothiazolidin-2-yl)benzoate (181 mg) described in Preparation Example 28 and 1-(3-cyclopropyl-5-trifluoromethylpyridin-2-yl)piperazine (136 mg) described in Preparation Example 90 and by the reaction and treatment in the same manner as in Example 109, the title compound (172 mg) was obtained.

MS (ESI) m/z: 587(M+H)⁺.

Example 185

Synthesis of [2,4-bis(1,1-dioxo-1λ⁶-isothiazolidin-2-yl)phenyl][4-(3-methyl-5-trifluoromethylpyridin-2-yl)piperazin-1-yl]methanone

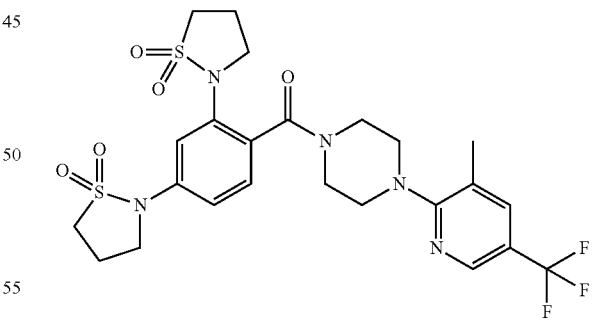

Using 2,4-bis(1,1-dioxo-1λ⁶-isothiazolidin-2-yl)benzoic acid (200 mg) described in Preparation Example 34 and 1-(3-methyl-5-trifluoromethylpyridin-2-yl)piperazine (136 mg) described in Preparation Example 84 and by the reaction and treatment in the same manner as in Example 87, the title compound (172 mg) was obtained.

MS (ESI) m/z: 588(M+H)⁺.

Example 186

Synthesis of [2,4-bis(1,1-dioxo-1λ⁶-isothiazolidin-2-yl)phenyl][4-(5-cyclopropyl-3-methylpyridin-2-yl)piperazin-1-yl]methanone

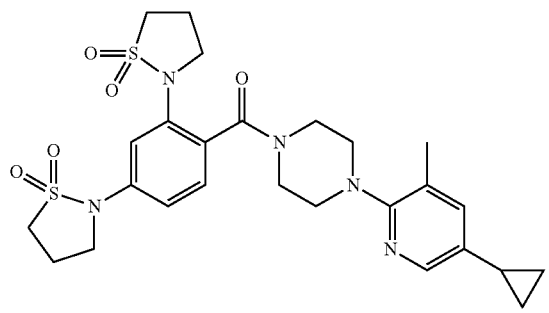 [SMILES: Cc1cc(C2CC2)cnc1N1CCN(C(=O)c2ccc(N3CCCS3(=O)=O)cc2N2CCCS2(=O)=O)CC1]

Using 2,4-bis(1,1-dioxo-1λ⁶-isothiazolidin-2-yl)benzoic acid (200 mg) described in Preparation Example 34 and 1-(5-cyclopropyl-3-methylpyridin-2-yl)piperazine hydrochloride (141 mg) described in Preparation Example 82 and by the reaction and treatment in the same manner as in Example 86, the title compound (115 mg) was obtained.

MS (ESI) m/z: 560(M+H)⁺.

Example 187

Synthesis of [2,4-bis(1,1-dioxo-1λ⁶-isothiazolidin-2-yl)phenyl][4-(3-cyclopropyl-5-methylpyridin-2-yl)piperazin-1-yl]methanone hydrochloride

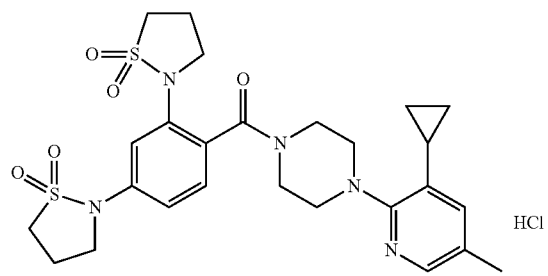 [SMILES: Cc1cnc(N2CCN(C(=O)c3ccc(N4CCCS4(=O)=O)cc3N3CCCS3(=O)=O)CC2)c(C2CC2)c1 ; Cl]

2,4-Bis(1,1-dioxo-1λ⁶-isothiazolidin-2-yl)benzoic acid (200 mg) described in Preparation Example 34, 1-(3-cyclopropyl-5-methylpyridin-2-yl)piperazine (121 mg) described in Preparation Example 86, and 1-hydroxybenzotriazole 1 hydrate (79 mg) were dissolved in N,N-dimethylformamide (3 mL), 1-ethyl-3-(3'-dimethylaminopropyl)carbodiimide hydrochloride (112 mg) was added, and the mixture was stirred at room temperature overnight. Water was added to the reaction mixture, and the mixture was extracted with ethyl acetate. The organic layer was washed with saturated brine, and the solvent was evaporated. The obtained residue was purified by column chromatography (ethyl acetate:hexane) to give [2,4-bis(1,1-dioxo-1λ⁶-isothiazolidin-2-yl)phenyl][4-(3-cyclopropyl-5-methylpyridin-2-yl)piperazin-1-yl]methanone. The obtained [2,4-bis(1,1-dioxo-1λ⁶-isothiazolidin-2-yl)phenyl][4-(3-cyclopropyl-5-methylpyridin-2-yl)piperazin-1-yl]methanone (240 mg) was dissolved in ethyl acetate, 4N hydrogen chloride/ethyl acetate (0.11 mL) was added, and the precipitate was collected by filtration to give the title compound (104 mg).

MS (ESI) m/z: 560(M+H)⁺.

Example 188

Synthesis of [2,4-bis(1,1-dioxo-1λ⁶-isothiazolidin-2-yl)phenyl][4-(3-cyclopropyl-5-trifluoromethylpyridin-2-yl)piperazin-1-yl]methanone

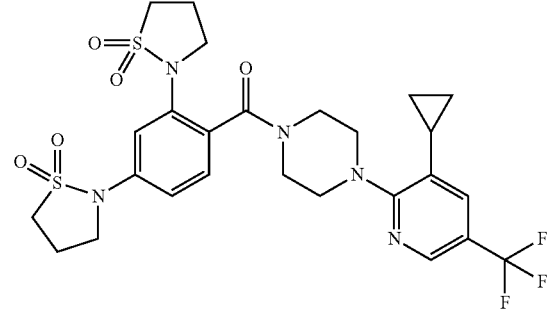 [SMILES: O=C(c1ccc(N2CCCS2(=O)=O)cc1N1CCCS1(=O)=O)N1CCN(c2ncc(C(F)(F)F)cc2C2CC2)CC1]

Using 2,4-bis(1,1-dioxo-1λ⁶-isothiazolidin-2-yl)benzoic acid (200 mg) described in Preparation Example 34 and 1-(3-cyclopropyl-5-trifluoromethylpyridin-2-yl)piperazine (150 mg) described in Preparation Example 90 and by the reaction and treatment in the same manner as in Example 87, the title compound (160 mg) was obtained.

MS (ESI) m/z: 614(M+H)⁺.

Example 189

Synthesis of [2,4-bis(1,1-dioxo-1λ⁶-isothiazolidin-2-yl)phenyl][4-(3,5-dicyclopropylpyridin-2-yl)piperazin-1-yl]mthanone

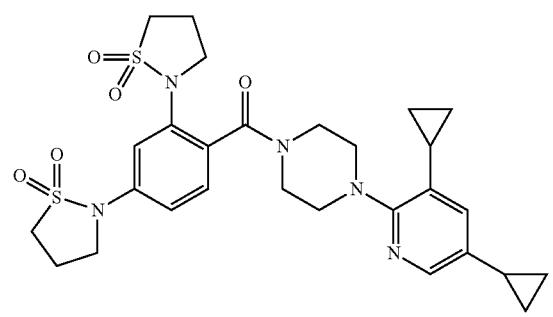 [SMILES: O=C(c1ccc(N2CCCS2(=O)=O)cc1N1CCCS1(=O)=O)N1CCN(c2ncc(C3CC3)cc2C2CC2)CC1]

Using 2,4-bis(1,1-dioxo-1λ⁶-isothiazolidin-2-yl)benzoic acid (200 mg) described in Preparation Example 34 and 1-(3,5-dicyclopropylpyridin-2-yl)piperazine (135 mg) described in Preparation Example 88 and by the reaction and treatment in the same manner as in Example 87, the title compound (59 mg) was obtained.

MS (ESI) m/z: 586(M+H)⁺.

Example 190

Synthesis of [2,4-bis(1,1-dioxo-1λ⁶-isothiazolidin-2-yl)phenyl][4-(3,5,6-trimethylpyridin-2-yl)piperazin-1-yl]methanone hydrochloride

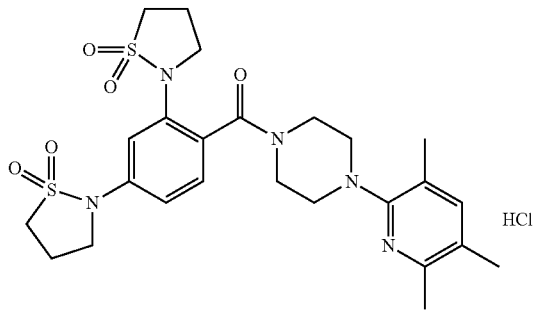 [SMILES: Cc1cc(C)c(N2CCN(C(=O)c3ccc(N4CCCS4(=O)=O)cc3N3CCCS3(=O)=O)CC2)nc1C ; Cl]

Using 2,4-bis(1,1-dioxo-1λ⁶-isothiazolidin-2-yl)benzoic acid (200 mg) described in Preparation Example 34 and 1-(3,5,6-trimethylpyridin-2-yl)piperazine (114 mg) described in Preparation Example 92 and by the reaction and treatment in the same manner as in Example 187, the title compound (124 mg) was obtained.

MS (ESI) m/z: 548(M+H)$^+$.

Example 191

Synthesis of [4-(1,1-dioxo-1λ⁶-isothiazolidin-2-yl)-2-methylphenyl][4-(3-methyl-5-trifluoromethylpyridin-2-yl)piperazin-1-yl]methanone

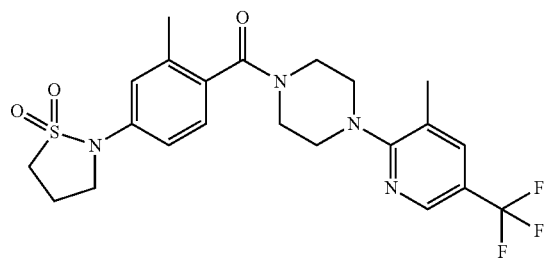 [SMILES: Cc1cc(N2CCCS2(=O)=O)ccc1C(=O)N1CCN(c2ncc(C(F)(F)F)cc2C)CC1]

Using 4-(1,1-dioxo-1λ⁶-isothiazolidin-2-yl)-2-methylbenzoic acid (255 mg) described in Preparation Example 29 and 1-(3-methyl-5-trifluoromethylpyridin-2-yl)piperazine (245 mg) described in Preparation Example 84 and by the reaction and treatment in the same manner as in Example 87, the title compound (230 mg) was obtained.

MS (ESI) m/z: 483(M+H)$^+$.

Example 192

Synthesis of [2,4-bis(1,1-dioxo-1λ⁶-isothiazolidin-2-yl)phenyl][4-(3,5-dimethylpyridin-2-yl)piperazin-1-yl]methanone hydrochloride

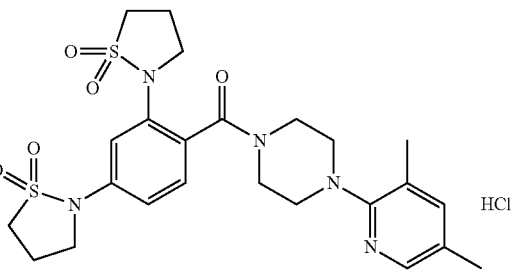

Using 2,4-bis(1,1-dioxo-1λ⁶-isothiazolidin-2-yl)benzoic acid (130 mg) described in Preparation Example 34 and 1-(3,5-dimethylpyridin-2-yl)piperazine (69 mg) described in Preparation Example 79 and by the reaction and treatment in the same manner as in Example 187, the title compound (40 mg) was obtained.

MS (ESI) m/z: 534(M+H)$^+$.

Example 193

Synthesis of [4-(5-cyclopropyl-3-methylpyridin-2-yl)piperazin-1-yl][4-(1,1-dioxo-1λ⁶-isothiazolidin-2-yl)-2-methylphenyl]methanone

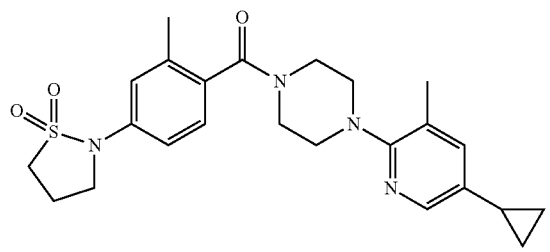 [SMILES: Cc1cc(N2CCCS2(=O)=O)ccc1C(=O)N1CCN(c2ncc(C3CC3)cc2C)CC1]

Using 4-(1,1-dioxo-1λ⁶-isothiazolidin-2-yl)-2-methylbenzoic acid (255 mg) described in Preparation Example 29 and 1-(5-cyclopropyl-3-methylpyridin-2-yl)piperazine hydrochloride (253 mg) described in Preparation Example 82 and by the reaction and treatment in the same manner as in Example 86, the title compound (74 mg) was obtained.

MS (ESI) m/z: 455(M+H)$^+$.

Example 194

Synthesis of [4-(3-cyclopropyl-5-methylpyridin-2-yl)piperazin-1-yl][4-(1,1-dioxo-1λ⁶-isothiazolidin-2-yl)-2-methylphenyl]methanone

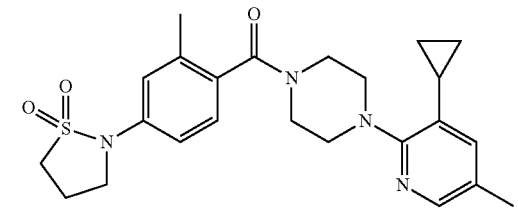 [SMILES: Cc1cnc(N2CCN(C(=O)c3ccc(N4CCCS4(=O)=O)cc3C)CC2)c(C2CC2)c1]

Using 4-(1,1-dioxo-1λ⁶-isothiazolidin-2-yl)-2-methylbenzoic acid (255 mg) described in Preparation Example 29 and 1-(3-cyclopropyl-5-methylpyridin-2-yl)piperazine (217 mg) described in Preparation Example 86 and by the reaction and treatment in the same manner as in Example 87, the title compound (198 mg) was obtained.

MS (ESI) m/z: 455(M+H)⁺.

Example 195

Synthesis of [4-(3-cyclopropyl-5-trifluoromethylpyridin-2-yl)piperazin-1-yl][4-(1,1-dioxo-1λ⁶-isothiazolidin-2-yl)-2-methylphenyl]methanone

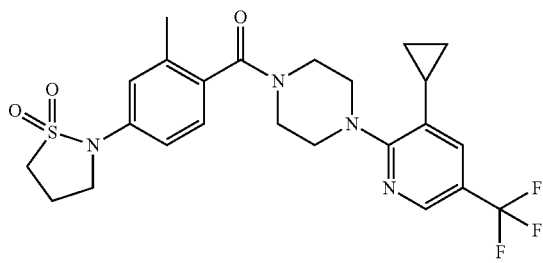 [SMILES: Cc1cc(N2CCCS2(=O)=O)ccc1C(=O)N1CCN(c2ncc(C(F)(F)F)cc2C2CC2)CC1]

Using 4-(1,1-dioxo-1λ⁶-isothiazolidin-2-yl)-2-methylbenzoic acid (255 mg) described in Preparation Example 29 and 1-(3-cyclopropyl-5-trifluoromethylpyridin-2-yl)piperazine (271 mg) described in Preparation Example 90 and by the reaction and treatment in the same manner as in Example 87, the title compound (390 mg) was obtained.

MS (ESI) m/z: 509(M+H)⁺.

Example 196

Synthesis of [4-(3,5-dicyclopropylpyridin-2-yl)piperazin-1-yl][4-(1,1-dioxo-1λ⁶-isothiazolidin-2-yl)-2-methylphenyl]methanone

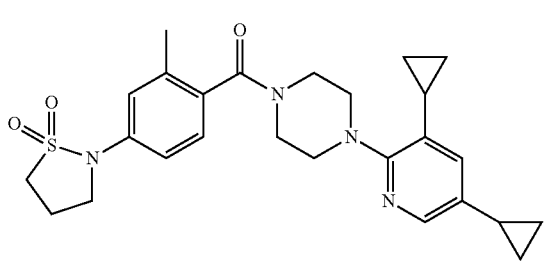 [SMILES: Cc1cc(N2CCCS2(=O)=O)ccc1C(=O)N1CCN(c2ncc(C3CC3)cc2C2CC2)CC1]

Using 4-(1,1-dioxo-1λ⁶-isothiazolidin-2-yl)-2-methylbenzoic acid (255 mg) described in Preparation Example 29 and 1-(3,5-dicyclopropylpyridin-2-yl)piperazine (243 mg) described in Preparation Example 88 and by the reaction and treatment in the same manner as in Example 87, the title compound (137 mg) was obtained.

MS (ESI) m/z: 481(M+H)⁺.

Example 197

Synthesis of [4-(1,1-dioxo-1λ⁶-isothiazolidin-2-yl)-2-methylphenyl][4-(3,5,6-trimethylpyridin-2-yl)piperazin-1-yl]methanone

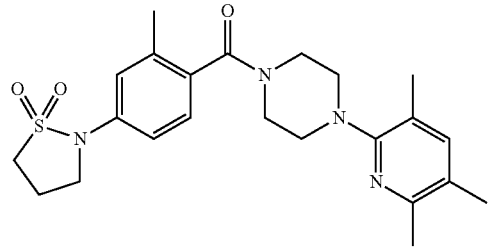 [SMILES: Cc1cc(N2CCCS2(=O)=O)ccc1C(=O)N1CCN(c2nc(C)c(C)cc2C)CC1]

Using 4-(1,1-dioxo-1λ⁶-isothiazolidin-2-yl)-2-methylbenzoic acid (128 mg) described in Preparation Example 29 and 1-(3,5,6-trimethylpyridin-2-yl)piperazine (103 mg) described in Preparation Example 92 and by the reaction and treatment in the same manner as in Example 87, the title compound (131 mg) was obtained.

MS (ESI) m/z: 443(M+H)⁺.

Example 198

Synthesis of [4-(3,5-dicyclopropylpyridin-2-yl)piperazin-1-yl][4-(1,1-dioxo-1λ⁶-isothiazolidin-2-yl)-2-methoxyphenyl]methanone

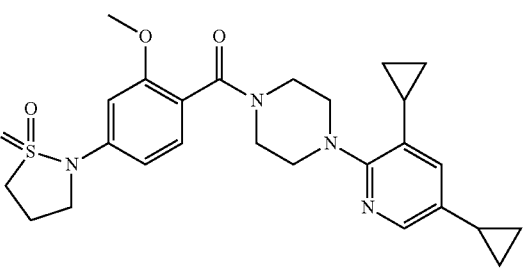

Using 4-(1,1-dioxo-1λ⁶-isothiazolidin-2-yl)-2-methoxybenzoic acid (271 mg) described in Preparation Example 19 and 1-(3,5-dicyclopropylpyridin-2-yl)piperazine hydrochloride (316 mg) described in Preparation Example 87 and by the reaction and treatment in the same manner as in Example 86, the title compound (347 mg) was obtained.

MS (ESI) m/z: 497(M+H)⁺.

Example 199

Synthesis of [4-(1,1-dioxo-1λ⁶-isothiazolidin-2-yl)-2-methoxyphenyl][4-(3,5,6-trimethylpyridin-2-yl)piperazin-1-yl]methanone

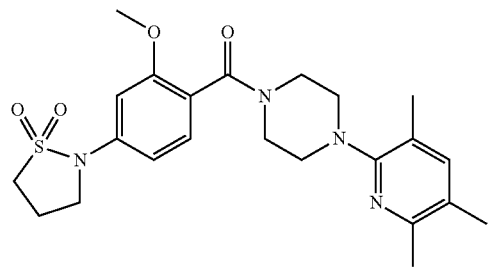 [SMILES: COc1cc(N2CCCS2(=O)=O)ccc1C(=O)N1CCN(c2nc(C)c(C)cc2C)CC1]

Using 4-(1,1-dioxo-1λ⁶-isothiazolidin-2-yl)-2-methoxybenzoic acid (136 mg) described in Preparation Example 19 and 1-(3,5,6-trimethylpyridin-2-yl)piperazine (103 mg) described in Preparation Example 92 and by the reaction and treatment in the same manner as in Example 87, the title compound (138 mg) was obtained.

MS (ESI) m/z: 459(M+H)⁺.

Example 200

Synthesis of [4-(5-cyclopropyl-3-methylpyridin-2-yl)piperazin-1-yl][6-(1,1-dioxo-1λ⁶-isothiazolidin-2-yl)pyridin-3-yl]methanone

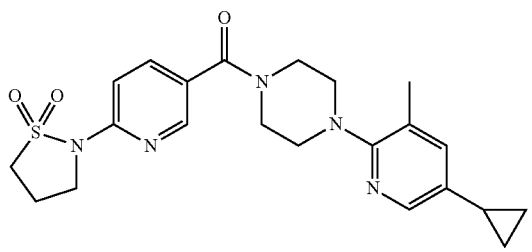

Using ethyl 6-(1,1-dioxo-1λ⁶-isothiazolidin-2-yl)nicotinate (270 mg) described in Preparation Example 25 and 1-(5-cyclopropyl-3-methylpyridin-2-yl)piperazine hydrochloride (254 mg) described in Preparation Example 82 and by the reaction and treatment in the same manner as in Example 170, the title compound (17 mg) was obtained.

MS (ESI) m/z: 442(M+H)⁺.

Example 201

Synthesis of [6-(1,1-dioxo-1λ⁶-isothiazolidin-2-yl)pyridin-3-yl][4-(3,5,6-trimethylpyridin-2-yl)piperazin-1-yl]methanone

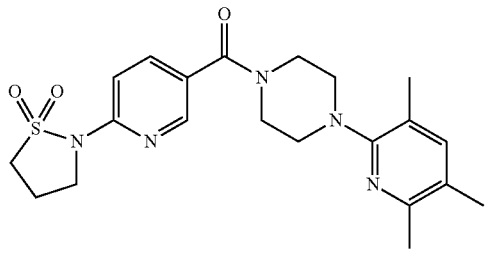

Using ethyl 6-(1,1-dioxo-1λ⁶-isothiazolidin-2-yl)nicotinate (135 mg) described in Preparation Example 25 and 1-(3,5,6-trimethylpyridin-2-yl)piperazine (103 mg) described in Preparation Example 92 and by the reaction and treatment in the same manner as in Example 109, the title compound (89 mg) was obtained.

MS (ESI) m/z: 430(M+H)⁺.

Example 202

Synthesis of [4-(4,4-dimethyl-1,1-dioxo-1λ⁶-isothiazolidin-2-yl)phenyl][4-(3,5-dimethylpyridin-2-yl)piperazin-1-yl]methanone

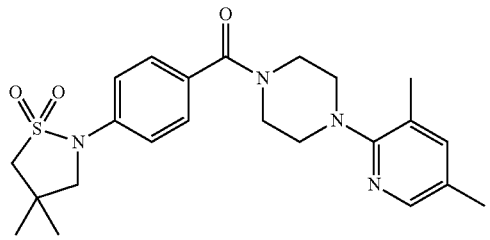 [SMILES: Cc1cnc(N2CCN(C(=O)c3ccc(N4CC(C)(C)CS4(=O)=O)cc3)CC2)c(C)c1]

Using ethyl 4-(4,4-dimethyl-1,1-dioxo-1λ⁶-isothiazolidin-2-yl)benzoate (127 mg) described in Preparation Example 30 and 1-(3,5-dimethylpyridin-2-yl)piperazine (82 mg) described in Preparation Example 79 and by the reaction and treatment in the same manner as in Example 109, the title compound (40 mg) was obtained.

MS (ESI) m/z: 443(M+H)⁺.

Example 203

Synthesis of [4-(3,5-dimethylpyridin-2-yl)piperazin-1-yl]{4-[1-(1,1-dioxo-1λ⁶-isothiazolidin-2-yl)cyclopropyl]phenyl}methanone hydrochloride

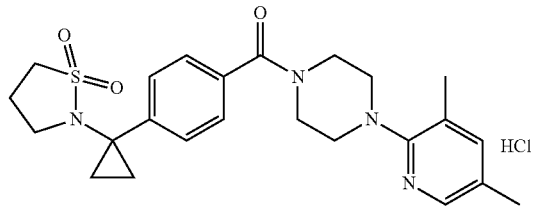 [SMILES: Cc1cnc(N2CCN(C(=O)c3ccc(C4(N5CCCS5(=O)=O)CC4)cc3)CC2)c(C)c1 ; Cl]

Using 4-[1-(1,1-dioxo-1λ⁶-isothiazolidin-2-yl)cyclopropyl]benzoic acid (141 mg) described in Preparation Example 31 and 1-(3,5-dimethylpyridin-2-yl)piperazine (82 mg) described in Preparation Example 79 and by the reaction and treatment in the same manner as in Example 187, the title compound (154 mg) was obtained.

MS (ESI) m/z: 455(M+H)⁺.

Example 204

Synthesis of [4-(5-cyclopropyl-3-methylpyridin-2-yl)piperazin-1-yl]{4-[1-(1,1-dioxo-1λ⁶-isothiazolidin-2-yl)cyclopropyl]phenyl}methanone

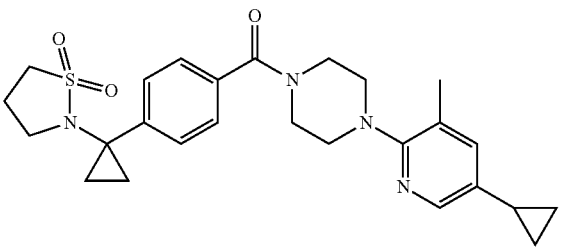 [SMILES: Cc1cc(C2CC2)cnc1N1CCN(C(=O)c2ccc(C3(N4CCCS4(=O)=O)CC3)cc2)CC1]

Using 4-[1-(1,1-dioxo-1λ⁶-isothiazolidin-2-yl)cyclopropyl]benzoic acid (141 mg) described in Preparation Example 31 and 1-(5-cyclopropyl-3-methylpyridin-2-yl)piperazine (114 mg) described in Preparation Example 83 and by the reaction and treatment in the same manner as in Example 87, the title compound (79 mg) was obtained.

MS (ESI) m/z: 481(M+H)⁺.

Example 205

Synthesis of [4-(2,4-dimethylphenyl)piperazin-1-yl]{4-[1-(1,1-dioxo-1λ⁶-isothiazolidin-2-yl)cyclopropyl]phenyl}methanone

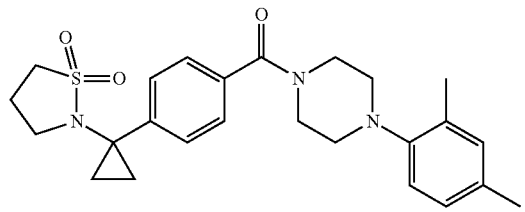 [SMILES: Cc1ccc(N2CCN(C(=O)c3ccc(C4(N5CCCS5(=O)=O)CC4)cc3)CC2)c(C)c1]

Using 4-[1-(1,1-dioxo-1λ⁶-isothiazolidin-2-yl)cyclopropyl]benzoic acid (141 mg) described in Preparation Example 31 and 1-(2,4-dimethylphenyl)piperazine (95.1 mg) and by the reaction and treatment in the same manner as in Example 87, the title compound (183 mg) was obtained.

MS (ESI) m/z: 454(M+H)⁺.

Example 206

Synthesis of 3-{2-[4-(3,5-dimethylpyridin-2-yl)piperazine-1-carbonyl]-5-(1,1-dioxo-1λ⁶-isothiazolidin-2-yl)phenyl}oxazolidin-2-one hydrochloride

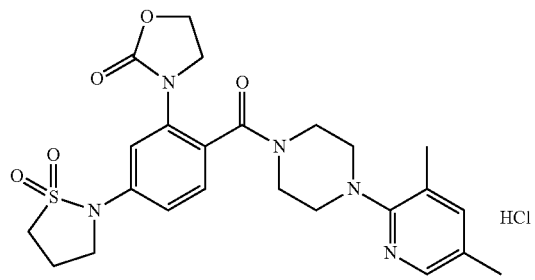 [SMILES: Cc1cnc(N2CCN(C(=O)c3ccc(N4CCCS4(=O)=O)cc3N3CCOC3=O)CC2)c(C)c1 ; Cl]

To methyl 4-(1,1-dioxo-1λ⁶-isothiazolidin-2-yl)-2-(2-oxooxazolidin-3-yl)benzoate (170 mg) described in Preparation Example 32 were added methanol (2.5 mL) and 1N aqueous sodium hydroxide solution (0.75 mL), and the mixture was stirred at 60° C. After completion of the reaction, the reaction mixture was neutralized with 1N hydrochloric acid (0.75 mL), 1-(3,5-dimethylpyridin-2-yl)piperazine (96 mg) described in Preparation Example 79 and 4-(4,6-dimethoxy[1.3.5]triazin-2-yl)-4-methylmorpholinium chloride hydrate (138 mg) were added, and the mixture was stirred at room temperature overnight. Water was added to the reaction mixture, the mixture was extracted with ethyl acetate, and the solvent was evaporated. The obtained residue was purified by silica gel column chromatography (ethyl acetate:methanol) to give 3-{2-[4-(3,5-dimethylpyridin-2-yl)piperazine-1-carbonyl]-5-(1,1-dioxo-1λ⁶-isothiazolidin-2-yl)phenyl}oxazolidin-2-one. The obtained 3-{2-[4-(3,5-dimethylpyridin-2-yl)piperazine-1-carbonyl]-5-(1,1-dioxo-1λ⁶-isothiazolidin-2-yl)phenyl}oxazolidin-2-one was dissolved in ethyl acetate, 4N hydrogen chloride/ethyl acetate (0.13 mL) was added, and the precipitate was collected by filtration to give the title compound (131 mg).

MS (ESI) m/z: 500(M+H)⁺.

Example 207

Synthesis of 3-{2-[4-(5-cyclopropyl-3-methylpyridin-2-yl)piperazine-1-carbonyl]-5-(1,1-dioxo-1λ⁶-isothiazolidin-2-yl)phenyl}oxazolidin-2-one

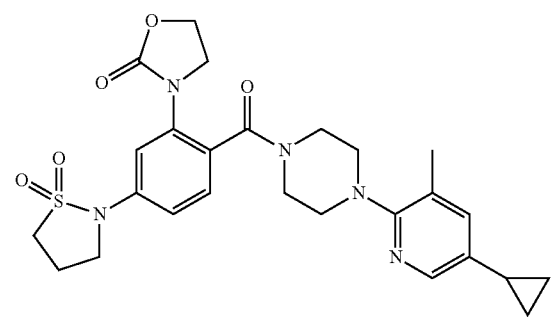 [SMILES: Cc1cc(C2CC2)cnc1N1CCN(C(=O)c2ccc(N3CCCS3(=O)=O)cc2N2CCOC2=O)CC1]

Using methyl 4-(1,1-dioxo-1λ⁶-isothiazolidin-2-yl)-2-(2-oxooxazolidin-3-yl)benzoate (170 mg) described in Preparation Example 32 and 1-(5-cyclopropyl-3-methylpyridin-2-yl)piperazine (110 mg) described in Preparation Example 83 and by the reaction and treatment in the same manner as in Example 109, the title compound (25 mg) was obtained.

MS (ESI) m/z: 526(M+H)⁺.

Example 208

Synthesis of 1-{2-[4-(3,5-dimethylpyridin-2-yl)piperazine-1-carbonyl]-5-(1,1-dioxo-1λ⁶-isothiazolidin-2-yl)phenyl}pyrrolidin-2-one

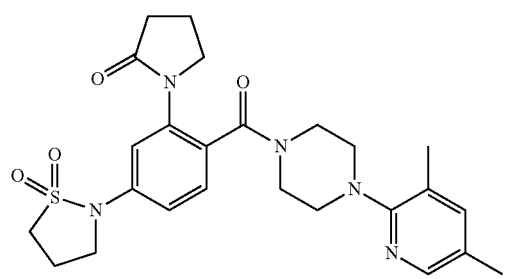 [SMILES: Cc1cnc(N2CCN(C(=O)c3ccc(N4CCCS4(=O)=O)cc3N3CCCC3=O)CC2)c(C)c1]

Using methyl 4-(1,1-dioxo-1λ⁶-isothiazolidin-2-yl)-2-(2-oxopyrrolidin-1-yl)benzoate (148 mg) described in Preparation Example 33 and 1-(3,5-dimethylpyridin-2-yl)piperazine (84 mg) described in Preparation Example 79 and by the reaction and treatment in the same manner as in Example 109, the title compound (5 mg) was obtained.

MS (ESI) m/z: 498(M+H)⁺.

Example 209

Synthesis of [2-chloro-4-(1,1-dioxo-1λ⁶-isothiazolidin-2-yl)phenyl][4-(3,5-dimethylpyridin-2-yl)piperazin-1-yl]methanone

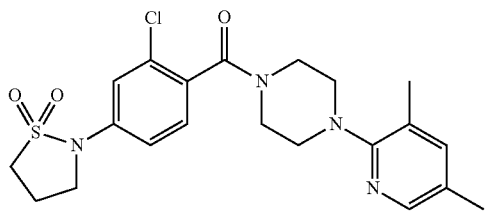 [SMILES: Cc1cnc(N2CCN(C(=O)c3ccc(N4CCCS4(=O)=O)cc3Cl)CC2)c(C)c1]

Using (4-bromo-2-chlorophenyl)[4-(3,5-dimethylpyridin-2-yl)piperazin-1-yl]methanone (408 mg) described in Preparation Example 119 and isothiazolidine 1,1-dioxide (121 mg) and by the reaction and treatment in the same manner as in Example 1, the title compound (59 mg) was obtained.
MS (ESI) m/z: 449(M+H)⁺.

Example 210

Synthesis of [2-cyclopropyl-4-(1,1-dioxo-1λ⁶-isothiazolidin-2-yl)phenyl][4-(3,5-dimethylpyridin-2-yl)piperazin-1-yl]methanone hydrochloride

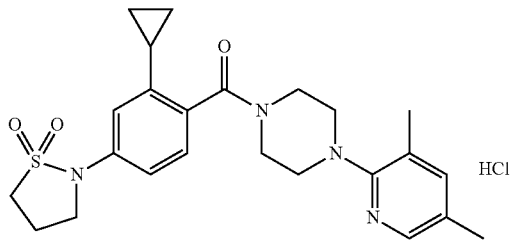 [SMILES: Cc1cnc(N2CCN(C(=O)c3ccc(N4CCCS4(=O)=O)cc3C3CC3)CC2)c(C)c1 ; Cl]

Using methyl 2-cyclopropyl-4-(1,1-dioxo-1λ⁶-isothiazolidin-2-yl)benzoate (168 mg) described in Preparation Example 35 and 1-(3,5-dimethylpyridin-2-yl)piperazine (109 mg) described in Preparation Example 79 and by the reaction and treatment in the same manner as in Example 206, the title compound (112 mg) was obtained.
MS (ESI) m/z: 455(M+H)⁺.

Example 211

Synthesis of [4-(3,5-dimethylpyridin-2-yl)piperazin-1-yl][4-(1,1-dioxo-1λ⁶-isothiazolidin-2-yl)-2-methylphenyl]methanone hydrobromide

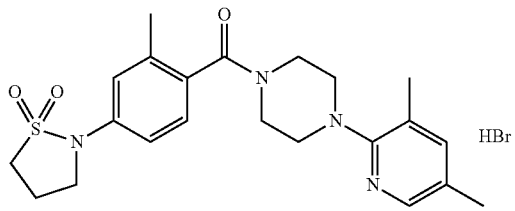 [SMILES: Cc1cnc(N2CCN(C(=O)c3ccc(N4CCCS4(=O)=O)cc3C)CC2)c(C)c1 ; Br]

[4-(3,5-Dimethylpyridin-2-yl)piperazin-1-yl][4-(1,1-dioxo-1λ⁶-isothiazolidin-2-yl)-2-methylphenyl]methanone (5.00 g) described in Example 154 was dissolved in acetic acid (20 mL), and 25% hydrogen bromide/acetic acid (3.3 mL) was added at 50° C. The reaction mixture was allowed to cool to room temperature, tetrahydrofuran (200 mL) was added, and the precipitate was collected by filtration. The obtained precipitate (5.52 g) was recrystallized from ethanol (110 mL) to give the title compound (4.67 g).
MS (ESI) m/z: 429(M+H)⁺.

Example 212

Synthesis of [4-(3,5-dimethylpyridin-2-yl)piperazin-1-yl][4-(1,1-dioxo-1λ⁶-[1,2]thiazinan-2-yl)phenyl]methanone

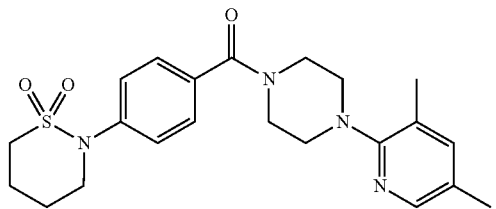 [SMILES: Cc1cnc(N2CCN(C(=O)c3ccc(N4CCCCS4(=O)=O)cc3)CC2)c(C)c1]

Using (4-bromophenyl)[4-(3,5-dimethylpyridin-2-yl)piperazin-1-yl]methanone (187 mg) described in Preparation Example 165 and [1,2]thiazinane 1,1-dioxide (68 mg) and by the reaction and treatment in the same manner as in Example 1, the title compound (118 mg) was obtained.
MS (ESI) m/z: 429(M+H)⁺.

Example 213

Synthesis of [4-(3,5-dimethylpyridin-2-yl)piperazin-1-yl][4-(1,1-dioxo-1λ⁶-[1,2]thiazinan-2-yl)-2-fluorophenyl]methanone

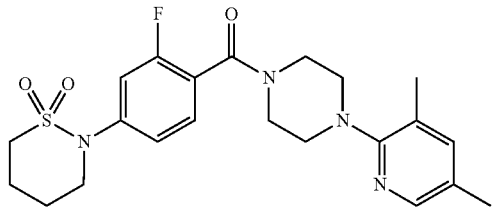 [SMILES: Cc1cnc(N2CCN(C(=O)c3ccc(N4CCCCS4(=O)=O)cc3F)CC2)c(C)c1]

Using (4-bromo-2-fluorophenyl)[4-(3,5-dimethylpyridin-2-yl)piperazin-1-yl]methanone (196 mg) described in Preparation Example 114 and [1,2]thiazinane 1,1-dioxide (68 mg) and by the reaction and treatment in the same manner as in Example 1, the title compound (109 mg) was obtained.
MS (ESI) m/z: 447(M+H)⁺.

Example 214

Synthesis of [4-(1,1-dioxo-1λ⁶-[1,2]thiazinan-2-yl)phenyl][4-(3,5,6-trimethylpyridin-2-yl)piperazin-1-yl]methanone

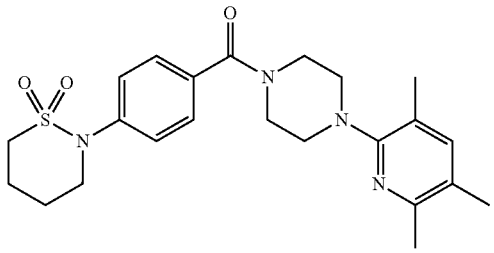 [SMILES: Cc1cc(C)c(N2CCN(C(=O)c3ccc(N4CCCCS4(=O)=O)cc3)CC2)nc1C]

Using (4-iodophenyl)[4-(3,5,6-trimethylpyridin-2-yl)piperazin-1-yl]methanone (218 mg) described in Preparation Example 120 and [1,2]thiazinane 1,1-dioxide (68 mg) and by the reaction and treatment in the same manner as in Example 1, the title compound (181 mg) was obtained.
MS (ESI) m/z: 443(M+H)⁺.

Example 215

Synthesis of [4-(3,5-dimethylpyridin-2-yl)piperazin-1-yl][6-(1,1-dioxo-1λ⁶-[1,2]thiazinan-2-yl)pyridin-3-yl]methanone

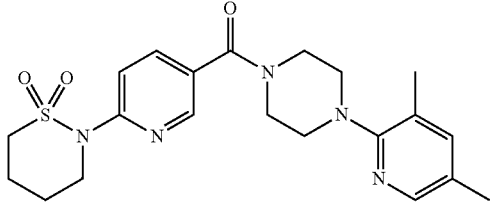 [SMILES: Cc1cnc(N2CCN(C(=O)c3ccc(N4CCCCS4(=O)=O)nc3)CC2)c(C)c1]

Using (6-bromopyridin-3-yl)[4-(3,5-dimethylpyridin-2-yl)piperazin-1-yl]methanone (188 mg) described in Preparation Example 127 and [1,2]thiazinane 1,1-dioxide (68 mg) and by the reaction and treatment in the same manner as in Example 1, the title compound (157 mg) was obtained.
MS (ESI) m/z: 430(M+H)⁺.

Example 216

Synthesis of [2-(3-aminopropoxy)-4-(1,1-dioxo-1λ⁶-isothiazolidin-2-yl)phenyl][4-(2,4-dimethylphenyl)piperazin-1-yl]methanone

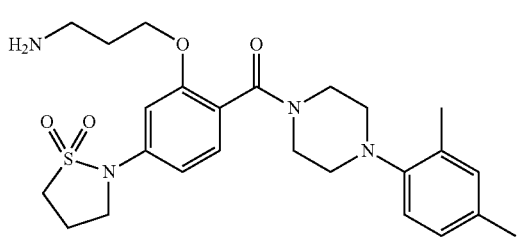 [SMILES: Cc1ccc(N2CCN(C(=O)c3ccc(N4CCCS4(=O)=O)cc3OCCCN)CC2)c(C)c1]

To a mixture of [4-(2,4-dimethylphenyl)piperazin-1-yl][4-(1,1-dioxo-1λ⁶-isothiazolidin-2-yl)-2-hydroxyphenyl]methanone (241 mg) described in Example 124, (3-bromopropyl)carbamic acid tert-butyl ester (200 mg) and cesium carbonate (548 mg) was added 2-butanone (4 mL), and the mixture was stirred with heating under reflux for 4 hr. Water was added to the reaction mixture, the mixture was extracted with ethyl acetate, and the solvent was evaporated. The obtained residue was purified by column chromatography (ethyl acetate:hexane) to give (3-{2-[4-(2,4-dimethylphenyl)piperazine-1-carbonyl]-5-(1,1-dioxo-1λ⁶-isothiazolidin-2-yl)phenoxy}propyl)carbamic acid tert-butyl ester (221 mg). The obtained (3-{2-[4-(2,4-dimethylphenyl)piperazine-1-carbonyl]-5-(1,1-dioxo-1λ⁶-isothiazolidin-2-yl)phenoxy}propyl)carbamic acid tert-butyl ester (221 mg) was dissolved in dichloromethane (2 mL), trifluoroacetic acid (0.46 mL) was added, and the mixture was stirred at room temperature overnight. The reaction mixture was poured into ice water, the mixture was neutralized with sodium hydrogen carbonate and extracted with chloroform, and the solvent was evaporated. The obtained residue was purified by NH-coated silica gel column chromatography (ethyl acetate:methanol) to give the title compound (74 mg).
MS (ESI) m/z: 487(M+H)⁺.

Example 217

Synthesis of methyl 4-{4-[4-(1,1-dioxo-1λ⁶-isothiazolidin-2-yl)benzoyl]piperazin-1-yl}-3-methylbenzoate

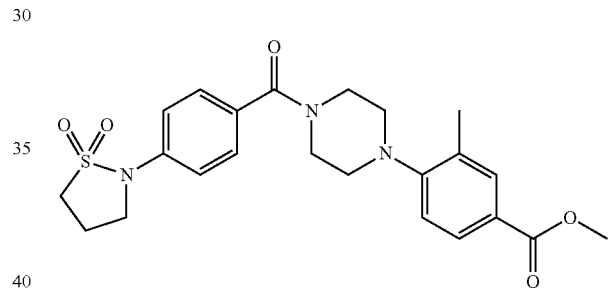

Using 4-(1,1-dioxo-1λ⁶-isothiazolidin-2-yl)benzoic acid (1.08 g) described in Preparation Example 16 and methyl 3-methyl-4-(piperazin-1-yl)benzoate (1.05 g) described in Preparation Example 97 and by the reaction and treatment in the same manner as in Example 87, the title compound (1.59 g) was obtained.
MS (ESI) m/z: 458(M+H)⁺.

Example 218

Synthesis of 4-{4-[4-(1,1-dioxo-1λ⁶-isothiazolidin-2-yl)benzoyl]piperazin-1-yl}-3-methylbenzoic acid

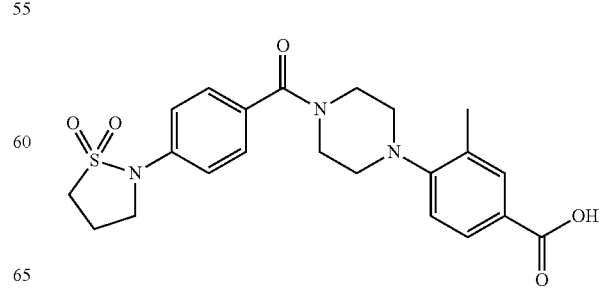

Methyl 4-{4-[4-(1,1-dioxo-1λ⁶-isothiazolidin-2-yl)benzoyl]piperazin-1-yl}-3-methylbenzoate (1.01 g) described in Example 217 was dissolved in methanol (8 mL), 1N aqueous sodium hydroxide solution (3.3 mL) was added, and the mixture was stirred at 60° C. for 4 hr. The reaction mixture was cooled and neutralized with dilute hydrochloric acid, and the precipitate was collected by filtration to give the title compound (844 mg).

MS (ESI) m/z: 444(M+H)⁺.

Example 219

Synthesis of [4-(1,1-dioxo-1λ⁶-isothiazolidin-2-yl)phenyl][4-(4-hydroxymethyl-2-methylphenyl)piperazin-1-yl]methanone

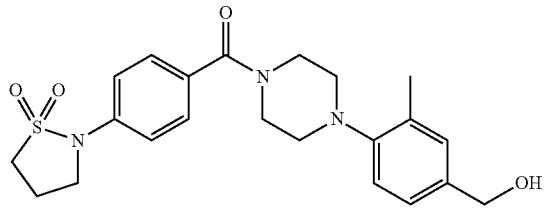 [SMILES: Cc1cc(CO)ccc1N1CCN(C(=O)c2ccc(N3CCCS3(=O)=O)cc2)CC1]

Using 4-(1,1-dioxo-1λ⁶-isothiazolidin-2-yl)benzoic acid (378 mg) described in Preparation Example 16 and [3-methyl-4-(piperazin-1-yl)phenyl]methanol (323 mg) described in Preparation Example 98 and by the reaction and treatment in the same manner as in Example 87, the title compound (351 mg) was obtained.

MS (ESI) m/z: 430(M+H)⁺.

Example 220

Synthesis of 4-{4-[4-(1,1-dioxo-1λ⁶-isothiazolidin-2-yl)benzoyl]piperazin-1-yl}-3,N,N-trimethylbenzamide

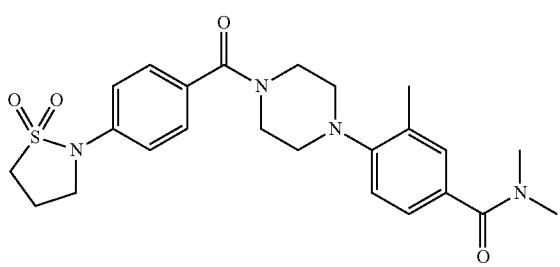 [SMILES: Cc1cc(C(=O)N(C)C)ccc1N1CCN(C(=O)c2ccc(N3CCCS3(=O)=O)cc2)CC1]

To 4-{4-[4-(1,1-dioxo-1λ⁶-isothiazolidin-2-yl)benzoyl]piperazin-1-yl}-3-methylbenzoic acid (116 mg) described in Example 218 were added 1,2-dichloroethane (5 mL) and thionyl chloride (1 mL), the mixture was stirred with heating under reflux for 2 hr, and the solvent was evaporated. The obtained residue was dissolved in 1,2-dichloroethane (3 mL), and the solution was added dropwise to a solution of 50% aqueous dimethylamine solution (5 mL) and 1,2-dichloroethane (2 mL) under ice-cooling. To the reaction mixture was added saturated brine, the mixture was extracted with chloroform, and the solvent was evaporated. The obtained residue was purified by column chromatography (chloroform:methanol) to give the title compound (74 mg).

MS (ESI) m/z: 471(M+H)⁺.

Example 221

Synthesis of [4-(1,1-dioxo-1λ⁶-isothiazolidin-2-yl)phenyl][4-(2-hydroxymethyl-4-methylphenyl)piperazin-1-yl]methanone

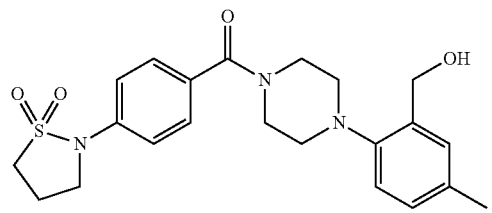 [SMILES: Cc1ccc(N2CCN(C(=O)c3ccc(N4CCCS4(=O)=O)cc3)CC2)c(CO)c1]

Using 4-(1,1-dioxo-1λ⁶-isothiazolidin-2-yl)benzoic acid (550 mg) described in Preparation Example 16 and [5-methyl-2-(piperazin-1-yl)phenyl]methanol (470 mg) described in Preparation Example 99 and by the reaction and treatment in the same manner as in Example 87, the title compound (264 mg) was obtained.

MS (ESI) m/z: 430(M+H)⁺.

Example 222

Synthesis of 4-{4-[4-(1,1-dioxo-1λ⁶-isothiazolidin-2-yl)benzoyl]piperazin-1-yl}-3-methylbenzamide

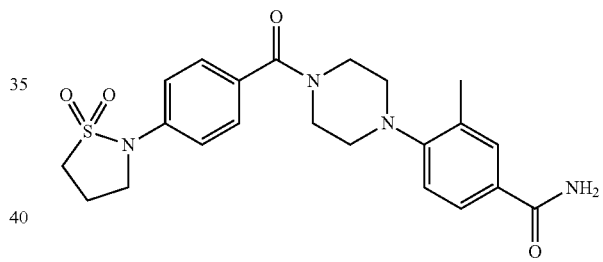

Using 4-{4-[4-(1,1-dioxo-1λ⁶-isothiazolidin-2-yl)benzoyl]piperazin-1-yl}-3-methylbenzoic acid (200 mg) described in Example 218 and 28% aqueous ammonia (5 mL) and by the reaction and treatment in the same manner as in Example 220, the title compound (68 mg) was obtained.

MS (ESI) m/z: 443(M+H)⁺.

Example 223

Synthesis of [4-(3,5-dimethylpyridin-2-yl)piperazin-1-yl][6-(1,1-dioxo-1λ⁶-isothiazolidin-2-yl)-4-methylpyridin-3-yl]methanone dihydrochloride

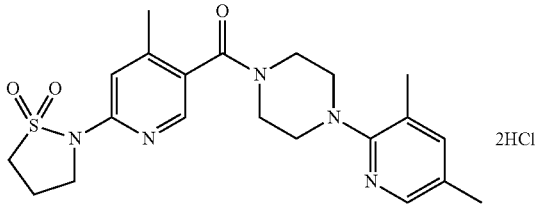 [SMILES: Cc1cnc(N2CCN(C(=O)c3cnc(N4CCCS4(=O)=O)cc3C)CC2)c(C)c1]

To [4-(3,5-dimethylpyridin-2-yl)piperazin-1-yl](6-fluoro-4-methylpyridin-3-yl)methanone (840 mg) described in Preparation Example 146 was added 4-methoxybenzylamine (2 mL), and the mixture was stirred at 160° C. for 2.5 hr. The reaction mixture was cooled, water was added, and the mixture was extracted with chloroform. The organic layer was washed with saturated brine, and the solvent was evaporated. To the obtained residue was added diethyl ether, and the insoluble material was collected by filtration to give [4-(3,5-dimethylpyridin-2-yl)piperazin-1-yl][6-(4-methoxybenzylamino)-4-methylpyridin-3-yl]methanone (790 mg). The obtained [4-(3,5-dimethylpyridin-2-yl)piperazin-1-yl][6-(4-methoxybenzylamino)-4-methylpyridin-3-yl]methanone (790 mg) was dissolved in dichloromethane (8 mL), trifluoroacetic acid (13 mL) was added, and the mixture was stirred at room temperature overnight. The solvent was evaporated from the reaction mixture, saturated aqueous sodium hydrogen carbonate solution was added, and the mixture was extracted with chloroform. The organic layer was washed with saturated brine, and the solvent was evaporated to give (6-amino-4-methylpyridin-3-yl)[4-(3,5-dimethylpyridin-2-yl)piperazin-1-yl]methanone. The obtained (6-amino-4-methylpyridin-3-yl)[4-(3,5-dimethylpyridin-2-yl)piperazin-1-yl]methanone and triethylamine (0.75 mL) were dissolved in dichloromethane (10 mL), 3-chloropropane-1-sulfonyl chloride (0.49 mL) was added under ice-cooling, and the mixture was stirred at room temperature for 3 hr. Water was added to the reaction mixture, and the mixture was extracted with chloroform. The organic layer was washed with saturated brine, and the solvent was evaporated. The obtained residue was dissolved in N,N-dimethylformamide (7 mL), 1,8-diazabicyclo[5.4.0]undec-7-ene (0.32 mL) was added, and the mixture was stirred at room temperature for 4.5 hr. Water was added to the reaction mixture, and the mixture was extracted with ethyl acetate. The organic layer was washed with water and saturated brine, and the solvent was evaporated. The obtained residue was purified by column chromatography to give [4-(3,5-dimethylpyridin-2-yl)piperazin-1-yl][6-(1,1-dioxo-1$\lambda^6$-isothiazolidin-2-yl)-4-methylpyridin-3-yl]methanone. The obtained [4-(3,5-dimethylpyridin-2-yl)piperazin-1-yl][6-(1,1-dioxo-1$\lambda^6$-isothiazolidin-2-yl)-4-methylpyridin-3-yl]methanone was dissolved in dichloromethane, 1N hydrogen chloride/diethyl ether was added, and the precipitate was collected by filtration to give the title compound (385 mg).

MS (ESI) m/z: 430(M+H)$^+$.

Example 224

Synthesis of [4-(2,4-dimethylphenyl)piperazin-1-yl][6-(1,1-dioxo-1$\lambda^6$-isothiazolidin-2-yl)-4-methylpyridin-3-yl]methanone hydrochloride

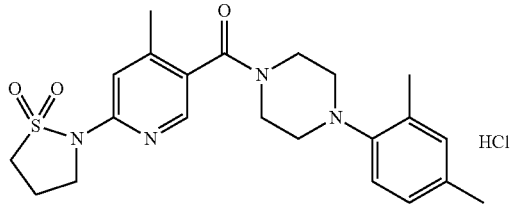 [SMILES: Cc1ccc(N2CCN(C(=O)c3cnc(N4CCCS4(=O)=O)cc3C)CC2)c(C)c1 ; Cl]

Using [4-(2,4-dimethylphenyl)piperazin-1-yl](6-fluoro-4-methylpyridin-3-yl)methanone (470 mg) described in Preparation Example 175, 4-methoxybenzylamine (1 mL) and 3-chloropropane-1-sulfonyl chloride (0.20 mL) and by the reaction and treatment in the same manner as in Example 223, the title compound (485 mg) was obtained via (6-amino-4-methylpyridin-3-yl)[4-(2,4-dimethylphenyl)piperazin-1-yl]methanone and [4-(2,4-dimethylphenyl)piperazin-1-yl][6-(1,1-dioxo-1$\lambda^6$-isothiazolidin-2-yl)-4-methylpyridin-3-yl]methanone.

MS (ESI) m/z: 429(M+H)$^+$.

Example 225

Synthesis of [4-(5-cyclopropyl-3-methylpyridin-2-yl)piperazin-1-yl][6-(1,1-dioxo-1$\lambda^6$-isothiazolidin-2-yl)-4-methylpyridin-3-yl]methanone dihydrochloride

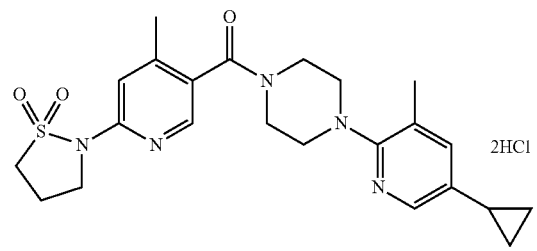 [SMILES: Cc1cc(N2CCCS2(=O)=O)ncc1C(=O)N1CCN(c2ncc(C3CC3)cc2C)CC1 ; "2HCl"]

Using [4-(5-cyclopropyl-3-methylpyridin-2-yl)piperazin-1-yl](6-fluoro-4-methylpyridin-3-yl)methanone (1.25 g) described in Preparation Example 140, 4-methoxybenzylamine (2 mL) and 3-chloropropane-1-sulfonyl chloride (0.55 ml) and by the reaction and treatment in the same manner as in Example 223, the title compound (950 mg) was obtained via (6-amino-4-methylpyridin-3-yl) [4-(5-cyclopropyl-3-methylpyridin-2-yl)piperazin-1-yl]methanone and [4-(5-cyclopropyl-3-methylpyridin-2-yl)piperazin-1-yl][6-(1,1-dioxo-1$\lambda^6$-isothiazolidin-2-yl)-4-methylpyridin-3-yl]methanone.

MS (ESI) m/z: 456(M+H)$^+$.

Example 226

Synthesis of [6-(1,1-dioxo-1$\lambda^6$-isothiazolidin-2-yl)pyridin-3-yl][4-(5-ethyl-3-methylpyridin-2-yl)piperazin-1-yl]methanone dihydrochloride

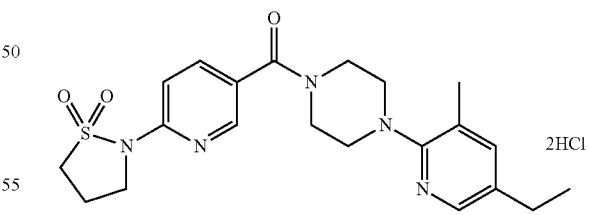

Using ethyl 6-(1,1-dioxo-1$\lambda^6$-isothiazolidin-2-yl)nicotinate (300 mg) described in Preparation Example 25 and 1-(5-ethyl-3-methylpyridin-2-yl)piperazine (228 mg) described in Preparation Example 81 and by the reaction and treatment in the same manner as in Example 206, the title compound (290 mg) was obtained via [6-(1,1-dioxo-1$\lambda^6$-isothiazolidin-2-yl)pyridin-3-yl][4-(5-ethyl-3-methylpyridin-2-yl)piperazin-1-yl]methanone.

MS (ESI) m/z: 430(M+H)$^+$.

Example 227

Synthesis of [4-(3-cyclopropyl-5-methylpyridin-2-yl)piperazin-1-yl][6-(1,1-dioxo-1λ⁶-isothiazolidin-2-yl)pyridin-3-yl]methanone

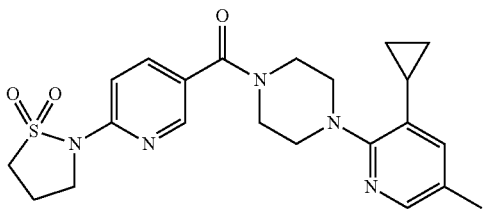 [SMILES: Cc1cnc(N2CCN(C(=O)c3ccc(N4CCCS4(=O)=O)nc3)CC2)c(C2CC2)c1]

Using ethyl 6-(1,1-dioxo-1λ⁶-isothiazolidin-2-yl)nicotinate (300 mg) described in Preparation Example 25 and 1-(3-cyclopropyl-5-methylpyridin-2-yl)piperazine (241 mg) described in Preparation Example 86 and by the reaction and treatment in the same manner as in Example 109, the title compound (225 mg) was obtained.
MS (ESI) m/z: 442(M+H)⁺.

Example 228

Synthesis of [4-(3,5-dicyclopropylpyridin-2-yl)piperazin-1-yl][6-(1,1-dioxo-1λ⁶-isothiazolidin-2-yl)pyridin-3-yl]methanone

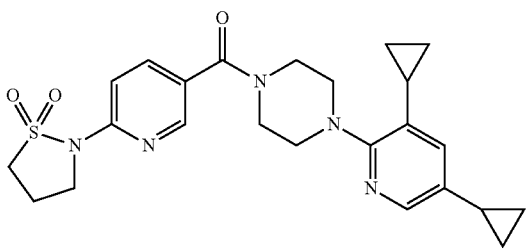

Using ethyl 6-(1,1-dioxo-1λ⁶-isothiazolidin-2-yl)nicotinate (300 mg) described in Preparation Example 25 and 1-(3,5-dicyclopropylpyridin-2-yl)piperazine (297 mg) described in Preparation Example 88 and by the reaction and treatment in the same manner as in Example 109, the title compound (347 mg) was obtained.
MS (ESI) m/z: 468(M+H)⁺.

Example 229

Synthesis of [6-(1,1-dioxo-1λ⁶-isothiazolidin-2-yl)-4-methylpyridin-3-yl][4-(5-ethyl-3-methylpyridin-2-yl)piperazin-1-yl]methanone

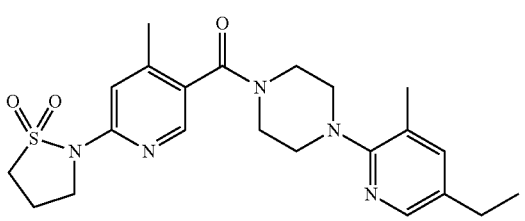 [SMILES: CCc1cnc(N2CCN(C(=O)c3cnc(N4CCCS4(=O)=O)cc3C)CC2)c(C)c1]

To [4-(5-ethyl-3-methylpyridin-2-yl)piperazin-1-yl](6-fluoro-4-methylpyridin-3-yl)methanone (320 mg) described in Preparation Example 176 was added 4-methoxybenzylamine (1 mL), and the mixture was stirred at 160° C. for 6 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give [4-(5-ethyl-3-methylpyridin-2-yl)piperazin-1-yl][6-(4-methoxybenzylamino)-4-methylpyridin-3-yl]methanone (330 mg). The obtained [4-(5-ethyl-3-methylpyridin-2-yl)piperazin-1-yl][6-(4-methoxybenzylamino)-4-methylpyridin-3-yl]methanone (330 mg) was dissolved in dichloromethane (5 mL), trifluoroacetic acid (10 mL) was added, and the mixture was stirred at room temperature overnight. The solvent was evaporated from the reaction mixture, 1N aqueous sodium hydroxide solution was added, and the mixture was extracted with chloroform. The organic layer was washed with saturated brine, and the solvent was evaporated. The obtained residue was purified by column chromatography to give (6-amino-4-methylpyridin-3-yl) [4-(5-ethyl-3-methylpyridin-2-yl)piperazin-1-yl]methanone. The obtained (6-amino-4-methylpyridin-3-yl)[4-(5-ethyl-3-methylpyridin-2-yl)piperazin-1-yl]methanone and triethylamine (0.30 mL) were dissolved in dichloromethane (10 mL), 3-chloropropane-1-sulfonyl chloride (0.18 mL) was added under ice-cooling, and the mixture was stirred at room temperature for 3.5 hr. Water was added to the reaction mixture, and the mixture was extracted with chloroform. The organic layer was washed with saturated brine, and the solvent was evaporated. The obtained residue was dissolved in N,N-dimethylformamide (10 mL), 1,8-diazabicyclo[5.4.0]undec-7-ene (0.16 mL) was added, and the mixture was stirred at room temperature overnight. Water was added to the reaction mixture, and the mixture was extracted with ethyl acetate. The organic layer was washed with water and saturated brine, and the solvent was evaporated. The obtained residue was purified by column chromatography to give the title compound (220 mg).
MS (ESI) m/z: 444(M+H)⁺.

Example 230

Synthesis of [4-(3-cyclopropyl-5-trifluoromethylpyridin-2-yl)piperazin-1-yl][6-(1,1-dioxo-1λ⁶-isothiazolidin-2-yl)pyridin-3-yl]methanone

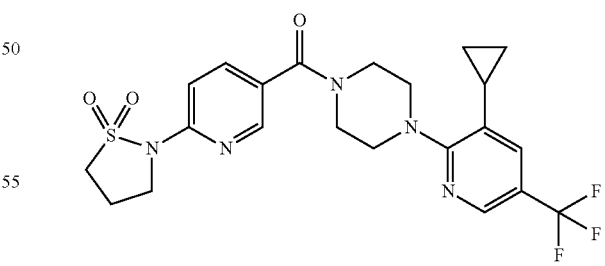

Using ethyl 6-(1,1-dioxo-1λ⁶-isothiazolidin-2-yl)nicotinate (300 mg) described in Preparation Example 25 and 1-(3-cyclopropyl-5-trifluoromethylpyridin-2-yl)piperazine (331 mg) described in Preparation Example 90 and by the reaction and treatment in the same manner as in Example 109, the title compound (375 mg) was obtained.
MS (ESI) m/z: 496(M+H)⁺.

Example 231

Synthesis of [4-(5-cyclopropyl-3-methylpyridin-2-yl)piperazin-1-yl][6-(1,1-dioxo-1λ$^6$-isothiazolidin-2-yl)pyridin-3-yl]methanone

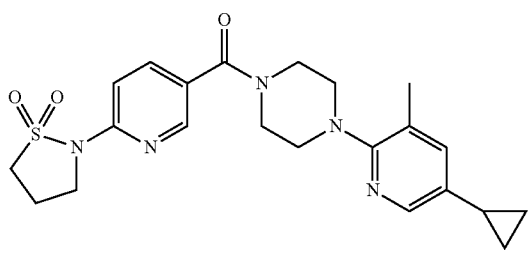

Using ethyl 6-(1,1-dioxo-1λ$^6$-isothiazolidin-2-yl)nicotinate (194 mg) described in Preparation Example 25 and 1-(5-cyclopropyl-3-methylpyridin-2-yl)piperazine (170 mg) described in Preparation Example 83 and by the reaction and treatment in the same manner as in Example 109, the title compound (95 mg) was obtained.

MS (ESI) m/z: 441(M+H)$^+$.

Example 232

Synthesis of [4-(3,5-dicyclopropylpyridin-2-yl)piperazin-1-yl][6-(1,1-dioxo-1λ$^6$-isothiazolidin-2-yl)-4-methylpyridin-3-yl]methanone

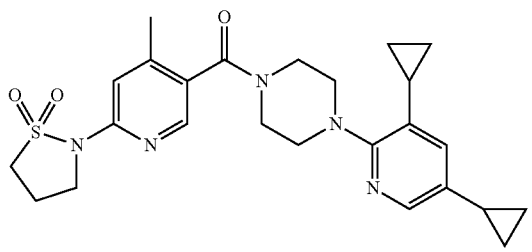

Using [4-(3,5-dicyclopropylpyridin-2-yl)piperazin-1-yl](6-fluoro-4-methylpyridin-3-yl)methanone (410 mg) described in Preparation Example 178, 4-methoxybenzylamine (2 mL) and 3-chloropropane-1-sulfonyl chloride (0.24 mL) and by the reaction and treatment in the same manner as in Example 229, the title compound (295 mg) was obtained via (6-amino-4-methylpyridin-3-yl)[4-(3,5-dicyclopropylpyridin-2-yl)piperazin-1-yl]methanone.

MS (ESI) m/z: 482(M+H)$^+$.

Example 233

Synthesis of [4-(2,4-dicyclopropylphenyl)piperazin-1-yl][6-(1,1-dioxo-1λ$^6$-isothiazolidin-2-yl)pyridin-3-yl]methanone

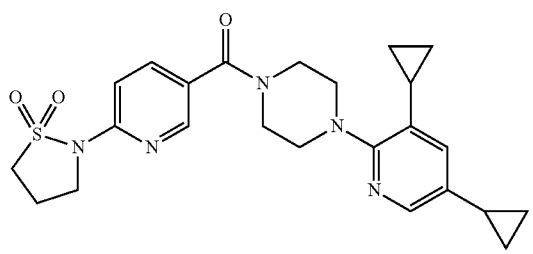

Using ethyl 6-(1,1-dioxo-1λ$^6$-isothiazolidin-2-yl)nicotinate (300 mg) described in Preparation Example 25 and 1-(2,4-dicyclopropylphenyl)piperazine (296 mg) described in Preparation Example 101 and by the reaction and treatment in the same manner as in Example 109, the title compound (375 mg) was obtained.

MS (ESI) m/z: 467(M+H)$^+$.

Example 234

Synthesis of [4-(2,4-dicyclopropylphenyl)piperazin-1-yl][6-(1,1-dioxo-1λ$^6$-isothiazolidin-2-yl)-4-methylpyridin-3-yl]methanone

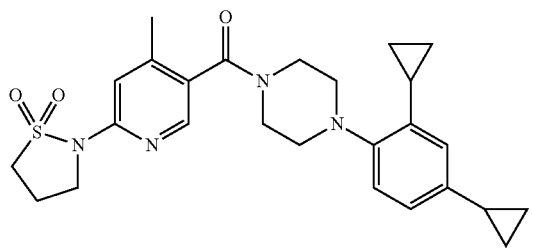

Using [4-(2,4-dicyclopropylphenyl)piperazin-1-yl](6-fluoro-4-methylpyridin-3-yl)methanone (480 mg) described in Preparation Example 179, 4-methoxybenzylamine (2 mL) and 3-chloropropane-1-sulfonyl chloride (0.31 mL) and by the reaction and treatment in the same manner as in Example 229, the title compound (450 mg) was obtained via (6-amino-4-methylpyridin-3-yl)[4-(2,4-dicyclopropylphenyl)piperazin-1-yl]methanone.

MS (ESI) m/z: 481(M+H)$^+$.

Example 235

Synthesis of [6-(1,1-dioxo-1λ$^6$-isothiazolidin-2-yl)pyridin-3-yl][4-(2,4,5-trimethylphenyl)piperazin-1-yl]methanone

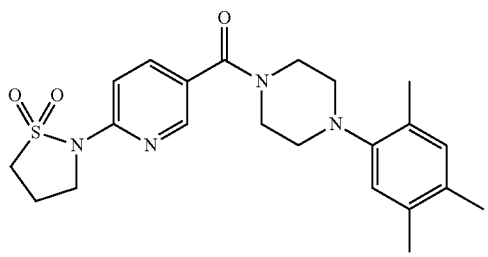 [SMILES: Cc1cc(C)c(N2CCN(C(=O)c3ccc(N4CCCS4(=O)=O)nc3)CC2)cc1C]

Using ethyl 6-(1,1-dioxo-1λ$^6$-isothiazolidin-2-yl)nicotinate (300 mg) described in Preparation Example 25 and 1-(2,4,5-trimethylphenyl)piperazine (249 mg) and by the reaction and treatment in the same manner as in Example 109, the title compound (337 mg) was obtained.

MS (ESI) m/z: 429(M+H)$^+$.

Example 236

Synthesis of [6-(1,1-dioxo-1λ$^6$-isothiazolidin-2-yl)-4-methylpyridin-3-yl][4-(2,4,5-trimethylphenyl)piperazin-1-yl]methanone

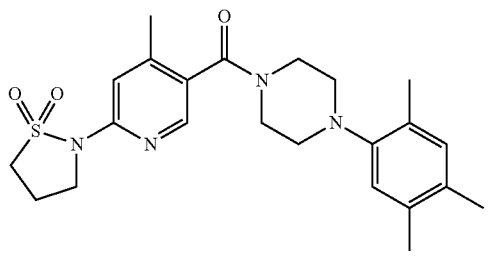 [SMILES: Cc1cc(C)c(N2CCN(C(=O)c3cnc(N4CCCS4(=O)=O)cc3C)CC2)cc1C]

Using (6-fluoro-4-methylpyridin-3-yl)[4-(2,4,5-trimethylphenyl)piperazin-1-yl]methanone (310 mg) described in Preparation Example 180, 4-methoxybenzylamine (2 mL) and 3-chloropropane-1-sulfonyl chloride (0.23 mL) and by the reaction and treatment in the same manner as in Example 229, the title compound (185 mg) was obtained via (6-amino-4-methylpyridin-3-yl)[4-(2,4,5-trimethylphenyl)piperazin-1-yl]methanone.

MS (ESI) m/z: 443(M+H)$^+$.

Example 237

Synthesis of [4-(3-cyclopropyl-5-methylpyridin-2-yl)piperazin-1-yl][6-(1,1-dioxo-1λ$^6$-isothiazolidin-2-yl)-4-methylpyridin-3-yl]methanone

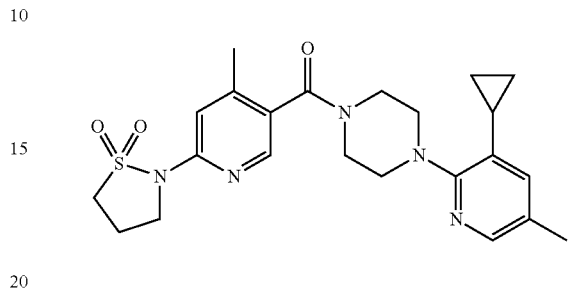

Using [4-(3-cyclopropyl-5-methylpyridin-2-yl)piperazin-1-yl](6-fluoro-4-methylpyridin-3-yl)methanone (180 mg) described in Preparation Example 181, 4-methoxybenzylamine (2 mL) and 3-chloropropane-1-sulfonyl chloride (0.12 mL) and by the reaction and treatment in the same manner as in Example 229, the title compound (125 mg) was obtained via (6-amino-4-methylpyridin-3-yl)[4-(3-cyclopropyl-5-methylpyridin-2-yl)piperazin-1-yl]methanone.

MS (ESI) m/z: 456(M+H)$^+$.

Example 238

Synthesis of [4-(3,5-dimethylpyridin-2-yl)piperazin-1-yl][6-(1,1-dioxo-1λ$^6$-isothiazolidin-2-yl)-2-methylpyridin-3-yl]methanone

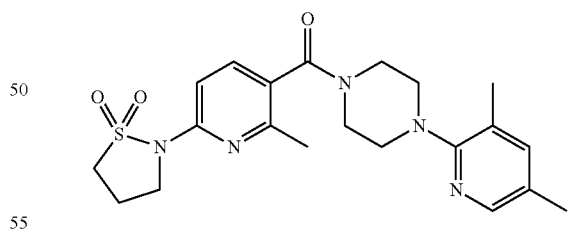

Using methyl 6-(1,1-dioxo-1λ$^6$-isothiazolidin-2-yl)-2-methylnicotinate (220 mg) described in Preparation Example 37 and 1-(3,5-dimethylpyridin-2-yl)piperazine (186 mg) described in Preparation Example 79 and by the reaction and treatment in the same manner as in Example 109, the title compound (235 mg) was obtained.

MS (ESI) m/z: 430(M+H)$^+$.

Example 239

Synthesis of [6-(1,1-dioxo-1λ⁶-isothiazolidin-2-yl)-2-methylpyridin-3-yl][4-(5-ethyl-3-methylpyridin-2-yl)piperazin-1-yl]methanone

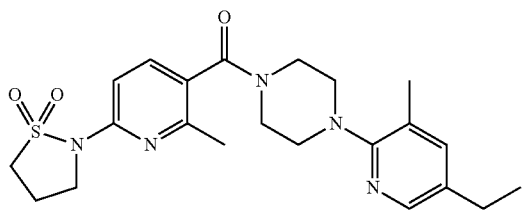 [SMILES: CCc1cnc(N2CCN(C(=O)c3ccc(N4CCCS4(=O)=O)nc3C)CC2)c(C)c1]

Using methyl 6-(1,1-dioxo-1λ⁶-isothiazolidin-2-yl)-2-methylnicotinate (300 mg) described in Preparation Example 37 and 1-(5-ethyl-3-methylpyridin-2-yl)piperazine (251 mg) described in Preparation Example 81 and by the reaction and treatment in the same manner as in Example 109, the title compound (25 mg) was obtained.
MS (ESI) m/z: 444(M+H)⁺.

Example 240

Synthesis of [6-(1,1-dioxo-1λ⁶-isothiazolidin-2-yl)-2-methylpyridin-3-yl][4-(3,5,6-trimethylpyridin-2-yl)piperazin-1-yl]methanone

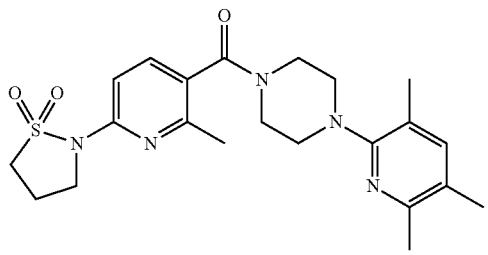 [SMILES: Cc1cc(C)c(N2CCN(C(=O)c3ccc(N4CCCS4(=O)=O)nc3C)CC2)nc1C]

Using methyl 6-(1,1-dioxo-1λ⁶-isothiazolidin-2-yl)-2-methylnicotinate (300 mg) described in Preparation Example 37 and 1-(3,5,6-trimethylpyridin-2-yl)piperazine (251 mg) described in Preparation Example 92 and by the reaction and treatment in the same manner as in Example 109, the title compound (307 mg) was obtained.
MS (ESI) m/z: 444(M+H)⁺.

Example 241

Synthesis of [4-(5-cyclopropyl-3-methylpyridin-2-yl)piperazin-1-yl][6-(1,1-dioxo-1λ⁶-isothiazolidin-2-yl)-2-methylpyridin-3-yl]methanone

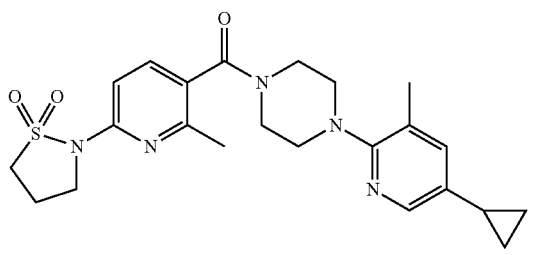 [SMILES: Cc1cc(C2CC2)cnc1N1CCN(C(=O)c2ccc(N3CCCS3(=O)=O)nc2C)CC1]

Using methyl 6-(1,1-dioxo-1λ⁶-isothiazolidin-2-yl)-2-methylnicotinate (300 mg) described in Preparation Example 37 and 1-(5-cyclopropyl-3-methylpyridin-2-yl)piperazine (265 mg) described in Preparation Example 83 and by the reaction and treatment in the same manner as in Example 109, the title compound (295 mg) was obtained.
MS (ESI) m/z: 456(M+H)⁺.

Example 242

Synthesis of [6-(1,1-dioxo-1λ⁶-isothiazolidin-2-yl)-4-methylpyridin-3-yl][4-(3,5,6-trimethylpyridin-2-yl)piperazin-1-yl]methanone

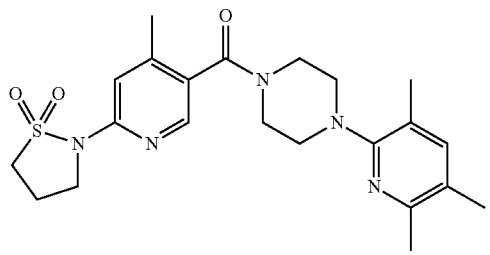 [SMILES: Cc1cc(N2CCCS2(=O)=O)ncc1C(=O)N1CCN(c2nc(C)c(C)cc2C)CC1]

Using (6-fluoro-4-methylpyridin-3-yl)[4-(3,5,6-trimethylpyridin-2-yl)piperazin-1-yl]methanone (220 mg) described in Preparation Example 182, 4-methoxybenzylamine (1.5 mL) and 3-chloropropane-1-sulfonyl chloride (0.16 mL) and by the reaction and treatment in the same manner as in Example 229, the title compound (175 mg) was obtained via (6-amino-4-methylpyridin-3-yl)[4-(3-cyclopropyl-5-methylpyridin-2-yl)piperazin-1-yl]methanone.
MS (ESI) m/z: 444(M+H)⁺.

Example 243

Synthesis of [4-(3,5-dicyclopropylpyridin-2-yl)piperazin-1-yl][6-(1,1-dioxo-1λ⁶-isothiazolidin-2-yl)-2-methylpyridin-3-yl]methanone

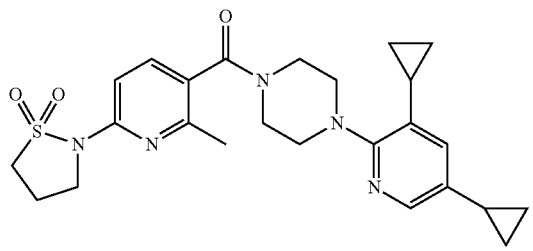 [SMILES: Cc1nc(N2CCCS2(=O)=O)ccc1C(=O)N1CCN(c2ncc(C3CC3)cc2C2CC2)CC1]

Using methyl 6-(1,1-dioxo-1λ⁶-isothiazolidin-2-yl)-2-methylnicotinate (300 mg) described in Preparation Example 37 and 1-(3,5-dicyclopropylpyridin-2-yl)piperazine (297 mg) described in Preparation Example 88 and by the reaction and treatment in the same manner as in Example 109, the title compound (355 mg) was obtained.
MS (ESI) m/z: 482(M+H)⁺.

Example 244

Synthesis of [4-(3,5-dimethylpyridin-2-yl)piperazin-1-yl][4-(1,1-dioxo-1λ$^6$-isothiazolidin-2-ylmethyl)phenyl]methanone hydrochloride

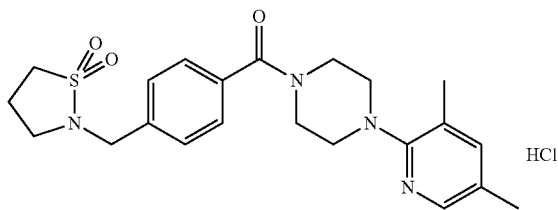 [SMILES: Cc1cnc(N2CCN(C(=O)c3ccc(CN4CCCS4(=O)=O)cc3)CC2)c(C)c1 ; Cl]

Using 4-(1,1-dioxo-1λ$^6$-isothiazolidin-2-ylmethyl)benzoic acid (123 mg) described in Preparation Example 18 and 1-(3,5-dimethylpyridin-2-yl)piperazine (96 mg) described in Preparation Example 79 and by the reaction and treatment in the same manner as in Example 187, the title compound (154 mg) was obtained.
MS (ESI) m/z: 429(M+H)$^+$.

Example 245

Synthesis of [4-(5-cyclopropyl-3-methylpyridin-2-yl)piperazin-1-yl][4-(1,1-dioxo-1λ$^6$-isothiazolidin-2-ylmethyl)phenyl]methanone

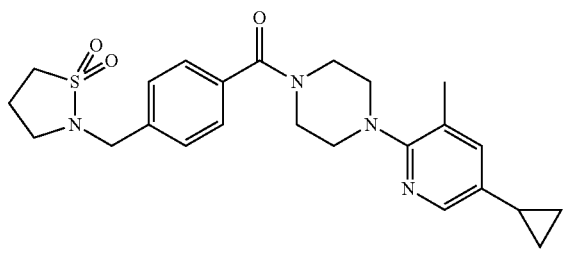 [SMILES: Cc1cc(C2CC2)cnc1N1CCN(C(=O)c2ccc(CN3CCCS3(=O)=O)cc2)CC1]

Using 4-(1,1-dioxo-1λ$^6$-isothiazolidin-2-ylmethyl)benzoic acid (153 mg) described in Preparation Example 18 and 1-(5-cyclopropyl-3-methylpyridin-2-yl)piperazine (196 mg) described in Preparation Example 83 and by the reaction and treatment in the same manner as in Example 87, the title compound (149 mg) was obtained.
MS (ESI) m/z: 455(M+H)$^+$.

Example 246

Synthesis of [4-(3,5-dimethylpyridin-2-yl)piperazin-1-yl] {4-[1-(1,1-dioxo-1λ$^6$-isothiazolidin-2-yl)-1-methylethyl]phenyl}methanone

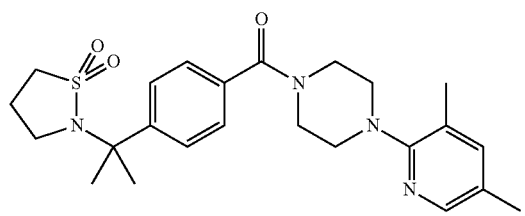 [SMILES: Cc1cnc(N2CCN(C(=O)c3ccc(C(C)(C)N4CCCS4(=O)=O)cc3)CC2)c(C)c1]

Using 4-[1-(1,1-dioxo-1λ$^6$-isothiazolidin-2-yl)-1-methylethyl]benzoic acid (170 mg) described in Preparation Example 39 and 1-(3,5-dimethylpyridin-2-yl)piperazine (138 mg) described in Preparation Example 79 and by the reaction and treatment in the same manner as in Example 87, the title compound (270 mg) was obtained.
MS (ESI) m/z: 457(M+H)$^+$.

Example 247

Synthesis of [4-(5-cyclopropyl-3-methylpyridin-2-yl)piperazin-1-yl]{4-[1-(1,1-dioxo-1λ$^6$-isothiazolidin-2-yl)-1-methylethyl]phenyl}methanone

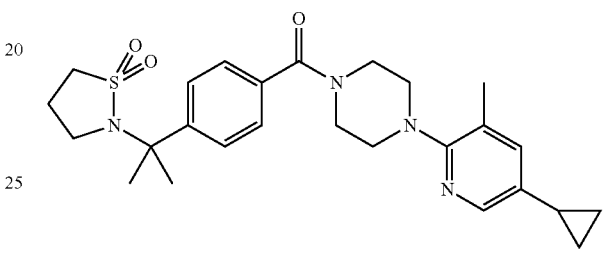

Using 4-[1-(1,1-dioxo-1λ$^6$-isothiazolidin-2-yl)-1-methylethyl]benzoic acid (170 mg) described in Preparation Example 39 and 1-(5-cyclopropyl-3-methylpyridin-2-yl)piperazine (156 mg) described in Preparation Example 83 and by the reaction and treatment in the same manner as in Example 87, the title compound (115 mg) was obtained.
MS (ESI) m/z: 483(M+H)$^+$.

Example 248

Synthesis of [4-(3,5-dimethylpyridin-2-yl)piperazin-1-yl]{4-[2-(1,1-dioxo-1λ$^6$-isothiazolidin-2-yl)ethyl]phenyl}methanone

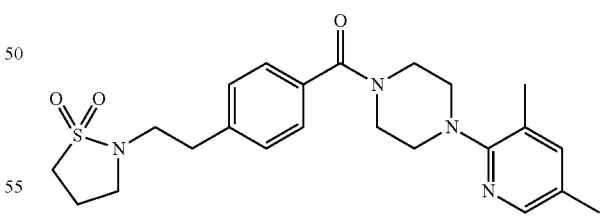

Using 4-[2-(1,1-dioxo-1λ$^6$-isothiazolidin-2-yl)ethyl]benzoic acid (162 mg) described in Preparation Example 41 and 1-(3,5-dimethylpyridin-2-yl)piperazine (115 mg) described in Preparation Example 79 and by the reaction and treatment in the same manner as in Example 87, the title compound (239 mg) was obtained.
MS (ESI) m/z: 443(M+H)$^+$.

Example 249

Synthesis of [4-(5-cyclopropyl-3-methylpyridin-2-yl)piperazin-1-yl]{4-[2-(1,1-dioxo-1λ$^6$-isothiazolidin-2-yl)ethyl]phenyl}methanone

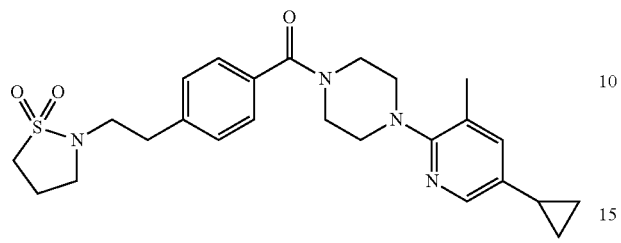

Using 4-[2-(1,1-dioxo-1λ$^6$-isothiazolidin-2-yl)ethyl]benzoic acid (162 mg) described in Preparation Example 41 and 1-(5-cyclopropyl-3-methylpyridin-2-yl)piperazine (130 mg) described in Preparation Example 83 and by the reaction and treatment in the same manner as in Example 87, the title compound (198 mg) was obtained.
MS (ESI) m/z: 469(M+H)$^+$.

Example 250

Synthesis of (R)-[4-(3,5-dimethylpyridin-2-yl)piperazin-1-yl][4-(3-methyl-1,1-dioxo-1λ$^6$-isothiazolidin-2-ylmethyl)phenyl]methanone

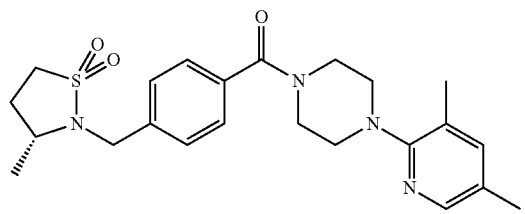 [SMILES: Cc1cnc(N2CCN(C(=O)c3ccc(CN4[C@H](C)CCS4(=O)=O)cc3)CC2)c(C)c1]

Using methyl (R)-4-(3-methyl-1,1-dioxo-1λ$^6$-isothiazolidin-2-ylmethyl)benzoate (79 mg) described in Preparation Example 42 and 1-(3,5-dimethylpyridin-2-yl)piperazine (53 mg) described in Preparation Example 79 and by the reaction and treatment in the same manner as in Example 109, the title compound (96 mg) was obtained.
MS (ESI) m/z: 443(M+H)$^+$.

Example 251

Synthesis of (R)-[4-(5-cyclopropyl-3-methylpyridin-2-yl)piperazin-1-yl][4-(3-methyl-1,1-dioxo-1λ$^6$-isothiazolidin-2-ylmethyl)phenyl]methanone

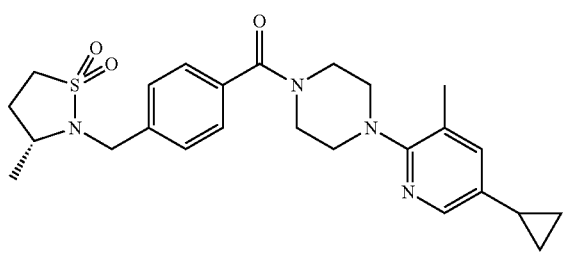 [SMILES: Cc1cc(C2CC2)cnc1N1CCN(C(=O)c2ccc(CN3[C@H](C)CCS3(=O)=O)cc2)CC1]

Using methyl (R)-4-(3-methyl-1,1-dioxo-1λ$^6$-isothiazolidin-2-ylmethyl)benzoate (79 mg) described in Preparation Example 42 and 1-(5-cyclopropyl-3-methylpyridin-2-yl)piperazine (61 mg) described in Preparation Example 83 and by the reaction and treatment in the same manner as in Example 109, the title compound (104 mg) was obtained.
MS (ESI) m/z: 469(M+H)$^+$.

Example 252

Synthesis of (S)-[4-(3,5-dimethylpyridin-2-yl)piperazin-1-yl]{4-[1-(1,1-dioxo-1λ$^6$-isothiazolidin-2-yl)ethyl]phenyl}methanone

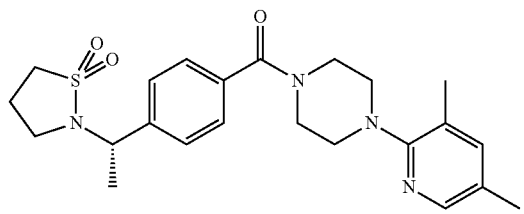 [SMILES: Cc1cnc(N2CCN(C(=O)c3ccc([C@H](C)N4CCCS4(=O)=O)cc3)CC2)c(C)c1]

Using (S)-4-[1-(1,1-dioxo-1λ$^6$-isothiazolidin-2-yl)ethyl]benzoic acid (162 mg) described in Preparation Example 44 and 1-(3,5-dimethylpyridin-2-yl)piperazine (126 mg) described in Preparation Example 79 and by the reaction and treatment in the same manner as in Example 87, the title compound (215 mg) was obtained.
MS (ESI) m/z: 443(M+H)$^+$.

Example 253

Synthesis of (S)-[4-(5-cyclopropyl-3-methylpyridin-2-yl)piperazin-1-yl]{4-[1-(1,1-dioxo-1λ$^6$-isothiazolidin-2-yl)ethyl]phenyl}methanone

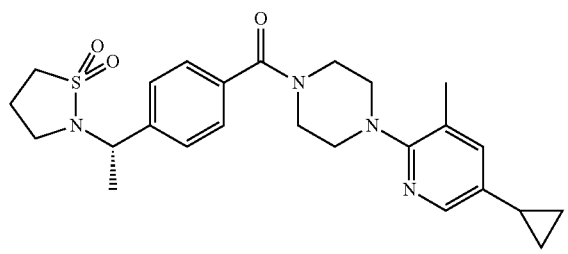 [SMILES: Cc1cc(C2CC2)cnc1N1CCN(C(=O)c2ccc([C@H](C)N3CCCS3(=O)=O)cc2)CC1]

Using (S)-4-[1-(1,1-dioxo-1λ$^6$-isothiazolidin-2-yl)ethyl]benzoic acid (162 mg) described in Preparation Example 44 and 1-(5-cyclopropyl-3-methylpyridin-2-yl)piperazine (143 mg) described in Preparation Example 83 and by the reaction and treatment in the same manner as in Example 87, the title compound (207 mg) was obtained.
MS (ESI) m/z: 469(M+H)$^+$.

Example 254

Synthesis of 6-[4-[6-(1,1-dioxo-1λ⁶-isothiazolidin-2-yl)pyridine-3-carbonyl]piperazin-1-yl]-5-methylnicotinonitrile

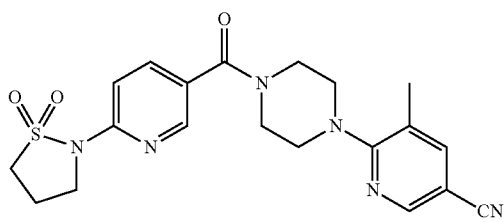 [SMILES: Cc1cc(C#N)cnc1N1CCN(C(=O)c2ccc(N3CCCS3(=O)=O)nc2)CC1]

Using 6-[4-(6-bromopyridine-3-carbonyl)piperazin-1-yl]-5-methylnicotinonitrile (200 mg) described in Preparation Example 160 and isothiazolidine 1,1-dioxide (94 mg) and by the reaction and treatment in the same manner as in Example 1, the title compound (128 mg) was obtained.
MS (ESI) m/z: 427(M+H)⁺.

Example 255

Synthesis of 6-(4-{4-[1-(1,1-dioxo-1λ⁶-isothiazolidin-2-yl)-1-methylethyl]benzoyl}piperazin-1-yl)-5-methylnicotinonitrile

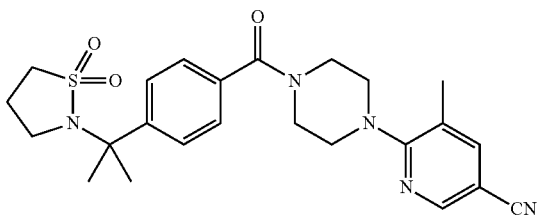 [SMILES: Cc1cc(C#N)cnc1N1CCN(C(=O)c2ccc(C(C)(C)N3CCCS3(=O)=O)cc2)CC1]

Using 4-[1-(1,1-dioxo-1λ⁶-isothiazolidin-2-yl)-1-methylethyl]benzoic acid (100 mg) described in Preparation Example 39 and 5-methyl-6-(piperazin-1-yl)nicotinonitrile (71 mg) described in Preparation Example 103 and by the reaction and treatment in the same manner as in Example 87, the title compound (142 mg) was obtained.
MS (ESI) m/z: 468(M+H)⁺.

Example 256

Synthesis of [(3,5-dimethylpyrazin-2-yl)piperazin-4-yl]{4-[1-(1,1-dioxo-1λ⁶-isothiazolidin-2-yl)-1-methylethyl]phenyl}methanone

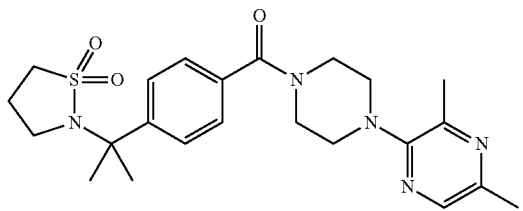 [SMILES: Cc1cnc(N2CCN(C(=O)c3ccc(C(C)(C)N4CCCS4(=O)=O)cc3)CC2)c(C)n1]

Using 4-[1-(1,1-dioxo-1λ⁶-isothiazolidin-2-yl)-1-methylethyl]benzoic acid (100 mg) described in Preparation Example 39 and (3,5-dimethylpyrazin-2-yl)piperazine hydrochloride (81 mg) described in Preparation Example 104 and by the reaction and treatment in the same manner as in Example 86, the title compound (87 mg) was obtained.
MS (ESI) m/z: 458(M+H)⁺.

Example 257

Synthesis of 2-(4-{4-[1-(1,1-dioxo-1λ⁶-isothiazolidin-2-yl)-1-methylethyl]benzoyl}piperazin-1-yl)-5-methylnicotinonitrile

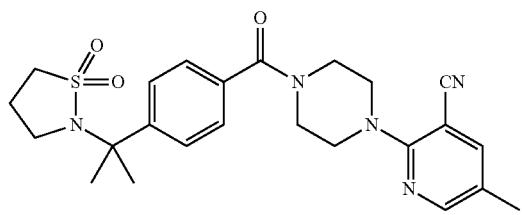 [SMILES: Cc1cnc(N2CCN(C(=O)c3ccc(C(C)(C)N4CCCS4(=O)=O)cc3)CC2)c(C#N)c1]

Using 4-[1-(1,1-dioxo-1λ⁶-isothiazolidin-2-yl)-1-methylethyl]benzoic acid (100 mg) described in Preparation Example 39 and 4-(3-cyano-5-methylpyridin-2-yl)piperazine (51 mg) described in Preparation Example 107 and by the reaction and treatment in the same manner as in Example 87, the title compound (94 mg) was obtained.
MS (ESI) m/z: 468(M+H)⁺.

Example 258

Synthesis of 2-[4-[6-(1,1-dioxo-1λ⁶-isothiazolidin-2-yl)pyridine-3-carbonyl]piperazin-1-yl]-5-methylnicotinonitrile

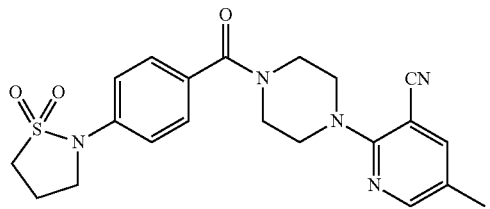 [SMILES: Cc1cnc(N2CCN(C(=O)c3ccc(N4CCCS4(=O)=O)cc3)CC2)c(C#N)c1]

Using 2-[4-(6-bromopyridine-3-carbonyl)piperazin-1-yl]-5-methylnicotinonitrile (150 mg) described in Preparation Example 184 and isothiazolidine 1,1-dioxide (71 mg) and by the reaction and treatment in the same manner as in Example 1, the title compound (114 mg) was obtained.
MS (ESI) m/z: 427(M+H)⁺.

Example 259

Synthesis of [4-(3,5-dimethylpyridin-2-yl)piperazin-1-yl][6-(1,1-dioxo-1λ$^6$-isothiazolidin-2-ylmethyl)pyridin-3-yl]methanone

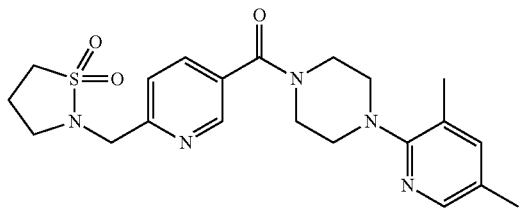 [SMILES: Cc1cnc(N2CCN(C(=O)c3ccc(CN4CCCS4(=O)=O)nc3)CC2)c(C)c1]

Using methyl 6-(1,1-dioxo-1λ$^6$-isothiazolidin-2-ylmethyl)nicotinate (108 mg) described in Preparation Example 45 and 1-(3,5-dimethylpyridin-2-yl)piperazine (77 mg) described in Preparation Example 79 and by the reaction and treatment in the same manner as in Example 109, the title compound (141 mg) was obtained.
MS (ESI) m/z: 430(M+H)$^+$.

Example 260

Synthesis of [4-(5-cyclopropyl-3-methylpyridin-2-yl)piperazin-1-yl][6-(1,1-dioxo-1λ$^6$-isothiazolidin-2-ylmethyl)pyridin-3-yl]methanone

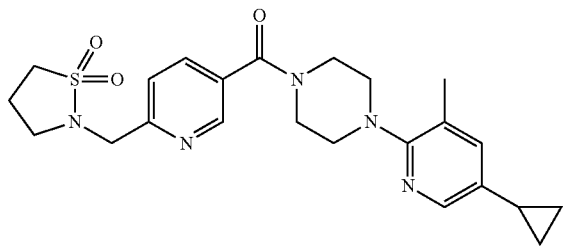 [SMILES: Cc1cc(C2CC2)cnc1N1CCN(C(=O)c2ccc(CN3CCCS3(=O)=O)nc2)CC1]

Using methyl 6-(1,1-dioxo-1λ$^6$-isothiazolidin-2-ylmethyl)nicotinate (108 mg) described in Preparation Example 45 and 1-(5-cyclopropyl-3-methylpyridin-2-yl)piperazine (87 mg) described in Preparation Example 83 and by the reaction and treatment in the same manner as in Example 109, the title compound (156 mg) was obtained.
MS (ESI) m/z: 456(M+H)$^+$.

Example 261

Synthesis of [4-(1,1-dioxo-1λ$^6$-isothiazolidin-2-ylmethyl)phenyl][4-(3,5,6-trimethylpyridin-2-yl)piperazin-1-yl]methanone

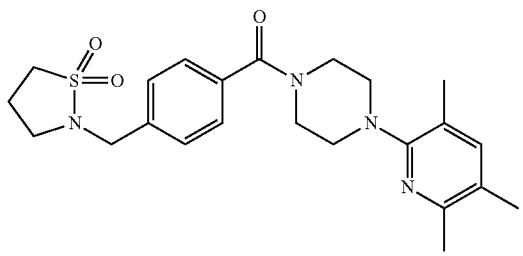 [SMILES: Cc1cc(C)c(N2CCN(C(=O)c3ccc(CN4CCCS4(=O)=O)cc3)CC2)nc1C]

Using 4-(1,1-dioxo-1λ$^6$-isothiazolidin-2-ylmethyl)benzoic acid (64 mg) described in Preparation Example 18 and 1-(3,5,6-trimethylpyridin-2-yl)piperazine (51 mg) described in Preparation Example 92 and by the reaction and treatment in the same manner as in Example 87, the title compound (83 mg) was obtained.
MS (ESI) m/z: 443(M+H)$^+$.

Example 262

Synthesis of 2-[4-(3,5-dimethylpyridin-2-yl)piperazine-1-carbonyl]-5-(1,1-dioxo-1λ$^6$-isothiazolidin-2-yl)benzonitrile

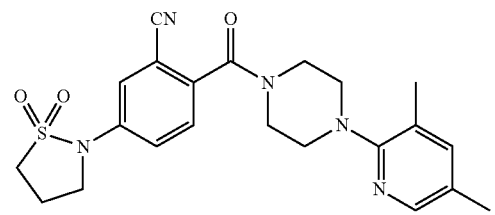

To a mixture of 5-bromo-2-[4-(3,5-dimethylpyridin-2-yl)piperazine-1-carbonyl]benzonitrile (599 mg) described in Preparation Example 187, isothiazolidine 1,1-dioxide (236 mg), 4,5-bisdiphenylphosphanyl-9,9-dimethyl-9H-xanthene (130 mg), palladium acetate (34 mg) and cesium carbonate (733 mg) was added 1,4-dioxane (2 mL), and the mixture was stirred with heating under reflux for 2 hr. The reaction mixture was cooled, saturated brine was added and the mixture was extracted with ethyl acetate. The organic layer was washed with saturated brine, dried over sodium sulfate, and the solvent was evaporated under reduced pressure. The obtained residue was purified by column chromatography (ethyl acetate:hexane) to give the title compound (470 mg).
MS (ESI) m/z: 440(M+H)$^+$.

Example 263

Synthesis of 2-[4-(2,4-dimethylphenyl)piperazine-1-carbonyl]-5-(1,1-dioxo-1λ$^6$-isothiazolidin-2-yl)benzonitrile

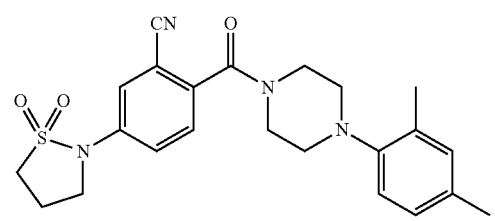

Using 5-bromo-2-[4-(2,4-dimethylphenyl)piperazine-1-carbonyl]benzonitrile (797 mg) described in Preparation Example 188 and isothiazolidine 1,1-dioxide (315 mg) and by the reaction and treatment in the same manner as in Example 262, the title compound (806 mg) was obtained.
MS (ESI) m/z: 439(M+H)$^+$.

Example 264

Synthesis of 2-[4-(5-cyclopropyl-3-methylpyridin-2-yl)piperazine-1-carbonyl]-5-(1,1-dioxo-1λ⁶-isothiazolidin-2-yl)benzonitrile

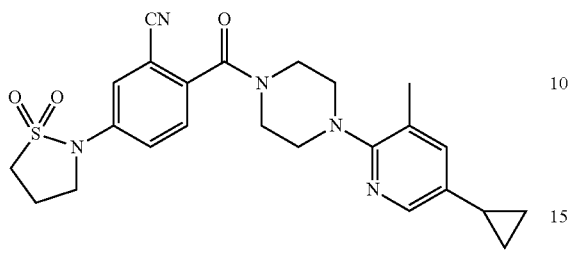

Using 5-bromo-2-[4-(5-cyclopropyl-3-methylpyridin-2-yl)piperazine-1-carbonyl]benzonitrile (425 mg) described in Preparation Example 189 and isothiazolidine 1,1-dioxide (158 mg) and by the reaction and treatment in the same manner as in Example 262, the title compound (386 mg) was obtained.
MS (ESI) m/z: 466(M+H)$^+$.

Example 265

Synthesis of 2-[4-(3,5-dimethylpyridin-2-yl)piperazine-1-carbonyl]-5-(1,1-dioxo-1λ⁶-[1,2]thiazinan-2-yl)benzonitrile

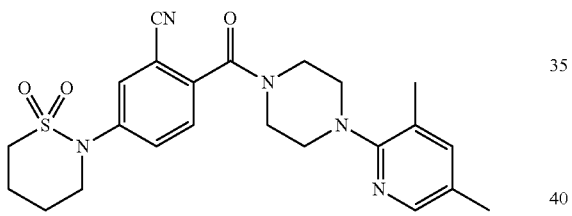

Using 5-bromo-2-[4-(3,5-dimethylpyridin-2-yl)piperazine-1-carbonyl]benzonitrile (399 mg) described in Preparation Example 187 and [1,2]thiazinane 1,1-dioxide (176 mg) and by the reaction and treatment in the same manner as in Example 262, the title compound (360 mg) was obtained.
MS (ESI) m/z: 454(M+H)$^+$.

Example 266

Synthesis of 2-[4-(5-cyclopropyl-3-methylpyridin-2-yl)piperazine-1-carbonyl]-5-(1,1-dioxo-1λ⁶-[1,2]thiazinan-2-yl)benzonitrile

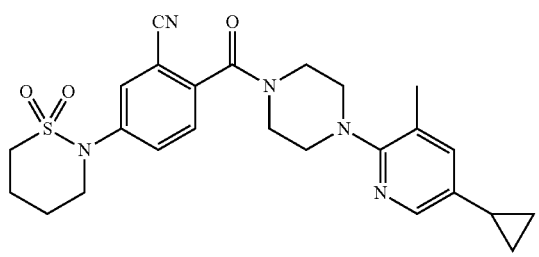 [SMILES: Cc1cc(C2CC2)cnc1N1CCN(C(=O)c2ccc(N3CCCCS3(=O)=O)cc2C#N)CC1]

Using 5-bromo-2-[4-(5-cyclopropyl-3-methylpyridin-2-yl)piperazine-1-carbonyl]benzonitrile (425 mg) described in Preparation Example 189 and [1,2]thiazinane 1,1-dioxide (176 mg) and by the reaction and treatment in the same manner as in Example 262, the title compound (317 mg) was obtained.
MS (ESI) m/z: 480(M+H)$^+$.

Example 267

Synthesis of 5-(1,1-dioxo-1λ⁶-[1,2]thiazinan-2-yl)-2-[4-(3,5,6-trimethylpyridin-2-yl)piperazine-1-carbonyl]benzonitrile

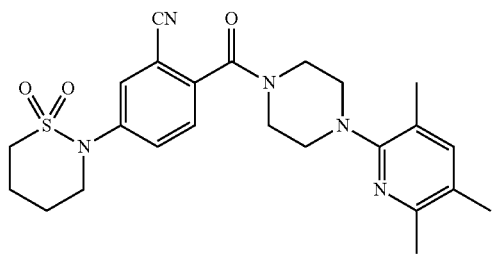 [SMILES: Cc1cc(C)c(N2CCN(C(=O)c3ccc(N4CCCCS4(=O)=O)cc3C#N)CC2)nc1C]

Using 5-bromo-2-[4-(3,5,6-trimethylpyridin-2-yl)piperazine-1-carbonyl]benzonitrile (413 mg) described in Preparation Example 172 and [1,2]thiazinane 1,1-dioxide (176 mg) and by the reaction and treatment in the same manner as in Example 262, the title compound (385 mg) was obtained.
MS (ESI) m/z: 468(M+H)$^+$.

Example 268

Synthesis of 5-(1,1-dioxo-1λ⁶-isothiazolidin-2-yl)-2-[4-(3,5,6-trimethylpyridin-2-yl)piperazine-1-carbonyl]benzonitrile

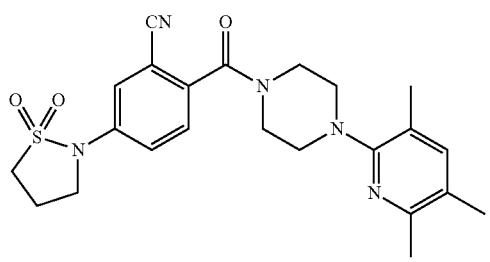 [SMILES: Cc1cc(C)c(N2CCN(C(=O)c3ccc(N4CCCS4(=O)=O)cc3C#N)CC2)nc1C]

Using 5-bromo-2-[4-(3,5,6-trimethylpyridin-2-yl)piperazine-1-carbonyl]benzonitrile (413 mg) described in Preparation Example 172 and isothiazolidine 1,1-dioxide (158 mg) and by the reaction and treatment in the same manner as in Example 262, the title compound (383 mg) was obtained.
MS (ESI) m/z: 454(M+H)$^+$.

Example 269

Synthesis of [4-(3,5-dimethylpyridin-2-yl)piperazin-1-yl][4-(1,1-dioxo-1λ⁶-[1,2,5]thiadiazolidin-2-yl)phenyl]methanone

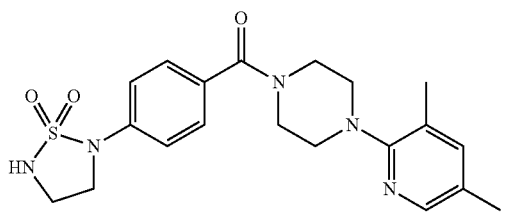

Using ethyl 4-(1,1-dioxo-1λ⁶-[1,2,5]thiadiazolidin-2-yl)benzoate (198 mg) described in Preparation Example 46 and 1-(3,5-dimethylpyridin-2-yl)piperazine (141 mg) described in Preparation Example 79 and by the reaction and treatment in the same manner as in Example 109, the title compound (222 mg) was obtained.

MS (ESI) m/z: 416(M+H)⁺.

Example 270

Synthesis of [4-(3,5-dimethylpyridin-2-yl)piperazin-1-yl][4-(5-methyl-1,1-dioxo-1λ⁶-[1,2,5]thiadiazolidin-2-yl)phenyl]methanone

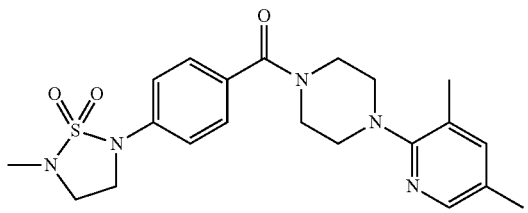

Using ethyl 4-(1,1-dioxo-1λ⁶-[1,2,5]thiadiazolidin-2-yl)benzoate (195 mg) described in Preparation Example 46 and methyl iodide (99 μL) and by the reaction and treatment in the same manner as in Example 36, crude ethyl 4-(5-methyl-1,1-dioxo-1λ⁶-[1,2,5]thiadiazolidin-2-yl)benzoate (107 mg) was obtained. Using the obtained crude ethyl 4-(5-methyl-1,1-dioxo-1λ⁶-[1,2,5]thiadiazolidin-2-yl)benzoate (107 mg) and 1-(3,5-dimethylpyridin-2-yl)piperazine (75.7 mg) described in Preparation Example 79 and by the reaction and treatment in the same manner as in Example 109, the title compound (120 mg) was obtained.

MS (ESI) m/z: 430(M+H)⁺.

Example 271

Synthesis of [4-(3,5-dimethylpyridin-2-yl)piperazin-1-yl][4-(1,1-dioxo-1λ⁶-[1,2,6]thiadiazinan-2-yl)phenyl]methanone

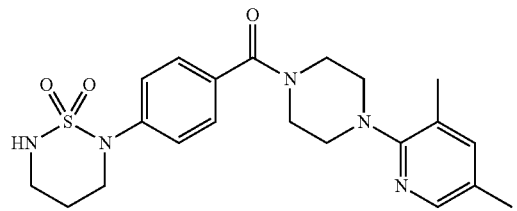 [SMILES: Cc1cnc(N2CCN(C(=O)c3ccc(N4CCCNS4(=O)=O)cc3)CC2)c(C)c1]

Using ethyl 4-(1,1-dioxo-1λ⁶-[1,2,6]thiadiazinan-2-yl)benzoate (300 mg) described in Preparation Example 47 and 1-(3,5-dimethylpyridin-2-yl)piperazine (202 mg) described in Preparation Example 79 and by the reaction and treatment in the same manner as in Example 109, the title compound (200 mg) was obtained.

MS (ESI) m/z: 430(M+H)⁺.

Example 272

Synthesis of [4-(3,5-dimethylpyridin-2-yl)piperazin-1-yl][4-(6-methyl-1,1-dioxo-1λ⁶-[1,2,6]thiadiazinan-2-yl)phenyl]methanone

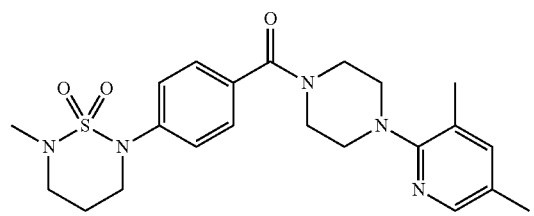

Using [4-(3,5-dimethylpyridin-2-yl)piperazin-1-yl][4-(1,1-dioxo-1λ⁶-[1,2,6]thiadiazinan-2-yl)phenyl]methanone (150 mg) described in Example 271 and methyl iodide (24 μL) and by the reaction and treatment in the same manner as in Example 36, the title compound (103 mg) was obtained.

MS (ESI) m/z: 444(M+H)⁺.

Example 273

Synthesis of [4-(3,5-dimethylpyridin-2-yl)piperazin-1-yl][6-(1,1-dioxo-1λ⁶-[1,2,5]thiadiazolidin-2-yl)pyridin-3-yl]methanone

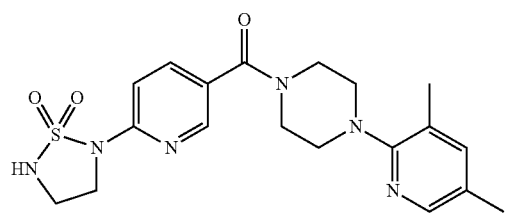 [SMILES: Cc1cnc(N2CCN(C(=O)c3ccc(N4CCNS4(=O)=O)nc3)CC2)c(C)c1]

Acetonitrile (15 mL) and sulfuryl chloride (6.08 mL) were added to 2-chloroethanamine hydrochloride (1.16 g), and the mixture was stirred at 80° C. for 8 hr, and the solvent was evaporated. A solution of the obtained residue in tetrahydrofuran (10 mL) was added dropwise to a solution of a mixture of methyl 6-aminonicotinate (761 mg) and triethylamine (2.8 mL) in tetrahydrofuran (5 mL) under ice-cooling. After stirring at room temperature overnight, water was added to the reaction mixture, and the mixture was extracted with ethyl acetate, and the solvent was evaporated. The obtained residue was dissolved in dimethyl sulfoxide (15 mL), potassium carbonate (1.38 g) was added, and the mixture was stirred at room temperature. Water was added to the reaction mixture, and the mixture was extracted with ethyl acetate, and the solvent was evaporated. The obtained residue was purified by column chromatography (ethyl acetate:hexane) to give crude methyl 6-(1,1-dioxo-1$\lambda^6$-[1,2,5] thiadiazolidin-2-yl)nicotinate (204 mg). Using the obtained crude methyl 6-(1,1-dioxo-1$\lambda^6$-[1,2,5]thiadiazolidin-2-yl)nicotinate (203.9 mg) and 1-(3,5-dimethylpyridin-2-yl)piperazine (152 mg) described in Preparation Example 79 and by the reaction and treatment in the same manner as in Example 109, the title compound (8 mg) was obtained.

MS (ESI) m/z: 417(M+H)$^+$.

Example 274

Synthesis of (S)-1-{4-[4-(3,5-dimethylpyridin-2-yl)piperazine-1-carbonyl]-3-methanesulfonylphenyl}-5-hydroxymethylpyrrolidin-2-one

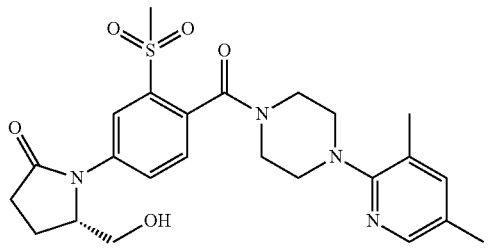 [SMILES: Cc1cnc(N2CCN(C(=O)c3ccc(N4C(=O)CC[C@H]4CO)cc3S(C)(=O)=O)CC2)c(C)c1]

Using (4-bromo-2-methanesulfonylphenyl)[4-(3,5-dimethylpyridin-2-yl)piperazin-1-yl]methanone (1.53 g) described in Preparation Example 112 and (S)-5-hydroxymethylpyrrolidin-2-one (428 mg) and by the reaction and treatment in the same manner as in Example 1, the title compound (1.05 g) was obtained.

MS (ESI) m/z: 487(M+H)$^+$.

Example 275

Synthesis of (S)-1-{4-[4-(3,5-dimethylpyridin-2-yl)piperazine-1-carbonyl]-3-methanesulfonylphenyl}-5-methoxymethylpyrrolidin-2-one

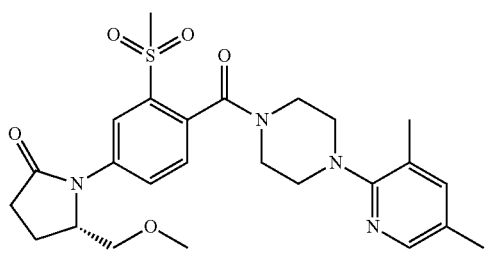 [SMILES: COC[C@@H]1CCC(=O)N1c1ccc(C(=O)N2CCN(c3ncc(C)cc3C)CC2)c(S(C)(=O)=O)c1]

Using (S)-1-{4-[4-(3,5-dimethylpyridin-2-yl)piperazine-1-carbonyl]-3-methanesulfonylphenyl}-5-hydroxymethylpyrrolidin-2-one (530 mg) described in Example 274 and methyl tosylate (203 mg) and by the reaction and treatment in the same manner as in Example 36, the title compound (151 mg) was obtained.

MS (ESI) m/z: 501(M+H)$^+$.

Example 276

Synthesis of 1-{4-[4-(3,5-dimethylpyridin-2-yl)piperazine-1-carbonyl]-3,5-difluorophenyl}pyrrolidin-2-one

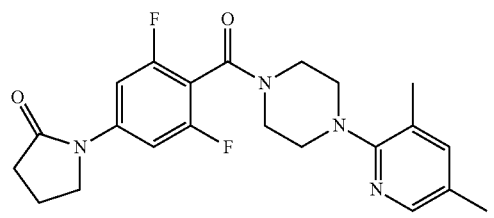

Using (4-bromo-2,6-difluorophenyl)[4-(3,5-dimethylpyridin-2-yl)piperazin-1-yl]methanone (200 mg) described in Preparation Example 111 and pyrrolidin-2-one (44 mg) and by the reaction and treatment in the same manner as in Example 1, the title compound (142 mg) was obtained.

MS (ESI) m/z: 415(M+H)$^+$.

Example 277

Synthesis of 1-{4-[4-(3,5-dimethylpyridin-2-yl)piperazine-1-carbonyl]-3-methanesulfonylphenyl}pyrrolidin-2-one

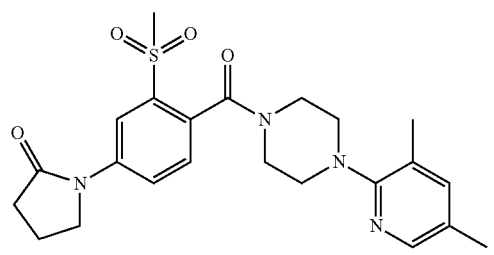 [SMILES: Cc1cnc(N2CCN(C(=O)c3ccc(N4CCCC4=O)cc3S(C)(=O)=O)CC2)c(C)c1]

Using pyrrolidin-2-one (119 mg) and (4-bromo-2-methanesulfonylphenyl)[4-(3,5-dimethylpyridin-2-yl)piperazin-1-yl]methanone (664 mg) described in Preparation Example 112 and by the reaction and treatment in the same manner as in Example 1, the title compound (206 mg) was obtained.

MS (ESI) m/z: 457(M+H)$^+$.

Example 278

Synthesis of 1-{4-[4-(3,5-dimethylpyridin-2-yl)piperazine-1-carbonyl]-3,5-difluorophenyl}-5-methylpyrrolidin-2-one

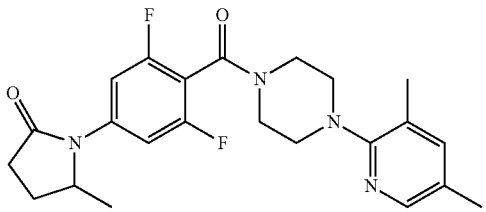 [SMILES: Cc1cnc(N2CCN(C(=O)c3c(F)cc(N4C(=O)CCC4C)cc3F)CC2)c(C)c1]

Using (4-bromo-2,6-difluorophenyl)[4-(3,5-dimethylpyridin-2-yl)piperazin-1-yl]methanone (200 mg) described in Preparation Example 111 and 5-methylpyrrolidin-2-one (48 mg) and by the reaction and treatment in the same manner as in Example 1, the title compound (81 mg) was obtained.
MS (ESI) m/z: 429(M+H)$^+$.

Example 279

Synthesis of 1-{4-[4-(3,5-dimethylpyridin-2-yl)piperazine-1-carbonyl]-3-fluorophenyl}-5-methylpyrrolidin-2-one

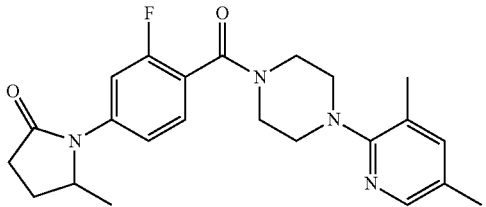 [SMILES: Cc1cnc(N2CCN(C(=O)c3ccc(N4C(=O)CCC4C)cc3F)CC2)c(C)c1]

Using 5-methylpyrrolidin-2-one (54 mg) and (4-bromo-2-fluorophenyl)[4-(3,5-dimethylpyridin-2-yl)piperazin-1-yl]methanone (240 mg) described in Preparation Example 114 and by the reaction and treatment in the same manner as in Example 1, the title compound (94 mg) was obtained.
MS (ESI) m/z: 411(M+H)$^+$.

Example 280

Synthesis of (R)-1-{4-[4-(3,5-dimethylpyridin-2-yl)piperazine-1-carbonyl]-3-fluorophenyl}-5-methoxymethylpyrrolidin-2-one hydrochloride

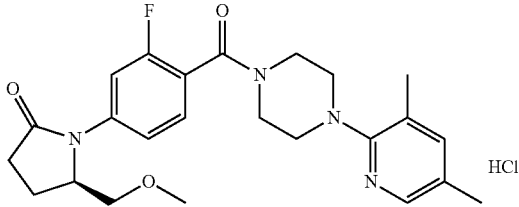 [SMILES: COC[C@H]1CCC(=O)N1c1ccc(C(=O)N2CCN(c3ncc(C)cc3C)CC2)c(F)c1 ; Cl]

Using (R)-5-hydroxymethylpyrrolidin-2-one (138 mg) and (4-bromo-2-fluorophenyl)[4-(3,5-dimethylpyridin-2-yl)piperazin-1-yl]methanone (392 mg) described in Preparation Example 114 and by the reaction and treatment in the same manner as in Example 1, (R)-1-{4-[4-(3,5-dimethylpyridin-2-yl)piperazine-1-carbonyl]-3-fluorophenyl}-5-hydroxymethylpyrrolidin-2-one (330 mg) was obtained. To a mixture of the obtained (R)-1-{4-[4-(3,5-dimethylpyridin-2-yl)piperazine-1-carbonyl]-3-fluorophenyl}-5-hydroxymethylpyrrolidin-2-one (330 mg) and sodium hydride (37 mg) were added tetrahydrofuran and N,N-dimethylformamide, and the mixture was stirred at room temperature for 15 min. To the reaction mixture was added methyl tosylate (117 µL), and the mixture was further stirred at room temperature overnight. Water was added to the reaction mixture, and the mixture was extracted with ethyl acetate. The organic layer was washed with saturated brine, dried over sodium sulfate, and the solvent was evaporated. The obtained residue was purified by column chromatography (hexane:ethyl acetate) to give (R)-1-{4-[4-(3,5-dimethylpyridin-2-yl)piperazine-1-carbonyl]-3-fluorophenyl}-5-methoxymethylpyrrolidin-2-one. The obtained (R)-1-{4-[4-(3,5-dimethylpyridin-2-yl)piperazine-1-carbonyl]-3-fluorophenyl}-5-methoxymethylpyrrolidin-2-one was dissolved in ethyl acetate, 4N hydrogen chloride/ethyl acetate was added and the mixture was stirred. The reaction mixture was concentrated under reduced pressure, diethyl ether was added, and the precipitate was collected by filtration to give the title compound (48 mg).
MS (ESI) m/z: 441(M+H)$^+$.

Example 281

Synthesis of 1-{5-[4-(4-chlorobenzoyl)piperidine-1-carbonyl]pyridin-2-yl}pyrrolidin-2-one

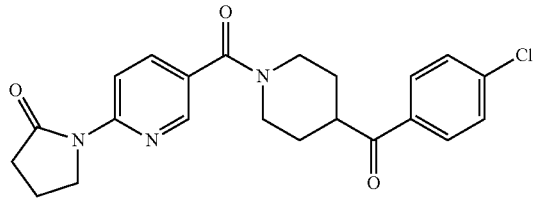 [SMILES: O=C(c1ccc(Cl)cc1)C1CCN(C(=O)c2ccc(N3CCCC3=O)nc2)CC1]

Using pyrrolidin-2-one (102 mg) and (6-bromopyridin-3-yl)[4-(4-chlorobenzoyl)piperidin-1-yl]methanone (408 mg) described in Preparation Example 190 and by the reaction and treatment in the same manner as in Example 1, the title compound (209 mg) was obtained.
MS (ESI) m/z: 412(M+H)$^+$.

Example 282

Synthesis of 1-{4-[4-(3,5-dimethylpyridin-2-yl)piperazine-1-carbonyl]-3-fluorophenyl}pyrrolidin-2-one

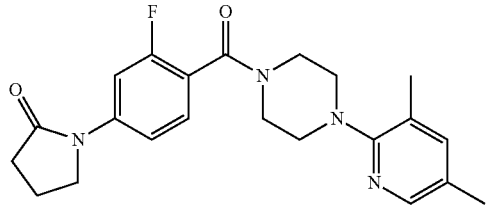

Using pyrrolidin-2-one (51 mg) and (4-bromo-2-fluorophenyl)[4-(3,5-dimethylpyridin-2-yl)piperazin-1-yl]methanone (240 mg) described in Preparation Example 114 and by the reaction and treatment in the same manner as in Example 1, the title compound (154 mg) was obtained.

MS (ESI) m/z: 397(M+H)⁺.

Example 283

Synthesis of 1-{5-[4-(2,4-dimethylphenyl)piperazine-1-carbonyl]pyridin-2-yl}pyrrolidin-2-one

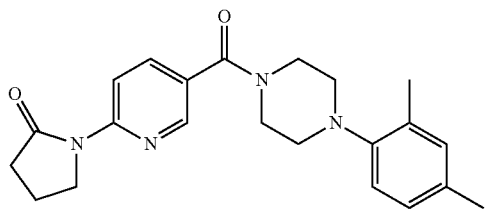

Using pyrrolidin-2-one (89 mg) and (6-bromopyridin-3-yl)[4-(2,4-dimethylphenyl)piperazin-1-yl]methanone (374 mg) described in Preparation Example 115 and by the reaction and treatment in the same manner as in Example 1, the title compound (214 mg) was obtained.

MS (ESI) m/z: 379(M+H)⁺.

Example 284

Synthesis of (R)-1-{4-[4-(3,5-dimethylpyridin-2-yl)piperazine-1-carbonyl]phenyl}-5-hydroxymethylpyrrolidin-2-one

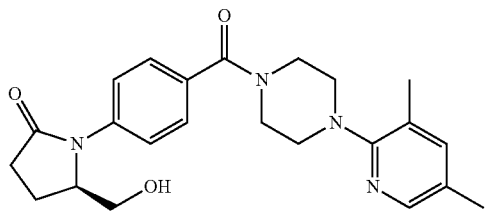 [SMILES: Cc1cnc(N2CCN(C(=O)c3ccc(N4C(=O)CC[C@@H]4CO)cc3)CC2)c(C)c1]

Using (R)-5-hydroxymethylpyrrolidin-2-one (137 mg) and [4-(3,5-dimethylpyridin-2-yl)piperazin-1-yl](4-iodophenyl)methanone (500 mg) described in Preparation Example 113 and by the reaction and treatment in the same manner as in Example 1, the title compound (231 mg) was obtained.

MS (ESI) m/z: 409(M+H)⁺.

Example 285

Synthesis of (R)-1-{4-[4-(3,5-dimethylpyridin-2-yl)piperazine-1-carbonyl]phenyl}-5-methoxymethylpyrrolidin-2-one hydrochloride

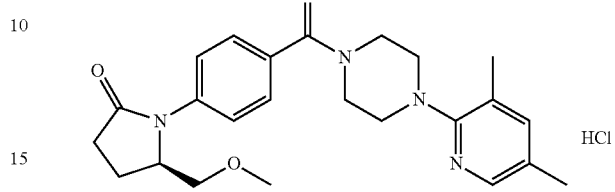

To a mixture of (R)-1-{4-[4-(3,5-dimethylpyridin-2-yl)piperazine-1-carbonyl]phenyl}-5-hydroxymethylpyrrolidin-2-one (200 mg) described in Example 284 and sodium hydride (22 mg) was added tetrahydrofuran, and the mixture was stirred at room temperature for 15 min. To the reaction mixture was added methyl tosylate (74 μL), and the mixture was further stirred at room temperature for 2 days. Water was added to the reaction mixture, and the mixture was extracted with ethyl acetate. The organic layer was washed with saturated brine, dried over sodium sulfate, and the solvent was evaporated. The obtained residue was purified by column chromatography (hexane:ethyl acetate) to give (R)-1-{4-[4-(3,5-dimethylpyridin-2-yl)piperazine-1-carbonyl]phenyl}-5-methoxymethylpyrrolidin-2-one. The obtained (R)-1-{4-[4-(3,5-dimethylpyridin-2-yl)piperazine-1-carbonyl]phenyl}-5-methoxymethylpyrrolidin-2-one was dissolved in ethyl acetate, 4N hydrogen chloride/ethyl acetate was added, and the precipitate was collected by filtration to give the title compound (113 mg).

MS (ESI) m/z: 423(M+H)⁺.

Example 286

Synthesis of (R)-1-{4-[4-(3,5-dimethylpyridin-2-yl)piperazine-1-carbonyl]-3,5-difluorophenyl}-5-hydroxymethylpyrrolidin-2-one

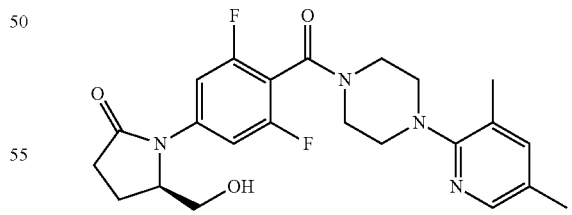

Using (R)-5-hydroxymethylpyrrolidin-2-one (116 mg) and (4-bromo-2,6-difluorophenyl)[4-(3,5-dimethylpyridin-2-yl)piperazin-1-yl]methanone (410 mg) described in Preparation Example 111 and by the reaction and treatment in the same manner as in Example 1, the title compound (210 mg) was obtained.

MS (ESI) m/z: 445(M+H)⁺.

Example 287

Synthesis of (R)-1-{4-[4-(3,5-dimethylpyridin-2-yl)piperazine-1-carbonyl]-3-methanesulfonylphenyl}-5-methoxymethylpyrrolidin-2-one

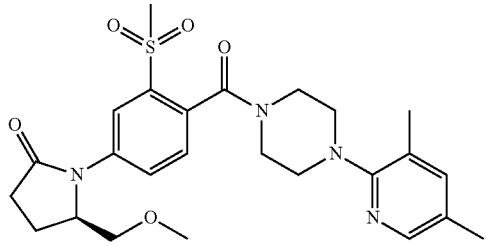 [SMILES: COC[C@H]1CCC(=O)N1c1ccc(C(=O)N2CCN(c3ncc(C)cc3C)CC2)c(S(C)(=O)=O)c1]

Using (R)-5-hydroxymethylpyrrolidin-2-one (409 mg) and (4-bromo-2-methanesulfonylphenyl)[4-(3,5-dimethylpyridin-2-yl)piperazin-1-yl]methanone (1.53 g) described in Preparation Example 112 and by the reaction and treatment in the same manner as in Example 1, (R)-1-{4-[4-(3,5-dimethylpyridin-2-yl)piperazine-1-carbonyl]-3-methanesulfonylphenyl}-5-hydroxymethylpyrrolidin-2-one (700 mg) was obtained. Using the obtained (R)-1-{4-[4-(3,5-dimethylpyridin-2-yl)piperazine-1-carbonyl]-3-methanesulfonylphenyl}-5-hydroxymethylpyrrolidin-2-one (700 mg) and methyl tosylate (0.21 mL) and by the reaction and treatment in the same manner as in Example 36, the title compound (319 mg) was obtained.

MS (ESI) m/z: 501(M+H)$^+$.

Example 288

Synthesis of (S)-1-{4-[4-(3,5-dimethylpyridin-2-yl)piperazine-1-carbonyl]-3-fluorophenyl}-5-hydroxymethylpyrrolidin-2-one

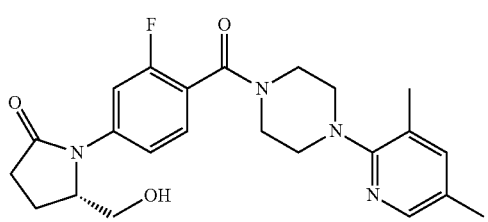 [SMILES: Cc1cnc(N2CCN(C(=O)c3ccc(N4C(=O)CC[C@H]4CO)cc3F)CC2)c(C)c1]

Using (S)-5-hydroxymethylpyrrolidin-2-one (127 mg) and (4-bromo-2-fluorophenyl)[4-(3,5-dimethylpyridin-2-yl)piperazin-1-yl]methanone (392 mg) described in Preparation Example 114 and by the reaction and treatment in the same manner as in Example 1, the title compound (317 mg) was obtained.

MS (ESI) m/z: 427(M+H)$^+$.

Example 289

Synthesis of (R)-1-{4-[4-(3,5-dimethylpyridin-2-yl)piperazine-1-carbonyl]-3,5-difluorophenyl}-5-methoxymethylpyrrolidin-2-one hydrochloride

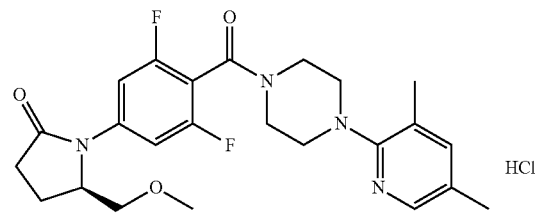 [SMILES: COC[C@H]1CCC(=O)N1c1cc(F)c(C(=O)N2CCN(c3ncc(C)cc3C)CC2)c(F)c1 ; Cl]

Using (R)-1-{4-[4-(3,5-dimethylpyridin-2-yl)piperazine-1-carbonyl]-3,5-difluorophenyl}-5-hydroxymethylpyrrolidin-2-one (180 mg) described in Example 286 and methyl tosylate (61 μL) and by the reaction and treatment in the same manner as in Example 285, the title compound (17 mg) was obtained.

MS (ESI) m/z: 459(M+H)$^+$.

Example 290

Synthesis of (S)-1-{4-[4-(3,5-dimethylpyridin-2-yl)piperazine-1-carbonyl]phenyl}-5-hydroxymethylpyrrolidin-2-one

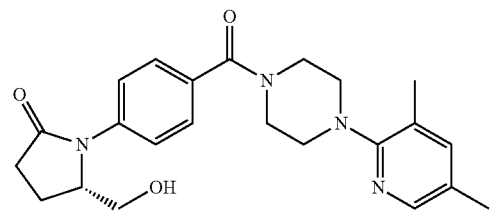 [SMILES: Cc1cnc(N2CCN(C(=O)c3ccc(N4C(=O)CC[C@H]4CO)cc3)CC2)c(C)c1]

Using (S)-5-hydroxymethylpyrrolidin-2-one (127 mg) and [4-(3,5-dimethylpyridin-2-yl)piperazin-1-yl](4-iodophenyl)methanone (421 mg) described in Preparation Example 113 and by the reaction and treatment in the same manner as in Example 1, the title compound (276 mg) was obtained.

MS (ESI) m/z: 409(M+H)$^+$.

Example 291

Synthesis of (S)-1-{4-[4-(3,5-dimethylpyridin-2-yl)piperazine-1-carbonyl]-3-fluorophenyl}-5-methoxymethylpyrrolidin-2-one hydrochloride

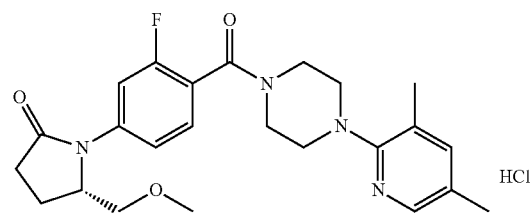 [SMILES: COC[C@@H]1CCC(=O)N1c1ccc(C(=O)N2CCN(c3ncc(C)cc3C)CC2)c(F)c1 ; Cl]

Using (S)-1-{4-[4-(3,5-dimethylpyridin-2-yl)piperazine-1-carbonyl]-3-fluorophenyl}-5-hydroxymethylpyrrolidin-2- one (250 mg) described in Example 288 and methyl tosylate (88 μL) and by the reaction and treatment in the same manner as in Example 285, the title compound (77 mg) was obtained.

MS (ESI) m/z: 441(M+H)⁺.

Example 292

Synthesis of (S)-1-{4-[4-(3,5-dimethylpyridin-2-yl)piperazine-1-carbonyl]phenyl}-5-methoxymethylpyrrolidin-2-one hydrochloride

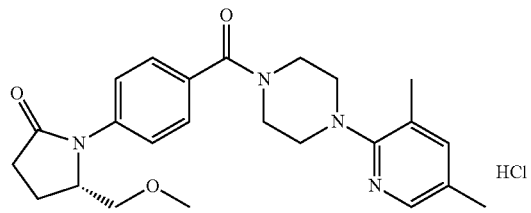 [SMILES: COC[C@@H]1CCC(=O)N1c1ccc(C(=O)N2CCN(c3ncc(C)cc3C)CC2)cc1 ; Cl]

Using (S)-1-{4-[4-(3,5-dimethylpyridin-2-yl)piperazine-1-carbonyl]phenyl}-5-hydroxymethylpyrrolidin-2-one (237 mg) described in Example 290 and methyl tosylate (88 μL) and by the reaction and treatment in the same manner as in Example 285, the title compound (68 mg) was obtained.

MS (ESI) m/z: 423(M+H)⁺.

Example 293

Synthesis of 1-{4-[4-(3,5-dicyclopropylpyridin-2-yl)piperazine-1-carbonyl]-3-fluorophenyl}pyrrolidin-2-one

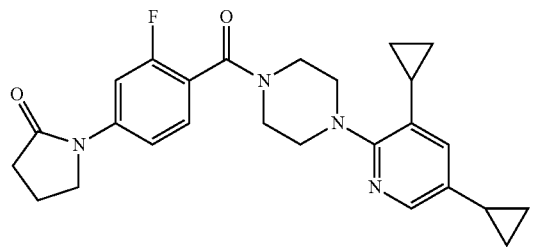 [SMILES: O=C(c1ccc(N2CCCC2=O)cc1F)N1CCN(c2ncc(C3CC3)cc2C2CC2)CC1]

Using pyrrolidin-2-one (35 mg) and [4-(3,5-dicyclopropylpyridin-2-yl)piperazin-1-yl](2-fluoro-4-iodophenyl)methanone (200 mg) described in Preparation Example 164 and by the reaction and treatment in the same manner as in Example 1, the title compound (115 mg) was obtained.

MS (ESI) m/z: 449(M+H)⁺.

Example 294

Synthesis of (S)-1-{4-[4-(3,5-dicyclopropylpyridin-2-yl)piperazine-1-carbonyl]-3-fluorophenyl}-5-hydroxymethylpyrrolidin-2-one

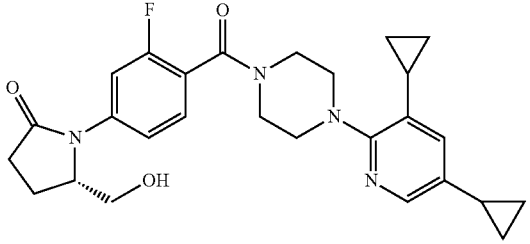 [SMILES: O=C(c1ccc(N2C(=O)CC[C@H]2CO)cc1F)N1CCN(c2ncc(C3CC3)cc2C2CC2)CC1]

Using (S)-5-hydroxymethylpyrrolidin-2-one (94 mg) and [4-(3,5-dicyclopropylpyridin-2-yl)piperazin-1-yl](2-fluoro-4-iodophenyl)methanone (400 mg) described in Preparation Example 164 and by the reaction and treatment in the same manner as in Example 1, the title compound (158 mg) was obtained.

MS (ESI) m/z: 479(M+H)⁺.

Example 295

Synthesis of (S)-1-{4-[4-(3,5-dicyclopropylpyridin-2-yl)piperazine-1-carbonyl]-3-fluorophenyl}-5-methoxymethylpyrrolidin-2-one

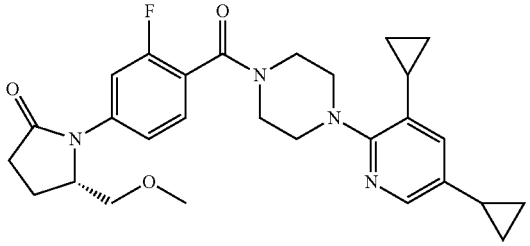 [SMILES: COC[C@@H]1CCC(=O)N1c1ccc(C(=O)N2CCN(c3ncc(C4CC4)cc3C3CC3)CC2)c(F)c1]

Using (S)-1-{4-[4-(3,5-dicyclopropylpyridin-2-yl)piperazine-1-carbonyl]-3-fluorophenyl}-5-hydroxymethylpyrrolidin-2-one (130 mg) described in Example 294 and methyl tosylate (41 μL) and by the reaction and treatment in the same manner as in Example 36, the title compound (8 mg) was obtained.

MS (ESI) m/z: 493(M+H)⁺.

Example 296

Synthesis of 1-{4-[4-(5-cyclopropyl-3-methylpyridin-2-yl)piperazine-1-carbonyl]-3-fluorophenyl}pyrrolidin-2-one

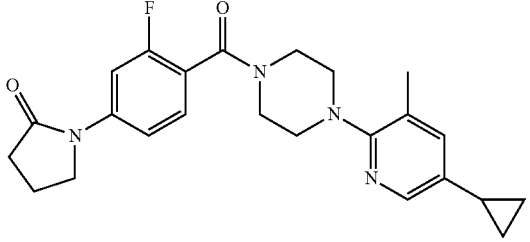 [SMILES: Cc1cc(C2CC2)cnc1N1CCN(C(=O)c2ccc(N3CCCC3=O)cc2F)CC1]

Using pyrrolidin-2-one (94 mg) and (4-bromo-2-fluorophenyl)[4-(5-cyclopropyl-3-methylpyridin-2-yl)piperazin-1-yl]methanone (418 mg) described in Preparation Example 121 and by the reaction and treatment in the same manner as in Example 1, the title compound (308 mg) was obtained.

MS (ESI) m/z: 423(M+H)$^+$.

Example 297

Synthesis of 1-{4-[4-(3,5-dimethylpyridin-2-yl)piperazine-1-carbonyl]-3-methylphenyl}pyrrolidin-2-one

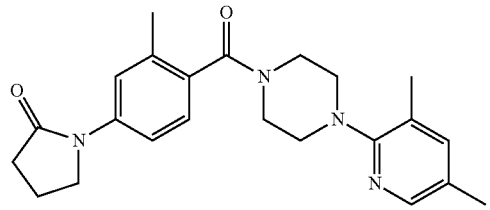 [SMILES: Cc1cnc(N2CCN(C(=O)c3ccc(N4CCCC4=O)cc3C)CC2)c(C)c1]

Using pyrrolidin-2-one (47 mg) and (4-bromo-2-methylphenyl)[4-(3,5-dimethylpyridin-2-yl)piperazin-1-yl]methanone (194 mg) described in Preparation Example 118 and by the reaction and treatment in the same manner as in Example 1, the title compound (88 mg) was obtained.

MS (ESI) m/z: 393(M+H)$^+$.

Example 298

Synthesis of (S)-1-{4-[4-(5-cyclopropyl-3-methylpyridin-2-yl)piperazine-1-carbonyl]-3-methanesulfonylphenyl}-5-hydroxymethylpyrrolidin-2-one

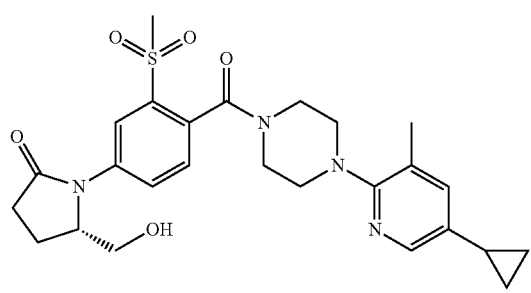 [SMILES: Cc1cc(C2CC2)cnc1N1CCN(C(=O)c2ccc(N3C(=O)CC[C@H]3CO)cc2S(C)(=O)=O)CC1]

Using (S)-5-hydroxymethylpyrrolidin-2-one (127 mg) and (4-bromo-2-methanesulfonylphenyl)[4-(5-cyclopropyl-3-methylpyridin-2-yl)piperazin-1-yl]methanone (478 mg) described in Preparation Example 126 and by the reaction and treatment in the same manner as in Example 1, the title compound (291 mg) was obtained.

MS (ESI) m/z: 513(M+H)$^+$.

Example 299

Synthesis of (S)-1-{4-[4-(5-cyclopropyl-3-methylpyridin-2-yl)piperazine-1-carbonyl]-3-methanesulfonylphenyl}-5-methoxymethylpyrrolidin-2-one

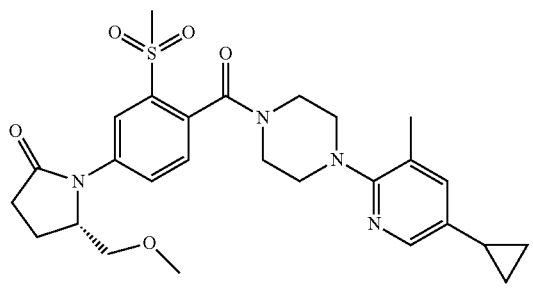 [SMILES: COC[C@@H]1CCC(=O)N1c1ccc(C(=O)N2CCN(c3ncc(C4CC4)cc3C)CC2)c(S(C)(=O)=O)c1]

Using (S)-1-{4-[4-(5-cyclopropyl-3-methylpyridin-2-yl)piperazine-1-carbonyl]-3-methanesulfonylphenyl}-5-hydroxymethylpyrrolidin-2-one (240 mg) described in Example 298 and methyl tosylate (71 μL) and by the reaction and treatment in the same manner as in Example 36, the title compound (28 mg) was obtained.

MS (ESI) m/z: 527(M+H)$^+$.

Example 300

Synthesis of (S)-1-{4-[4-(3,5-dimethylpyridin-2-yl)piperazine-1-carbonyl]-2-fluorophenyl}-5-hydroxymethylpyrrolidin-2-one

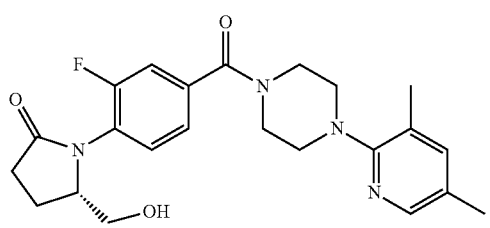 [SMILES: Cc1cnc(N2CCN(C(=O)c3ccc(N4C(=O)CC[C@H]4CO)c(F)c3)CC2)c(C)c1]

Using (S)-5-hydroxymethylpyrrolidin-2-one (127 mg) and (4-bromo-3-fluorophenyl)[4-(3,5-dimethylpyridin-2-yl)piperazin-1-yl]methanone (392 mg) described in Preparation Example 125 and by the reaction and treatment in the same manner as in Example 1, the title compound (155 mg) was obtained.

MS (ESI) m/z: 427(M+H)$^+$.

Example 301

Synthesis of 1-{4-[4-(3,5-dicyclopropylpyridin-2-yl)piperazine-1-carbonyl]-3-fluorophenyl}pyrrolidin-2-one hydrochloride

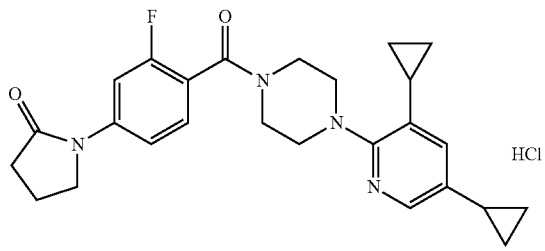 [SMILES: O=C(c1ccc(N2CCCC2=O)cc1F)N1CCN(c2ncc(C3CC3)cc2C2CC2)CC1 ; Cl]

Using [4-(3,5-dicyclopropylpyridin-2-yl)piperazin-1-yl](2-fluoro-4-iodophenyl)methanone (380 mg) described in Preparation Example 164 and pyrrolidin-2-one (80 mg) and by the reaction and treatment in the same manner as in Example 141, the title compound (84 mg) was obtained.
MS (ESI) m/z: 449(M+H)+.

Example 302

Synthesis of (S)-1-{4-[4-(3,5-dimethylpyridin-2-yl)piperazine-1-carbonyl]-3-methylphenyl}-5-hydroxymethylpyrrolidin-2-one

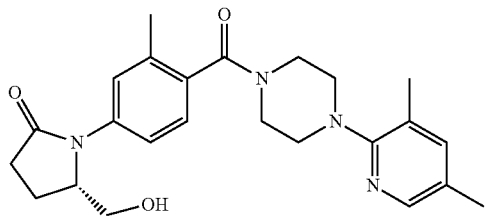 [SMILES: Cc1cnc(N2CCN(C(=O)c3ccc(N4C(=O)CC[C@H]4CO)cc3C)CC2)c(C)c1]

Using (S)-5-hydroxymethylpyrrolidin-2-one (168 mg) and (4-bromo-2-methylphenyl)[4-(3,5-dimethylpyridin-2-yl)piperazin-1-yl]methanone (516 mg) described in Preparation Example 118 and by the reaction and treatment in the same manner as in Example 1, the title compound (99 mg) was obtained.
MS (ESI) m/z: 423(M+H)+.

Example 303

Synthesis of (S)-1-{4-[4-(5-cyclopropyl-3-methylpyridin-2-yl)piperazine-1-carbonyl]-3-fluorophenyl}-5-hydroxymethylpyrrolidin-2-one

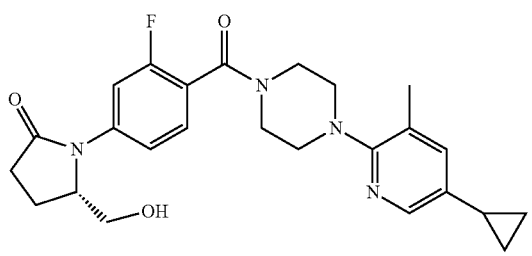

Using (S)-5-hydroxymethylpyrrolidin-2-one (127 mg) and (4-bromo-2-fluorophenyl)[4-(5-cyclopropyl-3-methylpyridin-2-yl)piperazin-1-yl]methanone (418 mg) described in Preparation Example 121 and by the reaction and treatment in the same manner as in Example 1, the title compound (36 mg) was obtained.
MS (ESI) m/z: 453(M+H)+.

Example 304

Synthesis of 1-{4-[4-(5-cyclopropyl-3-methylpyridin-2-yl)piperazine-1-carbonyl]-3-methanesulfonylphenyl}pyrrolidin-2-one

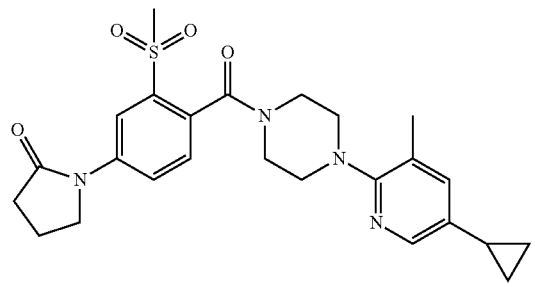 [SMILES: Cc1cc(C2CC2)cnc1N1CCN(C(=O)c2ccc(N3CCCC3=O)cc2S(C)(=O)=O)CC1]

Using pyrrolidin-2-one (47 mg) and (4-bromo-2-methanesulfonylphenyl)[4-(5-cyclopropyl-3-methylpyridin-2-yl)piperazin-1-yl]methanone (239 mg) described in Preparation Example 126 and by the reaction and treatment in the same manner as in Example 1, the title compound (204 mg) was obtained.
MS (ESI) m/z: 483(M+H)+.

Example 305

Synthesis of (S)-1-{4-[4-(5-cyclopropyl-3-methylpyridin-2-yl)piperazine-1-carbonyl]-3-methylphenyl}-5-hydroxymethylpyrrolidin-2-one

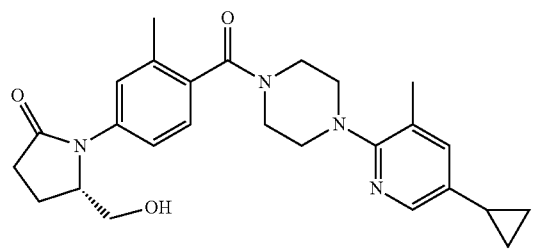 [SMILES: Cc1cc(N2C(=O)CC[C@H]2CO)ccc1C(=O)N1CCN(c2ncc(C3CC3)cc2C)CC1]

Using (S)-5-hydroxymethylpyrrolidin-2-one (153 mg) and (4-bromo-2-methylphenyl)[4-(5-cyclopropyl-3-methylpyridin-2-yl)piperazin-1-yl]methanone (500 mg) described in Preparation Example 124 and by the reaction and treatment in the same manner as in Example 1, the title compound (183 mg) was obtained.
MS (ESI) m/z: 449(M+H)+.

Example 306

Synthesis of 1-{3-fluoro-4-[4-(3,5,6-trimethylpyridin-2-yl)piperazine-1-carbonyl]phenyl}pyrrolidin-2-one

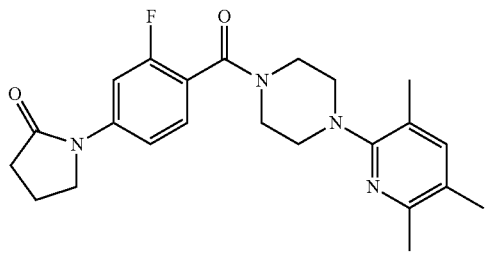 [SMILES: Cc1cc(C)c(N2CCN(C(=O)c3ccc(N4CCCC4=O)cc3F)CC2)nc1C]

Using pyrrolidin-2-one (94 mg) and (4-bromo-2-fluorophenyl) [4-(3,5,6-trimethylpyridin-2-yl)piperazin-1-yl]methanone (406 mg) described in Preparation Example 128 and by the reaction and treatment in the same manner as in Example 1, the title compound (368 mg) was obtained.
MS (ESI) m/z: 411(M+H)$^+$.

Example 307

Synthesis of (S)-1-{3-fluoro-4-[4-(3,5,6-trimethylpyridin-2-yl)piperazine-1-carbonyl]phenyl}-5-hydroxymethylpyrrolidin-2-one

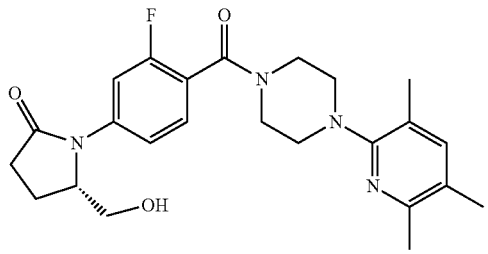 [SMILES: Cc1cc(C)c(N2CCN(C(=O)c3ccc(N4C(=O)CC[C@H]4CO)cc3F)CC2)nc1C]

Using (S)-5-hydroxymethylpyrrolidin-2-one and (4-bromo-2-fluorophenyl)[4-(3,5,6-trimethylpyridin-2-yl)piperazin-1-yl]methanone (406 mg) described in Preparation Example 128 and by the reaction and treatment in the same manner as in Example 1, the title compound (171 mg) was obtained.
MS (ESI) m/z: 441(M+H)$^+$.

Example 308

Synthesis of (S)-1-{4-[4-(3-cyclopropyl-5-trifluoromethylpyridin-2-yl)piperazine-1-carbonyl]-3-fluorophenyl}-5-hydroxymethylpyrrolidin-2-one

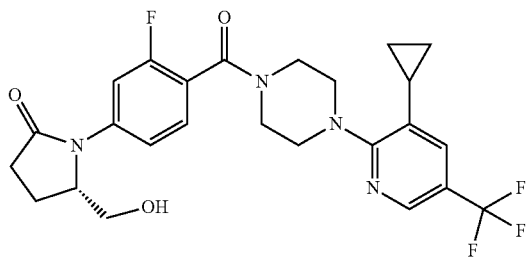 [SMILES: O=C(c1ccc(N2C(=O)CC[C@H]2CO)cc1F)N1CCN(c2ncc(C(F)(F)F)cc2C2CC2)CC1]

Using (S)-5-hydroxymethylpyrrolidin-2-one and (4-bromo-2-fluorophenyl)[4-(3-cyclopropyl-5-trifluoromethylpyridin-2-yl)piperazin-1-yl]methanone (945 mg) described in Preparation Example 123 and by the reaction and treatment in the same manner as in Example 1, the title compound (371 mg) was obtained.
MS (ESI) m/z: 507(M+H)$^+$.

Example 309

Synthesis of 1-{4-[4-(3,5,6-trimethylpyridin-2-yl)piperazine-1-carbonyl]phenyl}pyrrolidin-2-one

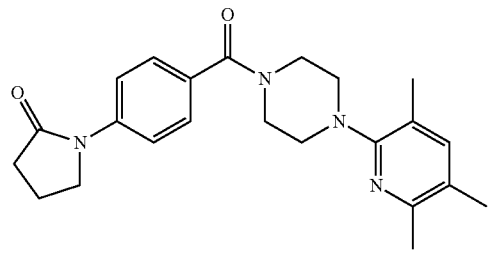 [SMILES: Cc1cc(C)c(N2CCN(C(=O)c3ccc(N4CCCC4=O)cc3)CC2)nc1C]

Using pyrrolidin-2-one (94 mg) and (4-iodophenyl)[4-(3,5,6-trimethylpyridin-2-yl)piperazin-1-yl]methanone (435 mg) described in Preparation Example 120 and by the reaction and treatment in the same manner as in Example 1, the title compound (234 mg) was obtained.
MS (ESI) m/z: 393(M+H)$^+$.

Example 310

Synthesis of (S)-5-hydroxymethyl-1-{4-[4-(3,5,6-trimethylpyridin-2-yl)piperazine-1-carbonyl]phenyl}pyrrolidin-2-one

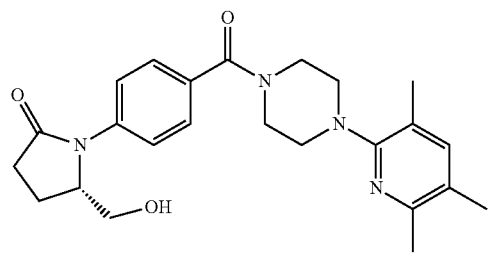 [SMILES: Cc1cc(C)c(N2CCN(C(=O)c3ccc(N4C(=O)CC[C@H]4CO)cc3)CC2)nc1C]

Using (S)-5-hydroxymethylpyrrolidin-2-one and (4-iodophenyl)[4-(3,5,6-trimethylpyridin-2-yl)piperazin-1-yl]methanone (871 mg) described in Preparation Example 120 and by the reaction and treatment in the same manner as in Example 1, the title compound (348 mg) was obtained.
MS (ESI) m/z: 423(M+H)$^+$.

Example 311

Synthesis of 1-{3-chloro-4-[4-(3,5-dimethylpyridin-2-yl)piperazine-1-carbonyl]phenyl}pyrrolidin-2-one

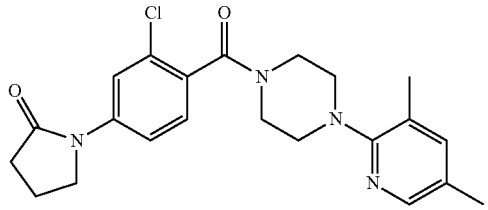

Using pyrrolidin-2-one (23 mg) and (4-bromo-2-chlorophenyl)[4-(3,5-dimethylpyridin-2-yl)piperazin-1-yl]methanone (100 mg) described in Preparation Example 119 and by the reaction and treatment in the same manner as in Example 1, the title compound (67 mg) was obtained.
MS (ESI) m/z: 413(M+H)$^+$.

Example 312

Synthesis of (S)-5-hydroxymethyl-1-{3-methanesulfonyl-4-[4-(3,5,6-trimethylpyridin-2-yl)piperazine-1-carbonyl]phenyl}pyrrolidin-2-one hydrochloride

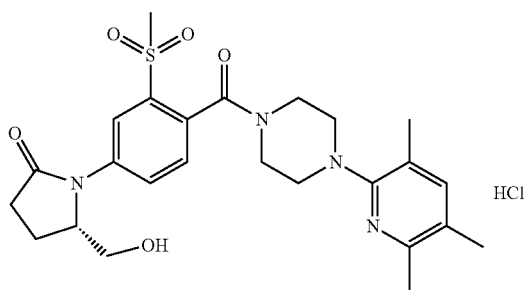 [SMILES: Cc1cc(C)c(N2CCN(C(=O)c3ccc(N4C(=O)CC[C@H]4CO)cc3S(C)(=O)=O)CC2)nc1C ; Cl]

Using (S)-5-hydroxymethylpyrrolidin-2-one and (4-bromo-2-methanesulfonylphenyl)[4-(3,5,6-trimethylpyridin-2-yl)piperazin-1-yl]methanone (233 mg) described in Preparation Example 122 and by the reaction and treatment in the same manner as in Example 141, the title compound was obtained.
MS (ESI) m/z: 501(M+H)$^+$.

Example 313

Synthesis of 1-{5-[4-(3,5-dimethylpyridin-2-yl)piperazine-1-carbonyl]pyridin-2-yl}pyrrolidin-2-one dihydrochloride

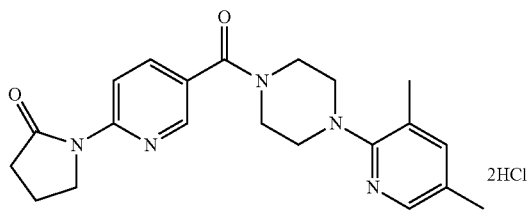 [SMILES: Cc1cnc(N2CCN(C(=O)c3ccc(N4CCCC4=O)nc3)CC2)c(C)c1 ; "2HCl"]

Using pyrrolidin-2-one (94 mg) and (6-bromopyridin-3-yl)[4-(3,5-dimethylpyridin-2-yl)piperazin-1-yl]methanone (375 mg) described in Preparation Example 127 and by the reaction and treatment in the same manner as in Example 141, the title compound (211 mg) was obtained.
MS (ESI) m/z: 380(M+H)$^+$.

Example 314

Synthesis of 1-{4-[4-(5-cyclopropyl-3-methylpyridin-2-yl)piperazine-1-carbonyl]phenyl}pyrrolidin-2-one

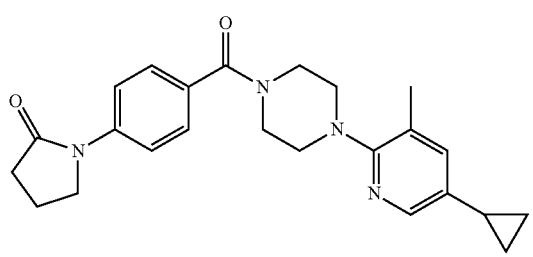 [SMILES: Cc1cc(C2CC2)cnc1N1CCN(C(=O)c2ccc(N3CCCC3=O)cc2)CC1]

Using pyrrolidin-2-one (94 mg) and [4-(5-cyclopropyl-3-methylpyridin-2-yl)piperazin-1-yl](4-iodophenyl)methanone (447 mg) described in Preparation Example 117 and by the reaction and treatment in the same manner as in Example 1, the title compound (246 mg) was obtained.
MS (ESI) m/z: 405(M+H)$^+$.

Example 315

Synthesis of 1-{6-[4-(3,5-dimethylpyridin-2-yl)piperazine-1-carbonyl]pyridin-3-yl}pyrrolidin-2-one

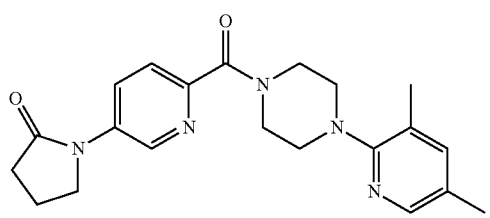 [SMILES: Cc1cnc(N2CCN(C(=O)c3ccc(N4CCCC4=O)cn3)CC2)c(C)c1]

Using pyrrolidin-2-one (94 mg) and (5-bromopyridin-2-yl)[4-(3,5-dimethylpyridin-2-yl)piperazin-1-yl]methanone (375 mg) described in Preparation Example 134 and by the reaction and treatment in the same manner as in Example 1, the title compound (272 mg) was obtained.
MS (ESI) m/z: 380(M+H)$^+$.

Example 316

Synthesis of 1-{6-[4-(5-cyclopropyl-3-methylpyridin-2-yl)piperazine-1-carbonyl]pyridin-3-yl}pyrrolidin-2-one

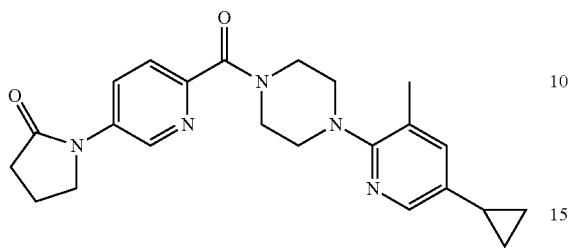

Using pyrrolidin-2-one (72 mg) and (5-bromopyridin-2-yl)[4-(5-cyclopropyl-3-methylpyridin-2-yl)piperazin-1-yl]methanone (310 mg) described in Preparation Example 135 and by the reaction and treatment in the same manner as in Example 1, the title compound (186 mg) was obtained.
MS (ESI) m/z: 406(M+H)$^+$.

Example 317

Synthesis of 1-{5-[4-(4-cyclopropylphenoxy)piperidine-1-carbonyl]pyridin-2-yl}pyrrolidin-2-one

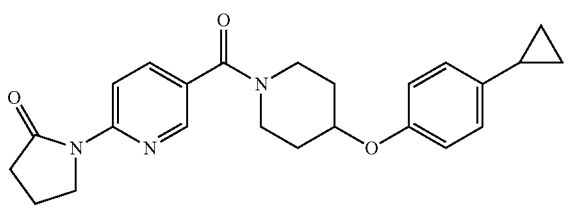 [SMILES: O=C(c1ccc(N2CCCC2=O)nc1)N1CCC(Oc2ccc(C3CC3)cc2)CC1]

Using pyrrolidin-2-one (94 mg) and (6-bromopyridin-3-yl)[4-(4-cyclopropylphenoxy)piperidin-1-yl]methanone (401 mg) described in Preparation Example 192 and by the reaction and treatment in the same manner as in Example 1, the title compound (238 mg) was obtained.
MS (ESI) m/z: 406(M+H)$^+$.

Example 318

Synthesis of 1-{5-[4-(3,5-dicyclopropylpyridin-2-yl)piperazine-1-carbonyl]pyridin-2-yl}pyrrolidin-2-one

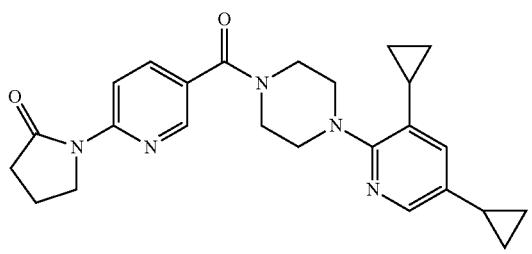 [SMILES: O=C(c1ccc(N2CCCC2=O)nc1)N1CCN(c2ncc(C3CC3)cc2C2CC2)CC1]

Using pyrrolidin-2-one (94 mg) and (6-bromopyridin-3-yl)[4-(3,5-dicyclopropylpyridin-2-yl)piperazin-1-yl]methanone (427 mg) described in Preparation Example 143 and by the reaction and treatment in the same manner as in Example 1, the title compound (210 mg) was obtained.
MS (ESI) m/z: 432(M+H)$^+$.

Example 319

Synthesis of 1-{5-[4-(5-cyclopropyl-3-methylpyridin-2-yl)piperazine-1-carbonyl]pyridin-2-yl}pyrrolidin-2-one

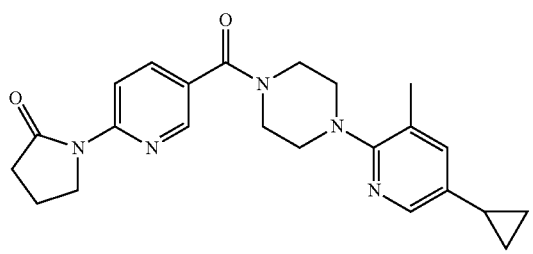 [SMILES: Cc1cc(C2CC2)cnc1N1CCN(C(=O)c2ccc(N3CCCC3=O)nc2)CC1]

Using pyrrolidin-2-one (130 mg) and (6-bromopyridin-3-yl)[4-(5-cyclopropyl-3-methylpyridin-2-yl)piperazin-1-yl]methanone (554 mg) described in Preparation Example 144 and by the reaction and treatment in the same manner as in Example 1, the title compound (25 mg) was obtained.
MS (ESI) m/z: 406(M+H)$^+$.

Example 320

Synthesis of 1-{5-[4-(5-ethyl-3-methylpyridin-2-yl)piperazine-1-carbonyl]pyridin-2-yl}pyrrolidin-2-one

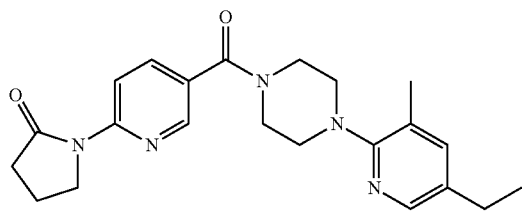 [SMILES: CCc1cnc(N2CCN(C(=O)c3ccc(N4CCCC4=O)nc3)CC2)c(C)c1]

Using pyrrolidin-2-one (49 mg) and (6-bromopyridin-3-yl)[4-(5-ethyl-3-methylpyridin-2-yl)piperazin-1-yl]methanone (200 mg) described in Preparation Example 145 and by the reaction and treatment in the same manner as in Example 1, the title compound (113 mg) was obtained.
MS (ESI) m/z: 394(M+H)$^+$.

Example 321

Synthesis of 1-{5-[4-(3,5-dimethylpyridin-2-yl)piperazine-1-carbonyl]pyridin-2-yl}-5-methylpyrrolidin-2-one

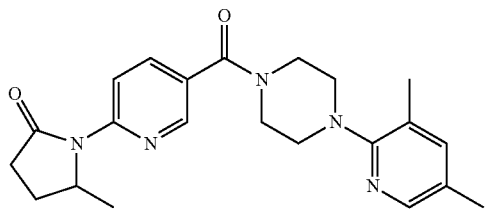 [SMILES: Cc1cnc(N2CCN(C(=O)c3ccc(N4C(=O)CCC4C)nc3)CC2)c(C)c1]

Using 5-methylpyrrolidin-2-one (99 mg) and (6-bromopyridin-3-yl) [4-(3,5-dimethylpyridin-2-yl)piperazin-1-yl]methanone (375 mg) described in Preparation Example 127 and by the reaction and treatment in the same manner as in Example 1, the title compound (171 mg) was obtained.
MS (ESI) m/z: 394(M+H)+.

Example 322

Synthesis of 1-{5-[4-(2,4-dimethylphenyl)piperazine-1-carbonyl]pyridin-2-yl}-5-methylpyrrolidin-2-one

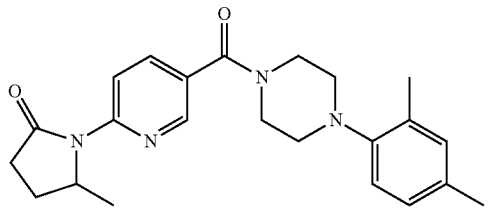 [SMILES: Cc1ccc(N2CCN(C(=O)c3ccc(N4C(=O)CCC4C)nc3)CC2)c(C)c1]

Using 5-methylpyrrolidin-2-one (99 mg) and (6-bromopyridin-3-yl)[4-(2,4-dimethylphenyl)piperazin-1-yl]methanone (374 mg) described in Preparation Example 115 and by the reaction and treatment in the same manner as in Example 1, the title compound (176 mg) was obtained.
MS (ESI) m/z: 393(M+H)+.

Example 323

Synthesis of 1-{5-[4-(3,5-dimethylpyridin-2-yl)piperazine-1-carbonyl]-4-methylpyridin-2-yl}pyrrolidin-2-one

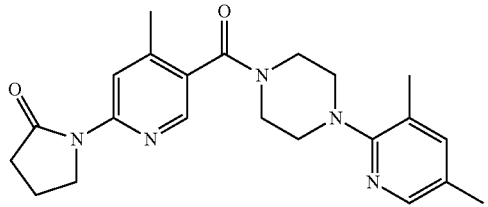 [SMILES: Cc1cnc(N2CCN(C(=O)c3cnc(N4CCCC4=O)cc3C)CC2)c(C)c1]

Pyrrolidin-2-one (322 mg) was dissolved in N,N-dimethylformamide (4 mL), sodium hydride (159 mg) was added, and the mixture was stirred for 30 min. To the reaction mixture was further added [4-(3,5-dimethylpyridin-2-yl)piperazin-1-yl](6-fluoro-4-methylpyridin-3-yl)methanone (620 mg) described in Preparation Example 146, and the mixture was stirred at 100° C. for 5 hr. The reaction mixture was cooled, water was added, and the mixture was extracted with ethyl acetate. The organic layer was washed with saturated brine, and the solvent was evaporated. The obtained residue was purified by column chromatography (hexane:ethyl acetate) to give the title compound (125 mg).
MS (ESI) m/z: 394(M+H)+.

Example 324

Synthesis of 1-{4-[4-(2,4-dimethylphenyl)piperazine-1-carbonyl]-3-(1,1-dioxo-1λ6-isoxazolidin-2-yl)phenyl}pyrrolidin-2-one

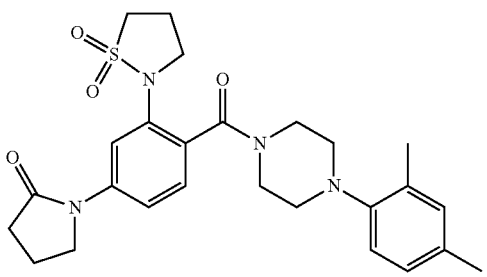 [SMILES: Cc1ccc(N2CCN(C(=O)c3ccc(N4CCCC4=O)cc3N3CCCS3(=O)=O)CC2)c(C)c1]

Using pyrrolidin-2-one (432 mg) and methyl 4-bromo-2-(1,1-dioxo-1λ6-isothiazolidin-2-yl)benzoate (1.54 g) described in Preparation Example 13 and by the reaction and treatment in the same manner as in Example 1, methyl 2-(1,1-dioxo-1λ6-isothiazolidin-2-yl)-4-(2-oxopyrrolidin-1-yl)benzoate (1.12 g) was obtained. The obtained methyl 2-(1,1-dioxo-1λ6-isothiazolidin-2-yl)-4-(2-oxopyrrolidin-1-yl)benzoate (1.12 g) was dissolved in a solution of methanol (5 mL) and tetrahydrofuran (5 mL), 1N aqueous sodium hydroxide solution (5 mL) was added, and the mixture was stirred at room temperature for 4 hr. The solvent was evaporated from the reaction mixture, and the mixture was neutralized with 1N hydrochloric acid, and extracted with chloroform. The organic layer was washed with saturated brine, dried over sodium sulfate, and the solvent was evaporated to give 2-(1,1-dioxo-1λ6-isothiazolidin-2-yl)-4-(2-oxopyrrolidin-1-yl)benzoic acid (720 mg). A mixture of the obtained 2-(1,1-dioxo-1λ6-isothiazolidin-2-yl)-4-(2-oxopyrrolidin-1-yl)benzoic acid (250 mg), 1-(2,4-dimethylphenyl)piperazine (154 mg) and 4-(4,6-dimethoxy[1.3.5]triazin-2-yl)-4-methylmorpholinium chloride hydrate (DMT-MM) (242 mg) was dissolved in ethanol (3 mL), and the mixture was stirred at room temperature overnight. The solvent was evaporated from the reaction mixture, water was added, and the mixture was extracted with ethyl acetate. The organic layer was washed with saturated brine, dried over sodium sulfate, and the solvent was evaporated. The obtained residue was purified by column chromatography (chloroform:methanol) to give the title compound (330 mg).
MS (ESI) m/z: 497(M+H)+.

Example 325

Synthesis of 1-{4-[4-(3,5-dicyclopropylpyridin-2-yl)piperazine-1-carbonyl]-3-(1,1-dioxo-1λ$^6$-isoxazolidin-2-yl)phenyl}pyrrolidin-2-one

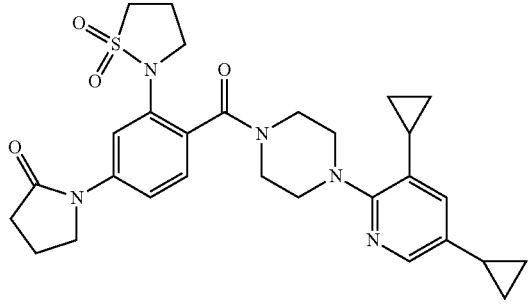 [SMILES: O=C(c1ccc(N2CCCC2=O)cc1N1CCCS1(=O)=O)N1CCN(c2ncc(C3CC3)cc2C2CC2)CC1]

Using 2-(1,1-dioxo-1λ$^6$-isothiazolidin-2-yl)-4-(2-oxopyrrolidin-1-yl)benzoic acid (243 mg), which is an intermediate described in Example 324, and 1-(3,5-dicyclopropylpyridin-2-yl)piperazine (200 mg) described in Preparation Example 88 and by the reaction and treatment in the same manner as in Example 93, the title compound (227 mg) was obtained.

MS (ESI) m/z: 550(M+H)$^+$.

Example 326

Synthesis of 1-{4-[4-(5-cyclopropyl-3-methylpyridin-2-yl)piperazine-1-carbonyl]-3-(1,1-dioxo-1λ$^6$-isoxazolidin-2-yl)phenyl}pyrrolidin-2-one

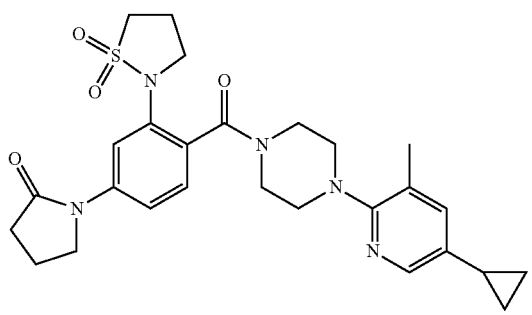 [SMILES: Cc1cc(C2CC2)cnc1N1CCN(C(=O)c2ccc(N3CCCC3=O)cc2N2CCCS2(=O)=O)CC1]

Using 2-(1,1-dioxo-1λ$^6$-isothiazolidin-2-yl)-4-(2-oxopyrrolidin-1-yl)benzoic acid (220 mg), which is an intermediate described in Example 324, and 1-(5-cyclopropyl-3-methylpyridin-2-yl)piperazine (162 mg) described in Preparation Example 83 and by the reaction and treatment in the same manner as in Example 93, the title compound (144 mg) was obtained.

MS (ESI) m/z: 524(M+H)$^+$.

Example 327

Synthesis of 1-{5-[4-(5-cyclopropyl-3-methylpyridin-2-yl)piperazine-1-carbonyl]pyridin-2-yl}-5-methylpyrrolidin-2-one

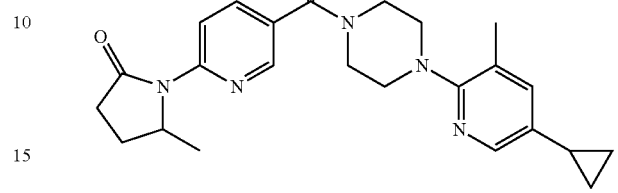

Using 5-methylpyrrolidin-2-one (64 mg) and (6-bromopyridin-3-yl) [4-(5-cyclopropyl-3-methylpyridin-2-yl)piperazin-1-yl]methanone (260 mg) described in Preparation Example 144 and by the reaction and treatment in the same manner as in Example 1, the title compound (66 mg) was obtained.

MS (ESI) m/z: 420(M+H)$^+$.

Example 328

Synthesis of 1-{5-[4-(3,5-dicyclopropylpyridin-2-yl)piperazine-1-carbonyl]pyridin-2-yl}-5-methylpyrrolidin-2-one

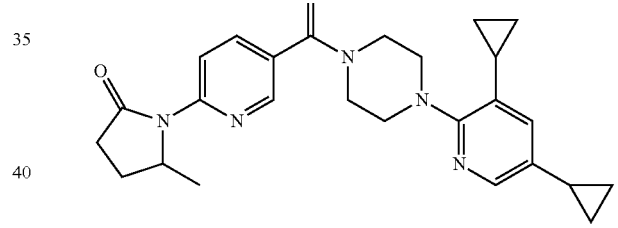

Using 5-methylpyrrolidin-2-one (99 mg) and (6-bromopyridin-3-yl) [4-(3,5-dicyclopropylpyridin-2-yl)piperazin-1-yl]methanone (4.27 mg) described in Preparation Example 143 and by the reaction and treatment in the same manner as in Example 1, the title compound (133 mg) was obtained.

MS (ESI) m/z: 446(M+H)$^+$.

Example 329

Synthesis of 1-{4-[4-(3,5-dimethylpyridin-2-yl)piperazine-1-carbonyl]-3,5-difluorophenyl}piperidin-2-one

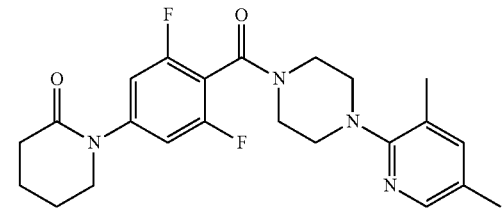 [SMILES: Cc1cnc(N2CCN(C(=O)c3c(F)cc(N4CCCCC4=O)cc3F)CC2)c(C)c1]

Using piperidin-2-one (51 mg) and (4-bromo-2,6-difluorophenyl)[4-(3,5-dimethylpyridin-2-yl)piperazin-1-yl]methanone (200 mg) described in Preparation Example 111 and by the reaction and treatment in the same manner as in Example 1, the title compound (101 mg) was obtained.

MS (ESI) m/z: 429(M+H)⁺.

Example 330

Synthesis of 1-{4-[4-(2,4-dimethylphenyl)piperazine-1-carbonyl]-3-methanesulfonylphenyl}piperidin-2-one

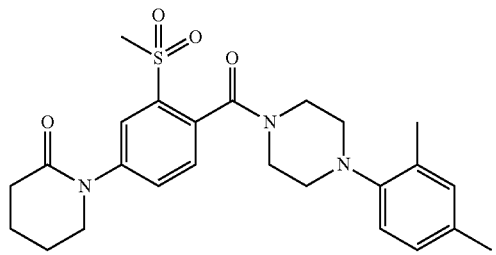 [SMILES: Cc1ccc(N2CCN(C(=O)c3ccc(N4CCCCC4=O)cc3S(C)(=O)=O)CC2)c(C)c1]

Using piperidin-2-one (104 mg) and (4-bromo-2-methanesulfonylphenyl)[4-(2,4-dimethylphenyl)piperazin-1-yl]methanone (451 mg) described in Preparation Example 110 and by the reaction and treatment in the same manner as in Example 1, the title compound (293 mg) was obtained.

MS (ESI) m/z: 470(M+H)⁺.

Example 331

Synthesis of 1-{5-[4-(3,5-dimethylpyridin-2-yl)piperazine-1-carbonyl]pyridin-2-yl}piperidin-2-one

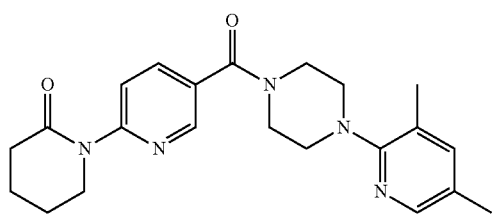

Using piperidin-2-one (58 mg) and (6-bromopyridin-3-yl)[4-(3,5-dimethylpyridin-2-yl)piperazin-1-yl]methanone (200 mg) described in Preparation Example 127 and by the reaction and treatment in the same manner as in Example 1, the title compound (42 mg) was obtained.

MS (ESI) m/z: 394(M+H)⁺.

Example 332

Synthesis of 1-{5-[4-(5-cyclopropyl-3-methylpyridin-2-yl)piperazine-1-carbonyl]pyridin-2-yl}piperidin-2-one

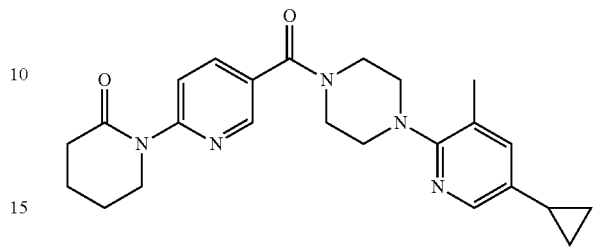

Using piperidin-2-one (14 mg) and (6-bromopyridin-3-yl)[4-(5-cyclopropyl-3-methylpyridin-2-yl)piperazin-1-yl]methanone (50 mg) described in Preparation Example 144 and by the reaction and treatment in the same manner as in Example 1, the title compound (20 mg) was obtained.

MS (ESI) m/z: 420(M+H)⁺.

Example 333

Synthesis of 1-{4-[4-(2,4-dimethylphenyl)piperazine-1-carbonyl]phenyl}-5-oxopyrrolidine-3-carboxylic acid

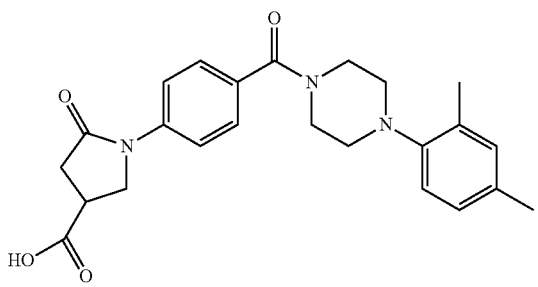 [SMILES: Cc1ccc(N2CCN(C(=O)c3ccc(N4CC(C(=O)O)CC4=O)cc3)CC2)c(C)c1]

4-Nitrobenzoic acid (2 g), 1-(2,4-dimethylphenyl)piperazine (2.28 g), and 1-hydroxybenzotriazole 1 hydrate (1.62 g) were dissolved in N,N-dimethylformamide (30 mL), 1-ethyl-3-(3'-dimethylaminopropyl)carbodiimide hydrochloride (2.31 g) was added, and the mixture was stirred at room temperature. Water was added to the reaction mixture, and the mixture was extracted with ethyl acetate. The organic layer was washed with saturated brine, and the solvent was evaporated. To the obtained residue was added ethyl acetate/diisopropyl ether and the insoluble material was collected by filtration to give [4-(2,4-dimethylphenyl)piperazin-1-yl](4-nitrophenyl)methanone (4.17 g). Then, ammonium chloride (3.71 g) and iron (2.68 g) were added to a solution of ethanol (61 mL) and water (17 mL), and the obtained [4-(2,4-dimethylphenyl)piperazin-1-yl](4-nitrophenyl)methanone (4.17 g) was added with stirring at 60° C.-70° C. After completion of the reaction, the insoluble material was filtered off, and the filtrate was concentrated. To the residue was added aqueous sodium hydrogen carbonate solution, and the mixture was extracted with ethyl acetate, and the solvent was evaporated to give crude (4-aminophenyl) [4-(2,4-dimethylphenyl)piperazin-1-yl]methanone (4.17 g). To the obtained crude (4-aminophenyl) [4-(2,4-dimethylphenyl)piperazin-1-yl]methanone (1 g) were added itaconic acid (0.42 g), water (5 mL), 1,2-dimethoxyethane (2 mL) and acetic acid (5 mL), and the mixture was stirred with heating under reflux for 13 hr. Water was added to the reaction mixture, and the mixture was extracted with ethyl acetate. The organic layer was washed with saturated brine, and the solvent was evaporated. To the obtained residue was added ethyl acetate, and the precipitate was collected by filtration to give the title compound (508 mg).

MS (ESI) m/z: 422(M+H)$^+$.

Example 334

Synthesis of 1-{4-[4-(2,4-dimethylphenyl)piperazine-1-carbonyl]phenyl}-4-(pyrrolidine-1-carbonyl)pyrrolidin-2-one

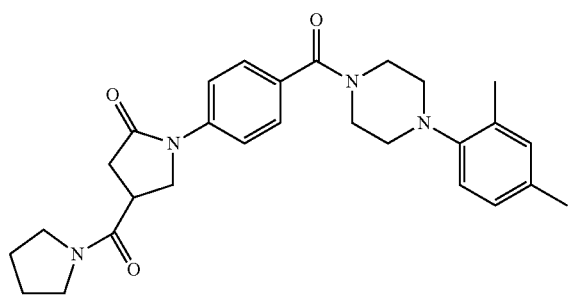 [SMILES: Cc1ccc(N2CCN(C(=O)c3ccc(N4CC(C(=O)N5CCCC5)CC4=O)cc3)CC2)c(C)c1]

Using 1-{4-[4-(2,4-dimethylphenyl)piperazine-1-carbonyl]phenyl}-5-oxopyrrolidine-3-carboxylic acid (100 mg) described in Example 333 and pyrrolidine (17 mg) and by the reaction and treatment in the same manner as in Example 87, the title compound (49 mg) was obtained.

MS (ESI) m/z: 475(M+H)$^+$.

Example 335

Synthesis of 1-{4-[4-(2,4-dimethylphenyl)piperazine-1-carbonyl]phenyl}-4-(4-morpholin-4-ylpiperidine-1-carbonyl)pyrrolidin-2-one

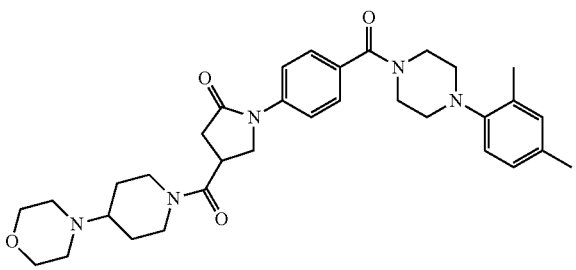 [SMILES: Cc1ccc(N2CCN(C(=O)c3ccc(N4CC(C(=O)N5CCC(N6CCOCC6)CC5)CC4=O)cc3)CC2)c(C)c1]

Using 1-{4-[4-(2,4-dimethylphenyl)piperazine-1-carbonyl]phenyl}-5-oxopyrrolidine-3-carboxylic acid (100 mg) described in Example 333 and 4-morpholinopiperidine (44 mg) and by the reaction and treatment in the same manner as in Example 87, the title compound (85 mg) was obtained.

MS (ESI) m/z: 574(M+H)$^+$.

Example 336

Synthesis of 4-[(S)-3-dimethylaminopyrrolidine-1-carbonyl]-1-{4-[4-(2,4-dimethylphenyl)piperazine-1-carbonyl]phenyl}pyrrolidin-2-one

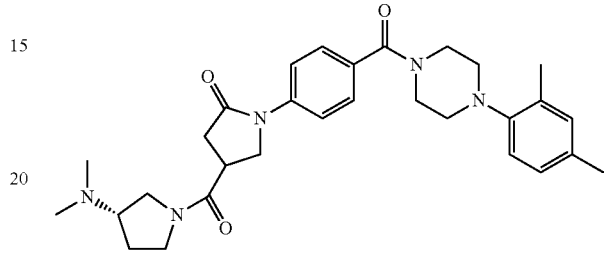

Using 1-{4-[4-(2,4-dimethylphenyl)piperazine-1-carbonyl]phenyl}-5-oxopyrrolidine-3-carboxylic acid (100 mg) described in Example 333 and (S)-3-(dimethylamino)pyrrolidine (27 mg) and by the reaction and treatment in the same manner as in Example 87, the title compound (48 mg) was obtained.

MS (ESI) m/z: 518(M+H)$^+$.

Example 337

Synthesis of 1-{4-[4-(2,4-dimethylphenyl)piperazine-1-carbonyl]phenyl}-5-oxopyrrolidine-3-carboxylic acid methyl ester

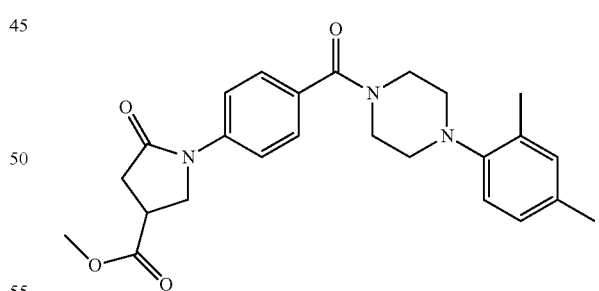

1-{4-[4-(2,4-Dimethylphenyl)piperazine-1-carbonyl]phenyl}-5-oxopyrrolidine-3-carboxylic acid (1.54 g) described in Example 333 was dissolved in methanol (10 mL), thionyl chloride (0.29 mL) was added under ice-cooling, and the mixture was stirred at room temperature for 3 hr. The solvent was evaporated from the reaction mixture, and the residue was purified by column chromatography (chloroform:methanol) to give the title compound (1.39 g).

MS (ESI) m/z: 436(M+H)$^+$.

Example 338

Synthesis of 1-{4-[4-(2,4-dimethylphenyl)piperazine-1-carbonyl]phenyl}-4-hydroxymethylpyrrolidin-2-one

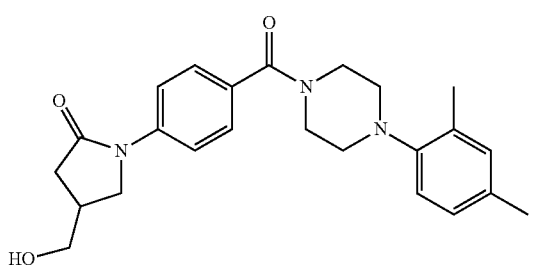 [SMILES: Cc1ccc(N2CCN(C(=O)c3ccc(N4CC(CO)CC4=O)cc3)CC2)c(C)c1]

To 1-{4-[4-(2,4-dimethylphenyl)piperazine-carbonyl]phenyl}-5-oxopyrrolidine-3-carboxylic acid methyl ester (1.3 g) described in Example 337 were added tetrahydrofuran (5 mL) and sodium borohydride (124 mg), methanol (0.9 mL) was added with heating under reflux, and the mixture was stirred for 1 hr. The reaction mixture was cooled, water was added, and the mixture was extracted with ethyl acetate. The organic layer was washed with saturated brine, and the solvent was evaporated. The obtained residue was purified by column chromatography (chloroform:methanol) to give the title compound (1.06 g).

MS (ESI) m/z: 408(M+H)$^+$.

Example 339

Synthesis of 1-{4-[4-(2,4-dimethylphenyl)piperazine-1-carbonyl]phenyl}-4-(3,3,4,4-tetrafluoropyrrolidine-1-carbonyl)pyrrolidin-2-one

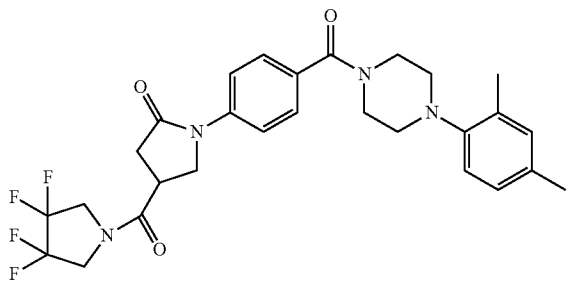 [SMILES: Cc1ccc(N2CCN(C(=O)c3ccc(N4CC(C(=O)N5CC(F)(F)C(F)(F)C5)CC4=O)cc3)CC2)c(C)c1]

Using 1-{4-[4-(2,4-dimethylphenyl)piperazine-1-carbonyl]phenyl}-5-oxopyrrolidine-3-carboxylic acid (100 mg) described in Example 333 and 3,3,4,4-tetrafluoropyrrolidine hydrochloride (43 mg) and by the reaction and treatment in the same manner as in Example 86, the title compound (40 mg) was obtained.

MS (ESI) m/z: 547(M+H)$^+$.

Example 340

Synthesis of 1-{4-[4-(2,4-dimethylphenyl)piperazine-1-carbonyl]phenyl}-4-[(S)-3-fluoropyrrolidine-1-carbonyl]pyrrolidin-2-one

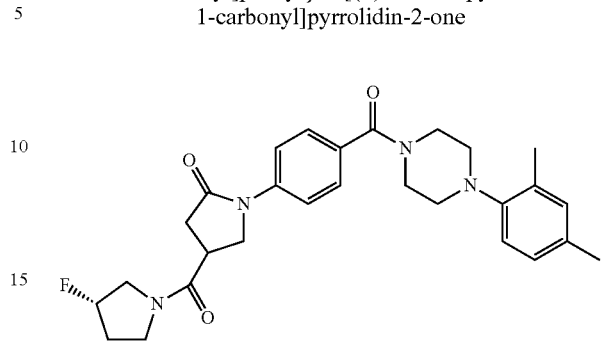

Using 1-{4-[4-(2,4-dimethylphenyl)piperazine-1-carbonyl]phenyl}-5-oxopyrrolidine-3-carboxylic acid (62 mg) described in Example 333 and (S)-3-fluoropyrrolidine hydrochloride (19 mg) and by the reaction and treatment in the same manner as in Example 86, the title compound (13 mg) was obtained.

MS (ESI) m/z: 493(M+H)$^+$.

Example 341

Synthesis of 1-{4-[4-(2,4-dimethylphenyl)piperazine-1-carbonyl]phenyl}-4-(pyrrolidin-1-ylmethyl)pyrrolidin-2-one hydrochloride

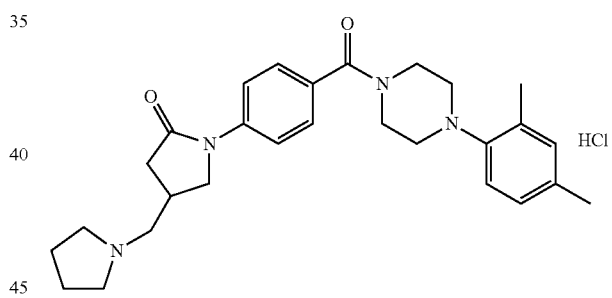

1-{4-[4-(2,4-Dimethylphenyl)piperazine-1-carbonyl]phenyl}-4-hydroxymethylpyrrolidin-2-one (150 mg) described in Example 338 was dissolved in dichloromethane (2 mL), triethylamine (0.16 mL) and mesyl chloride (0.06 mL) were added, and the mixture was stirred at room temperature. Water was added to the reaction mixture, and the mixture was extracted with chloroform. The organic layer was washed with saturated brine, and the solvent was evaporated. The obtained residue was dissolved in N,N-dimethylformamide (3 mL), pyrrolidine (0.15 mL) and potassium carbonate (51 mg) were added, and the mixture was stirred at 60° C.-70° C. for 9 hr. Water was added to the reaction mixture, and the mixture was extracted with ethyl acetate. The organic layer was washed with saturated brine, and the solvent was evaporated. The obtained residue was purified by column chromatography (chloroform:methanol) to give 1-{4-[4-(2,4-dimethylphenyl)piperazine-1-carbonyl]phenyl}-4-(pyrrolidin-1-ylmethyl)pyrrolidin-2-one. The obtained 1-{4-[4-(2,4-dimethylphenyl)piperazine-1-carbonyl]phenyl}-4-(pyrrolidin-1-ylmethyl)pyrrolidin-2-one was dissolved in

Example 342

Synthesis of (S)-1-{4-[4-(2,4-dimethylphenyl)piperazine-1-carbonyl]phenyl}-5-hydroxymethylpyrrolidin-2-one

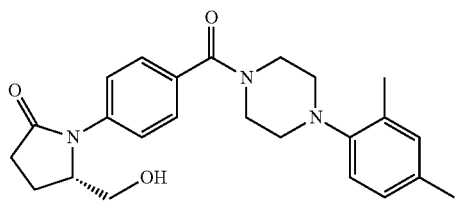 [SMILES: Cc1ccc(N2CCN(C(=O)c3ccc(N4C(=O)CC[C@H]4CO)cc3)CC2)c(C)c1]

Using (4-bromophenyl)[4-(2,4-dimethylphenyl)piperazin-1-yl]methanone (1.87 g) described in Preparation Example 170 and (S)-5-hydroxymethylpyrrolidin-2-one (556 mg) and by the reaction and treatment in the same manner as in Example 1, the title compound (1.00 g) was obtained.

MS (ESI) m/z: 408(M+H)⁺.

Example 343

Synthesis of (S)-1-{4-[4-(2,4-dimethylphenyl)piperazine-1-carbonyl]phenyl}-5-(pyrrolidin-1-ylmethyl)pyrrolidin-2-one hydrochloride

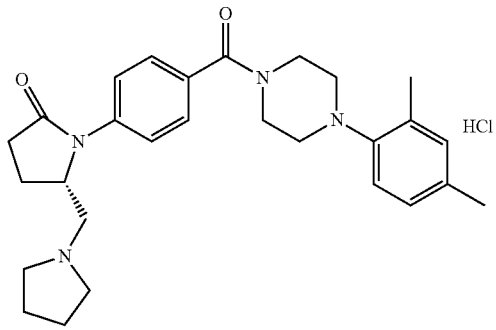 [SMILES: Cc1ccc(N2CCN(C(=O)c3ccc(N4C(=O)CC[C@H]4CN4CCCC4)cc3)CC2)c(C)c1 ; Cl]

Using (S)-1-{4-[4-(2,4-dimethylphenyl)piperazine-1-carbonyl]phenyl}-5-(hydroxymethyl)pyrrolidin-2-one (150 mg) described in Example 342 and pyrrolidine (0.15 mL) and by the reaction and treatment in the same manner as in Example 341, the title compound (88 mg) was obtained via (S)-1-{4-[4-(2,4-dimethylphenyl)piperazine-1-carbonyl]phenyl}-5-(pyrrolidin-1-ylmethyl)pyrrolidin-2-one.

MS (ESI) m/z: 461(M+H)⁺.

ethyl acetate, 4N hydrogen chloride/ethyl acetate (0.1 mL) was added, and the precipitate was collected by filtration to give the title compound (112 mg).

MS (ESI) m/z: 461(M+H)⁺.

Example 344

Synthesis of 1-{4-[4-(2,4-dimethylphenyl)piperazine-1-carbonyl]phenyl}-4-[(S)-2-(pyrrolidin-1-ylmethyl)pyrrolidin-1-ylmethyl]pyrrolidin-2-one dihydrochloride

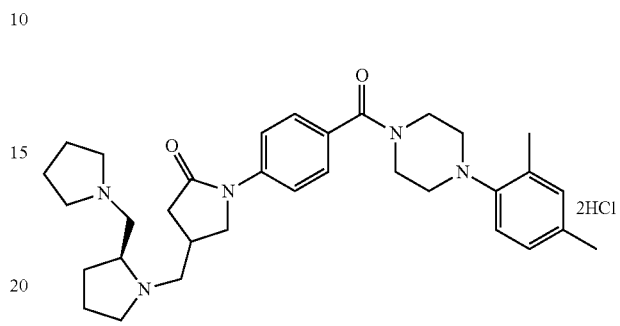

Using 1-{4-[4-(2,4-dimethylphenyl)piperazine-1-carbonyl]phenyl}-4-hydroxymethylpyrrolidin-2-one (300 mg) described in Example 338 and (S)-2-(1-pyrrolidinylmethyl)pyrrolidine (568 mg) and by the reaction and treatment in the same manner as in Example 341, the title compound (85 mg) was obtained.

MS (ESI) m/z: 544(M+H)⁺.

Example 345

Synthesis of (S)-1-{4-[4-(2,4-dimethylphenyl)piperazine-1-carbonyl]phenyl}-5-[(S)-2-(pyrrolidin-1-ylmethyl)pyrrolidin-1-ylmethyl]pyrrolidin-2-one dihydrochloride

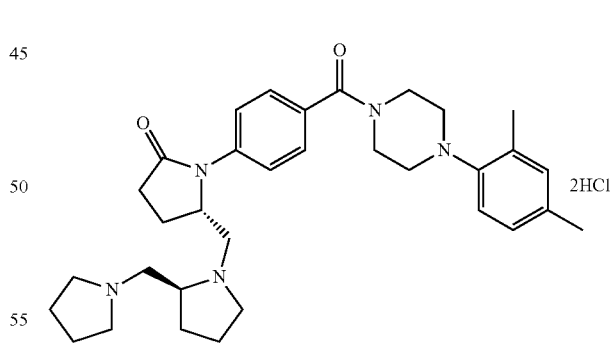

Using (S)-1-{4-[4-(2,4-dimethylphenyl)piperazine-1-carbonyl]phenyl}-5-(hydroxymethyl)pyrrolidin-2-one (300 mg) described in Example 342 and (S)-2-(1-pyrrolidinylmethyl)pyrrolidine (568 mg) and by the reaction and treatment in the same manner as in Example 341, the title compound (135 mg) was obtained.

MS (ESI) m/z: 544(M+H)⁺.

Example 346

Synthesis of 1-{4-[4-(3,5-dimethylpyridin-2-yl)piperazine-1-carbonyl]-3-(1,1-dioxo-1λ⁶-isothiazolidin-2-yl)phenyl}pyrrolidin-2-one

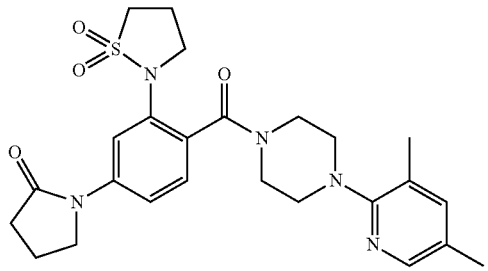 [SMILES: Cc1cnc(N2CCN(C(=O)c3ccc(N4CCCC4=O)cc3N3CCCS3(=O)=O)CC2)c(C)c1]

Using [4-bromo-2-(1,1-dioxo-1λ⁶-isothiazolidin-2-yl)phenyl][4-(3,5-dimethylpyridin-2-yl)piperazin-1-yl]methanone (247 mg) described in Preparation Example 166 and pyrrolidin-2-one (43 mg) and by the reaction and treatment in the same manner as in Example 1, the title compound (180 mg) was obtained.

MS (ESI) m/z: 498(M+H)⁺.

Example 347

Synthesis of 1-{4-[4-(3,5-dimethylpyridin-2-yl)piperazine-1-carbonyl]-3-(1,1-dioxo-1λ⁶-isothiazolidin-2-yl)phenyl}-5-methylpyrrolidin-2-one

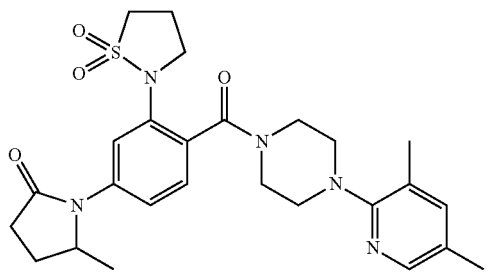 [SMILES: Cc1cnc(N2CCN(C(=O)c3ccc(N4C(=O)CCC4C)cc3N3CCCS3(=O)=O)CC2)c(C)c1]

Using [4-bromo-2-(1,1-dioxo-1λ⁶-isothiazolidin-2-yl)phenyl][4-(3,5-dimethylpyridin-2-yl)piperazin-1-yl]methanone (247 mg) described in Preparation Example 166 and 5-methylpyrrolidin-2-one (50 mg) and by the reaction and treatment in the same manner as in Example 1, the title compound (190 mg) was obtained.

MS (ESI) m/z: 512(M+H)⁺.

Example 348

Synthesis of 1-{4-[4-(3,5-dimethylpyridin-2-yl)piperazine-1-carbonyl]phenyl}-4-methylpyrrolidin-2-one hydrochloride

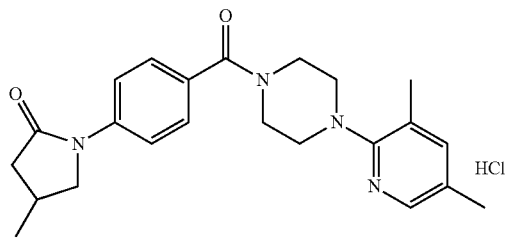 [SMILES: Cc1cnc(N2CCN(C(=O)c3ccc(N4CC(C)CC4=O)cc3)CC2)c(C)c1 ; Cl]

Using ethyl 4-(4-methyl-2-oxopyrrolidin-1-yl)benzoate (124 mg) described in Preparation Example 48 and 1-(3,5-dimethylpyridin-2-yl)piperazine (96 mg) described in Preparation Example 79 and by the reaction and treatment in the same manner as in Example 206, the title compound (163 mg) was obtained.

MS (ESI) m/z: 393(M+H)⁺.

Example 349

Synthesis of 1-{4-[4-(5-cyclopropyl-3-methylpyridin-2-yl)piperazine-1-carbonyl]phenyl}-4-methylpyrrolidin-2-one

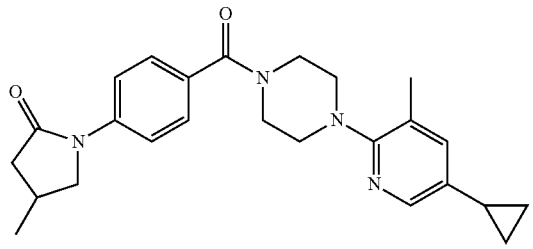 [SMILES: Cc1cc(C2CC2)cnc1N1CCN(C(=O)c2ccc(N3CC(C)CC3=O)cc2)CC1]

Using ethyl 4-(4-methyl-2-oxopyrrolidin-1-yl)benzoate (124 mg) described in Preparation Example 48 and 1-(5-cyclopropyl-3-methylpyridin-2-yl)piperazine (109 mg) described in Preparation Example 83 and by the reaction and treatment in the same manner as in Example 109, the title compound (48 mg) was obtained.

MS (ESI) m/z: 419(M+H)⁺.

Example 350

Synthesis of 1-{4-[4-(3,5-dimethylpyridin-2-yl)piperazine-1-carbonyl]phenyl}-4,4-dimethylpyrrolidin-2-one

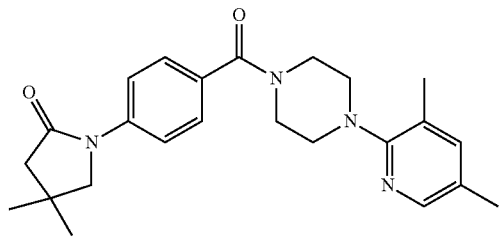

Using ethyl 4-(4,4-dimethyl-2-oxopyrrolidin-1-yl)benzoate (131 mg) described in Preparation Example 49 and 1-(3,5-dimethylpyridin-2-yl)piperazine (96 mg) described in Preparation Example 79 and by the reaction and treatment in the same manner as in Example 109, the title compound (134 mg) was obtained.

MS (ESI) m/z: 407(M+H)⁺.

Example 351

Synthesis of 1-{4-[4-(5-cyclopropyl-3-methylpyridin-2-yl)piperazine-1-carbonyl]phenyl}-4,4-dimethylpyrrolidin-2-one

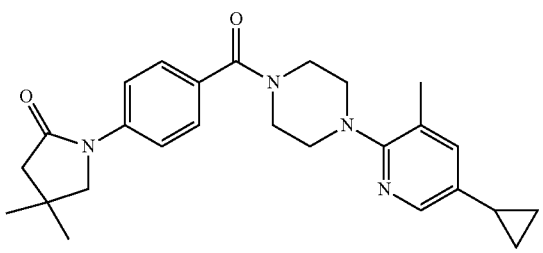 [SMILES: Cc1cc(C2CC2)cnc1N1CCN(C(=O)c2ccc(N3CC(C)(C)CC3=O)cc2)CC1]

Using ethyl 4-(4,4-dimethyl-2-oxopyrrolidin-1-yl)benzoate (131 mg) described in Preparation Example 49 and 1-(5-cyclopropyl-3-methylpyridin-2-yl)piperazine (109 mg) described in Preparation Example 83 and by the reaction and treatment in the same manner as in Example 109, the title compound (32 mg) was obtained.

MS (ESI) m/z: 433(M+H)⁺.

Example 352

Synthesis of 3-{2-[4-(3,5-dimethylpyridin-2-yl)piperazine-1-carbonyl]-5-(2-oxopyrrolidin-1-yl)phenyl}oxazolidin-2-one

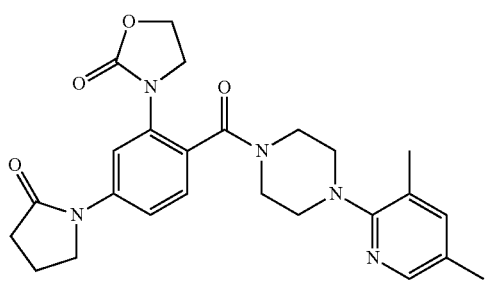 [SMILES: Cc1cnc(N2CCN(C(=O)c3ccc(N4CCCC4=O)cc3N3CCOC3=O)CC2)c(C)c1]

To a mixture of 3-{5-chloro-2-[4-(3,5-dimethylpyridin-2-yl)piperazine-1-carbonyl]phenyl}oxazolidin-2-one (207 mg) described in Preparation Example 168, pyrrolidin-2-one (43 mg), cesium carbonate (228 mg), tris(dibenzylideneacetone)dipalladium(0)-chloroform adduct (52 mg) and 2-di-tert-butylphosphino-3,4,5,6-tetramethyl-2',4',6'-triisopropyl-1,1'-biphenyl (24 mg) was added toluene (1 mL), and the mixture was stirred with heating under reflux for 8 hr. The reaction mixture was cooled, water was added, and the mixture was extracted with ethyl acetate, and the solvent was evaporated. The obtained residue was purified by column chromatography (ethyl acetate:methanol) to give the title compound (83 mg).

MS (ESI) m/z: 464(M+H)⁺.

Example 353

Synthesis of 3-{2-[4-(3,5-dimethylpyridin-2-yl)piperazine-1-carbonyl]-5-(2-methyl-5-oxopyrrolidin-1-yl)phenyl}oxazolidin-2-one

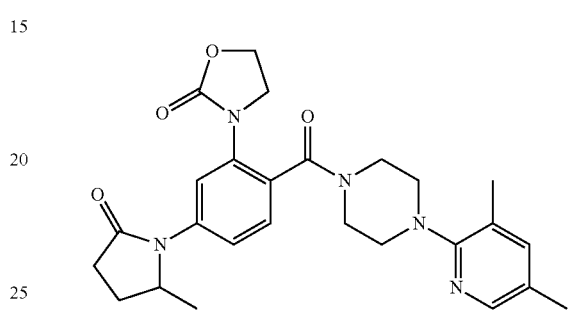

Using 3-{5-chloro-2-[4-(3,5-dimethylpyridin-2-yl)piperazine-1-carbonyl]phenyl}oxazolidin-2-one (207 mg) described in Preparation Example 168 and 5-methylpyrrolidin-2-one (50 mg) and by the reaction and treatment in the same manner as in Example 352, the title compound (50 mg) was obtained.

MS (ESI) m/z: 478(M+H)⁺.

Example 354

Synthesis of 1-{4-[4-(3,5-dimethylpyridin-2-yl)piperazine-1-carbonyl]phenyl}-5,5-dimethylpyrrolidin-2-one

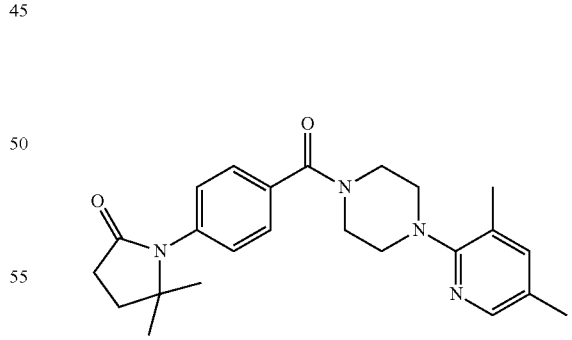

Using [4-(3,5-dimethylpyridin-2-yl)piperazin-1-yl](4-iodophenyl)methanone (295 mg) described in Preparation Example 113 and 5,5-dimethylpyrrolidin-2-one (79 mg) and by the reaction and treatment in the same manner as in Example 1, the title compound (51 mg) was obtained.

MS (ESI) m/z: 407(M+H)⁺.

Example 355

Synthesis of 1,1'-(4-{[4-(3,5-dimethylpyridin-2-yl)piperazin-1-yl]carbonyl}-1,3-phenylene)dipyrrolidin-2-one

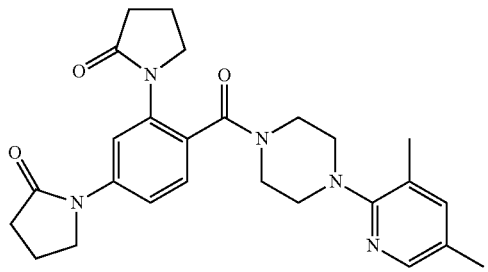 [SMILES: Cc1cnc(N2CCN(C(=O)c3ccc(N4CCCC4=O)cc3N3CCCC3=O)CC2)c(C)c1]

Using 1-{5-chloro-2-[4-(3,5-dimethylpyridin-2-yl)piperazine-1-carbonyl]phenyl}pyrrolidin-2-one (206 mg) described in Preparation Example 169 and pyrrolidin-2-one (43 mg) and by the reaction and treatment in the same manner as in Example 352, the title compound (73 mg) was obtained.
MS (ESI) m/z: 462(M+H)$^+$.

Example 356

Synthesis of 1-{4-[4-(3,5-dimethylpyridin-2-yl)piperazine-1-carbonyl]-3-(2-oxopyrrolidin-1-yl)phenyl}-5-methylpyrrolidin-2-one hydrochloride

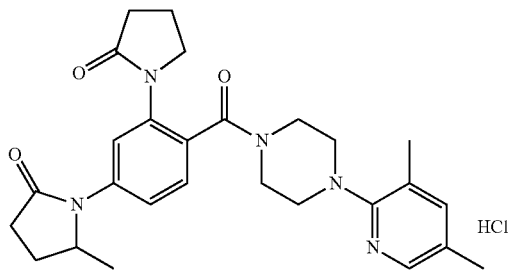 [SMILES: Cc1cnc(N2CCN(C(=O)c3ccc(N4C(=O)CCC4C)cc3N3CCCC3=O)CC2)c(C)c1 ; Cl]

To a mixture of 1-{5-chloro-2-[4-(3,5-dimethylpyridin-2-yl)piperazine-1-carbonyl]phenyl}pyrrolidin-2-one (220 mg) described in Preparation Example 169, 5-methylpyrrolidin-2-one (53 mg), cesium carbonate (243 mg), tris(dibenzylideneacetone)dipalladium(0)-chloroform adduct (55 mg) and 2-di-tert-butylphosphino-3,4,5,6-tetramethyl-2',4',6'-triisopropyl-1,1'-biphenyl (26 mg) was added toluene (1 mL), and the mixture was stirred with heating under reflux for 8 hr. The reaction mixture was cooled, water was added, and the mixture was extracted with ethyl acetate, and the solvent was evaporated. The obtained residue was purified by column chromatography (ethyl acetate:methanol) to give 1-{4-[4-(3,5-dimethylpyridin-2-yl)piperazine-1-carbonyl]-3-(2-oxopyrrolidin-1-yl)phenyl}-5-methylpyrrolidin-2-one. The obtained 1-{4-[4-(3,5-dimethylpyridin-2-yl)piperazine-1-carbonyl]-3-(2-oxopyrrolidin-1-yl)phenyl}-5-methylpyrrolidin-2-one was dissolved in ethyl acetate, 4N hydrogen chloride/ethyl acetate (0.13 mL) was added, and the precipitate was collected by filtration to give the title compound (37 mg).
MS (ESI) m/z: 476(M+H)$^+$.

Example 357

Synthesis of 1-{5-[4-(5-cyclopropyl-3-methylpyridin-2-yl)piperazine-1-carbonyl]-4-methylpyridin-2-yl}pyrrolidin-2-one dihydrochloride

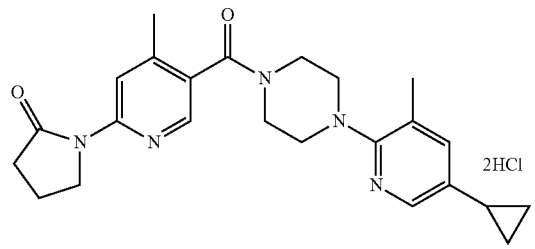 [SMILES: Cc1cc(N2CCCC2=O)ncc1C(=O)N1CCN(c2ncc(C3CC3)cc2C)CC1 ; "2HCl"]

Under a nitrogen stream, sodium hydride (47 mg) was suspended in N,N-dimethylformamide (10 mL), pyrrolidin-2-one (74 μL) was added, and the mixture was stirred at room temperature. Then, a solution of [4-(5-cyclopropyl-3-methylpyridin-2-yl)piperazin-1-yl](6-fluoro-4-methylpyridin-3-yl)methanone (210 mg) described in Preparation Example 140 in N,N-dimethylformamide (5 mL) was added, and the mixture was stirred at 95° C. The reaction mixture was cooled, water was added, and the mixture was extracted with ethyl acetate. The organic layer was washed with water and saturated brine, and the solvent was evaporated. The obtained residue was purified by column chromatography to give 1-{5-[4-(5-cyclopropyl-3-methylpyridin-2-yl)piperazine-1-carbonyl]-4-methylpyridin-2-yl}pyrrolidin-2-one. The obtained 1-{5-[4-(5-cyclopropyl-3-methylpyridin-2-yl)piperazine-1-carbonyl]-4-methylpyridin-2-yl}pyrrolidin-2-one was dissolved in dichloromethane, 1N hydrogen chloride/diethyl ether (5 mL) was added, and the precipitate was collected by filtration to give the title compound (12 mg).
MS (ESI) m/z: 420(M+H)$^+$.

Example 358

Synthesis of 1-{5-[4-(3,5-dicyclopropylpyridin-2-yl)piperazine-1-carbonyl]pyridin-2-yl}pyrrolidin-2-one

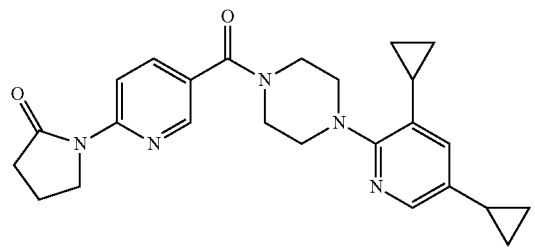 [SMILES: O=C(c1ccc(N2CCCC2=O)nc1)N1CCN(c2ncc(C3CC3)cc2C2CC2)CC1]

Using (6-bromopyridin-3-yl)[4-(3,5-dicyclopropylpyridin-2-yl)piperazin-1-yl]methanone (510 mg) described in Preparation Example 143 and pyrrolidin-2-one (131 μL) and by the reaction and treatment in the same manner as in Example 1, the title compound (297 mg) was obtained.
MS (ESI) m/z: 431(M+H)$^+$.

Example 359

Synthesis of 1-{5-[4-(2,4,5-trimethylphenyl)piperazine-1-carbonyl]pyridin-2-yl}pyrrolidin-2-one

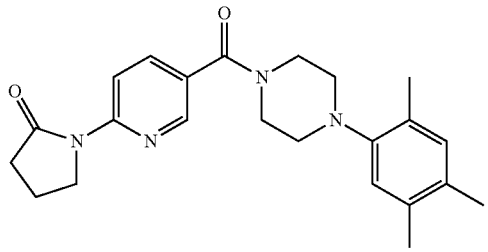 [SMILES: Cc1cc(C)c(N2CCN(C(=O)c3ccc(N4CCCC4=O)nc3)CC2)cc1C]

Using (6-bromopyridin-3-yl)[4-(2,4,5-trimethylphenyl)piperazin-1-yl]methanone (310 mg) described in Preparation Example 173 and pyrrolidin-2-one (93 μL) and by the reaction and treatment in the same manner as in Example 1, the title compound (187 mg) was obtained.
MS (ESI) m/z: 393(M+H)⁺.

Example 360

Synthesis of 1-{5-[4-(3,5-dicyclopropylpyridin-2-yl)piperazine-1-carbonyl]-4-methylpyridin-2-yl}pyrrolidin-2-one

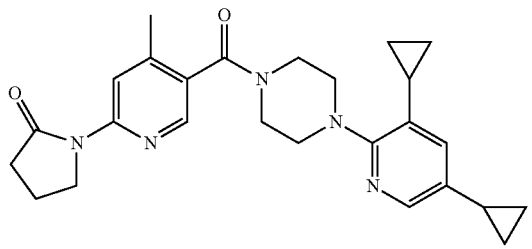

Using pyrrolidin-2-one (326 μL) and [4-(3,5-dicyclopropylpyridin-2-yl)piperazin-1-yl](6-fluoro-4-methylpyridin-3-yl)methanone (400 mg) described in Preparation Example 174 and by the reaction and treatment in the same manner as in Example 323, the title compound (187 mg) was obtained.
MS (ESI) m/z: 446(M+H)⁺.

Example 361

Synthesis of 1-{4-[4-(3,5-dimethylpyridin-2-yl)piperazine-1-carbonyl]benzyl}pyrrolidin-2-one hydrochloride

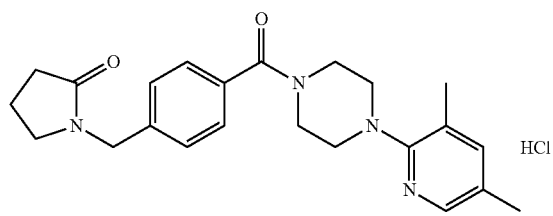 [SMILES: Cc1cnc(N2CCN(C(=O)c3ccc(CN4CCCC4=O)cc3)CC2)c(C)c1 ; Cl]

Using 4-(2-oxopyrrolidin-1-ylmethyl)benzoic acid (175 mg) and 1-(3,5-dimethylpyridin-2-yl)piperazine (153 mg) described in Preparation Example 79 and by the reaction and treatment in the same manner as in Example 187, the title compound (246 mg) was obtained.
MS (ESI) m/z: 393(M+H)⁺.

Example 362

Synthesis of 1-{4-[4-(5-cyclopropyl-3-methylpyridin-2-yl)piperazine-1-carbonyl]benzyl}pyrrolidin-2-one

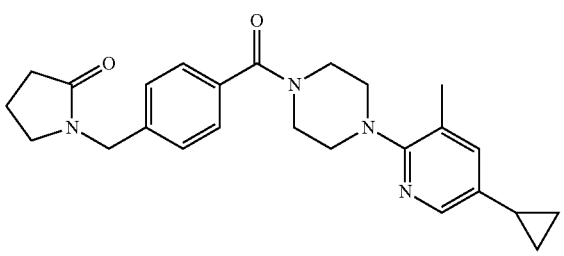 [SMILES: Cc1cc(C2CC2)cnc1N1CCN(C(=O)c2ccc(CN3CCCC3=O)cc2)CC1]

Using 4-(2-oxopyrrolidin-1-ylmethyl)benzoic acid (132 mg) and 1-(5-cyclopropyl-3-methylpyridin-2-yl)piperazine (156 mg) described in Preparation Example 83 and by the reaction and treatment in the same manner as in Example 87, the title compound (91 mg) was obtained.
MS (ESI) m/z: 419(M+H)⁺.

Example 363

Synthesis of 1-{2-[4-(5-cyclopropyl-3-methylpyridin-2-yl)piperazine-1-carbonyl]-5-(1,1-dioxo-1λ⁶-isothiazolidin-2-yl)phenyl}pyrrolidin-2-one

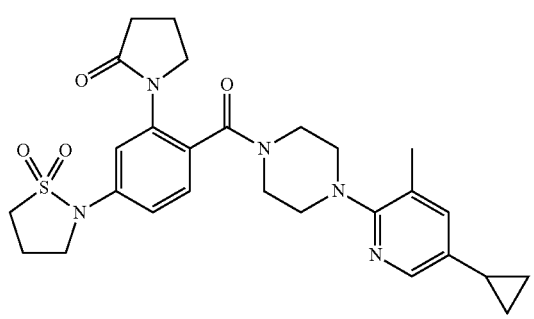 [SMILES: Cc1cc(C2CC2)cnc1N1CCN(C(=O)c2ccc(N3CCCS3(=O)=O)cc2N2CCCC2=O)CC1]

Using methyl 4-(1,1-dioxo-1λ⁶-isothiazolidin-2-yl)-2-(2-oxopyrrolidin-1-yl)benzoate (131 mg) described in Preparation Example 33 and 1-(5-cyclopropyl-3-methylpyridin-2-yl)piperazine (84 mg) described in Preparation Example 83 and by the reaction and treatment in the same manner as in Example 109, the title compound (8.3 mg) was obtained.
MS (ESI) m/z: 524(M+H)⁺.

Example 364

Synthesis of (S)-1-{4-[4-(2,4-dimethylphenyl)piperazine-1-carbonyl]phenyl}-4-hydroxypyrrolidin-2-one

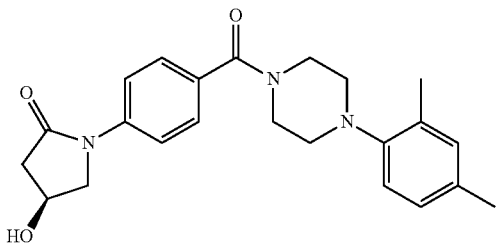 [SMILES: Cc1ccc(N2CCN(C(=O)c3ccc(N4C[C@@H](O)CC4=O)cc3)CC2)c(C)c1]

Using (4-bromophenyl) [4-(2,4-dimethylphenyl)piperazin-1-yl]methanone (1.87 g) described in Preparation Example 170 and (S)-4-hydroxypyrrolidin-2-one (556 mg) and by the reaction and treatment in the same manner as in Example 1, the title compound (760 mg) was obtained.
MS (ESI) m/z: 394(M+H)$^+$.

Example 365

Synthesis of 2-{4-[4-(2,4-dimethylphenyl)piperazine-1-carbonyl]phenyl}-2-azabicyclo[2.2.1]hept-5-en-3-one

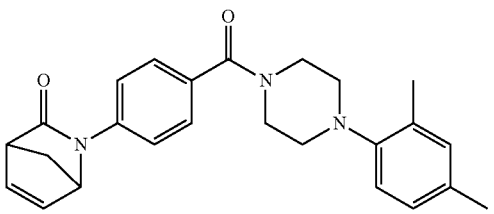 [SMILES: Cc1ccc(N2CCN(C(=O)c3ccc(N4C(=O)C5C=CC4C5)cc3)CC2)c(C)c1]

Using (4-bromophenyl)[4-(2,4-dimethylphenyl)piperazin-1-yl]methanone (747 mg) described in Preparation Example 170 and 2-azabicyclo[2.2.1]hept-5-en-3-one (218 mg) and by the reaction and treatment in the same manner as in Example 1, the title compound (121 mg) was obtained.
MS (ESI) m/z: 402(M+H)$^+$.

Example 366

Synthesis of 1-{4-[4-(2,4-dimethylphenyl)piperazine-1-carbonyl]phenyl}-5-methylpyrrolidin-2-one

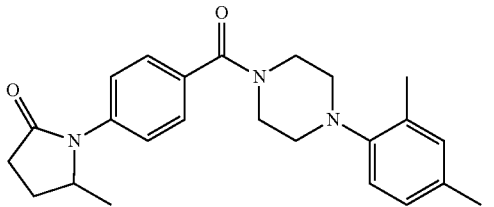

Using (4-bromophenyl)[4-(2,4-dimethylphenyl)piperazin-1-yl]methanone (747 mg) described in Preparation Example 170 and 5-methylpyrrolidin-2-one (198 mg) and by the reaction and treatment in the same manner as in Example 1, the title compound (367 mg) was obtained.
MS (ESI) m/z: 392(M+H)$^+$.

Example 367

Synthesis of 1-{4-[4-(2,4-dimethylphenyl)piperazine-1-carbonyl]-3,5-difluorophenyl}pyrrolidin-2-one

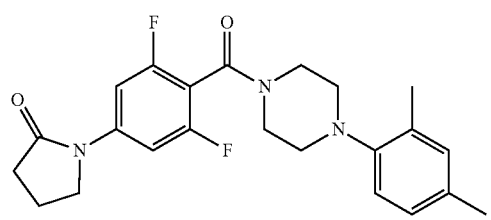 [SMILES: Cc1ccc(N2CCN(C(=O)c3c(F)cc(N4CCCC4=O)cc3F)CC2)c(C)c1]

Using (4-bromo-2,6-difluorophenyl)[4-(2,4-dimethylphenyl)piperazin-1-yl]methanone (819 mg) described in Preparation Example 109 and pyrrolidin-2-one (0.16 mL) and by the reaction and treatment in the same manner as in Example 1, the title compound (49 mg) was obtained.
MS (ESI) m/z: 414(M+H)$^+$.

Example 368

Synthesis of 1-{4-[4-(2,4-dimethylphenyl)piperazine-1-carbonyl]-3-methanesulfonylphenyl}pyrrolidin-2-one

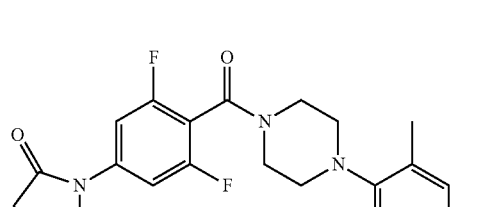

Using (4-bromo-2-methanesulfonylphenyl)[4-(2,4-dimethylphenyl)piperazin-1-yl]methanone (451 mg) described in Preparation Example 110 and pyrrolidin-2-one (80 μL) and by the reaction and treatment in the same manner as in Example 1, the title compound (244 mg) was obtained.
MS (ESI) m/z: 456(M+H)$^+$.

Example 369

Synthesis of 2-{4-[4-(2,4-dimethylphenyl)piperazine-1-carbonyl]phenyl}-2-azaspiro[4.5]decan-3-one

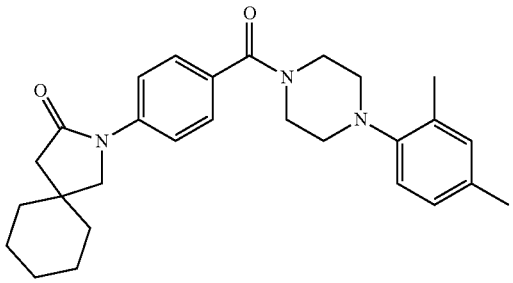 [SMILES: Cc1ccc(N2CCN(C(=O)c3ccc(N4CC5(CCCCC5)CC4=O)cc3)CC2)c(C)c1]

Using (4-bromophenyl) [4-(2,4-dimethylphenyl)piperazin-1-yl]methanone (747 mg) described in Preparation Example 170 and 2-azaspiro[4.5]decan-3-one (306 mg) and by the reaction and treatment in the same manner as in Example 1, the title compound (131 mg) was obtained.
MS (ESI) m/z: 446(M+H)+.

Example 370

Synthesis of 1-{4-[4-(2,4-dimethylphenyl)piperazine-1-carbonyl]-3-methanesulfonylphenyl}-5-methylpyrrolidin-2-one

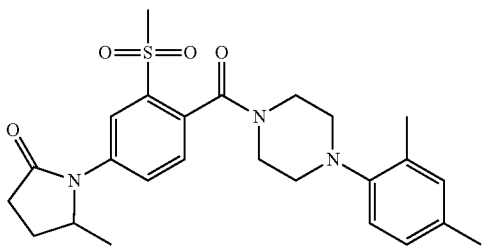

Using (4-bromo-2-methanesulfonylphenyl)[4-(2,4-dimethylphenyl)piperazin-1-yl]methanone (903 mg) described in Preparation Example 110 and 5-methylpyrrolidin-2-one (198 mg) and by the reaction and treatment in the same manner as in Example 1, the title compound (412 mg) was obtained.
MS (ESI) m/z: 470(M+H)+.

Example 371

Synthesis of (S)-1-{4-[4-(2,4-dimethylphenyl)piperazine-1-carbonyl]-3,5-difluorophenyl}-5-hydroxymethylpyrrolidin-2-one

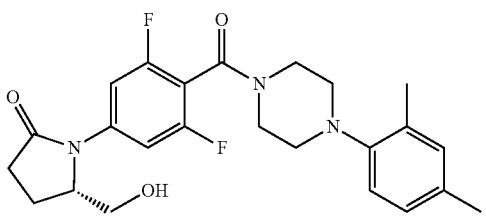 [SMILES: Cc1ccc(N2CCN(C(=O)c3c(F)cc(N4C(=O)CC[C@H]4CO)cc3F)CC2)c(C)c1]

Using (4-bromo-2,6-difluorophenyl)[4-(2,4-dimethylphenyl)piperazin-1-yl]methanone (819 mg) described in Preparation Example 109 and 5-hydroxymethylpyrrolidin-2-one (230 mg) and by the reaction and treatment in the same manner as in Example 1, the title compound (133 mg) was obtained.
MS (ESI) m/z: 444(M+H)+.

Example 372

Synthesis of (S)-1-{4-[4-(2,4-dimethylphenyl)piperazine-1-carbonyl]-3-methanesulfonylphenyl}-5-hydroxymethylpyrrolidin-2-one

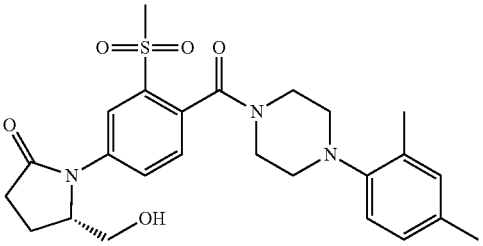 [SMILES: Cc1ccc(N2CCN(C(=O)c3ccc(N4C(=O)CC[C@H]4CO)cc3S(C)(=O)=O)CC2)c(C)c1]

Using (4-bromo-2-methanesulfonylphenyl)[4-(2,4-dimethylphenyl)piperazin-1-yl]methanone (903 mg) described in Preparation Example 110 and 5-hydroxymethylpyrrolidin-2-one (230 mg) and by the reaction and treatment in the same manner as in Example 1, the title compound (486 mg) was obtained.
MS (ESI) m/z: 486(M+H)+.

Example 373

Synthesis of 1-{4-[4-(2,4-dimethylphenyl)piperazine-1-carbonyl]-3-fluorophenyl}pyrrolidin-2-one

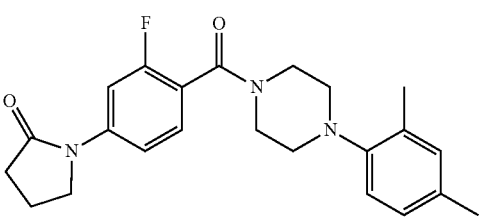 [SMILES: Cc1ccc(N2CCN(C(=O)c3ccc(N4CCCC4=O)cc3F)CC2)c(C)c1]

Using (4-bromo-2-fluorophenyl)[4-(2,4-dimethylphenyl)piperazin-1-yl]methanone (783 mg) described in Preparation Example 116 and pyrrolidin-2-one (0.16 mL) and by the reaction and treatment in the same manner as in Example 1, the title compound (313 mg) was obtained.
MS (ESI) m/z: 396(M+H)+.

Example 374

Synthesis of 1-{4-[4-(2,4-dimethylphenyl)piperazine-1-carbonyl]-3-methylphenyl}pyrrolidin-2-one

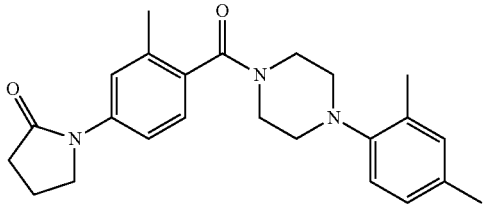 [SMILES: Cc1ccc(N2CCN(C(=O)c3ccc(N4CCCC4=O)cc3C)CC2)c(C)c1]

Using (4-bromo-2-methylphenyl)[4-(2,4-dimethylphenyl)piperazin-1-yl]methanone (775 mg) described in Preparation Example 130 and pyrrolidin-2-one (0.16 mL) and by the reaction and treatment in the same manner as in Example 1, the title compound (182 mg) was obtained.

MS (ESI) m/z: 392(M+H)⁺.

Example 375

Synthesis of 1-{2-chloro-4-[4-(2,4-dimethylphenyl)piperazine-1-carbonyl]phenyl}-4-(4-methylpiperazine-1-carbonyl)pyrrolidin-2-one hydrochloride

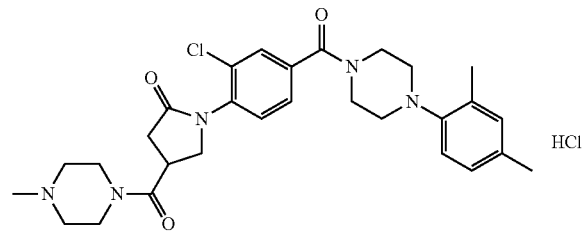

Using (4-bromo-3-chlorophenyl)[4-(2,4-dimethylphenyl)piperazin-1-yl]methanone (2.90 g) described in Preparation Example 171 and 5-oxopyrrolidine-3-carboxylic acid methyl ester (1.00 g) and by the reaction and treatment in the same manner as in Example 1, 1-{2-chloro-4-[4-(2,4-dimethylphenyl)piperazine-1-carbonyl]phenyl}-5-oxopyrrolidine-3-carboxylic acid methyl ester (2.80 g) was obtained. The so obtained 1-{2-chloro-4-[4-(2,4-dimethylphenyl)piperazine-1-carbonyl]phenyl}-5-oxopyrrolidine-3-carboxylic acid methyl ester (1.40 g) was dissolved in methanol (6 mL), 1N aqueous sodium hydroxide solution (6 mL) was added, and the mixture was stirred with heating under reflux for 3 hr. The reaction mixture was cooled, neutralized with 1N hydrochloric acid (6 mL), 1-methylpiperazine (0.33 mL) and 4-(4,6-dimethoxy[1.3.5]triazin-2-yl)-4-methylmorpholinium chloride hydrate (DMT-MM) (1.00 g) were added, and the mixture was stirred at room temperature overnight. The solvent was evaporated from the reaction mixture, water was added, and the mixture was extracted with chloroform. The organic layer was washed with water and saturated brine, and the solvent was evaporated. The obtained residue was purified by column chromatography (chloroform:methanol) to give 1-{2-chloro-4-[4-(2,4-dimethylphenyl)piperazine-1-carbonyl]phenyl}-4-(4-methylpiperazine-1-carbonyl)pyrrolidin-2-one. The obtained 1-{2-chloro-4-[4-(2,4-dimethylphenyl)piperazine-1-carbonyl]phenyl}-4-(4-methylpiperazine-1-carbonyl)pyrrolidin-2-one was dissolved in ethyl acetate, 4N hydrogen chloride/ethyl acetate (0.75 mL) was added, and the precipitate was collected by filtration to give the title compound (0.74 g).

MS (ESI) m/z: 538(M+H)⁺.

Example 376

Synthesis of 1-{3-methanesulfonyl-4-[4-(4-s methylbenzoyl)piperidine-1-carbonyl]phenyl}pyrrolidin-2-one

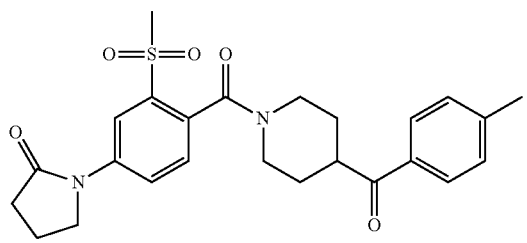 [SMILES: Cc1ccc(C(=O)C2CCN(C(=O)c3ccc(N4CCCC4=O)cc3S(C)(=O)=O)CC2)cc1]

To a mixture of (4-bromo-2-methanesulfonylphenyl)[4-(4-chlorobenzoyl)piperidin-1-yl]methanone (1.45 g) described in Preparation Example 191, pyrrolidin-2-one (0.24 mL), potassium carbonate (0.83 g) and copper(I) iodide (0.11 g) were added toluene (3 mL) and N,N'-dimethylethylenediamine (0.13 mL), and the mixture was stirred with heating under reflux for 8 hr. The reaction mixture was cooled, water was added, and the mixture was extracted with chloroform. The organic layer was washed with water and saturated brine, and the solvent was evaporated. The obtained residue was purified by column chromatography (chloroform:methanol) to give 1-{4-[4-(4-chlorobenzoyl)piperidine-1-carbonyl]-3-methanesulfonylphenyl}pyrrolidin-2-one. To a mixture of the obtained 1-{4-[4-(4-chlorobenzoyl)piperidine-1-carbonyl]-3-methanesulfonylphenyl}pyrrolidin-2-one, palladium (II) acetate (34 mg), 2-dicyclohexylphosphino-2',6'-dimethoxybiphenyl (123 mg), potassium fluoride (697 mg) and methylboronic acid (359 mg) was added tetrahydrofuran (9 mL), and the mixture was stirred with heating under reflux for 8 hr. Water was added to the reaction mixture, and the mixture was extracted with chloroform. The organic layer was washed with water and saturated brine, and the solvent was evaporated. The obtained residue was purified by column chromatography (chloroform:methanol) to give the title compound (408 mg).

MS (ESI) m/z: 469(M+H)⁺.

Example 377

Synthesis of 1-{4-[4-(3,5-dimethylpyridin-2-yl)piperazine-1-carbonyl]phenyl}pyrrolidin-2-one

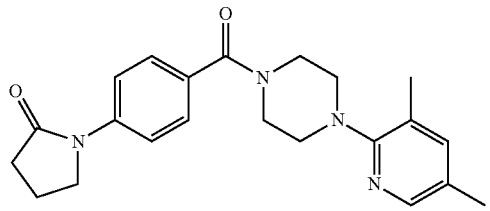 [SMILES: Cc1cnc(N2CCN(C(=O)c3ccc(N4CCCC4=O)cc3)CC2)c(C)c1]

Using [4-(3,5-dimethylpyridin-2-yl)piperazin-1-yl](4-iodophenyl)methanone (568 mg) described in Preparation Example 113 and pyrrolidin-2-one (0.12 mL) and by the reaction and treatment in the same manner as in Example 1, the title compound (427 mg) was obtained.

MS (ESI) m/z: 379(M+H)$^+$.

Example 378

Synthesis of 1-{4-[4-(3,5-dimethylpyridin-2-yl)piperazine-1-carbonyl]phenyl}-5-methylpyrrolidin-2-one

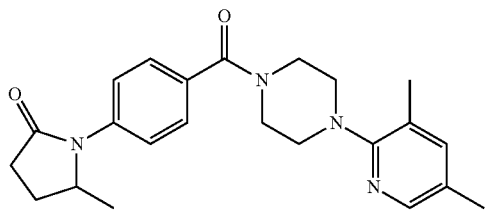 [SMILES: Cc1cnc(N2CCN(C(=O)c3ccc(N4C(=O)CCC4C)cc3)CC2)c(C)c1]

Using 4-(2-methyl-5-oxopyrrolidin-1-yl)benzoic acid (438 mg) described in Preparation Example 50 and 1-(3,5-dimethylpyridin-2-yl)piperazine (383 mg) described in Preparation Example 79 and by the reaction and treatment in the same manner as in Example 93, the title compound (406 mg) was obtained.

MS (ESI) m/z: 393(M+H)$^+$.

Example 379

Synthesis of 1-{4-[4-(3,5-dimethylpyridin-2-yl)piperazine-1-carbonyl]-3-fluorophenyl}-5-methylpyrrolidin-2-one hydrochloride

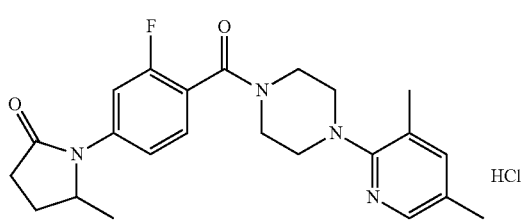 [SMILES: Cc1cnc(N2CCN(C(=O)c3ccc(N4C(=O)CCC4C)cc3F)CC2)c(C)c1 ; Cl]

Using (4-bromo-2-fluorophenyl)[4-(3,5-dimethylpyridin-2-yl)piperazin-1-yl]methanone (1.03 g) described in Preparation Example 114 and 5-methylpyrrolidin-2-one (258 mg) and by the reaction and treatment in the same manner as in Example 141, the title compound (300 mg) was obtained.

MS (ESI) m/z: 411(M+H)$^+$.

Example 380

Synthesis of 1-{4-[4-(3,5-dimethylpyridin-2-yl)piperazine-1-carbonyl]-3-methanesulfonylphenyl}-5-methylpyrrolidin-2-one

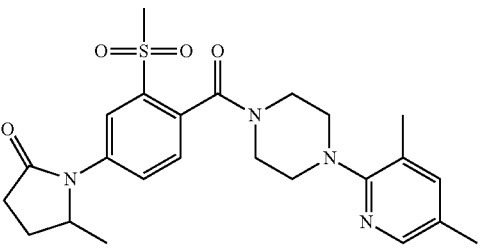 [SMILES: Cc1cnc(N2CCN(C(=O)c3ccc(N4C(=O)CCC4C)cc3S(C)(=O)=O)CC2)c(C)c1]

Using (4-bromo-2-methanesulfonylphenyl)[4-(3,5-dimethylpyridin-2-yl)piperazin-1-yl]methanone (864 mg) described in Preparation Example 112 and 5-methylpyrrolidin-2-one (258 mg) and by the reaction and treatment in the same manner as in Example 1, the title compound (304 mg) was obtained.

MS (ESI) m/z: 471(M+H)$^+$.

Example 381

Synthesis of 2-[4-(3,5-dimethylpyridin-2-yl)piperazine-1-carbonyl]-5-(2-oxopyrrolidin-1-yl)benzonitrile

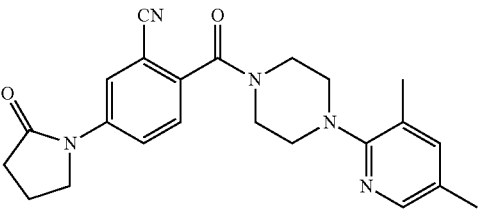

Using 5-bromo-2-[4-(3,5-dimethylpyridin-2-yl)piperazine-1-carbonyl]benzonitrile (399 mg) described in Preparation Example 187 and pyrrolidin-2-one (115 μL) and by the reaction and treatment in the same manner as in Example 262, the title compound (275 mg) was obtained.

MS (ESI) m/z: 404(M+H)$^+$.

Example 382

Synthesis of 2-[4-(2,4-dimethylphenyl)piperazine-1-carbonyl]-5-(2-oxopyrrolidin-1-yl)benzonitrile

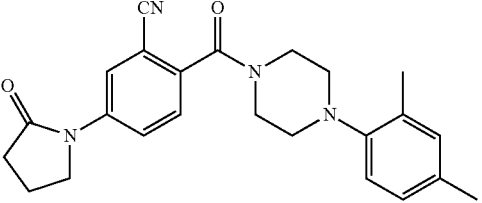 [SMILES: Cc1ccc(N2CCN(C(=O)c3ccc(N4CCCC4=O)cc3C#N)CC2)c(C)c1]

Using 5-bromo-2-[4-(2,4-dimethylphenyl)piperazine-1-carbonyl]benzonitrile (398 mg) described in Preparation Example 188 and pyrrolidin-2-one (115 μL) and by the reaction and treatment in the same manner as in Example 262, the title compound (377 mg) was obtained.

MS (ESI) m/z: 403(M+H)$^+$.

Example 383

Synthesis of 5-(2-oxopyrrolidin-1-yl)-2-[4-(3,5,6-trimethylpyridin-2-yl)piperazine-1-carbonyl]benzonitrile

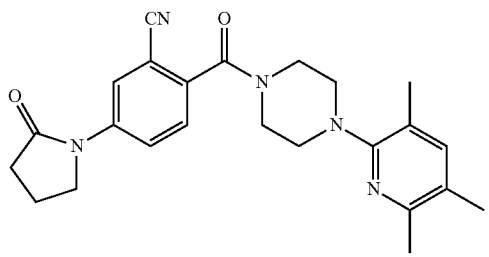

Using 5-bromo-2-[4-(3,5,6-trimethylpyridin-2-yl)piperazine-1-carbonyl]benzonitrile (413 mg) described in Preparation Example 172 and pyrrolidin-2-one (115 μL) and by the reaction and treatment in the same manner as in Example 262, the title compound (378 mg) was obtained.

MS (ESI) m/z: 418(M+H)$^+$.

Example 384

Synthesis of 2-[4-(5-cyclopropyl-3-methylpyridin-2-yl)piperazine-1-carbonyl]-5-(2-oxopyrrolidin-1-yl)benzonitrile

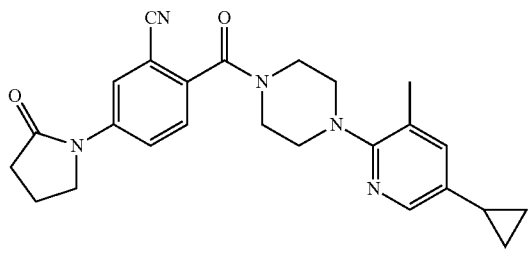 [SMILES: Cc1cc(C2CC2)cnc1N1CCN(C(=O)c2ccc(N3CCCC3=O)cc2C#N)CC1]

Using 5-bromo-2-[4-(5-cyclopropyl-3-methylpyridin-2-yl)piperazine-1-carbonyl]benzonitrile (723 mg) described in Preparation Example 189 and pyrrolidin-2-one (196 μL) and by the reaction and treatment in the same manner as in Example 20262, the title compound (668 mg) was obtained.

MS (ESI) m/z: 430(M+H)$^+$.

Example 385

Synthesis of 1-[(4-{4-(2,4-dimethylphenyl)piperazine-1-carbonyl]phenyl}piperidin-2-one

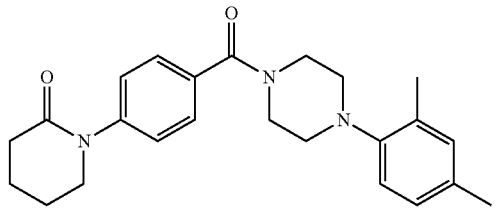 [SMILES: Cc1ccc(N2CCN(C(=O)c3ccc(N4CCCCC4=O)cc3)CC2)c(C)c1]

Using ethyl 4-(2-oxopiperidin-1-yl)benzoate (247 mg) and 1-(2,4-dimethylphenyl)piperazine (190 mg) and by the reaction and treatment in the same manner as in Example 109, the title compound (219 mg) was obtained.

MS (ESI) m/z: 392(M+H)$^+$.

Example 386

Synthesis of 1-acetyl-3-{6-[4-(3,5-dimethylpyridin-2-yl)piperazine-1-carbonyl]pyridin-3-yl}imidazolidin-2-one

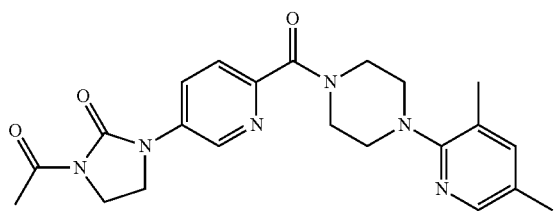 [SMILES: CC(=O)N1CCN(c2ccc(C(=O)N3CCN(c4ncc(C)cc4C)CC3)nc2)C1=O]

Using (5-bromopyridin-2-yl)[4-(3,5-dimethylpyridin-2-yl)piperazin-1-yl]methanone (550 mg) described in Preparation Example 134 and 1-acetyl-2-imidazolidinone (188 mg) and by the reaction and treatment in the same manner as in Example 1, the title compound (322 mg) was obtained.

MS (ESI) m/z: 423(M+H)$^+$.

Example 387

Synthesis of 1-{6-[4-(3,5-dimethylpyridin-2-yl)piperazine-1-carbonyl]pyridin-3-yl}imidazolidin-2-one

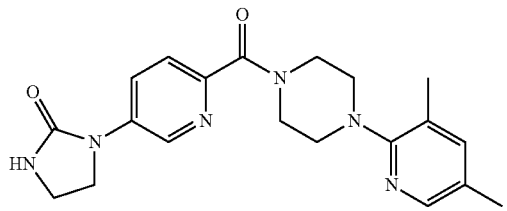 [SMILES: Cc1cnc(N2CCN(C(=O)c3ccc(N4CCNC4=O)cn3)CC2)c(C)c1]

The byproduct resulting from Example 386 was purified by column chromatography (chloroform:methanol) to give the title compound (26 mg).

MS (ESI) m/z: 381(M+H)$^+$.

Example 388

Synthesis of 1-acetyl-3-{6-[4-(2,4-dimethylphenyl)piperazine-1-carbonyl]pyridin-3-yl}imidazolidin-2-one

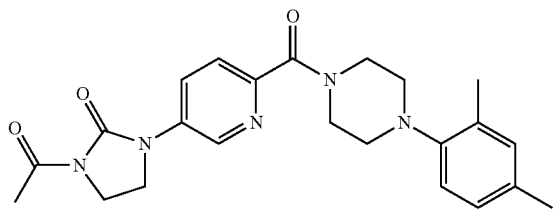 [SMILES: CC(=O)N1CCN(c2ccc(C(=O)N3CCN(c4ccc(C)cc4C)CC3)nc2)C1=O]

Using 1-acetyl-2-imidazolidinone (128 mg) and (5-bromopyridin-2-yl)[4-(2,4-dimethylphenyl)piperazin-1-yl]methanone (374 mg) described in Preparation Example 137 and by the reaction and treatment in the same manner as in Example 1, the title compound (155 mg) was obtained.
MS (ESI) m/z: 422(M+H)+.

Example 389

Synthesis of 1-{6-[4-(2,4-dimethylphenyl)piperazine-1-carbonyl]pyridin-3-yl}-3-methylimidazolidin-2-one

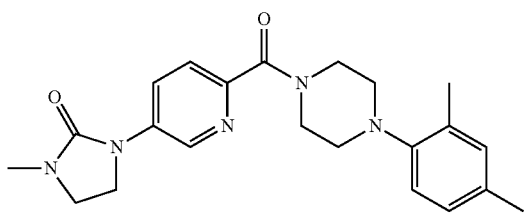

Using 1-methyl-2-imidazolidinone (37 mg) and (5-bromopyridin-2-yl)[4-(2,4-dimethylphenyl)piperazin-1-yl]methanone (140 mg) described in Preparation Example 137 and by the reaction and treatment in the same manner as in Example 1, the title compound (78 mg) was obtained.
MS (ESI) m/z: 394(M+H)+.

Example 390

Synthesis of 1-{6-[4-(3,5-dimethylpyridin-2-yl)piperazine-1-carbonyl]pyridin-3-yl}-3-methylimidazolidin-2-one

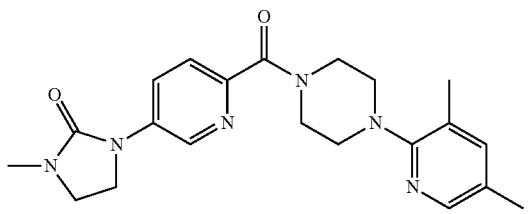

Using 1-methyl-2-imidazolidinone (53 mg) and (5-bromopyridin-2-yl)[4-(3,5-dimethylpyridin-2-yl)piperazin-1-yl]methanone (200 mg) described in Preparation Example 134 and by the reaction and treatment in the same manner as in Example 1, the title compound (130 mg) was obtained.
MS (ESI) m/z: 395(M+H)+.

Example 391

Synthesis of 1-{6-[4-(2,4-dimethylphenyl)piperazine-1-carbonyl]pyridin-3-yl}imidazolidin-2-one

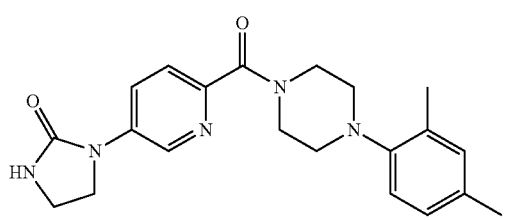

To a mixture of 1-acetyl-3-{6-[4-(2,4-dimethylphenyl)piperazine-1-carbonyl]pyridin-3-yl}imidazolidin-2-one (70 mg) described in Example 388 and potassium carbonate (35 mg) was added methanol (5 mL), and the mixture was stirred with heating under reflux for 1 hr. Water was added to the reaction mixture, and the mixture was extracted with ethyl acetate. The organic layer was washed with saturated brine, and the solvent was evaporated. The obtained residue was purified by column chromatography (chloroform:methanol) to give the title compound (23 mg).
MS (ESI) m/z: 380(M+H)+.

Example 392

Synthesis of 1-acetyl-3-{6-[4-(5-cyclopropyl-3-methylpyridin-2-yl)piperazine-1-carbonyl]pyridin-3-yl}imidazolidin-2-one

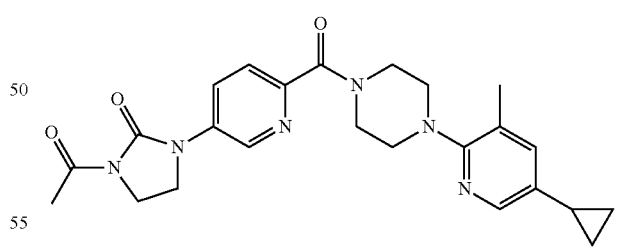

Using 1-acetyl-2-imidazolidinone (316 mg) and (5-bromopyridin-2-yl)[4-(5-cyclopropyl-3-methylpyridin-2-yl)piperazin-1-yl]methanone (900 mg) described in Preparation Example 135 and by the reaction and treatment in the same manner as in Example 1, the title compound (116 mg) was obtained.
MS (ESI) m/z: 449(M+H)+.

Example 393

Synthesis of 1-{6-[4-(5-cyclopropyl-3-methylpyridin-2-yl)piperazine-1-carbonyl]pyridin-3-yl}imidazolidin-2-one

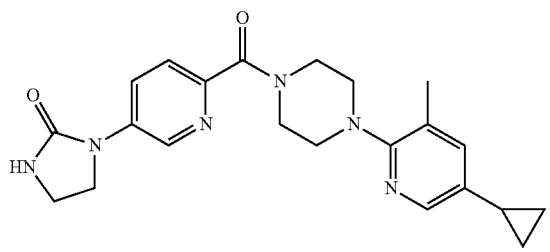 [SMILES: Cc1cc(C2CC2)cnc1N1CCN(C(=O)c2ccc(N3CCNC3=O)cn2)CC1]

Using 1-acetyl-3-{6-[4-(5-cyclopropyl-3-methylpyridin-2-yl)piperazine-1-carbonyl]pyridin-3-yl}imidazolidin-2-one (220 mg) described in Example 392 and by the reaction and treatment in the same manner as in Example 391, the title compound (157 mg) was obtained.
MS (ESI) m/z: 407(M+H)$^+$.

Example 394

Synthesis of 1-{6-[4-(5-cyclopropyl-3-methylpyridin-2-yl)piperazine-1-carbonyl]pyridin-3-yl}-3-methylimidazolidin-2-one

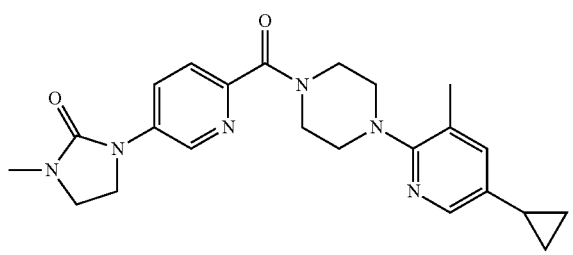 [SMILES: Cc1cc(C2CC2)cnc1N1CCN(C(=O)c2ccc(N3CCN(C)C3=O)cn2)CC1]

Using 1-{6-[4-(5-cyclopropyl-3-methylpyridin-2-yl)piperazine-1-carbonyl]pyridin-3-yl}imidazolidin-2-one (280 mg) described in Example 393 and methyl iodide (51 µL) and by the reaction and treatment in the same manner as in Example 36, the title compound (211 mg) was obtained.
MS (ESI) m/z: 421(M+H)$^+$.

Example 395

Synthesis of 1-acetyl-3-{6-[4-(3,5,6-trimethylpyridin-2-yl)piperazine-1-carbonyl]pyridin-3-yl}imidazolidin-2-one

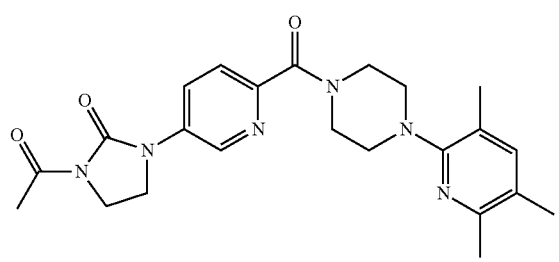 [SMILES: CC(=O)N1CCN(c2ccc(C(=O)N3CCN(c4nc(C)c(C)cc4C)CC3)nc2)C1=O]

Using 1-acetyl-2-imidazolidinone (655 mg) and (5-bromopyridin-2-yl)[4-(3,5,6-trimethylpyridin-2-yl)piperazin-1-yl]methanone (1.81 g) described in Preparation Example 147 and by the reaction and treatment in the same manner as in Example 1, the title compound (1.08 g) was obtained.
MS (ESI) m/z: 437(M+H)$^+$.

Example 396

Synthesis of 1-acetyl-3-{6-[4-(3,5-dicyclopropylpyridin-2-yl)piperazine-1-carbonyl]pyridin-3-yl}imidazolidin-2-one

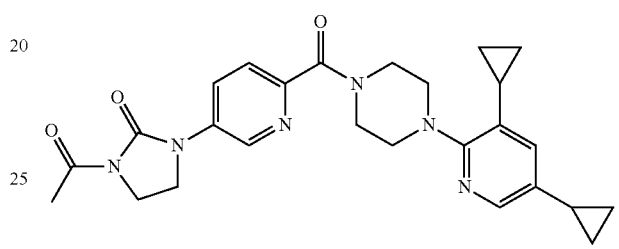

Using 1-acetyl-2-imidazolidinone (462 mg) and (5-bromopyridin-2-yl)[4-(3,5-dicyclopropylpyridin-2-yl)piperazin-1-yl]methanone (1.4 g) described in Preparation Example 142 and by the reaction and treatment in the same manner as in Example 1, the title compound (199 mg) was obtained.
MS (ESI) m/z: 475(M+H)$^+$.

Example 397

Synthesis of 1-{6-[4-(3,5,6-trimethylpyridin-2-yl)piperazine-1-carbonyl]pyridin-3-yl}imidazolidin-2-one

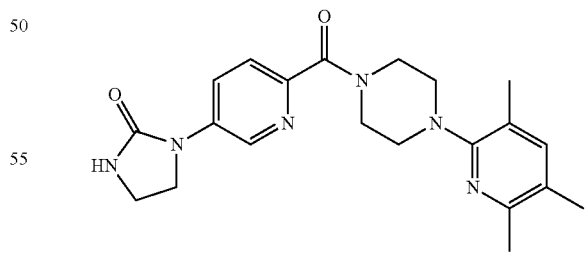

Using 1-acetyl-3-{6-[4-(3,5,6-trimethylpyridin-2-yl)piperazine-1-carbonyl]pyridin-3-yl}imidazolidin-2-one (470 mg) described in Example 395 and by the reaction and treatment in the same manner as in Example 391, the title compound (356 mg) was obtained.
MS (ESI) m/z: 395(M+H)$^+$.

Example 398

Synthesis of 1-methyl-3-{6-[4-(3,5,6-trimethylpyridin-2-yl)piperazine-1-carbonyl]pyridin-3-yl}imidazolidin-2-one

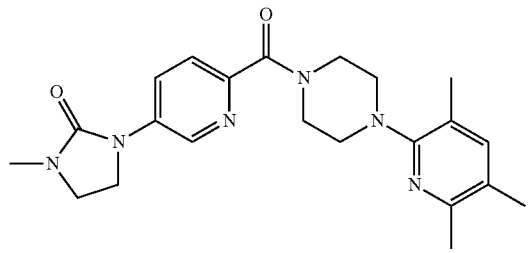

Using 1-{6-[4-(3,5,6-trimethylpyridin-2-yl)piperazine-1-carbonyl]pyridin-3-yl}imidazolidin-2-one (136 mg) described in Example 397 and methyl iodide (26 µL) and by the reaction and treatment in the same manner as in Example 36, the title compound (109 mg) was obtained.
MS (ESI) m/z: 409(M+H)+.

Example 399

Synthesis of 1-{6-[4-(3,5-dicyclopropylpyridin-2-yl)piperazine-1-carbonyl]pyridin-3-yl}-3-methylimidazolidin-2-one

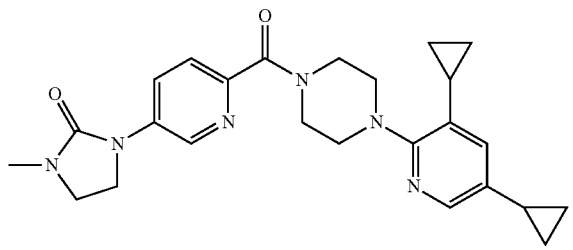 [SMILES: CN1CCN(c2ccc(C(=O)N3CCN(c4ncc(C5CC5)cc4C4CC4)CC3)nc2)C1=O]

Using 1-methyl-2-imidazolidinone (181 mg) and (5-bromopyridin-2-yl)[4-(3,5-dicyclopropylpyridin-2-yl)piperazin-1-yl]methanone (700 mg) described in Preparation Example 142 and by the reaction and treatment in the same manner as in Example 1, the title compound (253 mg) was obtained.
MS (ESI) m/z: 447(M+H)+.

Example 400

Synthesis of 1-{6-[4-(3,5-dicyclopropylpyridin-2-yl)piperazine-1-carbonyl]pyridin-3-yl}imidazolidin-2-one

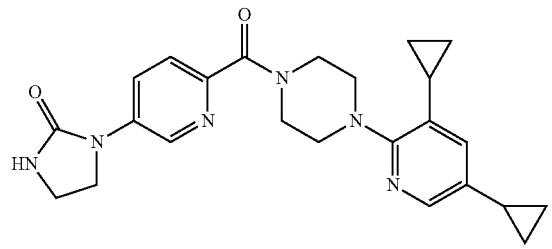

Using 1-acetyl-3-{6-[4-(3,5-dicyclopropylpyridin-2-yl)piperazine-1-carbonyl]pyridin-3-yl}imidazolidin-2-one (140 mg) described in Example 396 and by the reaction and treatment in the same manner as in Example 391, the title compound (84 mg) was obtained.
MS (ESI) m/z: 433(M+H)+.

Example 401

Synthesis of 1-{4-[4-(2,4-dimethylphenyl)piperazine-1-carbonyl]phenyl}imidazolidin-2-one

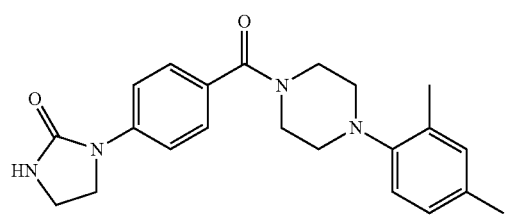

Using methyl 4-(3-acetyl-2-oxoimidazolidin-1-yl)benzoate (290 mg) described in Preparation Example 59 and 1-(2,4-dimethylphenyl)piperazine (209 mg) and by the reaction and treatment in the same manner as in Example 109, the title compound (188.5 mg) was obtained.
MS (ESI) m/z: 379(M+H)+.

Example 402

Synthesis of 1-benzyl-3-{4-[4-(2,4-dimethylphenyl)piperazine-1-carbonyl]phenyl}imidazolidin-2-one

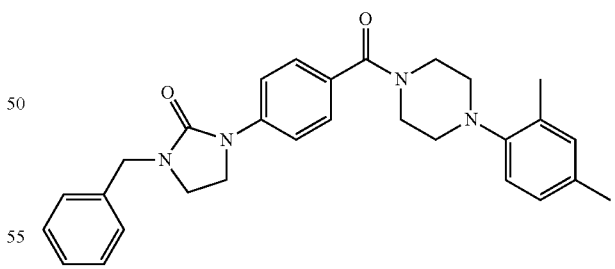

Using 1-{4-[4-(2,4-dimethylphenyl)piperazine-1-carbonyl]phenyl}imidazolidin-2-one (100 mg) described in Example 401 and benzyl bromide (35 µL) and by the reaction and treatment in the same manner as in Example 36, the title compound (63 mg) was obtained.
MS (ESI) m/z: 469(M+H)+.

Example 403

Synthesis of 1-{4-[4-(2,4-dimethylphenyl)piperazine-1-carbonyl]phenyl}-3-methylimidazolidin-2-one

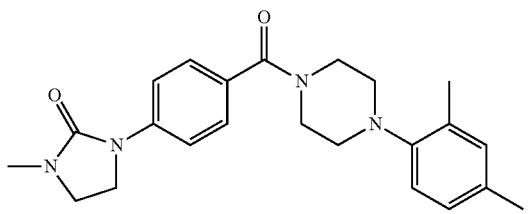

Using 1-{4-[4-(2,4-dimethylphenyl)piperazine-1-carbonyl]phenyl}imidazolidin-2-one (100 mg) described in Example 401 and methyl iodide (18 µL) and by the reaction and treatment in the same manner as in Example 36, the title compound (69 mg) was obtained.
MS (ESI) m/z: 393(M+H)$^+$.

Example 404

Synthesis of 1-acetyl-3-{4-[4-(3,5-dimethylpyridin-2-yl)piperazine-1-carbonyl]phenyl}imidazolidin-2-one

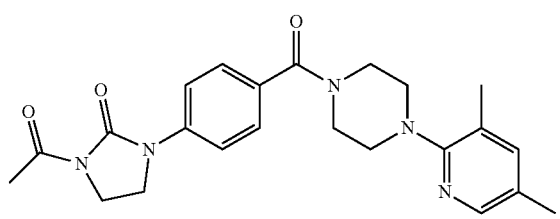 [SMILES: CC(=O)N1CCN(c2ccc(C(=O)N3CCN(c4ncc(C)cc4C)CC3)cc2)C1=O]

Using (4-bromophenyl)[4-(3,5-dimethylpyridin-2-yl)piperazin-1-yl]methanone (225 mg) described in Preparation Example 165 and 1-acetylimidazolidin-2-one (115 mg) and by the reaction and treatment in the same manner as in Example 1, the title compound (178 mg) was obtained.
MS (ESI) m/z: 422(M+H)$^+$.

Example 405

Synthesis of 1-acetyl-3-{4-[4-(5-cyclopropyl-3-methylpyridin-2-yl)piperazine-1-carbonyl]phenyl}imidazolidin-2-one

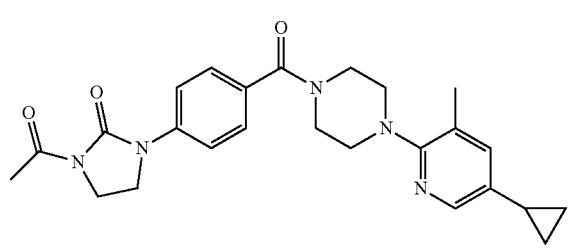 [SMILES: CC(=O)N1CCN(c2ccc(C(=O)N3CCN(c4ncc(C5CC5)cc4C)CC3)cc2)C1=O]

Using (4-bromophenyl)[4-(5-cyclopropyl-3-methylpyridin-2-yl)piperazin-1-yl]methanone (240 mg) described in Preparation Example 185 and 1-acetylimidazolidin-2-one (115 mg) and by the reaction and treatment in the same manner as in Example 1, the title compound (189 mg) was obtained.
MS (ESI) m/z: 448(M+H)$^+$.

Example 406

Synthesis of 1-{4-[4-(3,5-dimethylpyridin-2-yl)piperazine-1-carbonyl]phenyl}imidazolidin-2-one

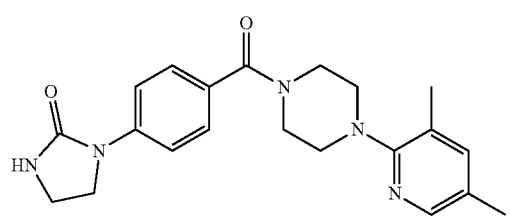 [SMILES: Cc1cnc(N2CCN(C(=O)c3ccc(N4CCNC4=O)cc3)CC2)c(C)c1]

Using 1-acetyl-3-{4-[4-(3,5-dimethylpyridin-2-yl)piperazine-1-carbonyl]phenyl}imidazolidin-2-one (135 mg) described in Example 404 and by the reaction and treatment in the same manner as in Example 391, the title compound (112 mg) was obtained.
MS (ESI) m/z: 380(M+H)$^+$.

Example 407

Synthesis of 1-{4-[4-(5-cyclopropyl-3-methylpyridin-2-yl)piperazine-1-carbonyl]phenyl}imidazolidin-2-one

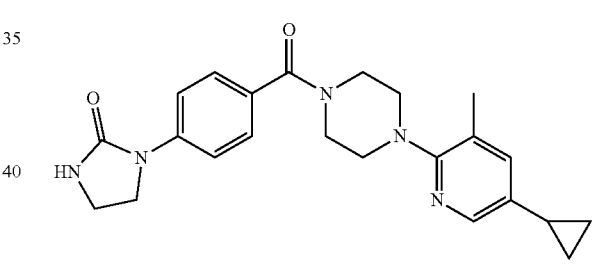

Using 1-acetyl-3-{4-[4-(5-cyclopropyl-3-methylpyridin-2-yl)piperazine-1-carbonyl]phenyl}imidazolidin-2-one (143 mg) described in Example 405 and by the reaction and treatment in the same manner as in Example 391, the title compound (123 mg) was obtained.
MS (ESI) m/z: 406(M+H)$^+$.

Example 408

Synthesis of 1-{4-[4-(3,5-dimethylpyridin-2-yl)piperazine-1-carbonyl]phenyl}-3-methylimidazolidin-2-one

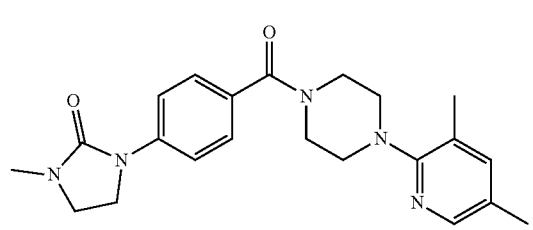

Using (4-bromophenyl)[4-(3,5-dimethylpyridin-2-yl)piperazin-1-yl]methanone (225 mg) described in Preparation Example 165 and 1-methylimidazolidin-2-one (90 mg) and by the reaction and treatment in the same manner as in Example 1, the title compound (58 mg) was obtained.

MS (ESI) m/z: 394(M+H)$^+$.

Example 409

Synthesis of 1-{4-[4-(5-cyclopropyl-3-methylpyridin-2-yl)piperazine-1-carbonyl]phenyl}-3-methylimidazolidin-2-one

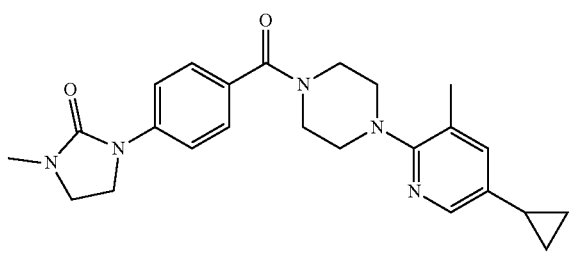 [SMILES: Cc1cc(C2CC2)cnc1N1CCN(C(=O)c2ccc(N3CCN(C)C3=O)cc2)CC1]

Using (4-bromophenyl)[4-(5-cyclopropyl-3-methylpyridin-2-yl)piperazin-1-yl]methanone (240 mg) described in Preparation Example 185 and 1-methylimidazolidin-2-one (90 mg) and by the reaction and treatment in the same manner as in Example 1, the title compound (24 mg) was obtained.

MS (ESI) m/z: 420(M+H)$^+$.

Example 410

Synthesis of 1-acetyl-3-{5-[4-(3,5-dimethylpyridin-2-yl)piperazine-1-carbonyl]pyridin-2-yl}imidazolidin-2-one

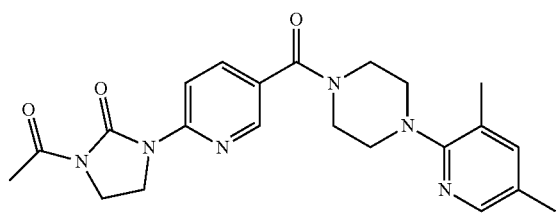 [SMILES: CC(=O)N1CCN(c2ccc(C(=O)N3CCN(c4ncc(C)cc4C)CC3)cn2)C1=O]

Using (6-bromopyridin-3-yl)[4-(3,5-dimethylpyridin-2-yl)piperazin-1-yl]methanone (225 mg) described in Preparation Example 127 and 1-acetylimidazolidin-2-one (115 mg) and by the reaction and treatment in the same manner as in Example 1, the title compound (161 mg) was obtained.

MS (ESI) m/z: 423(M+H)$^+$.

Example 411

Synthesis of 1-{5-[4-(3,5-dimethylpyridin-2-yl)piperazine-1-carbonyl]pyridin-2-yl}-3-methylimidazolidin-2-one

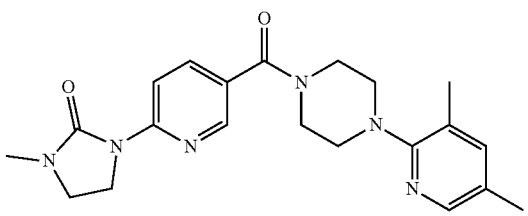

Using (6-bromopyridin-3-yl)[4-(3,5-dimethylpyridin-2-yl)piperazin-1-yl]methanone (225 mg) described in Preparation Example 127 and 1-methylimidazolidin-2-one (90 mg) and by the reaction and treatment in the same manner as in Example 1, the title compound (193 mg) was obtained.

MS (ESI) m/z: 395(M+H)$^+$.

Example 412

Synthesis of 1-acetyl-3-{4-[4-(3,5-dimethylpyridin-2-yl)piperazine-1-carbonyl]-3-methylphenyl}imidazolidin-2-one

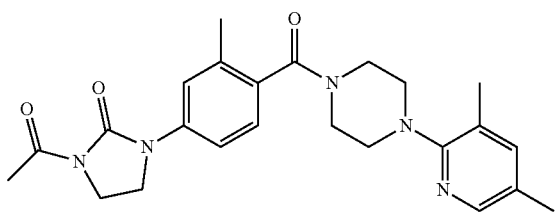 [SMILES: CC(=O)N1CCN(c2ccc(C(=O)N3CCN(c4ncc(C)cc4C)CC3)c(C)c2)C1=O]

Using (4-bromo-2-methylphenyl) [4-(3,5-dimethylpyridin-2-yl)piperazin-1-yl]methanone (233 mg) described in Preparation Example 118 and 1-acetylimidazolidin-2-one (115 mg) and by the reaction and treatment in the same manner as in Example 1, the title compound (163 mg) was obtained.

MS (ESI) m/z: 436(M+H)$^+$.

Example 413

Synthesis of 1-acetyl-3-{4-[4-(3,5-dimethylpyridin-2-yl)piperazine-1-carbonyl]-3-fluorophenyl}imidazolidin-2-one

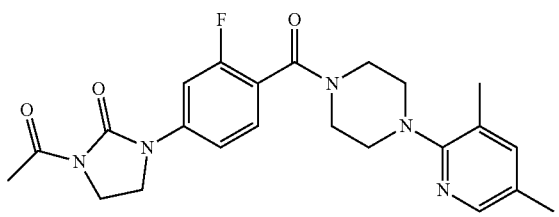 [SMILES: CC(=O)N1CCN(c2ccc(C(=O)N3CCN(c4ncc(C)cc4C)CC3)c(F)c2)C1=O]

Using (4-bromo-2-fluorophenyl)[4-(3,5-dimethylpyridin-2-yl)piperazin-1-yl]methanone (235 mg) described in Preparation Example 114 and 1-acetylimidazolidin-2-one (115 mg) and by the reaction and treatment in the same manner as in Example 1, the title compound (142 mg) was obtained.

MS (ESI) m/z: 440(M+H)+.

Example 414

Synthesis of 1-{5-[4-(3,5-dimethylpyridin-2-yl)piperazine-1-carbonyl]pyridin-2-yl}imidazolidin-2-one

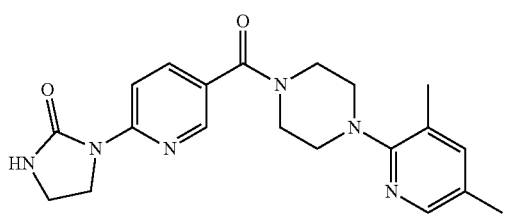 [SMILES: Cc1cnc(N2CCN(C(=O)c3ccc(N4CCNC4=O)nc3)CC2)c(C)c1]

Using 1-acetyl-3-{5-[4-(3,5-dimethylpyridin-2-yl)piperazine-1-carbonyl]pyridin-2-yl}imidazolidin-2-one (120 mg) described in Example 410 and by the reaction and treatment in the same manner as in Example 391, the title compound (108 mg) was obtained.

MS (ESI) m/z: 381(M+H)+.

Example 415

Synthesis of 1-{4-[4-(3,5-dimethylpyridin-2-yl)piperazine-1-carbonyl]-3-methylphenyl}imidazolidin-2-one

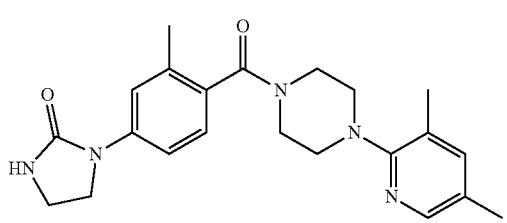

Using 1-acetyl-3-{4-[4-(3,5-dimethylpyridin-2-yl)piperazine-1-carbonyl]-3-methylphenyl}imidazolidin-2-one (120 mg) described in Example 412 and by the reaction and treatment in the same manner as in Example 391, the title compound (103 mg) was obtained.

MS (ESI) m/z: 394(M+H)+.

Example 416

Synthesis of 1-{4-[4-(3,5-dimethylpyridin-2-yl)piperazine-1-carbonyl]-3-fluorophenyl}imidazolidin-2-one

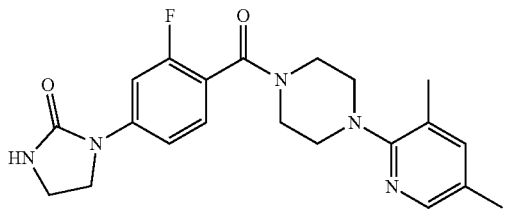 [SMILES: Cc1cnc(N2CCN(C(=O)c3ccc(N4CCNC4=O)cc3F)CC2)c(C)c1]

Using 1-acetyl-3-{4-[4-(3,5-dimethylpyridin-2-yl)piperazine-1-carbonyl]-3-fluorophenyl}imidazolidin-2-one (120 mg) described in Example 413 and by the reaction and treatment in the same manner as in Example 391, the title compound (106 mg) was obtained.

MS (ESI) m/z: 398(M+H)+.

Example 417

Synthesis of 1-acetyl-3-{5-[4-(5-cyclopropyl-3-methylpyridin-2-yl)piperazine-1-carbonyl]pyridin-2-yl}imidazolidin-2-one

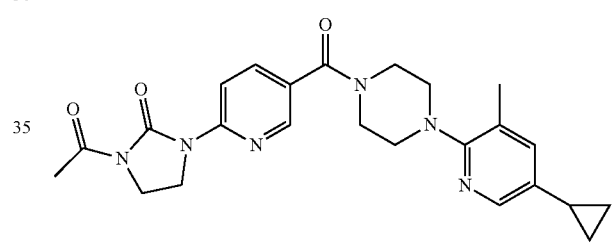

Using (6-bromopyridin-3-yl)[4-(5-cyclopropyl-3-methylpyridin-2-yl)piperazin-1-yl]methanone (241 mg) described in Preparation Example 144 and 1-acetylimidazolidin-2-one (115 mg) and by the reaction and treatment in the same manner as in Example 1, the title compound (151 mg) was obtained.

MS (ESI) m/z: 449(M+H)+.

Example 418

Synthesis of 1-{5-[4-(5-cyclopropyl-3-methylpyridin-2-yl)piperazine-1-carbonyl]pyridin-2-yl}-3-methylimidazolidin-2-one

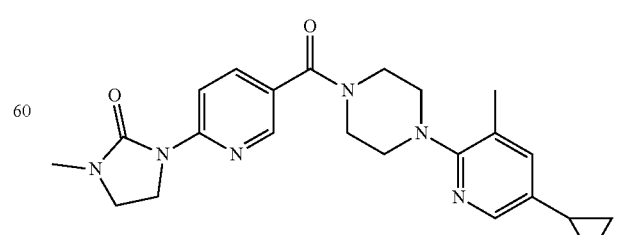

Using (6-bromopyridin-3-yl) [4-(5-cyclopropyl-3-methylpyridin-2-yl)piperazin-1-yl]methanone (241 mg) described in Preparation Example 144 and 1-methylimidazolidin-2-one (90 mg) and by the reaction and treatment in the same manner as in Example 1, the title compound (154 mg) was obtained.

MS (ESI) m/z: 421(M+H)⁺.

Example 419

Synthesis of 1-{5-[4-(5-cyclopropyl-3-methylpyridin-2-yl)piperazine-1-carbonyl]pyridin-2-yl}imidazolidin-2-one

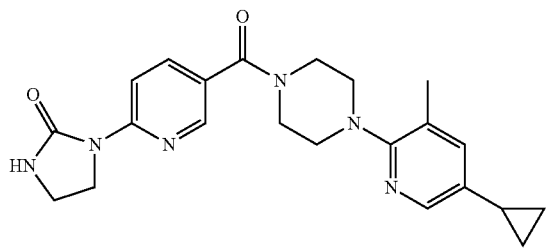

Using 1-acetyl-3-{5-[4-(5-cyclopropyl-3-methylpyridin-2-yl)piperazine-1-carbonyl]pyridin-2-yl}imidazolidin-2-one (120 mg) described in Example 417 and by the reaction and treatment in the same manner as in Example 391, the title compound (101 mg) was obtained.

MS (ESI) m/z: 407(M+H)⁺.

Example 420

Synthesis of 3-{4-[4-(3,5-dimethylpyridin-2-yl)piperazine-1-carbonyl]phenyl}-1-(4-methoxybenzyl)-4-methylimidazolidin-2-one

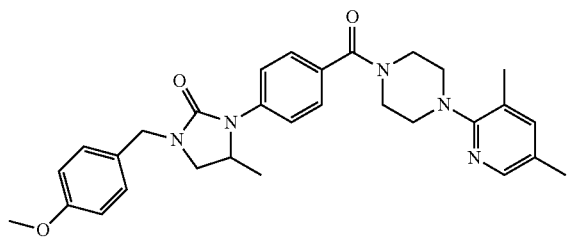

Using (4-bromophenyl)[4-(3,5-dimethylpyridin-2-yl)piperazin-1-yl]methanone (150 mg) described in Preparation Example 165 and 1-(4-methoxybenzyl)-4-methylimidazolidin-2-one (132 mg) described in Preparation Example 52 and by the reaction and treatment in the same manner as in Example 1, the title compound (130 mg) was obtained.

MS (ESI) m/z: 514(M+H)⁺.

Example 421

Synthesis of 1-{4-[4-(3,5-dimethylpyridin-2-yl)piperazine-1-carbonyl]phenyl}-5-methylimidazolidin-2-one

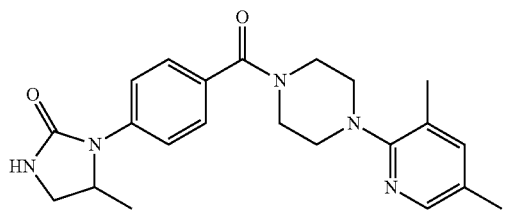 [SMILES: Cc1cnc(N2CCN(C(=O)c3ccc(N4C(=O)NCC4C)cc3)CC2)c(C)c1]

3-{4-[4-(3,5-dimethylpyridin-2-yl)piperazine-1-carbonyl]phenyl}-1-(4-methoxybenzyl)-4-methylimidazolidin-2-one (105 mg) described in Example 420 was dissolved in dichloromethane (1 mL), trifluoroacetic acid (2 mL) was added, and the mixture was stirred at room temperature overnight. The solvent was evaporated from the reaction mixture, 5% aqueous sodium hydrogen carbonate solution was added, and the mixture was extracted with chloroform/methanol (10/1). The organic layer was dried over sodium sulfate, and the solvent was evaporated. The obtained residue was suspension washing with IPE to give the title compound (86 mg).

MS (ESI) m/z: 394(M+H)⁺.

Example 422

Synthesis of 1-{4-[4-(3,5-dimethylpyridin-2-yl)piperazine-1-carbonyl]-3-methylphenyl}-3-methylimidazolidin-2-one

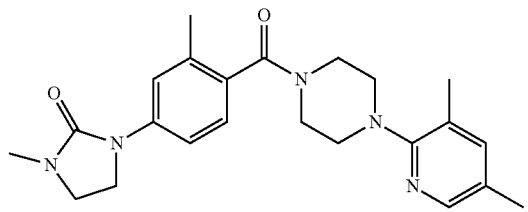

Using (4-bromo-2-methylphenyl) [4-(3,5-dimethylpyridin-2-yl)piperazin-1-yl]methanone (233 mg) described in Preparation Example 118 and 1-methylimidazolidin-2-one (90 mg) and by the reaction and treatment in the same manner as in Example 1, the title compound (203 mg) was obtained.

MS (ESI) m/z: 408(M+H)⁺.

Example 423

Synthesis of 1-{4-[4-(3,5-dimethylpyridin-2-yl)piperazine-1-carbonyl]-3-fluorophenyl}-3-methylimidazolidin-2-one

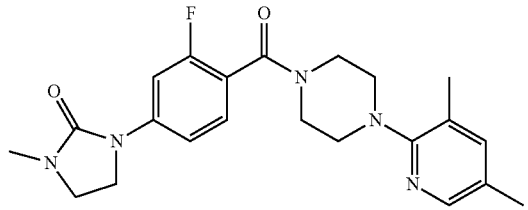

Using (4-bromo-2-fluorophenyl)[4-(3,5-dimethylpyridin-2-yl)piperazin-1-yl]methanone (235 mg) described in Preparation Example 114 and 1-methylimidazolidin-2-one (90 mg) and by the reaction and treatment in the same manner as in Example 1, the title compound (202 mg) was obtained.
MS (ESI) m/z: 412(M+H)⁺.

Example 424

Synthesis of 1-{4-[4-(3,5-dimethylpyridin-2-yl)piperazine-1-carbonyl]-3-methylphenyl}-5-methylimidazolidin-2-one

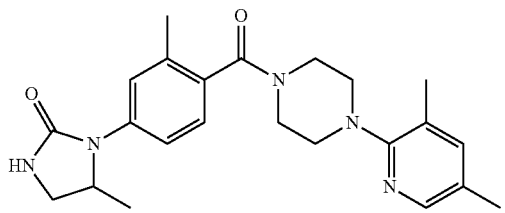 [SMILES: Cc1cnc(N2CCN(C(=O)c3ccc(N4C(=O)NCC4C)cc3C)CC2)c(C)c1]

Using (4-bromo-2-methylphenyl)[4-(3,5-dimethylpyridin-2-yl)piperazin-1-yl]methanone (155 mg) described in Preparation Example 118 and 1-(4-methoxybenzyl)-4-methylimidazolidin-2-one (132 mg) described in Preparation Example 52 and by the reaction and treatment in the same manner as in Example 1, 3-{4-[4-(3,5-dimethylpyridin-2-yl)piperazine-1-carbonyl]-3-methylphenyl}-1-(4-methoxybenzyl)-4-methylimidazolidin-2-one (90 mg) was obtained. Using the obtained 3-{4-[4-(3,5-dimethylpyridin-2-yl)piperazine-1-carbonyl]-3-methylphenyl}-1-(4-methoxybenzyl)-4-methylimidazolidin-2-one (90 mg) and by the reaction and treatment in the same manner as in Example 421, the title compound (53 mg) was obtained.
MS (ESI) m/z: 408(M+H)⁺.

Example 425

Synthesis of 1-{4-[4-(3,5-dimethylpyridin-2-yl)piperazine-1-carbonyl]-3-fluorophenyl}-5-methylimidazolidin-2-one

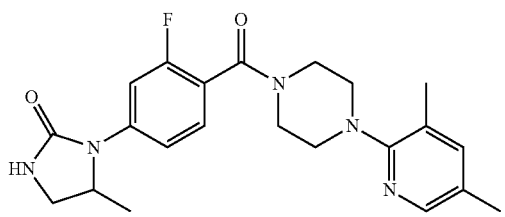 [SMILES: Cc1cnc(N2CCN(C(=O)c3ccc(N4C(=O)NCC4C)cc3F)CC2)c(C)c1]

Using (4-bromo-2-fluorophenyl)[4-(3,5-dimethylpyridin-2-yl)piperazin-1-yl]methanone (157 mg) described in Preparation Example 114 and 1-(4-methoxybenzyl)-4-methylimidazolidin-2-one (132 mg) described in Preparation Example 52 and by the reaction and treatment in the same manner as in Example 1, 3-{4-[4-(3,5-dimethylpyridin-2-yl)piperazine-1-carbonyl]-3-fluorophenyl}-1-(4-methoxybenzyl)-4-methylimidazolidin-2-one was obtained. Using the obtained 3-{4-[4-(3,5-dimethylpyridin-2-yl)piperazine-1-carbonyl]-3-fluorophenyl}-1-(4-methoxybenzyl)-4-methylimidazolidin-2-one and by the reaction and treatment in the same manner as in Example 421, the title compound (89 mg) was obtained.
MS (ESI) m/z: 412(M+H)⁺.

Example 426

Synthesis of 1-{5-[4-(3,5-dimethylpyridin-2-yl)piperazine-1-carbonyl]pyridin-2-yl}-5-methylimidazolidin-2-one

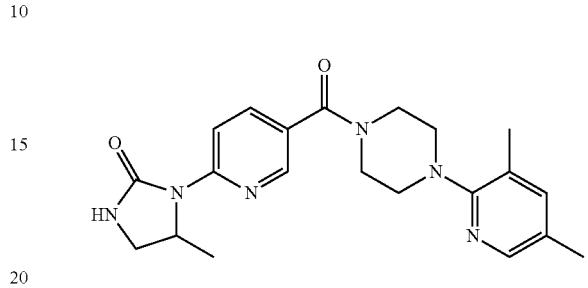

Using (6-bromopyridin-3-yl)[4-(3,5-dimethylpyridin-2-yl)piperazin-1-yl]methanone (150 mg) described in Preparation Example 127 and 1-(4-methoxybenzyl)-4-methylimidazolidin-2-one (106 mg) described in Preparation Example 52 and by the reaction and treatment in the same manner as in Example 1, 3-{5-[4-(3,5-dimethylpyridin-2-yl)piperazine-1-carbonyl]pyridin-2-yl}-1-(4-methoxybenzyl)-4-methylimidazolidin-2-one (132 mg) was obtained. The obtained 3-{5-[4-(3,5-dimethylpyridin-2-yl)piperazine-1-carbonyl]pyridin-2-yl}-1-(4-methoxybenzyl)-4-methylimidazolidin-2-one (132 mg) was dissolved in trifluoroacetic acid (2 mL), trifluoromethanesulfonic acid (0.11 mL) was added, and the mixture was stirred at room temperature for 30 min. To the reaction mixture was added 5% aqueous sodium hydrogen carbonate solution, and the solvent was evaporated, and the mixture was extracted with ethyl acetate. The organic layer was washed with 5% aqueous sodium hydrogen carbonate solution and saturated brine, and the solvent was evaporated. The obtained residue was purified by silica gel column chromatography (ethyl acetate:methanol) to give the title compound (83 mg).
MS (ESI) m/z: 395(M+H)⁺.

Example 427

Synthesis of 1-{4-[4-(3,5-dimethylpyridin-2-yl)piperazine-1-carbonyl]phenyl}-5,5-dimethylimidazolidin-2-one

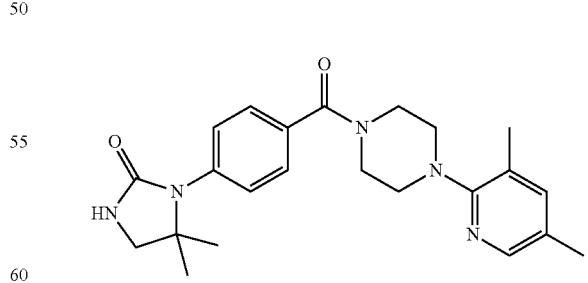

Using (4-bromophenyl) [4-(3,5-dimethylpyridin-2-yl)piperazin-1-yl]methanone (150 mg) described in Preparation Example 165 and 1-(4-methoxybenzyl)-4,4-dimethylimidazolidin-2-one (112 mg) described in Preparation Example 54 and by the reaction and treatment in the same manner as in Example 426, the title compound (57 mg) was obtained via 3-{4-[4-(3,5-dimethylpyridin-2-yl)piperazine-1-carbonyl]phenyl}-1-(4-methoxybenzyl)-4,4-dimethylimidazolidin-2-one.

MS (ESI) m/z: 408(M+H)⁺.

Example 428

Synthesis of 1-{5-[4-(3,5-dimethylpyridin-2-yl)piperazine-1-carbonyl]pyridin-2-yl}-5,5-dimethylimidazolidin-2-one

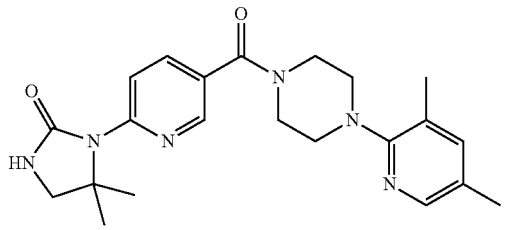 [SMILES: Cc1cnc(N2CCN(C(=O)c3ccc(N4C(=O)NCC4(C)C)nc3)CC2)c(C)c1]

Using (6-bromopyridin-3-yl)[4-(3,5-dimethylpyridin-2-yl)piperazin-1-yl]methanone (150 mg) described in Preparation Example 127 and 1-(4-methoxybenzyl)-4,4-dimethylimidazolidin-2-one (112 mg) described in Preparation Example 54 and by the reaction and treatment in the same manner as in Example 426, the title compound (56 mg) was obtained via 3-{5-[4-(3,5-dimethylpyridin-2-yl)piperazine-1-carbonyl]pyridin-2-yl}-1-(4-methoxybenzyl)-4,4-dimethylimidazolidin-2-one (119 mg).

MS (ESI) m/z: 409(M+H)⁺.

Example 429

Synthesis of 3-benzoyl-1-{4-[4-(3,5-dimethylpyridin-2-yl)piperazine-1-carbonyl]phenyl}-4-methylimidazolidin-2-one

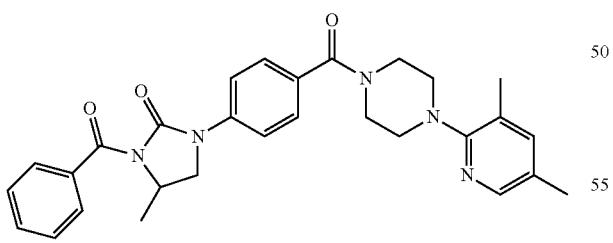

Using (4-bromophenyl)[4-(3,5-dimethylpyridin-2-yl)piperazin-1-yl]methanone (150 mg) described in Preparation Example 165 and 1-benzoyl-5-methylimidazolidin-2-one (98 mg) described in Preparation Example 56 and by the reaction and treatment in the same manner as in Example 1, the title compound (32 mg) was obtained.

MS (ESI) m/z: 498(M+H)⁺.

Example 430

Synthesis of 1-{4-[4-(3,5-dimethylpyridin-2-yl)piperazine-1-carbonyl]phenyl}-4-methylimidazolidin-2-one

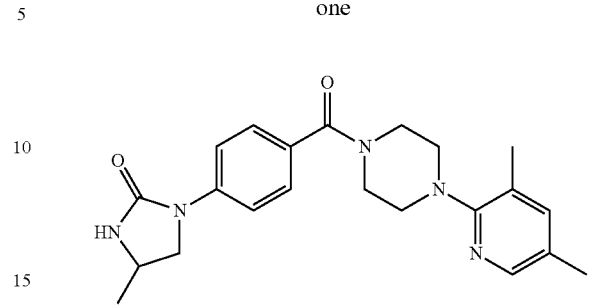

Using 3-benzoyl-1-{4-[4-(3,5-dimethylpyridin-2-yl)piperazine-1-carbonyl]phenyl}-4-methylimidazolidin-2-one (32 mg) described in Example 429 and by the reaction and treatment in the same manner as in Example 391, the title compound (18 mg) was obtained.

MS (ESI) m/z: 394(M+H)⁺.

Example 431

Synthesis of 3-benzoyl-1-{4-[4-(3,5-dimethylpyridin-2-yl)piperazine-1-carbonyl]phenyl}-4,4-dimethylimidazolidin-2-one

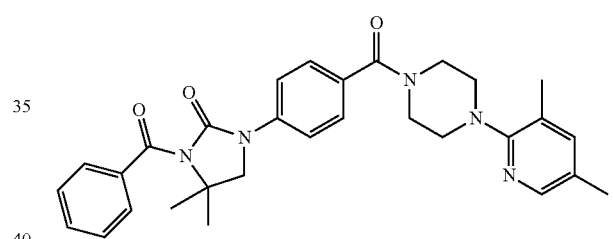

Using (4-bromophenyl)[4-(3,5-dimethylpyridin-2-yl)piperazin-1-yl]methanone (150 mg) described in Preparation Example 165 and 1-benzoyl-5,5-dimethylimidazolidin-2-one (105 mg) described in Preparation Example 58 and by the reaction and treatment in the same manner as in Example 1, the title compound (115 mg) was obtained.

MS (ESI) m/z: 512(M+H)⁺.

Example 432

Synthesis of 1-{4-[4-(3,5-dimethylpyridin-2-yl)piperazine-1-carbonyl]phenyl}-4,4-dimethylimidazolidin-2-one

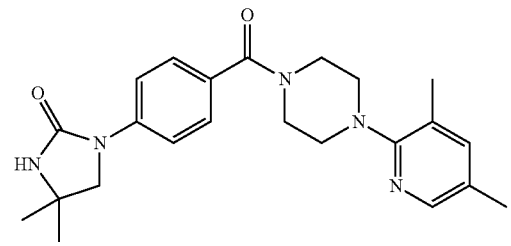

Using 3-benzoyl-1-{4-[4-(3,5-dimethylpyridin-2-yl)piperazine-1-carbonyl]phenyl}-4,4-dimethylimidazolidin-2-one (113 mg) described in Example 431 and by the reaction and treatment in the same manner as in Example 391, the title compound (73 mg) was obtained.

MS (ESI) m/z: 408(M+H)$^+$.

Example 433

Synthesis of 5-(3-acetyl-2-oxoimidazolidin-1-yl)-2-[4-(3,5-dimethylpyridin-2-yl)piperazine-1-carbonyl]benzonitrile

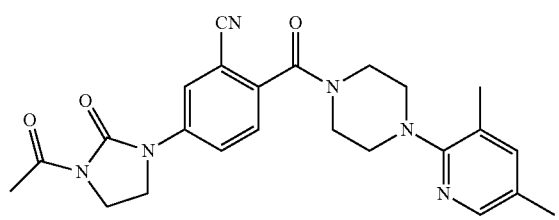 [SMILES: CC(=O)N1CCN(c2ccc(C(=O)N3CCN(c4ncc(C)cc4C)CC3)c(C#N)c2)C1=O]

Using 5-bromo-2-[4-(3,5-dimethylpyridin-2-yl)piperazine-1-carbonyl]benzonitrile (1.2 g) described in Preparation Example 187 and 1-acetylimidazolidin-2-one (461 mg) and by the reaction and treatment in the same manner as in Example 1, the title compound (919 mg) was obtained.

MS (ESI) m/z: 447(M+H)$^+$.

Example 434

Synthesis of 2-[4-(3,5-dimethylpyridin-2-yl)piperazine-1-carbonyl]-5-(2-oxoimidazolidin-1-yl)benzonitrile

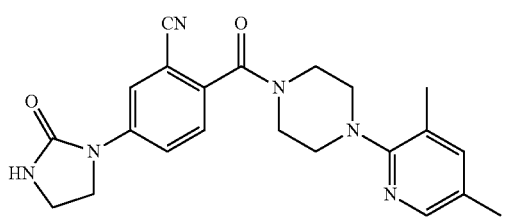 [SMILES: Cc1cnc(N2CCN(C(=O)c3ccc(N4CCNC4=O)cc3C#N)CC2)c(C)c1]

Using 5-(3-acetyl-2-oxoimidazolidin-1-yl)-2-[4-(3,5-dimethylpyridin-2-yl)piperazine-1-carbonyl]benzonitrile (713 mg) described in Example 433 and by the reaction and treatment in the same manner as in Example 391, the title compound (526 mg) was obtained.

MS (ESI) m/z: 405(M+H)$^+$.

Example 435

Synthesis of 5-(3-acetyl-2-oxoimidazolidin-1-yl)-2-[4-(2,4-dimethylphenyl)piperazine-1-carbonyl]benzonitrile

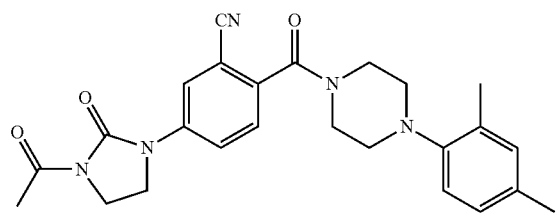 [SMILES: CC(=O)N1CCN(c2ccc(C(=O)N3CCN(c4ccc(C)cc4C)CC3)c(C#N)c2)C1=O]

Using 5-bromo-2-[4-(2,4-dimethylphenyl)piperazine-1-carbonyl]benzonitrile (996 mg) described in Preparation Example 188 and 1-acetylimidazolidin-2-one (384 mg) and by the reaction and treatment in the same manner as in Example 1, the title compound (679 mg) was obtained.

MS (ESI) m/z: 446(M+H)$^+$.

Example 436

Synthesis of 2-[4-(3,5-dimethylpyridin-2-yl)piperazine-1-carbonyl]-5-(3-methyl-2-oxoimidazolidin-1-yl)benzonitrile

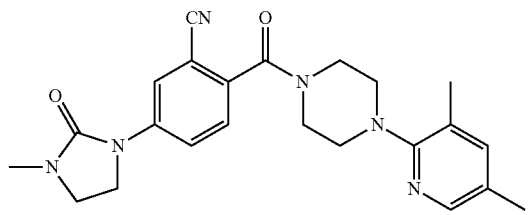

Using 5-bromo-2-[4-(3,5-dimethylpyridin-2-yl)piperazine-1-carbonyl]benzonitrile (399 mg) described in Preparation Example 187 and 1-methylimidazolidin-2-one (120 mg) and by the reaction and treatment in the same manner as in Example 1, the title compound (323 mg) was obtained.

MS (ESI) m/z: 419(M+H)$^+$.

Example 437

Synthesis of 2-[4-(2,4-dimethylphenyl)piperazine-1-carbonyl]-5-(2-oxoimidazolidin-1-yl)benzonitrile

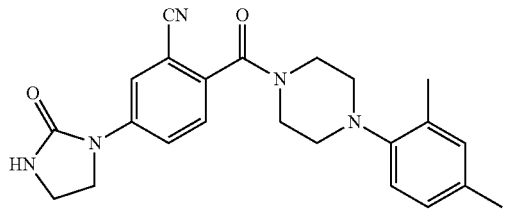 [SMILES: Cc1ccc(N2CCN(C(=O)c3ccc(N4CCNC4=O)cc3C#N)CC2)c(C)c1]

Using 5-(3-acetyl-2-oxoimidazolidin-1-yl)-2-[4-(2,4-dimethylphenyl)piperazine-1-carbonyl]benzonitrile (468 mg) described in Example 435 and by the reaction and treatment in the same manner as in Example 391, the title compound (193 mg) was obtained.

MS (ESI) m/z: 404(M+H)⁺.

Example 438

Synthesis of 5-(3-acetyl-2-oxoimidazolidin-1-yl)-2-[4-(5-cyclopropyl-3-methylpyridin-2-yl)piperazine-1-carbonyl]benzonitrile

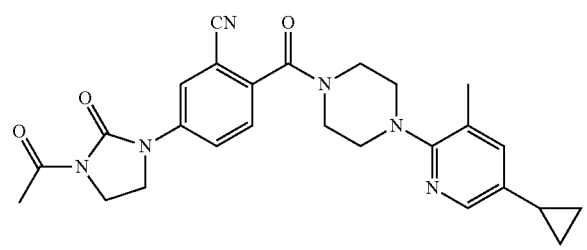 [SMILES: CC(=O)N1CCN(c2ccc(C(=O)N3CCN(c4ncc(C5CC5)cc4C)CC3)c(C#N)c2)C1=O]

Using 5-bromo-2-[4-(5-cyclopropyl-3-methylpyridin-2-yl)piperazine-1-carbonyl]benzonitrile (1.06 g) described in Preparation Example 189 and 1-acetylimidazolidin-2-one (384 mg) and by the reaction and treatment in the same manner as in Example 1, the title compound (494 mg) was obtained.

MS (ESI) m/z: 473(M+H)⁺.

Example 439

Synthesis of 2-[4-(2,4-dimethylphenyl)piperazine-1-carbonyl]-5-(3-methyl-2-oxoimidazolidin-1-yl)benzonitrile

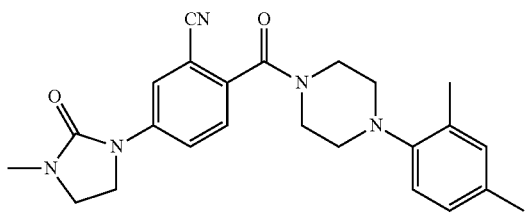

Using 5-bromo-2-[4-(2,4-dimethylphenyl)piperazine-1-carbonyl]benzonitrile (398 mg) described in Preparation Example 188 and 1-methylimidazolidin-2-one (120 mg) and by the reaction and treatment in the same manner as in Example 1, the title compound (349 mg) was obtained.

MS (ESI) m/z: 418(M+H)⁺.

Example 440

Synthesis of 2-[4-(5-cyclopropyl-3-methylpyridin-2-yl)piperazine-1-carbonyl]-5-(3-methyl-2-oxoimidazolidin-1-yl)benzonitrile

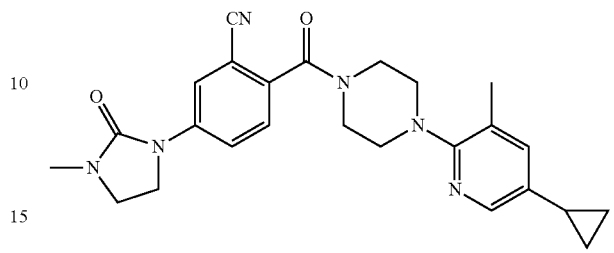

Using 5-bromo-2-[4-(5-cyclopropyl-3-methylpyridin-2-yl)piperazine-1-carbonyl]benzonitrile (425 mg) described in Preparation Example 189 and 1-methylimidazolidin-2-one (120 mg) and by the reaction and treatment in the same manner as in Example 1, the title compound (364 mg) was obtained.

MS (ESI) m/z: 445(M+H)⁺.

Example 441

Synthesis of 2-[4-(5-cyclopropyl-3-methylpyridin-2-yl)piperazine-1-carbonyl]-5-(2-oxoimidazolidin-1-yl)benzonitrile

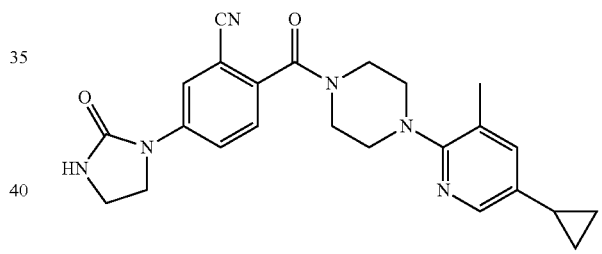

Using 5-(3-acetyl-2-oxoimidazolidin-1-yl)-2-[4-(5-cyclopropyl-3-methylpyridin-2-yl)piperazine-1-carbonyl]benzonitrile (378 mg) described in Example 438 and by the reaction and treatment in the same manner as in Example 391, the title compound (252 mg) was obtained.

MS (ESI) m/z: 431(M+H)⁺.

Example 442

Synthesis of 2-[4-(3,5-dimethylpyridin-2-yl)piperazine-1-carbonyl]-5-[3-(2-methoxyethyl)-2-oxoimidazolidin-1-yl]benzonitrile

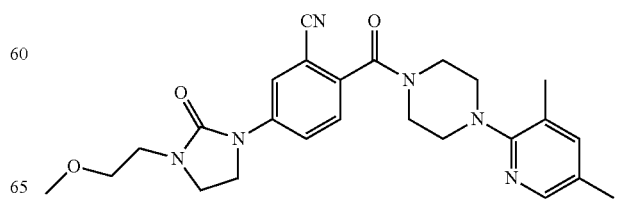

Using 2-[4-(3,5-dimethylpyridin-2-yl)piperazine-1-carbonyl]-5-(2-oxoimidazolidin-1-yl)benzonitrile (399 mg) described in Example 434 and 1-bromo-2-methoxyethane (165 mg) and by the reaction and treatment in the same manner as in Example 36, the title compound (337 mg) was obtained.

MS (ESI) m/z: 463(M+H)$^+$.

Example 443

Synthesis of 5-(3-methyl-2-oxoimidazolidin-1-yl)-2-[4-(3,5,6-trimethylpyridin-2-yl)piperazine-1-carbonyl]benzonitrile

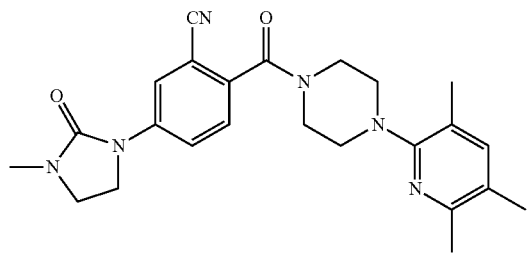

Using 5-bromo-2-[4-(3,5,6-trimethylpyridin-2-yl)piperazine-1-carbonyl]benzonitrile (413 mg) described in Preparation Example 172 and 1-methylimidazolidin-2-one (120 mg) and by the reaction and treatment in the same manner as in Example 1, the title compound (378 mg) was obtained.

MS (ESI) m/z: 433(M+H)$^+$.

Example 444

Synthesis of 5-(3-acetyl-2-oxoimidazolidin-1-yl)-2-[4-(3,5,6-trimethylpyridin-2-yl)piperazine-1-carbonyl]benzonitrile

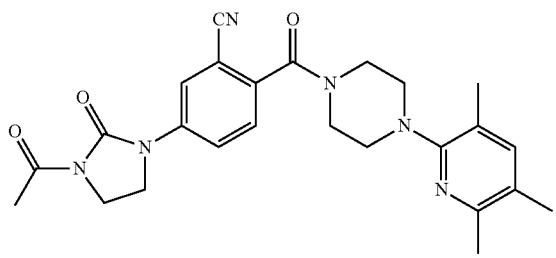 [SMILES: CC(=O)N1CCN(c2ccc(C(=O)N3CCN(c4nc(C)c(C)cc4C)CC3)c(C#N)c2)C1=O]

Using 5-bromo-2-[4-(3,5,6-trimethylpyridin-2-yl)piperazine-1-carbonyl]benzonitrile (1.24 g) described in Preparation Example 172 and 1-acetylimidazolidin-2-one (461 mg) and by the reaction and treatment in the same manner as in Example 1, the title compound (1.14 g) was obtained.

MS (ESI) m/z: 461(M+H)$^+$.

Example 445

Synthesis of 5-(2-oxoimidazolidin-1-yl)-2-[4-(3,5,6-trimethylpyridin-2-yl)piperazine-1-carbonyl]benzonitrile

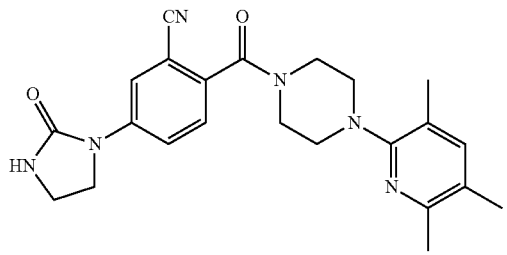 [SMILES: Cc1cc(C)c(N2CCN(C(=O)c3ccc(N4CCNC4=O)cc3C#N)CC2)nc1C]

Using 5-(3-acetyl-2-oxoimidazolidin-1-yl)-2-[4-(3,5,6-trimethylpyridin-2-yl)piperazine-1-carbonyl]benzonitrile (921 mg) described in Example 444 and by the reaction and treatment in the same manner as in Example 391, the title compound (743 mg) was obtained.

MS (ESI) m/z: 419(M+H)$^+$.

Example 446

Synthesis of 1-{4-[4-(3,5-dimethylpyridin-2-yl)piperazine-1-carbonyl]phenyl}tetrahydropyrimidin-2-one

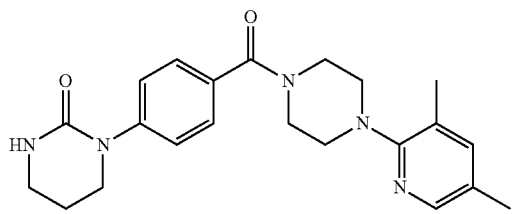 [SMILES: Cc1cnc(N2CCN(C(=O)c3ccc(N4CCCNC4=O)cc3)CC2)c(C)c1]

Using ethyl 4-(2-oxotetrahydropyrimidin-1-yl)benzoate (84 mg) described in Preparation Example 60 and 1-(3,5-dimethylpyridin-2-yl)piperazine (65 mg) described in Preparation Example 79 and by the reaction and treatment in the same manner as in Example 109, the title compound (103 mg) was obtained.

MS (ESI) m/z: 394(M+H)$^+$.

Example 447

Synthesis of 1-{4-[4-(3,5-dimethylpyridin-2-yl)piperazine-1-carbonyl]phenyl}-3-methyltetrahydropyrimidin-2-one

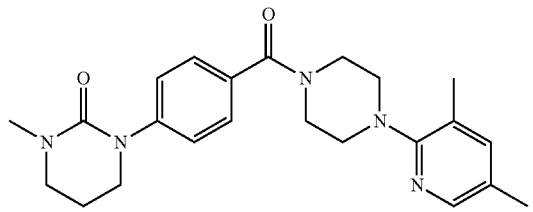

Using 1-{4-[4-(3,5-dimethylpyridin-2-yl)piperazine-1-carbonyl]phenyl}tetrahydropyrimidin-2-one (78 mg) described in Example 446 and methyl iodide (14 μL) and by the reaction and treatment in the same manner as in Example 36, the title compound (49 mg) was obtained.

MS (ESI) m/z: 408(M+H)⁺.

Example 448

Synthesis of 1-{4-[4-(3,5-dimethylpyridin-2-yl)piperazine-1-carbonyl]phenyl}-3-(4-methoxybenzyl)-5-methylimidazolidine-2,4-dione

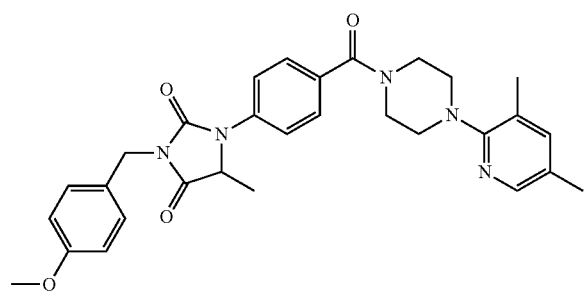

Using (4-bromophenyl)[4-(3,5-dimethylpyridin-2-yl)piperazin-1-yl]methanone (150 mg) described in Preparation Example 165 and 3-(4-methoxybenzyl)-5-methylimidazolidine-2,4-dione (141 mg) described in Preparation Example 51 and by the reaction and treatment in the same manner as in Example 1, the title compound (183 mg) was obtained.

MS (ESI) m/z: 528(M+H)⁺.

Example 449

Synthesis of 3-{4-[4-(3,5-dimethylpyridin-2-yl)piperazine-1-carbonyl]phenyl}-5-methylimidazolidine-2,4-dione

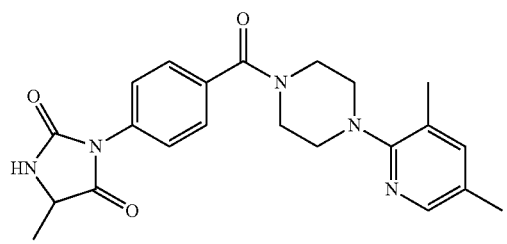 [SMILES: Cc1cnc(N2CCN(C(=O)c3ccc(N4C(=O)NC(C)C4=O)cc3)CC2)c(C)c1]

Using (4-bromophenyl) [4-(3,5-dimethylpyridin-2-yl)piperazin-1-yl]methanone (150 mg) described in Preparation Example 165 and 5-methylimidazolidine-2,4-dione (55 mg) and by the reaction and treatment in the same manner as in Example 1, the title compound (33 mg) was obtained.

MS (ESI) m/z: 408(M+H)⁺.

Example 450

Synthesis of 1-{4-[4-(3,5-dimethylpyridin-2-yl)piperazine-1-carbonyl]phenyl}-5-methylimidazolidine-2,4-dione

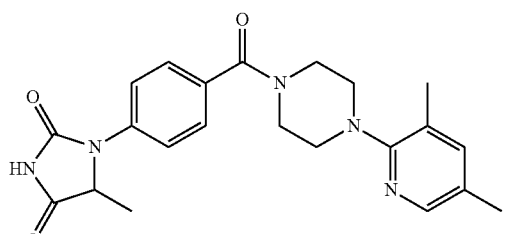

1-{4-[4-(3,5-Dimethylpyridin-2-yl)piperazine-1-carbonyl]phenyl}-3-(4-methoxybenzyl)-5-methylimidazolidine-2,4-dione (172 mg) described in Example 448 was dissolved in 1,2-dichloroethane (5 mL), trifluoromethanesulfonic acid (0.18 mL) was added, and the mixture was stirred at 80° C. for 30 min. To the reaction mixture was added 5% aqueous sodium hydrogen carbonate solution, and the mixture was extracted with chloroform/methanol (10:1). The organic layer was dried over sodium sulfate, and the solvent was evaporated. The obtained residue was purified by silica gel column chromatography (ethyl acetate:methanol) to give the title compound (92 mg).

MS (ESI) m/z: 408(M+H)⁺.

Example 451

Synthesis of 1-{4-[4-(3,5-dimethylpyridin-2-yl)piperazine-1-carbonyl]phenyl}-3,5-dimethylimidazolidine-2,4-dione

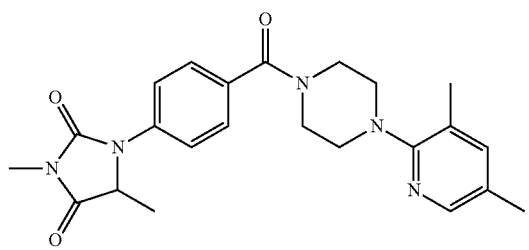

Using 1-{4-[4-(3,5-dimethylpyridin-2-yl)piperazine-1-carbonyl]phenyl}-5-methylimidazolidine-2,4-dione (50 mg) described in Example 450 and methyl iodide (9.2 μL) and by the reaction and treatment in the same manner as in Example 36, the title compound (26 mg) was obtained.

MS (ESI) m/z: 422(M+H)⁺.

Example 452

Synthesis of 3-{4-[4-(3,5-dimethylpyridin-2-yl)piperazine-1-carbonyl]benzyl}oxazolidin-2-one

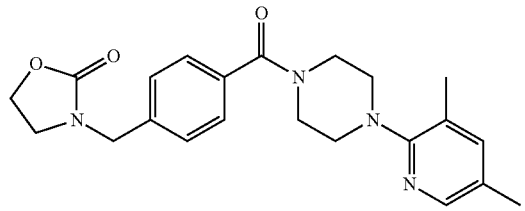 [SMILES: Cc1cnc(N2CCN(C(=O)c3ccc(CN4CCOC4=O)cc3)CC2)c(C)c1]

Using 4-(2-oxooxazolidin-3-ylmethyl)benzoic acid (133 mg) described in Preparation Example 62 and 1-(3,5-dimethylpyridin-2-yl)piperazine (115 mg) described in Preparation Example 79 and by the reaction and treatment in the same manner as in Example 87, the title compound (206 mg) was obtained.
MS (ESI) m/z: 395(M+H)$^+$.

Example 453

Synthesis of 3-{4-[4-(5-cyclopropyl-3-methylpyridin-2-yl)piperazine-1-carbonyl]benzyl}oxazolidin-2-one

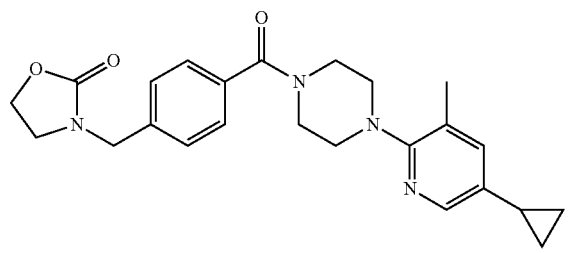

Using 4-(2-oxooxazolidin-3-ylmethyl)benzoic acid (133 mg) described in Preparation Example 62 and 1-(5-cyclopropyl-3-methylpyridin-2-yl)piperazine (156 mg) described in Preparation Example 83 and by the reaction and treatment in the same manner as in Example 87, the title compound (107 mg) was obtained.
MS (ESI) m/z: 421(M+H)$^+$.

Example 454

Synthesis of 3-(1-{4-[4-(3,5-dimethylpyridin-2-yl)piperazine-1-carbonyl]phenyl}cyclopropyl)oxazolidin-2-one

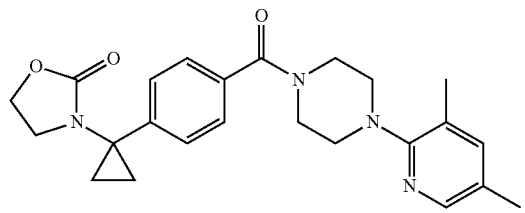 [SMILES: Cc1cnc(N2CCN(C(=O)c3ccc(C4(N5CCOC5=O)CC4)cc3)CC2)c(C)c1]

Using methyl 4-[1-(2-oxooxazolidin-3-yl)cyclopropyl]benzoate (52 mg) described in Preparation Example 69 and 1-(3,5-dimethylpyridin-2-yl)piperazine (38 mg) described in Preparation Example 79 and by the reaction and treatment in the same manner as in Example 109, the title compound (56 mg) was obtained.
MS (ESI) m/z: 421(M+H)$^+$.

Example 455

Synthesis of (R)-3-{4-[4-(3,5-dimethylpyridin-2-yl)piperazine-1-carbonyl]benzyl}-4-methyloxazolidin-2-one

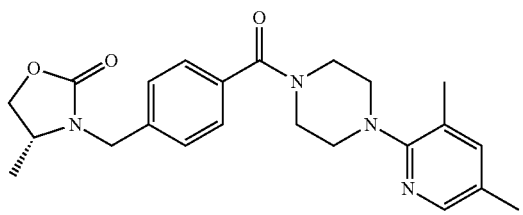 [SMILES: Cc1cnc(N2CCN(C(=O)c3ccc(CN4C(=O)OC[C@H]4C)cc3)CC2)c(C)c1]

Using (R)-4-(4-methyl-2-oxooxazolidin-3-ylmethyl)benzoic acid (141 mg) described in Preparation Example 64 and 1-(3,5-dimethylpyridin-2-yl)piperazine (126 mg) described in Preparation Example 79 and by the reaction and treatment in the same manner as in Example 87, the title compound (212 mg) was obtained.
MS (ESI) m/z: 409(M+H)$^+$.

Example 456

Synthesis of (R)-3-{4-[4-(5-cyclopropyl-3-methylpyridin-2-yl)piperazine-1-carbonyl]benzyl}-4-methyloxazolidin-2-one

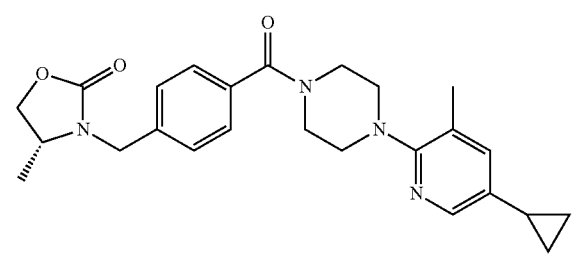 [SMILES: Cc1cc(C2CC2)cnc1N1CCN(C(=O)c2ccc(CN3C(=O)OC[C@H]3C)cc2)CC1]

Using (R)-4-(4-methyl-2-oxooxazolidin-3-ylmethyl)benzoic acid (141 mg) described in Preparation Example 64 and 1-(5-cyclopropyl-3-methylpyridin-2-yl)piperazine (156 mg) described in Preparation Example 83 and by the reaction and treatment in the same manner as in Example 87, the title compound (91 mg) was obtained.
MS (ESI) m/z: 435(M+H)$^+$.

Example 457

Synthesis of (S)-3-{4-[4-(3,5-dimethylpyridin-2-yl)piperazine-1-carbonyl]benzyl}-4-methyloxazolidin-2-one

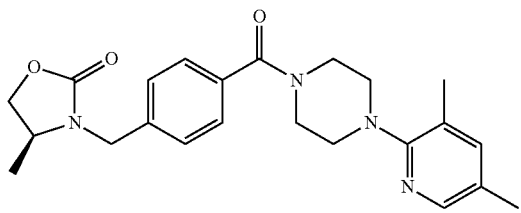 [SMILES: Cc1cnc(N2CCN(C(=O)c3ccc(CN4C(=O)OC[C@@H]4C)cc3)CC2)c(C)c1]

Using (S)-4-(4-methyl-2-oxooxazolidin-3-ylmethyl)benzoic acid (141 mg) described in Preparation Example 66 and 1-(3,5-dimethylpyridin-2-yl)piperazine (126 mg) described in Preparation Example 79 and by the reaction and treatment in the same manner as in Example 87, the title compound (234 mg) was obtained.

MS (ESI) m/z: 409(M+H)$^+$.

Example 458

Synthesis of (S)-3-{4-[4-(5-cyclopropyl-3-methylpyridin-2-yl)piperazine-1-carbonyl]benzyl}-4-methyloxazolidin-2-one

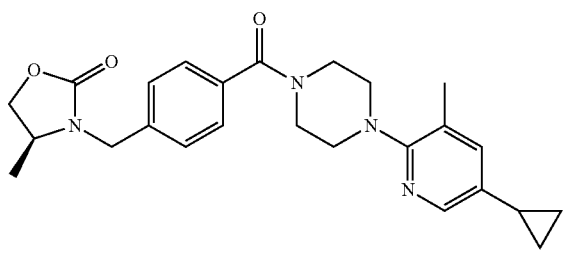 [SMILES: Cc1cc(C2CC2)cnc1N1CCN(C(=O)c2ccc(CN3C(=O)OC[C@@H]3C)cc2)CC1]

Using (S)-4-(4-methyl-2-oxooxazolidin-3-ylmethyl)benzoic acid (141 mg) described in Preparation Example 66 and 1-(5-cyclopropyl-3-methylpyridin-2-yl)piperazine (143 mg) described in Preparation Example 83 and by the reaction and treatment in the same manner as in Example 87, the title compound (212 mg) was obtained.

MS (ESI) m/z: 435(M+H)$^+$.

Example 459

Synthesis of 3-{4-[4-(3,5-dimethylpyridin-2-yl)piperazine-1-carbonyl]phenyl}-[1,3]oxazinan-2-one

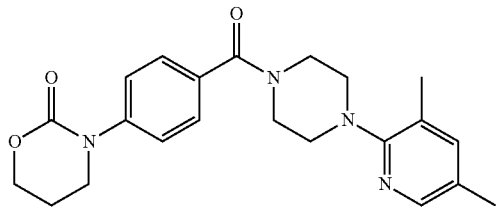 [SMILES: Cc1cnc(N2CCN(C(=O)c3ccc(N4CCCOC4=O)cc3)CC2)c(C)c1]

Using 4-(2-oxo[1,3]oxazinan-3-yl)benzoic acid (111 mg) and 1-(3,5-dimethylpyridin-2-yl)piperazine (96 mg) described in Preparation Example 79 and by the reaction and treatment in the same manner as in Example 87, the title compound (171 mg) was obtained.

MS (ESI) m/z: 395(M+H)$^+$.

Example 460

Synthesis of 3-{4-[4-(5-cyclopropyl-3-methylpyridin-2-yl)piperazine-1-carbonyl]phenyl}-[1,3]oxazinan-2-one

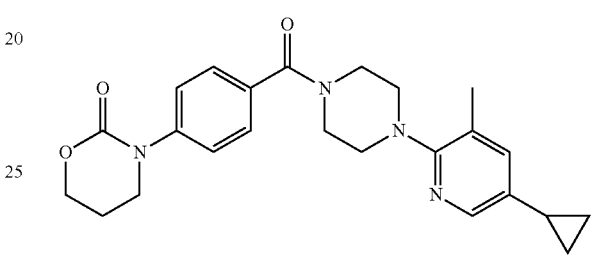

Using 4-(2-oxo[1,3]oxazinan-3-yl)benzoic acid (111 mg) and 1-(5-cyclopropyl-3-methylpyridin-2-yl)piperazine (109 mg) described in Preparation Example 83 and by the reaction and treatment in the same manner as in Example 87, the title compound (157 mg) was obtained.

MS (ESI) m/z: 421(M+H)$^+$.

Example 461

Synthesis of [2-bromo-4-(1,1-dioxo-1$\lambda^6$-isothiazolidin-2-ylmethyl)phenyl][4-(3,5-dimethylpyridin-2-yl)piperazin-1-yl]methanone

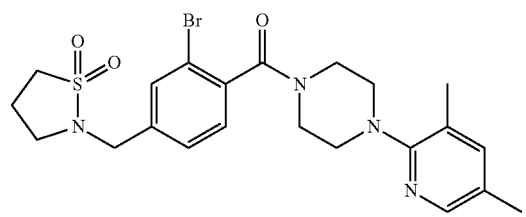

Using methyl 2-bromo-4-(1,1-dioxo-1$\lambda^6$-isothiazolidin-2-ylmethyl)benzoate (312 mg) described in Preparation Example 177 and 1-(3,5-dimethylpyridin-2-yl)piperazine (171 mg) described in Preparation Example 79 and by the reaction and treatment in the same manner as in Example 109, the title compound (384 mg) was obtained.

MS (ESI) m/z: 507(M+H)$^+$.

Example 462

Synthesis of N-{4-[4-(2,4-dimethylphenyl)piperazine-1-carbonyl]phenyl}-N-methylmethanesulfonamide

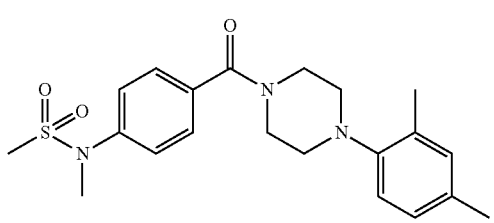

Using N-{4-[4-(2,4-dimethylphenyl)piperazine-1-carbonyl]phenyl}methanesulfonamide (194 mg) described in Example 461 and methyl iodide (34 µL) and by the reaction and treatment in the same manner as in Example 36, the title compound (57 mg) was obtained.

MS (ESI) m/z: 402(M+H)$^+$.

Example 463

Synthesis of N-{4-[4-(2,4-dimethylphenyl)piperazine-1-carbonyl]phenyl}-N-(2-hydroxyethyl)methanesulfonamide

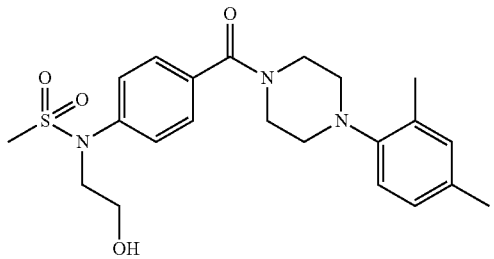

Using N-{4-[4-(2,4-dimethylphenyl)piperazine-1-carbonyl]phenyl}methanesulfonamide (271 mg) described in Example 461 and 2-(2-bromoethoxy)tetrahydropyran (1.21 mL) and by the reaction and treatment in the same manner as in Example 36, N-{4-[4-(2,4-dimethylphenyl)piperazine-1-carbonyl]phenyl}-N-[2-(tetrahydropyran-2-yloxy)ethyl]methanesulfonamide was obtained. The obtained N-{4-[4-(2,4-dimethylphenyl)piperazine-1-carbonyl]phenyl}-N-[2-(tetrahydropyran-2-yloxy)ethyl]methanesulfonamide was dissolved in methanol (5 mL), p-toluenesulfonic acid 1 hydrate (121 mg) was added, and the mixture was stirred at room temperature. To the reaction mixture was added 1N aqueous sodium hydroxide solution, and the mixture was extracted with ethyl acetate. The organic layer was washed with saturated brine, and the solvent was evaporated. The obtained residue was purified by column chromatography (chloroform:methanol) to give the title compound (185 mg).

MS (ESI) m/z: 432(M+H)$^+$.

Example 464

Synthesis of N-{4-[4-(2,4-dimethylphenyl)piperazine-1-carbonyl]phenyl}-N-(3-hydroxypropyl)methanesulfonamide

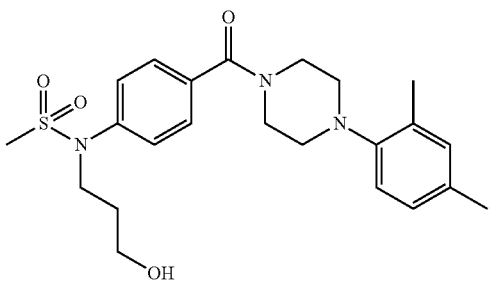

Using N-{4-[4-(2,4-dimethylphenyl)piperazine-1-carbonyl]phenyl}methanesulfonamide (271 mg) described in Example 461 and 2-(3-bromopropoxy)tetrahydropyran (0.6 mL) and by the reaction and treatment in the same manner as in Example 463, the title compound (41 mg) was obtained.

MS (ESI) m/z: 446(M+H)$^+$.

Example 465

Synthesis of N-{4-[4-(3,5-dimethylpyridin-2-yl)piperazine-1-carbonyl]phenyl}methanesulfonamide

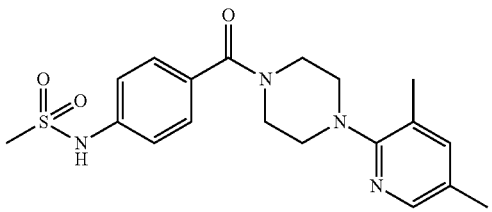

Using 4-methanesulfonylaminobenzoic acid (226 mg) and 1-(3,5-dichloropyridin-2-yl)piperazine (244 mg) and by the reaction and treatment in the same manner as in Example 87, N-{4-[4-(3,5-dichloropyridin-2-yl)piperazine-1-carbonyl]phenyl}methanesulfonamide (425 mg) was obtained. Using the obtained N-{4-[4-(3,5-dichloropyridin-2-yl)piperazine-1-carbonyl]phenyl}methanesulfonamide (425 mg) and methylboronic acid (504 mg) and by the reaction and treatment in the same manner as in Example 115, the title compound (91 mg) was obtained.

MS (ESI) m/z: 389(M+H)$^+$.

Example 466

Synthesis of N-{4-[4-(3,5-dimethylpyridin-2-yl)piperazine-1-carbonyl]phenyl}-N-methylmethanesulfonamide

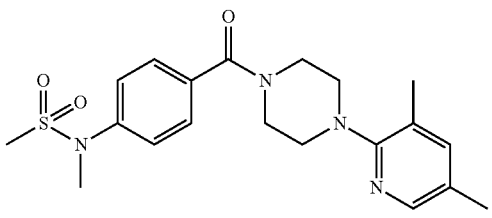

Using N-{4-[4-(3,5-dimethylpyridin-2-yl)piperazine-1-carbonyl]phenyl}methanesulfonamide (259.2 mg) described in Example 465 and methyl iodide (65 μL) and by the reaction and treatment in the same manner as in Example 36, the title compound (187 mg) was obtained.

MS (ESI) m/z: 403(M+H)$^+$.

Example 467

Synthesis of N,N-dimethyl-N'—(4-{[4-(3,5-dimethylpyridin-2-yl)piperazin-1-yl]carbonyl}phenyl)sulfamide hydrochloride

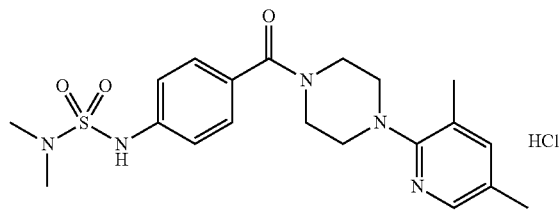

Using ethyl 4-{[(dimethylamino)sulfonyl]amino} benzoate (114 mg) and 1-(3,5-dimethylpyridin-2-yl)piperazine (80 mg) described in Preparation Example 79 and by the reaction and treatment in the same manner as in Example 206, the title compound (78 mg) was obtained.

MS (ESI) m/z: 418(M+H)$^+$.

Example 468

Synthesis of N-{4-[4-(3,5-dimethylpyridin-2-yl)piperazine-1-carbonyl]benzyl}methanesulfonamide

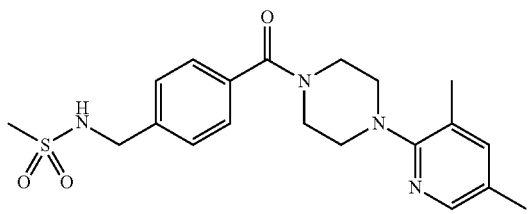

Using 4-(methanesulfonylaminomethyl)benzoic acid (183 mg) and 1-(3,5-dimethylpyridin-2-yl)piperazine (153 mg) described in Preparation Example 79 and by the reaction and treatment in the same manner as in Example 87, the title compound (260 mg) was obtained.

MS (ESI) m/z: 403(M+H)$^+$.

Example 469

Synthesis of N-{4-[4-(5-cyclopropyl-3-methylpyridin-2-yl)piperazine-1-carbonyl]benzyl}methanesulfonamide

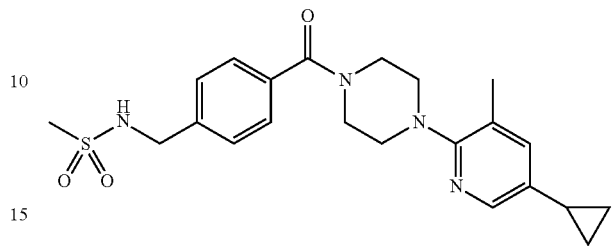

Using 4-(methanesulfonylaminomethyl)benzoic acid (138 mg) and 1-(5-cyclopropyl-3-methylpyridin-2-yl)piperazine (156 mg) described in Preparation Example 83 and by the reaction and treatment in the same manner as in Example 87, the title compound (100 mg) was obtained.

MS (ESI) m/z: 429(M+H)$^+$.

Example 470

Synthesis of N-(1-{4-[4-(3,5-dimethylpyridin-2-yl)piperazine-1-carbonyl]phenyl}-1-methylethyl)methanesulfonamide

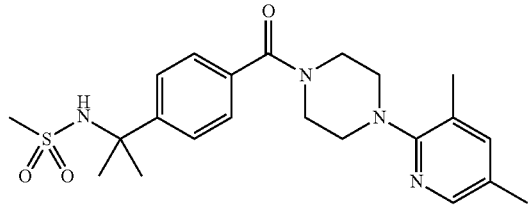

Using methyl 4-(1-methanesulfonylamino-1-methylethyl)benzoate (126 mg) described in Preparation Example 71 and 1-(3,5-dimethylpyridin-2-yl)piperazine (89 mg) described in Preparation Example 79 and by the reaction and treatment in the same manner as in Example 109, the title compound (157 mg) was obtained.

MS (ESI) m/z: 431(M+H)$^+$.

Example 471

Synthesis of N-(1-{4-[4-(5-cyclopropyl-3-methylpyridin-2-yl)piperazine-1-carbonyl]phenyl}-1-methylethyl)methanesulfonamide

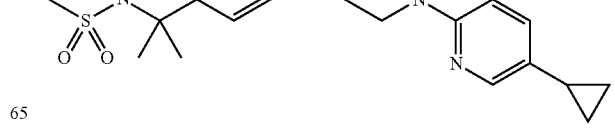

Using methyl 4-(1-methanesulfonylamino-1-methylethyl)benzoate (126 mg) described in Preparation Example 71 and 1-(5-cyclopropyl-3-methylpyridin-2-yl)piperazine (101 mg) described in Preparation Example 83 and by the reaction and treatment in the same manner as in Example 109, the title compound (162 mg) was obtained.

MS (ESI) m/z: 457(M+H)$^+$.

Example 472

Synthesis of (S)—N-(1-{4-[4-(3,5-dimethylpyridin-2-yl)piperazine-1-carbonyl]phenyl}ethyl)methanesulfonamide

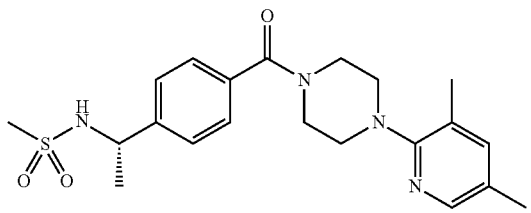

Using (S)-4-(1-methanesulfonylaminoethyl)benzoic acid (146 mg) described in Preparation Example 73 and 1-(3,5-dimethylpyridin-2-yl)piperazine (126 mg) described in Preparation Example 79 and by the reaction and treatment in the same manner as in Example 87, the title compound (261 mg) was obtained.

MS (ESI) m/z: 417(M+H)$^+$.

Example 473

Synthesis of (S)—N-(1-{4-[4-(5-cyclopropyldimethylpyridin-2-yl)piperazine-1-carbonyl]phenyl}ethyl)methanesulfonamide

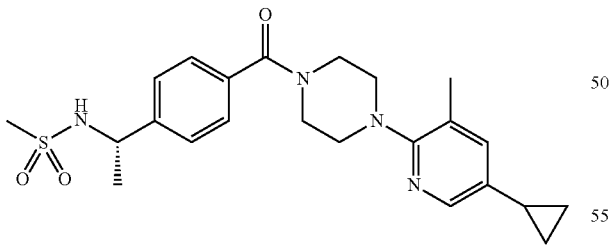

Using (S)-4-(1-methanesulfonylaminoethyl)benzoic acid (146 mg) described in Preparation Example 73 and 1-(5-cyclopropyl-3-methylpyridin-2-yl)piperazine (143 mg) described in Preparation Example 83 and by the reaction and treatment in the same manner as in Example 87, the title compound (276 mg) was obtained.

MS (ESI) m/z: 443(M+H)$^+$.

Example 474

Synthesis of N-{4-[4-(2,4-dimethylphenyl)piperazine-1-carbonyl]-3-methanesulfonylphenyl}acetamide

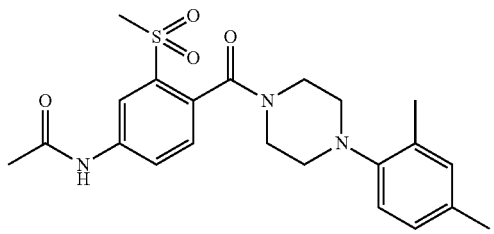 [SMILES: CC(=O)Nc1ccc(C(=O)N2CCN(c3ccc(C)cc3C)CC2)c(S(C)(=O)=O)c1]

Using (4-bromo-2-methanesulfonylphenyl)[4-(2,4-dimethylphenyl)piperazin-1-yl]methanone (526 mg) described in Preparation Example 110 and acetamide (75.7 mg) and by the reaction and treatment in the same manner as in Example 1, the title compound (54 mg) was obtained.

MS (ESI) m/z: 430(M+H)$^+$.

Example 475

Synthesis of N-{4-[4-(3,5-dicyclopropylpyridin-2-yl)piperazine-1-carbonyl]phenyl}acetamide

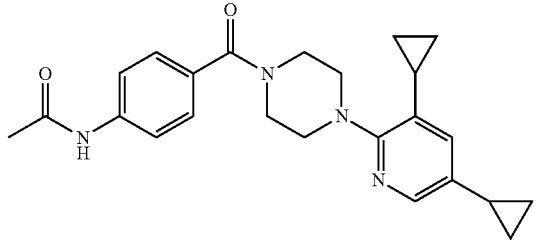 [SMILES: CC(=O)Nc1ccc(C(=O)N2CCN(c3ncc(C4CC4)cc3C3CC3)CC2)cc1]

Using [4-(3,5-dicyclopropylpyridin-2-yl)piperazin-1-yl](4-iodophenyl)methanone (473 mg) described in Preparation Example 186 and acetamide (89 mg) and by the reaction and treatment in the same manner as in Example 262, the title compound (294 mg) was obtained.

MS (ESI) m/z: 405(M+H)$^+$.

Example 476

Synthesis of N-{4-[4-(3,5-dicyclopropylpyridin-2-yl)piperazine-1-carbonyl]phenyl}formamide

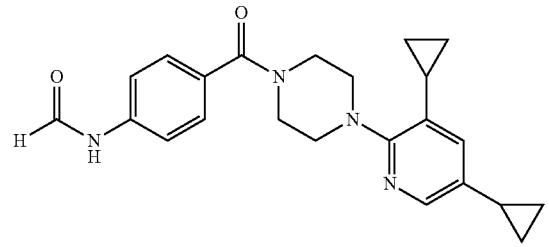 [SMILES: O=CNc1ccc(C(=O)N2CCN(c3ncc(C4CC4)cc3C3CC3)CC2)cc1]

Using [4-(3,5-dicyclopropylpyridin-2-yl)piperazin-1-yl](4-iodophenyl)methanone (710 mg) described in Preparation Example 186 and formamide (89 μL) and by the reaction and treatment in the same manner as in Example 262, the title compound (213 mg) was obtained.

MS (ESI) m/z: 391(M+H)⁺.

Example 477

Synthesis of {4-[4-(3,5-dicyclopropylpyridin-2-yl)piperazine-1-carbonyl]phenyl}carbamic acid ethyl ester

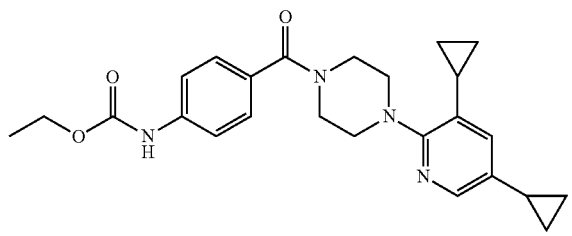 [SMILES: CCOC(=O)Nc1ccc(C(=O)N2CCN(c3ncc(C4CC4)cc3C3CC3)CC2)cc1]

Using [4-(3,5-dicyclopropylpyridin-2-yl)piperazin-1-yl](4-iodophenyl)methanone (473 mg) described in Preparation Example 186 and carbamic acid ethyl ester (137 mg) and by the reaction and treatment in the same manner as in Example 262, the title compound (209 mg) was obtained.

MS (ESI) m/z: 435(M+H)⁺.

Example 478

Synthesis of {4-[4-(3,5-dicyclopropylpyridin-2-yl)piperazine-1-carbonyl]phenyl}carbamic acid methyl ester

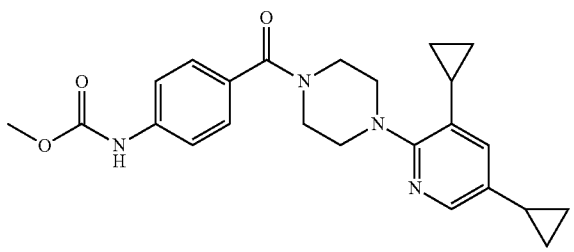 [SMILES: COC(=O)Nc1ccc(C(=O)N2CCN(c3ncc(C4CC4)cc3C3CC3)CC2)cc1]

Using [4-(3,5-dicyclopropylpyridin-2-yl)piperazin-1-yl](4-iodophenyl)methanone (473 mg) described in Preparation Example 186 and carbamic acid methyl ester (113 mg) and by the reaction and treatment in the same manner as in Example 262, the title compound (161 mg) was obtained.

MS (ESI) m/z: 421(M+H)⁺.

Example 479

Synthesis of {4-[4-(3,5-dicyclopropylpyridin-2-yl)piperazine-1-carbonyl]phenyl}methylcarbamic acid ethyl ester

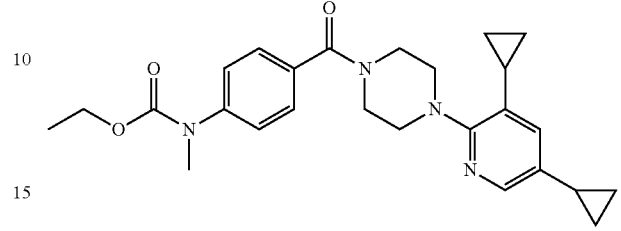

Using [4-(3,5-dicyclopropylpyridin-2-yl)piperazin-1-yl](4-iodophenyl)methanone (473 mg) described in Preparation Example 186 and methylcarbamic acid ethyl ester (152 μL) and by the reaction and treatment in the same manner as in Example 262, the title compound (203 mg) was obtained.

MS (ESI) m/z: 449(M+H)⁺.

Example 480

Synthesis of N-{4-[4-(3,5-dimethylpyridin-2-yl)piperazine-1-carbonyl]benzyl}acetamide

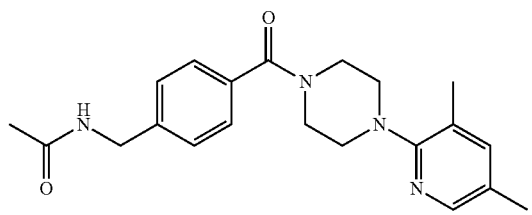 [SMILES: CC(=O)NCc1ccc(C(=O)N2CCN(c3ncc(C)cc3C)CC2)cc1]

Using 4-(acetylaminomethyl)benzoic acid (116 mg) and 1-(3,5-dimethylpyridin-2-yl)piperazine (115 mg) described in Preparation Example 79 and by the reaction and treatment in the same manner as in Example 87, the title compound (156 mg) was obtained.

MS (ESI) m/z: 367(M+H)⁺.

Example 481

Synthesis of N-{4-[4-(5-cyclopropyl-3-methylpyridin-2-yl)piperazine-1-carbonyl]benzyl}acetamide

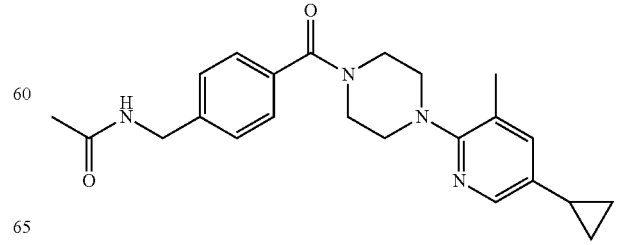

Using 4-(acetylaminomethyl)benzoic acid (116 mg) and 1-(5-cyclopropyl-3-methylpyridin-2-yl)piperazine (156 mg) described in Preparation Example 83 and by the reaction and treatment in the same manner as in Example 87, the title compound (96 mg) was obtained.

MS (ESI) m/z: 393(M+H)$^+$.

Example 482

Synthesis of (1-{4-[4-(3,5-dimethylpyridin-2-yl)piperazine-1-carbonyl]phenyl}-1-methylethyl)carbamic acid ethyl ester

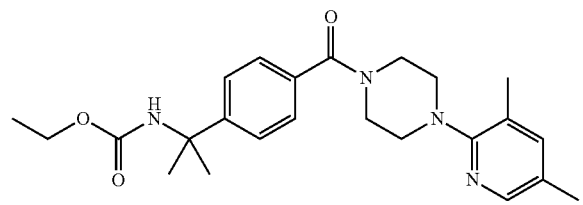 [SMILES: CCOC(=O)NC(C)(C)c1ccc(C(=O)N2CCN(c3ncc(C)cc3C)CC2)cc1]

Using methyl 4-(1-ethoxycarbonylamino-1-methylethyl)benzoate (174 mg) described in Preparation Example 70 and 1-(3,5-dimethylpyridin-2-yl)piperazine (138 mg) described in Preparation Example 79 and by the reaction and treatment in the same manner as in Example 109, the title compound (229 mg) was obtained.

MS (ESI) m/z: 425(M+H)$^+$.

Example 483

Synthesis of (1-{4-[4-(3,5-dimethylpyridin-2-yl)piperazine-1-carbonyl]phenyl}-1-methylethyl)carbamic acid ethyl ester

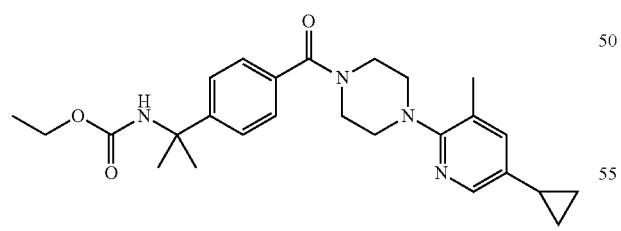

Using methyl 4-(1-ethoxycarbonylamino-1-methylethyl)benzoate (174 mg) described in Preparation Example 70 and 1-(5-cyclopropyl-3-methylpyridin-2-yl)piperazine (157 mg) described in Preparation Example 83 and by the reaction and treatment in the same manner as in Example 109, the title compound (235 mg) was obtained.

MS (ESI) m/z: 451(M+H)$^+$.

Example 484

Synthesis of 1-{4-[4-(2,4-dimethylphenyl)piperazine-1-carbonyl]-3-methanesulfonylphenyl}azepan-2-one

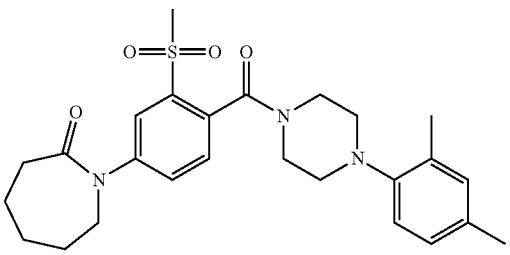 [SMILES: Cc1ccc(N2CCN(C(=O)c3ccc(N4CCCCCC4=O)cc3S(C)(=O)=O)CC2)c(C)c1]

Using (4-bromo-2-methanesulfonylphenyl)[4-(2,4-dimethylphenyl)piperazin-1-yl]methanone (451 mg) described in Preparation Example 110 and azepan-2-one (119 mg) and by the reaction and treatment in the same manner as in Example 1, the title compound (234 mg) was obtained.

MS (ESI) m/z: 484(M+H)$^+$.

Example 485

Synthesis of 1-{4-[4-(3,5-dimethylpyridin-2-yl)piperazine-1-carbonyl]-3,5-difluorophenyl}azepan-2-one

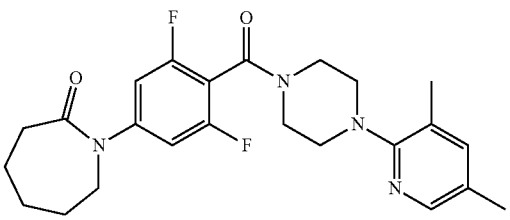 [SMILES: Cc1cnc(N2CCN(C(=O)c3c(F)cc(N4CCCCCC4=O)cc3F)CC2)c(C)c1]

Using (4-bromo-2,6-difluorophenyl)[4-(3,5-dimethylpyridin-2-yl)piperazin-1-yl]methanone (200 mg) described in Preparation Example 111 and azepan-2-one (58 mg) and by the reaction and treatment in the same manner as in Example 1, the title compound (41 mg) was obtained.

MS (ESI) m/z: 443(M+H)$^+$.

Example 486

Synthesis of 1-{4-[4-(3,5-dimethylpyridin-2-yl)piperazine-1-carbonyl]-3,5-difluorophenyl}azetidin-2-one

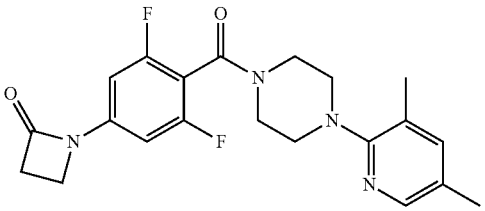 [SMILES: Cc1cnc(N2CCN(C(=O)c3c(F)cc(N4CCC4=O)cc3F)CC2)c(C)c1]

Using (4-bromo-2,6-difluorophenyl)[4-(3,5-dimethylpyridin-2-yl)piperazin-1-yl]methanone (410 mg) described in Preparation Example 111 and 2-azetidinone (75 mg) and by the reaction and treatment in the same manner as in Example 1, the title compound (219 mg) was obtained.

MS (ESI) m/z: 401(M+H)$^+$.

Example 487

Synthesis of 1-{4-[4-(3,5-dimethylpyridin-2-yl)piperazine-1-carbonyl]-3-fluorophenyl}azetidin-2-one

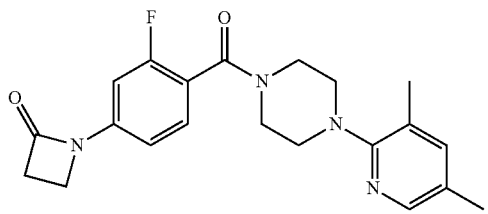 [SMILES: Cc1cnc(N2CCN(C(=O)c3ccc(N4CCC4=O)cc3F)CC2)c(C)c1]

Using (4-bromo-2-fluorophenyl) [4-(3,5-dimethylpyridin-2-yl)piperazin-1-yl]methanone (150 mg) described in Preparation Example 114 and 2-azetidinone (30 mg) and by the reaction and treatment in the same manner as in Example 1, the title compound (47 mg) was obtained.

MS (ESI) m/z: 383(M+H)$^+$.

Example 488

Synthesis of 1-{4-[4-(3,5-dimethylpyridin-2-yl)piperazine-1-carbonyl]-3-methanesulfonylphenyl}azetidin-2-one

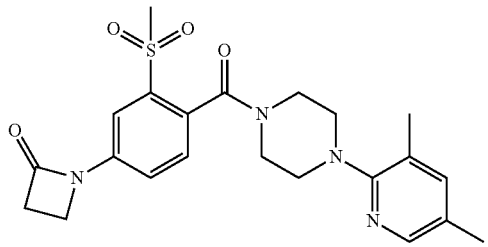 [SMILES: Cc1cnc(N2CCN(C(=O)c3ccc(N4CCC4=O)cc3S(C)(=O)=O)CC2)c(C)c1]

Using (4-bromo-2-methanesulfonylphenyl)[4-(3,5-dimethylpyridin-2-yl)piperazin-1-yl]methanone (420 mg) described in Preparation Example 112 and 2-azetidinone (70 mg) and by the reaction and treatment in the same manner as in Example 1, the title compound (144 mg) was obtained.

MS (ESI) m/z: 443(M+H)$^+$.

Example 489

Synthesis of 1-{4-[4-(2,4-dimethylphenyl)piperazine-1-carbonyl]-3-methanesulfonylphenyl}azetidin-2-one

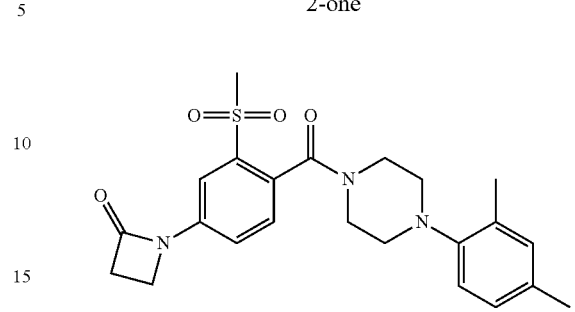

Using (4-bromo-2-methanesulfonylphenyl)[4-(2,4-dimethylphenyl)piperazin-1-yl]methanone (903 mg) described in Preparation Example 110 and azetidin-2-one (142 mg) and by the reaction and treatment in the same manner as in Example 1, the title compound (158 mg) was obtained.

MS (ESI) m/z: 442(M+H)$^+$.

Example 490

Synthesis of N-{4-[4-(4-chlorobenzoyl)piperidine-1-carbonyl]phenyl}methanesulfonamide

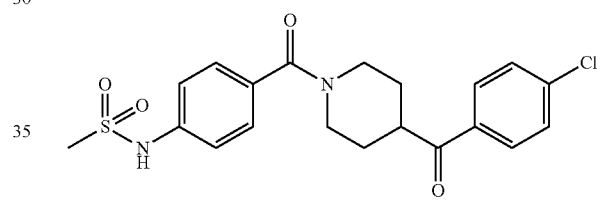

Using 4-methanesulfonylaminobenzoic acid (800 mg) and (4-chlorophenyl)(piperidin-4-yl)methanone hydrochloride (967 mg) and by the reaction and treatment in the same manner as in Example 86, the title compound (843 mg) was obtained.

MS (ESI) m/z: 421(M+H)$^+$.

Example 491

Synthesis of N-{4-[4-(4-chlorobenzoyl)piperidine-1-carbonyl]benzyl}methanesulfonamide

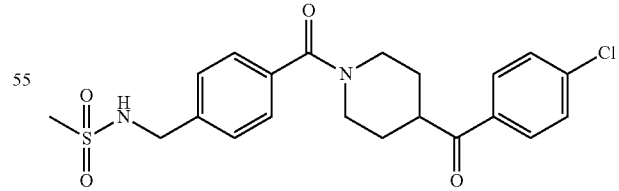

Using 4-(methanesulfonylaminomethyl)benzoic acid (100 mg) and (4-chlorophenyl)(piperidin-4-yl)methanone hydrochloride (113 mg) and by the reaction and treatment in the same manner as in Example 86, the title compound (103 mg) was obtained.

MS (ESI) m/z: 435(M+H)$^+$.

Example 492

Synthesis of N-{4-[4-(4-methylbenzoyl)piperidine-1-carbonyl]benzyl}methanesulfonamide

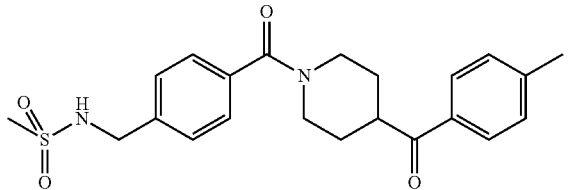

Using 4-(methanesulfonylaminomethyl)benzoic acid (145 mg) and (4-methylphenyl)(piperidin-4-yl)methanone hydrochloride (152 mg) and by the reaction and treatment in the same manner as in Example 86, the title compound (84 mg) was obtained.
MS (ESI) m/z: 415(M+H)$^+$.

Example 493

Synthesis of N-{4-[4-(4-methylbenzoyl)piperidine-1-carbonyl]phenyl}methanesulfonamide

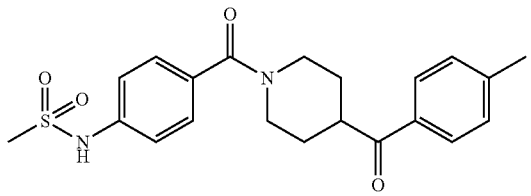

Using 4-methanesulfonylaminobenzoic acid (136 mg) and (4-methylphenyl)(piperidin-4-yl)methanone hydrochloride (152 mg) and by the reaction and treatment in the same manner as in Example 86, the title compound (37 mg) was obtained.
MS (ESI) m/z: 401(M+H)$^+$.

Example 494

Synthesis of N-{4-[4-(3,5-dimethylpyridin-2-yl)piperazine-1-carbonyl]-3-fluorophenyl}-N-methyl-methanesulfonamide

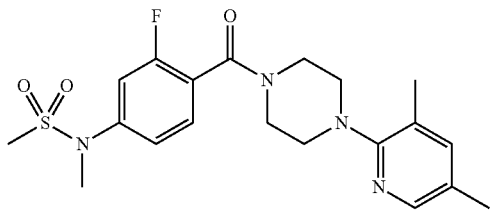

Using (4-bromo-2-fluorophenyl)[4-(3,5-dimethylpyridin-2-yl)piperazin-1-yl]methanone (624 mg) described in Preparation Example 114 and N-methylmethanesulfonamide (349 mg) and by the reaction and treatment in the same manner as in Example 4, the title compound (599 mg) was obtained.
MS (ESI) m/z: 421(M+H)$^+$.

Example 495

Synthesis of N-{4-[4-(2,4-dimethylphenyl)piperazine-1-carbonyl]phenyl}acetamide

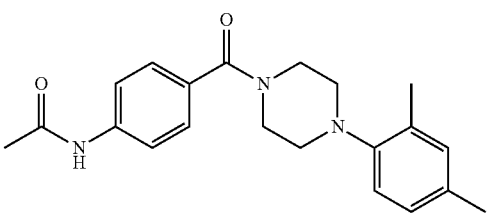 [SMILES: CC(=O)Nc1ccc(C(=O)N2CCN(c3ccc(C)cc3C)CC2)cc1]

Using 4-(acetylamino)benzoic acid (179 mg) and 1-(2,4-dimethylphenyl)piperazine (190 mg) and by the reaction and treatment in the same manner as in Example 93, the title compound (350 mg) was obtained.
MS (ESI) m/z: 352(M+H)$^+$.

Example 496

Synthesis of [4-(imidazo[4,5-b]pyridin-3-yl)phenyl][4-(4-methoxybenzoyl)piperidin-1-yl]methanone

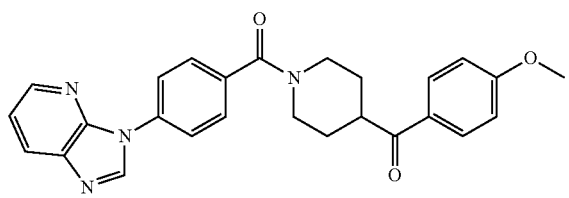 [SMILES: COc1ccc(C(=O)C2CCN(C(=O)c3ccc(-n4cnc5cccnc54)cc3)CC2)cc1]

Using ethyl 4-(imidazo[4,5-b]pyridin-3-yl)benzoate (300 mg) described in Preparation Example 77 and (4-methoxyphenyl)(piperidin-4-yl)methanone hydrochloride (287 mg) and by the reaction and treatment in the same manner as in Example 170, the title compound (329 mg) was obtained.
MS (ESI) m/z: 441(M+H)$^+$.

Example 497

Synthesis of [4-(imidazo[4,5-b]pyridin-3-yl)phenyl][4-(4-methylbenzoyl)piperidin-1-yl]methanone

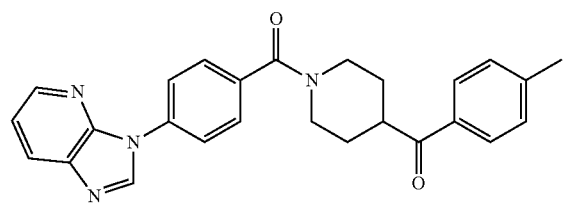 [SMILES: Cc1ccc(C(=O)C2CCN(C(=O)c3ccc(-n4cnc5cccnc54)cc3)CC2)cc1]

Using ethyl 4-(imidazo[4,5-b]pyridin-3-yl)benzoate (300 mg) described in Preparation Example 77 and (4-methylphenyl)(piperidin-4-yl)methanone hydrochloride (269 mg) and

Example 498

Synthesis of [6-(benzimidazol-1-yl)pyridin-3-yl][4-(4-methylbenzoyl)piperidin-1-yl]methanone

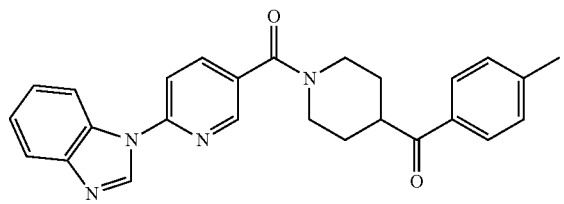 [SMILES: Cc1ccc(C(=O)C2CCN(C(=O)c3ccc(-n4cnc5ccccc54)nc3)CC2)cc1]

Using ethyl 6-(benzimidazol-1-yl)nicotinate (300 mg) described in Preparation Example 78, (4-methylphenyl)(piperidin-4-yl)methanone hydrochloride (269 mg) and by the reaction and treatment in the same manner as in Example 170, the title compound (217 mg) was obtained.
MS (ESI) m/z: 425(M+H)$^+$.

Example 499

Synthesis of [4-(benzimidazol-1-yl)phenyl][4-(2,4-dimethylphenyl)piperazin-1-yl]methanone

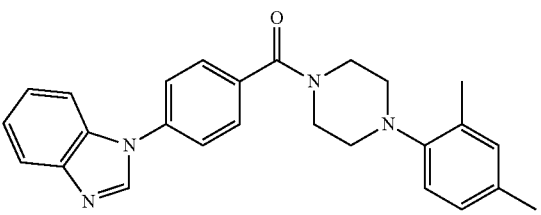 [SMILES: Cc1ccc(N2CCN(C(=O)c3ccc(-n4cnc5ccccc54)cc3)CC2)c(C)c1]

Using methyl 4-(benzimidazol-1-yl)benzoate (126 mg) and 1-(2,4-dimethylphenyl)piperazine (95 mg) and by the reaction and treatment in the same manner as in Example 109, the title compound (114 mg) was obtained.
MS (ESI) m/z: 411(M+H)$^+$.

Example 500

Preparation of 1-{4-[4-(2,4-dimethylphenyl)piperazine-1-carbonyl]phenyl}pyrrolidin-2-one

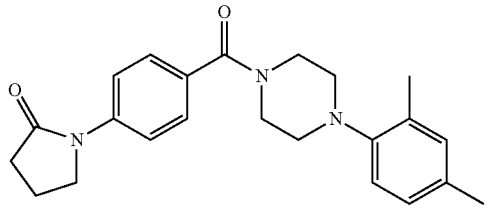 [SMILES: Cc1ccc(N2CCN(C(=O)c3ccc(N4CCCC4=O)cc3)CC2)c(C)c1]

Using [4-(2,4-dimethylphenyl)piperazin-1-yl](4-iodophenyl)methanone (6.0 g) described in Preparation Example 109 and pyrrolidin-2-one (1.3 mL) and by the reaction and treatment in the same manner as in Example 1, the title compound (1.80 g) was obtained.
MS (ESI) m/z: 378(M+H)$^+$.

Example 501

Synthesis of 2-[4-(3,5-dimethylpyridin-2-yl)piperazine-1-carbonyl]-5-(1,1-dioxo-1$\lambda^6$-isothiazolidin-2-ylmethyl)benzonitrile

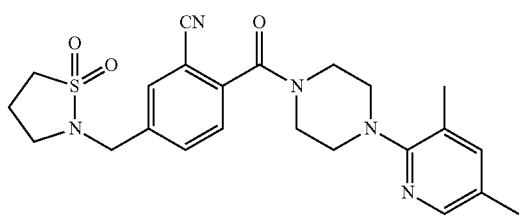 [SMILES: Cc1cnc(N2CCN(C(=O)c3ccc(CN4CCCS4(=O)=O)cc3C#N)CC2)c(C)c1]

Under a nitrogen stream, [2-bromo-4-(1,1-dioxo-1$\lambda^6$-isothiazolidin-2-ylmethyl)phenyl][4-(3,5-dimethylpyridin-2-yl)piperazin-1-yl]methanone (120 mg) described in Example 461 was dissolved in N,N-dimethylformamide (5 mL), zinc cyanide (28 mg) and tetrakistriphenylphosphine palladium(0)(55 mg) were added, and the mixture was stirred at 130° C. for 4 hr. After completion of the reaction, to the reaction mixture was added water/saturated aqueous ammonium chloride solution/28% aqueous ammonia (4:4:1), and the mixture was extracted with ethyl acetate. The organic layer was washed with water and saturated brine, and the solvent was evaporated. The obtained residue was purified by column chromatography (hexane:ethyl acetate) to give the title compound (68 mg).
MS (ESI) m/z: 454(M+H)$^+$.

Example 502

Synthesis of [4-(3,5-dimethylpyridin-2-yl)piperazin-1-yl][4-(1,1-dioxo-1$\lambda^6$-isothiazolidin-2-ylmethyl)-2-methylphenyl]methanone

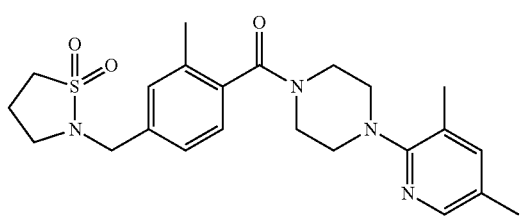

Using [2-bromo-4-(1,1-dioxo-1$\lambda^6$-isothiazolidin-2-ylmethyl)phenyl][4-(3,5-dimethylpyridin-2-yl)piperazin-1-yl]methanone (120 mg) described in Example 461 and methylboronic acid (42 mg) and by the reaction and treatment in the same manner as in Example 115, the title compound (90 mg) was obtained.
MS (ESI) m/z: 443(M+H)$^+$.

Example 503

Synthesis of [4-(3,5-dimethylpyridin-2-yl)piperazin-1-yl][4-(1,1-dioxo-1λ$^6$-isothiazolidin-2-ylmethyl)-2-fluorophenyl]methanone

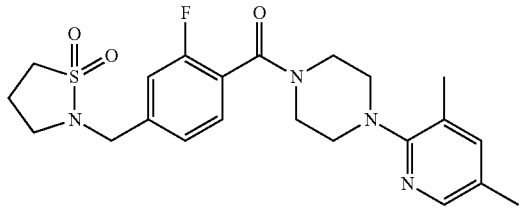 [SMILES: Cc1cnc(N2CCN(C(=O)c3ccc(CN4CCCS4(=O)=O)cc3C)CC2)c(C)c1]

Using methyl 4-(1,1-dioxo-1λ$^6$-isothiazolidin-2-ylmethyl)-2-fluorobenzoate (115 mg) described in Preparation Example 200 and 1-(3,5-dimethylpyridin-2-yl)piperazine (92 mg) described in Preparation Example 79 and by the reaction and treatment in the same manner as in Example 109, the title compound (157 mg) was obtained.
MS (ESI) m/z: 447(M+H)$^+$.

Example 504

Synthesis of [4-(5-cyclopropyl-3-methylpyridin-2-yl)piperazin-1-yl][4-(1,1-dioxo-1λ$^6$-isothiazolidin-2-ylmethyl)-2-fluorophenyl]methanone

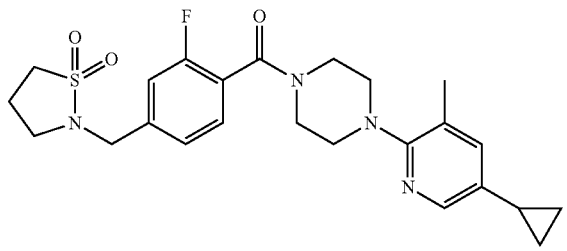 [SMILES: Cc1cc(C2CC2)cnc1N1CCN(C(=O)c2ccc(CN3CCCS3(=O)=O)cc2F)CC1]

Using methyl 4-(1,1-dioxo-1λ$^6$-isothiazolidin-2-ylmethyl)-2-fluorobenzoate (115 mg) described in Preparation Example 200 and 1-(5-cyclopropyl-3-methylpyridin-2-yl)piperazine (104 mg) described in Preparation Example 83 and by the reaction and treatment in the same manner as in Example 109, the title compound (157 mg) was obtained.
MS (ESI) m/z: 473(M+H)$^+$.

Example 505

Synthesis of 1-{4-[4-(3,5-dimethylpyridin-2-yl)piperazine-1-carbonyl]-3-fluorophenyl}-5,5-dimethylimidazolidin-2-one

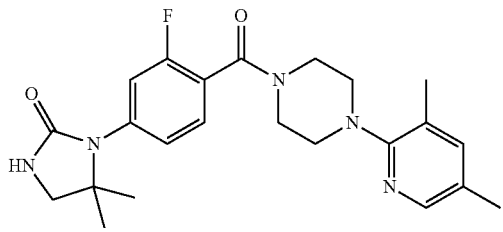 [SMILES: Cc1cnc(N2CCN(C(=O)c3ccc(N4C(=O)NCC4(C)C)cc3F)CC2)c(C)c1]

To a mixture of (4-bromo-2-fluorophenyl) [4-(3,5-dimethylpyridin-2-yl)piperazin-1-yl]methanone (157 mg) described in Preparation Example 114, 1-(4-methoxybenzyl)-4,4-dimethylimidazolidin-2-one (112 mg) described in Preparation Example 54, cesium carbonate (261 mg) and copper(I) iodide (38 mg) were added 1,4-dioxane (10 mL) and N,N'-dimethylethylenediamine (43 μL), and the mixture was stirred with heating under reflux for 32 hr. The reaction mixture was cooled, water was added, and the mixture was extracted with ethyl acetate. The organic layer was washed with saturated brine, dried over sodium sulfate, and the solvent was evaporated. The obtained residue was purified by column chromatography (hexane:ethyl acetate) to give 3-{4-[4-(3,5-dimethylpyridin-2-yl)piperazine-1-carbonyl]-3-fluorophenyl}-1-(4-methoxybenzyl)-4,4-dimethylimidazolidin-2-one. The obtained 3-{4-[4-(3,5-dimethylpyridin-2-yl)piperazine-1-carbonyl]-3-fluorophenyl}-1-(4-methoxybenzyl)-4,4-dimethylimidazolidin-2-one was dissolved in dichloromethane (5 mL), trifluoromethanesulfonic acid (75 μL) was added, and the mixture was stirred at room temperature for 4 hr. To the reaction mixture was added 5% aqueous sodium hydrogen carbonate solution, and the solvent was evaporated, and the mixture was extracted with ethyl acetate. The organic layer was washed with 5% aqueous sodium hydrogen carbonate solution, and saturated brine, dried over sodium sulfate, and the solvent was evaporated. The obtained residue was purified by silica gel column chromatography (ethyl acetate:methanol) to give the title compound (30 mg).
MS (ESI) m/z: 426(M+H)$^+$.

Example 506

Synthesis of 1-{4-[4-(3,5-dimethylpyridin-2-yl)piperazine-1-carbonyl]-3-methylphenyl}-5,5-dimethylimidazolidin-2-one

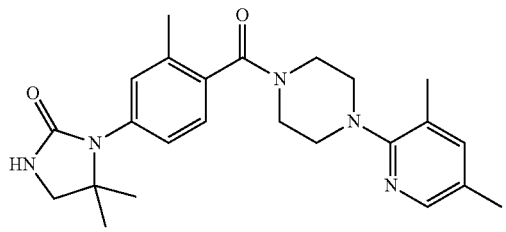 [SMILES: Cc1cnc(N2CCN(C(=O)c3ccc(N4C(=O)NCC4(C)C)cc3C)CC2)c(C)c1]

To a mixture of (4-bromo-2-methylphenyl)[4-(3,5-dimethylpyridin-2-yl)piperazin-1-yl]methanone (155 mg) described in Preparation Example 118, 1-(4-methoxybenzyl)-4,4-dimethylimidazolidin-2-one (112 mg) described in Preparation Example 54, cesium carbonate (261 mg) and copper(I) iodide (76 mg) were added toluene (10 mL) and N,N'-dimethylethylenediamine (86 μL), and the mixture was stirred with heating under reflux for 19 hr. The reaction mixture was cooled, water was added, and the mixture was extracted with ethyl acetate. The organic layer was washed with saturated brine, dried over sodium sulfate, and the solvent was evaporated. The obtained residue was purified by column chromatography (hexane:ethyl acetate) to give 3-{4-[4-(3,5-dimethylpyridin-2-yl)piperazine-1-carbonyl]-3-methylphenyl}-1-(4-methoxybenzyl)-4,4-dimethylimidazolidin-2-one. The obtained 3-{4-[4-(3,5-dimethylpyridin-2-yl)piperazine-1-carbonyl]-3-methylphenyl}-1-(4-methoxybenzyl)-4,4-dimethylimidazolidin-2-one was dissolved in trifluoroacetic acid (3 mL), and the mixture was stirred at room temperature for 22 hr. The solvent was evapo-

Example 507

Synthesis of 1-{4-[4-(2,4-dimethylphenyl)piperazine-1-carbonyl]phenyl}-5-methylimidazolidin-2-one

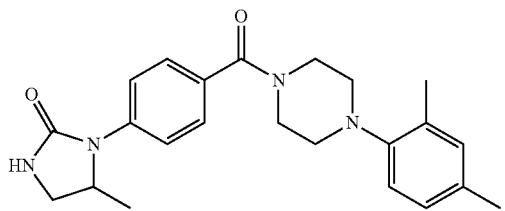 [SMILES: Cc1ccc(N2CCN(C(=O)c3ccc(N4C(=O)NCC4C)cc3)CC2)c(C)c1]

Using (4-bromophenyl)[4-(2,4-dimethylphenyl)piperazin-1-yl]methanone (149 mg) described in Preparation Example 170 and 1-(4-methoxybenzyl)-4-methylimidazolidin-2-one (106 mg) described in Preparation Example 52 and by the reaction and treatment in the same manner as in Example 506, the title compound (120 mg) was obtained via 3-{4-[4-(2,4-dimethylphenyl)piperazine-1-carbonyl]phenyl}-1-(4-methoxybenzyl)-4-methylimidazolidin-2-one.

MS (ESI) m/z: 393(M+H)$^+$.

Example 508

Synthesis of 1-{4-[4-(3,5-dimethylpyridin-2-yl)piperazine-1-carbonyl]phenyl}-5,5-dimethylimidazolidine-2,4-dione

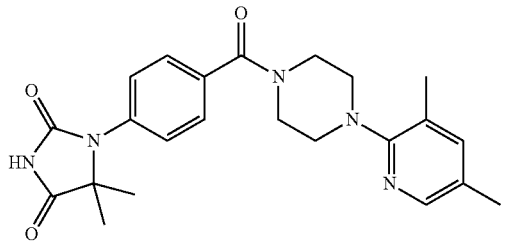 [SMILES: Cc1cnc(N2CCN(C(=O)c3ccc(N4C(=O)NC(=O)C4(C)C)cc3)CC2)c(C)c1]

To a mixture of (4-bromophenyl) [4-(3,5-dimethylpyridin-2-yl)piperazin-1-yl]methanone (150 mg) described in Preparation Example 165, 3-(4-methoxybenzyl)-5,5-dimethylimidazolidine-2,4-dione (119 mg) described in Preparation Example 53, cesium carbonate (260 mg) and copper(I) iodide (38 mg) were added toluene (8 mL) and N,N'-dimethylethylenediamine (43 μL), and the mixture was stirred with heating under reflux for 29 hr. The reaction mixture was cooled, water was added, and the mixture was extracted with ethyl acetate. The organic layer was washed with saturated brine, dried over sodium sulfate, and the solvent was evaporated. The obtained residue was purified by column chromatography (hexane: ethyl acetate) to give 1-{4-[4-(3,5-dimethylpyridin-2-yl)piperazine-1-carbonyl]phenyl}-3-(4-methoxybenzyl)-5,5-dimethylimidazolidine-2,4-dione. The obtained 1-{4-[4-(3,5-dimethylpyridin-2-yl)piperazine-1-carbonyl]phenyl}-3-(4-methoxybenzyl)-5,5-dimethylimidazolidine-2,4-dione was dissolved in 1,2-dichloroethane (4 mL), trifluoromethanesulfonic acid (92 μL) was added and the mixture was stirred at 80° C. for 13 hr. To the reaction mixture was added 5% aqueous sodium hydrogen carbonate solution, and the mixture was extracted with chloroform/methanol (10:1). The organic layer was dried over sodium sulfate, and the solvent was evaporated. The obtained residue was purified by silica gel column chromatography (ethyl acetate:methanol) to give the title compound (34 mg).

MS (ESI) m/z: 422(M+H)$^+$.

Example 509

Synthesis of 1-{5-[4-(3,5-dimethylpyridin-2-yl)piperazine-1-carbonyl]pyridin-2-yl}-4-methylimidazolidin-2-one

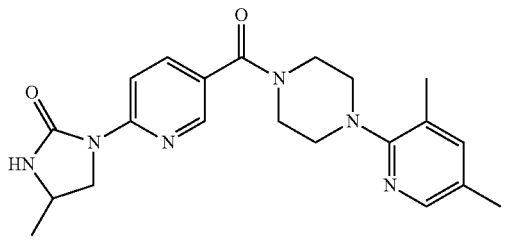 [SMILES: Cc1cnc(N2CCN(C(=O)c3ccc(N4CC(C)NC4=O)nc3)CC2)c(C)c1]

To a mixture of (6-bromopyridin-3-yl)[4-(3,5-dimethylpyridin-2-yl)piperazin-1-yl]methanone (150 mg) described in Preparation Example 127, 1-benzoyl-5-methylimidazolidin-2-one (105 mg) described in Preparation Example 56, cesium carbonate (260 mg) and copper(I) iodide (38 mg) were added 1,4-dioxane (8 mL) and N,N'-dimethylethylenediamine (43 μL), and the mixture was stirred with heating under reflux for 18 hr. The reaction mixture was cooled, water was added, and the mixture was extracted with ethyl acetate. The organic layer was washed with saturated brine, dried over sodium sulfate, and the solvent was evaporated. The obtained residue was purified by column chromatography (hexane:ethyl acetate) to give the title compound (68 mg) produced by debenzoylation that simultaneously proceeded during the reaction.

MS (ESI) m/z: 395(M+H)$^+$.

Example 510

Synthesis of 1-{5-[4-(3,5-dimethylpyridin-2-yl)piperazine-1-carbonyl]pyridin-2-yl}-4,4-dimethylimidazolidin-2-one

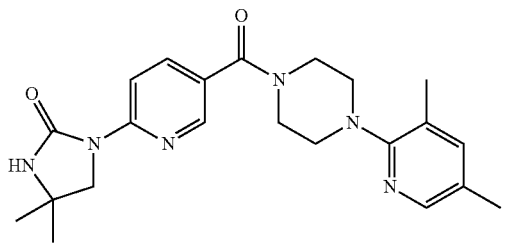

Using (6-bromopyridin-3-yl)[4-(3,5-dimethylpyridin-2-yl)piperazin-1-yl]methanone (150 mg) described in Preparation Example 127 and 1-benzoyl-5,5-dimethylimidazolidin-2-one (105 mg) described in Preparation Example 58 and by the reaction and treatment in the same manner as in Example 509 to give the title compound (60 mg) produced by debenzoylation that simultaneously proceeded during the reaction.

MS (ESI) m/z: 409(M+H)⁺.

Example 511

Synthesis of 3-benzoyl-1-{4-[4-(3,5-dimethylpyridin-2-yl)piperazin-1-carbonyl]-3-fluorophenyl}-4-methylimidazolidin-2-one

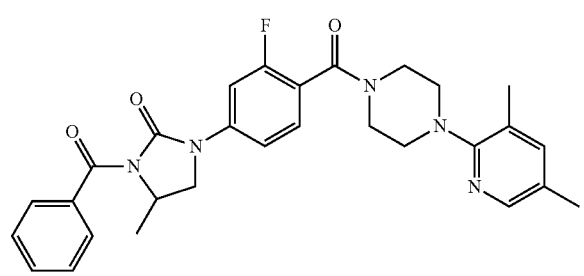 [SMILES: Cc1cnc(N2CCN(C(=O)c3ccc(N4CC(C)N(C(=O)c5ccccc5)C4=O)cc3F)CC2)c(C)c1]

To a mixture of (4-bromo-2-fluorophenyl)[4-(3,5-dimethylpyridin-2-yl)piperazin-1-yl]methanone (157 mg) described in Preparation Example 114, 1-benzoyl-5-methylimidazolidin-2-one (105 mg) described in Preparation Example 56, tripotassium phosphate (170 mg) and copper(I) iodide (76 mg) were added 1,4-dioxane (8 mL) and N,N'-dimethylethylenediamine (86 μL), and the mixture was stirred with heating under reflux for 10 hr. The reaction mixture was cooled, water was added, and the mixture was extracted with ethyl acetate. The organic layer was washed with saturated brine, dried over sodium sulfate, and the solvent was evaporated. The obtained residue was purified by column chromatography (hexane:ethyl acetate) to give the title compound (35 mg).

MS (ESI) m/z: 516(M+H)⁺.

Example 512

Synthesis of 1-{4-[4-(3,5-dimethylpyridin-2-yl)piperazine-1-carbonyl]-3-fluorophenyl}-4-methylimidazolidin-2-one

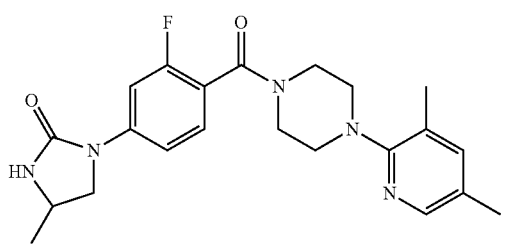 [SMILES: Cc1cnc(N2CCN(C(=O)c3ccc(N4CC(C)NC4=O)cc3F)CC2)c(C)c1]

Using 3-benzoyl-1-{4-[4-(3,5-dimethylpyridin-2-yl)piperazine-1-carbonyl]-3-fluorophenyl}-4-methylimidazolidin-2-one (35 mg) described in Example 511 and by the reaction and treatment in the same manner as in Example 391, the title compound (23 mg) was obtained.

MS (ESI) m/z: 412(M+H)⁺.

Example 513

Synthesis of 3-benzoyl-1-{4-[4-(3,5-dimethylpyridin-2-yl)piperazine-1-carbonyl]-3-fluorophenyl}-4,4-dimethylimidazolidin-2-one

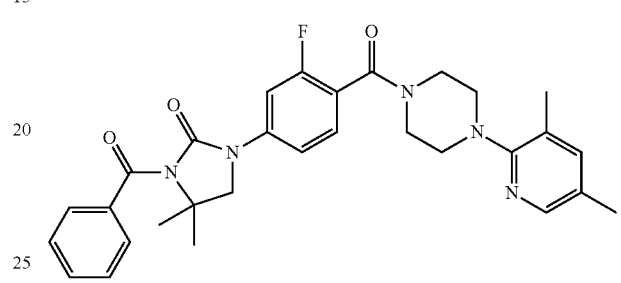

Using (4-bromo-2-fluorophenyl)[4-(3,5-dimethylpyridin-2-yl)piperazin-1-yl]methanone (157 mg) described in Preparation Example 114 and 1-benzoyl-5,5-dimethylimidazolidin-2-one (105 mg) described in Preparation Example 58 and by the reaction and treatment in the same manner as in Example 511, the title compound (123 mg) was obtained.

MS (ESI) m/z: 530(M+H)⁺.

Example 514

Synthesis of 1-{4-[4-(3,5-dimethylpyridin-2-yl)piperazine-1-carbonyl]-3-fluorophenyl}-4,4-dimethylimidazolidin-2-one

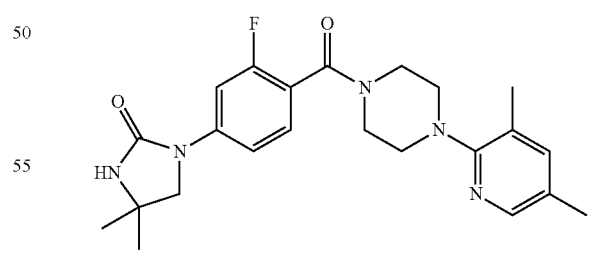

Using 3-benzoyl-1-{4-[4-(3,5-dimethylpyridin-2-yl)piperazine-1-carbonyl]-3-fluorophenyl}-4,4-dimethylimidazolidin-2-one (123 mg) described in Example 513 and by the reaction and treatment in the same manner as in Example 391, the title compound (71 mg) was obtained.

MS (ESI) m/z: 426(M+H)⁺.

Example 515

Synthesis of 1-{4-[4-(3,5-dimethylpyridin-2-yl)piperazine-1-carbonyl]-3-fluorophenyl}-5-methylimidazolidine-2,4-dione

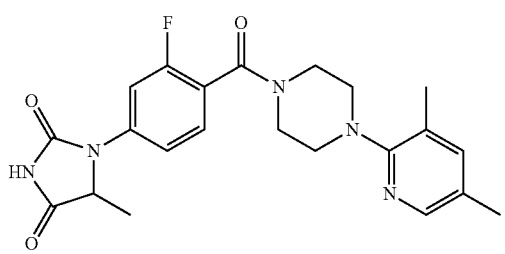 [SMILES: Cc1cnc(N2CCN(C(=O)c3ccc(N4C(=O)NC(=O)C4C)cc3F)CC2)c(C)c1]

Using (4-bromo-2-fluorophenyl)[4-(3,5-dimethylpyridin-2-yl)piperazin-1-yl]methanone (314 mg) described in Preparation Example 114 and 3-(4-methoxybenzyl)-5-methylimidazolidine-2,4-dione (225 mg) described in Preparation Example 51 and by the reaction and treatment in the same manner as in Example 508, the title compound (184 mg) was obtained via 1-{4-[4-(3,5-dimethylpyridin-2-yl)piperazine-1-carbonyl]-3-fluorophenyl}-3-(4-methoxybenzyl)-5-methylimidazolidine-2,4-dione.

MS (ESI) m/z: 426(M+H)$^+$.

Example 516

Synthesis of 1-{5-[4-(3,5-dimethylpyridin-2-yl)piperazine-1-carbonyl]pyridin-2-yl}-5-methylimidazolidine-2,4-dione

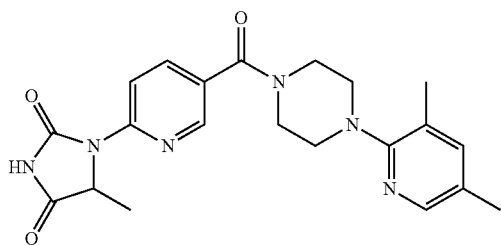 [SMILES: Cc1cnc(N2CCN(C(=O)c3ccc(N4C(=O)NC(=O)C4C)nc3)CC2)c(C)c1]

Using (6-bromopyridin-3-yl)[4-(3,5-dimethylpyridin-2-yl)piperazin-1-yl]methanone (300 mg) described in Preparation Example 127 and 3-(4-methoxybenzyl)-5-methylimidazolidine-2,4-dione (225 mg) described in Preparation Example 51 and by the reaction and treatment in the same manner as in Example 508, the title compound (92 mg) was obtained via 1-{5-[4-(3,5-dimethylpyridin-2-yl)piperazine-1-carbonyl]pyridin-2-yl}-3-(4-methoxybenzyl)-5-methylimidazolidine-2,4-dione.

MS (ESI) m/z: 409(M+H)$^+$.

Example 517

Synthesis of [6-(1,1-dioxo-1λ$^6$-isothiazolidin-2-ylmethyl)pyridin-3-yl][4-(3,5,6-trimethylpyridin-2-yl)piperazin-1-yl]methanone

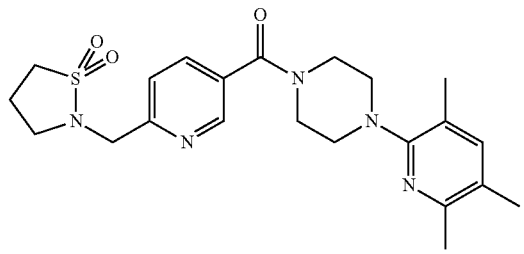 [SMILES: Cc1cc(C)c(N2CCN(C(=O)c3ccc(CN4CCCS4(=O)=O)nc3)CC2)nc1C]

Using methyl 6-(1,1-dioxo-1λ$^6$-isothiazolidin-2-ylmethyl)nicotinate (107 mg) described in Preparation Example 45 and 1-(3,5,6-trimethylpyridin-2-yl)piperazine (81 mg) described in Preparation Example 92 and by the reaction and treatment in the same manner as in Example 109, the title compound (118 mg) was obtained.

MS (ESI) m/z: 444(M+H)$^+$.

Example 518

Synthesis of 1-{4-[4-(3,5-dimethylpyridin-2-yl)piperazine-1-carbonyl]-3-fluorophenyl}-3,5-dimethylimidazolidine-2,4-dione

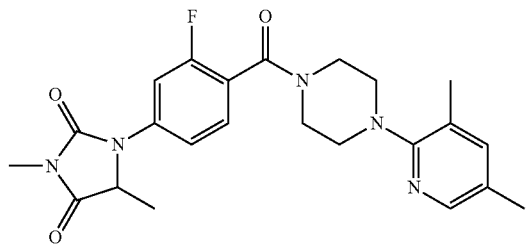

Using 1-{4-[4-(3,5-dimethylpyridin-2-yl)piperazine-1-carbonyl]-3-fluorophenyl}-5-methylimidazolidine-2,4-dione (80 mg) described in Example 515 and methyl iodide (12 µl) and by the reaction and treatment in the same manner as in Example 36, the title compound (12 mg) was obtained.

MS (ESI) m/z: 440(M+H)$^+$.

Example 519

Synthesis of 1-{5-[4-(3,5-dimethylpyridin-2-yl)piperazine-1-carbonyl]pyridin-2-yl}-3,5-dimethylimidazolidine-2,4-dione

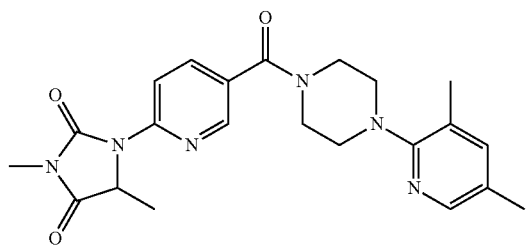

Using 1-{5-[4-(3,5-dimethylpyridin-2-yl)piperazine-1-carbonyl]pyridin-2-yl}-5-methylimidazolidine-2,4-dione (50 mg) described in Example 516 and methyl iodide (9 μL) and by the reaction and treatment in the same manner as in Example 36, the title compound (23 mg) was obtained.

MS (ESI) m/z: 423(M+H)⁺.

Example 520

Synthesis of [6-(1,1-dioxo-1λ⁶-isothiazolidin-2-ylmethyl)pyridin-3-yl][4-(5-ethyl-3-methylpyridin-2-yl)piperazin-1-yl]methanone dihydrochloride

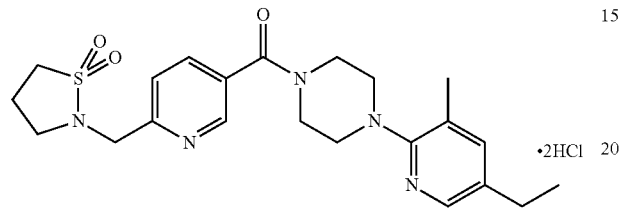

Using methyl 6-(1,1-dioxo-1λ⁶-isothiazolidin-2-ylmethyl)nicotinate (107 mg) described in Preparation Example 45 and 1-(5-ethyl-3-methylpyridin-2-yl)piperazine (81 mg) described in Preparation Example 81 and by the reaction and treatment in the same manner as in Example 109, [6-(1,1-dioxo-1λ⁶-isothiazolidin-2-ylmethyl)pyridin-3-yl][4-(5-ethyl-3-methylpyridin-2-yl)piperazin-1-yl]methanone (81 mg) was obtained. The obtained [6-(1,1-dioxo-1λ⁶-isothiazolidin-2-ylmethyl)pyridin-3-yl][4-(5-ethyl-3-methylpyridin-2-yl)piperazin-1-yl]methanone (81 mg) was dissolved in ethyl acetate/methanol, 2N hydrogen chloride/ethanol solution was added, and the solvent was evaporated under reduced pressure. The obtained residue was suspension washed with diisopropyl ether to give the title compound (83 mg).

MS (ESI) m/z: 444(M+H)⁺.

Example 521

Synthesis of (R)-1-{4-[4-(3,5-dimethylpyridin-2-yl)piperazine-1-carbonyl]-3-fluorophenyl}-5-methylimidazolidin-2-one

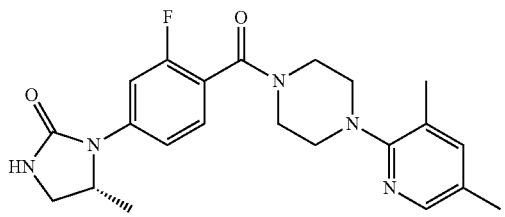 [SMILES: Cc1cnc(N2CCN(C(=O)c3ccc(N4C(=O)NC[C@H]4C)cc3F)CC2)c(C)c1]

Using (4-bromo-2-fluorophenyl)[4-(3,5-dimethylpyridin-2-yl)piperazin-1-yl]methanone (157 mg) described in Preparation Example 114 and (R)-1-(4-methoxybenzyl)-4-methylimidazolidin-2-one (106 mg) described in Preparation Example 202 and by the reaction and treatment in the same manner as in Example 1, (R)-3-{4-[4-(3,5-dimethylpyridin-2-yl)piperazine-1-carbonyl]-3-fluorophenyl}-1-(4-methoxybenzyl)-4-methylimidazolidin-2-one (173 mg) was obtained. Using the obtained (R)-3-{4-[4-(3,5-dimethylpyridin-2-yl)piperazine-1-carbonyl]-3-fluorophenyl}-1-(4-methoxybenzyl)-4-methylimidazolidin-2-one (173 mg) and by the reaction and treatment in the same manner as in Example 421, the title compound (106 mg) was obtained.

MS (ESI) m/z: 412(M+H)⁺.

Example 522

Synthesis of (R)-1-{5-[4-(3,5-dimethylpyridin-2-yl)piperazine-1-carbonyl]pyridin-2-yl}-5-methylimidazolidin-2-one

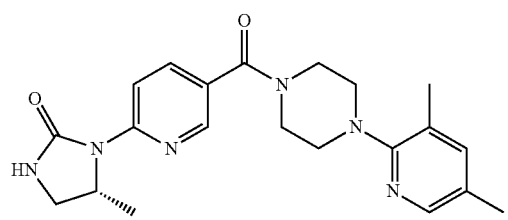 [SMILES: Cc1cnc(N2CCN(C(=O)c3ccc(N4C(=O)NC[C@H]4C)nc3)CC2)c(C)c1]

Using (6-bromopyridin-3-yl)[4-(3,5-dimethylpyridin-2-yl)piperazin-1-yl]methanone (150 mg) described in Preparation Example 127 and (R)-1-(4-methoxybenzyl)-4-methylimidazolidin-2-one (106 mg) described in Preparation Example 202 and by the reaction and treatment in the same manner as in Example 426, the title compound (81 mg) was obtained via (R)-3-{5-[4-(3,5-dimethylpyridin-2-yl)piperazine-1-carbonyl]pyridin-2-yl}-1-(4-methoxybenzyl)-4-methylimidazolidin-2-one.

MS (ESI) m/z: 395(M+H)⁺.

Example 523

Synthesis of (S)-1-{4-[4-(3,5-dimethylpyridin-2-yl)piperazine-1-carbonyl]-3-fluorophenyl}-5-methylimidazolidin-2-one

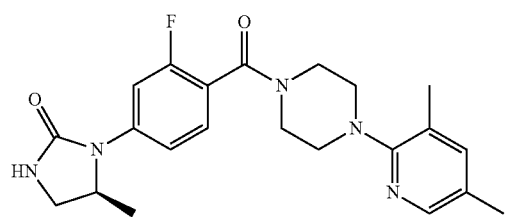 [SMILES: Cc1cnc(N2CCN(C(=O)c3ccc(N4C(=O)NC[C@@H]4C)cc3F)CC2)c(C)c1]

Using (4-bromo-2-fluorophenyl)[4-(3,5-dimethylpyridin-2-yl)piperazin-1-yl]methanone (157 mg) described in Preparation Example 114 and (S)-1-(4-methoxybenzyl)-4-methylimidazolidin-2-one (106 mg) described in Preparation Example 204 and by the reaction and treatment in the same manner as in Example 1, (S)-3-{4-[4-(3,5-dimethylpyridin-2-yl)piperazine-1-carbonyl]-3-fluorophenyl}-1-(4-methoxybenzyl)-4-methylimidazolidin-2-one (180 mg) was obtained. Using the obtained (S)-3-{4-[4-(3,5-dimethylpyridin-2-yl)piperazine-1-carbonyl]-3-fluorophenyl}-1-(4-methoxybenzyl)-4-methylimidazolidin-2-one (180 mg) and by the reaction and treatment in the same manner as in Example 421, the title compound (108 mg) was obtained.

MS (ESI) m/z: 412(M+H)⁺.

Example 524

Synthesis of (S)-1-{5-[4-(3,5-dimethylpyridin-2-yl)piperazine-1-carbonyl]pyridin-2-yl}-5-methylimidazolidin-2-one

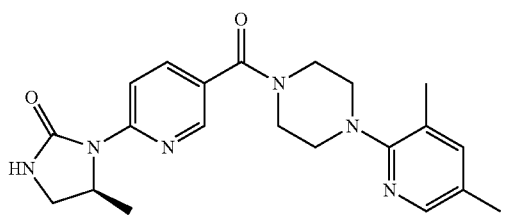 [SMILES: Cc1cnc(N2CCN(C(=O)c3ccc(N4C(=O)NC[C@@H]4C)nc3)CC2)c(C)c1]

Using (6-bromopyridin-3-yl)[4-(3,5-dimethylpyridin-2-yl)piperazin-1-yl]methanone (150 mg) described in Preparation Example 127 and (S)-1-(4-methoxybenzyl)-4-methylimidazolidin-2-one (106 mg) described in Preparation Example 204 and by the reaction and treatment in the same manner as in Example 426, the title compound (96 mg) was obtained via (S)-3-{5-[4-(3,5-dimethylpyridin-2-yl)piperazine-1-carbonyl]pyridin-2-yl}-1-(4-methoxybenzyl)-4-methylimidazolidin-2-one.

MS (ESI) m/z: 395(M+H)⁺.

Example 525

Synthesis of 1-{4-[4-(3,5-dimethylpyridin-2-yl)piperazine-1-carbonyl]-3-methylphenyl}-5-methylimidazolidine-2,4-dione

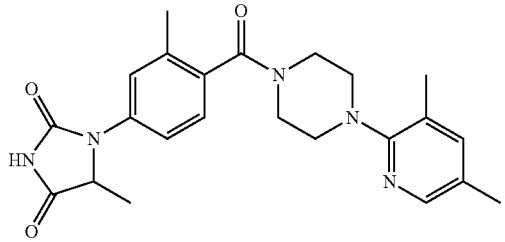

Using (4-bromo-2-methylphenyl)[4-(3,5-dimethylpyridin-2-yl)piperazin-1-yl]methanone (311 mg) described in Preparation Example 118 and 3-(4-methoxybenzyl)-5-methylimidazolidine-2,4-dione (225 mg) described in Preparation Example 51 and by the reaction and treatment in the same manner as in Example 508, the title compound (91 mg) was obtained via 1-{4-[4-(3,5-dimethylpyridin-2-yl)piperazine-1-carbonyl]-3-methylphenyl}-3-(4-methoxybenzyl)-5-methylimidazolidine-2,4-dione.

MS (ESI) m/z: 422(M+H)⁺.

Example 526

Synthesis of 1-{4-[4-(5-cyclopropyl-3-s methylpyridin-2-yl)piperazine-1-carbonyl]phenyl}-5-methylimidazolidin-2-one

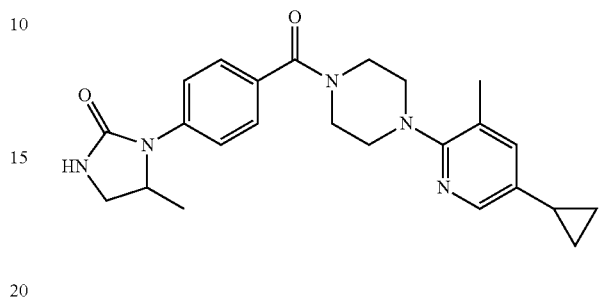

Using (4-bromophenyl)[4-(5-cyclopropyl-3-methylpyridin-2-yl)piperazin-1-yl]methanone (160 mg) described in Preparation Example 185 and 1-(4-methoxybenzyl)-4-methylimidazolidin-2-one (106 mg) described in Preparation Example 52 and by the reaction and treatment in the same manner as in Example 506, the title compound (113 mg) was obtained via 3-{4-[4-(5-cyclopropyl-3-methylpyridin-2-yl)piperazine-1-carbonyl]phenyl}-1-(4-methoxybenzyl)-4-methylimidazolidin-2-one.

MS (ESI) m/z: 420(M+H)⁺.

Example 527

Synthesis of 1-{5-[4-(5-cyclopropyl-3-methylpyridin-2-yl)piperazine-1-carbonyl]pyridin-2-yl}-5-methylimidazolidin-2-one

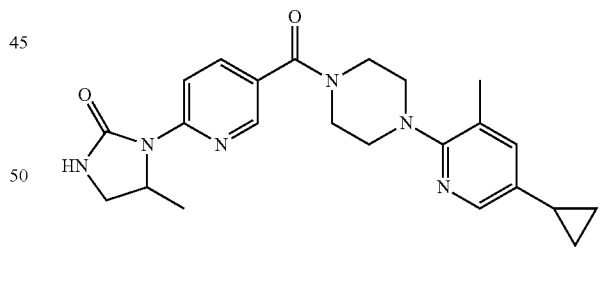

Using (6-bromopyridin-3-yl) [4-(5-cyclopropyl-3-methylpyridin-2-yl)piperazin-1-yl]methanone (160 mg) described in Preparation Example 144 and 1-(4-methoxybenzyl)-4-methylimidazolidin-2-one (106 mg) described in Preparation Example 52 and by the reaction and treatment in the same manner as in Example 505, the title compound (16 mg) was obtained via 3-{5-[4-(5-cyclopropyl-3-methylpyridin-2-yl)piperazine-1-carbonyl]pyridin-2-yl}-1-(4-methoxybenzyl)-4-methylimidazolidin-2-one.

MS (ESI) m/z: 421(M+H)⁺.

Example 528

Synthesis of 1-{4-[4-(3,5-dimethylpyridin-2-yl)piperazine-1-carbonyl]-2-fluorophenyl}-5-methylimidazolidine-2,4-dione

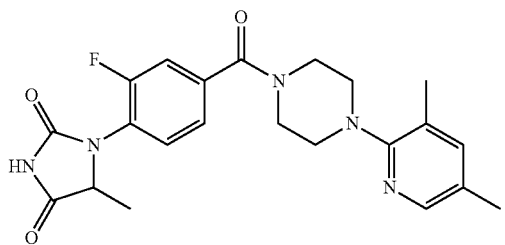

Using (4-bromo-3-fluorophenyl)[4-(3,5-dimethylpyridin-2-yl)piperazin-1-yl]methanone (314 mg) described in Preparation Example 125 and 3-(4-methoxybenzyl)-5-methylimidazolidine-2,4-dione (225 mg) described in Preparation Example 51 and by the reaction and treatment in the same manner as in Example 508, the title compound (141 mg) was obtained via 1-{4-[4-(3,5-dimethylpyridin-2-yl)piperazine-1-carbonyl]-2-fluorophenyl}-3-(4-methoxybenzyl)-5-methylimidazolidine-2,4-dione.

MS (ESI) m/z: 426(M+H)$^+$.

Example 529

Synthesis of 1-{4-[4-(3,5-dimethylpyridin-2-yl)piperazine-1-carbonyl]-3-methylphenyl}-3,5-dimethylimidazolidine-2,4-dione

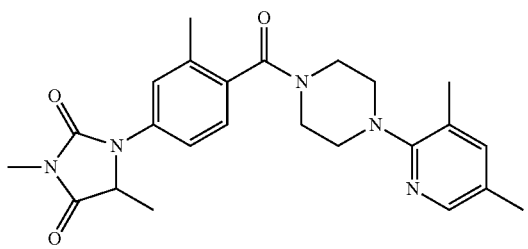

Using 1-{4-[4-(3,5-dimethylpyridin-2-yl)piperazine-1-carbonyl]-3-methylphenyl}-5-methylimidazolidine-2,4-dione (50 mg) described in Example 525 and methyl iodide (10 µL) and by the reaction and treatment in the same manner as in Example 36, the title compound (9 mg) was obtained.

MS (ESI) m/z: 436(M+H)$^+$.

Example 530

Synthesis of 1-{4-[4-(5-cyclopropyl-3-methylpyridin-2-yl)piperazine-1-carbonyl]-3-fluorophenyl}-5-methylimidazolidin-2-one

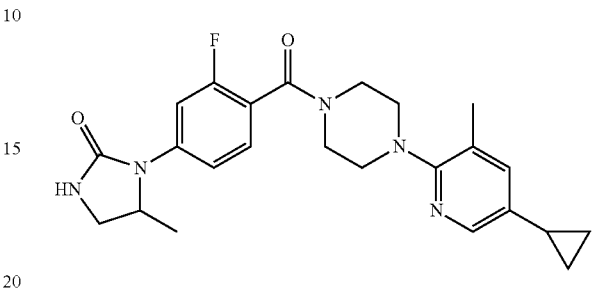

Using (4-bromo-2-fluorophenyl)[4-(5-cyclopropyl-3-methylpyridin-2-yl)piperazin-1-yl]methanone (167 mg) described in Preparation Example 121 and 1-(4-methoxybenzyl)-4-methylimidazolidin-2-one (106 mg) described in Preparation Example 52 and by the reaction and treatment in the same manner as in Example 506, the title compound (109 mg) was obtained via 3-{4-[4-(5-cyclopropyl-3-methylpyridin-2-yl)piperazine-1-carbonyl]-3-fluorophenyl}-1-(4-methoxybenzyl)-4-methylimidazolidin-2-one.

MS (ESI) m/z: 438(M+H)$^+$.

Example 531

Synthesis of 1-{4-[4-(3,5-dimethylpyridin-2-yl)piperazine-1-carbonyl]-2-fluorophenyl}-3,5-dimethylimidazolidine-2,4-dione

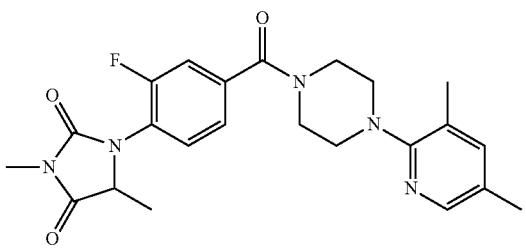

Using 1-{4-[4-(3,5-dimethylpyridin-2-yl)piperazine-1-carbonyl]-2-fluorophenyl}-5-methylimidazolidine-2,4-dione (90 mg) described in Example 528 and methyl iodide (17 µL) and by the reaction and treatment in the same manner as in Example 36, the title compound (22 mg) was obtained.

MS (ESI) m/z: 440(M+H)$^+$.

Example 532

Synthesis of 1-{4-[4-(3,5-dimethylpyridin-2-yl)piperazine-1-carbonyl]-2-fluorophenyl}-5-methylimidazolidin-2-one

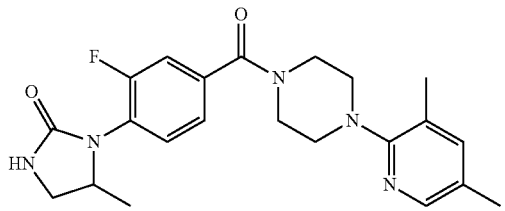

Using (4-bromo-3-fluorophenyl)[4-(3,5-dimethylpyridin-2-yl)piperazin-1-yl]methanone (157 mg) described in Preparation Example 125 and 1-(4-methoxybenzyl)-4-methylimidazolidin-2-one (106 mg) described in Preparation Example 52 and by the reaction and treatment in the same manner as in Example 506, the title compound (86 mg) was obtained via 3-{4-[4-(3,5-dimethylpyridin-2-yl)piperazine-1-carbonyl]-2-fluorophenyl}-1-(4-methoxybenzyl)-4-methylimidazolidin-2-one.

MS (ESI) m/z: 412(M+H)$^+$.

Example 533

Synthesis of 5-methyl-1-{5-[4-(3,5,6-trimethylpyridin-2-yl)piperazine-1-carbonyl]pyridin-2-yl}imidazolidin-2-one

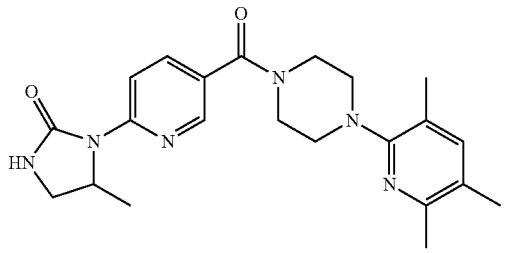 [SMILES: Cc1cc(C)c(N2CCN(C(=O)c3ccc(N4C(=O)NCC4C)nc3)CC2)nc1C]

Using (6-bromopyridin-3-yl)[4-(3,5,6-trimethylpyridin-2-yl)piperazin-1-yl]methanone (156 mg) described in Preparation Example 205 and 1-(4-methoxybenzyl)-4-methylimidazolidin-2-one (106 mg) described in Preparation Example 52 and by the reaction and treatment in the same manner as in Example 505, the title compound (101 mg) was obtained via 1-(4-methoxybenzyl)-4-methyl-3-{5-[4-(3,5,6-trimethylpyridin-2-yl)piperazine-1-carbonyl]pyridin-2-yl}imidazolidin-2-one.

MS (ESI) m/z: 409(M+H)$^+$.

Example 534

Synthesis of 1-{3-fluoro-4-[4-(3,5,6-trimethylpyridin-2-yl)piperazine-1-carbonyl]phenyl}-5-methylimidazolidin-2-one

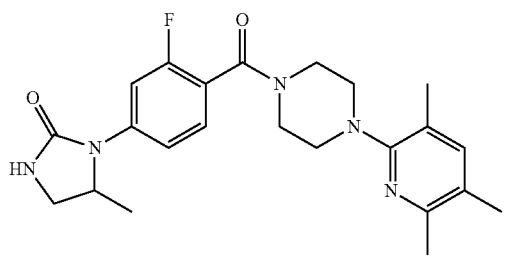

Using (4-bromo-2-fluorophenyl)[4-(3,5,6-trimethylpyridin-2-yl)piperazin-1-yl]methanone (163 mg) described in Preparation Example 128 and 1-(4-methoxybenzyl)-4-methylimidazolidin-2-one (106 mg) described in Preparation Example 52 and by the reaction and treatment in the same manner as in Example 506, the title compound (79 mg) was obtained via 3-{3-fluoro-4-[4-(3,5,6-trimethylpyridin-2-yl)piperazine-1-carbonyl]phenyl}-1-(4-methoxybenzyl)-4-methylimidazolidin-2-one.

MS (ESI) m/z: 426(M+H)$^+$.

Example 535

Synthesis of 5-methyl-1-{4-[4-(3,5,6-trimethylpyridin-2-yl)piperazine-1-carbonyl]phenyl}imidazolidin-2-one

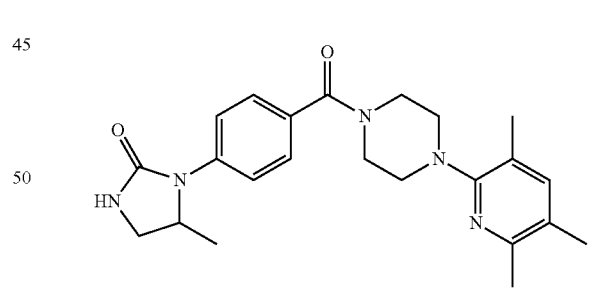

Using (4-iodophenyl)[4-(3,5,6-trimethylpyridin-2-yl)piperazin-1-yl]methanone (174 mg) described in Preparation Example 120 and 1-(4-methoxybenzyl)-4-methylimidazolidin-2-one (106 mg) described in Preparation Example 52 and by the reaction and treatment in the same manner as in Example 506, the title compound (135 mg) was obtained via 1-(4-methoxybenzyl)-4-methyl-3-{4-[4-(3,5,6-trimethylpyridin-2-yl)piperazine-1-carbonyl]phenyl}imidazolidin-2-one.

MS (ESI) m/z: 408(M+H)$^+$.

Example 536

Synthesis of 3-benzyloxymethyl-1-{4-[4-(5-cyclopropyl-3-methylpyridin-2-yl)piperazine-1-carbonyl]-3-fluorophenyl}-5-methylimidazolidine-2,4-dione

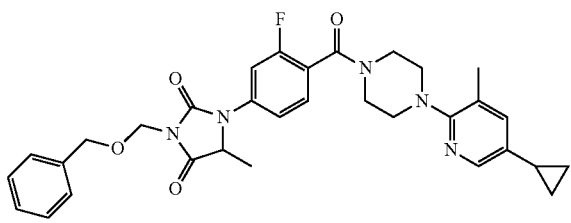

1,4-Dioxane (12 mL) and N,N'-dimethylethylenediamine (86 µL) were added to a mixture of (4-bromo-2-fluorophenyl)[4-(5-cyclopropyl-3-methylpyridin-2-yl)piperazin-1-yl]methanone (325 mg) described in Preparation Example 121, 3-benzyloxymethyl-5-methylimidazolidine-2,4-dione (225 mg) described in Preparation Example 206, cesium carbonate (521 mg) and copper(I) iodide (76 mg), and the mixture was stirred with heating under reflux for 10 hr. The reaction mixture was cooled, water was added, and the mixture was extracted with ethyl acetate. The organic layer was washed with saturated brine, dried over sodium sulfate, and the solvent was evaporated. The obtained residue was purified by column chromatography (hexane:ethyl acetate) to give the title is compound (270 mg).

MS (ESI) m/z: 572(M+H)$^+$.

Example 537

Synthesis of 1-{4-[4-(5-cyclopropyl-3-methylpyridin-2-yl)piperazine-1-carbonyl]-3-fluorophenyl}-5-methylimidazolidine-2,4-dione

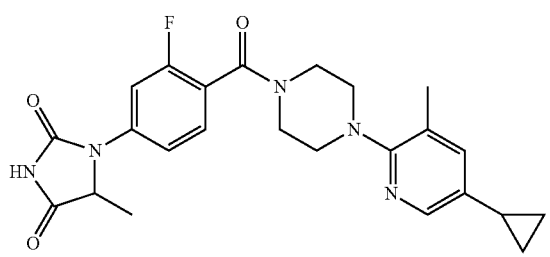 [SMILES: Cc1cc(C2CC2)cnc1N1CCN(C(=O)c2ccc(N3C(=O)NC(=O)C3C)cc2F)CC1]

3-Benzyloxymethyl-1-{4-[4-(5-cyclopropyl-3-methylpyridin-2-yl)piperazine-1-carbonyl]-3-fluorophenyl}-5-methylimidazolidine-2,4-dione (270 mg) described in Example 536 was dissolved in methanol (20 mL), formic acid (0.36 ml) and 10% palladium carbon catalyst (108 mg) were added, and the mixture was stirred with heating under reflux for 16 hr. The reaction mixture was cooled, the catalyst was removed by celite filtration, and the solvent was evaporated. To the residue were added methanol and 0.5N aqueous sodium hydroxide solution, and the mixture was stirred at room temperature. The reaction solution was neutralized with acetic acid, and the solvent was evaporated. Water was added to the residue, and the mixture was extracted with chloroform. The organic layer was dried over sodium sulfate, and the solvent was evaporated. The obtained residue was purified by column chromatography (chloroform:methanol) to give the title compound (40 mg).

MS (ESI) m/z: 452(M+H)$^+$.

Example 538

Synthesis of 3-benzyloxymethyl-1-{4-[4-(5-cyclopropyl-3-methylpyridin-2-yl)piperazine-1-carbonyl]phenyl}-5-methylimidazolidine-2,4-dione

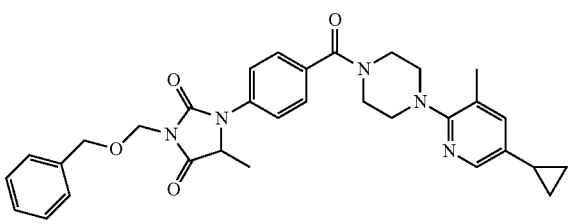 [SMILES: Cc1cc(C2CC2)cnc1N1CCN(C(=O)c2ccc(N3C(=O)N(COCc4ccccc4)C(=O)C3C)cc2)CC1]

Using (4-bromophenyl)[4-(5-cyclopropyl-3-methylpyridin-2-yl)piperazin-1-yl]methanone (320 mg) described in Preparation Example 185 and 3-benzyloxymethyl-5-methylimidazolidine-2,4-dione (225 mg) described in Preparation Example 206 and by the reaction and treatment in the same manner as in Example 536, the title compound (286 mg) was obtained.

MS (ESI) m/z: 554(M+H)$^+$.

Example 539

Synthesis of 1-{4-[4-(5-cyclopropyl-3-methylpyridin-2-yl)piperazine-1-carbonyl]phenyl}-5-methylimidazolidine-2,4-dione

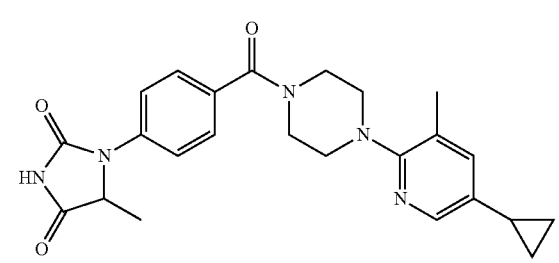 [SMILES: Cc1cc(C2CC2)cnc1N1CCN(C(=O)c2ccc(N3C(=O)NC(=O)C3C)cc2)CC1]

Using 3-benzyloxymethyl-1-{4-[4-(5-cyclopropyl-3-methylpyridin-2-yl)piperazine-1-carbonyl]phenyl}-5-methylimidazolidine-2,4-dione (286 mg) described in Example 538 and by the reaction and treatment in the same manner as in Example 537, the title compound (59 mg) was obtained.

MS (ESI) m/z: 434(M+H)$^+$.

Example 540

Synthesis of 3-benzyloxymethyl-1-{5-[4-(5-cyclopropyl-3-methylpyridin-2-yl)piperazine-1-carbonyl]pyridin-2-yl}-5-methylimidazolidine-2,4-dione

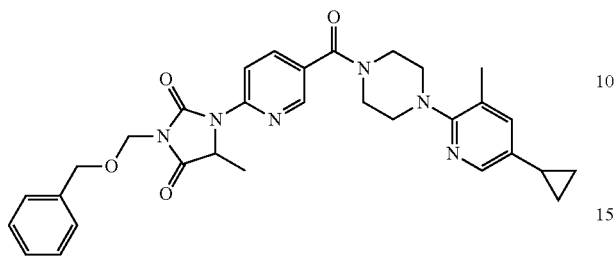

Using (6-bromopyridin-3-yl)[4-(5-cyclopropyl-3-methylpyridin-2-yl)piperazin-1-yl]methanone (321 mg) described in Preparation Example 144 and 3-benzyloxymethyl-5-methylimidazolidine-2,4-dione (225 mg) described in Preparation Example 206 and by the reaction and treatment in the same manner as in Example 536, the title compound (391 mg) was obtained.
MS (ESI) m/z: 555(M+H)+.

Example 541

Synthesis of 1-{5-[4-(5-cyclopropyl-3-methylpyridin-2-yl)piperazine-1-carbonyl]pyridin-2-yl}-5-methylimidazolidine-2,4-dione

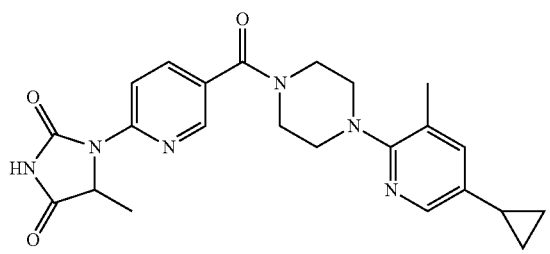 [SMILES: Cc1cc(C2CC2)cnc1N1CCN(C(=O)c2ccc(N3C(=O)NC(=O)C3C)nc2)CC1]

Using 3-benzyloxymethyl-1-{5-[4-(5-cyclopropyl-3-methylpyridin-2-yl)piperazine-1-carbonyl]pyridin-2-yl}-5-methylimidazolidine-2,4-dione (390 mg) described in Example 540 and by the reaction and treatment in the same manner as in Example 537, the title compound (9 mg) was obtained.
MS (ESI) m/z: 435(M+H)+.

Example 542

Synthesis of 1-{5-[4-(3,5-dimethylpyridin-2-yl)piperazine-1-carbonyl]pyridin-2-yl}-5-ethylimidazolidin-2-one

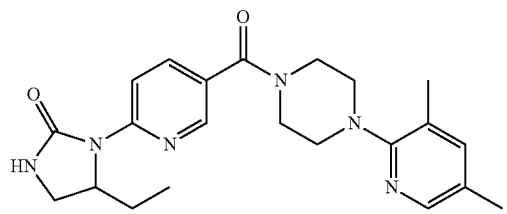

Using (6-bromopyridin-3-yl)[4-(3,5-dimethylpyridin-2-yl)piperazin-1-yl]methanone (225 mg) described in Preparation Example 127 and 4-ethyl-1-(4-methoxybenzyl)imidazolidin-2-one (140 mg) described in Preparation Example 208 and by the reaction and treatment in the same manner as in Example 505, the title compound (96 mg) was obtained via 3-{5-[4-(3,5-dimethylpyridin-2-yl)piperazine-1-carbonyl]pyridin-2-yl}-4-ethyl-1-(4-methoxybenzyl)imidazolidin-2-one.
MS (ESI) m/z: 409(M+H)+.

Example 543

Synthesis of 1-{4-[4-(3,5-dimethylpyridin-2-yl)piperazine-1-carbonyl]phenyl}-5-ethylimidazolidin-2-one

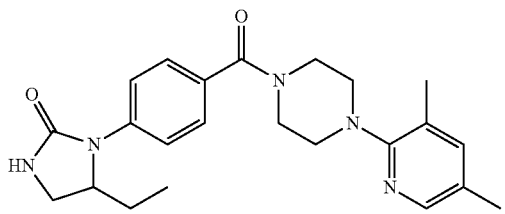 [SMILES: CCC1CNC(=O)N1c1ccc(C(=O)N2CCN(c3ncc(C)cc3C)CC2)cc1]

Using [4-(3,5-dimethylpyridin-2-yl)piperazin-1-yl](4-iodophenyl)methanone (253 mg) described in Preparation Example 113 and 4-ethyl-1-(4-methoxybenzyl)imidazolidin-2-one (140 mg) described in Preparation Example 208 and by the reaction and treatment in the same manner as in Example 506, the title compound (162 mg) was obtained via 3-{4-[4-(3,5-dimethylpyridin-2-yl)piperazine-1-carbonyl]phenyl}-4-ethyl-1-(4-methoxybenzyl)imidazolidin-2-one.
MS (ESI) m/z: 408(M+H)+.

Example 544

Synthesis of 1-{4-[4-(3,5-dimethylpyridin-2-yl)piperazine-1-carbonyl]phenyl}-5-isopropylimidazolidin-2-one

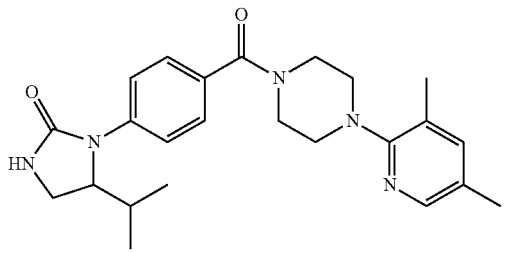 [SMILES: Cc1cnc(N2CCN(C(=O)c3ccc(N4C(=O)NCC4C(C)C)cc3)CC2)c(C)c1]

Using [4-(3,5-dimethylpyridin-2-yl)piperazin-1-yl](4-iodophenyl)methanone (253 mg) described in Preparation Example 113 and 4-isopropyl-1-(4-methoxybenzyl)imidazolidin-2-one (149 mg) described in Preparation Example 210 and by the reaction and treatment in the same manner as in Example 506, the title compound (145 mg) was obtained via 3-{4-[4-(3,5-dimethylpyridin-2-yl)piperazine-1-carbonyl]phenyl}-4-isopropyl-1-(4-methoxybenzyl)imidazolidin-2-one.
MS (ESI) m/z: 422(M+H)+.

Example 545

Synthesis of (R)-1-{5-[4-(3,5-dimethylpyridin-2-yl)piperazine-1-carbonyl]pyridin-2-yl}-5-methylpyrrolidin-2-one dihydrochloride

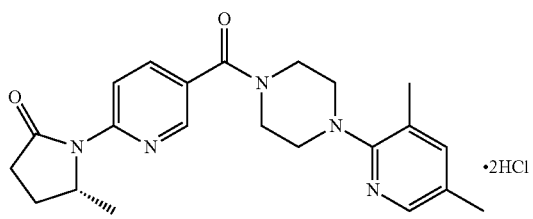 [SMILES: Cc1cnc(N2CCN(C(=O)c3ccc(N4C(=O)CC[C@H]4C)nc3)CC2)c(C)c1]

Using (6-bromopyridin-3-yl)[4-(3,5-dimethylpyridin-2-yl)piperazin-1-yl]methanone (188 mg) described in Preparation Example 127 and (R)-5-methylpyrrolidin-2-one (59 mg) described in Preparation Example 221 and by the reaction and treatment in the same manner as in Example 141, the title compound (105 mg) was obtained via (R)-1-{5-[4-(3,5-dimethylpyridin-2-yl)piperazine-1-carbonyl]pyridin-2-yl}-5-methylpyrrolidin-2-one.

MS (ESI) m/z: 394(M+H)$^+$.

Example 546

Synthesis of (S)-1-{5-[4-(3,5-dimethylpyridin-2-yl)piperazine-1-carbonyl]pyridin-2-yl}-5-methylpyrrolidin-2-one dihydrochloride

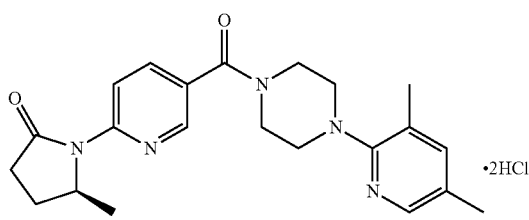 [SMILES: Cc1cnc(N2CCN(C(=O)c3ccc(N4C(=O)CC[C@@H]4C)nc3)CC2)c(C)c1]

Using (6-bromopyridin-3-yl)[4-(3,5-dimethylpyridin-2-yl)piperazin-1-yl]methanone (188 mg) described in Preparation Example 127 and (S)-5-methylpyrrolidin-2-one (59 mg) described in Preparation Example 224 and by the reaction and treatment in the same manner as in Example 141, the title compound (92 mg) was obtained via (S)-1-{5-[4-(3,5-dimethylpyridin-2-yl)piperazine-1-carbonyl]pyridin-2-yl}-5-methylpyrrolidin-2-one.

MS (ESI) m/z: 394(M+H)$^+$.

Example 547

Synthesis of 1-{5-[4-(3,5-dimethylpyridin-2-yl)piperazine-1-carbonyl]pyridin-2-yl}-5-isopropylimidazolidin-2-one

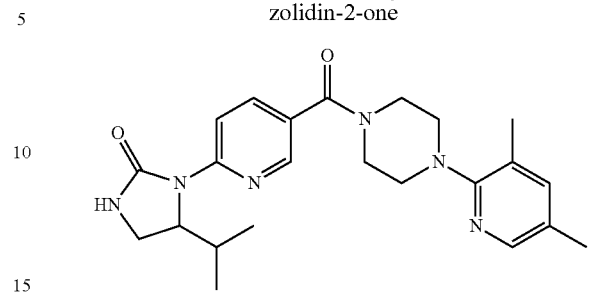

Using (6-bromopyridin-3-yl)[4-(3,5-dimethylpyridin-2-yl)piperazin-1-yl]methanone (225 mg) described in Preparation Example 127 and 4-isopropyl-1-(4-methoxybenzyl)imidazolidin-2-one (149 mg) described in Preparation Example 210 and by the reaction and treatment in the same manner as in Example 505, the title compound (52 mg) was obtained via 3-{5-[4-(3,5-dimethylpyridin-2-yl)piperazine-1-carbonyl]pyridin-2-yl}-4-isopropyl-1-(4-methoxybenzyl)imidazolidin-2-one.

MS (ESI) m/z: 423(M+H)$^+$.

Example 548

Synthesis of 3-{5-[4-(3,5-dimethylpyridin-2-yl)piperazine-1-carbonyl]pyridin-2-yl}-1,4-dimethylimidazolidin-2-one

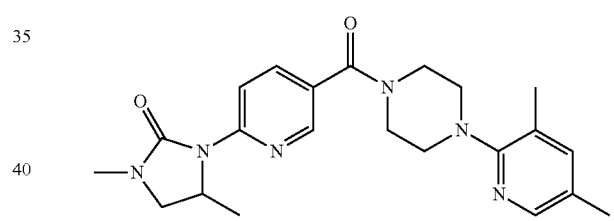

Using 1-{5-[4-(3,5-dimethylpyridin-2-yl)piperazine-1-carbonyl]pyridin-2-yl}-5-methylimidazolidin-2-one (166 mg) described in Example 426 and methyl iodide (31 μL) and by the reaction and treatment in the same manner as in Example 36, the title compound (123 mg) was obtained.

MS (ESI) m/z: 409(M+H)$^+$.

Example 549

Synthesis of 5-methyl-1-{5-[4-(3,5,6-trimethylpyridin-2-yl)piperazine-1-carbonyl]pyridin-2-yl}imidazolidine-2,4-dione

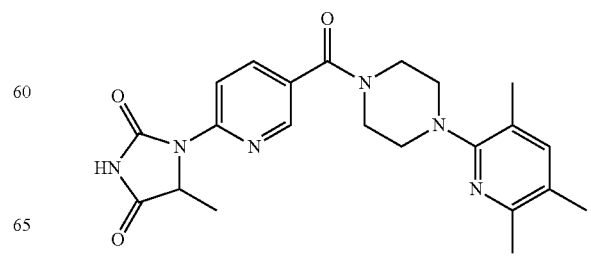

Using (6-bromopyridin-3-yl)[4-(3,5,6-trimethylpyridin-2-yl)piperazin-1-yl]methanone (311 mg) described in Preparation Example 205 and 3-(4-methoxybenzyl)-5-methylimidazolidine-2,4-dione (187 mg) described in Preparation Example 51 and by the reaction and treatment in the same manner as in Example 508, the title compound (110 mg) was obtained via 3-(4-methoxybenzyl)-5-methyl-1-{5-[4-(3,5,6-trimethylpyridin-2-yl)piperazine-1-carbonyl]pyridin-2-yl}imidazolidine-2,4-dione.

MS (ESI) m/z: 423(M+H)$^+$.

Example 550

Synthesis of 5-methyl-1-{4-[4-(3,5,6-trimethylpyridin-2-yl)piperazine-1-carbonyl]phenyl}imidazolidine-2,4-dione

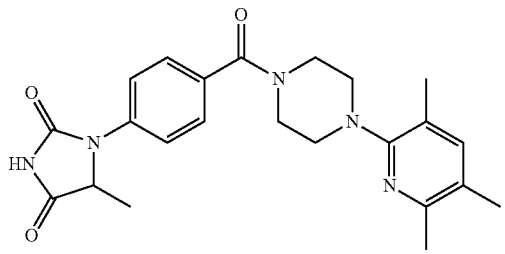 [SMILES: Cc1cc(C)c(N2CCN(C(=O)c3ccc(N4C(=O)NC(=O)C4C)cc3)CC2)nc1C]

Using (4-iodophenyl) [4-(3,5,6-trimethylpyridin-2-yl)piperazin-1-yl]methanone (348 mg) described in Preparation Example 120 and 3-(4-methoxybenzyl)-5-methylimidazolidine-2,4-dione (187 mg) described in Preparation Example 51 and by the reaction and treatment in the same manner as in Example 508, the title compound (166 mg) was obtained via 3-(4-methoxybenzyl)-5-methyl-1-{4-[4-(3,5,6-trimethylpyridin-2-yl)piperazine-1-carbonyl]phenyl}imidazolidine-2,4-dione.

MS (ESI) m/z: 422(M+H)$^+$.

Example 551

Synthesis of 3,5-dimethyl-1-{5-[4-(3,5,6-trimethylpyridin-2-yl)piperazine-1-carbonyl]pyridin-2-yl}-imidazolidine-2,4-dione

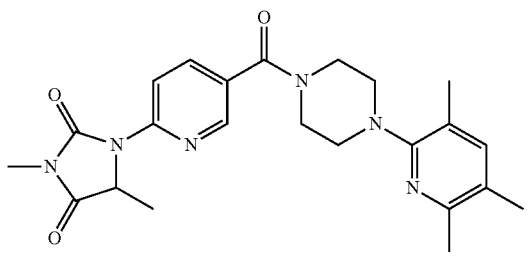

5-Methyl-1-{5-[4-(3,5,6-trimethylpyridin-2-yl)piperazine-1-carbonyl]pyridin-2-yl}imidazolidine-2,4-dione (60 mg) described in Example 549 was dissolved in tetrahydrofuran, potassium tert-butoxide (17 mg) and methyl iodide (9.3 μL) were added under ice-cooling, and the mixture was stirred at the same temperature for 15 min and at room temperature for 24 hr. Water was added to the reaction mixture, and the mixture was extracted with ethyl acetate. The organic layer was washed with water and saturated brine, dried over sodium sulfate, and the solvent was evaporated. The obtained residue was purified by column chromatography (hexane:ethyl acetate) to give the title compound (50 mg).

MS (ESI) m/z: 437(M+H)$^+$.

Example 552

Synthesis of 1-{3-fluoro-4-[4-(3,5,6-trimethylpyridin-2-yl)piperazine-1-carbonyl]phenyl}-5-methylimidazolidine-2,4-dione

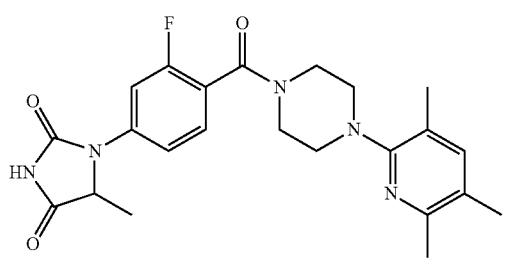 [SMILES: Cc1cc(C)c(N2CCN(C(=O)c3ccc(N4C(=O)NC(=O)C4C)cc3F)CC2)nc1C]

Using (4-bromo-2-fluorophenyl)[4-(3,5,6-trimethylpyridin-2-yl)piperazin-1-yl]methanone (325 mg) described in Preparation Example 128 and 3-(4-methoxybenzyl)-5-methylimidazolidine-2,4-dione (187 mg) described in Preparation Example 51 and by the reaction and treatment in the same manner as in Example 508, the title compound (169 mg) was obtained via 1-{3-fluoro-4-[4-(3,5,6-trimethylpyridin-2-yl)piperazine-1-carbonyl]phenyl}-3-(4-methoxybenzyl)-5-methylimidazolidine-2,4-dione.

MS (ESI) m/z: 440(M+H)$^+$.

Example 553

Synthesis of 3,5-dimethyl-1-{4-[4-(3,5,6-trimethylpyridin-2-yl)piperazine-1-carbonyl]phenyl}imidazolidine-2,4-dione

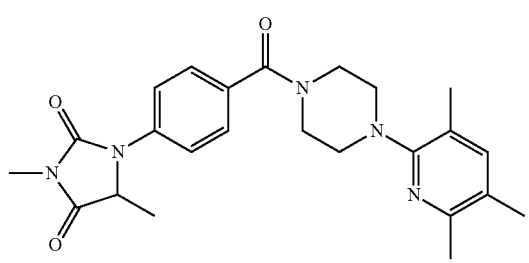

Using 5-methyl-1-{4-[4-(3,5,6-trimethylpyridin-2-yl)piperazine-1-carbonyl]phenyl}imidazolidine-2,4-dione (50 mg) described in Example 550 and methyl iodide (8.1 μL) and by the reaction and treatment in the same manner as in Example 551, the title compound (27 mg) was obtained.

MS (ESI) m/z: 436(M+H)$^+$.

Example 554

Synthesis of 1-{3-fluoro-4-[4-(3,5,6-trimethylpyridin-2-yl)piperazine-1-carbonyl]phenyl}-3,5-dimethylimidazolidine-2,4-dione

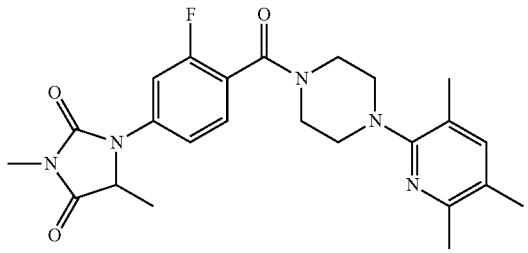

Using 1-{3-fluoro-4-[4-(3,5,6-trimethylpyridin-2-yl)piperazine-1-carbonyl]phenyl}-5-methylimidazolidine-2,4-dione (50 mg) described in Example 552 and methyl iodide (7.8 µL) and by the reaction and treatment in the same manner as in Example 551, the title compound (27 mg) was obtained.
MS (ESI) m/z: 454(M+H)+.

Example 555

Synthesis of 1-{4-[4-(3,5-dimethylpyridin-2-yl)piperazine-1-carbonyl]-3-fluorophenyl}imidazolidin-2-one hydrochloride

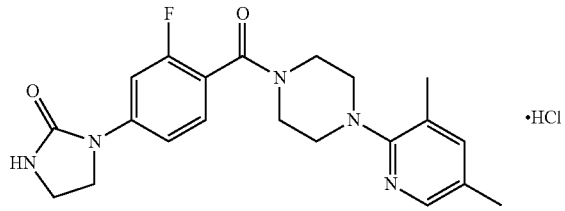 [SMILES: Cc1cnc(N2CCN(C(=O)c3ccc(N4CCNC4=O)cc3F)CC2)c(C)c1 ; Cl]

1-{4-[4-(3,5-Dimethylpyridin-2-yl)piperazine-1-carbonyl]-3-fluorophenyl}imidazolidin-2-one (840 mg) described in Example 416 was dissolved in chloroform/methanol, 2N hydrogen chloride/ethanol solution was added, and the solvent was evaporated under reduced pressure. The obtained residue was suspension washed with ethyl acetate to give the title compound (909 mg).
MS (ESI) m/z: 398(M+H)+.

Example 556

Synthesis of 1-{4-[4-(5-ethyl-3-methylpyridin-2-yl)piperazine-1-carbonyl]-3-fluorophenyl}-5-methylimidazolidin-2-one

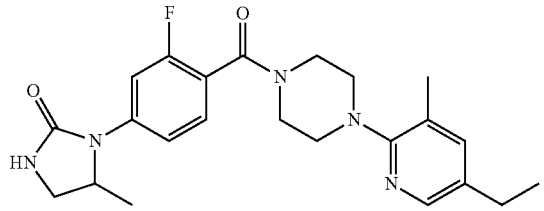 [SMILES: CCc1cnc(N2CCN(C(=O)c3ccc(N4C(=O)NCC4C)cc3F)CC2)c(C)c1]

Using (4-bromo-2-fluorophenyl)[4-(5-ethyl-3-methylpyridin-2-yl)piperazin-1-yl]methanone (163 mg) described in Preparation Example 211 and 1-(4-methoxybenzyl)-4-methylimidazolidin-2-one (88 mg) described in Preparation Example 52 and by the reaction and treatment in the same manner as in Example 506, the title compound (89 mg) was obtained via 3-{4-[4-(5-ethyl-3-methylpyridin-2-yl)piperazine-1-carbonyl]-3-fluorophenyl}-1-(4-methoxybenzyl)-4-methylimidazolidin-2-one.
MS (ESI) m/z: 426(M+H)+.

Example 557

Synthesis of 1-{5-[4-(5-ethyl-3-methylpyridin-2-yl)piperazine-1-carbonyl]pyridin-2-yl}-5-methylimidazolidin-2-one

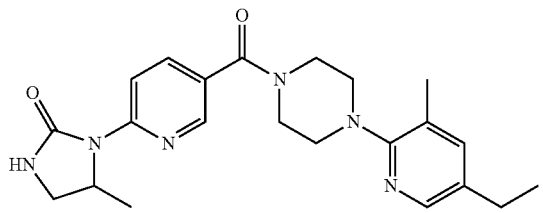 [SMILES: CCc1cnc(N2CCN(C(=O)c3ccc(N4C(=O)NCC4C)nc3)CC2)c(C)c1]

Using (6-bromopyridin-3-yl) [4-(5-ethyl-3-methylpyridin-2-yl)piperazin-1-yl]methanone (156 mg) described in Preparation Example 145 and 1-(4-methoxybenzyl)-4-methylimidazolidin-2-one (88 mg) described in Preparation Example 52 and by the reaction and treatment in the same manner as in Example 505, the title compound (110 mg) was obtained via 3-{5-[4-(5-ethyl-3-methylpyridin-2-yl)piperazine-1-carbonyl]pyridin-2-yl}-1-(4-methoxybenzyl)-4-methylimidazolidin-2-one.
MS (ESI) m/z: 409(M+H)+.

Example 558

Synthesis of 1-{4-[4-(5-ethyl-3-methylpyridin-2-yl)piperazine-1-carbonyl]phenyl}-5-methylimidazolidin-2-one

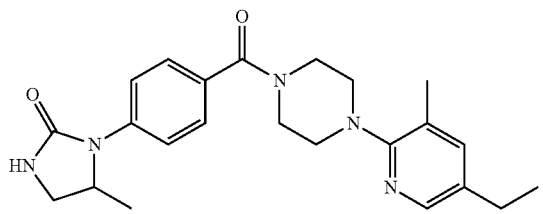 [SMILES: CCc1cnc(N2CCN(C(=O)c3ccc(N4C(=O)NCC4C)cc3)CC2)c(C)c1]

Using (4-bromophenyl)[4-(5-ethyl-3-methylpyridin-2-yl)piperazin-1-yl]methanone (155 mg) described in Preparation Example 212 and 1-(4-methoxybenzyl)-4-methylimidazolidin-2-one (88 mg) described in Preparation Example 52 and by the reaction and treatment in the same manner as in Example 506, the title compound (117 mg) was obtained via 3-{4-[4-(5-ethyl-3-methylpyridin-2-yl)piperazine-1-carbonyl]phenyl}-1-(4-methoxybenzyl)-4-methylimidazolidin-2-one.
MS (ESI) m/z: 408(M+H)+.

Example 559

Synthesis of 1-{4-[4-(3,5-dimethylpyridin-2-yl)piperazine-1-carbonyl]phenyl}imidazolidine-2,4-dione

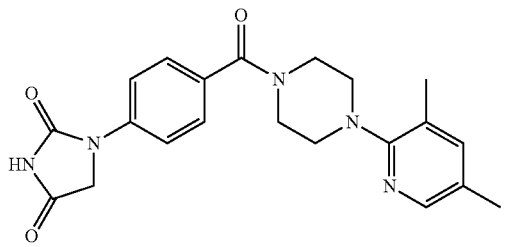 [SMILES: Cc1cnc(N2CCN(C(=O)c3ccc(N4CC(=O)NC4=O)cc3)CC2)c(C)c1]

Using [4-(3,5-dimethylpyridin-2-yl)piperazin-1-yl](4-iodophenyl)methanone (337 mg) described in Preparation Example 113 and 3-(4-methoxybenzyl)imidazolidine-2,4-dione (176 mg) described in Preparation Example 213 and by the reaction and treatment in the same manner as in Example 508, the title compound (61 mg) was obtained via 1-{4-[4-(3,5-dimethylpyridin-2-yl)piperazine-1-carbonyl]phenyl}-3-(4-methoxybenzyl)imidazolidine-2,4-dione.

MS (ESI) m/z: 394(M+H)$^+$.

Example 560

Synthesis of 1-{4-[4-(3,5-dimethylpyridin-2-yl)piperazine-1-carbonyl]-3-fluorophenyl}imidazolidine-2,4-dione

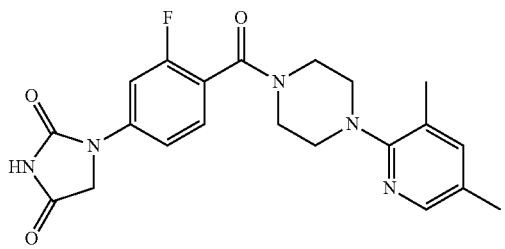

Using (4-bromo-2-fluorophenyl)[4-(3,5-dimethylpyridin-2-yl)piperazin-1-yl]methanone (314 mg) described in Preparation Example 114 and 3-(4-methoxybenzyl)imidazolidine-2,4-dione (176 mg) described in Preparation Example 213 and by the reaction and treatment in the same manner as in Example 508, the title compound (185 mg) was obtained via 1-{4-[4-(3,5-dimethylpyridin-2-yl)piperazine-1-carbonyl]-3-fluorophenyl}-3-(4-methoxybenzyl)imidazolidine-2,4-dione.

MS (ESI) m/z: 412(M+H)$^+$.

Example 561

Synthesis of 1-{5-[4-(3,5-dimethylpyridin-2-yl)piperazine-1-carbonyl]pyridin-2-yl}imidazolidine-2,4-dione

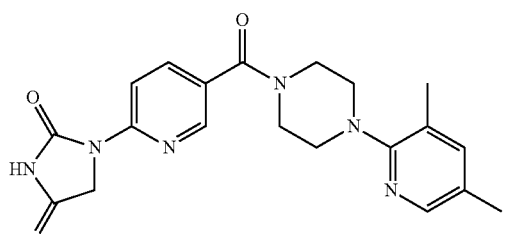

Using (6-bromopyridin-3-yl)[4-(3,5-dimethylpyridin-2-yl)piperazin-1-yl]methanone (300 mg) described in Preparation Example 127 and 3-(4-methoxybenzyl)imidazolidine-2,4-dione (176 mg) described in Preparation Example 213 and by the reaction and treatment in the same manner as in Example 508, the title compound (165 mg) was obtained via 1-{5-[4-(3,5-dimethylpyridin-2-yl)piperazine-1-carbonyl]pyridin-2-yl}-3-(4-methoxybenzyl)imidazolidine-2,4-dione.

MS (ESI) m/z: 395(M+H)$^+$.

Example 562

Synthesis of 1-{4-[4-(3,5-dimethylpyridin-2-yl)piperazine-1-carbonyl]phenyl}-3-methylimidazolidine-2,4-dione

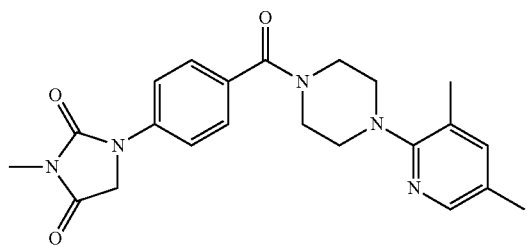

Using [4-(3,5-dimethylpyridin-2-yl)piperazin-1-yl](4-iodophenyl)methanone (169 mg) described in Preparation Example 113 and 3-methylimidazolidine-2,4-dione (46 mg) described in Preparation Example 214 and by the reaction and treatment in the same manner as in Example 536, the title compound (50 mg) was obtained.

MS (ESI) m/z: 408(M+H)$^+$.

Example 563

Synthesis of 1-{4-[4-(3,5-dimethylpyridin-2-yl)piperazine-1-carbonyl]-3-fluorophenyl}-3-methylimidazolidine-2,4-dione

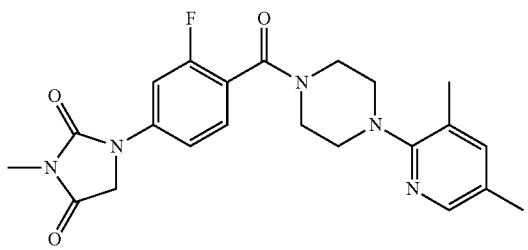

Using (4-bromo-2-fluorophenyl)[4-(3,5-dimethylpyridin-2-yl)piperazin-1-yl]methanone (157 mg) described in Preparation Example 114 and 3-methylimidazolidine-2,4-dione (46 mg) described in Preparation Example 214 and by the reaction and treatment in the same manner as in Example 536, the title compound (40 mg) was obtained.

MS (ESI) m/z: 426(M+H)$^+$.

Example 564

Synthesis of 1-{5-[4-(3,5-dimethylpyridin-2-yl)piperazine-1-carbonyl]pyridin-2-yl}-3-methylimidazolidine-2,4-dione

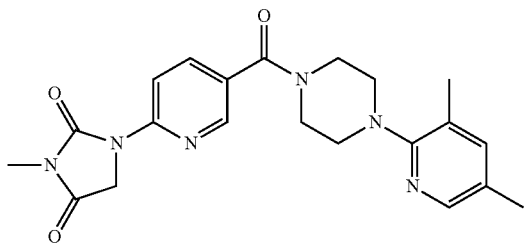

Using (6-bromopyridin-3-yl)[4-(3,5-dimethylpyridin-2-yl)piperazin-1-yl]methanone (150 mg) described in Preparation Example 127 and 3-methylimidazolidine-2,4-dione (46 mg) described in Preparation Example 214 and by the reaction and treatment in the same manner as in Example 536, the title compound (66 mg) was obtained.

MS (ESI) m/z: 409(M+H)$^+$.

Example 565

Synthesis of 1-{4-[4-(3,5-dimethylpyridin-2-yl)piperazine-1-carbonyl]phenyl}-5-ethylimidazolidine-2,4-one

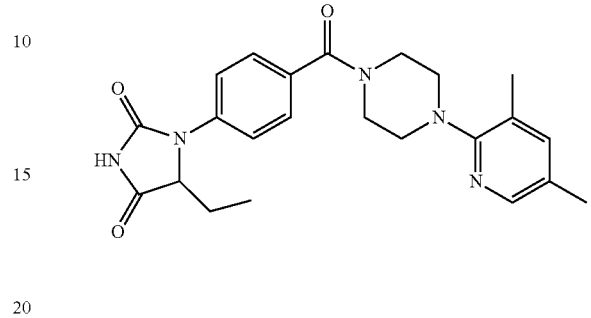

Using [4-(3,5-dimethylpyridin-2-yl)piperazin-1-yl](4-iodophenyl)methanone (337 mg) described in Preparation Example 113 and 5-ethyl-3-(4-methoxybenzyl)imidazolidine-2,4-dione (176 mg) described in Preparation Example 207 and by the reaction and treatment in the same manner as in Example 508, the title compound (205 mg) was obtained via 1-{4-[4-(3,5-dimethylpyridin-2-yl)piperazine-1-carbonyl]phenyl}-5-ethyl-3-(4-methoxybenzyl)imidazolidine-2,4-dione.

MS (ESI) m/z: 422(M+H)$^+$.

Example 566

Synthesis of 1-{4-[4-(3,5-dimethylpyridin-2-yl)piperazine-1-carbonyl]-3-fluorophenyl}-5-ethylimidazolidine-2,4-dione

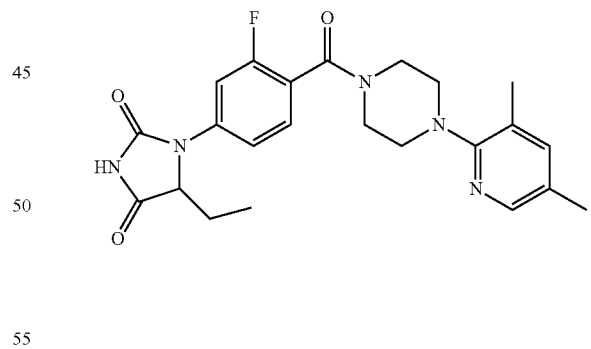

Using (4-bromo-2-fluorophenyl)[4-(3,5-dimethylpyridin-2-yl)piperazin-1-yl]methanone (314 mg) described in Preparation Example 114 and 5-ethyl-3-(4-methoxybenzyl)imidazolidine-2,4-dione (176 mg) described in Preparation Example 207 and by the reaction and treatment in the same manner as in Example 508, the title compound (190 mg) was obtained via 1-{4-[4-(3,5-dimethylpyridin-2-yl)piperazine-1-carbonyl]-3-fluorophenyl}-5-ethyl-3-(4-methoxybenzyl)imidazolidine-2,4-dione.

MS (ESI) m/z: 440(M+H)$^+$.

Example 567

Synthesis of 1-{5-[4-(3,5-dimethylpyridin-2-yl)piperazine-1-carbonyl]pyridin-2-yl}-5-ethylimidazolidine-2,4-dione

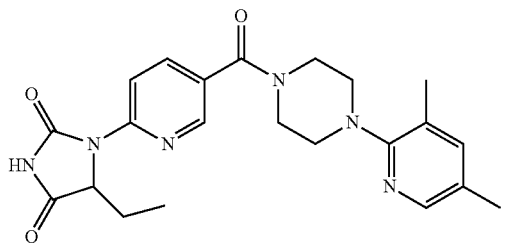 [SMILES: CCC1C(=O)NC(=O)N1c1ccc(C(=O)N2CCN(c3ncc(C)cc3C)CC2)cn1]

Using (6-bromopyridin-3-yl)[4-(3,5-dimethylpyridin-2-yl)piperazin-1-yl]methanone (300 mg) described in Preparation Example 127 and 5-ethyl-3-(4-methoxybenzyl)imidazolidine-2,4-dione (176 mg) described in Preparation Example 207 and by the reaction and treatment in the same manner as in Example 508, the title compound (153 mg) was obtained via 1-{5-[4-(3,5-dimethylpyridin-2-yl)piperazine-1-carbonyl]pyridin-2-yl}-5-ethyl-3-(4-methoxybenzyl)imidazolidine-2,4-dione.

MS (ESI) m/z: 423(M+H)⁺.

Example 568

Synthesis of 1-{4-[4-(3,5-dimethylpyridin-2-yl)piperazine-1-carbonyl]phenyl}-5-ethyl-3-methylimidazolidine-2,4-dione

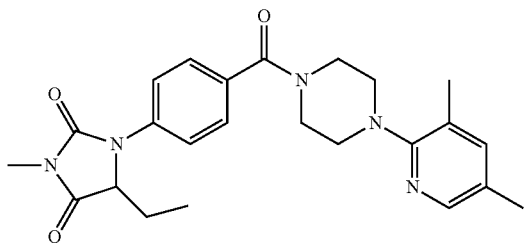

Using (4-bromophenyl)[4-(3,5-dimethylpyridin-2-yl)piperazin-1-yl]methanone (150 mg) described in Preparation Example 165 and 5-ethyl-3-methylimidazolidine-2,4-dione (63 mg) described in Preparation Example 215 and by the reaction and treatment in the same manner as in Example 536, the title compound (113 mg) was obtained.

MS (ESI) m/z: 436(M+H)⁺.

Example 569

Synthesis of 1-{4-[4-(3,5-dimethylpyridin-2-yl)piperazine-1-carbonyl]-3-fluorophenyl}-5-ethyl-3-methylimidazolidine-2,4-dione

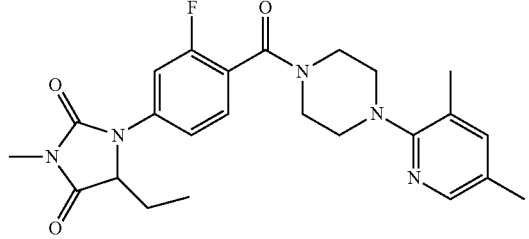

Using (4-bromo-2-fluorophenyl)[4-(3,5-dimethylpyridin-2-yl)piperazin-1-yl]methanone (157 mg) described in Preparation Example 114 and 5-ethyl-3-methylimidazolidine-2,4-dione (63 mg) described in Preparation Example 215 and by the reaction and treatment in the same manner as in Example 536, the title compound (114 mg) was obtained.

MS (ESI) m/z: 454(M+H)⁺.

Example 570

Synthesis of 1-{5-[4-(3,5-dimethylpyridin-2-yl)piperazine-1-carbonyl]pyridin-2-yl}-5-ethyl-3-methylimidazolidine-2,4-dione

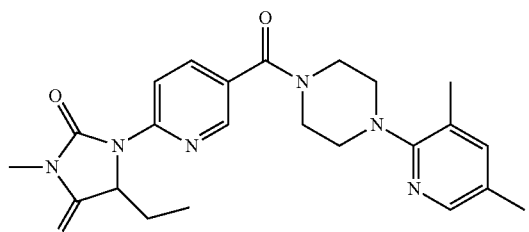

Using (6-bromopyridin-3-yl)[4-(3,5-dimethylpyridin-2-yl)piperazin-1-yl]methanone (150 mg) described in Preparation Example 127 and 5-ethyl-3-methylimidazolidine-2,4-dione (63 mg) described in Preparation Example 215 and by the reaction and treatment in the same manner as in Example 536, the title compound (95 mg) was obtained.

MS (ESI) m/z: 437(M+H)⁺.

Example 571

Synthesis of 1-{4-[4-(3,5-dimethylpyridin-2-yl)piperazine-1-carbonyl]phenyl}-5-isopropylimidazolidine-2,4-dione

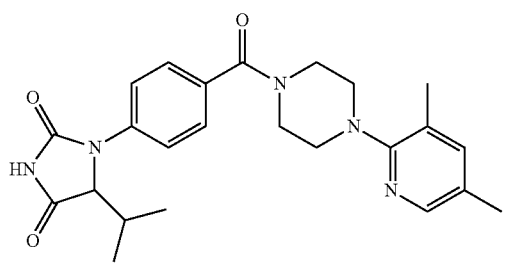 [SMILES: Cc1cnc(N2CCN(C(=O)c3ccc(N4C(=O)NC(=O)C4C(C)C)cc3)CC2)c(C)c1]

Using (4-bromophenyl)[4-(3,5-dimethylpyridin-2-yl)piperazin-1-yl]methanone (225 mg) described in Preparation Example 165 and 5-isopropyl-3-(4-methoxybenzyl)imidazolidine-2,4-dione (157 mg) described in Preparation Example 209 and by the reaction and treatment in the same manner as in Example 508, the title compound (169 mg) was obtained via 1-{4-[4-(3,5-dimethylpyridin-2-yl)piperazine-1-carbonyl]phenyl}-5-isopropyl-3-(4-methoxybenzyl)imidazolidine-2,4-dione.

MS (ESI) m/z: 436(M+H)+.

Example 572

Synthesis of 1-{4-[4-(3,5-dimethylpyridin-2-yl)piperazine-1-carbonyl]-3-fluorophenyl}-5-isopropylimidazolidine-2,4-dione

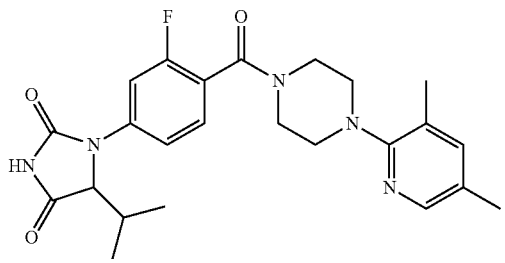 [SMILES: Cc1cnc(N2CCN(C(=O)c3ccc(N4C(=O)NC(=O)C4C(C)C)cc3F)CC2)c(C)c1]

Using (4-bromo-2-fluorophenyl)[4-(3,5-dimethylpyridin-2-yl)piperazin-1-yl]methanone (235 mg) described in Preparation Example 114 and 5-isopropyl-3-(4-methoxybenzyl)imidazolidine-2,4-dione (157 mg) described in Preparation Example 209 and by the reaction and treatment in the same manner as in Example 508, the title compound (144 mg) was obtained via 1-{4-[4-(3,5-dimethylpyridin-2-yl)piperazine-1-carbonyl]-3-fluorophenyl}-5-isopropyl-3-(4-methoxybenzyl)imidazolidine-2,4-dione.

MS (ESI) m/z: 454(M+H)+.

Example 573

Synthesis of 1-{5-[4-(3,5-dimethylpyridin-2-yl)piperazine-1-carbonyl]pyridin-2-yl}-5-isopropylimidazolidine-2,4-dione

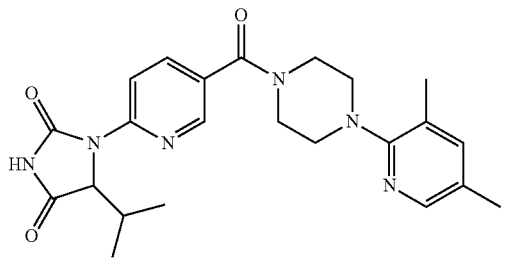 [SMILES: Cc1cnc(N2CCN(C(=O)c3ccc(N4C(=O)NC(=O)C4C(C)C)nc3)CC2)c(C)c1]

Using (6-bromopyridin-3-yl)[4-(3,5-dimethylpyridin-2-yl)piperazin-1-yl]methanone (225 mg) described in Preparation Example 127 and 5-isopropyl-3-(4-methoxybenzyl)imidazolidine-2,4-dione (157 mg) described in Preparation Example 209 and by the reaction and treatment in the same manner as in Example 508, the title compound (138 mg) was obtained via 1-{5-[4-(3,5-dimethylpyridin-2-yl)piperazine-1-carbonyl]pyridin-2-yl}-5-isopropyl-3-(4-methoxybenzyl)imidazolidine-2,4-dione.

MS (ESI) m/z: 437(M+H)+.

Example 574

Synthesis of 1-{4-[4-(3,5-dimethylpyridin-2-yl)piperazine-1-carbonyl]phenyl}-5-isopropyl-3-methylimidazolidine-2,4-dione

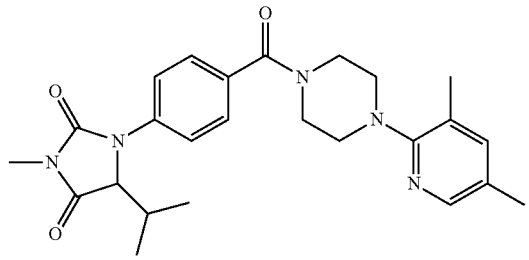

Using (4-bromophenyl)[4-(3,5-dimethylpyridin-2-yl)piperazin-1-yl]methanone (150 mg) described in Preparation Example 165 and 5-isopropyl-3-methylimidazolidine-2,4-dione (69 mg) described in Preparation Example 216 and by the reaction and treatment in the same manner as in Example 536, the title compound (95 mg) was obtained.

MS (ESI) m/z: 450(M+H)+.

Example 575

Synthesis of 1-{4-[4-(3,5-dimethylpyridin-2-yl)piperazine-1-carbonyl]-3-fluorophenyl}-5-isopropyl-3-methylimidazolidine-2,4-dione

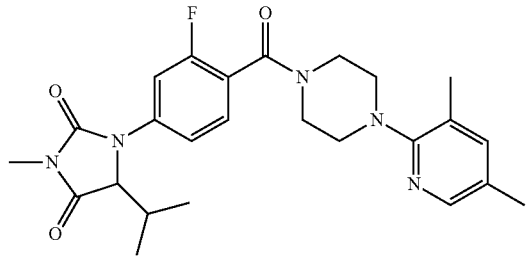

Using (4-bromo-2-fluorophenyl)[4-(3,5-dimethylpyridin-2-yl)piperazin-1-yl]methanone (157 mg) described in Preparation Example 114 and 5-isopropyl-3-methylimidazolidine-2,4-dione (69 mg) described in Preparation Example 216 and by the reaction and treatment in the same manner as in Example 536, the title compound (111 mg) was obtained.

MS (ESI) m/z: 468(M+H)+.

Example 576

Synthesis of 1-{5-[4-(3,5-dimethylpyridin-2-yl)piperazine-1-carbonyl]pyridin-2-yl}-5-isopropyl-3-methylimidazolidine-2,4-dione

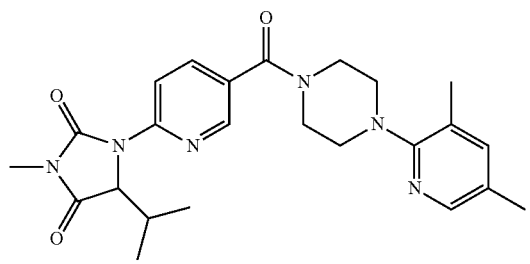

Using (6-bromopyridin-3-yl)[4-(3,5-dimethylpyridin-2-yl)piperazin-1-yl]methanone (150 mg) described in Preparation Example 127 and 5-isopropyl-3-methylimidazolidine-2,4-dione (69 mg) described in Preparation Example 216 and by the reaction and treatment in the same manner as in Example 536, the title compound (99 mg) was obtained.

MS (ESI) m/z: 451(M+H)$^+$.

Example 577

Synthesis of 1-{5-[4-(5-cyclopropyl-3-methylpyridin-2-yl)piperazine-1-carbonyl]pyridin-2-yl}-3,5-dimethylimidazolidine-2,4-dione

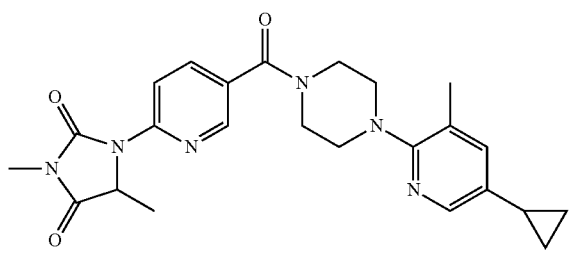 [SMILES: Cc1cc(C2CC2)cnc1N1CCN(C(=O)c2ccc(N3C(=O)N(C)C(=O)C3C)nc2)CC1]

Using (6-bromopyridin-3-yl) [4-(5-cyclopropyl-3-methylpyridin-2-yl)piperazin-1-yl]methanone (100 mg) described in Preparation Example 144 and 3,5-dimethylimidazolidine-2,4-dione (64 mg) described in Preparation Example 217 and by the reaction and treatment in the same manner as in Example 536, the title compound (13 mg) was obtained.

MS (ESI) m/z: 449(M+H)$^+$.

Example 578

Synthesis of 1-{4-[4-(3,5-dimethylpyridin-2-yl)piperazine-1-carbonyl]-3-fluorophenyl}-5,5-dimethylimidazolidine-2,4-dione

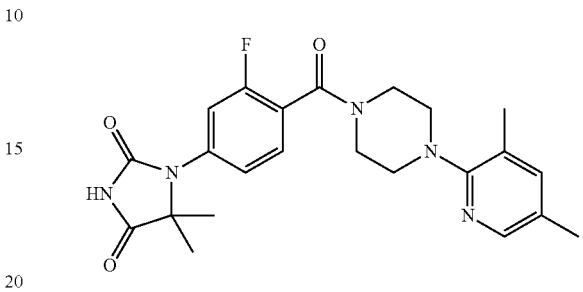

Using (4-bromo-2-fluorophenyl)[4-(3,5-dimethylpyridin-2-yl)piperazin-1-yl]methanone (235 mg) described in Preparation Example 114 and 3-(4-methoxybenzyl)-5,5-dimethylimidazolidine-2,4-dione (149 mg) described in Preparation Example 53 and by the reaction and treatment in the same manner as in Example 508, the title compound (130 mg) was obtained via 1-{4-[4-(3,5-dimethylpyridin-2-yl)piperazine-1-carbonyl]-3-fluorophenyl}-3-(4-methoxybenzyl)-5,5-dimethylimidazolidine-2,4-dione.

MS (ESI) m/z: 440(M+H)$^+$.

Example 579

Synthesis of 1-{5-[4-(3,5-dimethylpyridin-2-yl)piperazine-1-carbonyl]pyridin-2-yl}-5,5-dimethylimidazolidine-2,4-dione

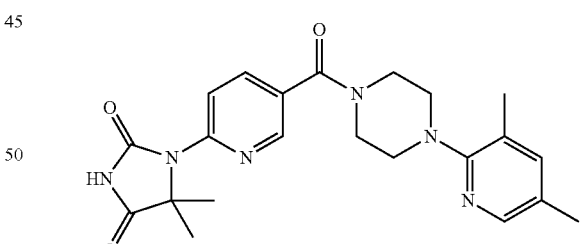

Using (6-bromopyridin-3-yl)[4-(3,5-dimethylpyridin-2-yl)piperazin-1-yl]methanone (225 mg) described in Preparation Example 127 and 3-(4-methoxybenzyl)-5,5-dimethylimidazolidine-2,4-dione (149 mg) described in Preparation Example 53 and by the reaction and treatment in the same manner as in Example 508, the title compound (120 mg) was obtained via 1-{5-[4-(3,5-dimethylpyridin-2-yl)piperazine-1-carbonyl]pyridin-2-yl}-3-(4-methoxybenzyl)-5,5-dimethylimidazolidine-2,4-dione.

MS (ESI) m/z: 423(M+H)$^+$.

Example 580

Synthesis of 1-{4-[4-(3,5-dimethylpyridin-2-yl)piperazine-1-carbonyl]-3-fluorophenyl}-3,5,5-trimethylimidazolidine-2,4-dione

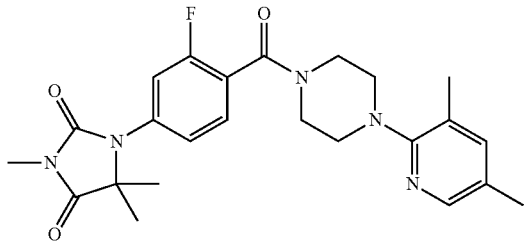

Using (4-bromo-2-fluorophenyl) [4-(3,5-dimethylpyridin-2-yl)piperazin-1-yl]methanone (157 mg) described in Preparation Example 114 and 3,5,5-trimethylimidazolidine-2,4-dione (63 mg) described in Preparation Example 218 and by the reaction and treatment in the same manner as in Example 536, the title compound (30 mg) was obtained.
MS (ESI) m/z: 453(M+H)$^+$.

Example 581

Synthesis of 1-{5-[4-(3,5-dimethylpyridin-2-yl)piperazine-1-carbonyl]pyridin-2-yl}-3,5,5-trimethylimidazolidine-2,4-dione

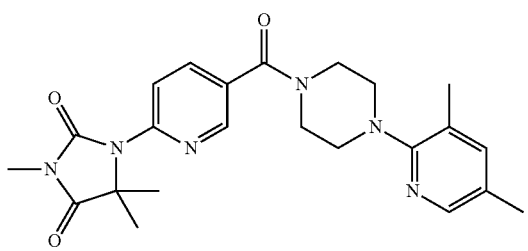

Using (6-bromopyridin-3-yl)[4-(3,5-dimethylpyridin-2-yl)piperazin-1-yl]methanone (150 mg) described in Preparation Example 127 and 3,5,5-trimethylimidazolidine-2,4-dione (63 mg) described in Preparation Example 218 and by the reaction and treatment in the same manner as in Example 536, the title compound (112 mg) was obtained.
MS (ESI) m/z: 437(M+H)$^+$.

Example 582

Synthesis of 1-{4-[4-(5-cyclopropyl-3-methylpyridin-2-yl)piperazine-1-carbonyl]phenyl}-3,5-dimethylimidazolidine-2,4-dione

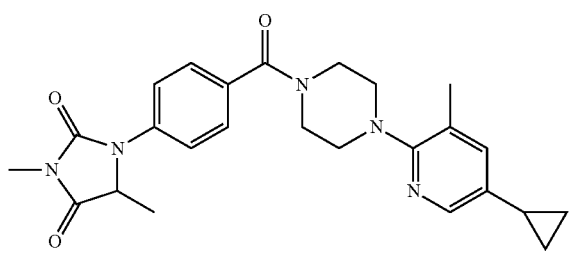

Using (4-bromophenyl) [4-(5-cyclopropyl-3-methylpyridin-2-yl)piperazin-1-yl]methanone (160 mg) described in Preparation Example 185 and 3,5-dimethylimidazolidine-2,4-dione (51 mg) described in Preparation Example 217 and by the reaction and treatment in the same manner as in Example 536, the title compound (20 mg) was obtained.
MS (ESI) m/z: 448(M+H)$^+$.

Example 583

Synthesis of 1-{4-[4-(5-cyclopropyl-3-methylpyridin-2-yl)piperazine-1-carbonyl]-3-fluorophenyl}-3,5-dimethylimidazolidine-2,4-dione

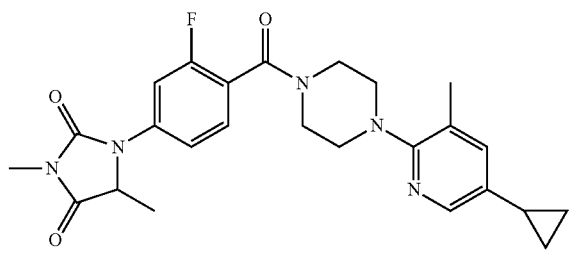 [SMILES: Cc1cc(C2CC2)cnc1N1CCN(C(=O)c2ccc(N3C(=O)N(C)C(=O)C3C)cc2F)CC1]

Using (4-bromo-2-fluorophenyl)[4-(5-cyclopropyl-3-methylpyridin-2-yl)piperazin-1-yl]methanone (167 mg) described in Preparation Example 121 and 3,5-dimethylimidazolidine-2,4-dione (51 mg) described in Preparation Example 217 and by the reaction and treatment in the same manner as in Example 536, the title compound (51 mg) was obtained.
MS (ESI) m/z: 466(M+H)$^+$.

Example 584

Synthesis of 1-{4-[4-(5-cyclopropyl-3-methylpyridin-2-yl)piperazine-1-carbonyl]-3-fluorophenyl}-3-methylimidazolidine-2,4-dione

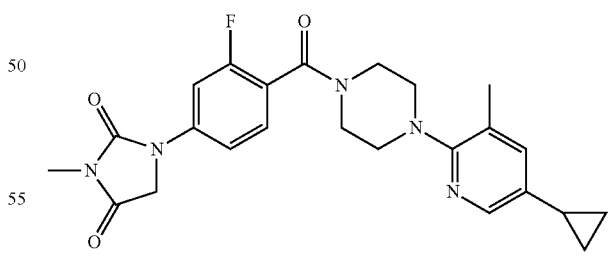

Using (4-bromo-2-fluorophenyl)[4-(5-cyclopropyl-3-methylpyridin-2-yl)piperazin-1-yl]methanone (167 mg) described in Preparation Example 121 and 3-methylimidazolidine-2,4-dione (68 mg) described in Preparation Example 214 and by the reaction and treatment in the same manner as in Example 536, the title compound (107 mg) was obtained.
MS (ESI) m/z: 452(M+H)$^+$.

Example 585

Synthesis of 1-{5-[4-(5-cyclopropyl-3-methylpyridin-2-yl)piperazine-1-carbonyl]pyridin-2-yl}-3-methylimidazolidine-2,4-dione

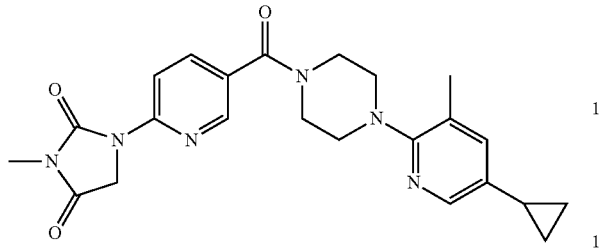

Using (6-bromopyridin-3-yl)[4-(5-cyclopropyl-3-methylpyridin-2-yl)piperazin-1-yl]methanone (161 mg) described in Preparation Example 144 and 3-methylimidazolidine-2,4-dione (68 mg) described in Preparation Example 214 and by the reaction and treatment in the same manner as in Example 536, the title compound (55 mg) was obtained.
MS (ESI) m/z: 435(M+H)$^+$.

Example 586

Synthesis of 1-{3-fluoro-4-[4-(3,5,6-trimethylpyridin-2-yl)piperazine-1-carbonyl]phenyl}-3-methylimidazolidine-2,4-dione

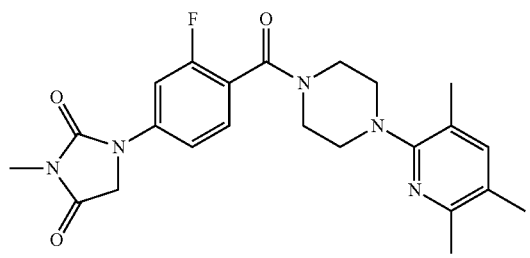

Using (4-bromo-2-fluorophenyl)[4-(3,5,6-trimethylpyridin-2-yl)piperazin-1-yl]methanone (163 mg) described in Preparation Example 128 and 3-methylimidazolidine-2,4-dione (68 mg) described in Preparation Example 214 and by the reaction and treatment in the same manner as in Example 536, the title compound (109 mg) was obtained.
MS (ESI) m/z: 440(M+H)$^+$.

Example 587

Synthesis of 3-methyl-1-{5-[4-(3,5,6-trimethylpyridin-2-yl)piperazine-1-carbonyl]pyridin-2-yl}imidazolidine-2,4-dione

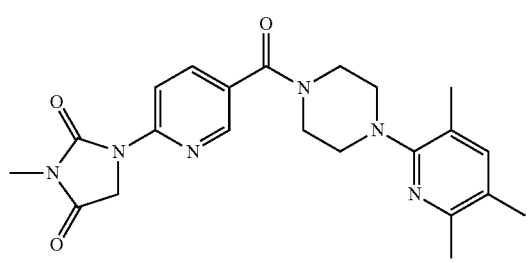

Using (6-bromopyridin-3-yl)[4-(3,5,6-trimethylpyridin-2-yl)piperazin-1-yl]methanone (156 mg) described in Preparation Example 205 and 3-methylimidazolidine-2,4-dione (68 mg) described in Preparation Example 214 and by the reaction and treatment in the same manner as in Example 536, the title compound (67 mg) was obtained.
MS (ESI) m/z: 423(M+H)$^+$.

Example 588

Synthesis of 1-{5-[4-(5-ethyl-3-methylpyridin-2-yl)piperazine-1-carbonyl]pyridin-2-yl}-3-methylimidazolidine-2,4-dione

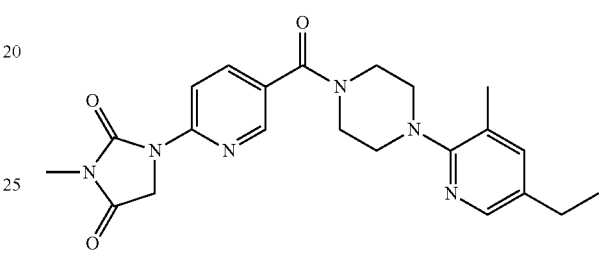

Using (6-bromopyridin-3-yl) [4-(5-ethyl-3-methylpyridin-2-yl)piperazin-1-yl]methanone (156 mg) described in Preparation Example 145 and 3-methylimidazolidine-2,4-dione (68 mg) described in Preparation Example 214 and by the reaction and treatment in the same manner as in Example 536, the title compound (61 mg) was obtained.
MS (ESI) m/z: 423(M+H)$^+$.

Example 589

Synthesis of 1-{4-[4-(5-ethyl-3-methylpyridin-2-yl)piperazine-1-carbonyl]-3-fluorophenyl}-3-methylimidazolidine-2,4-dione

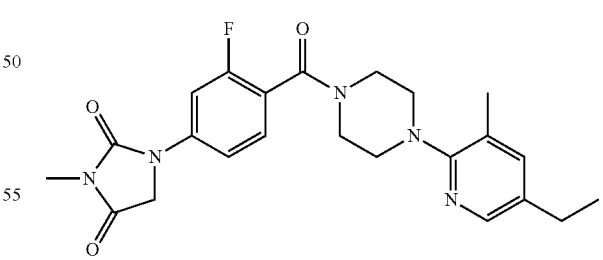

Using (4-bromo-2-fluorophenyl)[4-(5-ethyl-3-methylpyridin-2-yl)piperazin-1-yl]methanone (163 mg) described in Preparation Example 211 and 3-methylimidazolidine-2,4-dione (68 mg) described in Preparation Example 214 and by the reaction and treatment in the same manner as in Example 536, the title compound (115 mg) was obtained.
MS (ESI) m/z: 440(M+H)$^+$.

Example 590

Synthesis of 1-{5-[4-(5-cyclopropyl-3-methylpyridin-2-yl)piperazine-1-carbonyl]pyridin-2-yl}-3,5,5-trimethylimidazolidine-2,4-dione

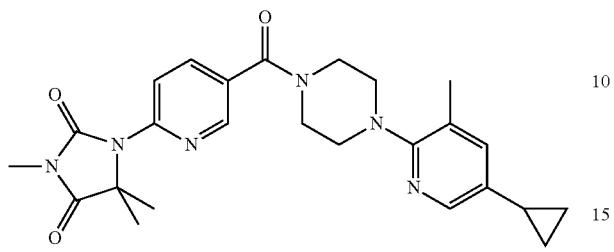

Using (6-bromopyridin-3-yl)[4-(5-cyclopropyl-3-methylpyridin-2-yl)piperazin-1-yl]methanone (161 mg) described in Preparation Example 144 and 3,5,5-trimethylimidazolidine-2,4-dione (63 mg) described in Preparation Example 218 and by the reaction and treatment in the same manner as in Example 536, the title compound (84 mg) was obtained.

MS (ESI) m/z: 463(M+H)$^+$.

Example 591

Synthesis of 1-{5-[4-(5-ethyl-3-methylpyridin-2-yl)piperazine-1-carbonyl]pyridin-2-yl}-3,5,5-trimethylimidazolidine-2,4-dione

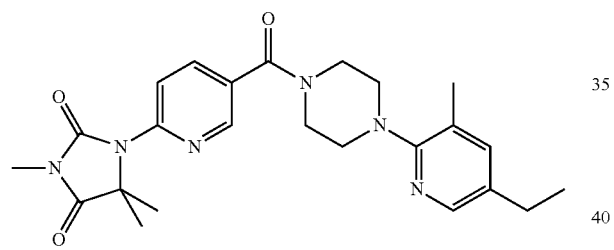

Using (6-bromopyridin-3-yl)[4-(5-ethyl-3-methylpyridin-2-yl)piperazin-1-yl]methanone (156 mg) described in Preparation Example 145 and 3,5,5-trimethylimidazolidine-2,4-dione (63 mg) m described in Preparation Example 218 and by the reaction and treatment in the same manner as in Example 536, the title compound (115 mg) was obtained.

MS (ESI) m/z: 451(M+H)$^+$.

Example 592

Synthesis of 1-{4-[4-(5-ethyl-3-methylpyridin-2-yl)piperazine-1-carbonyl]-3-fluorophenyl}-3,5,5-trimethylimidazolidine-2,4-dione

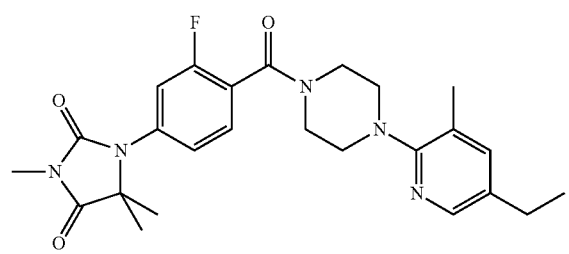 [SMILES: CCc1cnc(N2CCN(C(=O)c3ccc(N4C(=O)N(C)C(=O)C4(C)C)cc3F)CC2)c(C)c1]

Using (4-bromo-2-fluorophenyl)[4-(5-ethyl-3-methylpyridin-2-yl)piperazin-1-yl]methanone (163 mg) described in Preparation Example 211 and 3,5,5-trimethylimidazolidine-2,4-dione (63 mg) described in Preparation Example 218 and by the reaction and treatment in the same manner as in Example 536, the title compound (8 mg) was obtained.

MS (ESI) m/z: 468(M+H)$^+$.

Example 593

Synthesis of 1-{3-fluoro-4-[4-(3,5,6-trimethylpyridin-2-yl)piperazine-1-carbonyl]phenyl}-3,5,5-trimethylimidazolidine-2,4-dione

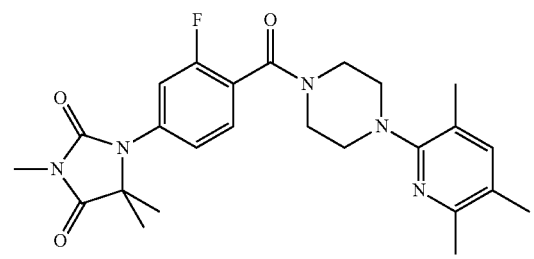

Using (4-bromo-2-fluorophenyl) [4-(3,5,6-trimethylpyridin-2-yl)piperazin-1-yl]methanone (163 mg) described in Preparation Example 128 and 3,5,5-trimethylimidazolidine-2,4-dione (63 mg) described in Preparation Example 218 and by the reaction and treatment in the same manner as in Example 536, the title compound (26 mg) was obtained.

MS (ESI) m/z: 468(M+H)$^+$.

Example 594

Synthesis of 3,5,5-trimethyl-1-{5-[4-(3,5,6-trimethylpyridin-2-yl)piperazine-1-carbonyl]pyridin-2-yl}imidazolidine-2,4-dione

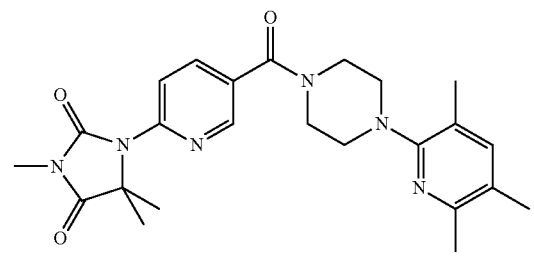

Using (6-bromopyridin-3-yl)[4-(3,5,6-trimethylpyridin-2-yl)piperazin-1-yl]methanone (156 mg) described in Preparation Example 205 and 3,5,5-trimethylimidazolidine-2,4-dione (63 mg) described in Preparation Example 218 and by the reaction and treatment in the same manner as in Example 536, the title compound (114 mg) was obtained.

MS (ESI) m/z: 451(M+H)$^+$.

Example 595

Synthesis of 1-{4-[4-(5-cyclopropyl-3-methylpyridin-2-yl)piperazine-1-carbonyl]-3-fluorophenyl}-3,5,5-trimethylimidazolidine-2,4-dione

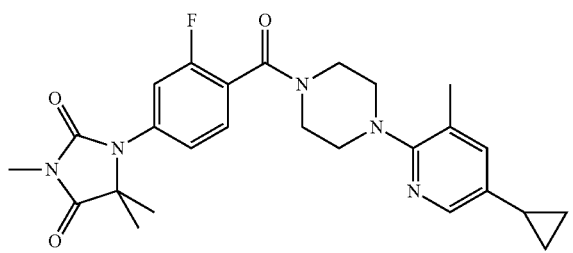 [SMILES: Cc1cc(C2CC2)cnc1N1CCN(C(=O)c2ccc(N3C(=O)N(C)C(=O)C3(C)C)cc2F)CC1]

Using (4-bromo-2-fluorophenyl)[4-(5-cyclopropyl-3-methylpyridin-2-yl)piperazin-1-yl]methanone (167 mg) described in Preparation Example 121 and 3,5,5-trimethylimidazolidine-2,4-dione (63 mg) described in Preparation Example 218 and by the reaction and treatment in the same manner as in Example 536, the title compound (20 mg) was obtained.

MS (ESI) m/z: 480(M+H)$^+$.

Example 596

Synthesis of N-{5-(3-acetyl-2-oxoimidazolidin-1-yl)-2-[4-(3,5-dimethylpyridin-2-yl)piperazine-1-carbonyl]phenyl}methanesulfonamide

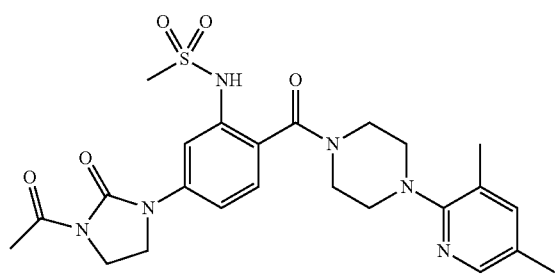 [SMILES: CC(=O)N1CCN(c2ccc(C(=O)N3CCN(c4ncc(C)cc4C)CC3)c(NS(C)(=O)=O)c2)C1=O]

Using N-{5-bromo-2-[4-(3,5-dimethylpyridin-2-yl)piperazine-1-carbonyl]phenyl}methanesulfonamide (806 mg) described in Preparation Example 226 and 1-acetylimidazolidin-2-one (221 mg) and by the reaction and treatment in the same manner as in Example 536, the title compound (115 mg) was obtained.

MS (ESI) m/z: 515(M+H)$^+$.

Example 597

Synthesis of N-{2-[4-(3,5-dimethylpyridin-2-yl)piperazine-1-carbonyl]-5-(2-oxoimidazolidin-1-yl)phenyl}methanesulfonamide

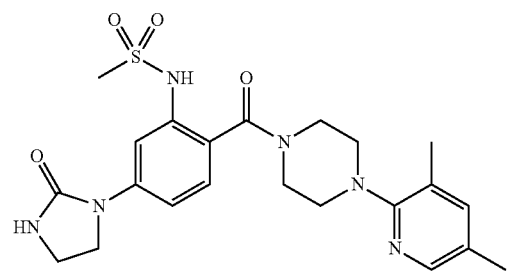 [SMILES: Cc1cnc(N2CCN(C(=O)c3ccc(N4CCNC4=O)cc3NS(C)(=O)=O)CC2)c(C)c1]

A product produced by deacetylation that simultaneously proceeded during synthesis of N-{5-(3-acetyl-2-oxoimidazolidin-1-yl)-2-[4-(3,5-dimethylpyridin-2-yl)piperazine-1-carbonyl]phenyl}methanesulfonamide described in Example 596 was purified by column chromatography (ethyl acetate: methanol) to give the title compound (24 mg).

MS (ESI) m/z: 473(M+H)$^+$.

Example 598

Synthesis of N-{5-(3-acetyl-2-oxoimidazolidin-1-yl)-2-[4-(3,5-dimethylpyridin-2-yl)piperazine-1-carbonyl]phenyl}-N-methylmethanesulfonamide

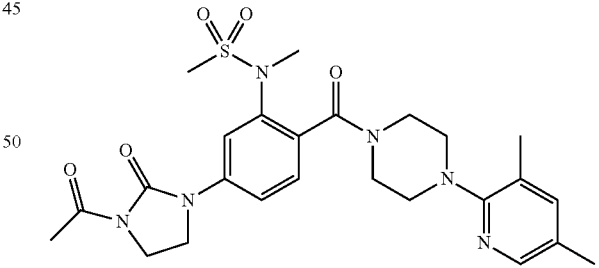

Using N-{5-(3-acetyl-2-oxoimidazolidin-1-yl)-2-[4-(3,5-dimethylpyridin-2-yl)piperazine-1-carbonyl]phenyl}methanesulfonamide (93 mg) described in Example 596 and methyl iodide (12.3 µL) and by the reaction and treatment in the same manner as in Example 36, the title compound (15 mg) was obtained.

MS (ESI) m/z: 529(M+H)$^+$.

Example 599

Synthesis of N-{2-[4-(3,5-dimethylpyridin-2-yl)piperazine-1-carbonyl]-5-(3-methyl-2-oxoimidazolidin-1-yl)phenyl}methanesulfonamide

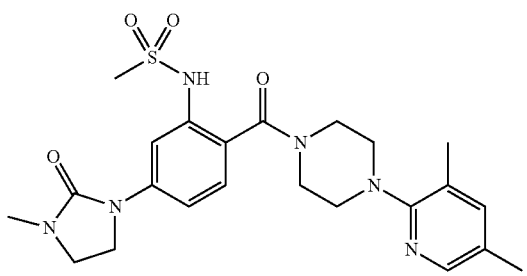

Using N-{5-bromo-2-[4-(3,5-dimethylpyridin-2-yl)piperazine-1-carbonyl]phenyl}methanesulfonamide (187 mg) described in Preparation Example 226 and 1-methylimidazolidin-2-one (40 mg) and by the reaction and treatment in the same manner as in Example 536, the title compound (52 mg) was obtained.

MS (ESI) m/z: 487(M+H)$^+$.

Example 600

Synthesis of N-{2-[4-(3,5-dimethylpyridin-2-yl)piperazine-1-carbonyl]-5-(3-methyl-2-oxoimidazolidin-1-yl)phenyl}-N-methylmethanesulfonamide

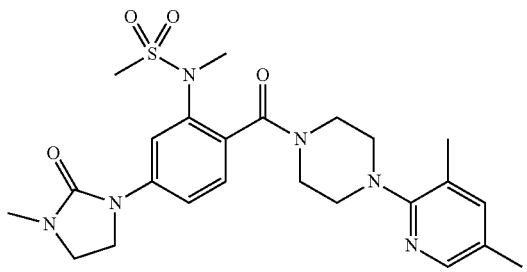

Using N-{5-bromo-2-[4-(3,5-dimethylpyridin-2-yl)piperazine-1-carbonyl]phenyl}-N-methylmethanesulfonamide (130 mg) described in Preparation Example 227 and 1-methylimidazolidin-2-one (27 mg) and by the reaction and treatment in the same manner as in Example 536, the title compound (95 mg) was obtained.

MS (ESI) m/z: 501(M+H)$^+$.

Example 601

Synthesis of N-{2-[4-(3,5-dimethylpyridin-2-yl)piperazine-1-carbonyl]-5-(2-oxoimidazolidin-1-yl)phenyl}-N-methylmethanesulfonamide

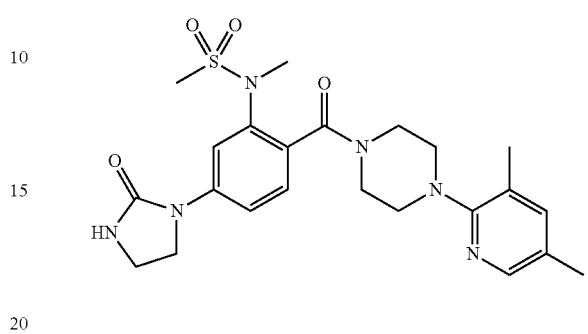

To a mixture of N-{5-bromo-2-[4-(3,5-dimethylpyridin-2-yl)piperazine-1-carbonyl]phenyl}-N-methylmethanesulfonamide (540 mg) described in Preparation Example 227 and 1-acetylimidazolidin-2-one (144 mg), cesium carbonate (731 mg), copper(I) iodide (107 mg) were added dioxane (3 mL) and N,N'-dimethylethylenediamine (121 µL), and the mixture was stirred under refluxing for 8 hr. After cooling, water was added to the reaction mixture, and the mixture was extracted with ethyl acetate. The solvent was evaporated, methanol (2 mL) and 1N aqueous sodium hydroxide solution (1.7 mL) were added to the obtained residue, and the mixture was stirred at 40° C. for 3 hr. After cooling, water was added to the reaction mixture, and the mixture was extracted with ethyl acetate. The solvent was evaporated, and the residue was purified by column chromatography (ethyl acetate: methanol) to give the title compound (330 mg).

MS (ESI) m/z: 487(M+H)$^+$.

Example 602

Synthesis of 1-acetyl-3-{4-[4-(5-cyclopropyl-3-methylpyridin-2-yl)piperazine-1-carbonyl]-3-fluorophenyl}imidazolidin-2-one

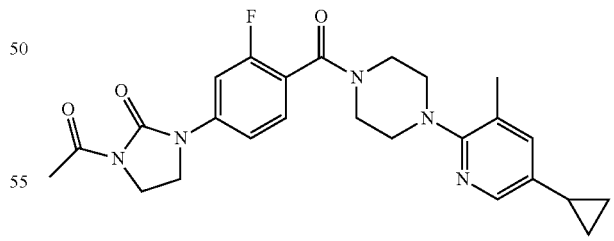

Using (4-bromo-2-fluorophenyl)[4-(5-cyclopropyl-3-methylpyridin-2-yl)piperazin-1-yl]methanone (418 mg) described in Preparation Example 121 and 1-acetylimidazolidin-2-one (128 mg) and by the reaction and treatment in the same manner as in Example 511, the title compound (156 mg) was obtained.

MS (ESI) m/z: 466(M+H)$^+$.

Example 603

Synthesis of 1-{4-[4-(5-cyclopropyl-3-methylpyridin-2-yl)piperazine-1-carbonyl]-3-fluorophenyl}imidazolidin-2-one

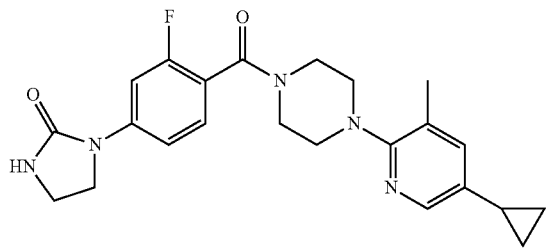 [SMILES: Cc1cc(C2CC2)cnc1N1CCN(C(=O)c2ccc(N3CCNC3=O)cc2F)CC1]

A product produced by deacetylation that simultaneously proceeded during synthesis of 1-acetyl-3-{4-[4-(5-cyclopropyl-3-methylpyridin-2-yl)piperazine-1-carbonyl]-3-fluorophenyl}imidazolidin-2-one described in Example 602 was purified by column chromatography (ethyl acetate:methanol) to give the title compound (26 mg).

MS (ESI) m/z: 424(M+H)⁺.

Example 604

Synthesis of 1-{4-[4-(5-cyclopropyl-3-methylpyridin-2-yl)piperazine-1-carbonyl]-3-fluorophenyl}-3-methylimidazolidin-2-one

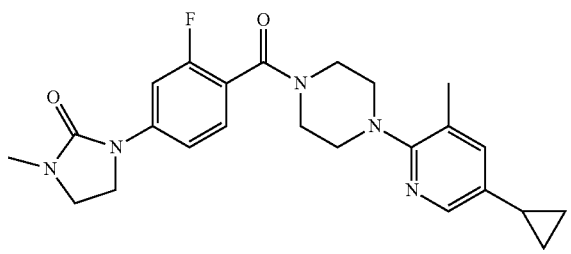 [SMILES: Cc1cc(C2CC2)cnc1N1CCN(C(=O)c2ccc(N3CCN(C)C3=O)cc2F)CC1]

Using (4-bromo-2-fluorophenyl)[4-(5-cyclopropyl-3-methylpyridin-2-yl)piperazin-1-yl]methanone (209 mg) described in Preparation Example 121 and 1-methylimidazolidin-2-one (50 mg) and by the reaction and treatment in the same manner as in Example 536, the title compound (104 mg) was obtained.

MS (ESI) m/z: 438(M+H)⁺.

Example 605

Synthesis of 1-acetyl-3-{5-[4-(3,5-dimethylpyridin-2-yl)piperazine-1-carbonyl]-4-methylpyridin-2-yl}imidazolidin-2-one

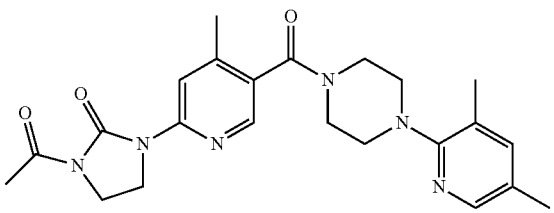 [SMILES: CC(=O)N1CCN(c2cc(C)c(C(=O)N3CCN(c4ncc(C)cc4C)CC3)cn2)C1=O]

Using (6-bromo-4-methylpyridin-3-yl)[4-(3,5-dimethylpyridin-2-yl)piperazin-1-yl]methanone (389 mg) described in Preparation Example 228 and 1-acetylimidazolidin-2-one (128 mg) and by the reaction and treatment in the same manner as in Example 511, the title compound (233 mg) was obtained.

MS (ESI) m/z: 437(M+H)⁺.

Example 606

Synthesis of 1-{5-[4-(3,5-dimethylpyridin-2-yl)piperazine-1-carbonyl]-4-methylpyridin-2-yl}imidazolidin-2-one

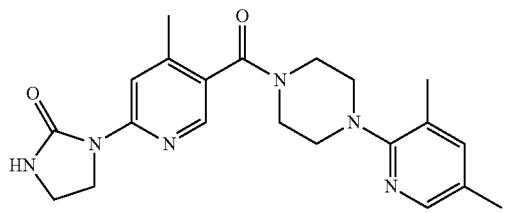

A product produced by deacetylation that simultaneously proceeded during synthesis of 1-acetyl-3-{5-[4-(3,5-dimethylpyridin-2-yl)piperazine-1-carbonyl]-4-methylpyridin-2-yl}imidazolidin-2-one described in Example 605 was purified by column chromatography (ethyl acetate:methanol) to give the title compound (28 mg).

MS (ESI) m/z: 395(M+H)⁺.

Example 607

Synthesis of 1-acetyl-3-{4-[4-(5-ethyl-3-methylpyridin-2-yl)piperazine-1-carbonyl]-3-fluorophenyl}imidazolidin-2-one

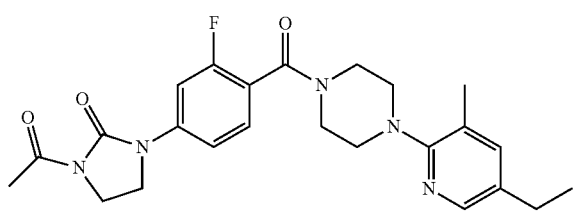 [SMILES: CCc1cnc(N2CCN(C(=O)c3ccc(N4CCN(C(C)=O)C4=O)cc3F)CC2)c(C)c1]

Using (4-bromo-2-fluorophenyl)[4-(5-ethyl-3-methylpyridin-2-yl)piperazin-1-yl]methanone (500 mg) described in Preparation Example 211 and 1-acetylimidazolidin-2-one (236 mg) and by the reaction and treatment in the same manner as in Example 511, the title compound (262 mg) was obtained.

MS (ESI) m/z: 454(M+H)$^+$.

Example 608

Synthesis of 1-{4-[4-(5-ethyl-3-methylpyridin-2-yl)piperazine-1-carbonyl]-3-fluorophenyl}imidazolidin-2-one

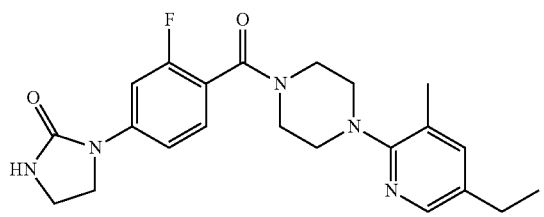 [SMILES: CCc1cnc(N2CCN(C(=O)c3ccc(N4CCNC4=O)cc3F)CC2)c(C)c1]

A product produced by deacetylation that simultaneously proceeded during synthesis of 1-acetyl-3-{4-[4-(5-ethyl-3-methylpyridin-2-yl)piperazine-1-carbonyl]-3-fluorophenyl}imidazolidin-2-one described in Example 607 was purified by column chromatography (ethyl acetate: methanol) to give the title compound (32 mg).

MS (ESI) m/z: 412(M+H)$^+$.

Example 609

Synthesis of 1-{5-[4-(3,5-dimethylpyridin-2-yl)piperazine-1-carbonyl]-4-methylpyridin-2-yl}-3-methylimidazolidin-2-one dihydrochloride

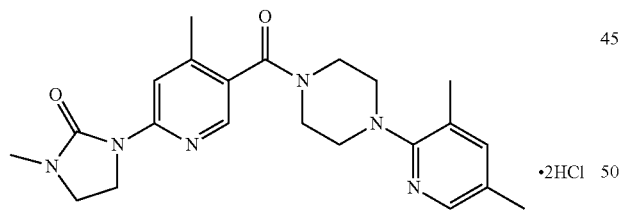

Using (6-bromo-4-methylpyridin-3-yl)[4-(3,5-dimethylpyridin-2-yl)piperazin-1-yl]methanone (195 mg) described in Preparation Example 228 and 1-methylimidazolidin-2-one (75 mg) and by the reaction and treatment in the same manner as in Example 511, 1-{5-[4-(3,5-dimethylpyridin-2-yl)piperazine-1-carbonyl]-4-methylpyridin-2-yl}-3-methylimidazolidin-2-one (160 mg) was obtained. The obtained 1-{5-[4-(3,5-dimethylpyridin-2-yl)piperazine-1-carbonyl]-4-methylpyridin-2-yl}-3-methylimidazolidin-2-one (160 mg) was dissolved in ethyl acetate, 4N hydrogen chloride/ethyl acetate (0.2 mL) was added, and the precipitate was collected by filtration to give the title compound (98 mg).

MS (ESI) m/z: 409(M+H)$^+$.

Example 610

Synthesis of 1-{4-[4-(5-ethyl-3-methylpyridin-2-yl)piperazine-1-carbonyl]-3-fluorophenyl}-3-methylimidazolidin-2-one

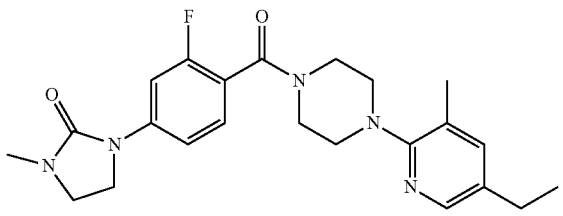 [SMILES: CCc1cnc(N2CCN(C(=O)c3ccc(N4CCN(C)C4=O)cc3F)CC2)c(C)c1]

Using (4-bromo-2-fluorophenyl)[4-(5-ethyl-3-methylpyridin-2-yl)piperazin-1-yl]methanone (203 mg) described in Preparation Example 211 and 1-methylimidazolidin-2-one (60 mg) and by the reaction and treatment in the same manner as in Example 511, the title compound (86 mg) was obtained.

MS (ESI) m/z: 426(M+H)$^+$.

Example 611

Synthesis of 1-acetyl-3-{3-fluoro-4-[4-(3,5,6-trimethylpyridin-2-yl)piperazine-1-carbonyl]phenyl}imidazolidin-2-one

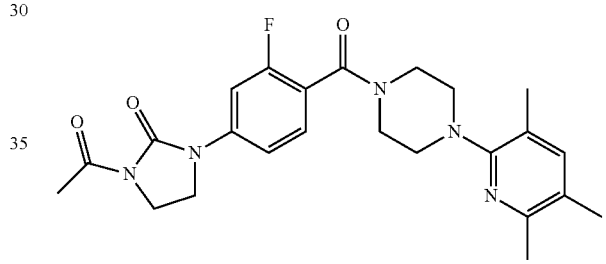

Using (4-bromo-2-fluorophenyl)[4-(3,5,6-trimethylpyridin-2-yl)piperazin-1-yl]methanone (406 mg) described in Preparation Example 128 and 1-acetylimidazolidin-2-one (192 mg) and by the reaction and treatment in the same manner as in Example 511, the title compound (236 mg) was obtained.

MS (ESI) m/z: 454(M+H)$^+$.

Example 612

Synthesis of 1-{3-fluoro-4-[4-(3,5,6-trimethylpyridin-2-yl)piperazine-1-carbonyl]phenyl}imidazolidin-2-one

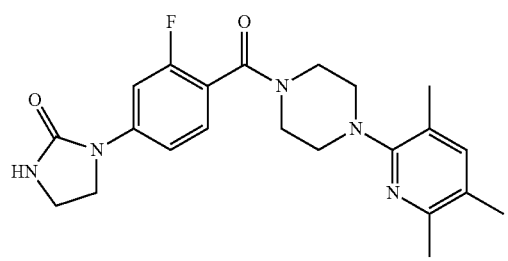

To 1-acetyl-3-{(3-fluoro-4-[4-(3,5,6-trimethylpyridin-2-yl)piperazine-1-carbonyl]phenyl}imidazolidin-2-one (140 mg) described in Example 611 were added methanol (1 mL) and 1N aqueous sodium hydroxide solution (0.46 mL), and the mixture was stirred at 40° C. for 2 hr. After cooling, water was added to the reaction mixture, and the mixture was extracted with ethyl acetate. The solvent was evaporated, diisopropyl ether and ethyl acetate were added, and the precipitated solid was collected by filtration to give the title compound (115 mg).

MS (ESI) m/z: 411(M+H)$^+$.

Example 613

Synthesis of 1-{3-fluoro-4-[4-(3,5,6-trimethylpyridin-2-yl)piperazine-1-carbonyl]phenyl}-3-methylimidazolidin-2-one

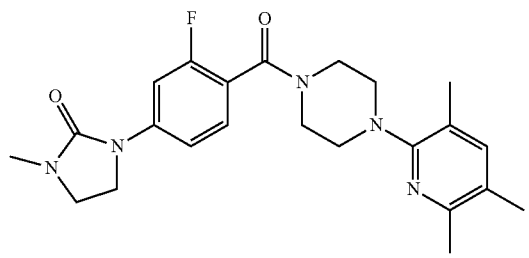

Using (4-bromo-2-fluorophenyl)[4-(3,5,6-trimethylpyridin-2-yl)piperazin-1-yl]methanone (203 mg) described in Preparation Example 128 and 1-methylimidazolidin-2-one (60 mg) and by the reaction and treatment in the same manner as in Example 511, the title compound (17 mg) was obtained.

MS (ESI) m/z: 426(M+H)$^+$.

Example 614

Synthesis of 1-acetyl-3-{3-chloro-4-[4-(3,5-dimethylpyridin-2-yl)piperazine-1-carbonyl]phenyl}imidazolidin-2-one

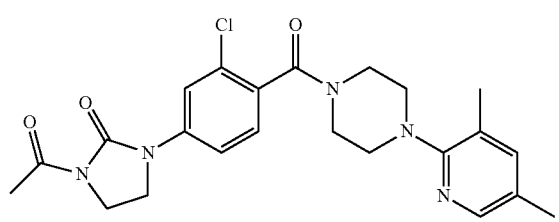 [SMILES: CC(=O)N1CCN(c2ccc(C(=O)N3CCN(c4ncc(C)cc4C)CC3)c(Cl)c2)C1=O]

Using (4-bromo-2-chlorophenyl)[4-(3,5-dimethylpyridin-2-yl)piperazin-1-yl]methanone (409 mg) described in Preparation Example 119 and 1-acetylimidazolidin-2-one (192 mg) and by the reaction and treatment in the same manner as in Example 511, the title compound (242 mg) was obtained.

MS (ESI) m/z: 456(M+H)$^+$.

Example 615

Synthesis of 1-{3-chloro-4-[4-(3,5-dimethylpyridin-2-yl)piperazine-1-carbonyl]phenyl}imidazolidin-2-one

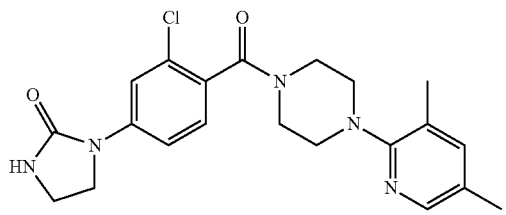

A product produced by deacetylation that simultaneously proceeded during synthesis of 1-acetyl-3-{3-chloro-4-[4-(3,5-dimethylpyridin-2-yl)piperazine-1-carbonyl]phenyl}imidazolidin-2-one described in Example 614 was purified by column chromatography (ethyl acetate:methanol) to give the title compound (37 mg).

MS (ESI) m/z: 414(M+H)$^+$.

Example 616

Synthesis of 1-{3-chloro-4-[4-(3,5-dimethylpyridin-2-yl)piperazine-1-carbonyl]phenyl}-3-methylimidazolidin-2-one

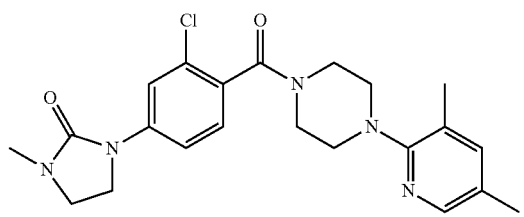

Using (4-bromo-2-chlorophenyl)[4-(3,5-dimethylpyridin-2-yl)piperazin-1-yl]methanone (204 mg) described in Preparation Example 119 and 1-methylimidazolidin-2-one (60 mg) and by the reaction and treatment in the same manner as in Example 511, the title compound (13 mg) was obtained.

MS (ESI) m/z: 428(M+H)$^+$.

Example 617

Synthesis of 3-{4-[4-(3,5-dimethylpyridin-2-yl)piperazine-1-carbonyl]phenyl}thiazolidin-4-one

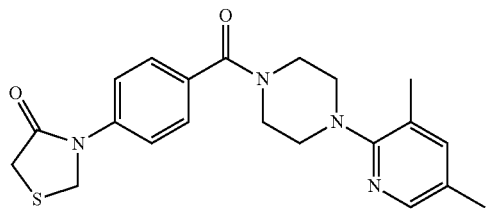

Using 4-(4-oxothiazolidin-3-yl)benzoic acid (112 mg) and 1-(3,5-dimethylpyridin-2-yl)piperazine (96 mg) described in Preparation Example 79 and by the reaction and treatment in the same manner as in Example 11, the title compound (148 mg) was obtained.

MS (ESI) m/z: 397(M+H)$^+$.

Example 618

Synthesis of [4-(3,5-dimethylpyridin-2-yl)piperazin-1-yl][5-(1,1-dioxo-1λ$^6$-isothiazolidin-2-yl)pyrimidin-2-yl]methanone

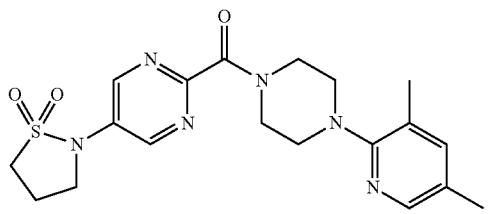 [SMILES: Cc1cnc(N2CCN(C(=O)c3ncc(N4CCCS4(=O)=O)cn3)CC2)c(C)c1]

Using (5-bromopyrimidin-2-yl)[4-(3,5-dimethylpyridin-2-yl)piperazin-1-yl]methanone (188 mg) described in Preparation Example 229 and isothiazolidine 1,1-dioxide (61 mg) and by the reaction and treatment in the same manner as in Example 4, the title compound (114 mg) was obtained.

MS (ESI) m/z: 417(M+H)$^+$.

Example 619

Synthesis of 1-acetyl-3-{2-[4-(3,5-dimethylpyridin-2-yl)piperazine-1-carbonyl]pyrimidin-5-yl}imidazolidin-2-one

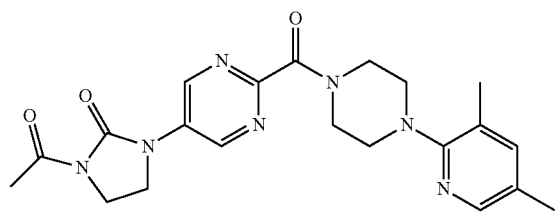 [SMILES: CC(=O)N1CCN(c2cnc(C(=O)N3CCN(c4ncc(C)cc4C)CC3)nc2)C1=O]

Using (5-bromopyrimidin-2-yl)[4-(3,5-dimethylpyridin-2-yl)piperazin-1-yl]methanone (376 mg) described in Preparation Example 229 and 1-acetylimidazolidin-2-one (192 mg) and by the reaction and treatment in the same manner as in Example 511, the title compound (37 mg) was obtained.

MS (ESI) m/z: 424(M+H)$^+$.

Example 620

Synthesis of 1-{2-[4-(3,5-dimethylpyridin-2-yl)piperazine-1-carbonyl]pyrimidin-5-yl}imidazolidin-2-one

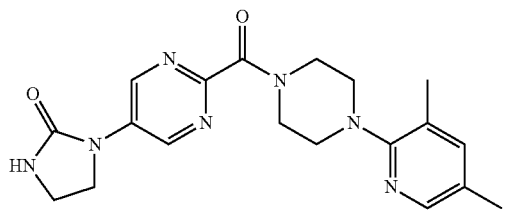

A product produced by deacetylation that simultaneously proceeded during synthesis of 1-acetyl-3-{2-[4-(3,5-dimethylpyridin-2-yl)piperazine-1-carbonyl]pyrimidin-5-yl}imidazolidin-2-one described in Example 619 was purified by column chromatography (ethyl acetate:methanol) to give the title compound (58 mg).

MS (ESI) m/z: 382(M+H)$^+$.

Example 621

Synthesis of 1-{2-[4-(3,5-dimethylpyridin-2-yl)piperazine-1-carbonyl]pyrimidin-5-yl}-3-methylimidazolidin-2-one

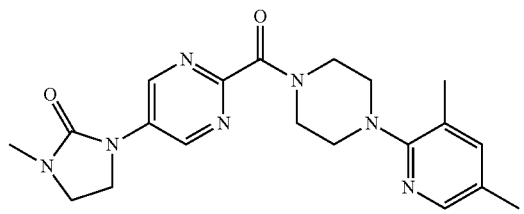

Using (5-bromopyrimidin-2-yl)[4-(3,5-dimethylpyridin-2-yl)piperazin-1-yl]methanone (188 mg) described in Preparation Example 229 and 1-methylimidazolidin-2-one (50 mg) and by the reaction and treatment in the same manner as in Example 536, the title compound (80 mg) was obtained.

MS (ESI) m/z: 396(M+H)$^+$.

Example 622

Synthesis of (R)-3-{6-[4-(3,5-dimethylpyridin-2-yl)piperazine-1-carbonyl]pyridazin-3-yl}-4-methyloxazolidin-2-one

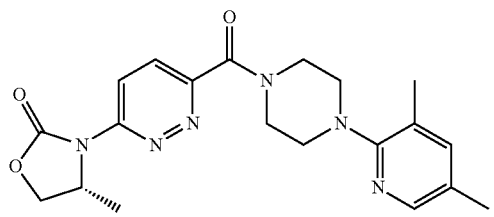 [SMILES: Cc1cnc(N2CCN(C(=O)c3ccc(N4C(=O)OC[C@H]4C)nn3)CC2)c(C)c1]

Using (6-chloropyridazin-3-yl)[4-(3,5-dimethylpyridin-2-yl)piperazin-1-yl]methanone (28 mg) described in Preparation Example 230 and (R)-4-methyloxazolidin-2-one (10 mg) and by the reaction and treatment in the same manner as in Example 1, the title compound (17 mg) was obtained.
MS (ESI) m/z: 397(M+H)+.

Example 623

Synthesis of [4-(3,5-dimethylpyridin-2-yl)piperazin-1-yl][4-(1,1-dioxo-1λ6-[1,2]thiazetidin-2-yl)phenyl]methanone

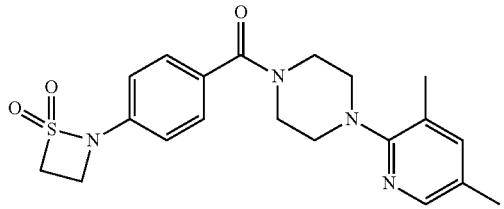 [SMILES: Cc1cnc(N2CCN(C(=O)c3ccc(N4CCS4(=O)=O)cc3)CC2)c(C)c1]

Using (4-bromophenyl)[4-(3,5-dimethylpyridin-2-yl)piperazin-1-yl]methanone (188 mg) described in Preparation Example 165 and [1,2]thiazetidine 1,1-dioxide (54 mg) and by the reaction and treatment in the same manner as in Example 536, the title compound (4 mg) was obtained.
MS (ESI) m/z: 401(M+H)+.

Example 624

Synthesis of [4-(2,4-dimethylphenyl)piperazin-1-yl][4-(1,1-dioxo-1λ6-[1, 2]thiazetidin-2-yl)phenyl]methanone

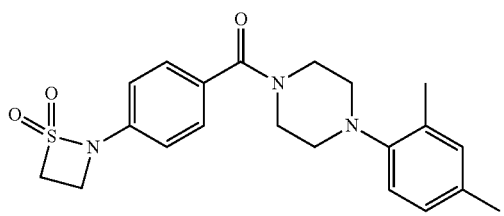 [SMILES: Cc1ccc(N2CCN(C(=O)c3ccc(N4CCS4(=O)=O)cc3)CC2)c(C)c1]

Using [4-(2,4-dimethylphenyl)piperazin-1-yl](4-iodophenyl)methanone (210 mg) described in Preparation Example 108 and [1,2]thiazetidine 1,1-dioxide (54 mg) and by the reaction and treatment in the same manner as in Example 536, the title compound (15 mg) was obtained.
MS (ESI) m/z: 400(M+H)+.

Example 625

Synthesis of [4-(3,5-dimethylpyridin-2-yl)piperazin-1-yl][6-(1,1-dioxo-1λ6-[1,2]thiazetidin-2-yl)pyridin-3-yl]methanone

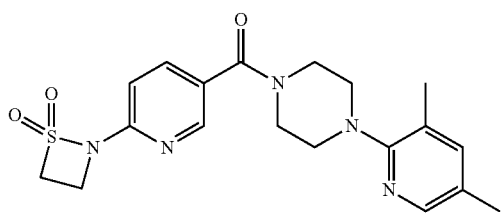 [SMILES: Cc1cnc(N2CCN(C(=O)c3ccc(N4CCS4(=O)=O)nc3)CC2)c(C)c1]

Using (6-bromopyridin-3-yl)[4-(3,5-dimethylpyridin-2-yl)piperazin-1-yl]methanone (188 mg) described in Preparation Example 127 and [1,2]thiazetidine 1,1-dioxide (54 mg) and by the reaction and treatment in the same manner as in Example 536, the title compound (7 mg) was obtained.
MS (ESI) m/z: 402(M+H)+.

Example 626

Synthesis of [4-(3,5-dimethylpyridin-2-yl)piperazin-1-yl][2-(1,1-dioxo-1λ6-isothiazolidin-2-yl)pyrimidin-5-yl]methanone

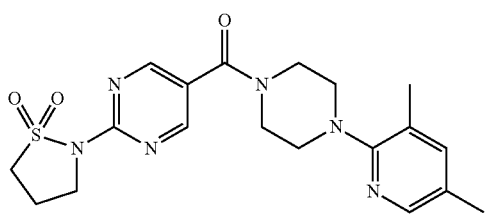 [SMILES: Cc1cnc(N2CCN(C(=O)c3cnc(N4CCCS4(=O)=O)nc3)CC2)c(C)c1]

Using methyl 2-(1,1-dioxo-1λ6-isothiazolidin-2-yl)pyrimidine-5-carboxylate (100 mg) described in Preparation Example 231 and 1-(3,5-dimethylpyridin-2-yl)piperazine (74 mg) described in Preparation Example 79 and by the reaction and treatment in the same manner as in Example 109, the title compound (28 mg) was obtained.
MS (ESI) m/z: 417(M+H)+.

Example 627

Synthesis of [4-(5-cyclopropyl-3-methylpyridin-2-yl)piperazin-1-yl][2-(1,1-dioxo-1λ6-isothiazolidin-2-yl)pyrimidin-5-yl]methanone

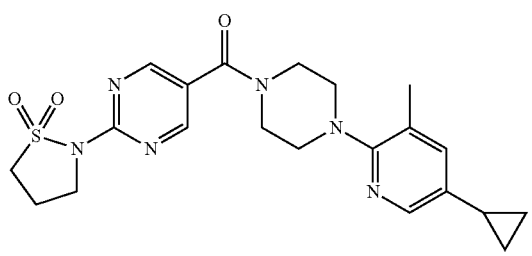 [SMILES: Cc1cc(C2CC2)cnc1N1CCN(C(=O)c2cnc(N3CCCS3(=O)=O)nc2)CC1]

Using methyl 2-(1,1-dioxo-1λ6-isothiazolidin-2-yl)pyrimidine-5-carboxylate (85 mg) described in Preparation Example 231 and 1-(5-cyclopropyl-3-methylpyridin-2-yl)piperazine (72 mg) described in Preparation Example 83 and by the reaction and treatment in the same manner as in Example 109, the title compound (10 mg) was obtained.
MS (ESI) m/z: 443(M+H)+.

Example 628

Synthesis of (R)-3-{5-[4-(3,5-dimethylpyridin-2-yl)piperazine-1-carbonyl]pyrazin-2-yl}-4-methyloxazolidin-2-one

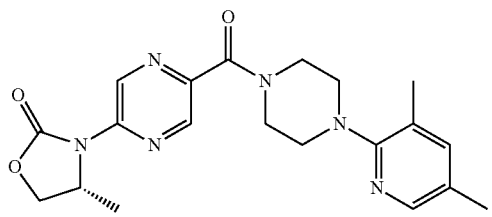 [SMILES: Cc1cnc(N2CCN(C(=O)c3cnc(N4C(=O)OC[C@H]4C)cn3)CC2)c(C)c1]

Using (5-bromopyrazin-2-yl) [4-(3,5-dimethylpyridin-2-yl)piperazin-1-yl]methanone (130 mg) described in Preparation Example 232 and (R)-4-methyloxazolidin-2-one (35 mg) and by the reaction and treatment in the same manner as in Example 1, the title compound (110 mg) was obtained.
MS (ESI) m/z: 397(M+H)+.

Example 629

Synthesis of [4-(3,5-dimethylpyridin-2-yl)piperazin-1-yl][5-(1,1-dioxo-1$\lambda^6$-isothiazolidin-2-yl)pyrazin-2-yl]methanone

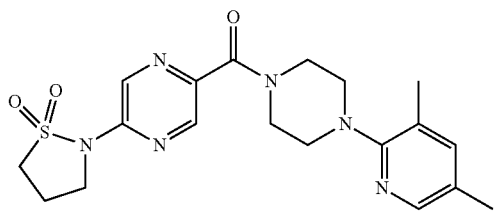 [SMILES: Cc1cnc(N2CCN(C(=O)c3cnc(N4CCCS4(=O)=O)cn3)CC2)c(C)c1]

Using (5-bromopyrazin-2-yl)[4-(3,5-dimethylpyridin-2-yl)piperazin-1-yl]methanone (49 mg) described in Preparation Example 232 and isothiazolidine 1,1-dioxide (16 mg) and by the reaction and treatment in the same manner as in Example 1, the title compound (28 mg) was obtained.
MS (ESI) m/z: 417(M+H)+.

Example 630

Synthesis of 1-acetyl-3-{5-[4-(3,5-dimethylpyridin-2-yl)piperazine-1-carbonyl]pyrazin-2-yl}imidazolidin-2-one

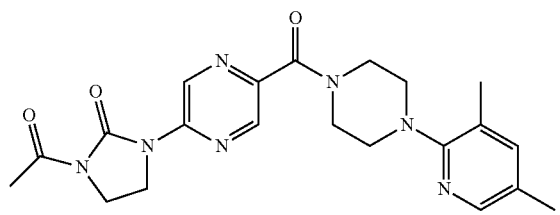 [SMILES: CC(=O)N1CCN(c2cnc(C(=O)N3CCN(c4ncc(C)cc4C)CC3)cn2)C1=O]

Using (5-bromopyrazin-2-yl)[4-(3,5-dimethylpyridin-2-yl)piperazin-1-yl]methanone (188 mg) described in Preparation Example 232 and 1-acetylimidazolidin-2-one (64 mg) and by the reaction and treatment in the same manner as in Example 511, the title compound (93 mg) was obtained.
MS (ESI) m/z: 424(M+H)+.

Example 631

Synthesis of 1-{5-[4-(3,5-dimethylpyridin-2-yl)piperazine-1-carbonyl]pyrazin-2-yl}imidazolidin-2-one

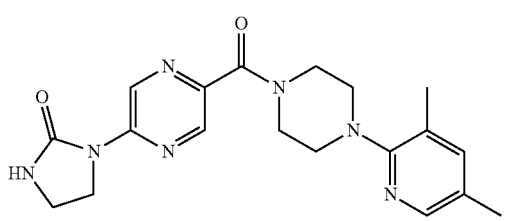 [SMILES: Cc1cnc(N2CCN(C(=O)c3cnc(N4CCNC4=O)cn3)CC2)c(C)c1]

A product produced by deacetylation that simultaneously proceeded during synthesis of 1-acetyl-3-{5-[4-(3,5-dimethylpyridin-2-yl)piperazine-1-carbonyl]pyrazin-2-yl}imidazolidin-2-one described in Example 630 was purified by column chromatography (ethyl acetate:methanol) to give the title compound (23 mg).
MS (ESI) m/z: 382(M+H)+.

Example 632

Synthesis of 1-{5-[4-(3,5-dimethylpyridin-2-yl)piperazine-1-carbonyl]pyrazin-2-yl}-3-methylimidazolidin-2-one

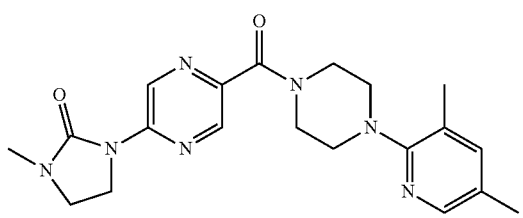

Using (5-bromopyrazin-2-yl)[4-(3,5-dimethylpyridin-2-yl)piperazin-1-yl]methanone (188 mg) described in Preparation Example 232 and 1-methylimidazolidin-2-one (50 mg) and by the reaction and treatment in the same manner as in Example 536, the title compound (122 mg) was obtained.
MS (ESI) m/z: 396(M+H)+.

Example 633

Synthesis of (R)-3-{6-[4-(5-cyclopropyl-3-methylpyridin-2-yl)piperazine-1-carbonyl]pyridazin-3-yl}-4-methyloxazolidin-2-one

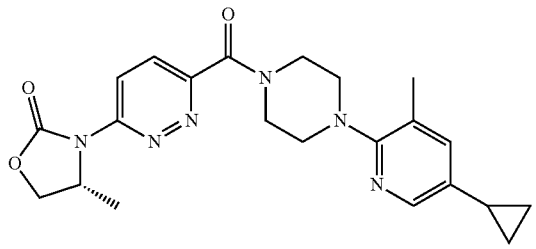 [SMILES: Cc1cc(C2CC2)cnc1N1CCN(C(=O)c2ccc(N3C(=O)OC[C@H]3C)nn2)CC1]

Using (6-chloropyridazin-3-yl)[4-(5-cyclopropyl-3-methylpyridin-2-yl)piperazin-1-yl]methanone (179 mg) described in Preparation Example 233 and (R)-4-methyloxazolidin-2-one (51 mg) and by the reaction and treatment in the same manner as in Example 1, the title compound (97 mg) was obtained.

MS (ESI) m/z: 423(M+H)$^+$.

Example 634

Synthesis of 3-{4-[4-(3,5-dimethylpyridin-2-yl)piperazine-1-carbonyl]phenyl}-4-oxoimidazolidine-1-carboxylic acid tert-butyl ester

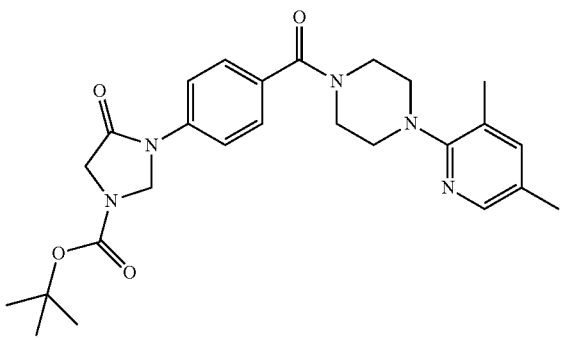 [SMILES: Cc1cnc(N2CCN(C(=O)c3ccc(N4CN(C(=O)OC(C)(C)C)CC4=O)cc3)CC2)c(C)c1]

Using [4-(3,5-dimethylpyridin-2-yl)piperazin-1-yl](4-iodophenyl)methanone (211 mg) described in Preparation Example 113 and 4-oxoimidazolidine-1-carboxylic acid tert-butyl ester (93 mg) and by the reaction and treatment in the same manner as in Example 1, the title compound (210 mg) was obtained.

MS (ESI) m/z: 480(M+H)$^+$.

Example 635

Synthesis of 3-{4-[4-(3,5-dimethylpyridin-2-yl)piperazine-1-carbonyl]phenyl}imidazolidin-4-one

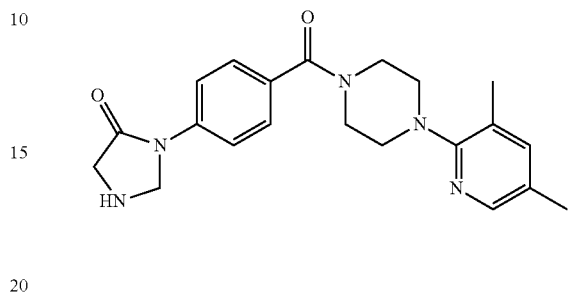

To 3-{4-[4-(3,5-dimethylpyridin-2-yl)piperazine-1-carbonyl]phenyl}-4-oxoimidazolidine-1-carboxylic acid tert-butyl ester (200 mg) described in Example 634 were added methanol (3 mL) and 2N hydrogen chloride/methanol (1.05 mL), and the mixture was stirred at room temperature for 8 hr. To the reaction mixture was added aqueous sodium hydrogen carbonate solution, and the mixture was extracted with chloroform. The solvent was evaporated, and the residue was purified by column chromatography (ethyl acetate:methanol) to give the title compound (33 mg).

MS (ESI) m/z: 380(M+H)$^+$.

Example 636

Synthesis of [4-(5-cyclopropyl-3-methylpyridin-2-yl)piperazin-1-yl][6-(1,1-dioxo-1$\lambda^6$-isothiazolidin-2-yl)pyridazin-3-yl]methanone

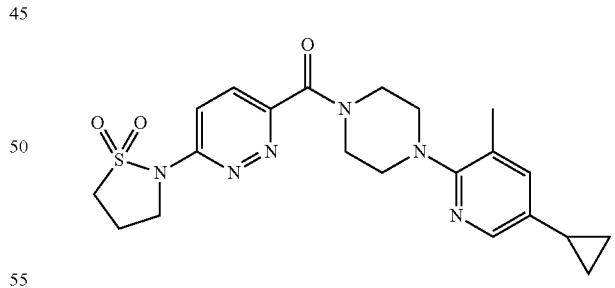

Using (6-chloropyridazin-3-yl) [4-(5-cyclopropyl-3-methylpyridin-2-yl)piperazin-1-yl]methanone (179 mg) described in Preparation Example 233 and isothiazolidine 1,1-dioxide (61 mg) and by the reaction and treatment in the same manner as in Example 1, the title compound (88 mg) was obtained.

MS (ESI) m/z: 443(M+H)$^+$.

Example 637

Synthesis of 3-{4-[4-(3,5-dimethylpyridin-2-yl)piperazine-1-carbonyl]phenyl}-1-methanesulfonylimidazolidin-4-one

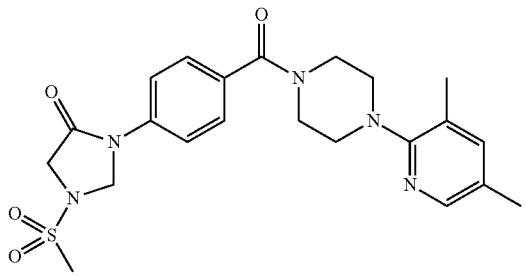 [SMILES: Cc1cnc(N2CCN(C(=O)c3ccc(N4CN(S(C)(=O)=O)CC4=O)cc3)CC2)c(C)c1]

A mixture of 3-{4-[4-(3,5-dimethylpyridin-2-yl)piperazine-1-carbonyl]phenyl}imidazolidin-4-one (48 mg) described in Example 635 and triethylamine (0.12 mL) was dissolved in tetrahydrofuran (1 mL), and methanesulfonyl chloride (15 μL) was added under ice-cooling. After stirring at room temperature for 8 hr, water was added to the reaction mixture, and the mixture was extracted with chloroform. The solvent was evaporated, and the residue was purified by column chromatography (ethyl acetate:hexane) to give the title compound (34 mg).

MS (ESI) m/z: 458(M+H)$^+$.

Example 638

Synthesis of 1-{6-[4-(5-cyclopropyl-3-methylpyridin-2-yl)piperazine-1-carbonyl]pyridazin-3-yl}imidazolidin-2-one

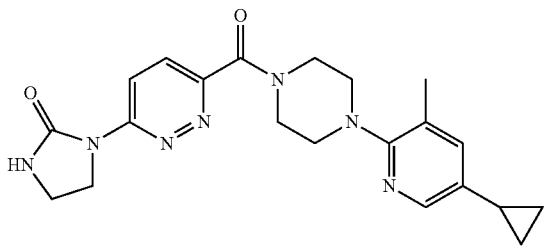 [SMILES: Cc1cc(C2CC2)cnc1N1CCN(C(=O)c2ccc(N3CCNC3=O)nn2)CC1]

Using (6-chloropyridazin-3-yl)[4-(5-cyclopropyl-3-methylpyridin-2-yl)piperazin-1-yl]methanone (179 mg) described in Preparation Example 233 and 1-acetylimidazolidin-2-one (64 mg) and by the reaction and treatment in the same manner as in Example 511, 1-acetyl-3-{6-[4-(5-cyclopropyl-3-methylpyridin-2-yl)piperazine-1-carbonyl]pyridazin-3-yl}imidazolidin-2-one was obtained as a crude product (170 mg). Methanol (1.2 mL) and 1N aqueous sodium hydroxide solution (0.57 mL) were added to the obtained crude product (170 mg) of 1-acetyl-3-{6-[4-(5-cyclopropyl-3-methylpyridin-2-yl)piperazine-1-carbonyl]pyridazin-3-yl}imidazolidin-2-one, and the mixture was stirred at 40° C. for 1 hr. After cooling, water was added to the reaction mixture, and the mixture was extracted with ethyl acetate. The solvent was evaporated, and the residue was purified by column chromatography (ethyl acetate:methanol) to give the title compound (48 mg).

MS (ESI) m/z: 408(M+H)$^+$.

Example 639

Synthesis of 1-{6-[4-(5-cyclopropyl-3-methylpyridin-2-yl)piperazine-1-carbonyl]pyridazin-3-yl}-3-methylimidazolidin-2-one

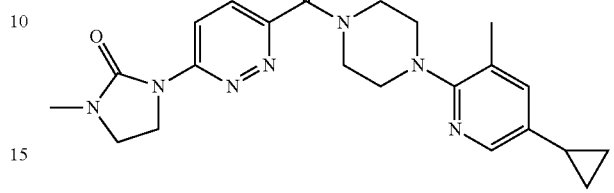

Using (6-chloropyridazin-3-yl)[4-(5-cyclopropyl-3-methylpyridin-2-yl)piperazin-1-yl]methanone (179 mg) described in Preparation Example 233 and 1-methylimidazolidin-2-one (50 mg) and by the reaction and treatment in the same manner as in Example 536, the title compound (92 mg) was obtained.

MS (ESI) m/z: 422(M+H)$^+$.

Example 640

Synthesis of 3-{6-[4-(5-cyclopropyl-3-methylpyridin-2-yl)piperazine-1-carbonyl]pyridazin-3-yl}oxazolidin-2-one

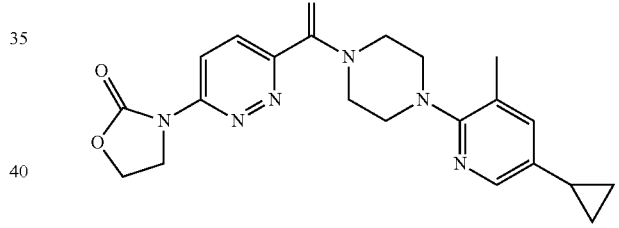

Using (6-chloropyridazin-3-yl)[4-(5-cyclopropyl-3-methylpyridin-2-yl)piperazin-1-yl]methanone (107 mg) described in Preparation Example 233 and oxazolidin-2-one (26 mg) and by the reaction and treatment in the same manner as in Example 1, the title compound (52 mg) was obtained.

MS (ESI) m/z: 409(M+H)$^+$.

Example 641

Synthesis of 1-{5-[4-(3,5-dimethylpyridin-2-yl)piperazine-1-carbonyl]pyridin-2-yl}-3-methanesulfonylimidazolidin-2-one

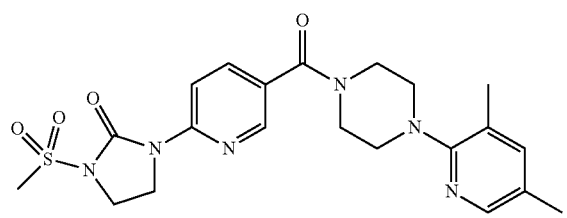

Using (6-bromopyridin-3-yl)[4-(3,5-dimethylpyridin-2-yl)piperazin-1-yl]methanone (188 mg) described in Preparation Example 127 and 1-methanesulfonylimidazolidin-2-one (82 mg) and by the reaction and treatment in the same manner as in Example 511, the title compound (170 mg) was obtained.
MS (ESI) m/z: 459(M+H)+.

Example 642

Synthesis of (R)-3-{6-[4-(5-cyclopropyl-3-methylpyridin-2-yl)piperazine-1-carbonyl]pyridazin-3-yl}-4-ethyloxazolidin-2-one

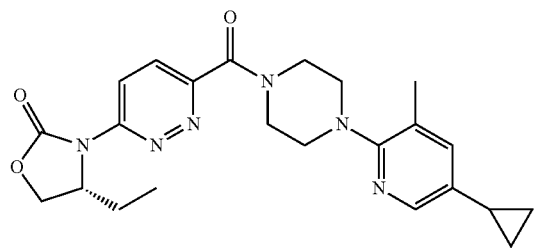 [SMILES: CC[C@@H]1COC(=O)N1c1ccc(C(=O)N2CCN(c3ncc(C4CC4)cc3C)CC2)nn1]

Using (6-chloropyridazin-3-yl)[4-(5-cyclopropyl-3-methylpyridin-2-yl)piperazin-1-yl]methanone (107 mg) described in Preparation Example 233 and (R)-4-ethyloxazolidin-2-one (35 mg) and by the reaction and treatment in the same manner as in Example 1, the title compound (8 mg) was obtained.
MS (ESI) m/z: 437(M+H)+.

Example 643

Synthesis of 3-{6-[4-(5-cyclopropyl-3-methylpyridin-2-yl)piperazine-1-carbonyl]pyridazin-3-yl}-5,5-dimethyloxazolidin-2-one

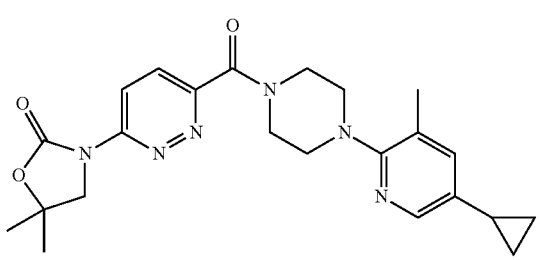 [SMILES: Cc1cc(C2CC2)cnc1N1CCN(C(=O)c2ccc(N3CC(C)(C)OC3=O)nn2)CC1]

Using (6-chloropyridazin-3-yl)[4-(5-cyclopropyl-3-methylpyridin-2-yl)piperazin-1-yl]methanone (107 mg) described in Preparation Example 233 and 5,5-dimethyloxazolidin-2-one (35 mg) and by the reaction and treatment in the same manner as in Example 1, the title compound (21 mg) was obtained.
MS (ESI) m/z: 437(M+H)+.

Example 644

Synthesis of 1-{6-[4-(5-cyclopropyl-3-methylpyridin-2-yl)piperazine-1-carbonyl]pyridazin-3-yl}pyrrolidin-2-one

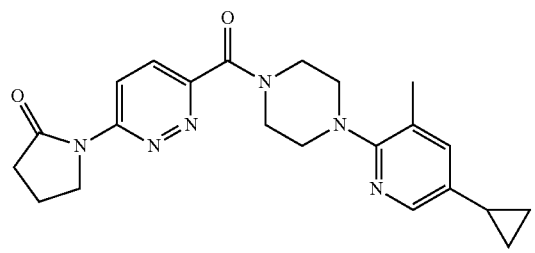 [SMILES: Cc1cc(C2CC2)cnc1N1CCN(C(=O)c2ccc(N3CCCC3=O)nn2)CC1]

Using (6-chloropyridazin-3-yl)[4-(5-cyclopropyl-3-methylpyridin-2-yl)piperazin-1-yl]methanone (107 mg) described in Preparation Example 233 and pyrrolidin-2-one (26 mg) and by the reaction and treatment in the same manner as in Example 1, the title compound (11 mg) was obtained.
MS (ESI) m/z: 407(M+H)+.

Example 645

Synthesis of 1-{6-[4-(5-cyclopropyl-3-methylpyridin-2-yl)piperazine-1-carbonyl]pyridazin-3-yl}-5-methylpyrrolidin-2-one

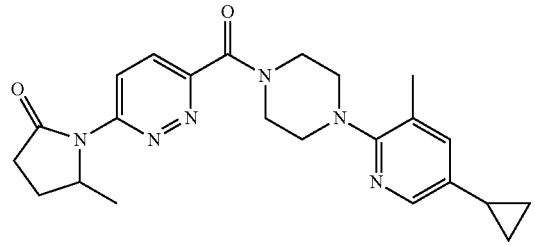

Using (6-chloropyridazin-3-yl)[4-(5-cyclopropyl-3-methylpyridin-2-yl)piperazin-1-yl]methanone (107 mg) described in Preparation Example 233 and 5-methylpyrrolidin-2-one (30 mg) and by the reaction and treatment in the same manner as in Example 1, the title compound (14 mg) was obtained.
MS (ESI) m/z: 421(M+H)+.

Example 646

Synthesis of (R)-3-{5-[4-(3,5-dimethylpyridin-2-yl)piperazine-1-carbonyl]pyrazin-2-yl}-4-ethyloxazolidin-2-one

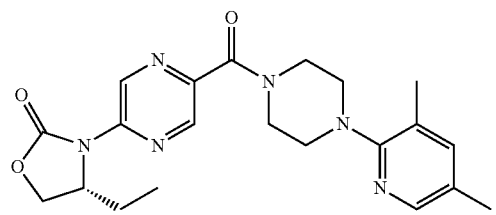 [SMILES: CC[C@@H]1COC(=O)N1c1cnc(C(=O)N2CCN(c3ncc(C)cc3C)CC2)cn1]

415

Using (5-bromopyrazin-2-yl)[4-(3,5-dimethylpyridin-2-yl)piperazin-1-yl]methanone (113 mg) described in Preparation Example 232 and (R)-4-ethyloxazolidin-2-one (52 mg) and by the reaction and treatment in the same manner as in Example 1, the title compound (105 mg) was obtained.

MS (ESI) m/z: 411(M+H)$^+$.

Example 647

Synthesis of 3-{5-[4-(3,5-dimethylpyridin-2-yl)piperazine-1-carbonyl]pyrazin-2-yl}-5,5-dimethyloxazolidin-2-one

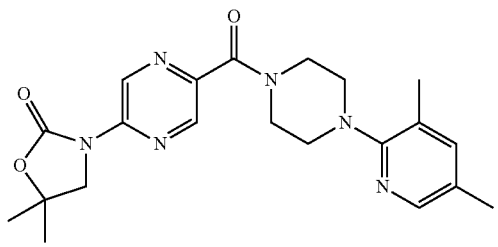

Using (5-bromopyrazin-2-yl)[4-(3,5-dimethylpyridin-2-yl)piperazin-1-yl]methanone (113 mg) described in Preparation Example 232 and 5,5-dimethyloxazolidin-2-one (52 mg) and by the reaction and treatment in the same manner as in Example 1, the title compound (65 mg) was obtained.

MS (ESI) m/z: 411(M+H)$^+$.

Example 648

Synthesis of 1-{5-[4-(3,5-dimethylpyridin-2-yl)piperazine-1-carbonyl]pyrazin-2-yl}-5-methylpyrrolidin-2-one

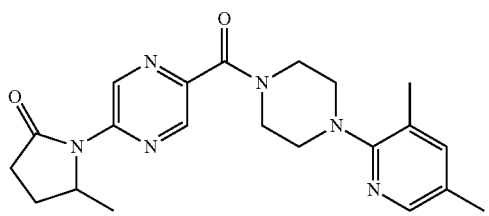

Using (5-bromopyrazin-2-yl)[4-(3,5-dimethylpyridin-2-yl)piperazin-1-yl]methanone (113 mg) described in Preparation Example 232 and 5-methylpyrrolidin-2-one (36 mg) and by the reaction and treatment in the same manner as in Example 1, the title compound (38 mg) was obtained.

MS (ESI) m/z: 395(M+H)$^+$.

416

Example 649

Synthesis of 1-{2-[4-(3,5-dimethylpyridin-2-yl)piperazine-1-carbonyl]-5-(2-oxopyrrolidin-1-yl)phenyl}imidazolidin-2-one

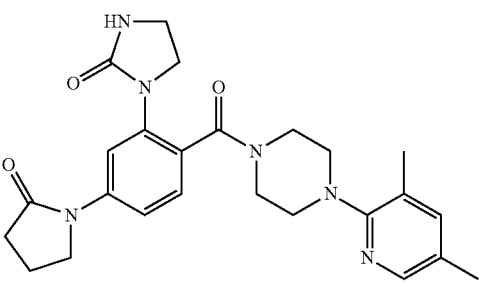 [SMILES: Cc1cnc(N2CCN(C(=O)c3ccc(N4CCCC4=O)cc3N3CCNC3=O)CC2)c(C)c1]

To a mixture of 1-acetyl-3-{5-chloro-2-[4-(3,5-dimethylpyridin-2-yl)piperazine-1-carbonyl]phenyl}imidazolidin-2-one (228 mg) described in Preparation Example 234, pyrrolidin-2-one (64 mg), tripotassium phosphate (149 mg), tris(dibenzylideneacetone)dipalladium(0)-chloroform adduct (52 mg) and 2-di-tert-butylphosphino-3,4,5,6-tetramethyl-2',4',6'-triisopropyl-1,1'-biphenyl (24 mg) was added tert-butanol (1.5 mL), and the mixture was stirred with heating under reflux for 8 hr. The reaction mixture was cooled, water was added, and the mixture was extracted with ethyl acetate. The solvent was evaporated and methanol (1.6 mL), 1N aqueous sodium hydroxide solution (0.75 mL) were added to the obtained crude product of 1-acetyl-3-[2-[4-(3,5-dimethylpyridin-2-yl)piperazine-1-carbonyl]-5-(2-oxopyrrolidin-1-yl)phenyl}imidazolidin-2-one, and the mixture was stirred at 40° C. for 3 hr. After cooling, water was added to the reaction mixture, and the mixture was extracted with ethyl acetate. The solvent was evaporated, and the residue was purified by column chromatography (ethyl acetate:methanol) to give the title compound (69 mg).

MS (ESI) m/z: 463(M+H)$^+$.

Example 650

Synthesis of 3-{4-[4-(3,5-dimethylpyridin-2-yl)piperazine-1-carbonyl]phenyl}-1,1-dimethylurea

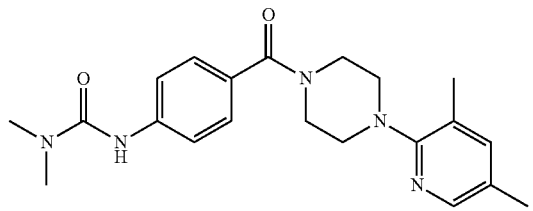

Using [4-(3,5-dimethylpyridin-2-yl)piperazin-1-yl](4-iodophenyl)methanone (211 mg) described in Preparation Example 113 and 1,1-dimethylurea (66 mg) and by the reaction and treatment in the same manner as in Example 262, the title compound (22 mg) was obtained.

MS (ESI) m/z: 382(M+H)$^+$.

Example 651

Synthesis of 1-[2-[4-(3,5-dimethylpyridin-2-yl)piperazine-1-carbonyl]-5-(2-methyl-5-oxopyrrolidin-1-yl)phenyl]imidazolidin-2-one

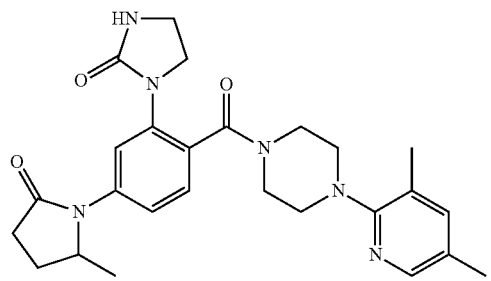

Using 1-acetyl-3-{(5-chloro-2-[4-(3,5-dimethylpyridin-2-yl)piperazine-1-carbonyl]phenyl}imidazolidin-2-one (228 mg) described in Preparation Example 234 and 5-methylpyrrolidin-2-one (74 mg) and by the reaction and treatment in the same manner as in Example 649, the title compound (31 mg) was obtained.

MS (ESI) m/z: 477(M+H)$^+$.

Example 652

Synthesis of 1-[4-[4-(3,5-dimethylpyridin-2-yl)piperazine-1-carbonyl]-3-(1,1-dioxo-1$\lambda^6$-isothiazolidin-2-yl)phenyl]imidazolidin-2-one

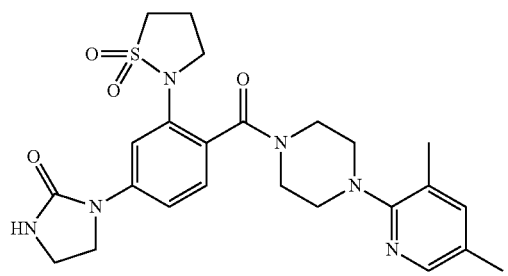 [SMILES: Cc1cnc(N2CCN(C(=O)c3ccc(N4CCNC4=O)cc3N3CCCS3(=O)=O)CC2)c(C)c1]

Using [4-bromo-2-(1,1-dioxo-1$\lambda^6$-isothiazolidin-2-yl)phenyl][4-(3,5-dimethylpyridin-2-yl)piperazin-1-yl]methanone (247 mg) described in Preparation Example 166 and 1-acetylimidazolidin-2-one (96 mg) and by the reaction and treatment in the same manner as in Example 638, the title compound (40 mg) was obtained.

MS (ESI) m/z: 499(M+H)$^+$.

Example 653

Synthesis of 1-[4-[4-(3,5-dimethylpyridin-2-yl)piperazine-1-carbonyl]-3-(1,1-dioxo-1$\lambda^6$-isothiazolidin-2-yl)phenyl]-3-methylimidazolidin-2-one

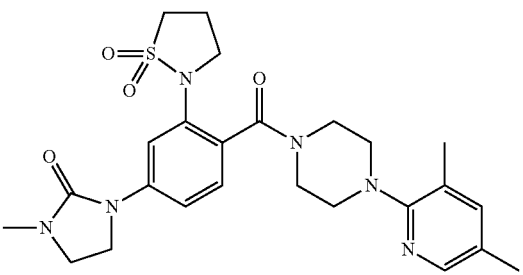

Using [4-bromo-2-(1,1-dioxo-1$\lambda^6$-isothiazolidin-2-yl)phenyl][4-(3,5-dimethylpyridin-2-yl)piperazin-1-yl]methanone (247 mg) described in Preparation Example 166 and 1-methylimidazolidin-2-one (60 mg) and by the reaction and treatment in the same manner as in Example 536, the title compound (35 mg) was obtained.

MS (ESI) m/z: 513(M+H)$^+$.

Example 654

Synthesis of 1-[2-[4-(3,5-dimethylpyridin-2-yl)piperazine-1-carbonyl]-5-(1,1-dioxo-1$\lambda^6$-isothiazolidin-2-yl)phenyl]imidazolidin-2-one

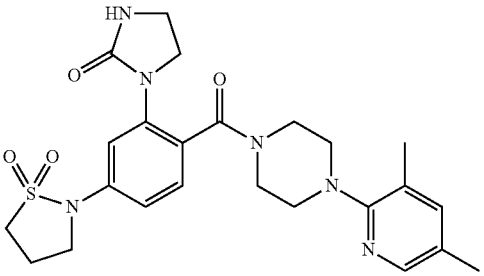 [SMILES: Cc1cnc(N2CCN(C(=O)c3ccc(N4CCCS4(=O)=O)cc3N3CCNC3=O)CC2)c(C)c1]

Using 1-acetyl-3-{5-chloro-2-[4-(3,5-dimethylpyridin-2-yl)piperazine-1-carbonyl]phenyl}imidazolidin-2-one (117 mg) described in Preparation Example 234 and isothiazolidine 1,1-dioxide (47 mg) and by the reaction and treatment in the same manner as in Example 649, the title compound (36 mg) was obtained.

MS (ESI) m/z: 499(M+H)$^+$.

Example 655

Synthesis of 3-{5-[4-(3,5-dimethylpyridin-2-yl)piperazine-1-carbonyl]pyridin-2-yl}-1,1-dimethylurea

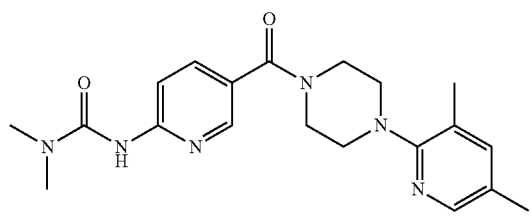

Using (6-bromopyridin-3-yl)[4-(3,5-dimethylpyridin-2-yl)piperazin-1-yl]methanone (188 mg) described in Preparation Example 127 and 1,1-dimethylurea (66 mg) and by the reaction and treatment in the same manner as in Example 262, the title compound (55 mg) was obtained.

MS (ESI) m/z: 383(M+H)$^+$.

Example 656

Synthesis of 1-[2-[4-(5-cyclopropyl-3-methylpyridin-2-yl)piperazine-1-carbonyl]-5-(2-oxopyrrolidin-1-yl)phenyl]imidazolidin-2-one

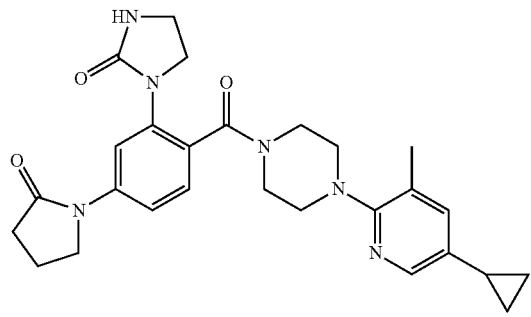 [SMILES: Cc1cc(C2CC2)cnc1N1CCN(C(=O)c2ccc(N3CCCC3=O)cc2N2CCNC2=O)CC1]

Using 1-acetyl-3-{5-chloro-2-[4-(5-cyclopropyl-3-methylpyridin-2-yl)piperazine-1-carbonyl]phenyl}imidazolidin-2-one (165 mg) described in Preparation Example 236 and pyrrolidin-2-one (44 mg) and by the reaction and treatment in the same manner as in Example 649, the title compound (75 mg) was obtained.

MS (ESI) m/z: 489(M+H)$^+$.

Example 657

Synthesis of [2,4-bis(2-oxoimidazolidin-1-yl)phenyl][4-(3,5-dimethylpyridin-2-yl)piperazin-1-yl]methanone

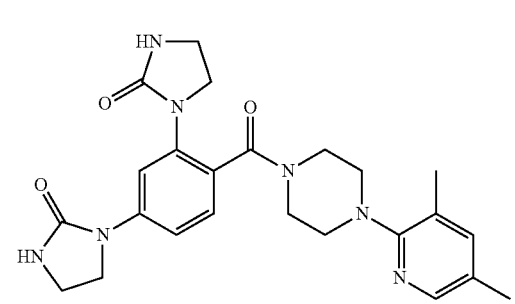 [SMILES: Cc1cnc(N2CCN(C(=O)c3ccc(N4CCNC4=O)cc3N3CCNC3=O)CC2)c(C)c1]

Using (2,4-dibromophenyl)[4-(3,5-dimethylpyridin-2-yl)piperazin-1-yl]methanone (258 mg) described in Preparation Example 237 and 1-acetylimidazolidin-2-one (219 mg) and by the reaction and treatment in the same manner as in Example 638, the title compound (71 mg) was obtained.

MS (ESI) m/z: 464(M+H)$^+$.

Example 658

Synthesis of 1-[2-[4-(5-cyclopropyl-3-methylpyridin-2-yl)piperazine-1-carbonyl]-5-(2-methyl-5-oxopyrrolidin-1-yl)phenyl]imidazolidin-2-one

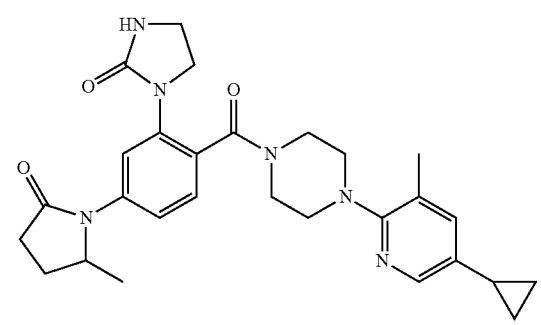 [SMILES: Cc1cc(C2CC2)cnc1N1CCN(C(=O)c2ccc(N3C(=O)CCC3C)cc2N2CCNC2=O)CC1]

Using 1-acetyl-3-{5-chloro-2-[4-(5-cyclopropyl-3-methylpyridin-2-yl)piperazine-1-carbonyl]phenyl}imidazolidin-2-one (239 mg) described in Preparation Example 236 and 5-methylpyrrolidin-2-one (74 mg) and by the reaction and treatment in the same manner as in Example 649, the title compound (67 mg) was obtained.

MS (ESI) m/z: 503(M+H)$^+$.

Example 659

Synthesis of 1-[2-[4-(5-cyclopropyl-3-methylpyridin-2-yl)piperazine-1-carbonyl]-5-(1,1-dioxo-1λ$^6$-isothiazolidin-2-yl)phenyl]imidazolidin-2-one

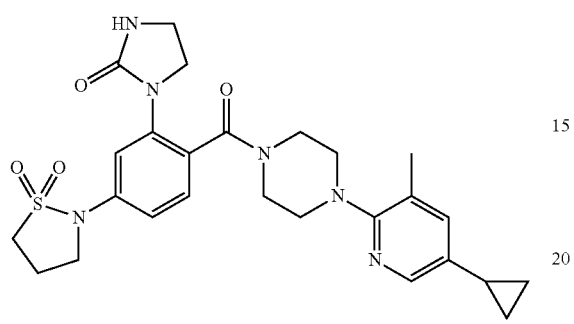

Using 1-acetyl-3-{5-chloro-2-[4-(5-cyclopropyl-3-methylpyridin-2-yl)piperazine-1-carbonyl]phenyl}imidazolidin-2-one (152 mg) described in Preparation Example 236 and isothiazolidine 1,1-dioxide (57 mg) and by the reaction and treatment in the same manner as in Example 649, the title compound (47 mg) was obtained.

MS (ESI) m/z: 525(M+H)$^+$.

Example 660

Synthesis of [2,4-bis(3-methyl-2-oxoimidazolidin-1-yl)phenyl][4-(3,5-dimethylpyridin-2-yl)piperazin-1-yl]methanone

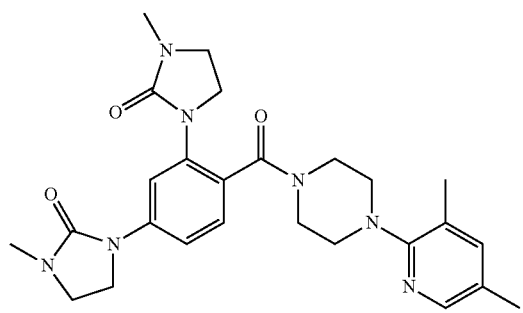

Using (2,4-dibromophenyl)[4-(3,5-dimethylpyridin-2-yl)piperazin-1-yl]methanone (136 mg) described in Preparation Example 237 and 1-methylimidazolidin-2-one (90 mg) and by the reaction and treatment in the same manner as in Example 536, the title compound (44 mg) was obtained.

MS (ESI) m/z: 492(M+H)$^+$.

Example 661

Synthesis of 1-{4-[4-(3,5-dimethylpyridin-2-yl)piperazine-1-carbonyl]phenyl}-1,3,3-trimethylurea

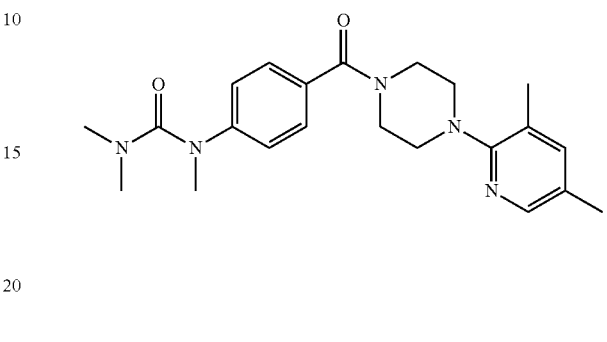

Using [4-(3,5-dimethylpyridin-2-yl)piperazin-1-yl](4-iodophenyl)methanone (211 mg) described in Preparation Example 113 and trimethylurea (77 mg) and by the reaction and treatment in the same manner as in Example 262, the title compound (127 mg) was obtained.

MS (ESI) m/z: 396(M+H)$^+$.

Example 662

Synthesis of [2,4-bis(2-oxoimidazolidin-1-yl)phenyl][4-(5-cyclopropyl-3-methylpyridin-2-yl)piperazin-1-yl]methanone

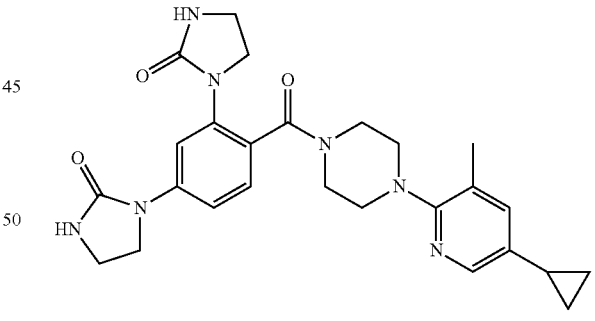

Using [4-(5-cyclopropyl-3-methylpyridin-2-yl)piperazin-1-yl](2,4-dibromophenyl)methanone (250 mg) described in Preparation Example 238 and 1-acetylimidazolidin-2-one (200 mg) and by the reaction and treatment in the same manner as in Example 638, the title compound (102 mg) was obtained.

MS (ESI) m/z: 490(M+H)$^+$.

Example 663

Synthesis of [2,4-bis(3-methyl-2-oxoimidazolidin-1-yl)phenyl][4-(5-cyclopropyl-3-methylpyridin-2-yl)piperazin-1-yl]methanone

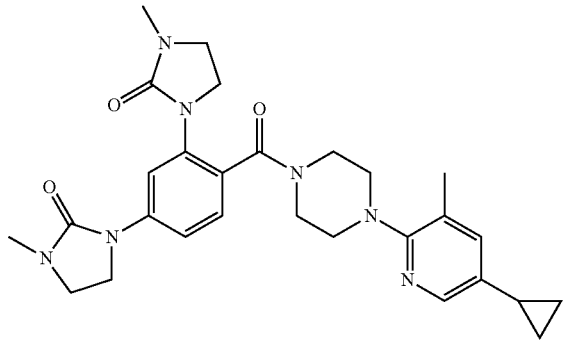 [SMILES: Cc1cc(C2CC2)cnc1N1CCN(C(=O)c2ccc(N3CCN(C)C3=O)cc2N2CCN(C)C2=O)CC1]

Using [4-(5-cyclopropyl-3-methylpyridin-2-yl)piperazin-1-yl](2,4-dibromophenyl)methanone (238 mg) described in Preparation Example 238 and 1-methylimidazolidin-2-one (149 mg) and by the reaction and treatment in the same manner as in Example 536, the title compound (66 mg) was obtained.

MS (ESI) m/z: 518(M+H)$^+$.

Example 664

Synthesis of 1-[4-[4-(5-cyclopropyl-3-methylpyridin-2-yl)piperazine-1-carbonyl]-3-(1,1-dioxo-1$\lambda^6$-isothiazolidin-2-yl)phenyl]imidazolidin-2-one

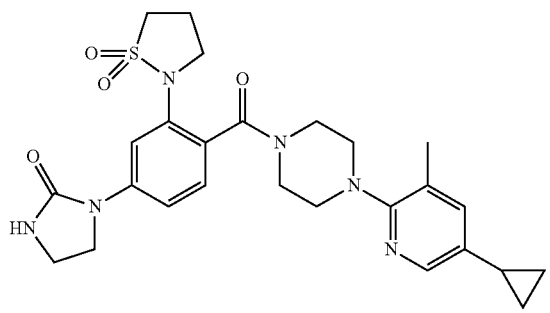 [SMILES: Cc1cc(C2CC2)cnc1N1CCN(C(=O)c2ccc(N3CCNC3=O)cc2N2CCCS2(=O)=O)CC1]

Using [4-bromo-2-(1,1-dioxo-1$\lambda^6$-isothiazolidin-2-yl)phenyl][4-(5-cyclopropyl-3-methylpyridin-2-yl)piperazin-1-yl]methanone (223 mg) described in Preparation Example 240 and 1-acetylimidazolidin-2-one (83 mg) and by the reaction and treatment in the same manner as in Example 638, the title compound (137 mg) was obtained.

MS (ESI) m/z: 525(M+H)$^+$.

Example 665

Synthesis of 1-[4-[4-(5-cyclopropyl-3-methylpyridin-2-yl)piperazine-1-carbonyl]-3-(1,1-dioxo-1$\lambda^6$-isothiazolidin-2-yl)phenyl]-3-methylimidazolidin-2-one

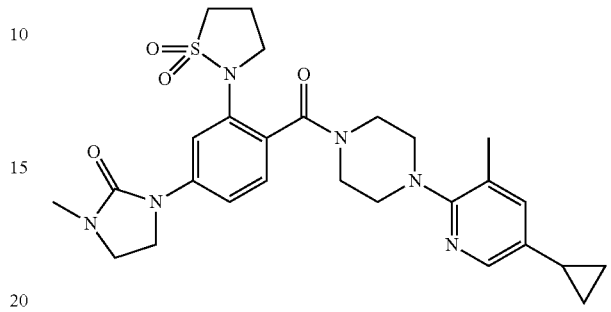

Using [4-bromo-2-(1,1-dioxo-1$\lambda^6$-isothiazolidin-2-yl)phenyl][4-(5-cyclopropyl-3-methylpyridin-2-yl)piperazin-1-yl]methanone (205 mg) described in Preparation Example 240 and 1-methylimidazolidin-2-one (59 mg) and by the reaction and treatment in the same manner as in Example 536, the title compound (139 mg) was obtained.

MS (ESI) m/z: 539(M+H)$^+$.

Example 666

Synthesis of 1-[2-[4-(3,5-dimethylpyridin-2-yl)piperazine-1-carbonyl]-5-(2-oxopyrrolidin-1-yl)phenyl]-3-methylimidazolidin-2-one

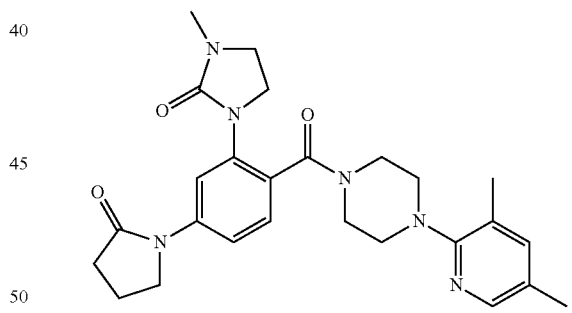

To a mixture of 1-{5-chloro-2-[4-(3,5-dimethylpyridin-2-yl)piperazine-1-carbonyl]phenyl}-3-methylimidazolidin-2-one (116 mg) described in Preparation Example 241, pyrrolidin-2-one (35 mg), tripotassium phosphate (81 mg), tris(dibenzylideneacetone)dipalladium(0)-chloroform adduct (28 mg) and 2-di-tert-butylphosphino-3,4,5,6-tetramethyl-2',4',6'-triisopropyl-1,1'-biphenyl (13 mg) was added tert-butanol (1.5 mL), and the mixture was stirred with heating under reflux for 8 hr. After cooling, water was added to the reaction mixture, and the mixture was extracted with ethyl acetate. The solvent was evaporated, and the residue was purified by column chromatography (ethyl acetate:methanol) to give the title compound (62 mg).

MS (ESI) m/z: 477(M+H)$^+$.

Example 667

Synthesis of 1-[2-[4-(3,5-dimethylpyridin-2-yl)piperazine-1-carbonyl]-5-(2-methyl-5-oxopyrrolidin-1-yl)phenyl]-3-methylimidazolidin-2-one

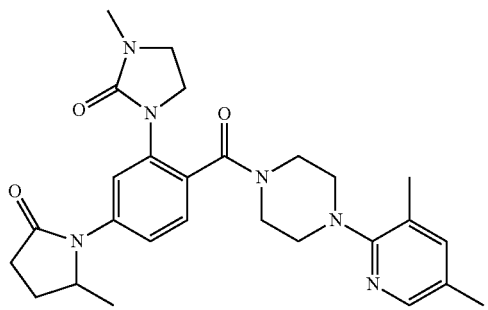 [SMILES: Cc1cnc(N2CCN(C(=O)c3ccc(N4C(=O)CCC4C)cc3N3CCN(C)C3=O)CC2)c(C)c1]

Using 1-{5-chloro-2-[4-(3,5-dimethylpyridin-2-yl)piperazine-1-carbonyl]phenyl}-3-methylimidazolidin-2-one (116 mg) described in Preparation Example 241 and 5-methylpyrrolidin-2-one (40 mg) and by the reaction and treatment in the same manner as in Example 666, the title compound (17 mg) was obtained.

MS (ESI) m/z: 491(M+H)$^+$.

Example 668

Synthesis of 1-[2-[4-(3,5-dimethylpyridin-2-yl)piperazine-1-carbonyl]-5-(1,1-dioxo-1$\lambda^6$-isothiazolidin-2-yl)phenyl]-3-methylimidazolidin-2-one

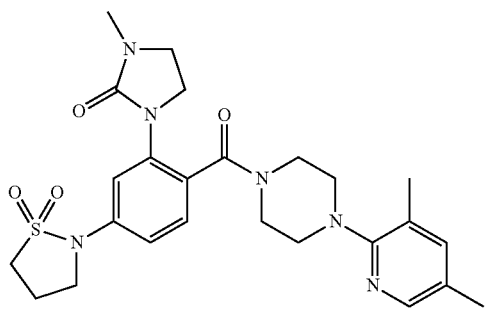 [SMILES: Cc1cnc(N2CCN(C(=O)c3ccc(N4CCCS4(=O)=O)cc3N3CCN(C)C3=O)CC2)c(C)c1]

Using 1-{5-chloro-2-[4-(3,5-dimethylpyridin-2-yl)piperazine-1-carbonyl]phenyl}-3-methylimidazolidin-2-one (85 mg) described in Preparation Example 241 and isothiazolidine 1,1-dioxide (36 mg) and by the reaction and treatment in the same manner as in Example 666, the title compound (45 mg) was obtained.

MS (ESI) m/z: 513(M+H)$^+$.

Example 669

Synthesis of 1-[2-[4-(5-cyclopropyl-3-methylpyridin-2-yl)piperazine-1-carbonyl]-5-(2-oxopyrrolidin-1-yl)phenyl]-3-methylimidazolidin-2-one

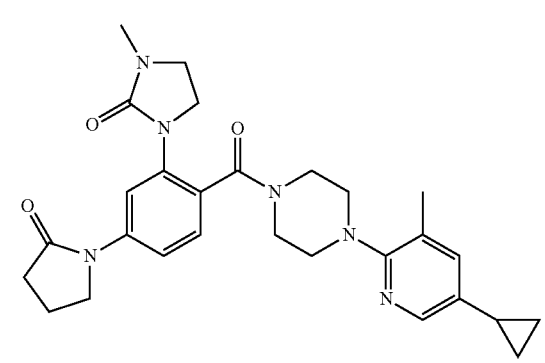 [SMILES: Cc1cc(C2CC2)cnc1N1CCN(C(=O)c2ccc(N3CCCC3=O)cc2N2CCN(C)C2=O)CC1]

Using 1-{5-chloro-2-[4-(5-cyclopropyl-3-methylpyridin-2-yl)piperazine-1-carbonyl]phenyl}-3-methylimidazolidin-2-one (82 mg) described in Preparation Example 242 and pyrrolidin-2-one (23 mg) and by the reaction and treatment in the same manner as in Example 666, the title compound (43 mg) was obtained.

MS (ESI) m/z: 503(M+H)$^+$.

Example 670

Synthesis of 1-[2-[4-(5-cyclopropyl-3-methylpyridin-2-yl)piperazine-1-carbonyl]-5-(2-methyl-5-oxopyrrolidin-1-yl)phenyl]-3-methylimidazolidin-2-one

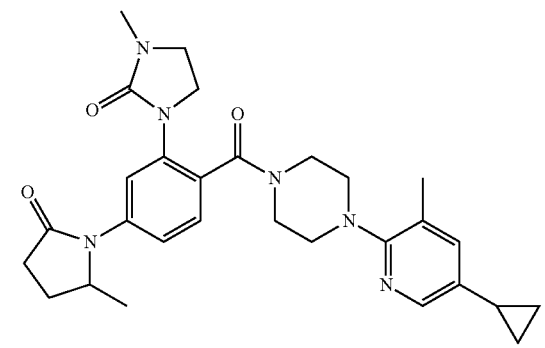 [SMILES: Cc1cc(C2CC2)cnc1N1CCN(C(=O)c2ccc(N3C(=O)CCC3C)cc2N2CCN(C)C2=O)CC1]

Using 1-{5-chloro-2-[4-(5-cyclopropyl-3-methylpyridin-2-yl)piperazine-1-carbonyl]phenyl}-3-methylimidazolidin-2-one (84 mg) described in Preparation Example 242 and 5-methylpyrrolidin-2-one (27.4 mg) and by the reaction and treatment in the same manner as in Example 666, the title compound (8 mg) was obtained.

MS (ESI) m/z: 517(M+H)$^+$.

Example 671

Synthesis of 1-[2-[4-(5-cyclopropyl-3-methylpyridin-2-yl)piperazine-1-carbonyl]-5-(1,1-dioxo-1λ⁶-isothiazolidin-2-yl)phenyl]-3-methylimidazolidin-2-one

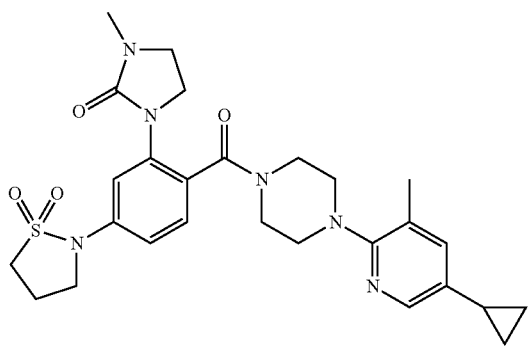 [SMILES: Cc1cc(C2CC2)cnc1N1CCN(C(=O)c2ccc(N3CCCS3(=O)=O)cc2N2CCN(C)C2=O)CC1]

Using 1-{5-chloro-2-[4-(5-cyclopropyl-3-methylpyridin-2-yl)piperazine-1-carbonyl]phenyl}-3-methylimidazolidin-2-one (79 mg) described in Preparation Example 242 and isothiazolidine 1,1-dioxide (32 mg) and by the reaction and treatment in the same manner as in Example 666, the title compound (36 mg) was obtained.
MS (ESI) m/z: 539(M+H)⁺.

Example 672

Synthesis of 3-{6-[4-(3,5-dimethylpyridin-2-yl)piperazine-1-carbonyl]pyridazin-3-yl}oxazolidin-2-one

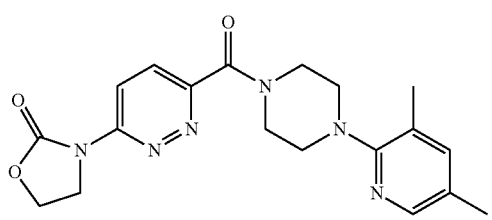 [SMILES: Cc1cnc(N2CCN(C(=O)c3ccc(N4CCOC4=O)nn3)CC2)c(C)c1]

Using (6-chloropyridazin-3-yl)[4-(3,5-dimethylpyridin-2-yl)piperazin-1-yl]methanone (152 mg) described in Preparation Example 230 and oxazolidin-2-one (40 mg) and by the reaction and treatment in the same manner as in Example 1, the title compound (44 mg) was obtained.
MS (ESI) m/z: 383(M+H)⁺.

Example 673

Synthesis of (R)-3-{6-[4-(3,5-dimethylpyridin-2-yl)piperazine-1-carbonyl]pyridazin-3-yl}-4-ethyloxazolidin-2-one

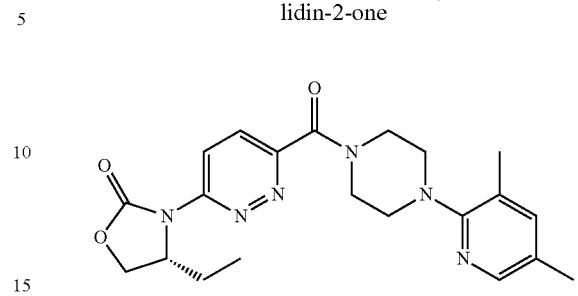

Using (6-chloropyridazin-3-yl)[4-(3,5-dimethylpyridin-2-yl)piperazin-1-yl]methanone (152 mg) described in Preparation Example 230 and (R)-4-ethyloxazolidin-2-one (79 mg) and by the reaction and treatment in the same manner as in Example 1, the title compound (60 mg) was obtained.
MS (ESI) m/z: 411(M+H)⁺.

Example 674

Synthesis of 3-{6-[4-(3,5-dimethylpyridin-2-yl)piperazine-1-carbonyl]pyridazin-3-yl}-5,5-dimethyloxazolidin-2-one

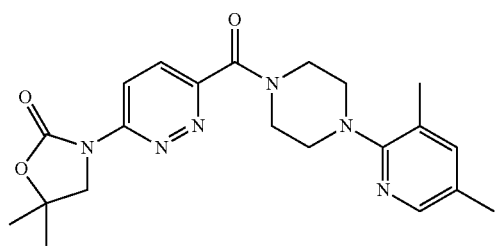

Using (6-chloropyridazin-3-yl)[4-(3,5-dimethylpyridin-2-yl)piperazin-1-yl]methanone (150 mg) described in Preparation Example 230 and 5,5-dimethyloxazolidin-2-one (63 mg) and by the reaction and treatment in the same manner as in Example 1, the title compound (81 mg) was obtained.
MS (ESI) m/z: 411(M+H)⁺.

Example 675

Synthesis of [4-(3,5-dimethylpyridin-2-yl)piperazin-1-yl][6-(1,1-dioxo-1λ⁶-isothiazolidin-2-yl)pyridazin-3-yl]methanone

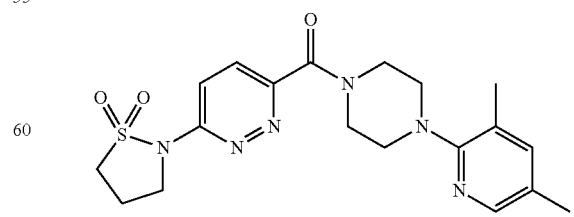

Using (6-chloropyridazin-3-yl)[4-(3,5-dimethylpyridin-2-yl)piperazin-1-yl]methanone (150 mg) described in Prepara-

Example 676

Synthesis of 1-{6-[4-(3,5-dimethylpyridin-2-yl)piperazine-1-carbonyl]pyridazin-3-yl}imidazolidin-2-one

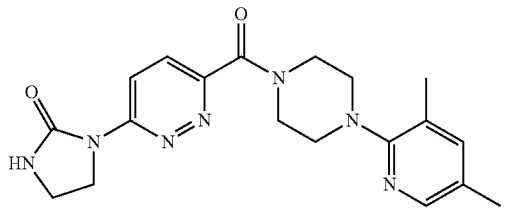

Using (6-chloropyridazin-3-yl)[4-(3,5-dimethylpyridin-2-yl)piperazin-1-yl]methanone (150 mg) described in Preparation Example 230 and 1-acetylimidazolidin-2-one (87 mg) and by the reaction and treatment in the same manner as in Example 638, the title compound (21 mg) was obtained.
MS (ESI) m/z: 382(M+H)$^+$.

Example 677

Synthesis of 1-{6-[4-(3,5-dimethylpyridin-2-yl)piperazine-1-carbonyl]pyridazin-3-yl}-3-methylimidazolidin-2-one

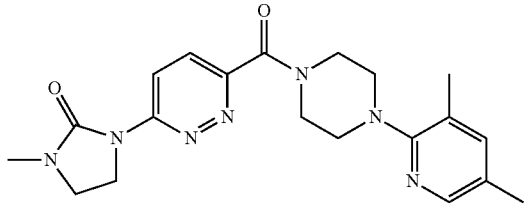

Using (6-chloropyridazin-3-yl)[4-(3,5-dimethylpyridin-2-yl)piperazin-1-yl]methanone (150 mg) described in Preparation Example 230 and 1-methylimidazolidin-2-one (68 mg) and by the reaction and treatment in the same manner as in Example 536, the title compound (62 mg) was obtained.
MS (ESI) m/z: 396(M+H)$^+$.

Example 678

Synthesis of 1-{6-[4-(3,5-dimethylpyridin-2-yl)piperazine-1-carbonyl]pyridazin-3-yl}pyrrolidin-2-one

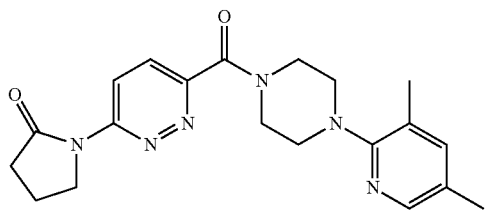 [SMILES: Cc1cnc(N2CCN(C(=O)c3ccc(N4CCCC4=O)nn3)CC2)c(C)c1]

Using (6-chloropyridazin-3-yl)[4-(3,5-dimethylpyridin-2-yl)piperazin-1-yl]methanone (150 mg) described in Preparation Example 230 and pyrrolidin-2-one (46 mg) and by the reaction and treatment in the same manner as in Example 1, the title compound (16 mg) was obtained.
MS (ESI) m/z: 381(M+H)$^+$.

Example 679

Synthesis of 1-{6-[4-(3,5-dimethylpyridin-2-yl)piperazine-1-carbonyl]pyridazin-3-yl}-5-methylpyrrolidin-2-one

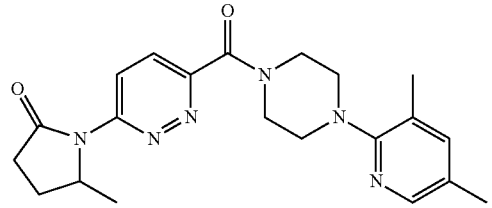 [SMILES: Cc1cnc(N2CCN(C(=O)c3ccc(N4C(=O)CCC4C)nn3)CC2)c(C)c1]

Using (6-chloropyridazin-3-yl)[4-(3,5-dimethylpyridin-2-yl)piperazin-1-yl]methanone (150 mg) described in Preparation Example 230 and 5-methylpyrrolidin-2-one (54 mg) and by the reaction and treatment in the same manner as in Example 1, the title compound (18 mg) was obtained.
MS (ESI) m/z: 395(M+H)$^+$.

Example 680

Synthesis of 3-{5-[4-(5-cyclopropyl-3-methylpyridin-2-yl)piperazine-1-carbonyl]pyrazin-2-yl}-5,5-dimethyloxazolidin-2-one

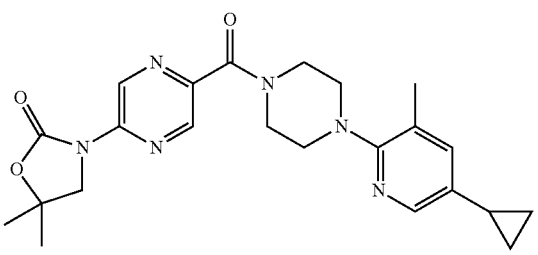 [SMILES: Cc1cc(C2CC2)cnc1N1CCN(C(=O)c2cnc(N3CC(C)(C)OC3=O)cn2)CC1]

Using (5-bromopyrazin-2-yl)[4-(5-cyclopropyl-3-methylpyridin-2-yl)piperazin-1-yl]methanone (150 mg) described in Preparation Example 243 and 5,5-dimethyloxazolidin-2-one (52 mg) and by the reaction and treatment in the same manner as in Example 1, the title compound (29 mg) was obtained.
MS (ESI) m/z: 437(M+H)$^+$.

Example 681

Synthesis of [4-(5-cyclopropyl-3-methylpyridin-2-yl)piperazin-1-yl][5-(1,1-dioxo-1λ$^6$-isothiazolidin-2-yl)pyrazin-2-yl]methanone

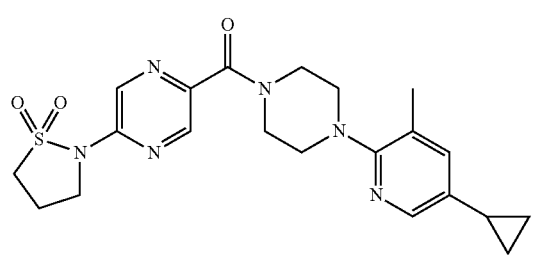

Using (5-bromopyrazin-2-yl)[4-(5-cyclopropyl-3-methylpyridin-2-yl)piperazin-1-yl]methanone (150 mg) described in Preparation Example 243 and isothiazolidine 1,1-dioxide (54 mg) and by the reaction and treatment in the same manner as in Example 1, the title compound (109 mg) was obtained.

MS (ESI) m/z: 443(M+H)$^+$.

Example 682

Synthesis of 1-{5-[4-(5-cyclopropyl-3-methylpyridin-2-yl)piperazine-1-carbonyl]pyrazin-2-yl}imidazolidin-2-one

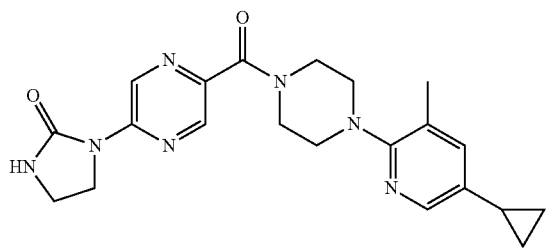 [SMILES: Cc1cc(C2CC2)cnc1N1CCN(C(=O)c2cnc(N3CCNC3=O)cn2)CC1]

Using (5-bromopyrazin-2-yl)[4-(5-cyclopropyl-3-methylpyridin-2-yl)piperazin-1-yl]methanone (150 mg) described in Preparation Example 243 and 1-acetylimidazolidin-2-one (72 mg) and by the reaction and treatment in the same manner as in Example 638, the title compound (78 mg) was obtained.

MS (ESI) m/z: 408(M+H)$^+$.

Example 683

Synthesis of 1-{5-[4-(5-cyclopropyl-3-methylpyridin-2-yl)piperazine-1-carbonyl]pyrazin-2-yl}-3-methylimidazolidin-2-one

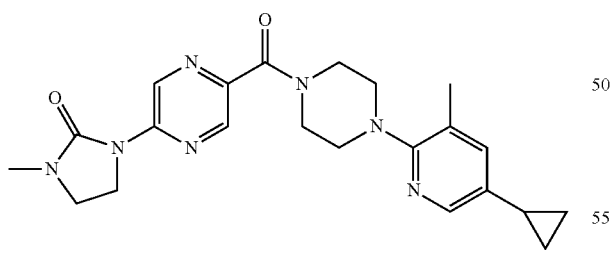

Using (5-bromopyrazin-2-yl)[4-(5-cyclopropyl-3-methylpyridin-2-yl)piperazin-1-yl]methanone (150 mg) described in Preparation Example 243 and 1-methylimidazolidin-2-one (56 mg) and by the reaction and treatment in the same manner as in Example 536, the title compound (86 mg) was obtained.

MS (ESI) m/z: 422(M+H)$^+$.

Example 684

Synthesis of (R)-3-{5-[4-(5-cyclopropyl-3-methylpyridin-2-yl)piperazine-1-carbonyl]pyrazin-2-yl}-4-methyloxazolidin-2-one

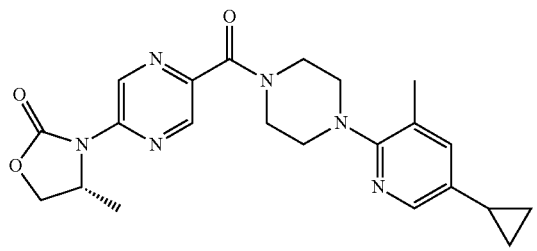 [SMILES: Cc1cc(C2CC2)cnc1N1CCN(C(=O)c2cnc(N3C(=O)OC[C@H]3C)cn2)CC1]

Using (5-bromopyrazin-2-yl)[4-(5-cyclopropyl-3-methylpyridin-2-yl)piperazin-1-yl]methanone (175 mg) described in Preparation Example 243 and (R)-4-methyloxazolidin-2-one (53 mg) and by the reaction and treatment in the same manner as in Example 1, the title compound (31 mg) was obtained.

MS (ESI) m/z: 423(M+H)$^+$.

Example 685

Synthesis of (R)-3-{5-[4-(5-cyclopropyl-3-methylpyridin-2-yl)piperazine-1-carbonyl]pyrazin-2-yl}-4-ethyloxazolidin-2-one

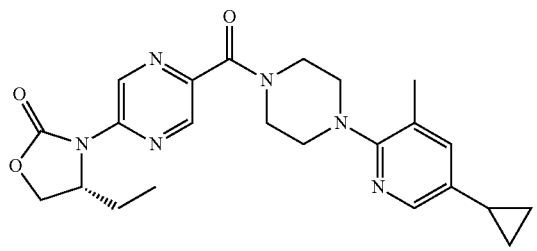 [SMILES: CC[C@@H]1COC(=O)N1c1cnc(C(=O)N2CCN(c3ncc(C4CC4)cc3C)CC2)cn1]

Using (5-bromopyrazin-2-yl)[4-(5-cyclopropyl-3-methylpyridin-2-yl)piperazin-1-yl]methanone (158 mg) described in Preparation Example 243 and (R)-4-ethyloxazolidin-2-one (68 mg) and by the reaction and treatment in the same manner as in Example 1, the title compound (54 mg) was obtained.

MS (ESI) m/z: 437(M+H)$^+$.

Example 686

Synthesis of 3-{5-[4-(5-cyclopropyl-3-methylpyridin-2-yl)piperazine-1-carbonyl]pyrazin-2-yl}oxazolidin-2-one

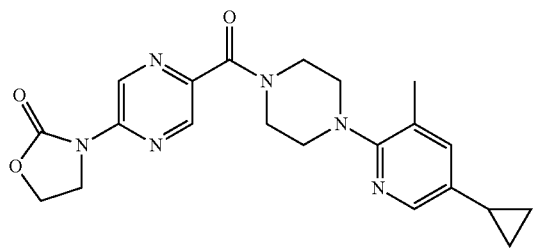 [SMILES: Cc1cc(C2CC2)cnc1N1CCN(C(=O)c2cnc(N3CCOC3=O)cn2)CC1]

Using (5-bromopyrazin-2-yl) [4-(5-cyclopropyl-3-methylpyridin-2-yl)piperazin-1-yl]methanone (100 mg) described in Preparation Example 243 and oxazolidin-2-one (26 mg) and by the reaction and treatment in the same manner as in Example 1, the title compound (48 mg) was obtained.

MS (ESI) m/z: 409(M+H)$^+$.

Example 687

Synthesis of 1-{5-[4-(5-cyclopropyl-3-methylpyridin-2-yl)piperazine-1-carbonyl]pyrazin-2-yl}-5-methylpyrrolidin-2-one

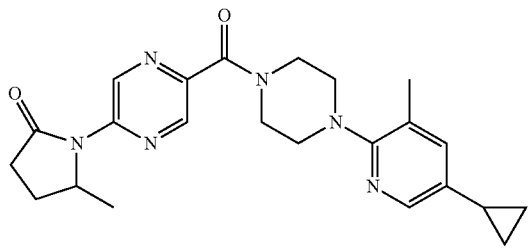

Using (5-bromopyrazin-2-yl)[4-(5-cyclopropyl-3-methylpyridin-2-yl)piperazin-1-yl]methanone (150 mg) described in Preparation Example 243 and 5-methylpyrrolidin-2-one (44 mg) and by the reaction and treatment in the same manner as in Example 1, the title compound (42 mg) was obtained.

MS (ESI) m/z: 421(M+H)$^+$.

Example 688

Synthesis of 1-{5-[4-(5-cyclopropyl-3-methylpyridin-2-yl)piperazine-1-carbonyl]pyrazin-2-yl}pyrrolidin-2-one

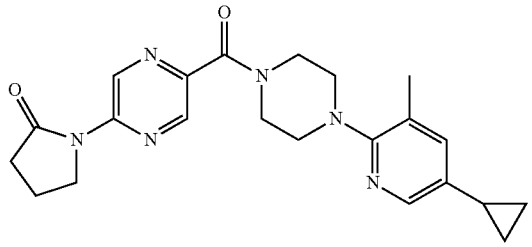

Using (5-bromopyrazin-2-yl) [4-(5-cyclopropyl-3-methylpyridin-2-yl)piperazin-1-yl]methanone (100 mg) described in Preparation Example 243 and pyrrolidin-2-one (25 mg) and by the reaction and treatment in the same manner as in Example 1, the title compound (2 mg) was obtained.

MS (ESI) m/z: 407(M+H)$^+$.

Example 689

Synthesis of (R)-3-{4-[4-(3,5-dimethylpyridin-2-yl)piperazine-1-carbonyl]thiophen-2-yl}-4-methyloxazolidin-2-one

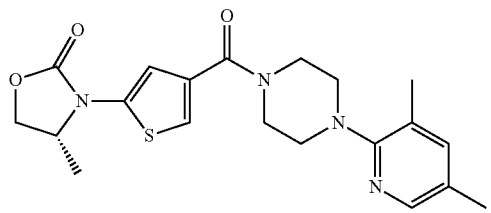 [SMILES: Cc1cnc(N2CCN(C(=O)c3csc(N4C(=O)OC[C@H]4C)c3)CC2)c(C)c1]

Using (5-bromothiophen-3-yl) [4-(3,5-dimethylpyridin-2-yl)piperazin-1-yl]methanone (107 mg) described in Preparation Example 244 and (R)-4-methyloxazolidin-2-one (34 mg) and by the reaction and treatment in the same manner as in Example 1, the title compound (65 mg) was obtained.

MS (ESI) m/z: 401(M+H)$^+$.

Example 690

Synthesis of [4-(3,5-dimethylpyridin-2-yl)piperazin-1-yl][5-(1,1-dioxo-1λ$^6$-isothiazolidin-2-yl)thiophen-3-yl]methanone

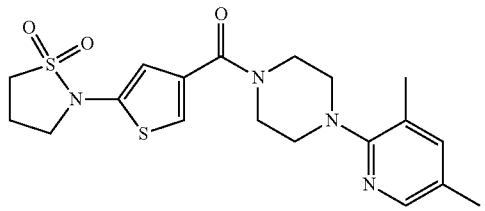 [SMILES: Cc1cnc(N2CCN(C(=O)c3csc(N4CCCS4(=O)=O)c3)CC2)c(C)c1]

Using (5-bromothiophen-3-yl)[4-(3,5-dimethylpyridin-2-yl)piperazin-1-yl]methanone (107 mg) described in Preparation Example 244 and isothiazolidine 1,1-dioxide (41 mg) and by the reaction and treatment in the same manner as in Example 1, the title compound (60 mg) was obtained.

MS (ESI) m/z: 421(M+H)$^+$.

Example 691

Synthesis of 1-acetyl-3-{6-methyl-5-[4-(3,5,6-trimethylpyridin-2-yl)piperazine-1-carbonyl]pyridin-2-yl}imidazolidin-2-one

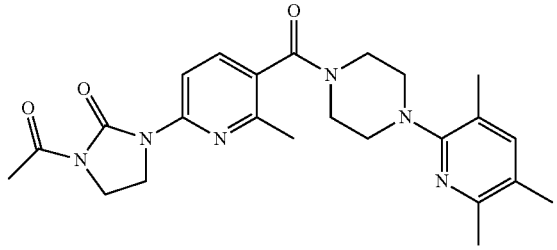 [SMILES: CC(=O)N1CCN(c2ccc(C(=O)N3CCN(c4nc(C)c(C)cc4C)CC3)c(C)n2)C1=O]

Using (6-bromo-2-methylpyridin-3-yl)[4-(3,5,6-trimethylpyridin-2-yl)piperazin-1-yl]methanone (202 mg) described in Preparation Example 248 and 1-acetylimidazolidin-2-one (77 mg) and by the reaction and treatment in the same manner as in Example 1, the title compound (164 mg) was obtained.

MS (ESI) m/z: 451(M+H)$^+$.

Example 692

Synthesis of 1-acetyl-3-{5-[4-(5-cyclopropyl-3-methylpyridin-2-yl)piperazine-1-carbonyl]-6-methylpyridin-2-yl}imidazolidin-2-one

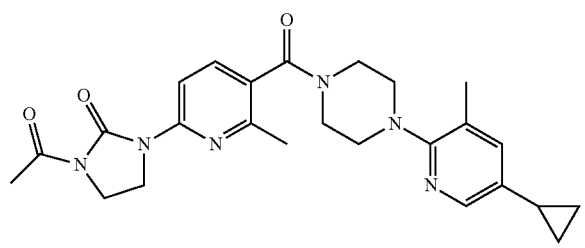 [SMILES: CC(=O)N1CCN(c2ccc(C(=O)N3CCN(c4ncc(C5CC5)cc4C)CC3)c(C)n2)C1=O]

Using (6-bromo-2-methylpyridin-3-yl) [4-(5-cyclopropyl-3-methylpyridin-2-yl)piperazin-1-yl]methanone (208 mg) described in Preparation Example 249 and 1-acetylimidazolidin-2-one (77 mg) and by the reaction and treatment in the same manner as in Example 1, the title compound (174 mg) was obtained.

MS (ESI) m/z: 463(M+H)$^+$.

Example 693

Synthesis of 1-acetyl-3-{5-[4-(5-ethyl-3-methylpyridin-2-yl)piperazine-1-carbonyl]-6-methylpyridin-2-yl}imidazolidin-2-one

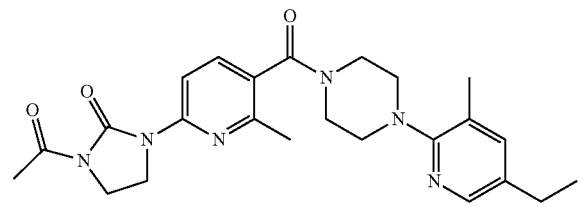 [SMILES: CCc1cnc(N2CCN(C(=O)c3ccc(N4CCN(C(C)=O)C4=O)nc3C)CC2)c(C)c1]

Using 6-bromo-2-methylpyridin-3-yl)[4-(5-ethyl-3-methylpyridin-2-yl)piperazin-1-yl]methanone (202 mg) described in Preparation Example 250 and 1-acetylimidazolidin-2-one (77 mg) and by the reaction and treatment in the same manner as in Example 1, the title compound (179 mg) was obtained.

MS (ESI) m/z: 451(M+H)$^+$.

Example 694

Synthesis of 1-acetyl-3-{5-[4-(3,5-dicyclopropylpyridin-2-yl)piperazine-1-carbonyl]-6-methylpyridin-2-yl}imidazolidin-2-one

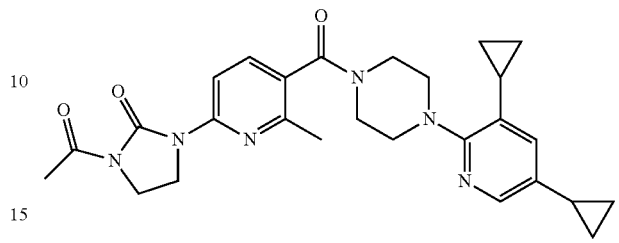

Using (6-bromo-2-methylpyridin-3-yl)[4-(3,5-dicyclopropylpyridin-2-yl)piperazin-1-yl]methanone (221 mg) described in Preparation Example 251 and 1-acetylimidazolidin-2-one (77 mg) and by the reaction and treatment in the same manner as in Example 1, the title compound (213 mg) was obtained.

MS (ESI) m/z: 489(M+H)$^+$.

Example 695

Synthesis of 1-methyl-3-{4-[4-(3,5,6-trimethylpyridin-2-yl)piperazine-1-carbonyl]phenyl}imidazolidin-2-one

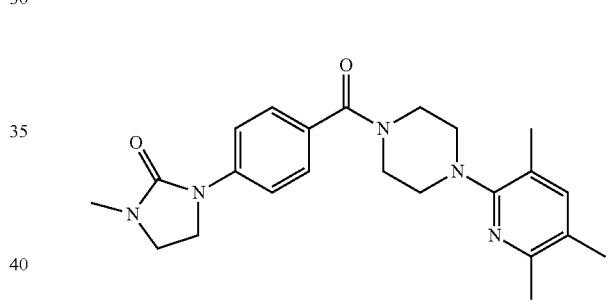

Using (4-iodophenyl)[4-(3,5,6-trimethylpyridin-2-yl)piperazin-1-yl]methanone (435 mg) described in Preparation Example 120 and 1-methylimidazolidin-2-one (120 mg) and by the reaction and treatment in the same manner as in Example 1, the title compound (369 mg) was obtained.

MS (ESI) m/z: 408(M+H)$^+$.

Example 696

Synthesis of 1-acetyl-3-{4-[4-(3,5,6-trimethylpyridin-2-yl)piperazine-1-carbonyl]phenyl}imidazolidin-2-one

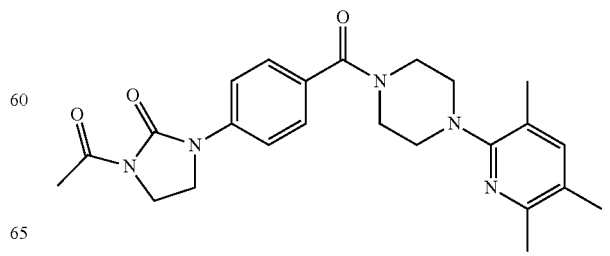

Using (4-iodophenyl)[4-(3,5,6-trimethylpyridin-2-yl)piperazin-1-yl]methanone (1.31 g) described in Preparation Example 120 and 1-acetylimidazolidin-2-one (461 mg) and by the reaction and treatment in the same manner as in Example 1, the title compound (1.14 g) was obtained.

MS (ESI) m/z: 436(M+H)$^+$.

Example 697

Synthesis of 1-{4-[4-(3,5,6-trimethylpyridin-2-yl)piperazine-1-carbonyl]phenyl}imidazolidin-2-one

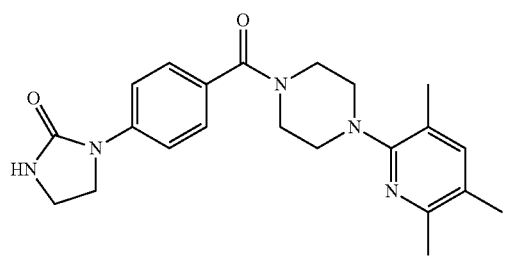

Using 1-acetyl-3-{4-[4-(3,5,6-trimethylpyridin-2-yl)piperazine-1-carbonyl]phenyl}imidazolidin-2-one (932 mg) described in Example 696 and by the reaction and treatment in the same manner as in Example 391, the title compound (826 mg) was obtained.

MS (ESI) m/z: 394(M+H)$^+$.

Example 698

Synthesis of 1-{4-[4-(3,5-dimethylpyridin-2-yl)piperazine-1-carbonyl]-3,5-difluorophenyl}-3-methylimidazolidin-2-one

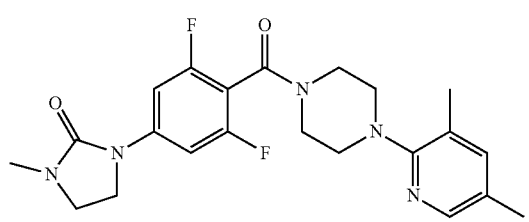

Using (4-bromo-2,6-difluorophenyl)[4-(3,5-dimethylpyridin-2-yl)piperazin-1-yl]methanone (410 mg) described in Preparation Example 111 and 1-methylimidazolidin-2-one (120 mg) and by the reaction and treatment in the same manner as in Example 1, the title compound (367 mg) was obtained.

MS (ESI) m/z: 430(M+H)$^+$.

Example 699

Synthesis of 1-acetyl-3-{4-[4-(3,5-dimethylpyridin-2-yl)piperazine-1-carbonyl]-3,5-difluorophenyl}imidazolidin-2-one

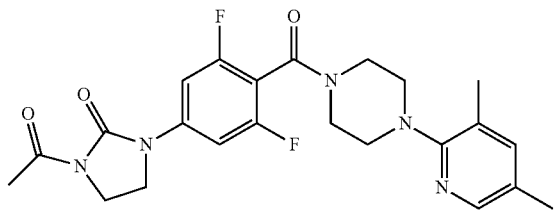 [SMILES: CC(=O)N1CCN(c2cc(F)c(C(=O)N3CCN(c4ncc(C)cc4C)CC3)c(F)c2)C1=O]

Using (4-bromo-2,6-difluorophenyl)[4-(3,5-dimethylpyridin-2-yl)piperazin-1-yl]methanone (1.23 g) described in Preparation Example 111 and 1-acetylimidazolidin-2-one (461 mg) and by the reaction and treatment in the same manner as in Example 1, the title compound (912 mg) was obtained.

MS (ESI) m/z: 458(M+H)$^+$.

Example 700

Synthesis of 1-{4-[4-(3,5-dimethylpyridin-2-yl)piperazine-1-carbonyl]-3,5-difluorophenyl}imidazolidin-2-one

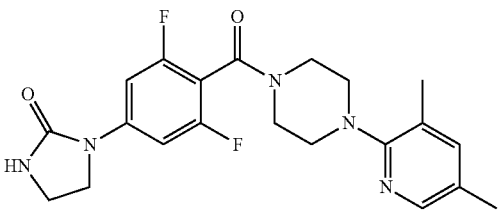 [SMILES: Cc1cnc(N2CCN(C(=O)c3c(F)cc(N4CCNC4=O)cc3F)CC2)c(C)c1]

Using 1-acetyl-3-{4-[4-(3,5-dimethylpyridin-2-yl)piperazine-1-carbonyl]-3,5-difluorophenyl}imidazolidin-2-one (693 mg) described in Example 699 and by the reaction and treatment in the same manner as in Example 391, the title compound (562 mg) was obtained.

MS (ESI) m/z: 416(M+H)$^+$.

Example 701

Synthesis of [4-(3,5-dimethylpyridin-2-yl)piperazin-1-yl][4-(1,1-dioxo-1$\lambda^6$-[1,2]thiazinan-2-yl)-2,6-difluorophenyl]methanone

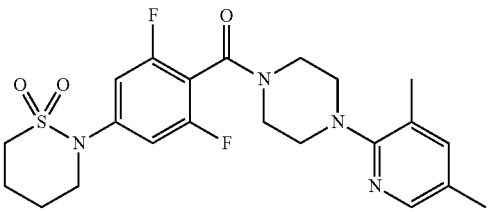 [SMILES: Cc1cnc(N2CCN(C(=O)c3c(F)cc(N4CCCCS4(=O)=O)cc3F)CC2)c(C)c1]

Using (4-bromo-2,6-difluorophenyl)[4-(3,5-dimethylpyridin-2-yl)piperazin-1-yl]methanone (429 mg) described in Preparation Example 111 and [1,2]thiazinane 1,1-dioxide (176 mg) and by the reaction and treatment in the same manner as in Example 262, the title compound (425 mg) was obtained.

MS (ESI) m/z: 465(M+H)+.

Example 702

Synthesis of 1-{4-[4-(3,5-dimethylpyridin-2-yl)piperazine-1-carbonyl]-2-fluorophenyl}-3-methylimidazolidin-2-one

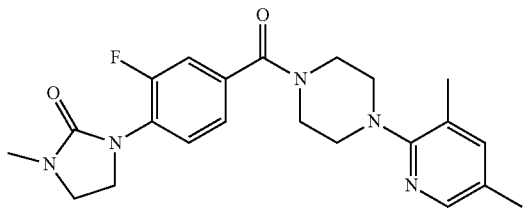

Using (4-bromo-3-fluorophenyl)[4-(3,5-dimethylpyridin-2-yl)piperazin-1-yl]methanone (353 mg) described in Preparation Example 125 and 1-methylimidazolidin-2-one (108 mg) and by the reaction and treatment in the same manner as in Example 1, the title compound (243 mg) was obtained.

MS (ESI) m/z: 412(M+H)+. Example 703: Synthesis of 1-acetyl-3-{4-[4-(3,5-dimethylpyridin-2-yl)piperazine-1-carbonyl]-2-fluorophenyl}imidazolidin-2-one

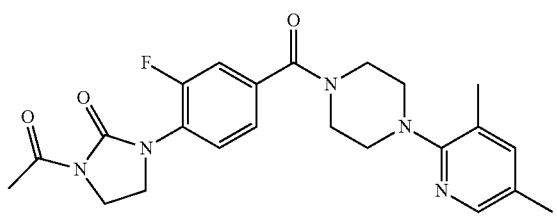 [SMILES: CC(=O)N1CCN(c2ccc(C(=O)N3CCN(c4ncc(C)cc4C)CC3)cc2F)C1=O]

Using (4-bromo-3-fluorophenyl)[4-(3,5-dimethylpyridin-2-yl)piperazin-1-yl]methanone (839 mg) described in Preparation Example 125 and 1-acetylimidazolidin-2-one (329 mg) and by the reaction and treatment in the same manner as in Example 1, the title compound (638 mg) was obtained.

MS (ESI) m/z: 440(M+H)+.

Example 704

Synthesis of 2-[4-(3,5-dicyclopropylpyridin-2-yl)piperazine-1-carbonyl]-5-(3-methyl-2-oxoimidazolidin-1-yl)benzonitrile

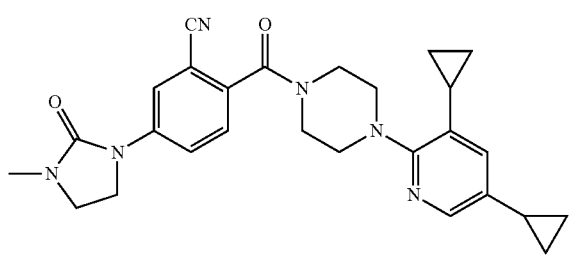 [SMILES: CN1CCN(c2ccc(C(=O)N3CCN(c4ncc(C5CC5)cc4C4CC4)CC3)c(C#N)c2)C1=O]

Using 5-bromo-2-[4-(3,5-dicyclopropylpyridin-2-yl)piperazine-1-carbonyl]benzonitrile (451 mg) described in Preparation Example 245 and 1-methylimidazolidin-2-one (120 mg) and by the reaction and treatment in the same manner as in Example 1, the title compound (377 mg) was obtained.

MS (ESI) m/z: 471(M+H)+.

Example 705

Synthesis of 5-(3-acetyl-2-oxoimidazolidin-1-yl)-2-[4-(3,5-dicyclopropylpyridin-2-yl)piperazine-1-carbonyl]benzonitrile

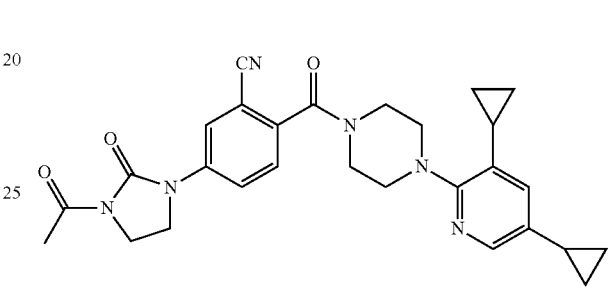

Using 5-bromo-2-[4-(3,5-dicyclopropylpyridin-2-yl)piperazine-1-carbonyl]benzonitrile (1.35 g) described in Preparation Example 245 and 1-acetylimidazolidin-2-one (461 mg) and by the reaction and treatment in the same manner as in Example 1, the title compound (702 mg) was obtained.

MS (ESI) m/z: 499(M+H)+.

Example 706

Synthesis of 1-{4-[4-(3,5-dimethylpyridin-2-yl)piperazine-1-carbonyl]-2-fluorophenyl}imidazolidin-2-one

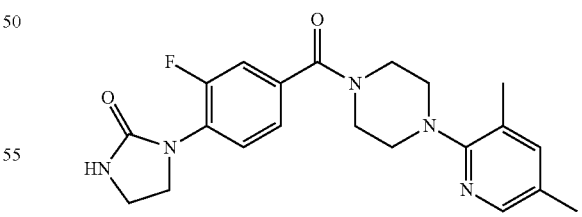

Using 1-acetyl-3-{4-[4-(3,5-dimethylpyridin-2-yl)piperazine-1-carbonyl]-2-fluorophenyl}imidazolidin-2-one (473 mg) described in Example 703 and by the reaction and treatment in the same manner as in Example 391, the title compound (362 mg) was obtained.

MS (ESI) m/z: 398(M+H)+.

Example 707

Synthesis of 2-[4-(3,5-dicyclopropylpyridin-2-yl) piperazine-1-carbonyl]-5-(2-oxoimidazolidin-1-yl) benzonitrile

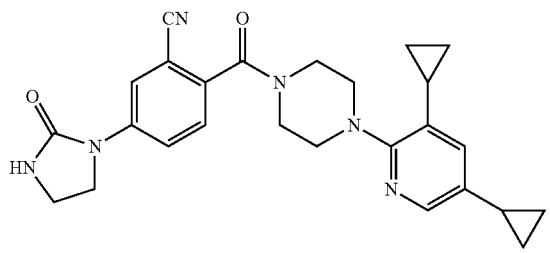 [SMILES: N#Cc1cc(N2CCNC2=O)ccc1C(=O)N1CCN(c2ncc(C3CC3)cc2C2CC2)CC1]

Using 5-(3-acetyl-2-oxoimidazolidin-1-yl)-2-[4-(3,5-dicyclopropylpyridin-2-yl)piperazine-1-carbonyl]benzonitrile (499 mg) described in Example 705 and by the reaction and treatment in the same manner as in Example 391, the title compound (373 mg) was obtained.
MS (ESI) m/z: 457(M+H)$^+$.

Example 708

Synthesis of 2-[4-(3,5-dicyclopropylpyridin-2-yl) piperazine-1-carbonyl]-5-(2-oxopyrrolidin-1-yl)benzonitrile

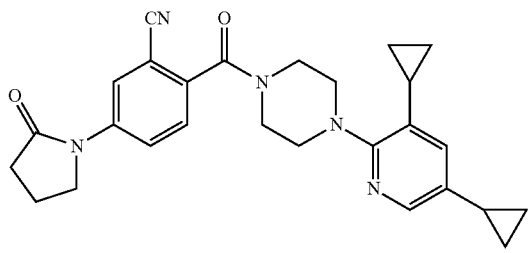 [SMILES: N#Cc1cc(N2CCCC2=O)ccc1C(=O)N1CCN(c2ncc(C3CC3)cc2C2CC2)CC1]

Using 5-bromo-2-[4-(3,5-dicyclopropylpyridin-2-yl)piperazine-1-carbonyl]benzonitrile (451 mg) described in Preparation Example 245 and pyrrolidin-2-one (115 µL) and by the reaction and treatment in the same manner as in Example 262, the title compound (440 mg) was obtained.
MS (ESI) m/z: 456(M+H)$^+$.

Example 709

Synthesis of 2-[4-(3,5-dicyclopropylpyridin-2-yl) piperazine-1-carbonyl]-5-(1,1-dioxo-1$\lambda^6$-isothiazolidin-2-yl)benzonitrile

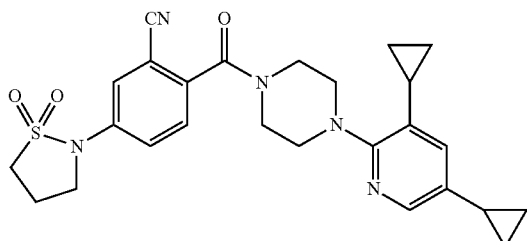

Using 5-bromo-2-[4-(3,5-dicyclopropylpyridin-2-yl)piperazine-1-carbonyl]benzonitrile (451 mg) described in Preparation Example 245 and isothiazolidine 1,1-dioxide (158 mg) and by the reaction and treatment in the same manner as in Example 262, the title compound (443 mg) was obtained.
MS (ESI) m/z: 492(M+H)$^+$.

Example 710

Synthesis of 2-[4-(3,5-dicyclopropylpyridin-2-yl) piperazine-1-carbonyl]-5-(1,1-dioxo-1$\lambda^6$-[1,2]thiazinan-2-yl)benzonitrile

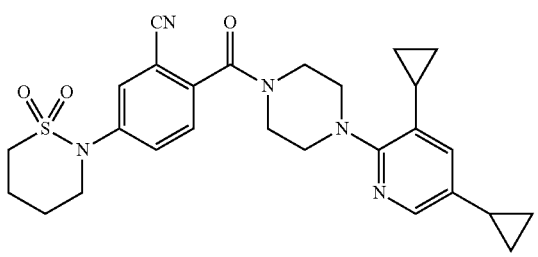 [SMILES: N#Cc1cc(N2CCCCS2(=O)=O)ccc1C(=O)N1CCN(c2ncc(C3CC3)cc2C2CC2)CC1]

Using 5-bromo-2-[4-(3,5-dicyclopropylpyridin-2-yl)piperazine-1-carbonyl]benzonitrile (451 mg) described in Preparation Example 245 and [1,2]thiazinane 1,1-dioxide (176 mg) and by the reaction and treatment in the same manner as in Example 262, the title compound (438 mg) was obtained.
MS (ESI) m/z: 506(M+H)$^+$.

Example 711

Synthesis of 1-{4-[4-(3,5-dicyclopropylpyridin-2-yl) piperazine-1-carbonyl]phenyl}-3-methylimidazolidin-2-one

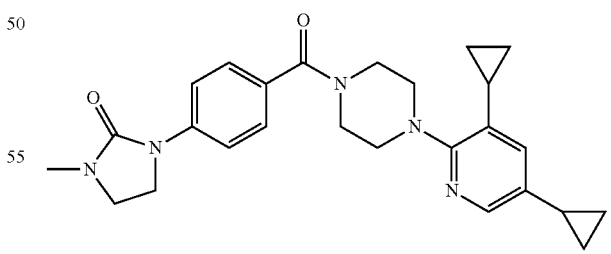

Using [4-(3,5-dicyclopropylpyridin-2-yl)piperazin-1-yl](4-iodophenyl)methanone (473 mg) described in Preparation Example 186 and 1-methylimidazolidin-2-one (120 mg) and by the reaction and treatment in the same manner as in Example 1, the title compound (336 mg) was obtained.
MS (ESI) m/z: 446(M+H)$^+$.

Example 712

Synthesis of 1-acetyl-3-{4-[4-(3,5-dicyclopropylpyridin-2-yl)piperazine-1-carbonyl]phenyl}imidazolidin-2-one

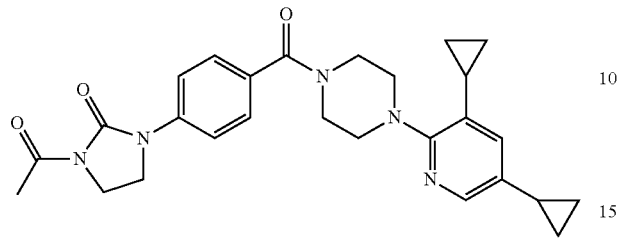

Using [4-(3,5-dicyclopropylpyridin-2-yl)piperazin-1-yl](4-iodophenyl)methanone (1.34 g) described in Preparation Example 186 and 1-acetylimidazolidin-2-one (461 mg) and by the reaction and treatment in the same manner as in Example 1, the title compound (1.14 g) was obtained.
MS (ESI) m/z: 474(M+H)$^+$.

Example 713

Synthesis of 1-{4-[4-(3,5-dicyclopropylpyridin-2-yl)piperazine-1-carbonyl]phenyl}imidazolidin-2-one

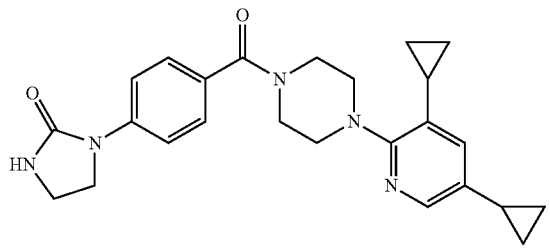

Using 1-acetyl-3-{4-[4-(3,5-dicyclopropylpyridin-2-yl)piperazine-1-carbonyl]phenyl}imidazolidin-2-one (908 mg) described in Example 712 and by the reaction and treatment in the same manner as in Example 391, the title compound (813 mg) was obtained.
MS (ESI) m/z: 432(M+H)$^+$.

Example 714

Synthesis of [4-(3,5-dicyclopropylpyridin-2-yl)piperazin-1-yl][4-(1,1-dioxo-1λ$^6$-[1,2]thiazinan-2-yl)phenyl]methanone

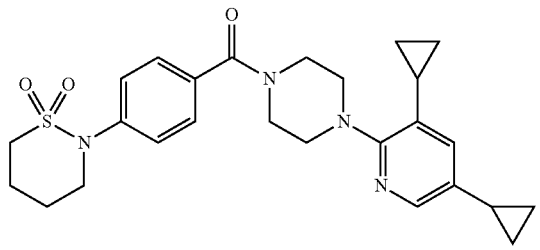 [SMILES: O=C(c1ccc(N2CCCCS2(=O)=O)cc1)N1CCN(c2ncc(C3CC3)cc2C2CC2)CC1]

Using [4-(3,5-dicyclopropylpyridin-2-yl)piperazin-1-yl](4-iodophenyl)methanone (446 mg) described in Preparation Example 186 and [1,2]thiazinane 1,1-dioxide (176 mg) and by the reaction and treatment in the same manner as in Example 262, the title compound (328 mg) was obtained.
MS (ESI) m/z: 481(M+H)$^+$.

Example 715

Synthesis of 1-{4-[4-(3,5-dimethylpyridin-2-yl)piperazine-1-carbonyl]-3-methanesulfonylphenyl}-3-methylimidazolidin-2-one

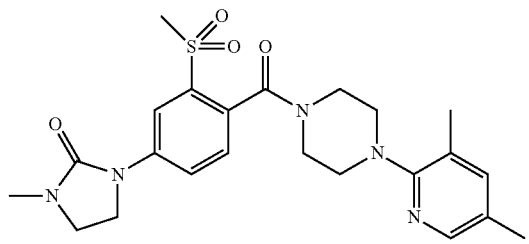

Using (4-bromo-2-methanesulfonylphenyl)[4-(3,5-dimethylpyridin-2-yl)piperazin-1-yl]methanone (452 mg) described in Preparation Example 112 and 1-methylimidazolidin-2-one (120 mg) and by the reaction and treatment in the same manner as in Example 1, the title compound (370 mg) was obtained.
MS (ESI) m/z: 472(M+H)$^+$.

Example 716

Synthesis of 1-acetyl-3-{4-[4-(3,5-dimethylpyridin-2-yl)piperazine-1-carbonyl]-3-methanesulfonylphenyl}imidazolidin-2-one

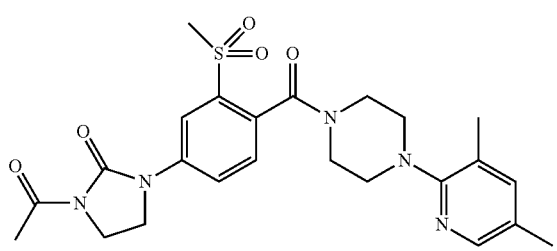 [SMILES: CC(=O)N1CCN(c2ccc(C(=O)N3CCN(c4ncc(C)cc4C)CC3)c(S(C)(=O)=O)c2)C1=O]

Using (4-bromo-2-methanesulfonylphenyl)[4-(3,5-dimethylpyridin-2-yl)piperazin-1-yl]methanone (1.36 g) described in Preparation Example 112 and 1-acetylimidazolidin-2-one (461 mg) and by the reaction and treatment in the same manner as in Example 1, the title compound (1.20 g) was obtained.
MS (ESI) m/z: 500(M+H)$^+$.

Example 717

Synthesis of 1-{4-[4-(3,5-dimethylpyridin-2-yl)piperazine-1-carbonyl]-3-methanesulfonylphenyl}imidazolidin-2-one

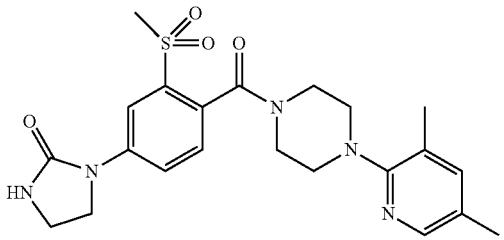 [SMILES: Cc1cnc(N2CCN(C(=O)c3ccc(N4CCNC4=O)cc3S(C)(=O)=O)CC2)c(C)c1]

Using 1-acetyl-3-{4-[4-(3,5-dimethylpyridin-2-yl)piperazine-1-carbonyl]-3-methanesulfonylphenyl}imidazolidin-2-one (968 mg) described in Example 716 and by the reaction and treatment in the same manner as in Example 391, the title compound (745 mg) was obtained.
MS (ESI) m/z: 458(M+H)$^+$.

Example 718

Synthesis of [4-(3,5-dimethylpyridin-2-yl)piperazin-1-yl][4-(1,1-dioxo-1$\lambda^6$-[1,2]thiazinan-2-yl)-2-methanesulfonylphenyl]methanone

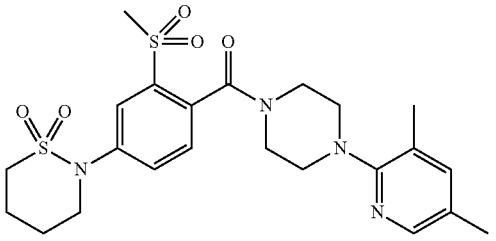 [SMILES: Cc1cnc(N2CCN(C(=O)c3ccc(N4CCCCS4(=O)=O)cc3S(C)(=O)=O)CC2)c(C)c1]

Using (4-bromo-2-methanesulfonylphenyl)[4-(3,5-dimethylpyridin-2-yl)piperazin-1-yl]methanone (452 mg) described in Preparation Example 112 and [1,2]thiazinane 1,1-dioxide (176 mg) and by the reaction and treatment in the same manner as in Example 262, the title compound (359 mg) was obtained.
MS (ESI) m/z: 507(M+H)$^+$.

Example 719

Synthesis of 1-{5-[4-(5-ethyl-3-methylpyridin-2-yl)piperazine-1-carbonyl]pyridin-2-yl}-3-methylimidazolidin-2-one

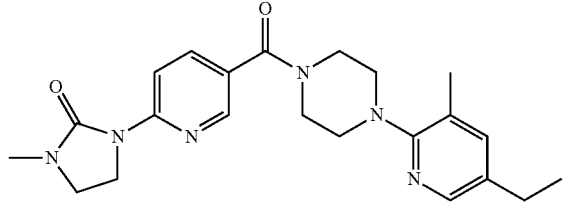 [SMILES: CCc1cnc(N2CCN(C(=O)c3ccc(N4CCN(C)C4=O)nc3)CC2)c(C)c1]

Using (6-bromopyridin-3-yl)[4-(5-ethyl-3-methylpyridin-2-yl)piperazin-1-yl]methanone (389 mg) described in Preparation Example 145 and 1-methylimidazolidin-2-one (120 mg) and by the reaction and treatment in the same manner as in Example 1, the title compound (313 mg) was obtained.
MS (ESI) m/z: 409(M+H)$^+$.

Example 720

Synthesis of 1-acetyl-3-{5-[4-(5-ethyl-3-methylpyridin-2-yl)piperazine-1-carbonyl]pyridin-2-yl}imidazolidin-2-one

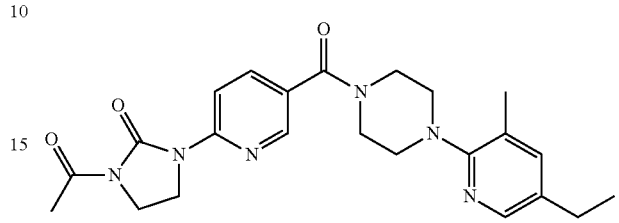

Using (6-bromopyridin-3-yl)[4-(5-ethyl-3-methylpyridin-2-yl)piperazin-1-yl]methanone (1.17 g) described in Preparation Example 145 and 1-acetylimidazolidin-2-one (461 mg) and by the reaction and treatment in the same manner as in Example 1, the title compound (834 mg) was obtained.
MS (ESI) m/z: 437(M+H)$^+$.

Example 721

Synthesis of [6-(1,1-dioxo-1$\lambda^6$-[1,2]thiazinan-2-yl)pyridin-3-yl][4-(5-ethyl-3-methylpyridin-2-yl)piperazin-1-yl]methanone

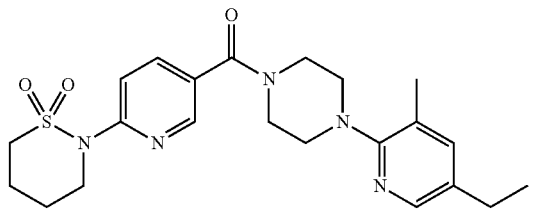 [SMILES: CCc1cnc(N2CCN(C(=O)c3ccc(N4CCCCS4(=O)=O)nc3)CC2)c(C)c1]

Using (6-bromopyridin-3-yl)[4-(5-ethyl-3-methylpyridin-2-yl)piperazin-1-yl]methanone (389 mg) described in Preparation Example 145 and [1,2]thiazinane 1,1-dioxide (176 mg) and by the reaction and treatment in the same manner as in Example 20262, the title compound (353 mg) was obtained.
MS (ESI) m/z: 444(M+H)$^+$.

Example 722

Synthesis of 5-(2-oxoimidazolidin-1-yl)-2-[4-(3,5,6-trimethylpyridin-2-yl)piperazine-1-carbonyl]benzamide

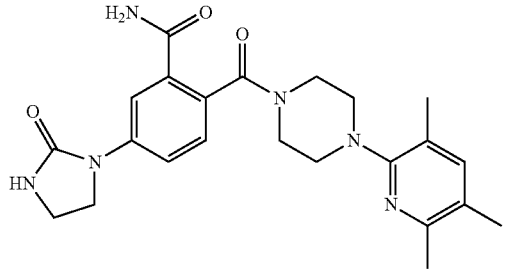 [SMILES: Cc1cc(C)c(N2CCN(C(=O)c3ccc(N4CCNC4=O)cc3C(N)=O)CC2)nc1C]

5-(2-Oxoimidazolidin-1-yl)-2-[4-(3,5,6-trimethylpyridin-2-yl)piperazine-1-carbonyl]benzonitrile (418 mg) described in Example 445 was added to a solution of trifluoroacetic acid (1.12 mL) and concentrated sulfuric acid (0.28 mL) under cooling, and the mixture was stirred at 10° C. for 1 hr. Then, the reaction mixture was added to water under ice-cooling, neutralized with 4N aqueous sodium hydroxide solution and the to mixture was stirred for 1 hr. The obtained precipitate was collected by filtration to give the title compound (363 mg).

MS (ESI) m/z: 437(M+H)$^+$.

Example 723

Synthesis of 1-{5-[4-(5-ethyl-3-methylpyridin-2-yl)piperazine-1-carbonyl]pyridin-2-yl}imidazolidin-2-one

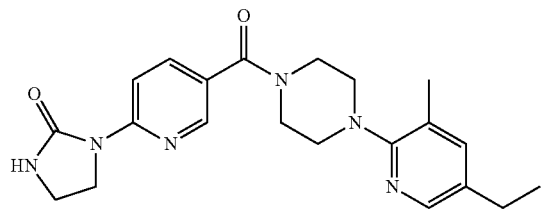 [SMILES: CCc1cnc(N2CCN(C(=O)c3ccc(N4CCNC4=O)nc3)CC2)c(C)c1]

Using 1-acetyl-3-{5-[4-(5-ethyl-3-methylpyridin-2-yl)piperazine-1-carbonyl]pyridin-2-yl}imidazolidin-2-one (622 mg) described in Example 720 and by the reaction and treatment in the same manner as in Example 391, the title compound (486 mg) was obtained.

MS (ESI) m/z: 395(M+H)$^+$.

Example 724

Synthesis of 2-[4-(5-cyclopropyl-3-methylpyridin-2-yl)piperazine-1-carbonyl]-5-(2-oxopyrrolidin-1-yl)benzamide

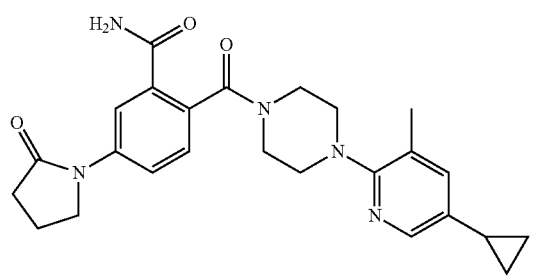 [SMILES: Cc1cc(C2CC2)cnc1N1CCN(C(=O)c2ccc(N3CCCC3=O)cc2C(N)=O)CC1]

Using 2-[4-(5-cyclopropyl-3-methylpyridin-2-yl)piperazine-1-carbonyl]-5-(2-oxopyrrolidin-1-yl)benzonitrile (430 mg) described in Example 384 and by the reaction and treatment in the same manner as in Example 722, the title compound (322 mg) was obtained.

MS (ESI) m/z: 448(M+H)$^+$.

Example 725

Synthesis of 2-[4-(3,5-dimethylpyridin-2-yl)piperazine-1-carbonyl]-5-(3-methyl-2-oxoimidazolidin-1-yl)benzamide

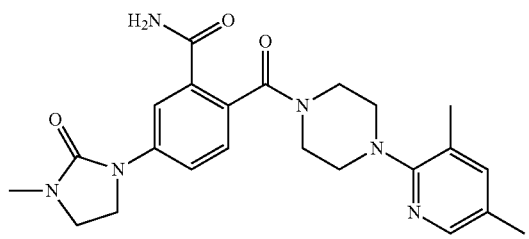

Using 2-[4-(3,5-dimethylpyridin-2-yl)piperazine-1-carbonyl]-5-(3-methyl-2-oxoimidazolidin-1-yl)benzonitrile (270 mg) described in Example 436 and by the reaction and treatment in the same manner as in Example 722, the title compound (228 mg) was obtained.

MS (ESI) m/z: 437(M+H)$^+$.

Example 726

Synthesis of 1-{5-[4-(3,5-dimethylpyridin-2-yl)piperazine-1-carbonyl]-6-methylpyridin-2-yl}-3-methylimidazolidin-2-one

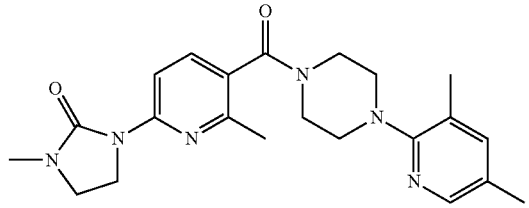

Using (6-bromo-2-methylpyridin-3-yl)[4-(3,5-dimethylpyridin-2-yl)piperazin-1-yl]methanone (234 mg) described in Preparation Example 247 and 1-methylimidazolidin-2-one (72 mg) and by the reaction and treatment in the same manner as in Example 1, the title compound (190 mg) was obtained.

MS (ESI) m/z: 409(M+H)$^+$.

Example 727

Synthesis of 1-acetyl-3-{5-[4-(3,5-dimethylpyridin-2-yl)piperazine-1-carbonyl]-6-methylpyridin-2-yl}imidazolidin-2-one

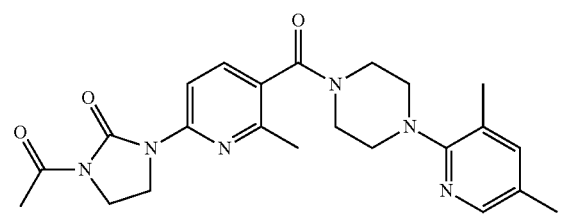 [SMILES: CC(=O)N1CCN(c2ccc(C(=O)N3CCN(c4ncc(C)cc4C)CC3)c(C)n2)C1=O]

Using (6-bromo-2-methylpyridin-3-yl)[4-(3,5-dimethylpyridin-2-yl)piperazin-1-yl]methanone (655 mg) described in Preparation Example 247 and 1-acetylimidazolidin-2-one (259 mg) and by the reaction and treatment in the same manner as in Example 1, the title compound (642 mg) was obtained.

MS (ESI) m/z: 437(M+H)$^+$.

Example 728

Synthesis of 1-{4-[4-(5-ethyl-3-methylpyridin-2-yl)piperazine-1-carbonyl]phenyl}-3-methylimidazolidin-2-one

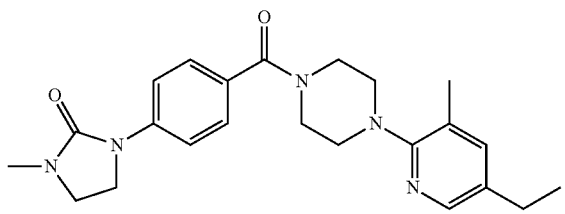 [SMILES: CCc1cnc(N2CCN(C(=O)c3ccc(N4CCN(C)C4=O)cc3)CC2)c(C)c1]

Using [4-(5-ethyl-3-methylpyridin-2-yl)piperazin-1-yl](4-iodophenyl)methanone (348 mg) described in Preparation Example 133 and 1-methylimidazolidin-2-one (96 mg) and by the reaction and treatment in the same manner as in Example 1, the title compound (278 mg) was obtained.

MS (ESI) m/z: 408(M+H)$^+$.

Example 729

Synthesis of 1-{5-[4-(3,5-dimethylpyridin-2-yl)piperazine-1-carbonyl]-6-methylpyridin-2-yl}imidazolidin-2-one

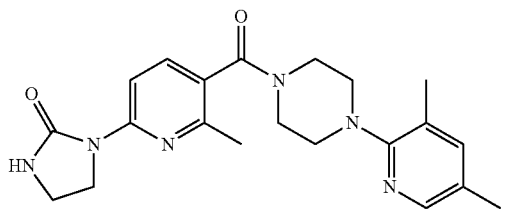

Using 1-acetyl-3-{5-[4-(3,5-dimethylpyridin-2-yl)piperazine-1-carbonyl]-6-methylpyridin-2-yl}imidazolidin-2-one (430 mg) described in Example 727 and by the reaction and treatment in the same manner as in Example 391, the title compound (385 mg) was obtained.

MS (ESI) m/z: 395(M+H)$^+$.

Example 730

Synthesis of 1-acetyl-3-{4-[4-(5-ethyl-3-methylpyridin-2-yl)piperazine-1-carbonyl]phenyl}imidazolidin-2-one

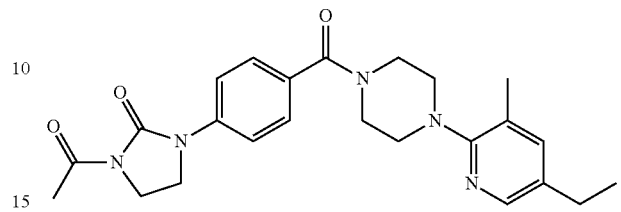

Using [4-(5-ethyl-3-methylpyridin-2-yl)piperazin-1-yl](4-iodophenyl)methanone (1.09 g) described in Preparation Example 133 and 1-acetylimidazolidin-2-one (384 mg) and by the reaction and treatment in the same manner as in Example 1, the title compound (1.00 g) was obtained.

MS (ESI) m/z: 436(M+H)$^+$.

Example 731

Synthesis of [4-(1,1-dioxo-1$\lambda^6$-isothiazolidin-2-yl)phenyl][4-(5-ethyl-3-methylpyridin-2-yl)piperazin-1-yl]methanone

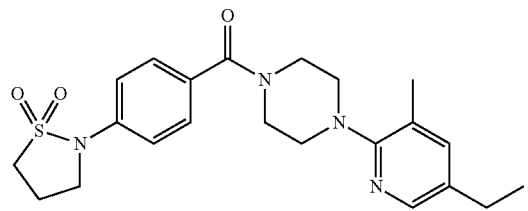 [SMILES: CCc1cnc(N2CCN(C(=O)c3ccc(N4CCCS4(=O)=O)cc3)CC2)c(C)c1]

Using [4-(5-ethyl-3-methylpyridin-2-yl)piperazin-1-yl](4-iodophenyl)methanone (435 mg) described in Preparation Example 133 and isothiazolidine 1,1-dioxide (158 mg) and by the reaction and treatment in the same manner as in Example 262, the title compound (310 mg) was obtained.

MS (ESI) m/z: 429(M+H)$^+$.

Example 732

Synthesis of 1-{4-[4-(5-ethyl-3-methylpyridin-2-yl)piperazine-1-carbonyl]phenyl}imidazolidin-2-one

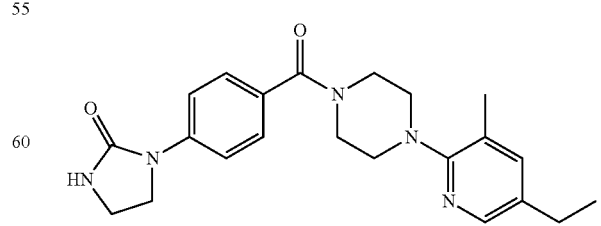

Using 1-acetyl-3-{4-[4-(5-ethyl-3-methylpyridin-2-yl)piperazine-1-carbonyl]phenyl}imidazolidin-2-one (753 mg)

451 described in Example 730 and by the reaction and treatment in the same manner as in Example 391, the title compound (686 mg) was obtained.

MS (ESI) m/z: 394(M+H)$^+$.

Example 733

Synthesis of 1-{4-[4-(5-ethyl-3-methylpyridin-2-yl)piperazine-1-carbonyl]phenyl}pyrrolidin-2-one

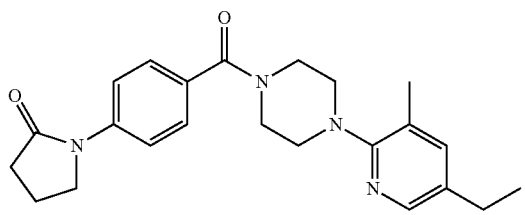

Using [4-(5-ethyl-3-methylpyridin-2-yl)piperazin-1-yl](4-iodophenyl)methanone (435 mg) described in Preparation Example 133 and pyrrolidin-2-one (115 μL) and by the reaction and treatment in the same manner as in Example 262, the title compound (234 mg) was obtained.

MS (ESI) m/z: 393(M+H)$^+$.

Example 734

Synthesis of [4-(1,1-dioxo-1λ$^6$-[1,2]thiazinan-2-yl)phenyl][4-(5-ethyl-3-methylpyridin-2-yl)piperazin-1-yl]methanone

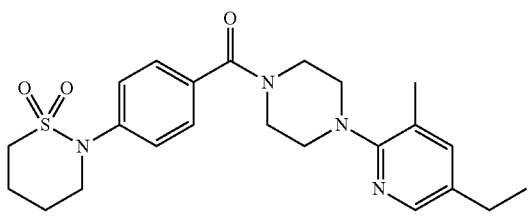 [SMILES: CCc1cnc(N2CCN(C(=O)c3ccc(N4CCCCS4(=O)=O)cc3)CC2)c(C)c1]

Using [4-(5-ethyl-3-methylpyridin-2-yl)piperazin-1-yl](4-iodophenyl)methanone (348 mg) described in Preparation Example 133 and [1,2]thiazinane 1,1-dioxide (141 mg) and by the reaction and treatment in the same manner as in Example 262, the title compound (207 mg) was obtained.

MS (ESI) m/z: 443(M+H)$^+$.

452

Example 735

Synthesis of 2-[4-(5-ethyl-3-methylpyridin-2-yl)piperazine-1-carbonyl]-5-(3-methyl-2-oxoimidazolidin-1-yl)benzonitrile

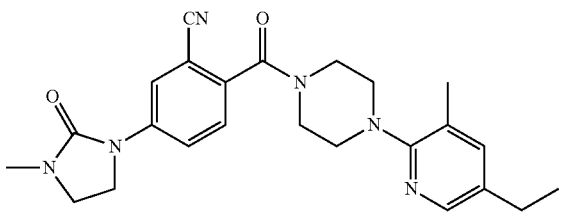 [SMILES: CCc1cnc(N2CCN(C(=O)c3ccc(N4CCN(C)C4=O)cc3C#N)CC2)c(C)c1]

Using 5-bromo-2-[4-(5-ethyl-3-methylpyridin-2-yl)piperazine-1-carbonyl]benzonitrile (827 mg) described in Preparation Example 246 and 1-methylimidazolidin-2-one (240 mg) and by the reaction and treatment in the same manner as in Example 1, the title compound (742 mg) was obtained.

MS (ESI) m/z: 433(M+H)$^+$.

Example 736

Synthesis of 5-(3-acetyl-2-oxoimidazolidin-1-yl)-2-[4-(5-ethyl-3-methylpyridin-2-yl)piperazine-1-carbonyl]benzonitrile

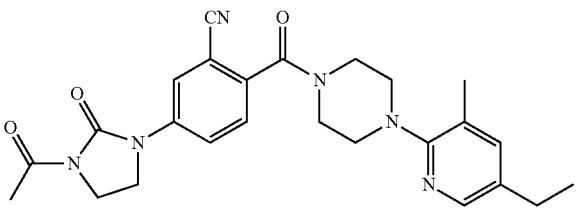 [SMILES: CCc1cnc(N2CCN(C(=O)c3ccc(N4CCN(C(C)=O)C4=O)cc3C#N)CC2)c(C)c1]

Using 5-bromo-2-[4-(5-ethyl-3-methylpyridin-2-yl)piperazine-1-carbonyl]benzonitrile (2.48 g) described in Preparation Example 246 and 1-acetylimidazolidin-2-one (923 mg) and by the reaction and treatment in the same manner as in Example 1, the title compound (1.79 g) was obtained.

MS (ESI) m/z: 461(M+H)$^+$.

Example 737

Synthesis of 1-{4-[4-(3,5-dimethylpyridin-2-yl)piperazine-1-carbonyl]-3-methoxyphenyl}-3-methylimidazolidin-2-one

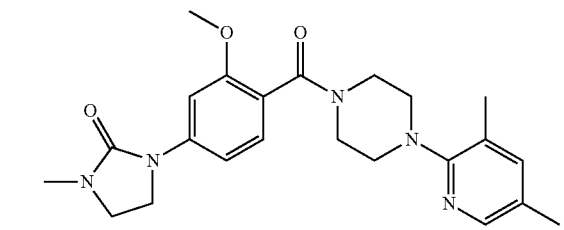

Using (4-bromo-2-methoxyphenyl)[4-(3,5-dimethylpyridin-2-yl)piperazin-1-yl]methanone (404 mg) described in Preparation Example 252 and 1-methylimidazolidin-2-one (120 mg) and by the reaction and treatment in the same manner as in Example 1, the title compound (347 mg) was obtained.

MS (ESI) m/z: 424(M+H)+.

Example 738

Synthesis of 2-[4-(5-ethyl-3-methylpyridin-2-yl)piperazine-1-carbonyl]-5-(2-oxoimidazolidin-1-yl)benzonitrile

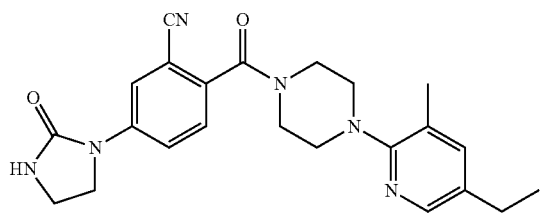 [SMILES: CCc1cnc(N2CCN(C(=O)c3ccc(N4CCNC4=O)cc3C#N)CC2)c(C)c1]

Using 5-(3-acetyl-2-oxoimidazolidin-1-yl)-2-[4-(5-ethyl-3-methylpyridin-2-yl)piperazine-1-carbonyl]benzonitrile (726 mg) described in Example 736 and by the reaction and treatment in the same manner as in Example 391, the title compound (616 mg) was obtained.

MS (ESI) m/z: 419(M+H)+.

Example 739

Synthesis of 1-acetyl-3-{4-[4-(3,5-dimethylpyridin-2-yl)piperazine-1-carbonyl]-3-methoxyphenyl}imidazolidin-2-one

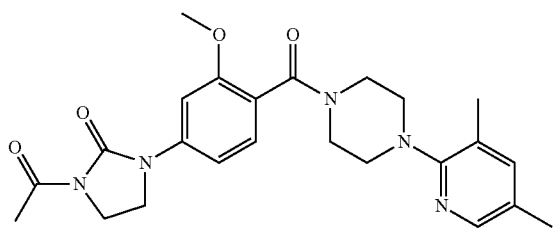 [SMILES: COc1cc(N2CCN(C(C)=O)C2=O)ccc1C(=O)N1CCN(c2ncc(C)cc2C)CC1]

Using (4-bromo-2-methoxyphenyl)[4-(3,5-dimethylpyridin-2-yl)piperazin-1-yl]methanone (1.01 g) described in Preparation Example 252 and 1-acetylimidazolidin-2-one (0.38 g) and by the reaction and treatment in the same manner as in Example 1, the title compound (0.66 g) was obtained.

MS (ESI) m/z: 452(M+H)+.

Example 740

Synthesis of 1-{4-[4-(3,5-dimethylpyridin-2-yl)piperazine-1-carbonyl]-3-methoxyphenyl}imidazolidin-2-one

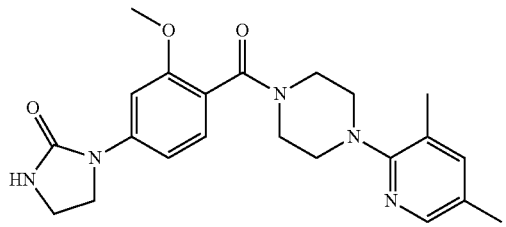 [SMILES: COc1cc(N2CCNC2=O)ccc1C(=O)N1CCN(c2ncc(C)cc2C)CC1]

Using 1-acetyl-3-{4-[4-(3,5-dimethylpyridin-2-yl)piperazine-1-carbonyl]-3-methoxyphenyl}imidazolidin-2-one (450 mg) described in Example 739 and by the reaction and treatment in the same manner as in Example 391, the title compound (405 mg) was obtained.

MS (ESI) m/z: 410(M+H)+.

Example 741

Synthesis of 5-(3-acetyl-2-oxoimidazolidin-1-yl)-2-[4-(5-ethyl-3-methylpyridin-2-yl)piperazine-1-carbonyl]benzamide

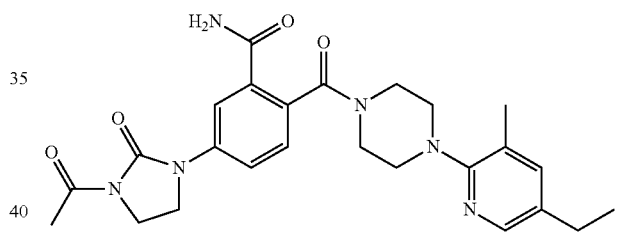

Using 5-(3-acetyl-2-oxoimidazolidin-1-yl)-2-[4-(5-ethyl-3-methylpyridin-2-yl)piperazine-1-carbonyl]benzonitrile (691 mg) described in Example 736 and by the reaction and treatment in the same manner as in Example 722, the title compound (566 mg) was obtained.

MS (ESI) m/z: 479(M+H)+.

Example 742

Synthesis of 2-[4-(5-ethyl-3-methylpyridin-2-yl)piperazine-1-carbonyl]-5-(3-methyl-2-oxoimidazolidin-1-yl)benzamide

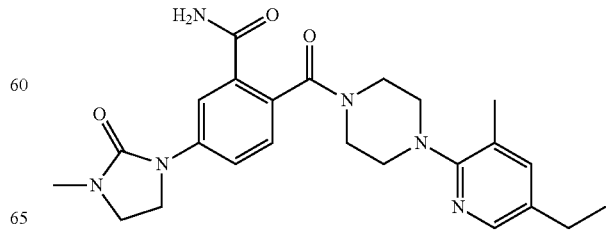

Using 2-[4-(5-ethyl-3-methylpyridin-2-yl)piperazine-1-carbonyl]-5-(3-methyl-2-oxoimidazolidin-1-yl)benzonitrile (530 mg) described in Example 735 and by the reaction and treatment in the same manner as in Example 722, the title compound (419 mg) was obtained.

MS (ESI) m/z: 451(M+H)+.

Example 743

Synthesis of [4-(3,5-dimethylpyridin-2-yl)piperazin-1-yl][4-(1,1-dioxo-1λ6-[1,2]thiazinan-2-yl)-2-methoxyphenyl]methanone

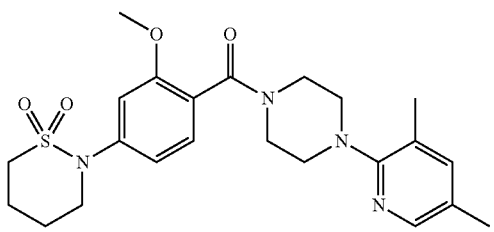 [SMILES: COc1cc(N2CCCCS2(=O)=O)ccc1C(=O)N1CCN(c2ncc(C)cc2C)CC1]

Using (4-bromo-2-methoxyphenyl)[4-(3,5-dimethylpyridin-2-yl)piperazin-1-yl]methanone (404 mg) described in Preparation Example 252 and [1,2]thiazinane 1,1-dioxide (176 mg) and by the reaction and treatment in the same manner as in Example 262, the title compound (340 mg) was obtained.

MS (ESI) m/z: 459(M+H)+.

Example 744

Synthesis of 2-[4-(5-ethyl-3-methylpyridin-2-yl)piperazine-1-carbonyl]-5-(2-oxoimidazolidin-1-yl)benzamide

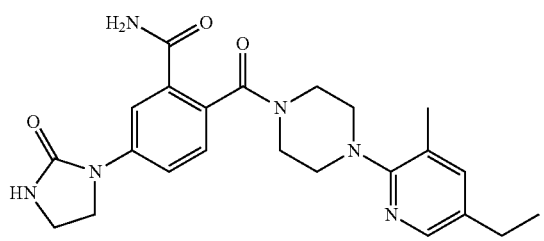 [SMILES: CCc1cnc(N2CCN(C(=O)c3ccc(N4CCNC4=O)cc3C(N)=O)CC2)c(C)c1]

Using 2-[4-(5-ethyl-3-methylpyridin-2-yl)piperazine-1-carbonyl]-5-(2-oxoimidazolidin-1-yl)benzonitrile (611 mg) described in Example 738 and by the reaction and treatment in the same manner as in Example 722, the title compound (313 mg) was obtained.

MS (ESI) m/z: 437(M+H)+.

Example 745

Synthesis of 5-(1,1-dioxo-1λ6-isothiazolidin-2-yl)-2-[4-(5-ethyl-3-methylpyridin-2-yl)piperazine-1-carbonyl]benzonitrile

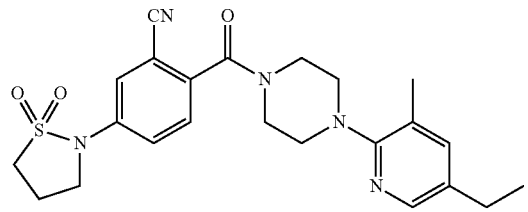 [SMILES: CCc1cnc(N2CCN(C(=O)c3ccc(N4CCCS4(=O)=O)cc3C#N)CC2)c(C)c1]

Using 5-bromo-2-[4-(5-ethyl-3-methylpyridin-2-yl)piperazine-1-carbonyl]benzonitrile (1.24 g) described in Preparation Example 246 and isothiazolidine 1,1-dioxide (0.47 g) and by the reaction and treatment in the same manner as in Example 262, the title compound (1.26 g) was obtained.

MS (ESI) m/z: 454(M+H)+.

Example 746

Synthesis of 2-[4-(5-ethyl-3-methylpyridin-2-yl)piperazine-1-carbonyl]-5-(2-oxopyrrolidin-1-yl)benzonitrile

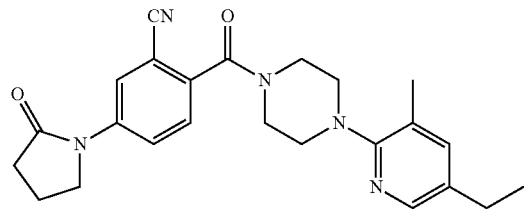 [SMILES: CCc1cnc(N2CCN(C(=O)c3ccc(N4CCCC4=O)cc3C#N)CC2)c(C)c1]

Using 5-bromo-2-[4-(5-ethyl-3-methylpyridin-2-yl)piperazine-1-carbonyl]benzonitrile (827 mg) described in Preparation Example 246 and pyrrolidin-2-one (230 μL) and by the reaction and treatment in the same manner as in Example 262, the title compound (817 mg) was obtained.

MS (ESI) m/z: 418(M+H)+.

Example 747

Synthesis of 5-(1,1-dioxo-1λ6-isothiazolidin-2-yl)-2-[4-(5-ethyl-3-methylpyridin-2-yl)piperazine-1-carbonyl]benzamide

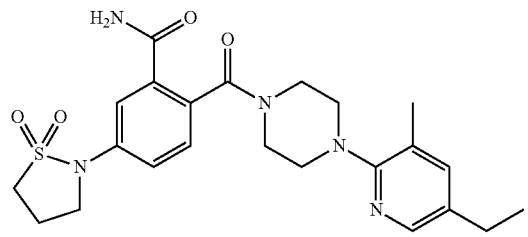 [SMILES: CCc1cnc(N2CCN(C(=O)c3ccc(N4CCCS4(=O)=O)cc3C(N)=O)CC2)c(C)c1]

Using 5-(1,1-dioxo-1λ$^6$-isothiazolidin-2-yl)-2-[4-(5-ethyl-3-methylpyridin-2-yl)piperazine-1-carbonyl]benzonitrile (500 mg) described in Example 745 and by the reaction and treatment in the same manner as in Example 722, the title compound (491 mg) was obtained.

MS (ESI) m/z: 472(M+H)$^+$.

Example 748

Synthesis of 2-[4-(5-ethyl-3-methylpyridin-2-yl)piperazine-1-carbonyl]-5-(2-oxopyrrolidin-1-yl)benzamide

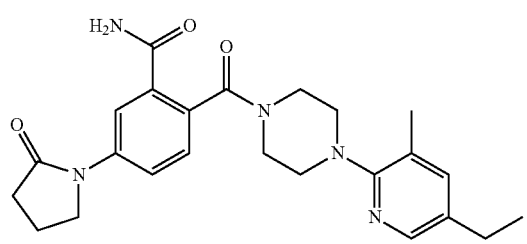 [SMILES: CCc1cnc(N2CCN(C(=O)c3ccc(N4CCCC4=O)cc3C(N)=O)CC2)c(C)c1]

Using 2-[4-(5-ethyl-3-methylpyridin-2-yl)piperazine-1-carbonyl]-5-(2-oxopyrrolidin-1-yl)benzonitrile (545 mg) described in Example 746 and by the reaction and treatment in the same manner as in Example 722, the title compound (529 mg) was obtained.

MS (ESI) m/z: 436(M+H)$^+$.

Example 749

Synthesis of 5-(1,1-dioxo-1λ$^6$-[1,2]thiazinan-2-yl)-2-[4-(5-ethyl-3-methylpyridin-2-yl)piperazine-1-carbonyl]benzonitrile

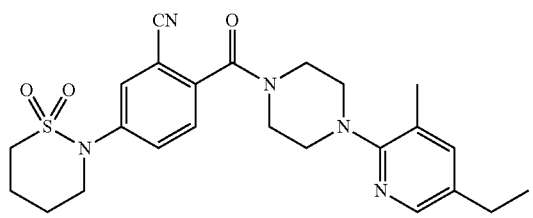 [SMILES: CCc1cnc(N2CCN(C(=O)c3ccc(N4CCCCS4(=O)=O)cc3C#N)CC2)c(C)c1]

Using 5-bromo-2-[4-(5-ethyl-3-methylpyridin-2-yl)piperazine-1-carbonyl]benzonitrile (827 mg) described in Preparation Example 246 and [1,2]thiazinane 1,1-dioxide (351 mg) and by the reaction and treatment in the same manner as in Example 262, the title compound (810 mg) was obtained.

MS (ESI) m/z: 468(M+H)$^+$.

Example 750

Synthesis of 5-(1,1-dioxo-1λ$^6$-[1,2]thiazinan-2-yl)-2-[4-(5-ethyl-3-methylpyridin-2-yl)piperazine-1-carbonyl]benzamide

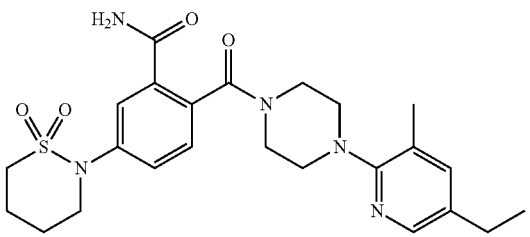 [SMILES: CCc1cnc(N2CCN(C(=O)c3ccc(N4CCCCS4(=O)=O)cc3C(N)=O)CC2)c(C)c1]

Using 5-(1,1-dioxo-1λ$^6$-[1,2]thiazinan-2-yl)-2-[4-(5-ethyl-3-methylpyridin-2-yl)piperazine-1-carbonyl]benzonitrile (538 mg) described in Example 749 and by the reaction and treatment in the same manner as in Example 722, the title compound (349 mg) was obtained.

MS (ESI) m/z: 486(M+H)$^+$.

Example 751

Synthesis of 2-[4-(3,5-dimethylpyridin-2-yl)piperazine-1-carbonyl]-5-(1,1-dioxo-1λ$^6$-[1,2]thiazinan-2-yl)benzamide

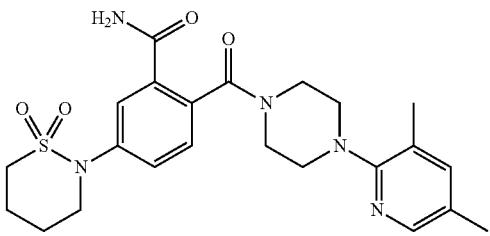 [SMILES: Cc1cnc(N2CCN(C(=O)c3ccc(N4CCCCS4(=O)=O)cc3C(N)=O)CC2)c(C)c1]

Using 2-[4-(3,5-dimethylpyridin-2-yl)piperazine-1-carbonyl]-5-(1,1-dioxo-1λ$^6$-[1,2]thiazinan-2-yl)benzonitrile (329 mg) described in Example 265 and by the reaction and treatment in the same manner as in Example 722, the title compound (338 mg) was obtained.

MS (ESI) m/z: 472(M+H)$^+$.

Example 752

Synthesis of 5-(3-acetyl-2-oxoimidazolidin-1-yl)-2-[4-(3,5-dimethylpyridin-2-yl)piperazine-1-carbonyl]benzamide

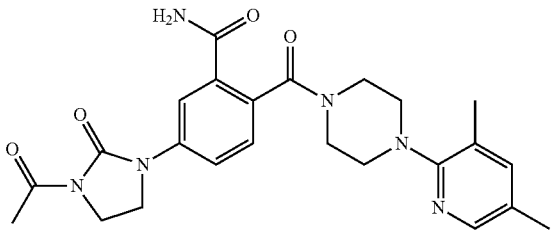 [SMILES: CC(=O)N1CCN(c2ccc(C(=O)N3CCN(c4ncc(C)cc4C)CC3)c(C(N)=O)c2)C1=O]

Using 5-(3-acetyl-2-oxoimidazolidin-1-yl)-2-[4-(3,5-dimethylpyridin-2-yl)piperazine-1-carbonyl]benzonitrile (456 mg) described in Example 433 and by the reaction and treatment in the same manner as in Example 722, the title compound (375 mg) was obtained.

MS (ESI) m/z: 465(M+H)$^+$.

Example 753

Synthesis of 2-[4-(3,5-dimethylpyridin-2-yl)piperazine-1-carbonyl]-5-(2-oxoimidazolidin-1-yl)benzamide

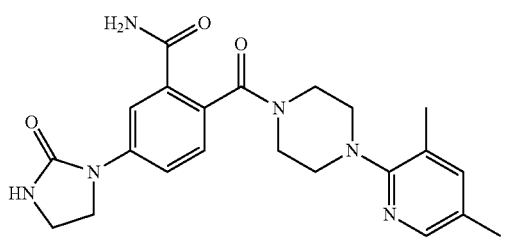 [SMILES: Cc1cnc(N2CCN(C(=O)c3ccc(N4CCNC4=O)cc3C(N)=O)CC2)c(C)c1]

Using 2-[4-(3,5-dimethylpyridin-2-yl)piperazine-1-carbonyl]-5-(2-oxoimidazolidin-1-yl)benzonitrile (452 mg) described in Example 434 and by the reaction and treatment in the same manner as in Example 722, the title compound (429 mg) was obtained.

MS (ESI) m/z: 423(M+H)$^+$.

Example 754

Synthesis of [4-(1,1-dioxo-1$\lambda^6$-isothiazolidin-2-yl)-2-fluorophenyl][4-(5-ethyl-3-methylpyridin-2-yl)piperazin-1-yl]methanone

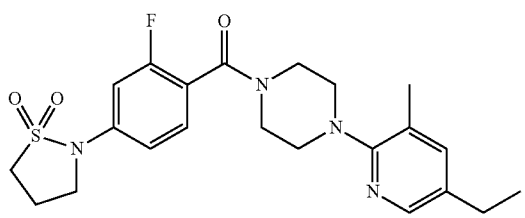

Using (4-bromo-2-fluorophenyl)[4-(5-ethyl-3-methylpyridin-2-yl)piperazin-1-yl]methanone (406 mg) described in Preparation Example 211 and isothiazolidine 1,1-dioxide (158 mg) and by the reaction and treatment in the same manner as in Example 262, the title compound (386 mg) was obtained.

MS (ESI) m/z: 447(M+H)$^+$.

Example 755

Synthesis of 1-{4-[4-(5-ethyl-3-methylpyridin-2-yl)piperazine-1-carbonyl]-3-fluorophenyl}pyrrolidin-2-one

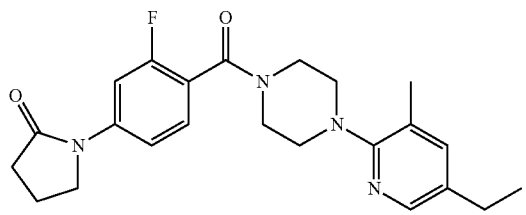

Using (4-bromo-2-fluorophenyl)[4-(5-ethyl-3-methylpyridin-2-yl)piperazin-1-yl]methanone (406 mg) described in Preparation Example 211 and pyrrolidin-2-one (115 μL) and by the reaction and treatment in the same manner as in Example 262, the title compound (350 mg) was obtained.

MS (ESI) m/z: 411(M+H)$^+$.

Example 756

Synthesis of [4-(1,1-dioxo-1$\lambda^6$-[1,2]thiazinan-2-yl)-2-fluorophenyl][4-(5-ethyl-3-methylpyridin-2-yl)piperazin-1-yl]methanone

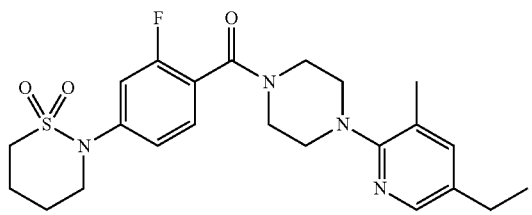 [SMILES: CCc1cnc(N2CCN(C(=O)c3ccc(N4CCCCS4(=O)=O)cc3F)CC2)c(C)c1]

Using (4-bromo-2-fluorophenyl)[4-(5-ethyl-3-methylpyridin-2-yl)piperazin-1-yl]methanone (406 mg) described in Preparation Example 211 and [1,2]thiazinane 1,1-dioxide (176 mg) and by the reaction and treatment in the same manner as in Example 262, the title compound (415 mg) was obtained.

MS (ESI) m/z: 461(M+H)$^+$.

Example 757

Synthesis of [4-(1,1-dioxo-1$\lambda^6$-[1,2]thiazinan-2-yl)-2-methylphenyl][4-(5-ethyl-3-methylpyridin-2-yl)piperazin-1-yl]methanone

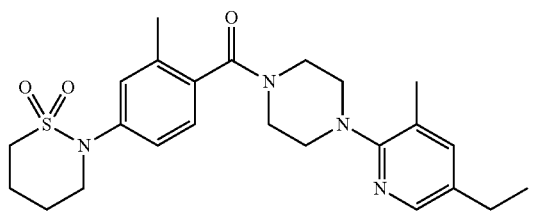 [SMILES: CCc1cnc(N2CCN(C(=O)c3ccc(N4CCCCS4(=O)=O)cc3C)CC2)c(C)c1]

Using (4-bromo-2-methylphenyl)[4-(5-ethyl-3-methylpyridin-2-yl)piperazin-1-yl]methanone (402 mg) described in Preparation Example 253 and [1,2]thiazinane 1,1-dioxide (176 mg) and by the reaction and treatment in the same manner as in Example 262, the title compound (307 mg) was obtained.

MS (ESI) m/z: 457(M+H)$^+$.

Example 758

Synthesis of 1-{4-[4-(5-ethyl-3-methylpyridin-2-yl)piperazine-1-carbonyl]-3-methylphenyl}pyrrolidin-2-one

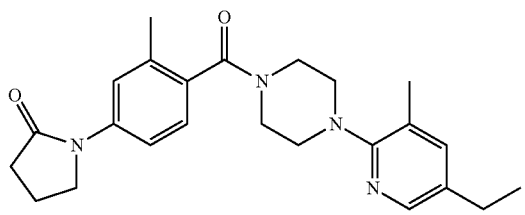 [SMILES: CCc1cnc(N2CCN(C(=O)c3ccc(N4CCCC4=O)cc3C)CC2)c(C)c1]

Using (4-bromo-2-methylphenyl) [4-(5-ethyl-3-methylpyridin-2-yl)piperazin-1-yl]methanone (402 mg) described in Preparation Example 253 and pyrrolidin-2-one (115 μL) and by the reaction and treatment in the same manner as in Example 262, the title compound (356 mg) was obtained.

MS (ESI) m/z: 407(M+H)$^+$.

Example 759

Synthesis of [4-(1,1-dioxo-1$\lambda^6$-isothiazolidin-2-yl)-2-methylphenyl][4-(5-ethyl-3-methylpyridin-2-yl)piperazin-1-yl]methanone

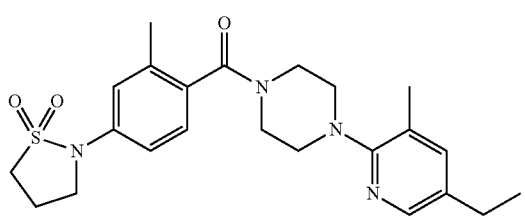 [SMILES: CCc1cnc(N2CCN(C(=O)c3ccc(N4CCCS4(=O)=O)cc3C)CC2)c(C)c1]

Using (4-bromo-2-methylphenyl) [4-(5-ethyl-3-methylpyridin-2-yl)piperazin-1-yl]methanone (402 mg) described in Preparation Example 253 and isothiazolidine 1,1-dioxide (158 mg) and by the reaction and treatment in the same manner as in Example 262, the title compound (304 mg) was obtained.

MS (ESI) m/z: 443(M+H)$^+$.

Example 760

Synthesis of [4-(1,1-dioxo-1$\lambda^6$-isothiazolidin-2-yl)-2-methanesulfonylphenyl][4-(5-ethyl-3-methylpyridin-2-yl)piperazin-1-yl]methanone

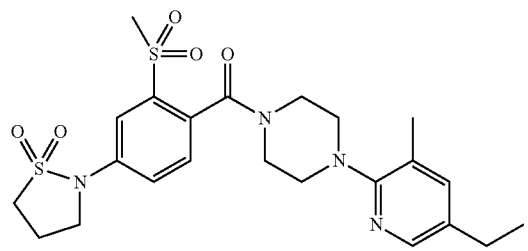 [SMILES: CCc1cnc(N2CCN(C(=O)c3ccc(N4CCCS4(=O)=O)cc3S(C)(=O)=O)CC2)c(C)c1]

Using (4-bromo-2-methanesulfonylphenyl)[4-(5-ethyl-3-methylpyridin-2-yl)piperazin-1-yl]methanone (466 mg) described in Preparation Example 254 and isothiazolidine 1,1-dioxide (158 mg) and by the reaction and treatment in the same manner as in Example 262, the title compound (274 mg) was obtained.

MS (ESI) m/z: 507(M+H)$^+$.

Example 761

Synthesis of 1-{4-[4-(5-ethyl-3-methylpyridin-2-yl)piperazine-1-carbonyl]-3-methanesulfonylphenyl}pyrrolidin-2-one

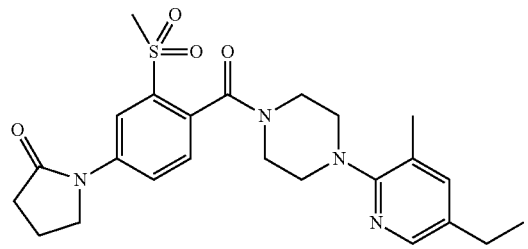 [SMILES: CCc1cnc(N2CCN(C(=O)c3ccc(N4CCCC4=O)cc3S(C)(=O)=O)CC2)c(C)c1]

Using (4-bromo-2-methanesulfonylphenyl)[4-(5-ethyl-3-methylpyridin-2-yl)piperazin-1-yl]methanone (466 mg) described in Preparation Example 254 and pyrrolidin-2-one (115 μL) and by the reaction and treatment in the same manner as in Example 262, the title compound (420 mg) was obtained.

MS (ESI) m/z: 471(M+H)$^+$.

Example 762

Synthesis of 1-{4-[4-(5-ethyl-3-methylpyridin-2-yl)piperazine-1-carbonyl]-3-methanesulfonylphenyl}-3-methylimidazolidin-2-one

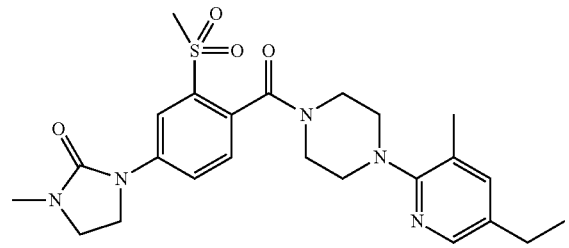 [SMILES: CCc1cnc(N2CCN(C(=O)c3ccc(N4CCN(C)C4=O)cc3S(C)(=O)=O)CC2)c(C)c1]

Using (4-bromo-2-methanesulfonylphenyl)[4-(5-ethyl-3-methylpyridin-2-yl)piperazin-1-yl]methanone (466 mg) described in Preparation Example 254 and 1-methylimidazolidin-2-one (120 mg) and by the reaction and treatment in the same manner as in Example 1, the title compound (412 mg) was obtained.

MS (ESI) m/z: 486(M+H)$^+$.

Example 763

Synthesis of 1-acetyl-3-{4-[4-(5-ethyl-3-methylpyridin-2-yl)piperazine-1-carbonyl]-3-methanesulfonylphenyl}imidazolidin-2-one

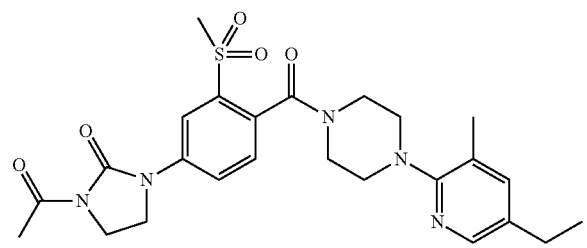 [SMILES: CCc1cnc(N2CCN(C(=O)c3ccc(N4CCN(C(C)=O)C4=O)cc3S(C)(=O)=O)CC2)c(C)c1]

Using (4-bromo-2-methanesulfonylphenyl)[4-(5-ethyl-3-methylpyridin-2-yl)piperazin-1-yl]methanone (1.17 g) described in Preparation Example 254 and 1-acetylimidazolidin-2-one (0.38 g) and by the reaction and treatment in the same manner as in Example 1, the title compound (1.00 g) was obtained.

MS (ESI) m/z: 514(M+H)$^+$.

Example 764

Synthesis of 2-[4-(3,5-dimethylpyridin-2-yl)piperazine-1-carbonyl]-5-(2-oxopyrrolidin-1-yl)benzamide

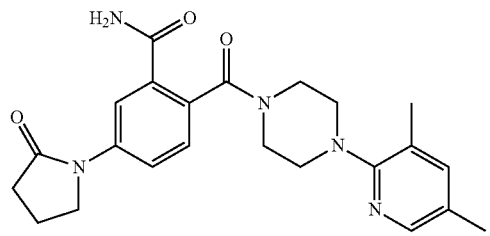 [SMILES: Cc1cnc(N2CCN(C(=O)c3ccc(N4CCCC4=O)cc3C(N)=O)CC2)c(C)c1]

Using 2-[4-(3,5-dimethylpyridin-2-yl)piperazine-1-carbonyl]-5-(2-oxopyrrolidin-1-yl)benzonitrile (2.65 g) described in Example 381 and by the reaction and treatment in the same manner as in Example 722, the title compound (2.97 g) was obtained.

MS (ESI) m/z: 422(M+H)$^+$.

Example 765

Synthesis of 1-{4-[4-(5-ethyl-3-methylpyridin-2-yl)piperazine-1-carbonyl]-3-methanesulfonylphenyl}imidazolidin-2-one

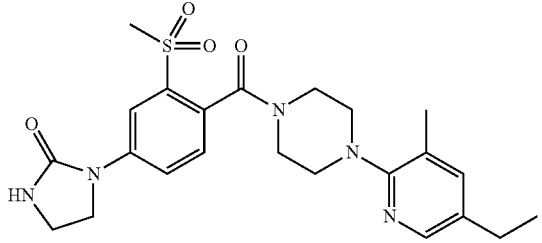 [SMILES: CCc1cnc(N2CCN(C(=O)c3ccc(N4CCNC4=O)cc3S(C)(=O)=O)CC2)c(C)c1]

Using 1-acetyl-3-{4-[4-(5-ethyl-3-methylpyridin-2-yl)piperazine-1-carbonyl]-3-methanesulfonylphenyl}imidazolidin-2-one (786 mg) described in Example 763 and by the reaction and treatment in the same manner as in Example 391, the title compound (689 mg) was obtained.

MS (ESI) m/z: 472(M+H)$^+$.

Example 766

Synthesis of [4-(1,1-dioxo-1$\lambda^6$-[1,2]thiazinan-2-yl)-2-methanesulfonylphenyl][4-(5-ethyl-3-methylpyridin-2-yl)piperazin-1-yl]methanone

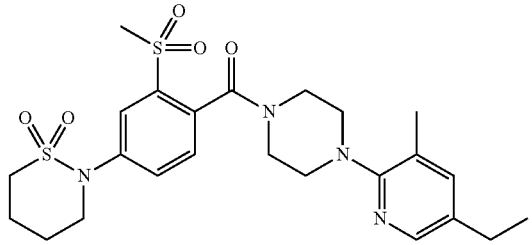 [SMILES: CCc1cnc(N2CCN(C(=O)c3ccc(N4CCCCS4(=O)=O)cc3S(C)(=O)=O)CC2)c(C)c1]

Using (4-bromo-2-methanesulfonylphenyl)[4-(5-ethyl-3-methylpyridin-2-yl)piperazin-1-yl]methanone (271 mg) described in Preparation Example 254 and [1,2]thiazinane 1,1-dioxide (102 mg) and by the reaction and treatment in the same manner as in Example 262, the title compound (247 mg) was obtained.

MS (ESI) m/z: 521(M+H)$^+$.

Example 767

Synthesis of 5-(1,1-dioxo-1$\lambda^6$-isothiazolidin-2-yl)-2-[4-(3,5,6-trimethylpyridin-2-yl)piperazine-1-carbonyl]benzamide

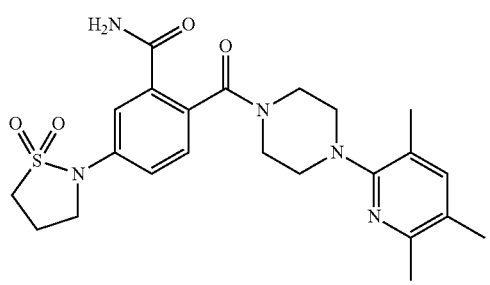 [SMILES: Cc1cc(C)c(N2CCN(C(=O)c3ccc(N4CCCS4(=O)=O)cc3C(N)=O)CC2)nc1C]

Using 5-(1,1-dioxo-1λ$^6$-isothiazolidin-2-yl)-2-[4-(3,5,6-trimethylpyridin-2-yl)piperazine-1-carbonyl]benzonitrile (1.32 g) described in Example 268 and by the reaction and treatment in the same manner as in Example 722, the title compound (488 mg) was obtained.

MS (ESI) m/z: 472(M+H)$^+$.

Example 768

Synthesis of N,N-di-tert-butyloxycarbonyl-5-(1,1-dioxo-1λ$^6$-isothiazolidin-2-yl)-2-[4-(3,5,6-trimethylpyridin-2-yl)piperazine-1-carbonyl]benzamide

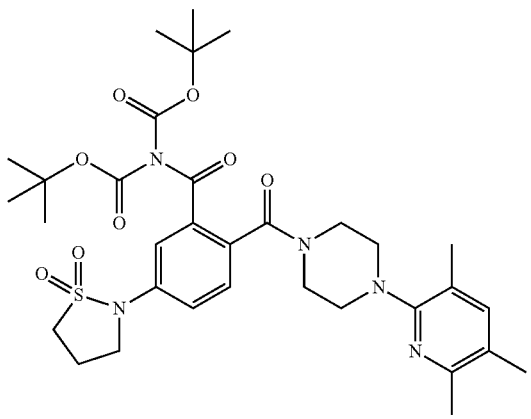 [SMILES: Cc1cc(C)c(N2CCN(C(=O)c3ccc(N4CCCS4(=O)=O)cc3C(=O)N(C(=O)OC(C)(C)C)C(=O)OC(C)(C)C)CC2)nc1C]

5-(1,1-Dioxo-1λ$^6$-isothiazolidin-2-yl)-2-[4-(3,5,6-trimethylpyridin-2-yl)piperazine-1-carbonyl]benzamide (472 mg) described in Example 767 was dissolved in acetonitrile (4.2 mL), di-tert-butyl dicarbonate (458 mg) and 4-dimethylaminopyridine (12 mg) were added, and the mixture was stirred for 10 min with heating under reflux. The solvent was evaporated from the reaction mixture, and the obtained residue was purified by column chromatography (hexane:ethyl acetate) to give the title compound (646 mg).

MS (ESI) m/z: 672(M+H)$^+$.

Example 769

Synthesis of N,N-di-tert-butyloxycarbonyl-2-[4-(3,5-dimethylpyridin-2-yl) piperazine-1-carbonyl]-5-(2-oxopyrrolidin-1-yl) benzamide

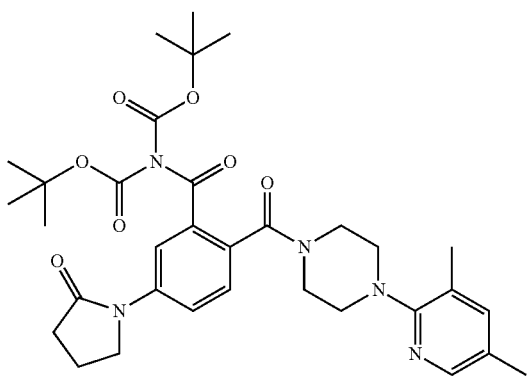 [SMILES: Cc1cnc(N2CCN(C(=O)c3ccc(N4CCCC4=O)cc3C(=O)N(C(=O)OC(C)(C)C)C(=O)OC(C)(C)C)CC2)c(C)c1]

Using 2-[4-(3,5-dimethylpyridin-2-yl)piperazine-1-carbonyl]-5-(2-oxopyrrolidin-1-yl)benzamide (1.92 g) described in Example 764 and di-tert-butyl dicarbonate (4.18 g) and by the reaction and treatment in the same manner as in Example 768, the title compound (2.27 g) was obtained.

MS (ESI) m/z: 622(M+H)$^+$.

Example 770

Synthesis of 5-(1,1-dioxo-1λ$^6$-isothiazolidin-2-yl)-N-methyl-2-[4-(3,5,6-trimethylpyridin-2-yl)piperazine-1-carbonyl]benzamide

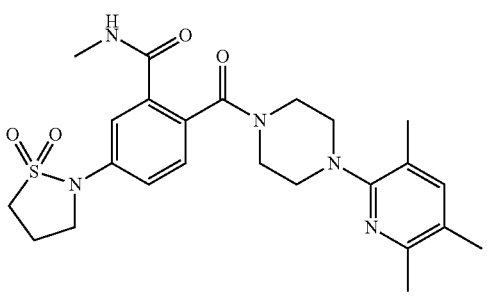 [SMILES: CNC(=O)c1cc(N2CCCS2(=O)=O)ccc1C(=O)N1CCN(c2nc(C)c(C)cc2C)CC1]

N,N-Di-tert-butyloxycarbonyl-5-(1,1-dioxo-1λ$^6$-isothiazolidin-2-yl -2-[4-(3,5,6-trimethylpyridin-2-yl) piperazine-1-carbonyl]benzamide (202 mg) described in Example 768 was dissolved in dichloromethane (1 mL), 2 mol/L methylamine tetrahydrofuran solution (180 μL) was added, and the mixture was stirred at room temperature for 1 hr. The reaction mixture was concentrated under reduced pressure, and the obtained residue was purified by column chromatography (chloroform:methanol) to give the title compound (109 mg).

MS (ESI) m/z: 486(M+H)$^+$.

Example 771

Synthesis of 2-[4-(3,5-dimethylpyridin-2-yl piperazine-1-carbonyl]-N-methyl-5-(2-oxopyrrolidin-1-yl enzamide

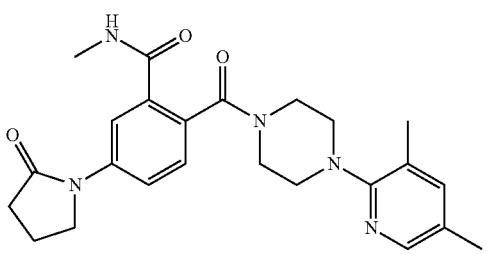 [SMILES: CNC(=O)c1cc(N2CCCC2=O)ccc1C(=O)N1CCN(c2ncc(C)cc2C)CC1]

Using N,N-di-tert-butyloxycarbonyl-2-[4-(3,5-dimethylpyridin-2-yl) piperazine-1-carbonyl]-5-(2-oxopyrrolidin-1-yl) benzamide (187 mg) described in Example 769 and 2 mol/L methylamine tetrahydrofuran solution (180 μL) and by the reaction and treatment in the same manner as in Example 770, the title compound (71 mg) was obtained.

MS (ESI) m/z: 436(M+H)$^+$.

Example 772

Synthesis of 1-{6-methyl-5-[4-(3,5,6-trimethylpyridin-2-yl) piperazine-1-carbonyl]pyridin-2-yl}pyrrolidin-2-one

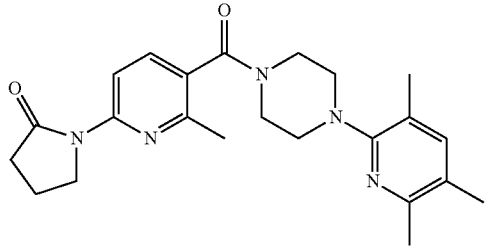 [SMILES: Cc1cc(C)c(N2CCN(C(=O)c3ccc(N4CCCC4=O)nc3C)CC2)nc1C]

Using (6-bromo-2-methylpyridin-3-yl)[4-(3,5,6-trimethylpyridin-2-yl) piperazin-1-yl]methanone (145 mg) described in Preparation Example 248 and pyrrolidin-2-one (41 μL) and by the reaction and treatment in the same manner as in Example 262, the title compound (148 mg) was obtained.
MS (ESI) m/z: 408(M+H)$^+$.

Example 773

Synthesis of 1-{6-methyl-5-[4-(3,5,6-trimethylpyridin-2-yl) piperazine-1-carbonyl]pyridin-2-yl}imidazolidin-2-one

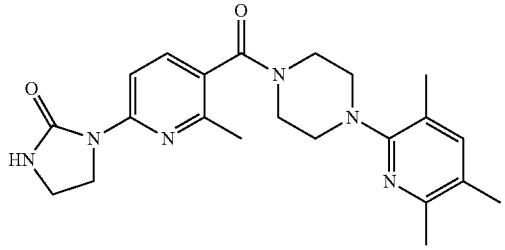 [SMILES: Cc1cc(C)c(N2CCN(C(=O)c3ccc(N4CCNC4=O)nc3C)CC2)nc1C]

Using 1-acetyl-3-{6-methyl-5-[4-(3,5,6-trimethylpyridin-2-yl)piperazine-1-carbonyl]pyridin-2-yl}imidazolidin-2-one (161 mg) described in Example 691 and by the reaction and treatment in the same manner as in Example 391, the title compound (143 mg) was obtained.
MS (ESI) m/z: 409(M+H)$^+$.

Example 774

Synthesis of 2-[4-(3,5-dimethylpyridin-2-yl) piperazine-1-carbonyl]-N,N-dimethyl-5-(2-oxopyrrolidin-1-yl) benzamide

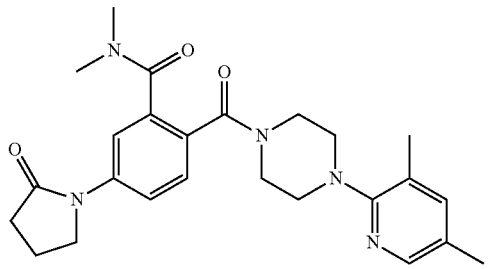

Using N,N-di-tert-butyloxycarbonyl-2-[4-(3,5-dimethylpyridin-2-yl) piperazine-1-carbonyl]-5-(2-oxopyrrolidin-1-yl) benzamide (186 mg) described in Example 769 and 2 mol/L dimethylamine tetrahydrofuran solution (180 μL) and by the reaction and treatment in the same manner as in Example 770, the title compound (60 mg) was obtained.
MS (ESI) m/z: 450(M+H)$^+$.

Example 775

Synthesis of 5-methyl-1-{6-methyl-5-[4-(3,5,6-trimethylpyridin-2-yl)piperazine-1-carbonyl]pyridin-2-yl}pyrrolidin-2-one

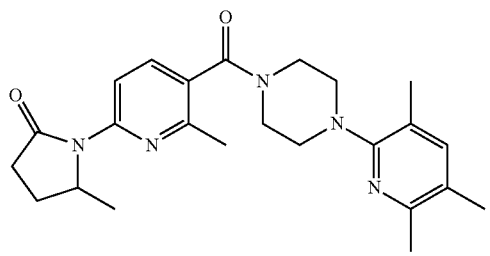 [SMILES: Cc1cc(C)c(N2CCN(C(=O)c3ccc(N4C(=O)CCC4C)nc3C)CC2)nc1C]

Using (6-bromo-2-methylpyridin-3-yl)[4-(3,5,6-trimethylpyridin-2-yl)piperazin-1-yl]methanone (145 mg) described in Preparation Example 248 and 5-methylpyrrolidin-2-one (54 mg) and by the reaction and treatment in the same manner as in Example 262, the title compound (130 mg) was obtained.
MS (ESI) m/z: 422(M+H)$^+$.

Example 776

Synthesis of 1-{4-[4-(3,5-dimethylpyridin-2-yl)piperazine-1-carbonyl]-3-(pyrrolidine-1-carbonyl) phenyl}pyrrolidin-2-one

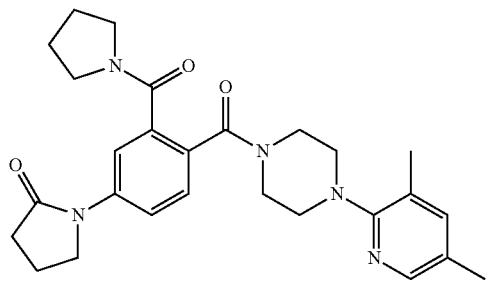 [SMILES: Cc1cnc(N2CCN(C(=O)c3ccc(N4CCCC4=O)cc3C(=O)N3CCCC3)CC2)c(C)c1]

Using N,N-di-tert-butyloxycarbonyl-2-[4-(3,5-dimethylpyridin-2-yl)piperazine-1-carbonyl]-5-(2-oxopyrrolidin-1-yl)benzamide (249 mg) described in Example 769 and pyrrolidine (40 μL) and by the reaction and treatment in the same manner as in Example 770, the title compound (138 mg) was obtained.
MS (ESI) m/z: 476(M+H)$^+$.

Example 777

Synthesis of 1-[4-[4-(3,5-dimethylpyridin-2-yl)piperazine-1-carbonyl]-3-(morpholine-4-carbonyl)phenyl]pyrrolidin-2-one

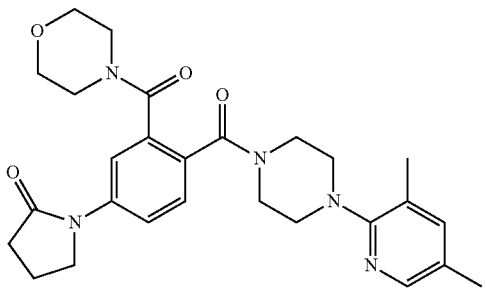 [SMILES: Cc1cnc(N2CCN(C(=O)c3ccc(N4CCCC4=O)cc3C(=O)N3CCOCC3)CC2)c(C)c1]

Using N,N-di-tert-butyloxycarbonyl-2-[4-(3,5-dimethylpyridin-2-yl)piperazine-1-carbonyl]-5-(2-oxopyrrolidin-1-yl)benzamide (249 mg) described in Example 769 and morpholine (42 μL) and by the reaction and treatment in the same manner as in Example 770, the title compound (60 mg) was obtained.
MS (ESI) m/z: 492(M+H)$^+$.

Example 778

Synthesis of 1-{5-[4-(5-cyclopropyl-3-methylpyridin-2-yl)piperazine-1-carbonyl]-6-methylpyridin-2-yl}pyrrolidin-2-one

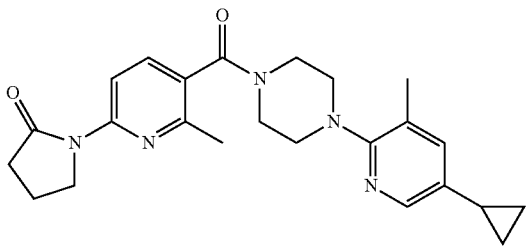 [SMILES: Cc1cc(C2CC2)cnc1N1CCN(C(=O)c2ccc(N3CCCC3=O)nc2C)CC1]

Using (6-bromo-2-methylpyridin-3-yl)[4-(5-cyclopropyl-3-methylpyridin-2-yl)piperazin-1-yl]methanone (150 mg) described in Preparation Example 249 and pyrrolidin-2-one (41 μL) and by the reaction and treatment in the same manner as in Example 262, the title compound (137 mg) was obtained.
MS (ESI) m/z: 420(M+H)$^+$.

Example 779

Synthesis of 1-{5-[4-(5-cyclopropyl-3-methylpyridin-2-yl)piperazine-1-carbonyl]-6-methylpyridin-2-yl}-5-methylpyrrolidin-2-one

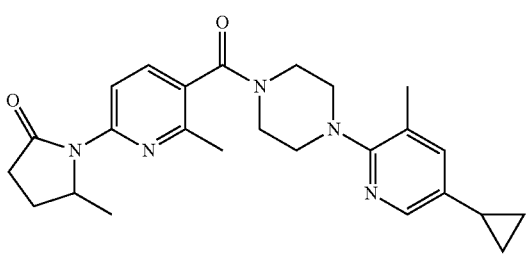 [SMILES: Cc1cc(C2CC2)cnc1N1CCN(C(=O)c2ccc(N3C(=O)CCC3C)nc2C)CC1]

Using (6-bromo-2-methylpyridin-3-yl)[4-(5-cyclopropyl-3-methylpyridin-2-yl)piperazin-1-yl]methanone (150 mg) described in Preparation Example 249 and 5-methylpyrrolidin-2-one (54 mg) and by the reaction and treatment in the same manner as in Example 262, the title compound (138 mg) was obtained.
MS (ESI) m/z: 434(M+H)$^+$.

Example 780

Synthesis of 1-{5-[4-(5-cyclopropyl-3-methylpyridin-2-yl)piperazine-1-carbonyl]-6-methylpyridin-2-yl}imidazolidin-2-one

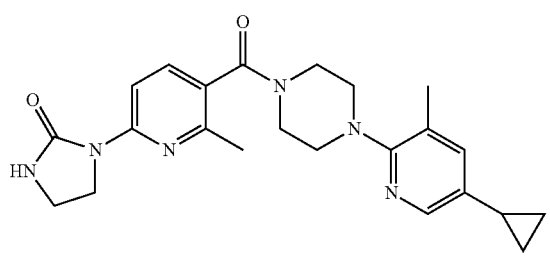 [SMILES: Cc1cc(C2CC2)cnc1N1CCN(C(=O)c2ccc(N3CCNC3=O)nc2C)CC1]

Using 1-acetyl-3-{5-[4-(5-cyclopropyl-3-methylpyridin-2-yl)piperazine-1-carbonyl]-6-methylpyridin-2-yl}imidazolidin-2-one (170 mg) described in Example 692 and by the reaction and treatment in the same manner as in Example 391, the title compound (134 mg) was obtained.
MS (ESI) m/z: 421(M+H)$^+$.

Example 781

Synthesis of 1-{5-[4-(5-ethyl-3-methylpyridin-2-yl)piperazine-1-carbonyl]-6-methylpyridin-2-yl}-5-methylpyrrolidin-2-one

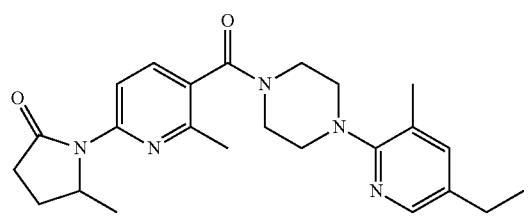 [SMILES: CCc1cnc(N2CCN(C(=O)c3ccc(N4C(=O)CCC4C)nc3C)CC2)c(C)c1]

Using 6-bromo-2-methylpyridin-3-yl) [4-(5-ethyl-3-methylpyridin-2-yl)piperazin-1-yl]methanone (145 mg) described in Preparation Example 250 and 5-methylpyrrolidin-2-one (54 mg) and by the reaction and treatment in the same manner as in Example 262, the title compound (125 mg) was obtained.
MS (ESI) m/z: 422(M+H)$^+$.

Example 782

Synthesis of 1-{5-[4-(5-ethyl-3-methylpyridin-2-yl)piperazine-1-carbonyl]-6-methylpyridin-2-yl}imidazolidin-2-one

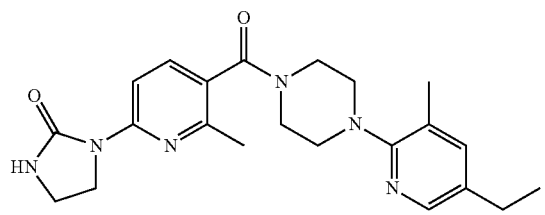 [SMILES: CCc1cnc(N2CCN(C(=O)c3ccc(N4CCNC4=O)nc3C)CC2)c(C)c1]

Using 1-acetyl-3-{(5-[4-(5-ethyl-3-methylpyridin-2-yl)piperazine-1-carbonyl]-6-methylpyridin-2-yl}imidazolidin-2-one (173 mg) described in Example 693 and by the reaction and treatment in the same manner as in Example 391, the title compound (151 mg) was obtained.

MS (ESI) m/z: 409(M+H)$^+$.

Example 783

Synthesis of 5-(1,1-dioxo-1$\lambda^6$-isothiazolidin-2-yl)-N,N-dimethyl-2-[4-(3,5,6-trimethylpyridin-2-yl)piperazine-1-carbonyl]benzamide

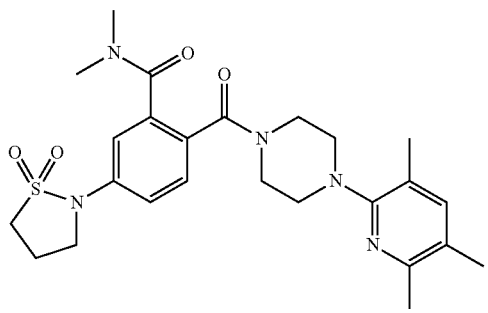 [SMILES: Cc1cc(C)c(N2CCN(C(=O)c3ccc(N4CCCS4(=O)=O)cc3C(=O)N(C)C)CC2)nc1C]

Using N,N-di-tert-butyloxycarbonyl-5-(1,1-dioxo-1$\lambda^6$-isothiazolidin-2-yl)-2-[4-(3,5,6-trimethylpyridin-2-yl)piperazine-1-carbonyl]benzamide (202 mg) described in Example 768 and 2 mol/L dimethylamine tetrahydrofuran solution (180 µL) and by the reaction and treatment in the same manner as in Example 770, the title compound (65 mg) was obtained.

MS (ESI) m/z: 500(M+H)$^+$.

Example 784

Synthesis of [4-(1,1-dioxo-1$\lambda^6$-isothiazolidin-2-yl)-2-(pyrrolidine-1-carbonyl)phenyl][4-(3,5,6-trimethylpyridin-2-yl)piperazin-1-yl]methanone

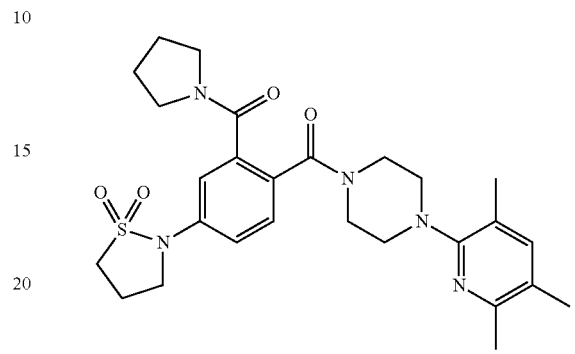

Using N,N-di-tert-butyloxycarbonyl-5-(1,1-dioxo-1$\lambda^6$-isothiazolidin-2-yl)-2-[4-(3,5,6-trimethylpyridin-2-yl)piperazine-1-carbonyl]benzamide (202 mg) described in Example 768 and pyrrolidine (30 µL) and by the reaction and treatment in the same manner as in Example 770, the title compound (127 mg) was obtained.

MS (ESI) m/z: 526(M+H)$^+$.

Example 785

Synthesis of N,N-di-tert-butyloxycarbonyl-5-(1,1-dioxo-1$\lambda^6$-isothiazolidin-2-yl)-2-[4-(5-ethyl-3-methylpyridin-2-yl)piperazine-1-carbonyl]benzamide

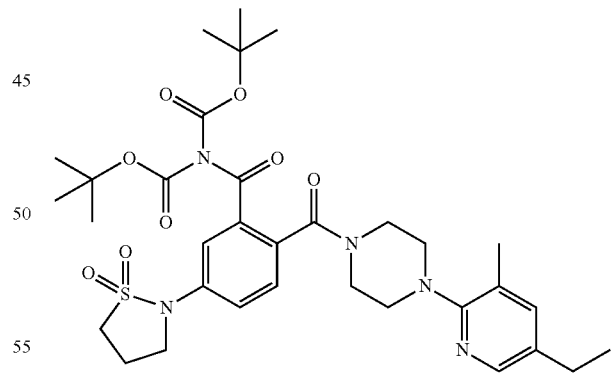

Using 5-(1,1-dioxo-1$\lambda^6$-isothiazolidin-2-yl)-2-[4-(5-ethyl-3-methylpyridin-2-yl)piperazine-1-carbonyl]benzamide (940 mg) described in Example 747 and di-tert-butyl dicarbonate (1.83 g) and by the reaction and treatment in the same manner as in Example 768, the title compound (1.13 g) was obtained.

MS (ESI) m/z: 672(M+H)$^+$.

Example 786

Synthesis of 5-(1,1-dioxo-1λ⁶-isothiazolidin-2-yl)-2-[4-(5-ethyl-3-methylpyridin-2-yl)piperazine-1-carbonyl]-N-methylbenzamide

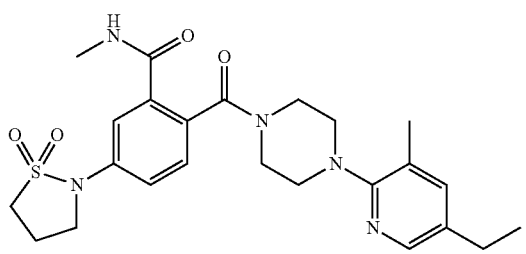 [SMILES: CCc1cnc(N2CCN(C(=O)c3ccc(N4CCCS4(=O)=O)cc3C(=O)NC)CC2)c(C)c1]

Using N,N-di-tert-butyloxycarbonyl-5-(1,1-dioxo-1λ⁶-isothiazolidin-2-yl)-2-[4-(5-ethyl-3-methylpyridin-2-yl)piperazine-1-carbonyl]benzamide (202 mg) described in Example 785 and 2 mol/L methylamine tetrahydrofuran solution (180 µL) and by the reaction and treatment in the same manner as in Example 770, the title compound (96 mg) was obtained.

MS (ESI) m/z: 486(M+H)⁺.

Example 787

Synthesis of [4-(1,1-dioxo-1λ⁶-isothiazolidin-2-yl)-2-(pyrrolidine-1-carbonyl)phenyl][4-(5-ethyl-3-methylpyridin-2-yl)piperazin-1-yl]methanone

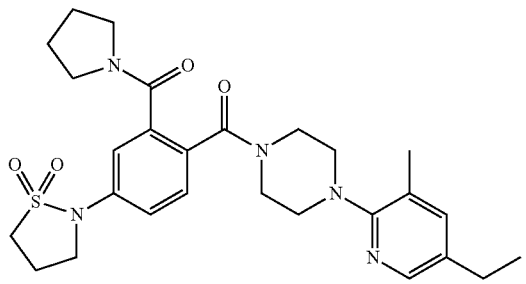 [SMILES: CCc1cnc(N2CCN(C(=O)c3ccc(N4CCCS4(=O)=O)cc3C(=O)N3CCCC3)CC2)c(C)c1]

Using N,N-di-tert-butyloxycarbonyl-5-(1,1-dioxo-1λ⁶-isothiazolidin-2-yl)-2-[4-(5-ethyl-3-methylpyridin-2-yl)piperazine-1-carbonyl]benzamide (202 mg) described in Example 785 and pyrrolidine (30 µL) and by the reaction and treatment in the same manner as in Example 770, the title compound (118 mg) was obtained.

MS (ESI) m/z: 526(M+H)⁺.

Example 788

Synthesis of 5-(1,1-dioxo-1λ⁶-isothiazolidin-2-yl)-2-[4-(5-ethyl-3-methylpyridin-2-yl)piperazine-1-carbonyl]-N,N-dimethyl-benzamide

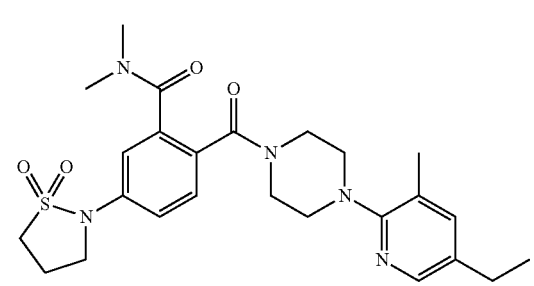 [SMILES: CCc1cnc(N2CCN(C(=O)c3ccc(N4CCCS4(=O)=O)cc3C(=O)N(C)C)CC2)c(C)c1]

Using N,N-di-tert-butyloxycarbonyl-5-(1,1-dioxo-1λ⁶-isothiazolidin-2-yl)-2-[4-(5-ethyl-3-methylpyridin-2-yl)piperazine-1-carbonyl]benzamide (202 mg) described in Example 785 and 2M dimethylamine tetrahydrofuran solution (180 µL) and by the reaction and treatment in the same manner as in Example 770, the title compound (81 mg) was obtained.

MS (ESI) m/z: 500(M+H)⁺.

Example 789

Synthesis of 1-{5-[4-(3,5-dicyclopropylpyridin-2-yl)piperazine-1-carbonyl]-6-methylpyridin-2-yl}imidazolidin-2-one

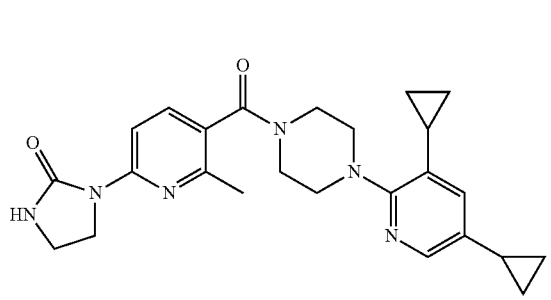 [SMILES: Cc1nc(N2CCNC2=O)ccc1C(=O)N1CCN(c2ncc(C3CC3)cc2C2CC2)CC1]

Using (1-acetyl-3-{5-[4-(3,5-dicyclopropylpyridin-2-yl)piperazine-1-carbonyl]-6-methylpyridin-2-yl}imidazolidin-2-one (204 mg) described in Example 694 and by the reaction and treatment in the same manner as in Example 391, the title compound (182 mg) was obtained.

MS (ESI) m/z: 447(M+H)⁺.

Example 790

Synthesis of [4-(1,1-dioxo-1λ⁶-isothiazolidin-2-yl)-2-(morpholine-4-carbonyl)phenyl][4-(5-ethyl-3-methylpyridin-2-yl)piperazin-1-yl]methanone

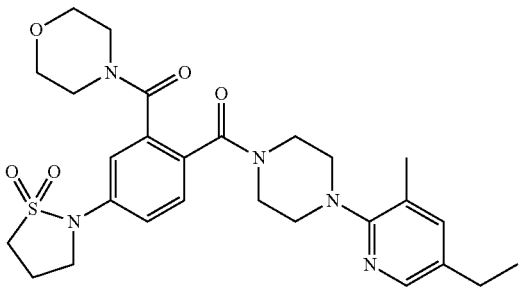 [SMILES: CCc1cnc(N2CCN(C(=O)c3ccc(N4CCCS4(=O)=O)cc3C(=O)N3CCOCC3)CC2)c(C)c1]

Using N,N-di-tert-butyloxycarbonyl-5-(1,1-dioxo-1λ⁶-isothiazolidin-2-yl)-2-[4-(5-ethyl-3-methylpyridin-2-yl)piperazine-1-carbonyl]benzamide (249 mg) described in Example 785 and morpholine (39 μL) and by the reaction and treatment in the same manner as in Example 770, the title compound (58 mg) was obtained.

MS (ESI) m/z: 542(M+H)⁺.

Example 791

Synthesis of 1-{5-[4-(3,5-dimethylpyridin-2-yl)piperazine-1-carbonyl]-6-methylpyridin-2-yl}pyrrolidin-2-one

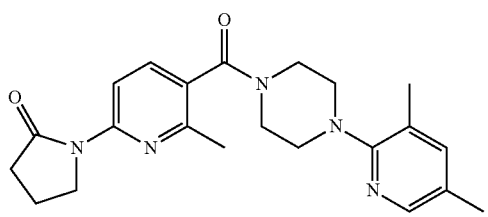 [SMILES: Cc1cnc(N2CCN(C(=O)c3ccc(N4CCCC4=O)nc3C)CC2)c(C)c1]

Ethyl 6-amino-2-methylnicotinate (450 mg) and triethylamine (0.42 mL) were dissolved in methylene chloride (5 mL), 4-chlorobutyryl chloride (0.31 mL) was added, and the mixture was stirred at room temperature for 3 days. To the reaction mixture was added saturated brine, and the mixture was extracted with methylene chloride. The solvent was evaporated, and the obtained residue was purified by column chromatography (ethyl acetate:hexane). The solvent was evaporated, and to the obtained residue were added N,N-dimethylformamide (3 mL) and sodium hydrogen carbonate (420 mg), and the mixture was stirred at 80° C. After completion of the reaction, to the reaction mixture was added saturated brine, and the mixture was extracted with ethyl acetate. The solvent was evaporated, ethanol (2 mL) and 1N aqueous sodium hydroxide solution (2 mL) were added to the obtained crude product (300 mg) of ethyl 2-methyl-6-(2-oxopyrrolidin-1-yl)nicotinate, and the mixture was stirred at room temperature for 2 hr. The reaction mixture was neutralized with 1N hydrochloric acid, saturated brine was added, and the mixture was extracted with ethyl acetate. The solvent was evaporated to give a crude product of 2-methyl-6-(2-oxopyrrolidin-1-yl)nicotinic acid. Using the obtained crude product (0.605 mmol) of 2-methyl-6-(2-oxopyrrolidin-1-yl)nicotinic acid and 1-(3,5-dimethylpyridin-2-yl)piperazine (116 mg) described in Preparation Example 79 and by the reaction and treatment in the same manner as in Example 93, the title compound (9 mg) was obtained.

MS (ESI) m/z: 394(M+H)⁺.

Example 792

Synthesis of 1-{5-[4-(5-ethyl-3-methylpyridin-2-yl)piperazine-1-carbonyl]-6-methylpyridin-2-yl}pyrrolidin-2-one

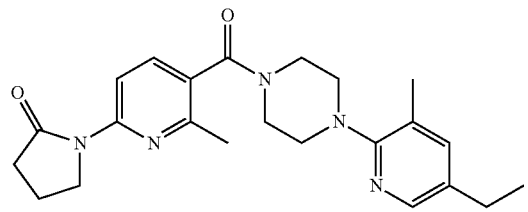 [SMILES: CCc1cnc(N2CCN(C(=O)c3ccc(N4CCCC4=O)nc3C)CC2)c(C)c1]

Using a crude product (0.605 mmol) of 2-methyl-6-(2-oxopyrrolidin-1-yl)nicotinic acid which is an intermediate described in Example 791, and 1-(5-ethyl-3-methylpyridin-2-yl)piperazine (124 mg) described in Preparation Example 81 and by the reaction and treatment in the same manner as in Example 93, the title compound (4 mg) was obtained.

MS (ESI) m/z: 408(M+H)⁺.

Example 793

Synthesis of 1-{5-[4-(3,5-dimethylpyridin-2-yl)piperazine-1-carbonyl]-6-methylpyridin-2-yl}-3,5-dimethylimidazolidine-2,4-dione

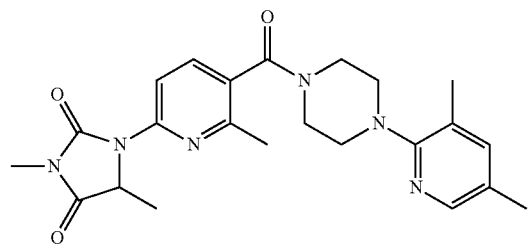

Using methyl 6-(3,5-dimethyl-2,4-dioxoimidazolidin-1-yl)-2-methylnicotinate (19 mg) described in Preparation Example 255 and 1-(3,5-dimethylpyridin-2-yl)piperazine (13 mg) described in Preparation Example 79 and by the reaction and treatment in the same manner as in Example 109, the title compound (24 mg) was obtained.

MS (ESI) m/z: 437(M+H)⁺.

Example 794

Synthesis of 1-[2-[4-(3,5-dimethylpyridin-2-yl)piperazine-1-carbonyl]-5-(1,1-dioxo-1λ⁶-isothiazolidin-2-yl)phenyl]-3-methylimidazolidine-2,4-dione

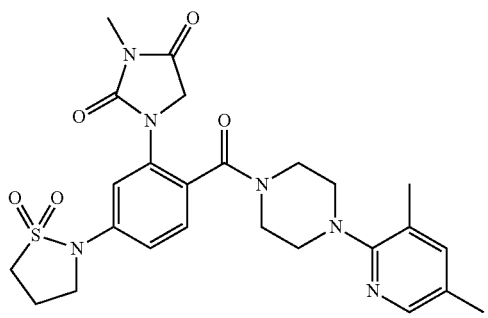 [SMILES: Cc1cnc(N2CCN(C(=O)c3ccc(N4CCCS4(=O)=O)cc3N3CC(=O)N(C)C3=O)CC2)c(C)c1]

Using 1-{5-chloro-2-[4-(3,5-dimethylpyridin-2-yl)piperazine-1-carbonyl]phenyl}-3-methylimidazolidine-2,4-dione (149 mg) described in Preparation Example 256 and isothiazolidine 1,1-dioxide (61 mg) and by the reaction and treatment in the same manner as in Example 666, the title compound (66 mg) was obtained.
MS (ESI) m/z: 527(M+H)⁺.

Example 795

Synthesis of 1-[2-[4-(3,5-dimethylpyridin-2-yl)piperazine-1-carbonyl]-5-(2-methyl-5-oxopyrrolidin-1-yl)phenyl]-3-methylimidazolidine-2,4-dione

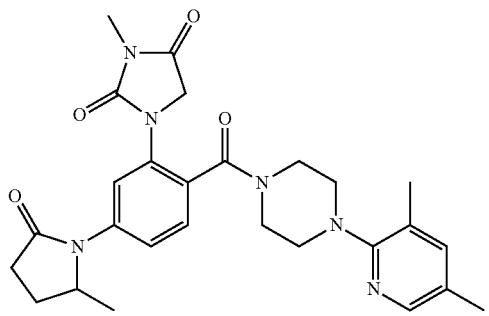 [SMILES: Cc1cnc(N2CCN(C(=O)c3ccc(N4C(=O)CCC4C)cc3N3CC(=O)N(C)C3=O)CC2)c(C)c1]

Using 1-{5-chloro-2-[4-(3,5-dimethylpyridin-2-yl)piperazine-1-carbonyl]phenyl}-3-methylimidazolidine-2,4-dione (155 mg) described in Preparation Example 256 and 5-methylpyrrolidin-2-one (52 mg) and by the reaction and treatment in the same manner as in Example 666, the title compound (21 mg) was obtained.
MS (ESI) m/z: 505(M+H)⁺.

Example 796

Synthesis of [4-(4-fluoro-2-methoxyphenyl)piperazin-1-yl][4-(imidazo[4,5-b]pyridin-3-yl)phenyl]methanone

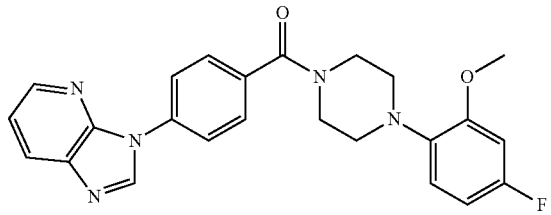 [SMILES: COc1cc(F)ccc1N1CCN(C(=O)c2ccc(-n3cnc4cccnc43)cc2)CC1]

Using ethyl 4-(imidazo[4,5-b]pyridin-3-yl)benzoate (300 mg) described in Preparation Example 77 and 1-(4-fluoro-2-methoxyphenyl)piperazine (236 mg) and by the reaction and treatment in the same manner as in Example 170, the title compound (78 mg) was obtained.
MS (ESI) m/z: 432(M+H)⁺.

Example 797

Synthesis of [4-(2,4-dimethylbenzoyl)piperidin-1-yl][4-(imidazo[4,5-b]pyridin-3-yl)phenyl]methanone

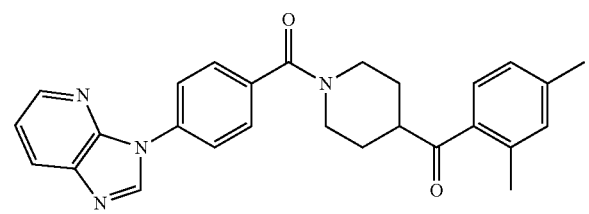 [SMILES: Cc1ccc(C(=O)C2CCN(C(=O)c3ccc(-n4cnc5cccnc54)cc3)CC2)c(C)c1]

Using ethyl 4-(imidazo[4,5-b]pyridin-3-yl)benzoate (300 mg) described in Preparation Example 77 and (2,4-dimethylphenyl)(piperidin-4-yl)methanone hydrochloride (285 mg) and by the reaction and treatment in the same manner as in Example 170, the title compound (312 mg) was obtained.
MS (ESI) m/z: 439(M+H)⁺.

Example 798

Synthesis of 1-{4-[4-(2,4-dimethylphenyl)piperazine-1-carbonyl]phenyl}azepan-2-one Using [4-(2,4-dimethylphenyl)piperazin-1-yl](4-iodophenyl)methanone (205 mg) described in Preparation Example 108 and azepan-2-one (58 mg) and by the reaction and treatment in the same manner as in Example 1, the title compound (151 mg) was obtained.
MS (ESI) m/z: 406(M+H)⁺.

Example 799

Synthesis of 4-{4-[4-(3,5-dimethylpyridin-2-yl)piperazine-1-carbonyl]phenyl}piperazine-1-carboxylic acid dimethylamide

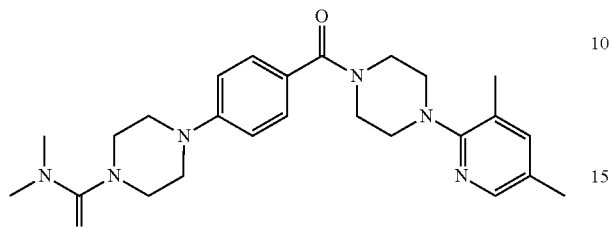

To a mixture of [4-(3,5-dimethylpyridin-2-yl)piperazin-1-yl](4-iodophenyl)methanone (270 mg) described in Preparation Example 113, palladium acetate (8 mg), 2-(dicyclohexylphosphino)biphenyl (22 mg), tripotassium phosphate (190 mg) and piperazine-1-carboxylic acid dimethylamide (111 mg) was added 1,2-dimethoxyethane (5 mL), and the mixture was stirred with heating under reflux for 7 hr. Water was added to the reaction mixture, and the mixture was extracted with ethyl acetate. The organic layer was washed with saturated brine, and the solvent was evaporated. The obtained residue was purified by NH coated silica gel column chromatography (ethyl acetate:hexane) to give the title compound (58 mg).

MS (ESI) m/z: 451(M+H)$^+$.

Example 800

Synthesis of N-cyclopentyl-2-[4-(3,5-dimethylpyridin-2-yl)piperazine-1-carbonyl]-5-(2-oxopyrrolidin-1-yl)benzamide

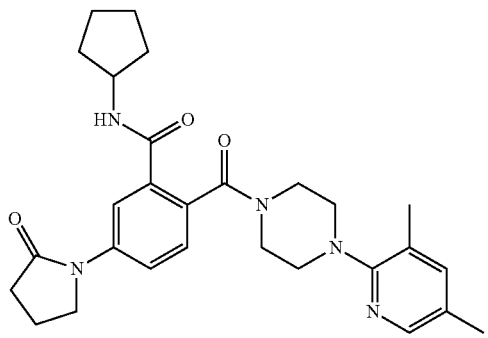 [SMILES: Cc1cnc(N2CCN(C(=O)c3ccc(N4CCCC4=O)cc3C(=O)NC3CCCC3)CC2)c(C)c1]

Using N,N-di-tert-butyloxycarbonyl-2-[4-(3,5-dimethylpyridin-2-yl)piperazine-1-carbonyl]-5-(2-oxopyrrolidin-1-yl)benzamide (187 mg) described in Example 769 and cyclopentylamine (36 μL) and by the reaction and treatment in the same manner as in Example 770, the title compound (87 mg) was obtained.

MS (ESI) m/z: 490(M+H)$^+$.

Example 801

Synthesis of 2-[4-(3,5-dimethylpyridin-2-yl)piperazine-1-carbonyl]-5-(2-oxopyrrolidin-1-yl)-N-pyridin-3-ylmethylbenzamide

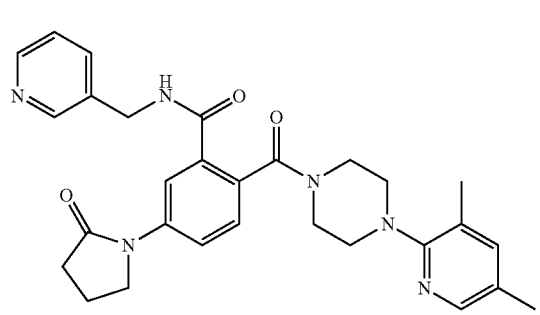 [SMILES: Cc1cnc(N2CCN(C(=O)c3ccc(N4CCCC4=O)cc3C(=O)NCc3cccnc3)CC2)c(C)c1]

Using N,N-di-tert-butyloxycarbonyl-2-[4-(3,5-dimethylpyridin-2-yl)piperazine-1-carbonyl]-5-(2-oxopyrrolidin-1-yl)benzamide (187 mg) described in Example 769 and C-pyridin-3-yl-methylamine (36 μL) and by the reaction and treatment in the same manner as in Example 770, the title compound (111 mg) was obtained.

MS (ESI) m/z: 513(M+H)$^+$.

Example 802

Synthesis of 2-[4-(3,5-dimethylpyridin-2-yl)piperazine-1-carbonyl]-N-(3-methoxybenzyl)-5-(2-oxopyrrolidin-1-yl)benzamide

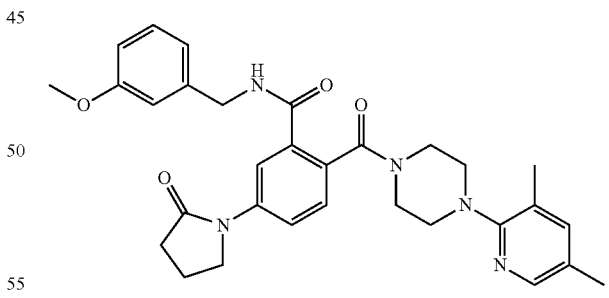

Using N,N-di-tert-butyloxycarbonyl-2-[4-(3,5-dimethylpyridin-2-yl)piperazine-1-carbonyl]-5-(2-oxopyrrolidin-1-yl)benzamide (187 mg) described in Example 769 and 3-methoxybenzylamine (36 μL) and by the reaction and treatment in the same manner as in Example 770, the title compound (120 mg) was obtained.

MS (ESI) m/z: 542(M+H)$^+$.

Example 803

Synthesis of 2-[4-(5-cyclopropyl-3-methylpyridin-2-yl)piperazine-1-carbonyl]-5-(1,1-dioxo-1λ$^6$-isothiazolidin-2-yl)benzamide

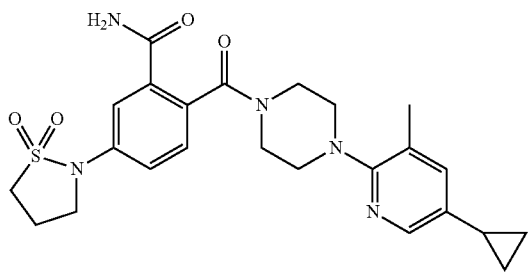 [SMILES: Cc1cc(C2CC2)cnc1N1CCN(C(=O)c2ccc(N3CCCS3(=O)=O)cc2C(N)=O)CC1]

Using 2-[4-(5-cyclopropyl-3-methylpyridin-2-yl)piperazine-1-carbonyl]-5-(1,1-dioxo-1λ$^6$-isothiazolidin-2-yl)benzonitrile (364 mg) described in Example 264 and by the reaction and treatment in the same manner as in Example 722, the title compound (366 mg) was obtained.

MS (ESI) m/z: 484(M+H)$^+$.

Example 804

Synthesis of 2-[4-(3,5-dimethylpyridin-2-yl)piperazine-1-carbonyl]-5-(1,1-dioxo-1λ$^6$-isothiazolidin-2-yl)benzamide

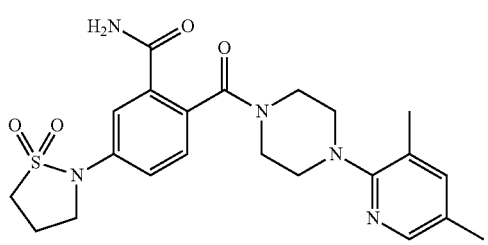

Using 2-[4-(3,5-dimethylpyridin-2-yl)piperazine-1-carbonyl]-5-(1,1-dioxo-1λ$^6$-isothiazolidin-2-yl)benzonitrile (574 mg) described in Example 262 and by the reaction and treatment in the same manner as in Example 722, the title compound (202 mg) was obtained.

MS (ESI) m/z: 458(M+H)$^+$.

Example 805

Synthesis of N,N-di-tert-butyloxycarbonyl-2-[4-(5-cyclopropyl-3-methylpyridin-2-yl)piperazine-1-carbonyl]-5-(1,1-dioxo-1λ$^6$-isothiazolidin-2-yl)benzamide

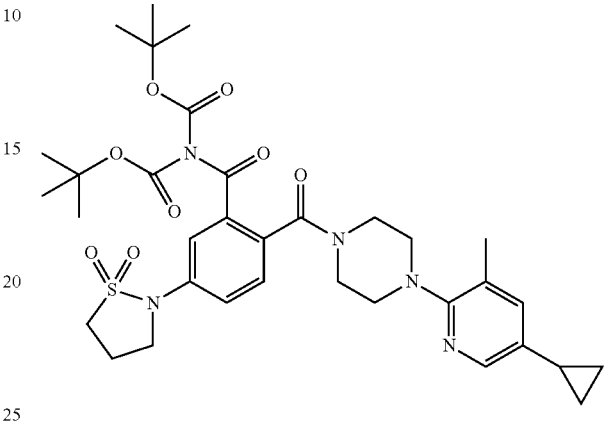

Using 2-[4-(5-cyclopropyl-3-methylpyridin-2-yl)piperazine-1-carbonyl]-5-(1,1-dioxo-1λ$^6$-isothiazolidin-2-yl)benzamide (343 mg) described in Example 803 and di-tert-butyl dicarbonate (325 mg) and by the reaction and treatment in the same manner as in Example 768, the title compound (370 mg) was obtained.

MS (ESI) m/z: 684(M+H)$^+$.

Example 806

Synthesis of 1-[4-[4-(3,5-dimethylpyridin-2-yl)piperazine-1-carbonyl]-3-(piperidine-1-carbonyl)phenyl]pyrrolidin-2-one

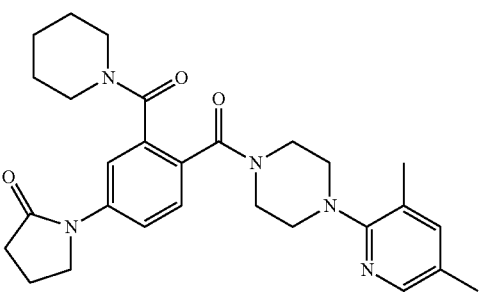 [SMILES: Cc1cnc(N2CCN(C(=O)c3ccc(N4CCCC4=O)cc3C(=O)N3CCCCC3)CC2)c(C)c1]

Using N,N-di-tert-butyloxycarbonyl-2-[4-(3,5-dimethylpyridin-2-yl)piperazine-1-carbonyl]-5-(2-oxopyrrolidin-1-yl)benzamide (137 mg) described in Example 769 and piperidine (26 µL) and by the reaction and treatment in the same manner as in Example 770, the title compound (54 mg) was obtained.

MS (ESI) m/z: 490(M+H)$^+$.

Example 807

Synthesis of [4-(5-cyclopropyl-3-methylpyridin-2-yl)piperazin-1-yl][4-(1,1-dioxo-1λ$^6$-isothiazolidin-2-yl)-2-(morpholine-4-carbonyl)phenyl]methanone

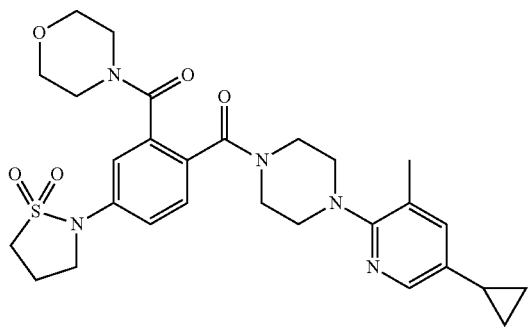 [SMILES: Cc1cc(C2CC2)cnc1N1CCN(C(=O)c2ccc(N3CCCS3(=O)=O)cc2C(=O)N2CCOCC2)CC1]

Using N,N-di-tert-butyloxycarbonyl-2-[4-(5-cyclopropyl-3-methylpyridin-2-yl)piperazine-1-carbonyl]-5-(1,1-dioxo-1λ$^6$-isothiazolidin-2-yl)benzamide (155 mg) described in Example 805 and morpholine (24 μL) and by the reaction and treatment in the same manner as in Example 770, the title compound (36 mg) was obtained.

MS (ESI) m/z: 553(M+H)$^+$.

Example 808

Synthesis of N,N-di-tert-butyloxycarbonyl-2-[4-(3,5-dimethylpyridin-2-yl)piperazine-1-carbonyl]-5-(1,1-dioxo-1λ$^6$-isothiazolidin-2-yl)benzamide

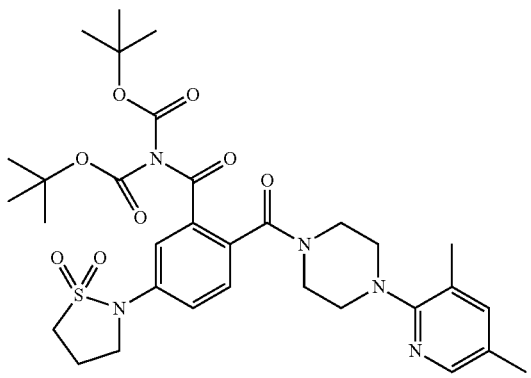 [SMILES: Cc1cnc(N2CCN(C(=O)c3ccc(N4CCCS4(=O)=O)cc3C(=O)N(C(=O)OC(C)(C)C)C(=O)OC(C)(C)C)CC2)c(C)c1]

Using 2-[4-(3,5-dimethylpyridin-2-yl)piperazine-1-carbonyl]-5-(1,1-dioxo-1λ$^6$-isothiazolidin-2-yl)benzamide (187 mg) described in Example 804 and di-tert-butyl dicarbonate (187 mg) and by the reaction and treatment in the same manner as in Example 768, the title compound (226 mg) was obtained.

MS (ESI) m/z: 657(M+H)$^+$.

Example 809

Synthesis of N,N-di-tert-butyloxycarbonyl-2-[4-(5-ethyl-3-methylpyridin-2-yl)piperazine-1-carbonyl]-5-(2-oxopyrrolidin-1-yl)benzamide

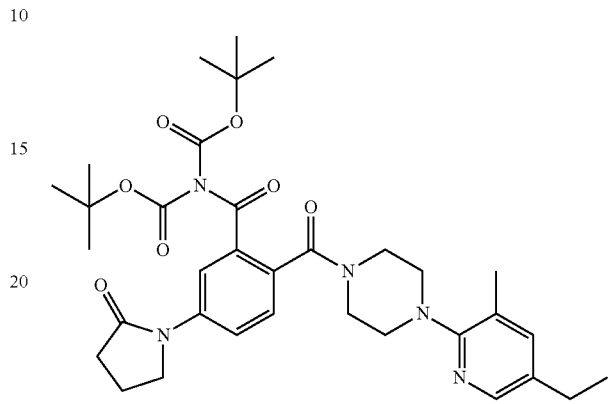

Using 2-[4-(5-ethyl-3-methylpyridin-2-yl)piperazine-1-carbonyl]-5-(2-oxopyrrolidin-1-yl)benzamide (250 mg) described in Example 748 and di-tert-butyl dicarbonate (276 mg) and by the reaction and treatment in the same manner as in Example 768, the title compound (296 mg) was obtained.

MS (ESI) m/z: 636(M+H)$^+$.

Example 810

Synthesis of 2-[4-(5-ethyl-3-methylpyridin-2-yl)piperazine-1-carbonyl]-N-methyl-5-(2-oxopyrrolidin-1-yl)benzamide

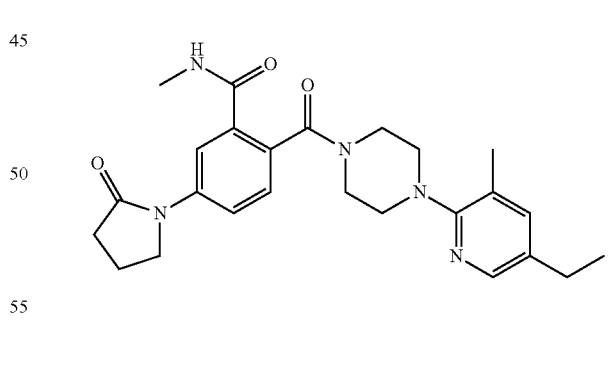

Using N,N-di-tert-butyloxycarbonyl-2-[4-(5-ethyl-3-methylpyridin-2-yl)piperazine-1-carbonyl]-5-(2-oxopyrrolidin-1-yl)benzamide (70 mg) described in Example 809 and 2 mol/L methylamine tetrahydrofuran solution (220 μL) and by the reaction and treatment in the same manner as in Example 770, the title compound (7 mg) was obtained.

MS (ESI) m/z: 450(M+H)$^+$.

Example 811

Synthesis of 2-[4-(5-ethyl-3-methylpyridin-2-yl)piperazine-1-carbonyl]-N,N-dimethyl-5-(2-oxopyrrolidin-1-yl)benzamide

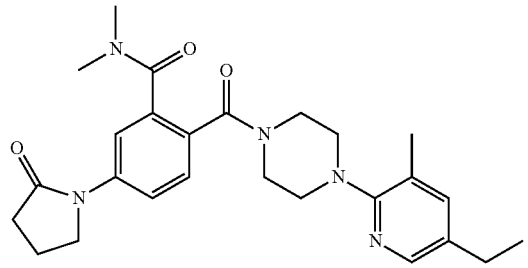 [SMILES: CCc1cnc(N2CCN(C(=O)c3ccc(N4CCCC4=O)cc3C(=O)N(C)C)CC2)c(C)c1]

Using N,N-di-tert-butyloxycarbonyl-2-[4-(5-ethyl-3-methylpyridin-2-yl)piperazine-1-carbonyl]-5-(2-oxopyrrolidin-1-yl)benzamide (70 mg) described in Example 809 and 2 mol/L dimethylamine tetrahydrofuran solution (220 μL) and by the reaction and treatment in the same manner as in Example 770, the title compound (27 mg) was obtained.

MS (ESI) m/z: 464(M+H)$^+$.

Example 812

Synthesis of 1-[4-[4-(5-ethyl-3-methylpyridin-2-yl)piperazine-1-carbonyl]-3-(pyrrolidine-1-carbonyl)phenyl]pyrrolidin-2-one

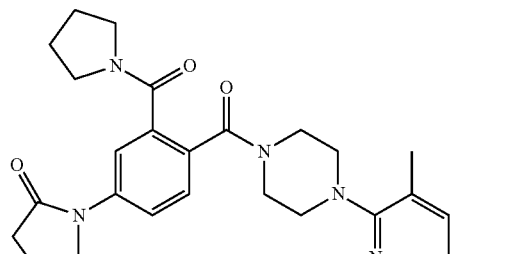

Using N,N-di-tert-butyloxycarbonyl-2-[4-(5-ethyl-3-methylpyridin-2-yl)piperazine-1-carbonyl]-5-(2-oxopyrrolidin-1-yl)benzamide (70 mg) described in Example 809 and pyrrolidine (36 μL) and by the reaction and treatment in the same manner as in Example 770, the title compound (33 mg) was obtained.

MS (ESI) m/z: 490(M+H)$^+$.

Example 813

Synthesis of 1-[4-[4-(5-ethyl-3-methylpyridin-2-yl)piperazine-1-carbonyl]-3-(morpholine-4-carbonyl)phenyl]pyrrolidin-2-one

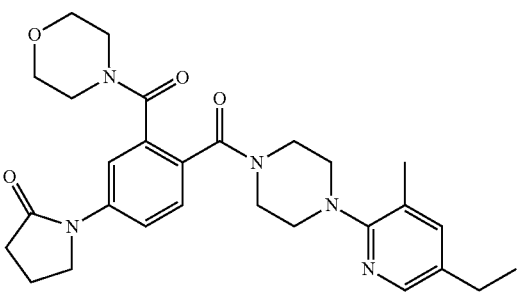 [SMILES: CCc1cnc(N2CCN(C(=O)c3ccc(N4CCCC4=O)cc3C(=O)N3CCOCC3)CC2)c(C)c1]

Using N,N-di-tert-butyloxycarbonyl-2-[4-(5-ethyl-3-methylpyridin-2-yl)piperazine-1-carbonyl]-5-(2-oxopyrrolidin-1-yl)benzamide (70 mg) described in Example 809 and morpholine (41 μL) and by the reaction and treatment in the same manner as in Example 770, the title compound (19 mg) was obtained.

MS (ESI) m/z: 506(M+H)$^+$.

Example 814

Synthesis of N,N-di-tert-butyloxycarbonyl-2-[4-(5-cyclopropyl-3-methylpyridin-2-yl)piperazine-1-carbonyl]-5-(2-oxopyrrolidin-1-yl)benzamide

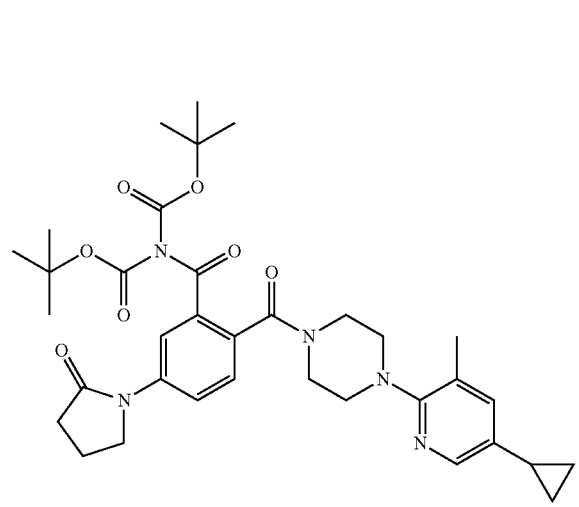 [SMILES: Cc1cc(C2CC2)cnc1N1CCN(C(=O)c2ccc(N3CCCC3=O)cc2C(=O)N(C(=O)OC(C)(C)C)C(=O)OC(C)(C)C)CC1]

Using 2-[4-(5-cyclopropyl-3-methylpyridin-2-yl)piperazine-1-carbonyl]-5-(2-oxopyrrolidin-1-yl)benzamide (270 mg) described in Example 724 and di-tert-butyl dicarbonate (600 mg) and by the reaction and treatment in the same manner as in Example 768, the title compound (352 mg) was obtained.

MS (ESI) m/z: 648(M+H)$^+$.

Example 815

Synthesis of 2-[4-(5-cyclopropyl-3-methylpyridin-2-yl)piperazine-1-carbonyl]-N-methyl-5-(2-oxopyrrolidin-1-yl)benzamide

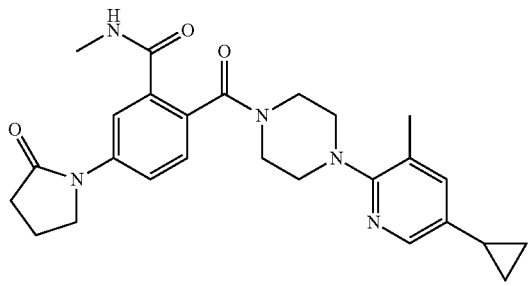 [SMILES: CNC(=O)c1cc(N2CCCC2=O)ccc1C(=O)N1CCN(c2ncc(C3CC3)cc2C)CC1]

Using N,N-di-tert-butyloxycarbonyl-2-[4-(5-cyclopropyl-3-methylpyridin-2-yl)piperazine-1-carbonyl]-5-(2-oxopyrrolidin-1-yl)benzamide (70 mg) described in Example 814 and 2 mol/L methylamine tetrahydrofuran solution (216 μL) and by the reaction and treatment in the same manner as in Example 770, the title compound (18 mg) was obtained.

MS (ESI) m/z: 462(M+H)$^+$.

Example 816

Synthesis of 2-[4-(5-cyclopropyl-3-methylpyridin-2-yl)piperazine-1-carbonyl]-N,N-dimethyl-5-(2-oxopyrrolidin-1-yl)benzamide

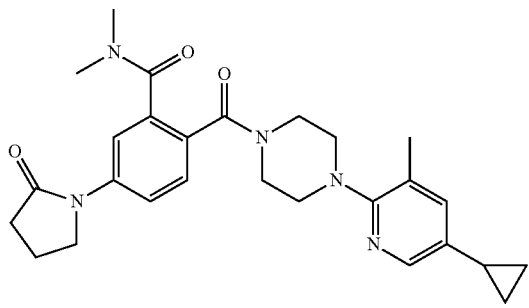 [SMILES: Cc1cc(C2CC2)cnc1N1CCN(C(=O)c2ccc(N3CCCC3=O)cc2C(=O)N(C)C)CC1]

Using N,N-di-tert-butyloxycarbonyl-2-[4-(5-cyclopropyl-3-methylpyridin-2-yl)piperazine-1-carbonyl]-5-(2-oxopyrrolidin-1-yl)benzamide (70 mg) described in Example 814 and 2 mol/L dimethylamine tetrahydrofuran solution (216 μL) and by the reaction and treatment in the same manner as in Example 770, the title compound (27 mg) was obtained.

MS (ESI) m/z: 476(M+H)$^+$.

Example 817

Synthesis of 1-[4-[4-(5-cyclopropyl-3-methylpyridin-2-yl)piperazine-1-carbonyl]-3-(pyrrolidine-1-carbonyl)phenyl]pyrrolidin-2-one

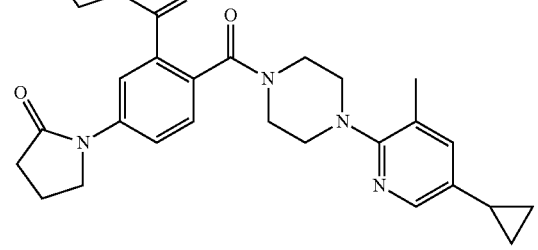

Using N,N-di-tert-butyloxycarbonyl-2-[4-(5-cyclopropyl-3-methylpyridin-2-yl)piperazine-1-carbonyl]-5-(2-oxopyrrolidin-1-yl)benzamide (70 mg) described in Example 814 and pyrrolidine (36 μL) and by the reaction and treatment in the same manner as in Example 770, the title compound (45 mg) was obtained.

MS (ESI) m/z: 502(M+H)$^+$.

Example 818

Synthesis of 1-[4-[4-(5-cyclopropyl-3-methylpyridin-2-yl)piperazine-1-carbonyl]-3-(morpholine-4-carbonyl)phenyl]pyrrolidin-2-one

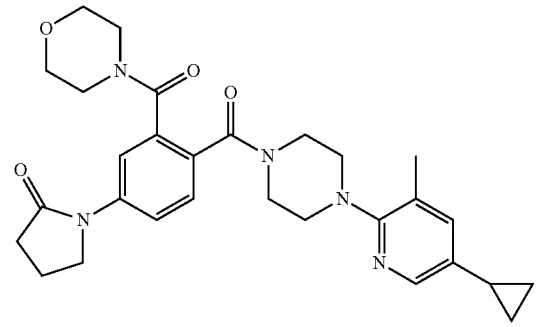 [SMILES: Cc1cc(C2CC2)cnc1N1CCN(C(=O)c2ccc(N3CCCC3=O)cc2C(=O)N2CCOCC2)CC1]

Using N,N-di-tert-butyloxycarbonyl-2-[4-(5-cyclopropyl-3-methylpyridin-2-yl)piperazine-1-carbonyl]-5-(2-oxopyrrolidin-1-yl)benzamide (70 mg) described in Example 814 and morpholine (38 μL) and by the reaction and treatment in the same manner as in Example 770, the title compound (20 mg) was obtained.

MS (ESI) m/z: 518(M+H)$^+$.

Example 819

Synthesis of 1-{5-[4-(3,5-dicyclopropylpyridin-2-yl)piperazine-1-carbonyl]-6-methylpyridin-2-yl}pyrrolidin-2-one

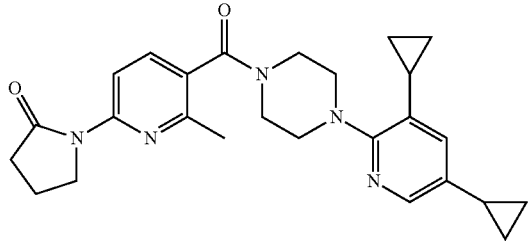 [SMILES: Cc1nc(N2CCCC2=O)ccc1C(=O)N1CCN(c2ncc(C3CC3)cc2C2CC2)CC1]

Using (6-bromo-2-methylpyridin-3-yl)[4-(3,5-dicyclopropylpyridin-2-yl)piperazin-1-yl]methanone (100 mg) described in Preparation Example 251 and pyrrolidin-2-one (29 mg) and by the reaction and treatment in the same manner as in Example 262, the title compound (104 mg) was obtained.
MS (ESI) m/z: 446(M+H)$^+$.

Example 820

Synthesis of 1-{5-[4-(3,5-dicyclopropylpyridin-2-yl)piperazine-1-carbonyl]-6-methylpyridin-2-yl}-5-methylpyrrolidin-2-one

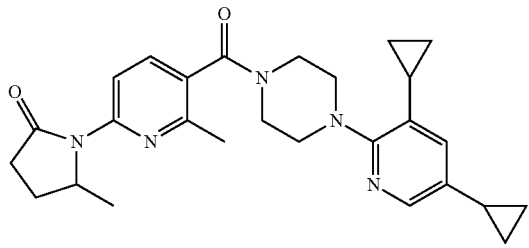 [SMILES: Cc1nc(N2C(=O)CCC2C)ccc1C(=O)N1CCN(c2ncc(C3CC3)cc2C2CC2)CC1]

Using (6-bromo-2-methylpyridin-3-yl)[4-(3,5-dicyclopropylpyridin-2-yl)piperazin-1-yl]methanone (100 mg) described in Preparation Example 251 and 5-methylpyrrolidin-2-one (34 mg) and by the reaction and treatment in the same manner as in Example 262, the title compound (61 mg) was obtained.
MS (ESI) m/z: 460(M+H)$^+$.

Example 821

Synthesis of 2-[4-(3,5-dimethylpyridin-2-yl)piperazine-1-carbonyl]-N-ethyl-N-methyl-5-(2-oxopyrrolidin-1-yl)benzamide

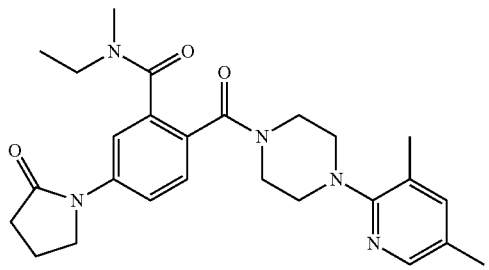 [SMILES: CCN(C)C(=O)c1cc(N2CCCC2=O)ccc1C(=O)N1CCN(c2ncc(C)cc2C)CC1]

Using N,N-di-tert-butyloxycarbonyl-2-[4-(3,5-dimethylpyridin-2-yl)piperazine-1-carbonyl]-5-(2-oxopyrrolidin-1-yl)benzamide (150 mg) described in Example 769 and ethyl(methyl)amine (86 µL) and by the reaction and treatment in the same manner as in Example 770, the title compound (33 mg) was obtained.
MS (ESI) m/z: 464(M+H)$^+$.

Example 822

Synthesis of 2-[4-(3,5-dimethylpyridin-2-yl)piperazine-1-carbonyl]-N-(2-methoxyethyl)-N-methyl-5-(2-oxopyrrolidin-1-yl)benzamide

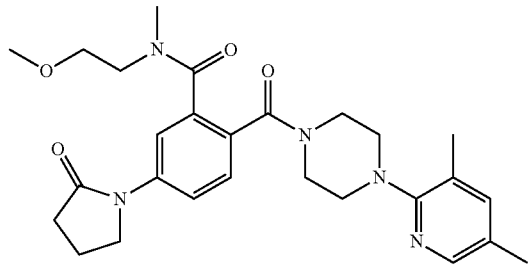

Using N,N-di-tert-butyloxycarbonyl-2-[4-(3,5-dimethylpyridin-2-yl)piperazine-1-carbonyl]-5-(2-oxopyrrolidin-1-yl)benzamide (150 mg) described in Example 769 and (2-methoxyethyl)(methyl)amine (108 µL) and by the reaction and treatment in the same manner as in Example 770, the title compound (58 mg) was obtained.
MS (ESI) m/z: 494(M+H)$^+$.

Example 823

Synthesis of 2-[4-(3,5-dimethylpyridin-2-yl)piperazine-1-carbonyl]-N-(2-methoxyethyl)-5-(2-oxopyrrolidin-1-yl)benzamide

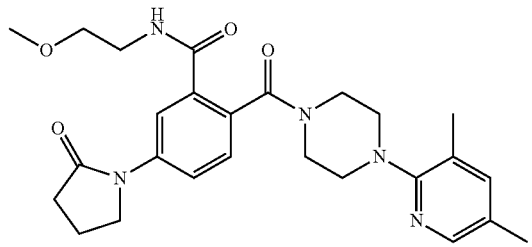

Using N,N-di-tert-butyloxycarbonyl-2-[4-(3,5-dimethylpyridin-2-yl)piperazine-1-carbonyl]-5-(2-oxopyrrolidin-1-yl)benzamide (150 mg) described in Example 769 and 2-methoxyethylamine (84 µL) and by the reaction and treatment in the same manner as in Example 770, the title compound (68 mg) was obtained.
MS (ESI) m/z: 480(M+H)$^+$.

Example 824

Synthesis of N-(2-cyanoethyl)-2-[4-(3,5-dimethylpyridin-2-yl)piperazine-1-carbonyl]-N-methyl-5-(2-oxopyrrolidin-1-yl)benzamide

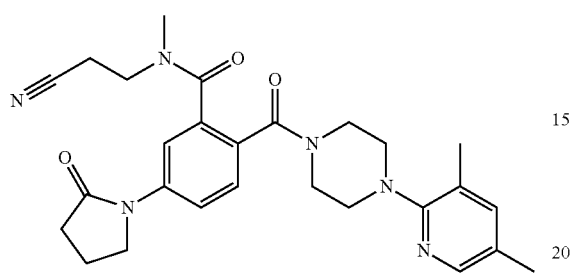

Using N,N-di-tert-butyloxycarbonyl-2-[4-(3,5-dimethylpyridin-2-yl)piperazine-1-carbonyl]-5-(2-oxopyrrolidin-1-yl)benzamide (150 mg) described in Example 769 and 3-methylaminopropionitrile (90 μL) and by the reaction and treatment in the same manner as in Example 770, the title compound (26 mg) was obtained.

MS (ESI) m/z: 489(M+H)$^+$.

Example 825

Synthesis of 1-{5-(2-oxopyrrolidin-1-yl)-2-[4-(3,5,6-trimethylpyridin-2-yl)piperazine-1-carbonyl]phenyl}imidazolidin-2-one

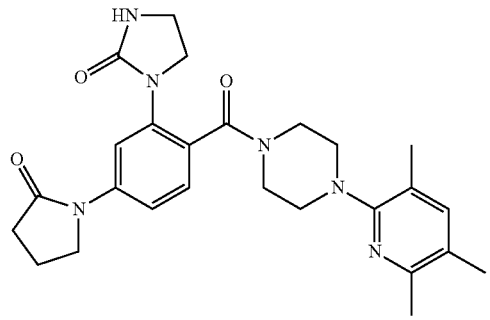 [SMILES: Cc1cc(C)c(N2CCN(C(=O)c3ccc(N4CCCC4=O)cc3N3CCNC3=O)CC2)nc1C]

Using 1-acetyl-3-{5-chloro-2-[4-(3,5,6-trimethylpyridin-2-yl)piperazine-1-carbonyl]phenyl}imidazolidin-2-one (188 mg) described in Preparation Example 258 and pyrrolidin-2-one (51 mg) and by the reaction and treatment in the same manner as in Example 649, the title compound (93 mg) was obtained.

MS (ESI) m/z: 477(M+H)$^+$.

Example 826

Synthesis of 1-{5-(2-methyl-5-oxopyrrolidin-1-yl)-2-[4-(3,5,6-trimethylpyridin-2-yl)piperazine-1-carbonyl]phenyl}imidazolidin-2-one

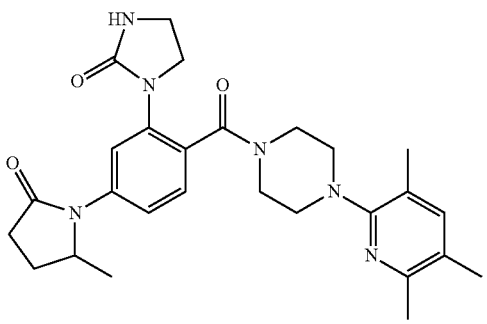 [SMILES: Cc1cc(C)c(N2CCN(C(=O)c3ccc(N4C(=O)CCC4C)cc3N3CCNC3=O)CC2)nc1C]

Using 1-acetyl-3-{5-chloro-2-[4-(3,5,6-trimethylpyridin-2-yl)piperazine-1-carbonyl]phenyl}imidazolidin-2-one (182 mg) described in Preparation Example 258 and 5-methylpyrrolidin-2-one (58 mg) and by the reaction and treatment in the same manner as in Example 649, the title compound (36 mg) was obtained.

MS (ESI) m/z: 491(M+H)$^+$.

Example 827

Synthesis of 1-{5-(1,1-dioxo-1$\lambda^6$-isothiazolidin-2-yl)-2-[4-(3,5,6-trimethylpyridin-2-yl)piperazine-1-carbonyl]phenyl}imidazolidin-2-one

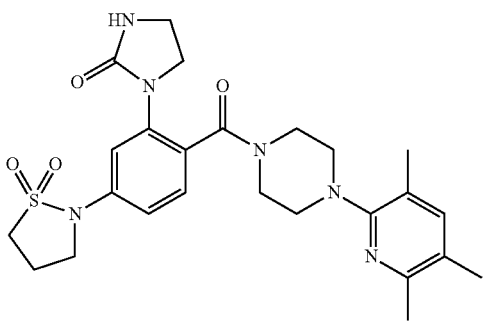 [SMILES: Cc1cc(C)c(N2CCN(C(=O)c3ccc(N4CCCS4(=O)=O)cc3N3CCNC3=O)CC2)nc1C]

Using 1-acetyl-3-{5-chloro-2-[4-(3,5,6-trimethylpyridin-2-yl)piperazine-1-carbonyl]phenyl}imidazolidin-2-one (190 mg) described in Preparation Example 258 and isothiazolidine 1,1-dioxide (73 mg) and by the reaction and treatment in the same manner as in Example 649, the title compound (109 mg) was obtained.

MS (ESI) m/z: 513(M+H)$^+$.

Example 828

Synthesis of 1-methyl-3-{5-(2-oxopyrrolidin-1-yl)-2-[4-(3,5,6-trimethylpyridin-2-yl)piperazine-1-carbonyl]phenyl}imidazolidin-2-one

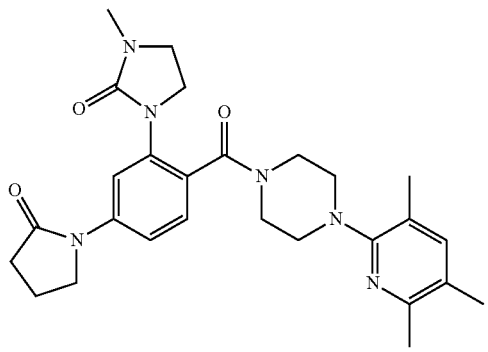 [SMILES: Cc1cc(C)c(N2CCN(C(=O)c3ccc(N4CCCC4=O)cc3N3CCN(C)C3=O)CC2)nc1C]

Using 1-{5-chloro-2-[4-(3,5,6-trimethylpyridin-2-yl)piperazine-1-carbonyl]phenyl}-3-methylimidazolidin-2-one (55 mg) described in Preparation Example 259 and pyrrolidin-2-one (16 mg) and by the reaction and treatment in the same manner as in Example 666, the title compound (30 mg) was obtained.

MS (ESI) m/z: 491(M+H)$^+$.

Example 829

Synthesis of 1-{5-(1,1-dioxo-1$\lambda^6$-isothiazolidin-2-yl)-2-[4-(3,5,6-trimethylpyridin-2-yl)piperazine-1-carbonyl]phenyl}-3-methylimidazolidin-2-one

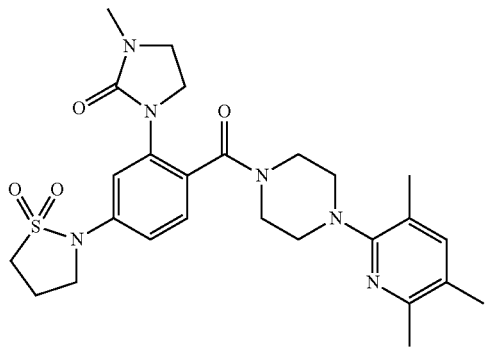 [SMILES: Cc1cc(C)c(N2CCN(C(=O)c3ccc(N4CCCS4(=O)=O)cc3N3CCN(C)C3=O)CC2)nc1C]

Using 1-{5-chloro-2-[4-(3,5,6-trimethylpyridin-2-yl)piperazine-1-carbonyl]phenyl}-3-methylimidazolidin-2-one (57 mg) described in Preparation Example 259 and isothiazolidine 1,1-dioxide (24 mg) and by the reaction and treatment in the same manner as in Example 666, the title compound (28 mg) was obtained.

MS (ESI) m/z: 527(M+H)$^+$.

Example 830

Synthesis of [4-(5-cyclopropyl-3-methylpyridin-2-yl)piperazin-1-yl][4-(1,1-dioxo-1$\lambda^6$-isothiazolidin-2-yl)-2-(pyrrolidine-1-carbonyl)phenyl]methanone

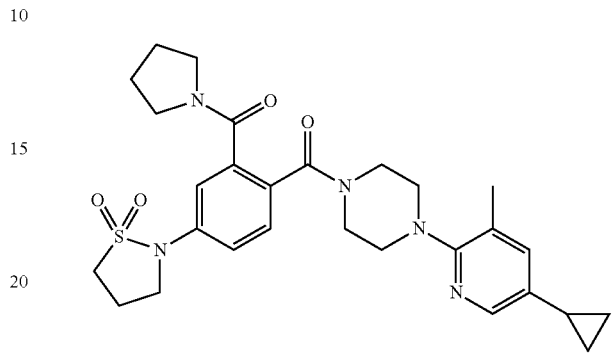

Using N,N-di-tert-butyloxycarbonyl-2-[4-(5-cyclopropyl-3-methylpyridin-2-yl)piperazine-1-carbonyl]-5-(1,1-dioxo-1$\lambda^6$-isothiazolidin-2-yl)benzamide (90 mg) described in Example 805 and pyrrolidine (13 μL) and by the reaction and treatment in the same manner as in Example 770, the title compound (59 mg) was obtained.

MS (ESI) m/z: 538(M+H)$^+$.

Example 831

Synthesis of 2-[4-(5-cyclopropyl-3-methylpyridin-2-yl)piperazine-1-carbonyl]-5-(1,1-dioxo-1$\lambda^6$-isothiazolidin-2-yl)-N,N-dimethylbenzamide

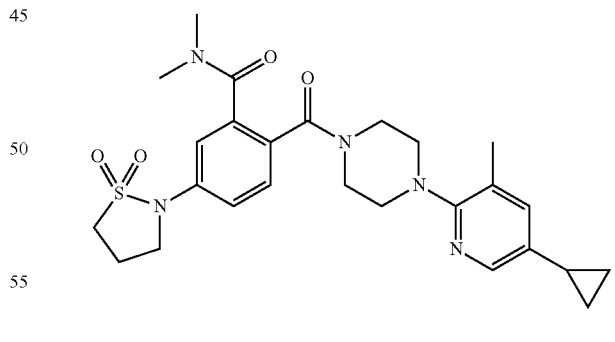

Using N,N-di-tert-butyloxycarbonyl-2-[4-(5-cyclopropyl-3-methylpyridin-2-yl)piperazine-1-carbonyl]-5-(1,1-dioxo-1$\lambda^6$-isothiazolidin-2-yl)benzamide (100 mg) described in Example 805 and 2 mol/L dimethylamine tetrahydrofuran solution (88 μL) and by the reaction and treatment in the same manner as in Example 770, the title compound (41 mg) was obtained.

MS (ESI) m/z: 512(M+H)$^+$.

Example 832

Synthesis of [4-(3,5-dimethylpyridin-2-yl)piperazin-1-yl][4-(1,1-dioxo-1λ$^6$-isothiazolidin-2-yl)-2-(pyrrolidine-1-carbonyl)phenyl]methanone

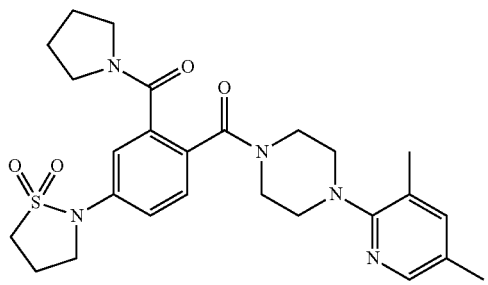 [SMILES: Cc1cnc(N2CCN(C(=O)c3ccc(N4CCCS4(=O)=O)cc3C(=O)N3CCCC3)CC2)c(C)c1]

Using N,N-di-tert-butyloxycarbonyl-2-[4-(3,5-dimethylpyridin-2-yl)piperazine-1-carbonyl]-5-(1,1-dioxo-1λ$^6$-isothiazolidin-2-yl)benzamide (100 mg) described in Example 808 and pyrrolidine (15 μL) and by the reaction and treatment in the same manner as in Example 770, the title compound (56 mg) was obtained.

MS (ESI) m/z: 512(M+H)$^+$.

Example 833

Synthesis of 2-[4-(3,5-dimethylpyridin-2-yl)piperazine-1-carbonyl]-5-(1,1-dioxo-1λ$^6$-isothiazolidin-2-yl)-N,N-dimethylbenzamide

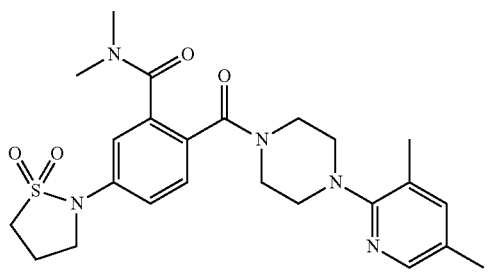 [SMILES: Cc1cnc(N2CCN(C(=O)c3ccc(N4CCCS4(=O)=O)cc3C(=O)N(C)C)CC2)c(C)c1]

Using N,N-di-tert-butyloxycarbonyl-2-[4-(3,5-dimethylpyridin-2-yl)piperazine-1-carbonyl]-5-(1,1-dioxo-1λ$^6$-isothiazolidin-2-yl)benzamide (115 mg) described in Example 808 and 2 mol/L dimethylamine tetrahydrofuran solution (105 μL) and by the reaction and treatment in the same manner as in Example 770, the title compound (39 mg) was obtained.

MS (ESI) m/z: 486(M+H)$^+$.

Example 834

Synthesis of [4-(3,5-dimethylpyridin-2-yl)piperazin-1-yl][4-(1,1-dioxo-1λ$^6$-isothiazolidin-2-yl)-2-(piperidine-1-carbonyl)phenyl]methanone

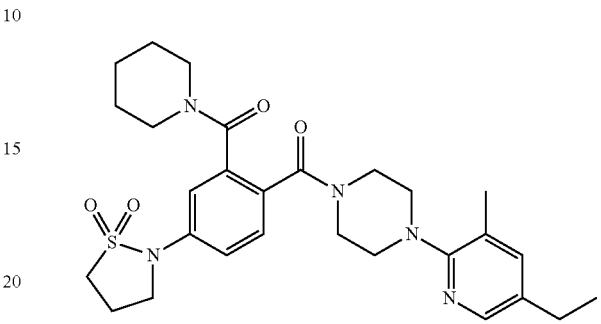

Using N,N-di-tert-butyloxycarbonyl-5-(1,1-dioxo-1λ$^6$-isothiazolidin-2-yl)-2-[4-(5-ethyl-3-methylpyridin-2-yl)piperazine-1-carbonyl]benzamide (192 mg) described in Example 785 and piperidine (34 μL) and by the reaction and treatment in the same manner as in Example 770, the title compound (86 mg) was obtained.

MS (ESI) m/z: 540(M+H)$^+$.

Example 835

Synthesis of 2-[4-(3,5-dimethylpyridin-2-yl)piperazine-1-carbonyl]-5-(2-methyl-5-oxopyrrolidin-1-yl)benzonitrile

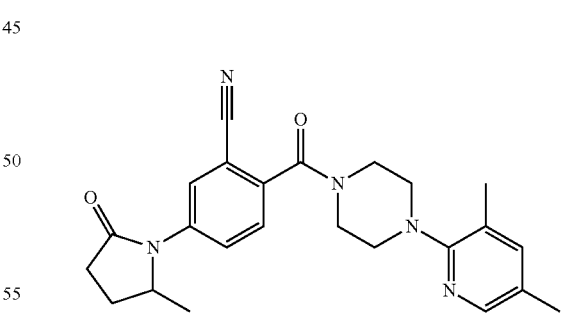

Using 5-bromo-2-[4-(3,5-dimethylpyridin-2-yl)piperazine-1-carbonyl]benzonitrile (1 g) described in Preparation Example 187 and 5-methylpyrrolidin-2-one (372 mg) and by the reaction and treatment in the same manner as in Example 262, the title compound (965 mg) was obtained.

MS (ESI) m/z: 418(M+H)$^+$.

Example 836

Synthesis of 2-[4-(3,5-dimethylpyridin-2-yl)piperazine-1-carbonyl]-5-(2-methyl-5-oxopyrrolidin-1-yl)benzamide

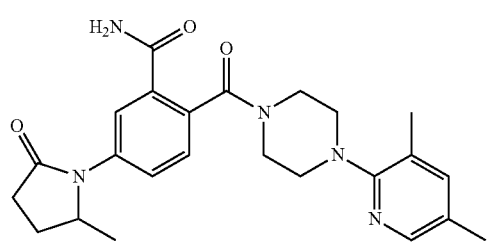 [SMILES: Cc1cnc(N2CCN(C(=O)c3ccc(N4C(=O)CCC4C)cc3C(N)=O)CC2)c(C)c1]

Using 2-[4-(3,5-dimethylpyridin-2-yl)piperazine-1-carbonyl]-5-(2-methyl-5-oxopyrrolidin-1-yl)benzonitrile (700 mg) described in Example 835 and by the reaction and treatment in the same manner as in Example 722, the title compound (684 mg) was obtained.

MS (ESI) m/z: 436(M+H)$^+$.

Example 837

Synthesis of N,N-di-tert-butyloxycarbonyl-2-[4-(3,5-dimethylpyridin-2-yl)piperazine-1-carbonyl]-5-(2-methyl-5-oxopyrrolidin-1-yl)benzamide

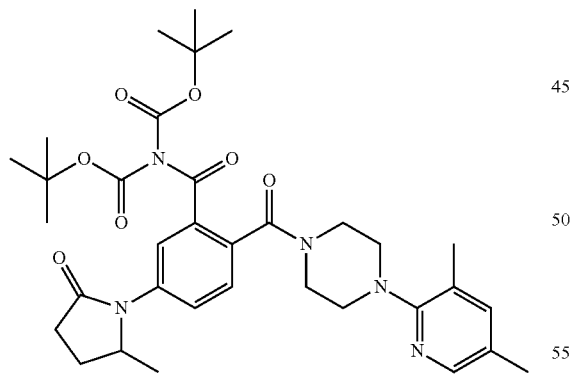

Using 2-[4-(3,5-dimethylpyridin-2-yl)piperazine-1-carbonyl]-5-(2-methyl-5-oxopyrrolidin-1-yl)benzamide (500 mg) described in Example 836 and di-tert-butyl dicarbonate (1128 mg) and by the reaction and treatment in the same manner as in Example 768, the title compound (679 mg) was obtained.

MS (ESI) m/z: 636(M+H)$^+$.

Example 838

Synthesis of 2-[4-(3,5-dimethylpyridin-2-yl)piperazine-1-carbonyl]-N,N-dimethyl-5-(2-methyl-5-oxopyrrolidin-1-yl)benzamide

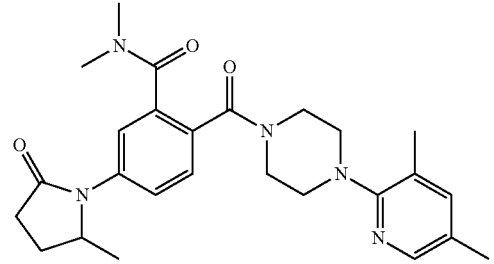 [SMILES: Cc1cnc(N2CCN(C(=O)c3ccc(N4C(=O)CCC4C)cc3C(=O)N(C)C)CC2)c(C)c1]

Using N,N-di-tert-butyloxycarbonyl-2-[4-(3,5-dimethylpyridin-2-yl)piperazine-1-carbonyl]-5-(2-methyl-5-oxopyrrolidin-1-yl)benzamide (70 mg) described in Example 837 and 2 mol/L dimethylamine tetrahydrofuran solution (220 μL) and by the reaction and treatment in the same manner as in Example 770, the title compound (26 mg) was obtained.

MS (ESI) m/z: 464(M+H)$^+$.

Example 839

Synthesis of 1-[4-[4-(3,5-dimethylpyridin-2-yl)piperazine-1-carbonyl]-3-(pyrrolidine-1-carbonyl)phenyl]-5-methylpyrrolidin-2-one

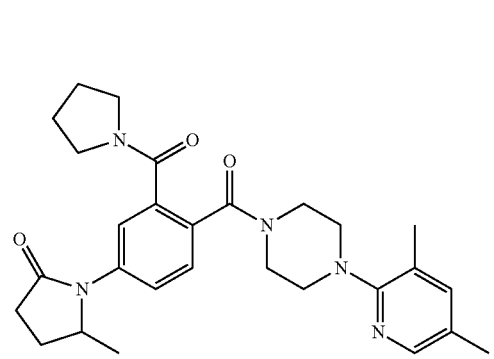 [SMILES: Cc1cnc(N2CCN(C(=O)c3ccc(N4C(=O)CCC4C)cc3C(=O)N3CCCC3)CC2)c(C)c1]

Using N,N-di-tert-butyloxycarbonyl-2-[4-(3,5-dimethylpyridin-2-yl)piperazine-1-carbonyl]-5-(2-methyl-5-oxopyrrolidin-1-yl)benzamide (70 mg) described in Example 837 and pyrrolidine (36 μL) and by the reaction and treatment in the same manner as in Example 770, the title compound (38 mg) was obtained.

MS (ESI) m/z: 490(M+H)$^+$.

Example 840

Synthesis of 1-[4-[4-(3,5-dimethylpyridin-2-yl)piperazine-1-carbonyl]-3-(piperidine-1-carbonyl)phenyl]-5-methylpyrrolidin-2-one

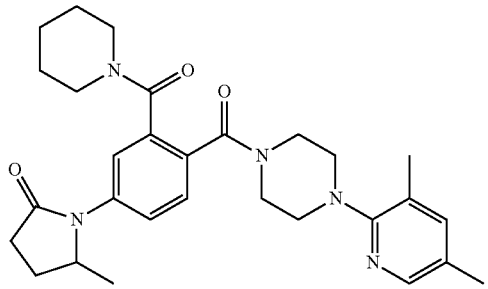 [SMILES: Cc1cnc(N2CCN(C(=O)c3ccc(N4C(=O)CCC4C)cc3C(=O)N3CCCCC3)CC2)c(C)c1]

Using N,N-di-tert-butyloxycarbonyl-2-[4-(3,5-dimethylpyridin-2-yl)piperazine-1-carbonyl]-5-(2-methyl-5-oxopyrrolidin-1-yl)benzamide (70 mg) described in Example 837 and piperidine (44 μL) and by the reaction and treatment in the same manner as in Example 770, the title compound (34 mg) was obtained.

MS (ESI) m/z: 504(M+H)$^+$.

Example 841

Synthesis of 1-[4-[4-(3,5-dimethylpyridin-2-yl)piperazine-1-carbonyl]-3-(morpholine-4-carbonyl)phenyl]-5-methylpyrrolidin-2-one

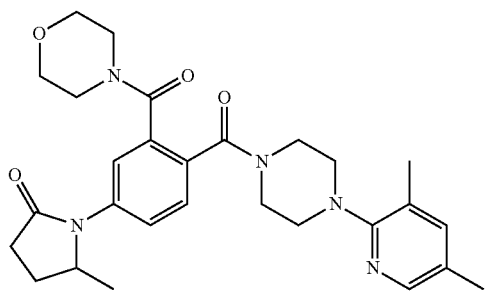 [SMILES: Cc1cnc(N2CCN(C(=O)c3ccc(N4C(=O)CCC4C)cc3C(=O)N3CCOCC3)CC2)c(C)c1]

Using N,N-di-tert-butyloxycarbonyl-2-[4-(3,5-dimethylpyridin-2-yl)piperazine-1-carbonyl]-5-(2-methyl-5-oxopyrrolidin-1-yl)benzamide (70 mg) described in Example 837 and morpholine (39 μL) and by the reaction and treatment in the same manner as in Example 770, the title compound (18 mg) was obtained.

MS (ESI) m/z: 506(M+H)$^+$.

Example 842

Synthesis of 2-[4-(3,5-dimethylpyridin-2-yl)piperazine-1-carbonyl]-N-(2-methoxyethyl)-N-methyl-5-(2-methyl-5-oxopyrrolidin-1-yl)benzamide

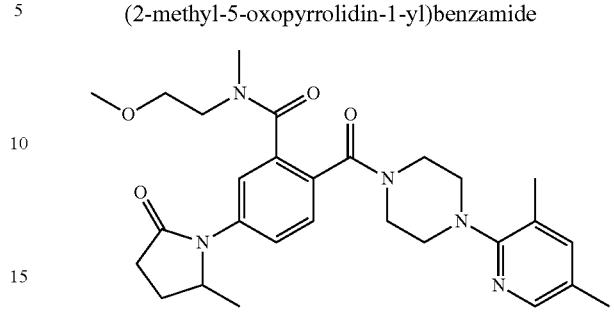

Using N,N-di-tert-butyloxycarbonyl-2-[4-(3,5-dimethylpyridin-2-yl)piperazine-1-carbonyl]-5-(2-methyl-5-oxopyrrolidin-1-yl)benzamide (70 mg) described in Example 837 and (2-methoxyethyl)(methyl)amine (49 μL) and by the reaction and treatment in the same manner as in Example 770, the title compound (28 mg) was obtained.

MS (ESI) m/z: 508(M+H)$^+$.

Example 843

Synthesis of 1-[4-[4-(3,5-dimethylpyridin-2-yl)piperazine-1-carbonyl]-3-(4-methylpiperazine-1-carbonyl)phenyl]pyrrolidin-2-one

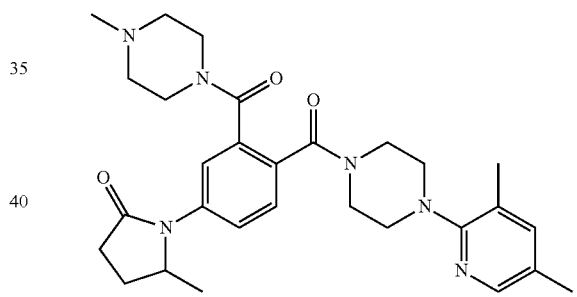

Using N,N-di-tert-butyloxycarbonyl-2-[4-(3,5-dimethylpyridin-2-yl)piperazine-1-carbonyl]-5-(2-methyl-5-oxopyrrolidin-1-yl)benzamide (80 mg) described in Example 837 and 1-methylpiperazine (52 mg) and by the reaction and treatment in the same manner as in Example 770, the title compound (37 mg) was obtained.

MS (ESI) m/z: 505(M+H)$^+$.

Experimental Example 1

Action of human TNFα stimulated THP-1 cell on proMMP-9 production

THP-1 cell (human monocytic leukemia cell line) was adjusted to $1\times10^7$ cells/mL in a culture medium (10% fetal bovine serum/RPMI1640 medium), and dispensed to a 96 well multiplate. This was equilibrated under the conditions of 37° C./5% $CO_2$, and a culture medium containing human TNFα (final concentration 10 ng/mL) and a test compound was added thereto. After incubation under the conditions of 37° C./5% $CO_2$ for 24 hr, the culture medium was centrifuged and the culture supernatant was collected, which was subjected to the following measurement.

Quantification of proMMP-9 in Culture Supernatant

The proMMP-9 concentration of the collected culture supernatant was quantified using a commercially available measurement reagent (manufactured by GE Healthcare, MMP-9, Human, Biotrak ELISA System).

Calculation of proMMP-9 Suppression Rate

The proMMP-9 suppression rate of the test compound was calculated from the following formula:

% suppression=100−((Test−Min)/(Max−Min)×100)

wherein Max is proMMP-9 concentration of culture supernatant induced by stimulation with human TNFα, without addition of a test compound (added with solvent alone)

Min is proMMP-9 concentration of culture supernatant without addition of a test compound (added with solvent alone) and without stimulation with human TNFα, and Test is proMMP-9 concentration of culture supernatant induced by stimulation with human TNFα when a test compound is added.

Furthermore, the concentration of the test compound necessary for suppressing proMMP-9 production by human TNFα stimulated THP-1 cell by 50% ($IC_H$ value) was calculated from 3 points of proMMP-9 suppression rate at test compound concentrations of 10, 100 and 1,000 nmol/L.

Experimental Example 2

Action of THP-1 cell on hemostatic type proMMP-2 production

THP-1 cell (human monocytic leukemia cell line) was adjusted to $1 \times 10^7$ cells/mL in a culture medium (10% fetal bovine serum/RPMI1640 medium), and dispensed to a 96 well multiplate. This was equilibrated under the conditions of 37° C./5% $CO_2$, and a culture medium containing a test compound was added thereto. After incubation under the conditions of 37° C./5% $CO_2$ for 24 hr, the culture medium was centrifuged and the culture supernatant was collected, which was subjected to the following measurement.

Quantification of proMMP-2 in Culture Supernatant

The proMMP-2 concentration of the collected culture supernatant was quantified using a commercially available measurement reagent (manufactured by GE Healthcare, MMP-2, Human, Biotrak ELISA System).

Calculation of proMMP-2 Suppression Rate

The proMMP-2 suppression rate of the test compound was calculated from the following formula:

% suppress=100−((Test/Cont)×100).

wherein Cont is proMMP-2 concentration of culture supernatant without addition of a test compound (added with solvent alone) and Test is proMMP-2 concentration of culture supernatant with addition of a test compound.

The results of the Example compounds of the present invention in Experimental Examples 1 and 2 are shown in the following Table 1 and Table 2.

TABLE 1

| Example compounds | Experimental Example 1 proMMP-9 production suppression ($IC_{50}$, nM) |
|---|---|
| 130 | 44 |
| 154 | 82 |
| 245 | 73 |

TABLE 1-continued

| Example compounds | Experimental Example 1 proMMP-9 production suppression ($IC_{50}$, nM) |
|---|---|
| 282 | 76 |
| 416 | 10 |
| 474 | 36 |
| 494 | 102 |
| 549 | 7 |
| 687 | 41 |

TABLE 2

| Example compounds | Experimental Example 2 MMP-2 production suppression (% suppression, 2 μM) |
|---|---|
| 130 | 8.0 |
| 154 | 13.0 |

MMP-9 is produced as a precursor proMMP-9 by the stimulated cells, extracellularly activated and expresses the physiological activity as MMP-9. That is, evaluation of the suppression of proMMP-9 produced by the cell means evaluation of the suppression of production of MMP-9. The same applies to MMP-2, and evaluation of the suppression of proMMP-2 produced by the cell means evaluation of the suppression of production is of MMP-2.

Experimental Example 3

Suppressive Action on Hindpaw Edema of Rat Adjuvant Induced Arthritis Model

Anesthetized rats (LEW, male, 6-week-old) were immunized with M. Butyricum (5 mg/mL) at a dose of 0.1 mL/body by subcutaneous administration from the tail root. On day 15, the hindpaw volume was measured (rat hindpaw edema volume measuring apparatus, Plethysmometer, manufactured by: Unicom (Yachiyo. Chiba, Japan) standard: TK-101 Series No.:101 GH1), and the rats were allocated such that each test group had a uniform hindpaw volume. The test compound was orally administered once a day from immediately after allocation on day 15 to day 20 at doses of 3 and 30 mg/kg, and the hindpaw volume was measured again on day 21. The amount of hindpaw edema was the difference in the amount between hindpaw volume on day 15 and that on day 21.

The results of the Example compound of the present invention in Experimental Example 3 are shown in Table 3 below.

TABLE 3

| compound administered | dose | hindpaw edema volume of disease group (administered with solvent) | hindpaw edema volume of compound administration group |
|---|---|---|---|
| Example 11 | 10 mg/kg | 0.63 ± 0.13 | 0.24 ± 0.10 |

Experimental Example 4

Suppressive Action on Articular Joints Injury of Rat Monoiodoacetic Acid-Induced Osteoarthritis Model Monoiodoacetic acid solution (0.3 mg/25 μL) was injected into the right hindpaw knee joint cavity of anesthetized rats (LEW, male, 7-week-old). A test compound was orally administered once a day from immediately after monoiodoacetic acid injection to day 6 at a dose of 10 mg/kg. On day 7, right hindpaw knee joint was taken from euthanized rats, and fixed with 10% neutral formalin solution. A pathology specimen of knee joint was prepared, stained with Hematoxylin Eosin and Safranine O, and the state of joint cartilage injury was scored under microscopic observation. For articular joint injury scores, changes in each pathological finding in medial condyle of femur and medial condyle of tibia (cartilage surface tuberosity, erosion/ulcer/fibrillation, chondrocyte disorganization/disappearance/hypertrophy, reduction of Safranine staining) were divided into mild, moderate and severe according to the method of Kobayashi et al. (Kobayashi K et al. J. Vet. Med. Sci. 65, 1195 1199 2003), and indicated in the scores of 1, 2 and 3 and totaled. Furthermore, an average of the score of medial condyle of femur and that of medial condyle of tibia was determined and used as an articular joint injury score.

The results of the Example compounds of the present invention in Experimental Example 4 are shown in Table 4 below.

TABLE 4

| compound administered | dose | articular joint injury score of disease group (administered with solvent) | articular joint injury score of compound administration group |
|---|---|---|---|
| Example 154 | 10 mg/kg | 5.8 ± 0.2 | 4.6 ± 0.4 |

Experimental Example 5

Suppressive Action on Large Intestine Weight Increase of Rat Dinitrobenzene-Induced Colitis Model A dinitrobenzene solution (30 mg/0.1 mL) was injected into the large intestine of anesthetized rats (Wistar, male, 6-week-old). A test compound was orally administered once a day from the previous day of the dinitrobenzene injection to day 7 at a dose of 30 mg/kg. On day 8, the large intestine was isolated from euthanized rats, and the wet weight thereof was measured. The large intestine weight was amended to the weight per 100 g body weight of the rats on day 8.

The results of the Example compound of the present invention in Experimental Example 5 are shown in Table 5 below.

TABLE 5

| test group | dose | large intestine weight (g/100 g body weight) |
|---|---|---|
| normal group without treatment | | 0.215 ± 0.011 |
| pathology group | | 0.633 ± 0.041 |
| Example compound 11 | 10 mg/kg | 0.509 ± 0.051 |

As is clear from the results of Tables 1 and 2, the compound of the present invention has a selective MMP-9 production suppressive action, and is a highly safe compound showing suppressed expression of side effects caused by the suppression of MMP-2 production. Furthermore, since the compound of the present invention has a suppressive action on the hindpaw edema of an adjuvant-induced arthritis model (Table 3), autoimmune diseases such as rheumatoid arthritis and the like, a suppressive action on the increase of large intestine weight of a dinitrobenzene-induced colitis model (Table 5), and a suppressive action on inflammatory bowel disease (ulcerative colitis, Crohn's disease) and articular joint injury of monoiodoacetic acid-induced osteoarthritis models (Table 4), it is useful as a prophylactic and/or therapeutic drug for osteoarthritis.

Industrial Applicability

According to the present invention, a compound having a selective MMP-9 production suppressive action, and a medicament containing same as an active ingredient can be provided.

This application is based on patent application No. 2010-101953 filed in Japan, the contents of which are encompassed in full herein.

The invention claimed is:
1. An amide derivative represented by formula (I)

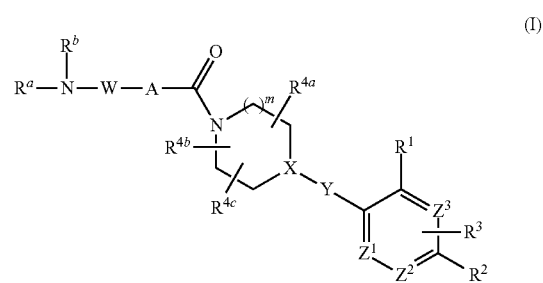

wherein A is a 5-membered heteroarylene containing 1-3 atoms selected from a nitrogen atom, an oxygen atom and a sulfur atom or phenylene or a 6-membered heteroarylene represented by the formula

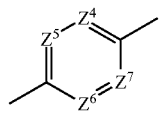

wherein $Z^4$, $Z^5$, $Z^6$ and $Z^7$ are each a carbon atom or a nitrogen atom, the phenylene and heteroarylene are optionally substituted by one or the same or different 2 or 3 substituents selected from a halogen atom; a hydroxyl group; nitro; cyano; mercapto; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$ $C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ acyloxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; $C_3$-$C_6$ cycloalkylthio; $C_3$-$C_6$ cycloalkylsulfinyl; $C_3$-$C_6$ cycloalkylsulfonyl; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; aminocarbonyl wherein the amino moiety is optionally mono- or di-substituted by $C_1$-$C_6$ alkyl (wherein $C_1$-$C_6$ alkyl is optionally substituted by a halogen atom, a hydroxyl group, cyano, $C_1$-$C_6$ alkoxy, amino optionally mono- or di-substituted by $C_1$-$C_6$ alkyl, $C_6$-$C_{10}$ aryl optionally substituted by substituent B shown below or heteroaryl containing 1-6 atoms selected from a nitrogen atom, an oxygen atom and a sulfur atom and having 5-10 ring-constituting atoms, which is optionally substituted by substituent B shown below), $C_3$-$C_6$ cycloalkyl (wherein $C_3$-$C_6$ cycloalkyl is optionally substituted by substituent B shown below), $C_2$-$C_7$ alkoxycarbonyl, $C_6$-$C_{10}$ aryl optionally substituted by substituent B shown below, heteroaryl containing 1-6 atoms selected from a nitrogen atom, an oxygen atom and a sulfur atom and having 5-10 ring-constituting atoms, which is optionally substituted by substituent B shown below, or a nonaromatic heterocyclic group containing 1-4 atoms selected from a nitrogen atom, an oxygen atom and a sulfur atom and having 3-7 ring-constituting atoms, which is optionally substituted by substituent B shown below; $C_1$-$C_6$ alkylsulfonylamino wherein the amino moiety is optionally substituted by $C_1$-$C_6$ alkyl; $C_3$-$C_6$ cycloalkylsulfonylamino wherein the amino moiety is optionally substituted by $C_1$-$C_6$ alkyl; a nonaromatic heterocyclic group containing 1-4 atoms selected from a nitrogen atom, an oxygen atom and a sulfur atom, and having 3-7 ring-constituting atoms, which is optionally substituted by a halogen atom, a hydroxyl group, oxo, dioxo, $C_1$-$C_6$ alkyl (which is optionally substituted by amino optionally mono- or di-substituted by $C_1$-$C_6$ alkyl, a halogen atom, a hydroxyl group, $C_1$-$C_6$ alkoxy, arylalkyl wherein the $C_6$-$C_{10}$ aryl moiety is optionally substituted by substituent B shown below and the alkyl moiety has 1-6 carbon atoms, arylalkyloxy wherein the $C_6$-$C_{10}$ aryl moiety is optionally substituted by substituent B shown below and the alkyl moiety has 1-6 carbon atoms, heteroarylalkyl wherein the heteroaryl moiety containing 1-6 atoms selected from a nitrogen atom, an oxygen atom and a sulfur atom, and having 5-10 ring-constituting atoms is optionally substituted by substituent B shown below and the alkyl moiety has 1-6 carbon atoms or heteroarylalkyloxy wherein the heteroaryl moiety containing 1-6 atoms selected from a nitrogen atom, an oxygen atom and a sulfur atom, and having 5-10 ring-constituting atoms is optionally substituted by substituent B shown below and the alkyl moiety has 1-6 carbon atoms), $C_1$-$C_6$ alkoxy (which is optionally substituted by amino optionally mono- or di-substituted by $C_1$-$C_6$ alkyl, a halogen atom, a hydroxyl group or $C_1$-$C_6$ alkoxy) or $C_2$-$C_7$ acyl; carbonyl substituted by a nonaromatic heterocyclic group containing at least one nitrogen atom and 0-3 atoms selected from a nitrogen atom, an oxygen atom and a sulfur atom, and having 3-7 ring-constituting atoms, which is optionally substituted by substituent B shown below (wherein the carbonyl is bonded to a nitrogen atom on a nonaromatic heterocyclic group); and R'—NH—CO—NH— (wherein R' is $C_1$-$C_6$ alkyl optionally substituted by a halogen atom; $C_3$-$C_6$ cycloalkyl optionally substituted by a halogen atom; a nonaromatic heterocyclic group containing 1-4 atoms selected from a nitrogen atom, an oxygen atom and a sulfur atom, and having 3-7 ring-constituting atoms, which is optionally substituted by a halogen atom; $C_6$-$C_{10}$ aryl optionally substituted by substituent B shown below; or heteroaryl containing 1-6 atoms selected from a nitrogen atom, an oxygen atom and a sulfur atom and having 5-10 ring-constituting atoms, which is optionally substituted by substituent B shown below), the right bond is bonded to carbonyl, and the left bond is bonded to substituent W, $R^1$ is a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ alkoxycarbonyl; carboxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; $C_1$-$C_6$ alkylsulfonylamino wherein the amino moiety is optionally substituted by $C_1$-$C_6$ alkyl; or $C_3$-$C_6$ cycloalkylsulfonylamino wherein the amino moiety is optionally substituted by $C_1$-$C_6$ alkyl, $R^2$ is a halogen atom; a hydroxyl group; nitro; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; $C_1$-$C_6$ alkylsulfonylamino wherein the amino moiety is optionally substituted by $C_1$-$C_6$ alkyl; or $C_3$-$C_6$ cycloalkylsulfonylamino wherein the amino moiety is optionally substituted by $C_1$-$C_6$ alkyl, $R^3$ is a hydrogen atom; a halogen atom; a hydroxyl group; nitro; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ alkoxycarbonyl; or carboxy, $R^{4a}$, $R^{4b}$ and $R^{4c}$ are the same or different and each is a hydrogen atom, $C_1$-$C_6$ alkyl, oxo or $C_1$-$C_6$ alkoxy, W is a bond, $C_1$-$C_6$ alkylene or $C_3$-$C_6$ cycloalkylidene, X is a carbon atom (any of $R^{4a}$, $R^{4b}$ and $R^{4c}$ may be bonded to the carbon atom, but the carbon atom is not substituted by oxo) or a nitrogen atom (when Y is a bond, the nitrogen atom may be oxidized to form N-oxide), Y is a bond, carbonyl, $C_1$-$C_6$ alkylene, an oxygen atom or —NH—, m is 1 or 2, $Z^1$, $Z^2$ and $Z^3$ are the same or different and each is a carbon atom or a nitrogen atom, wherein $Z^1$, $Z^2$ and $Z^3$ are not nitrogen atoms at the same time, $R^a$ and $R^b$, together with the adjacent nitrogen atom, form a nitrogen-containing cyclic group selected from

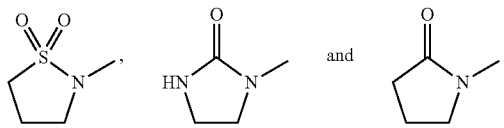

which is optionally substituted with $C_1$-$C_6$ alkoxy, oxo, or $C_1$-$C_6$ alkyl optionally substituted with a hydroxyl group, when the formula (I) is

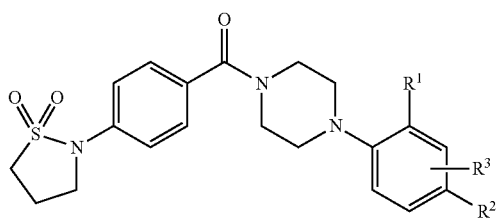

then $R^1$ and $R^2$ are not methyl groups at the same time, and wherein substituent B is a halogen atom; a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group or amino; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl or $C_3$-$C_6$ cycloalkyl; aminocarbonyl wherein the amino moiety is optionally mono- or di-substituted by $C_1$-$C_6$ alkyl or $C_3$-$C_6$ cycloalkyl; or carbonyl which is substituted by a nonaromatic heterocyclic group containing 1-4 atoms selected from a nitrogen atom, an oxygen atom and a sulfur atom and having 3-7 ring-constituting atoms and optionally substituted by a halogen atom, a hydroxyl group, oxo, dioxo, $C_1$-$C_6$ alkyl or $C_1$-$C_6$ alkoxy, or a pharmacologically acceptable salt thereof.

2. The amide derivative according to claim 1, wherein X is a nitrogen atom or N-oxide wherein nitrogen atom is oxidized and Y is a bond, or a pharmacologically acceptable salt thereof.

3. The amide derivative according to claim 1, wherein A is 5-membered heteroarylene containing 1-3 atoms selected from a nitrogen atom, an oxygen atom and a sulfur atom, or phenylene or 6-membered heteroarylene represented by the formula

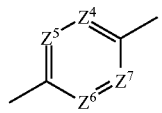

wherein $Z^4$, $Z^5$, $Z^6$ and $Z^7$ are each a carbon atom or a nitrogen atom, the phenylene and heteroarylene are optionally substituted by one or the same or different 2 or 3 substituents selected from a halogen atom; a hydroxyl group; nitro; cyano; mercapto; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_6$ alkenyl; $C_2$-$C_6$ alkynyl; $C_3$-$C_6$ cycloalkyl optionally substituted by a halogen atom, a hydroxyl group or amino; $C_6$-$C_{10}$ aryl optionally substituted by substituent B shown below; heteroaryl containing 1-6 atoms selected from a nitrogen atom, an oxygen atom and a sulfur atom and having 5-10 ring-constituting atoms, which is optionally substituted by substituent B shown below; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ acyloxy; $C_1$-$C_6$ alkylthio wherein the alkyl moiety is optionally substituted by a halogen atom or a hydroxyl group; $C_1$-$C_6$ alkylsulfinyl wherein the alkyl moiety is optionally substituted by a halogen atom or a hydroxyl group; $C_1$-$C_6$ alkylsulfonyl wherein the alkyl moiety is optionally substituted by a halogen atom or a hydroxyl group; $C_3$-$C_6$ cycloalkylthio; $C_3$-$C_6$ cycloalkylsulfinyl; $C_3$-$C_6$ cycloalkylsulfonyl; amino optionally mono- or di-substituted by $C_1$-$C_6$ alkyl or $C_3$-$C_6$ cycloalkyl; $C_2$-$C_7$ acylamino wherein the amino moiety is optionally substituted by $C_1$-$C_6$ alkyl; aminocarbonyl wherein the amino moiety is optionally mono- or di-substituted by $C_1$-$C_6$ alkyl or $C_3$-$C_6$ cycloalkyl; $C_1$-$C_6$ alkylsulfonylamino wherein the amino moiety is optionally substituted by $C_1$-$C_6$ alkyl; $C_3$-$C_6$ cycloalkylsulfonylamino wherein the amino moiety is optionally substituted by $C_1$-$C_6$ alkyl; a nonaromatic heterocyclic group containing 1-4 atoms selected from a nitrogen atom, an oxygen atom and a sulfur atom, and having 3-7 ring-constituting atoms, which is optionally substituted by a halogen atom, a hydroxyl group, oxo, dioxo, $C_1$-$C_6$ alkyl or $C_1$-$C_6$ alkoxy; and R'—NH—CO—NH— (wherein R' is $C_1$-$C_6$ alkyl optionally substituted by a halogen atom; $C_3$-$C_6$ cycloalkyl optionally substituted by a halogen atom; a nonaromatic heterocyclic group containing 1-4 atoms selected from a nitrogen atom, an oxygen atom and a sulfur atom, and having 3-7 ring-constituting atoms, which is optionally substituted by a halogen atom; $C_6$-$C_{10}$ aryl optionally substituted by substituent B shown below; or heteroaryl containing 1-6 atoms selected from a nitrogen atom, an oxygen atom and a sulfur atom and having 5-10 ring-constituting atoms, which is optionally substituted by substituent B shown below, the right bond is bonded to carbonyl, and the left bond is bonded to substituent W, and wherein substituent B is
  a halogen atom; a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group or amino; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl or $C_3$-$C_6$ cycloalkyl; aminocarbonyl wherein the amino moiety is optionally mono- or di-substituted by $C_1$-$C_6$ alkyl or $C_3$-$C_6$ cycloalkyl; or carbonyl which is substituted by a nonaromatic heterocyclic group containing 1-4 atoms selected from a nitrogen atom, an oxygen atom and a sulfur atom and having 3-7 ring-constituting atoms and optionally substituted by a halogen atom, a hydroxyl group, oxo, dioxo, $C_1$-$C_6$ alkyl or $C_1$-$C_6$ alkoxy,
or a pharmacologically acceptable salt thereof.

4. The amide derivative according to claim 1, wherein A is phenylene or 6-membered heteroarylene, or a pharmacologically acceptable salt thereof.

5. The amide derivative according to claim 1, wherein W is a bond, or a pharmacologically acceptable salt thereof.

6. The amide derivative according to claim 1, wherein $Z^2$ and $Z^3$ are carbon atoms, or a pharmacologically acceptable salt thereof.

7. The amide derivative according to claim 1, wherein $R^1$ is $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino,
  $R^2$ is $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino, and
  $R^3$ is a hydrogen atom; a halogen atom; $C_1$-$C_6$ alkyl optionally substituted by a halogen atom; $C_2$-$C_6$ alkenyl; $C_2$-$C_6$ alkynyl; or $C_3$-$C_6$ cycloalkyl optionally substituted by a halogen atom, a hydroxyl group or amino, or a pharmacologically acceptable salt thereof.

8. The amide derivative according to claim 1, wherein $R_{4a}$, $R^{4b}$ and $R^{4c}$ are hydrogen atoms, or a pharmacologically acceptable salt thereof.

9. [4-(3,5-dimethylpyridin-2-yl)piperazin-1-yl][4-(1,1-dioxo-1$\lambda^6$-isothiazolidin-2-yl)-2-fluorophenyl]methanone,
  [4-(5-cyclopropyl-3-methylpyridin-2-yl)piperazin-1-yl][6-(1,1-dioxo-1$\lambda^6$-isothiazolidin-2-yl)-2-methylpyridin-3-yl]methanone,
  1-{4-[4-(3,5-dimethylpyridin-2-yl)piperazine-1-carbonyl]-3-fluorophenyl}imidazolidin-2-one, or
  1-{4-[4-(3,5-dimethylpyridin-2-yl)piperazine-1-carbonyl]-3-fluorophenyl}-3,5-dimethylimidazolidine-2,4-dione.

10. A pharmaceutical composition comprising the amide derivative according to claim 1, or a pharmacologically acceptable salt thereof, and a pharmaceutically acceptable additive.

11. A method of suppressing MMP-9 production in a mammal, comprising administering an effective amount of the amide derivative according to claim 1, or a pharmacologically acceptable salt thereof to the mammal, thereby suppressing MMP-9 production in the mammal.

12. A method of treating osteoarthritis, comprising administering an effective amount of the amide derivative according to claim 1, or a pharmacologically acceptable salt thereof to the mammal, thereby treating osteoarthritis in the mammal.

13. A method of treating an autoimmune disease in a mammal, wherein the autoimmune disease is rheumatoid arthritis, multiple sclerosis or systemic lupus erythematosus, comprising administering an effective amount of the amide derivative according to claim 1, or a pharmacologically acceptable salt thereof to the mammal, thereby treating the autoimmune disease in the mammal.

14. A method of treating an inflammatory bowel disease in a mammal, wherein the inflammatory bowel disease is Crohn's disease or ulcerative colitis, comprising administering an effective amount of the amide derivative according to claim 1, or a pharmacologically acceptable salt thereof to the mammal, thereby treating the inflammatory bowel disease in the mammal.

* * * * *